United States Patent
Long et al.

(10) Patent No.: US 11,827,657 B2
(45) Date of Patent: Nov. 28, 2023

(54) BORON CONTAINING PYRAZOLE COMPOUNDS, COMPOSITIONS COMPRISING THEM, METHODS AND USES THEREOF

(71) Applicants: BOEHRINGER INGELHEIM ANIMAL HEALTH USA INC., Duluth, GA (US); BORAH, INC., Nashville, TN (US)

(72) Inventors: Alan Long, Warthausen (DE); Chun Yu Liu, Durham, NC (US); Chunliang Liu, Cary, NC (US); Yasheen Zhou, Moraga, CA (US); Shon R. Pulley, Trenton, SC (US); Keith Andrew Newton Graham, Berlin (DE)

(73) Assignees: BOEHRINGER INGELHEIM ANIMAL HEALTH USA INC., Duluth, GA (US); BORAH, INC., Nashville, TN (US)

( * ) Notice: Subject to any disclaimer, the term of this patent is extended or adjusted under 35 U.S.C. 154(b) by 0 days.

(21) Appl. No.: 17/644,023

(22) Filed: Dec. 13, 2021

(65) Prior Publication Data

US 2022/0194965 A1   Jun. 23, 2022

Related U.S. Application Data

(60) Provisional application No. 63/127,329, filed on Dec. 18, 2020.

(51) Int. Cl.
*C07F 5/02* (2006.01)

(52) U.S. Cl.
CPC .................................. *C07F 5/025* (2013.01)

(58) Field of Classification Search
CPC ....................................................... C07F 5/025
See application file for complete search history.

(56) References Cited

U.S. PATENT DOCUMENTS

| | | | |
|---|---|---|---|
| 6,890,929 B2 | 5/2005 | Blumenkopf et al. | |
| 7,687,507 B2 | 3/2010 | Blumenkopf et al. | |
| 8,133,899 B2 | 3/2012 | Mitton-Fry et al. | |
| 8,987,283 B2 | 3/2015 | Mitton-Fry et al. | |
| 9,522,151 B2 | 12/2016 | Gonzales et al. | |
| 10,766,883 B2 * | 9/2020 | Fuller | C07D 413/14 |

FOREIGN PATENT DOCUMENTS

| | | |
|---|---|---|
| WO | 2013041042 A1 | 3/2013 |
| WO | 2018108969 A1 | 6/2018 |
| WO | 2020118597 A1 | 6/2020 |
| WO | 2020120673 A1 | 6/2020 |
| WO | 2020120679 A1 | 6/2020 |
| WO | 2020221914 A1 | 11/2020 |

OTHER PUBLICATIONS

Gonzales et al., Oclacitinib (APOQUEL®) is a novel Janus kinase inhibitor with activity against cytokines involved in allergy. J. Vet Pharmacol. Therap. 2014, 37, 317-324.

Siu et al., The Discovery of 3-((4-Chloro-3-methoxyphenyl)amino)-1-((3R,4S)-4-cyanotetrahydro-2H-pyran-3-yl)-1H-pyrazole-4-carboxamide, a Highly Ligand Efficient and Efficacious Janus Kinase 1 Selective Inhibitor with Favorable Pharmacokinetic Properties. J. Med. Chem. 2017, 60, 9676-9690.

International Preliminary Report on Patentability dated Jun. 29, 2023 for PCT/US2021/072885.

* cited by examiner

*Primary Examiner* — Golam M Shameem

(74) *Attorney, Agent, or Firm* — Barnes & Thornburg LLP

(57) ABSTRACT

The present invention describes novel boron containing pyrazole compounds, or their pharmaceutically acceptable salts, pharmaceutical compositions containing them, and their medical uses. The compounds of the invention have activity as Janus kinase (JAK) inhibitors and are useful in the in the treatment or control of inflammation, auto-immune diseases, cancer, and other disorders and indications where modulation of JAK would be desirable. Also described are methods of treating inflammation, auto-immune diseases, cancer, and other conditions that are susceptible to the inhibition of a Janus kinase by administering a compound herein described.

8 Claims, No Drawings

BORON CONTAINING PYRAZOLE COMPOUNDS, COMPOSITIONS COMPRISING THEM, METHODS AND USES THEREOF

CROSS REFERENCE TO RELATED APPLICATIONS

This application claims the benefit of U.S. Provisional Application No. 63/127,329, filed Dec. 18, 2020, which is incorporated herein by reference, in its entirety.

FIELD OF THE INVENTION

The present invention describes novel boron-containing compounds, or their pharmaceutically acceptable salts, pharmaceutical compositions containing them, and their medical uses. The compounds of the invention have activity as Janus kinase (JAK) inhibitors and are useful in the treatment or control of inflammation, auto-immune diseases, cancer, and other disorders and indications where modulation of JAK would be desirable. Also described herein are methods of treating inflammation, auto-immune diseases, cancer, and other conditions susceptible to inhibition of JAK by administering a compound of the invention.

BACKGROUND OF THE INVENTION

Protein kinases are families of enzymes that catalyze the phosphorylation of specific residues in proteins, broadly classified into tyrosine and serine/threonine kinases. Inappropriate kinase activity, arising from mutation, over-expression, or inappropriate regulation, dys-regulation, or de-regulation, as well as over- or under-production of growth factors or cytokines has been implicated in many diseases, including but not limited to cancer, cardiovascular diseases, allergies, asthma and other respiratory diseases, autoimmune diseases, inflammatory diseases, bone diseases, metabolic disorders, and neurological and neurodegenerative disorders such as Alzheimer's disease. Inappropriate kinase activity triggers a variety of biological cellular responses relating to cell growth, cell differentiation, survival, apoptosis, mitogenesis, cell cycle control, and cell mobility implicated in the aforementioned and related diseases. Thus, protein kinases have emerged as an important class of enzymes as targets for therapeutic intervention. In particular, the JAK family of cellular protein tyrosine kinases (JAK-1, JAK-2, JAK-3, and Tyk-2) play a central role in cytokine signaling (Kisseleva et al, Gene, 2002, 285, 1; Yamaoka et al. Genome Biology 2004, 5, 253)). Upon binding to their receptors, cytokines activate JAK, which then phosphorylate the cytokine receptor, thereby creating docking sites for signaling molecules, notably, members of the signal transducer and activator of transcription (STAT) family that ultimately lead to gene expression, which stimulates biologic responses such as an itch signal. Activation of the JAK-STAT pathway also results in several other ancillary biologic activities that contribute to the inflammation and pruritic processes that contribute to acute allergy in animals but can also exacerbate clinical signs and contribute to chronic allergy.

Atopic dermatitis (AD), also known as eczema, is a common chronic inflammatory skin disease, affecting approximately 20% of children and up to 10% of adults and it imposes a significant financial and societal burden because of the direct medical costs and decreased productivity of individuals with AD. The burden of AD appears to be related mainly to the limited methods of treatment. Furthermore, according to the AD treatment guidelines, there is no standard of care and treatment may be tailored to an individual's needs. Topical interventions are the mainstay of AD therapy. Until now, topical corticosteroids have been the first-line treatment. Their use, however, may be limited by potential local and systemic adverse effects. Topical calcineurin inhibitors are classified as second-line anti-inflammatory therapy for AD, with advantages in long-term maintenance and application to special sites. Topical calcineurin inhibitors inhibit calcineurin-dependent T-cell activation; however, a black box warning about the potential for developing malignant neoplasms with the use of topical calcineurin inhibitors reduces patients' adherence to treatment.

Psoriasis and psoriatic arthritis are associated with aberrant inflammation and the production of proinflammatory mediators. Psoriasis and psoriatic arthritis are inflammatory diseases with overlapping features and shared immunologic mechanisms. Psoriasis is a systemic disease in that it primarily affects the skin but up to 40% of individuals with psoriasis may go on to develop psoriatic arthritis. Psoriatic arthritis typically affects the peripheral joints and may occasionally affect the spine and sacroiliac area. Enthesitis, dactylitis, and nail changes such as pitting and discoloration are also common manifestations of psoriatic disease in patients with joint involvement.

Pruritus is commonly a significant clinical sign associated with flea associated dermatitis in dogs. Medical management of for pruritus may be sought in cases where the cause of itching is not identifiable, or treatment of underlying disease does not eliminate itching. However, control of itching with antihistamines is usually ineffective, and while treatment with glucocorticoids can be effective, long term use is not ideal due to adverse side effects including excessive hunger, thirst, and urination, and increased risk of diabetes and urinary tract infections.

JAK inhibition may provide a therapeutic strategy for various immune and inflammatory diseases, including rheumatoid arthritis (RA), arthritis, ulcerative colitis, Crohn's disease, inflammatory bowel disease (IBD), psoriasis, alopecia areata, atopic dermatitis, vitiligo, palmoplantar pustulosis, mucocutaneous disease erythema multiforme, mycosis fungoides, graft-versus-host disease, cutaneous lupus, transplant rejection, systemic lupus erythematosus (SLE), dermatomyositis, Sjogren's syndrome, dry eye disease, secondary hypereosinophilic syndrome (HES), allergy, allergic dermatitis, asthma, vasculitis, multiple sclerosis, diabetic nephropathy, cardiovascular disease, artherosclerosis, and cancer. Reference is made to Schwartz et al., *JAK inhibition as a therapeutic strategy for immune and inflammatory diseases*, Nat Rev Drug Discov., 2017 Dec. 28, 17(1):78, herein incorporated by reference with regard to the rationale for targeting JAKs.

Various classes of compounds have been shown to inhibit JAK enzymes. For example, U.S. Pat. No. 8,133,899 B2 (to Pfizer) discloses use of pyrrolo[2,3-D]pyrimidine compounds as JAK inhibitors. In particular, oclacitinib (APOQUEL®) is a cyclohexylamino pyrrolopyrimidine demonstrated to be a Janus kinase inhibitor that controls clinical signs of allergic skin disease in dogs (as disclosed in J. Vet. Pharmacol. Therap. 2014 August 37(4): 317-324). In addition, published patent application nos. US 2020/0339585, WO 2009/114512 A1 and U.S. Pat. No. 7,598,257 B2 describe various other JAK inhibitor compounds.

Published patent applications filed by Merck Sharp & Dohme Corporation and Intervet Inc. relating to pyrazole carboxamide compounds as JAK inhibitors include WO 2013/041042 A1, WO 2018/108969 A1, WO 2020/118597 A1, WO 2020/120673 A1, WO 2020/120679 A1, and WO2020221914 A1 (all incorporated by reference herein in their entirety).

Reference is made to Siu et al., *The Discovery of 3-((4-Chloro-3-methoxyphenyl)amino)-1-((3R,4S)-4-cyanotetrahydro-2H-pyran-3-yl)-1H-pyrazole-4-carboxamide, a Highly Ligand Efficient and Efficacious Janus Kinase 1 Selective Inhibitor with Favorable Pharmacokinetic Properties*, J. Med. Chem. 2017 Dec. 14; 60(23): 9676-9690, herein incorporated by reference, with regard to pyrazole carboxamide Janus Kinase 1 inhibitors and their synthesis. There remains a need for therapies targeting and modulating JAK kinases for the treatment or control of inflammation, auto-immune diseases, cancer, and other disorders and indications where modulation of JAK modulation would be desirable.

INCORPORATION BY REFERENCE

Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

SUMMARY OF THE INVENTION

In a first aspect, the present invention provides for novel and inventive boron containing pyrazole compounds, or their pharmaceutically acceptable salts, pharmaceutical compositions containing them, and their medical uses. The compounds of the invention have activity as Janus kinase (JAK) inhibitors and are useful in the treatment or control of inflammation, auto-immune diseases, cancer, and other disorders and indications where modulation of JAK would be desirable.

In one embodiment, the invention of the present disclosure includes a compound of formula (I) and formula (II) below, or a pharmaceutically acceptable salt or a stereoisomer or a tautomer thereof, wherein A is selected from the group consisting of benzo[c][1,2]oxaborol-1(3H)-ol, 3,4-dihydro-1H-benzo[c][1,2]oxaborinin-1-ol, and 2H-benzo[e][1,2]oxaborinin-2-ol, or a derivative thereof, and the variables $R^2$, $R^3$, $R^4$, $R^{4a}$, $R^{4b}$, $R^{5a}$, X, n, and p are defined herein.

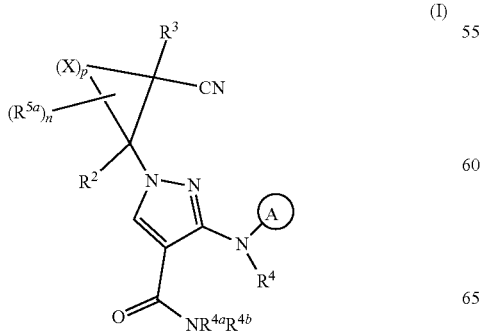

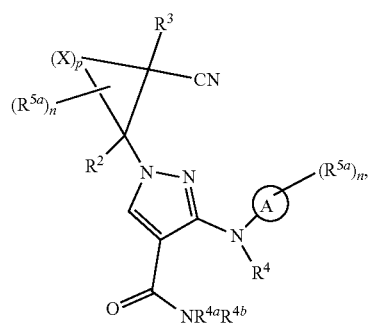

In another embodiment, the invention of the present disclosure provides a compound of formula (III), or a pharmaceutically acceptable salt or a stereoisomer or a tautomer thereof, wherein A is selected from the group consisting of benzo[c][1,2]oxaborol-1(3H)-ol, 3,4-dihydro-1H-benzo[c][1,2]oxaborinin-1-ol, and 2H-benzo[e][1,2]oxaborinin-2-ol, or a derivative thereof, and the variables R, $R^4$, $R^{4a}$, and $R^{4b}$ are defined herein.

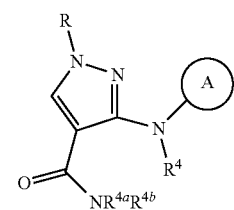

In one embodiment, the variable A in the compound of formula (I), (II), and III is selected from

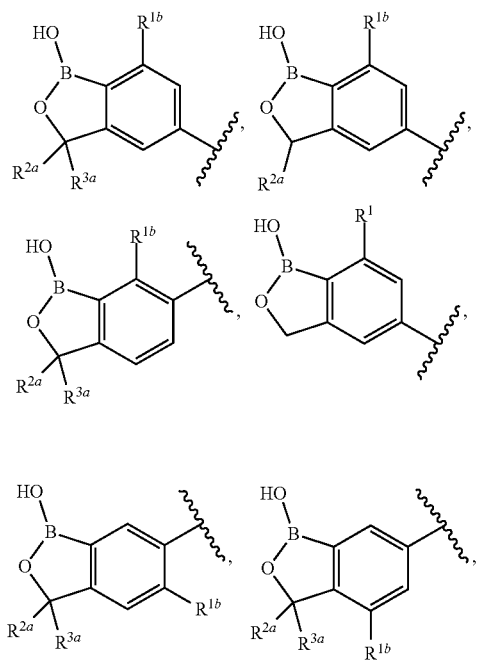

-continued

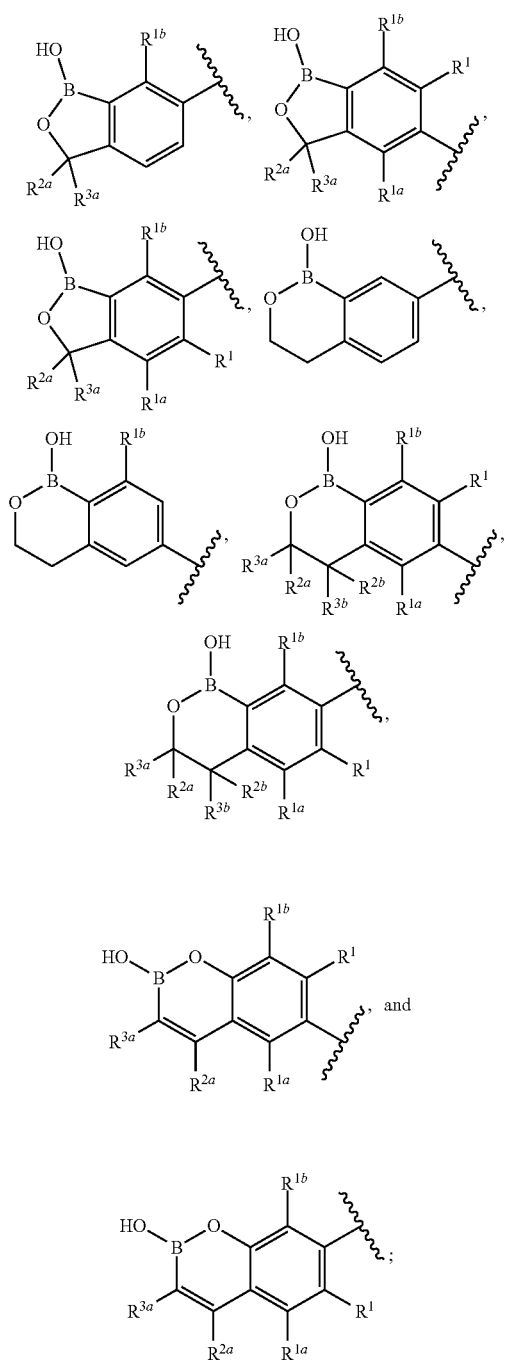

wherein the variables $R^{1a}$, $R^{1b}$, $R^{2a}$, $R^{2b}$, $R^{3a}$, and $R^{3b}$ are defined herein.

In one embodiment, the invention of the present disclosure provides a compound of formula (IV), (IVa) or (IVb), or a pharmaceutically acceptable salt or a stereoisomer or a tautomer thereof, wherein A is selected from the group consisting of benzo[c][1,2]oxaborol-1(3H)-ol, 3,4-dihydro-1H-benzo[c][1,2]oxaborinin-1-ol, and 2H-benzo[e][1,2]oxaborinin-2-ol, or a derivative thereof, such as a moiety selected from any one of $A_1$-$A_6$ as defined herein, and the variables $R^4$ and $R^{5-14}$ in respect of compounds of formula (IV), (IVa) and (IV)b are defined herein.

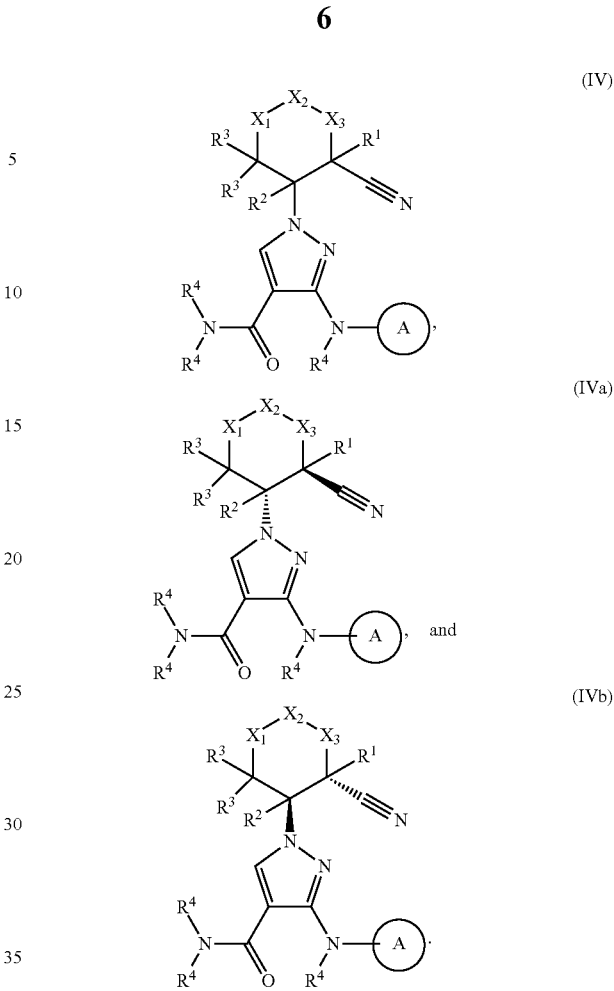

One embodiment of the invention of the present disclosure includes a method for treating a patient having a disease or disorder susceptible to modulation of JAK comprising administering a therapeutically effective amount of a compound of the present disclosure. In one aspect, the disease or disorder is one or more of atopic dermatitis, flea allergy dermatitis, eczema, pruritus, psoriasis, psoriatic arthritis, Bechet's disease, *Pityriasis rubra* pilaris, alopecia areata, discoid lupus erythematosus, vitiligo, palmoplantar pustulosis, mucocutaneous disease erythema multiforme, mycosis fungoides, graft-versus-host disease, cutaneous lupus, rheumatoid arthritis (RA), arthritis, ulcerative colitis, Crohn's disease, inflammatory bowel disease (IBD), transplant rejection, systemic lupus erythematosus (SLE), dermatomyositis, Sjogren's syndrome, dry eye disease, secondary hypereosinophilic syndrome (HES), allergy, allergic dermatitis, asthma, vasculitis, multiple sclerosis, diabetic nephropathy, cardiovascular disease, artherosclerosis, and cancer. In one aspect, the disease or disorder is one or more of atopic dermatitis, flea allergy dermatitis, psoriasis, and rheumatoid arthritis. In one aspect, the compound is administered in an amount to perturb an immune regulatory pathway in a cell. In one aspect, the perturbation results in an effect on the JAK-STAT pathway.

One embodiment of the present disclosure includes a method of inhibiting JAK in a mammalian cell comprising contacting the mammalian cell with a compound of the present disclosure. In one aspect, the mammalian cell is a cell from a subject having an inflammatory condition.

One embodiment of the invention of the present disclosure includes a composition comprising a compound of the present invention and a pharmaceutically or veterinary acceptable carrier.

One embodiment of the invention of the present disclosure includes a combination comprising a compound of the present disclosure, and one or more other pharmaceutical or veterinary active substances.

In another aspect, the invention of the present disclosure provides methods of treating inflammation, auto-immune diseases, cancer, and other conditions susceptible to inhibition of JAK by administering a compound herein described.

In one embodiment of the present disclosure, the invention provides a method for treating one or more diseases or disorders of inflammation, auto-immune dysfunction, and cancer comprising administering to a subject in need thereof an effective amount of a compound of the present disclosure. In one aspect, the disease or disorder is atopic dermatitis, flea allergy dermatitis, psoriasis, or rheumatoid arthritis. In one embodiment, the subject is a mammal. In one embodiment, the subject is a non-human animal. In one embodiment, the subject is selected from livestock mammals, domestic mammals, or companion animals. In one aspect, the subject is selected from cattle, sheep, goats, llamas, alpacas, pigs, horses, donkeys, dogs, and cats. In one aspect, the subject is a human.

One embodiment of the invention of the present disclosure includes a compound of the present disclosure for use in medicine.

One embodiment of the invention of the present disclosure includes a compound of the present disclosure for the manufacture of a medicament for the treatment of one or more diseases or disorder of inflammation, auto-immune dysfunction, and cancer. In one aspect, the disease or disorder is atopic dermatitis, psoriasis, or rheumatoid arthritis.

One embodiment of the invention of the present disclosure includes a use of a compound of the present disclosure for the treatment of one or more diseases or disorders of inflammation, auto-immune dysfunction, and cancer. In one aspect, the disease or disorder is atopic dermatitis, psoriasis, or rheumatoid arthritis.

One or more aspects and embodiments may be incorporated in a different embodiment although not specifically described. That is, all aspects and embodiments may be combined in any way or combination.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to the described variable.

It is an object of the invention to not encompass within the invention any previously known product, process of making the product, or method of using the product such that the Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

These and other embodiments are disclosed or are obvious from and encompassed by the following Detailed Description.

DETAILED DESCRIPTION

In a first aspect, the present invention provides for novel and inventive boron containing pyrazole compounds, or their pharmaceutically acceptable salts, pharmaceutical compositions containing them, and their medical uses.

The compounds of the invention have activity as Janus kinase (JAK) inhibitors and are useful in the treatment or control of inflammation, auto-immune diseases, cancer, and other disorders and indications where modulation of JAK would be desirable.

In one embodiment, the present invention provides for a compound of formula (I) or formula (II) or a pharmaceutically acceptable salt or a stereoisomer or a tautomer thereof:

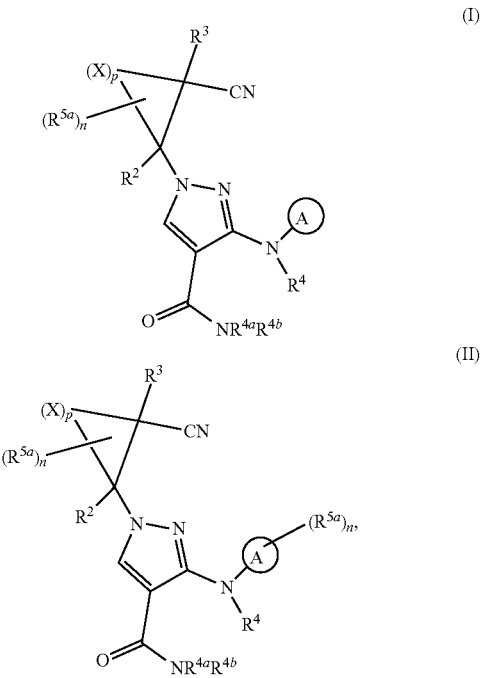

wherein:
$R^4$, $R^{4U}$, and $R^{4b}$ are independently selected from hydrogen, $C_{1-4}$alkyl, and $CH_2(oxy)C_{1-4}$alkyl; each occurrence of n is independently 0, 1, 2, 3, 4, 5, 6, 7, 8 or 9;
p is 2, 3, 4, or 5;
X is independently selected from C, N, S, and O, wherein at least one X is other than carbon;
A is selected from the group consisting of benzo[c][1,2]oxaborol-1(3H)-ol, 3,4-dihydro-1H-benzo[c][1,2]oxaborinin-1-ol, and 2H-benzo[e][1,2]oxaborinin-2-ol, or a derivative thereof,
$R^2$ and $R^3$ are each independently selected from:
hydrogen,
halogen,
$C_{1-10}$ alkyl,
$C_{2-10}$ alkenyl,
$C_{1-10}$ heteroalkyl,
aryl $C_{0-10}$ alkyl$C_{0-10}$ alkyl, $C_{3-8}$ cycloalkyl $C_{0-10}$ alkyl, heteroaryl $C_{0-10}$ alkyl, and $(C_{3-8})$heterocycloalkyl $C_{0-10}$ alkyl, wherein each of R² and R³ are independently substituted with 0, 1, 2, 3, or 4 R$^{5a}$ substituents;
  each R$^{5a}$ is independently selected from:
    hydrogen,
    halogen, except R$^{5a}$ is not halogen where substitution position is geminal to X that is O,
    $C_{1-10}$ alkyl(oxy)$_{0-1}$(carbonyl)$_{0-1}C_{0-10}$ alkyl,
    $C_{1-10}$ heteroalkyl(oxy)$_{0-1}$(carbonyl)$_{0-1}C_{0-10}$ alkyl,
    $C_{2-10}$ alkenyl(oxy)$_{0-1}$(carbonyl)$_{0-1}C_{0-10}$ alkyl,
    $C_{2-10}$ alkynyl(oxy)$_{0-1}$(carbonyl)$_{0-1}C_{0-10}$ alkyl, aryl $C_{0-10}$ alkyl(oxy)$_{0-1}$(carbonyl)$_{0-1}C_{0-10}$ alkyl,
    aryl $C_{2-10}$ alkenyl(oxy)$_{0-1}$(carbonyl)$_{0-1}C_{0-10}$ alkyl,
    aryl $C_{2-10}$ alkynyl(oxy)$_{0-1}$(carbonyl)$_{0-1}C_{0-10}$ alkyl,
    $C_{3-8}$ cycloalkyl $C_{0-10}$ alkyl(oxy)$_{0-1}$(carbonyl)$_{0-1}C_{0-10}$ alkyl,
    heteroaryl $C_{0-10}$ alkyl(oxy)$_{0-1}$(carbonyl)$_{0-1}C_{0-10}$ alkyl,
    $(C_{3-8})$heterocycloalkyl $C_{0-10}$ alkyl(oxy)$_{0-1}$(carbonyl)$_{0-1}C_{0-10}$ alkyl,
    $C_{1-10}$ alkyl(carbonyl)$_{0-1}$oxy$C_{0-10}$ alkyl,
    $C_{1-10}$ heteroalkyl(carbonyl)$_{0-1}$oxy$C_{0-10}$ alkyl,
    $C_{2-10}$ alkenyl(carbonyl)$_{0-1}$oxy$C_{0-10}$ alkyl,
    $C_{1-10}$ heteroalkyl(carbonyl)$_{0-1}$oxy$C_{0-10}$ alkyl,
    aryl $C_{0-10}$ alkyl (carbonyl)$_{0-1}$ oxy$C_{0-10}$ alkyl,
    $(C_{3-8})$cycloalkyl $C_{0-10}$ alkyl(carbonyl)$_{0-1}$oxy$C_{0-10}$ alkyl,
    heteroaryl$C_{0-10}$ alkyl(carbonyl)$_{0-1}$oxy$C_{0-10}$ alkyl,
    $(C_{3-8})$heterocycloalkyl $C_{0-10}$ alkyl(carbonyl)$_{0-1}$oxy$C_{0-10}$ alkyl,
    $((C_{0-10})$alkyl)$_{1-2}$aminocarbonyloxy,
    $(C_{0-10})$heteroalkylaminocarbonyloxy,
    aryl $(C_{0-10})$alkylaminocarbonyloxy,
    $(C_{3-8})$cycloalkyl$(C_{0-10})$alkylaminocarbonyloxy,
    heteroaryl$(C_{0-10})$alkylaminocarbonyloxy,
    $(C_{3-8})$heterocycloalkyl$(C_{0-10})$alkylaminocarbonyloxy,
    $C_{1-10}$ alkylamino(oxy)$_{0-1}$carbonyl$C_{0-10}$ alkyl,
    $(C_{0-10})$heteroalkylamino(oxy)$_{0-1}$carbonyl$C_{0-10}$ alkyl,
    $C_{3-8}$ cycloalkyl $C_{0-10}$ alkylamino(oxy)$_{0-1}$carbonyl$C_{0-10}$ alkyl,
    aryl $C_{0-10}$alkylamino(oxy)$_{0-1}$carbonyl$C_{0-10}$ alkyl,
    heteroaryl$C_{0-10}$ alkylamino(oxy)$_{0-1}$carbonyl$C_{0-10}$ alkyl,
    $(C_{3-8})$heterocycloalkyl$C_{0-10}$ alkylamino(oxy)$_{0-1}$carbonyl$C_{0-10}$ alkyl,
    $C_{1-10}$ alkyl(oxy)$_{0-1}$carbonylamino$C_{0-10}$ alkyl,
    $C_{1-10}$ heteroalkyl (oxy)$_{0-1}$carbonylamino$C_{0-10}$ alkyl,
    $C_{3-8}$ cycloalkyl $C_{0-10}$ alkyl (oxy)$_{0-1}$carbonylamino$C_{0-10}$ alkyl,
    aryl $C_{0-10}$ alkyl(oxy)$_{0-1}$carbonylamino$C_{0-10}$ alkyl,
    heteroaryl $C_{0-10}$ alkyl(oxy)$_{0-1}$carbonylamino$C_{0-10}$ alkyl,
    $(C_{3-8})$heterocycloalkyl $C_{0-10}$ alkyl(oxy)$_{0-1}$carbonylamino$C_{0-10}$ alkyl,
    —$CO_2(C_{0-10}$ alkyl),
    —$(C_{0-10}$ alkyl)$CO_2H$,
    Oxo (=O),
    $C_{1-10}$ alkylsulfonyl,
    $C_{1-10}$ heteroalkylsulfonyl, $(C_{3-8})$ cycloalkylsulfonyl,
    $(C_{3-8})$ cycloheteroalkylsulfonyl,
    heteroarylsulfonyl,
    arylsulfonyl,
    aminosulfonyl,
    —$SO_2N(C_{1-6}$alkyl)$_{1-2}$,
    —$SO_2C_{1-6}$alkyl,
    —$SO_2CF_3$,
    —$SO_2CF_2H$,
    $C_{1-10}$alkylsulfinyl,
    amino,
    $(C_{0-10}$ alkyl)$_{1-2}$ amino,
    $C_{1-4}$acylamino $C_{0-10}$ alkyl,
    hydroxy,
    $C_{0-10}$ alkylalkoxy,
    cyano,
    $C_{1-6}$alkylcyano, and
    $C_{1-6}$haloalkyl;
wherein R$^{5a}$ is each optionally substituted with 0, 1, 2, 3, or 4 R$^6$ substituents, and R$^6$ is independently selected from:
    halogen,
    $C_{1-10}$ alkyl(oxy)$_{0-1}$(carbonyl)$_{0-1}C_{0-10}$ alkyl,
    $C_{1-10}$ heteroalkyl(oxy)$_{0-1}$(carbonyl)$_{0-1}C_{0-10}$ alkyl,
    $C_{2-10}$ alkenyl(oxy)$_{0-1}$(carbonyl)$_{0-1}C_{0-10}$ alkyl,
    aryl $C_{0-10}$ alkyl(oxy)$_{0-1}$(carbonyl)$_{0-1}C_{0-10}$ alkyl,
    aryl $C_{2-10}$ alkenyl(oxy)$_{0-1}$(carbonyl)$_{0-1}C_{0-10}$ alkyl,
    aryl $C_{2-10}$ alkynyl(oxy)$_{0-1}$(carbonyl)$_{0-1}C_{0-10}$ alkyl,
    $C_{3-8}$ cycloalkyl $C_{0-10}$ alkyl(oxy)$_{0-1}$(carbonyl)$_{0-1}C_{0-10}$ alkyl,
    heteroaryl $C_{0-10}$ alkyl(oxy)$_{0-1}$(carbonyl)$_{0-1}C_{0-10}$ alkyl,
    $(C_{3-8})$heterocycloalkyl $C_{0-10}$ alkyl(oxy)$_{0-1}$(carbonyl)$_{0-1}C_{0-10}$ alkyl,
    $C_{1-10}$ alkyl(carbonyl)$_{0-1}$oxy$C_{0-10}$ alkyl,
    $C_{2-10}$ alkenyl(carbonyl)$_{0-1}$oxy$C_{0-10}$ alkyl,
    $C_{1-10}$heteroalkyl(carbonyl)$_{0-1}$oxy$C_{0-10}$ alkyl,
    aryl $C_{0-10}$ alkyl (carbonyl)$_{0-1}$oxy$C_{0-10}$ alkyl,
    $(C_{3-8})$cycloalkyl $C_{0-10}$ alkyl(carbonyl)$_{0-1}$oxy$C_{0-10}$ alkyl,
    heteroaryl$C_{0-10}$alkyl(carbonyl)$_{0-1}$oxy$C_{0-10}$ alkyl,
    $(C_{3-8})$heterocycloalkyl $C_{0-10}$ alkyl(carbonyl)$_{0-1}$oxy$C_{0-10}$ alkyl,
    $((C_{0-10})$alkyl)$_{1-2}$aminocarbonyloxy,
    aryl $(C_{0-10})$alkylaminocarbonyloxy,
    $(C_{3-8})$cycloalkyl$(C_{0-10})$alkylaminocarbonyloxy,
    heteroaryl$(C_{0-10})$alkylaminocarbonyloxy,
    $(C_{3-8})$heterocycloalkyl$(C_{0-10})$alkylaminocarbonyloxy,
    $C_{1-10}$ alkylamino(oxy)$_{0-1}$carbonyl$C_{0-10}$ alkyl,
    $C_{3-8}$ cycloalkyl $C_{0-10}$ alkylamino(oxy)$_{0-1}$carbonyl$C_{0-10}$ alkyl,
    aryl $C_{0-10}$alkylamino(oxy)$_{0-1}$carbonyl$C_{0-10}$ alkyl,
    heteroaryl $C_{0-10}$ alkylamino(oxy)$_{0-1}$carbonyl$C_{0-10}$ alkyl,
    $(C_{3-8})$heterocycloalkyl $C_{0-10}$ alkylamino(oxy)$_{0-1}$carbonyl$C_{0-10}$ alkyl,
    $C_{1-10}$ alkyl (oxy)$_{0-1}$carbonylamino$C_{0-10}$ alkyl,
    $C_{3-8}$ cycloalkyl $C_{1-10}$ alkyl (oxy)$_{0-1}$carbonylamino$C_{0-10}$alkyl,
    aryl $C_{0-10}$alkyl(oxy)$_{0-1}$carbonylamino$C_{0-10}$ alkyl,
    heteroaryl $C_{0-10}$ alkyl(oxy)$_{0-1}$carbonylamino$C_{0-10}$ alkyl,
    $(C_{3-8})$heterocycloalkyl $C_{0-10}$ alkyl(oxy)$_{0-1}$carbonylamino$C_{0-10}$ alkyl,
    —$CO_2(C_{0-10}$ alkyl),
    —$(C_{0-10}$ alkyl)$CO_2H$,
    Oxo (=O),
    $C_{1-10}$alkylsulfonyl,
    $C_{1-10}$heteroalkylsulfonyl,
    $(C_{3-8})$ cycloalkylsulfonyl,
    $(C_{3-8})$ cycloheteroalkylsulfonyl,
    heteroarylsulfonyl,
    arylsulfonyl,
    aminosulfonyl,
    —$SO_2N(C_{1-6}$alkyl)$_{1-2}$,
    —$SO_2C_{1-6}$alkyl,
    —$SO_2CF_3$,
    —$SO_2CF_2H$,
    $C_{1-10}$ alkylsulfinyl,
    —$OSi(C_{1-10}$ alkyl)$_3$ amino, $(C_{0-10} \text{ alkyl})_{1-2}$ amino, $(\text{oxy})_{0-1}$ $(\text{carbonyl})_{0-1}\text{N}(C_{0-10}\text{alkyl})$ 1-2

$C_{1-4}$acylamino $C_{0-10}$alkyl, hydroxy, $C_{1-10}$ alkoxy, cyano, and $C_{1-6}$ haloalkyl; and $R^6$ is optionally substituted with 0, 1, 2, or 3 substituents independently selected from hydroxy, $(C_{1-6})$ alkoxy, halogen, $CO_2H$, —$(C_{0-6})$alkylCN, —$O(C=O)C_1$-$C_6$ alkyl, $NO_2$, trifluoromethoxy, trifluoroethoxy, —N—C(O)O$(C_{0-6})$alkyl, $C_{1-10}$ alkylsulfonyl, $C_{1-10}$ heteroalkylsulfonyl, oxo (O=), $(C_{3-8})$ cycloalkylsulfonyl, $(C_{3-8})$ cycloheteroalkylsulfonyl, heteroarylsulfonyl, arylsulfonyl, aminosulfonyl, —$SO_2N(C_{1-6}\text{alkyl})_{1-2}$, —$SO_2C_{1-6}$alkyl, —$SO_2CF_3$, —$SO_2CF_2H$, —$C_{1-10}$ alkylsulfinyl, —$OSi(C_{1-10} \text{ alkyl})_3$, —$O_{(0-1)}(C_{1-10})$haloalkyl, and $NH_2$.

In one embodiment of formula (I) or formula (II) or a pharmaceutically acceptable salt or a stereoisomer or a tautomer thereof, the variable A is selected from the following:

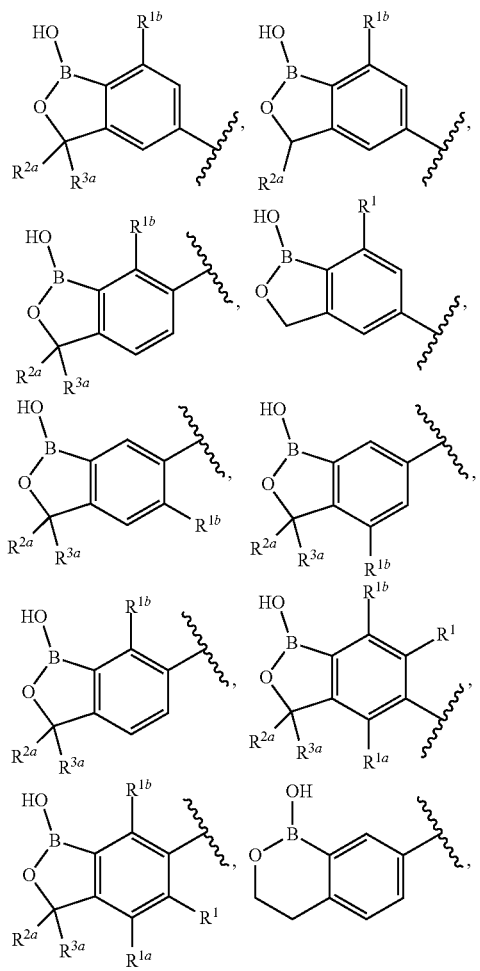

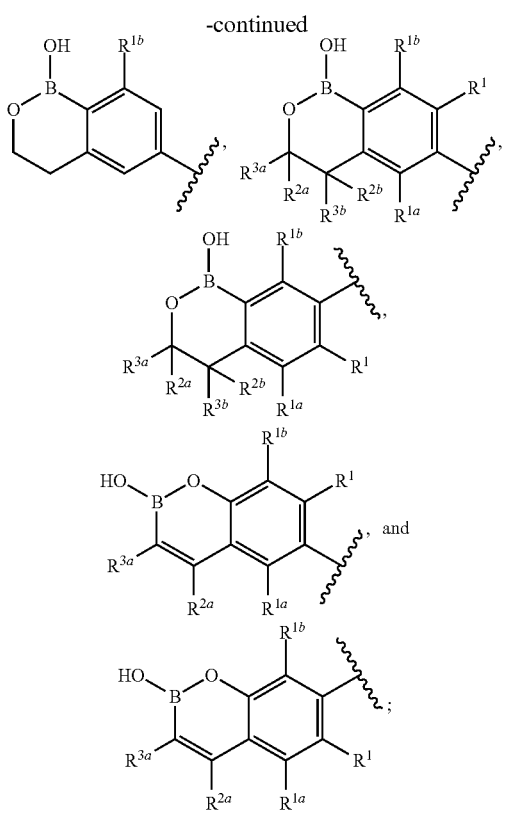

wherein:

$R^1$, $R^{1a}$ and $R^{1b}$ are independently selected from the group consisting of hydrogen, halogen, $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, partially or fully halogenated cyclopropyl, $O(C_1$-$C_3$ alkyl), and $O(C_1$-$C_3$ haloalkyl);

$R^{2a}$ and $R^{3a}$ are independently selected from the group consisting of hydrogen, halogen, $C_1$-$C_3$ alkyl, $C_2$-$C_3$ alkenyl, $C_2$-$C_3$ alkynyl, or $R^{2a}$ together with $R^{3a}$ form cyclopropyl, cyclobutyl, oxetane, or cyclobutanone, wherein each of $R^{2a}$ and $R^{3a}$ is independently unsubstituted or substituted with one or more of halogen, hydroxy, amino, alkyl- or di(alkyl) amino, alkyl, cycloalkyl, haloalkyl, alkenyl, haloalkenyl, alkynyl, haloalkynyl, alkoxy, haloalkoxy, alkylthio, haloalkylthio, $R^7S(O)$—, $R^7S(O)_2$—, $R^7C(O)$—, $R^7R^8NC(O)$—, $R^7OC(O)$—, $R^7C(O)O$—, $R^7C(O)NR^8$—, —CN or —$NO_2$; and $R^{2b}$ and $R^{3b}$ are independently selected from the group consisting of: hydrogen, $C_1$-$C_3$ alkyl, $C_2$-$C_3$ alkenyl, $C_2$-$C_3$ alkynyl, or $R^{2b}$ together with $R^{3b}$ form cyclopropyl, cyclobutyl, oxetane, or cyclobutane, wherein each of $R^{2b}$ and $R^{3b}$ is independently unsubstituted or substituted with one or more of halogen, hydroxy, amino, alkyl- or di(alkyl) amino, alkyl, cycloalkyl, haloalkyl, alkenyl, haloalkenyl, alkynyl, haloalkynyl, alkoxy, haloalkoxy, alkylthio, haloalkylthio, $R^7S(O)$—, $R^7S(O)_2$—, $R^7C(O)$—, $R^7R^8NC(O)$—, $R^7OC(O)$—, $R^7C(O)O$—, $R^7C(O)NR^8$—, —CN or —$NO_2$; and $R^7$ and $R^8$ are independently hydrogen, alkyl, haloalkyl, thioalkyl, alkylthioalkyl, hydroxyalkyl, alkoxy-alkyl, alkenyl, haloalkenyl, alkynyl or haloalkynyl.

In one embodiment, $R^1$, $R^{1a}$ and $R^{1b}$ are independently selected from the group consisting of hydrogen, fluorine, chlorine, bromine, iodine, $C_{1-3}$ alkyl, $C_1$-$C_3$ haloalkyl, $O(C_1$-$C_3$alkyl), and $O(C_1$-$C_3$ haloalkyl).

In one embodiment, $R^{2a}$, $R^{3a}$, $R^{2b}$, and $R^{3b}$ are independently selected from the group consisting of hydrogen and $C_1$-$C_3$ alkyl.

In one embodiment, $R^1$, $R^{1a}$ and $R^{1b}$ are independently selected from the group consisting of hydrogen, fluorine, chlorine, and $C_1$-$C_3$ alkyl.

In one embodiment, $R^1$, $R^{1a}$, and $R^{1b}$ are independently selected from the group consisting of hydrogen and fluorine when $R^1$, $R^{1a}$ and/or $R^{1b}$ is ortho position to the position where A is attached to nitrogen.

In another embodiment, each of $R^1$, $R^{1a}$ and $R^{1b}$ is independently H or $C_1$-$C_3$ alkyl, and each of $R^{2a}$, $R^{3a}$, $R^{2b}$, and $R^{3b}$ is independently $C_1$-$C_3$ alkyl.

In another embodiment, $R^4$, $R^{4a}$, and $R^{4b}$ are each hydrogen.

In one embodiment $R^2$ is not halogen. In another embodiment, $R^3$ is hydrogen, and $R^2$ is not halogen.

In one embodiment, each $R^{5a}$ is independently selected from:
hydrogen,
halogen,
$C_{1-10}$alkyl(oxy)$_{0-1}$(carbonyl)$_{0-1}$$C_{0-10}$alkyl,
$C_{1-10}$ heteroalkyl(oxy)$_{0-1}$(carbonyl)$_{0-1}$$C_{0-10}$alkyl,
$C_{2-10}$alkynyl(oxy)$_{0-1}$(carbonyl)$_{0-1}$$C_{0-10}$ alkyl,
$C_{2-10}$ alkenyl(oxy)$_{0-1}$(carbonyl)$_{0-1}$$C_{0-10}$ alkyl,
aryl $C_{0-10}$ alkyl(oxy)$_{0-1}$(carbonyl)$_{0-1}$$C_{0-10}$ alkyl,
aryl $C_{2-10}$ alkenyl(oxy)$_{0-1}$(carbonyl)$_{0-1}$$C_{0-10}$alkyl,
aryl $C_{2-10}$ alkynyl(oxy)$_{0-1}$(carbonyl)$_{0-1}$$C_{0-10}$ alkyl,
$C_{3-8}$cycloalkyl $C_{0-10}$alkyl(oxy)$_{0-1}$(carbonyl)$_{0-1}$$C_{0-10}$alkyl,
heteroaryl $C_{0-10}$alkyl(oxy)$_{0-1}$(carbonyl)$_{0-1}$$C_{0-10}$alkyl,
$(C_{3-8})$heterocycloalkyl $C_{0-10}$alkyl(oxy)$_{0-1}$(carbonyl)$_{0-1}$$C_{0-10}$alkyl,
$C_{1-10}$alkyl(carbonyl)$_{0-1}$ oxy$C_{0-10}$alkyl,
$((C_{0-10})$alkyl)$_{1-2}$aminocarbonyloxy,
$C_{1-10}$alkylamino(oxy)$_{0-1}$carbonyl$C_{0-10}$alkyl,
$C_{1-10}$ alkyl(oxy)$_{0-1}$carbonylamino$C_{0-10}$alkyl,
—CO$_2$($C_{0-10}$alkyl),
—($C_{0-10}$ alkyl)CO$_2$H,
Oxo (=O),
$C_{0-10}$alkylsulfonyl,
$C_{1-10}$heteroalkylsulfonyl,
$C_{3-8}$cycloalkylsulfonyl,
$C_{3-8}$cycloheteroalkylsulfonyl,
heteroarylsulfonyl,
arylsulfonyl,
aminosulfonyl,
—SO$_2$N($C_{1-6}$alkyl)$_{1-2}$,
—SO$_2$$C_{1-6}$alkyl,
—SO$_2$CF$_3$,
—SO$_2$CF$_2$H,
$C_{1-10}$alkylsulfinyl,
amino,
($C_{0-10}$ alkyl)$_{1-2}$ amino,
hydroxy,
$C_{0-10}$alkylalkoxy,
cyano,
$C_{1-6}$alkylcyano, and
$C_{1-6}$haloalkyl;
wherein $R^{5a}$ is each optionally substituted with 0, 1, 2, 3, or 4 substituent that is $R^6$.

In one embodiment, $R^3$ is selected from hydrogen, $C_{1-10}$alkyl, $(C_{3-8})$heterocycloalkyl $C_{0-10}$ alkyl, and $C_{3-8}$cycloalkyl$C_{0-10}$ alkyl, wherein $R^3$ is substituted with 0, 1, 2, 3, or 4 $R^{5a}$ substituents.

As would be understood by one skilled in the art, the IUPAC names for the variable A in Formula (I), (II) and (III) herein correspond to the following chemical structures:

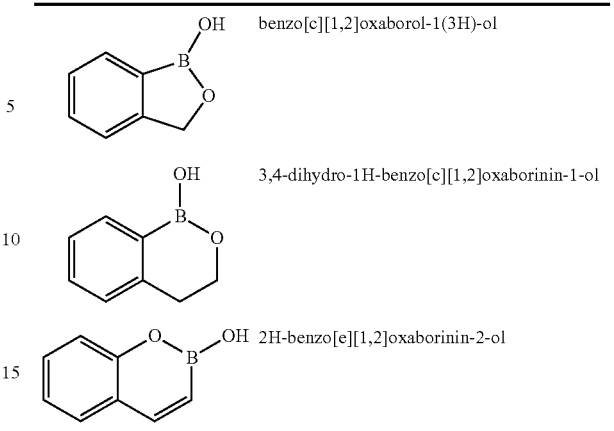

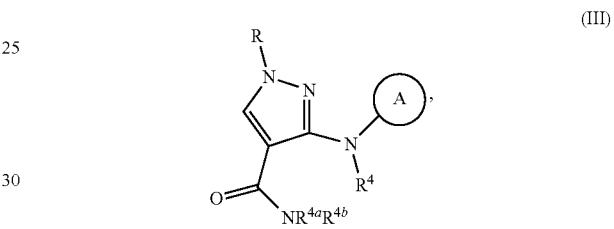

In one embodiment, the present invention provides for a compound of formula (III) or a pharmaceutically acceptable salt or a stereoisomer or a tautomer thereof:

(III)

wherein:
A is selected from the group consisting of benzo[c][1,2]oxaborol-1(3H)-ol, 3,4-dihydro-1H-benzo[c][1,2]oxaborinin-1-ol, and 2H-benzo[e][1,2]oxaborinin-2-ol, or a derivative thereof,
R is selected from the group consisting of:

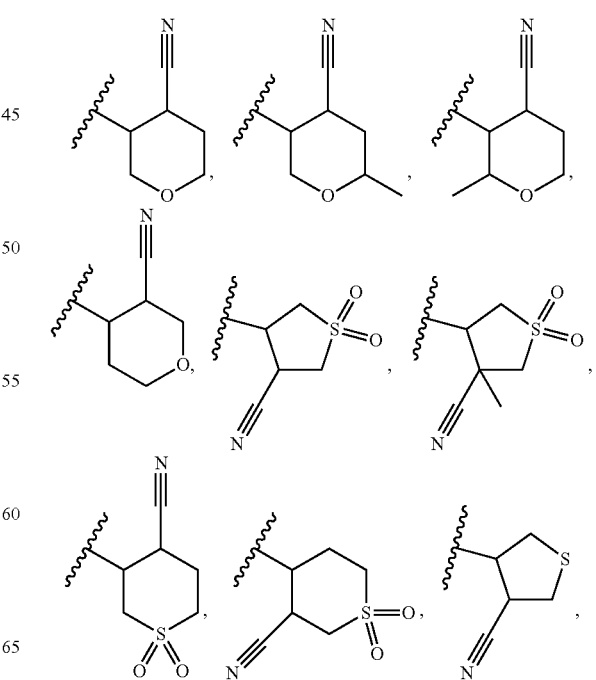

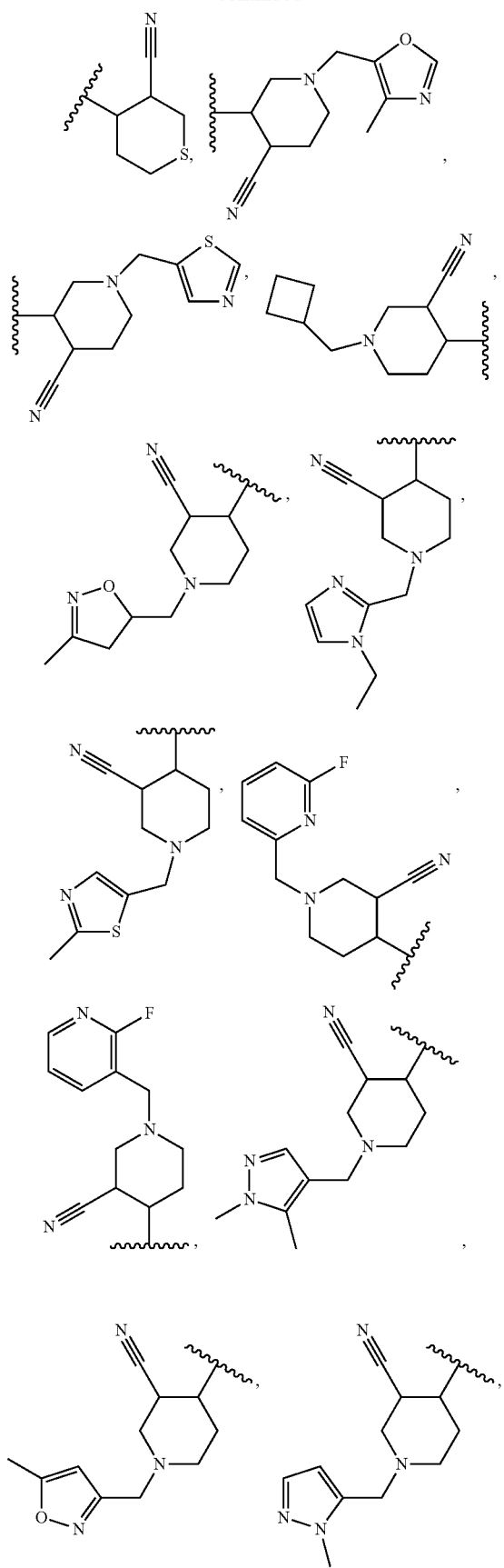
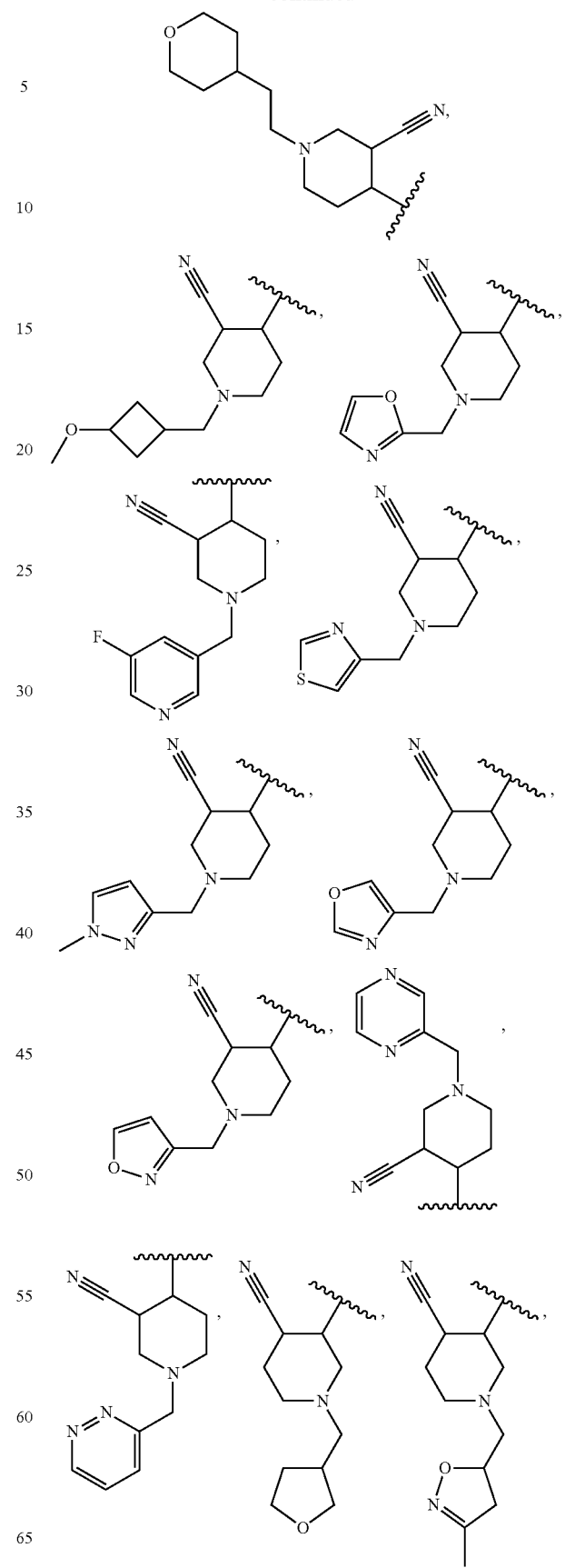

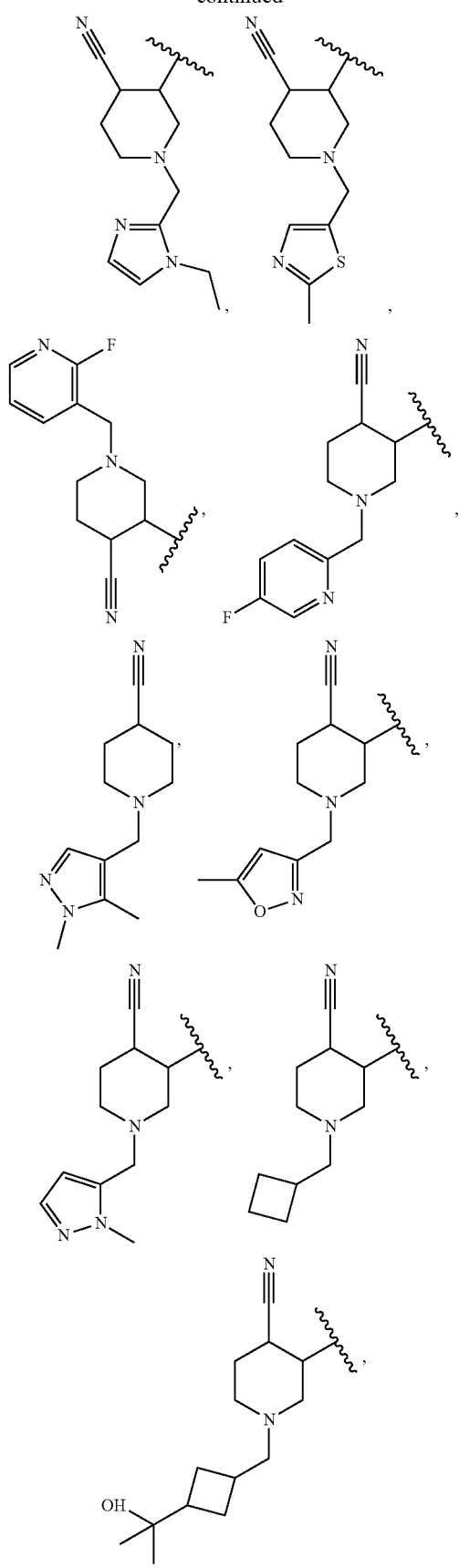
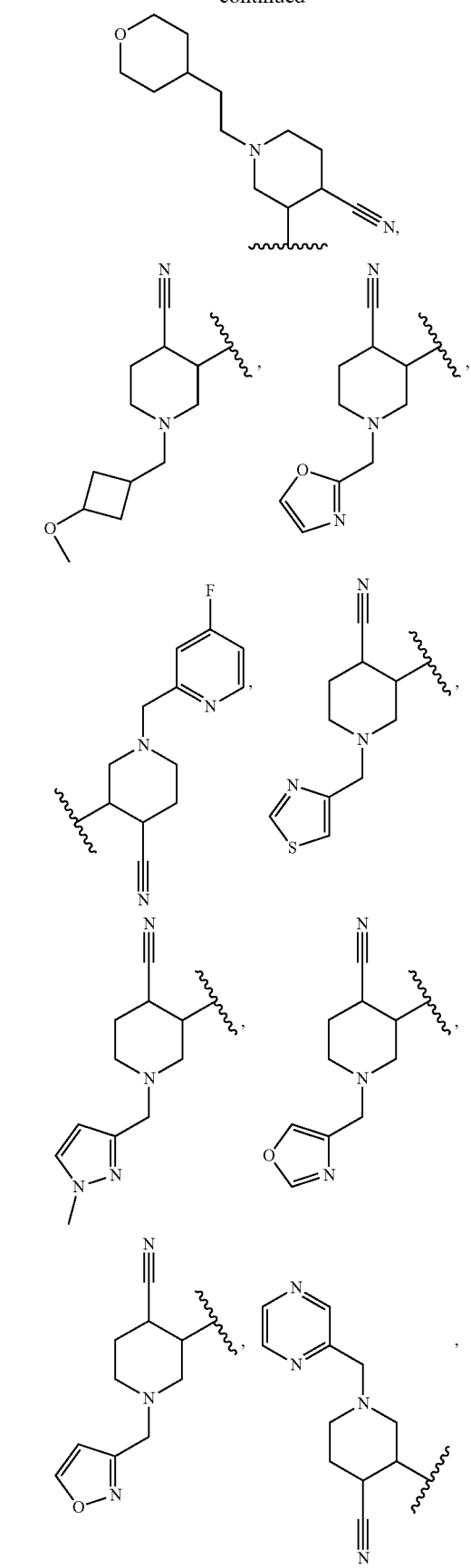

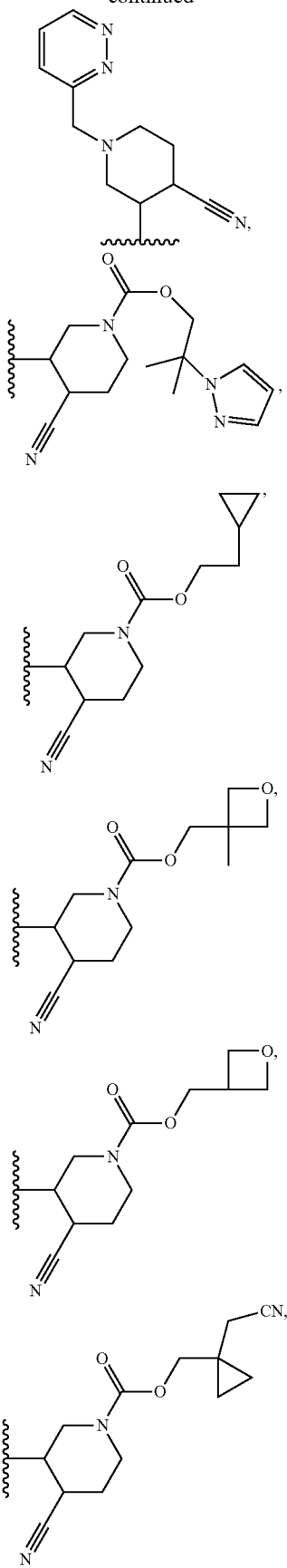
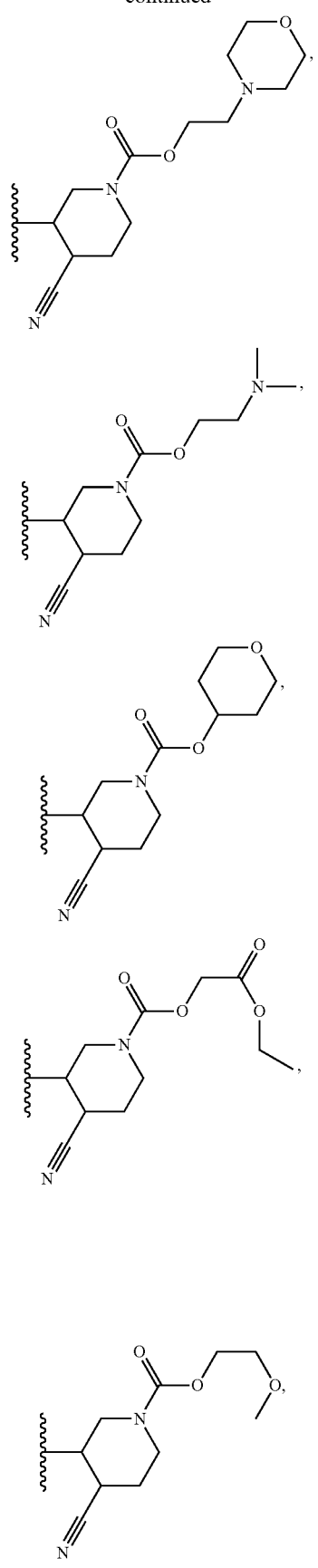

21
-continued
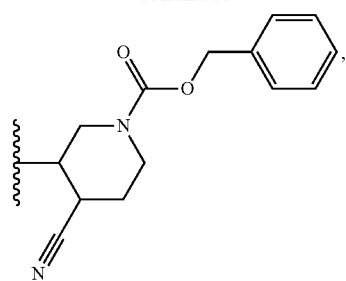,
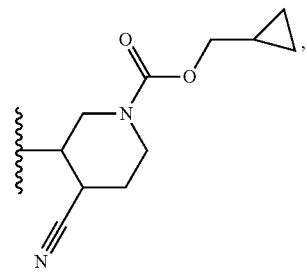,
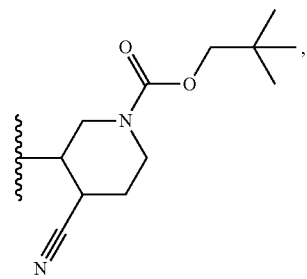,
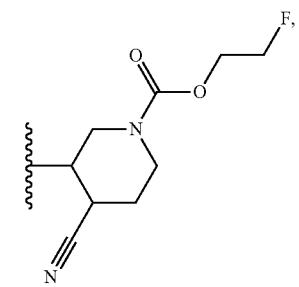,
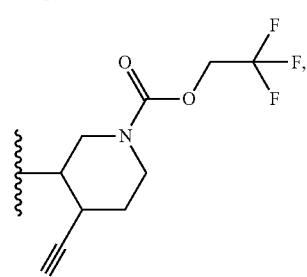,
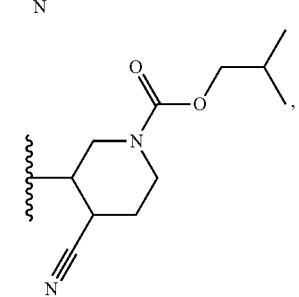,
22
-continued
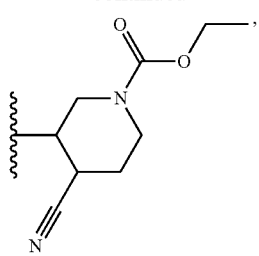,
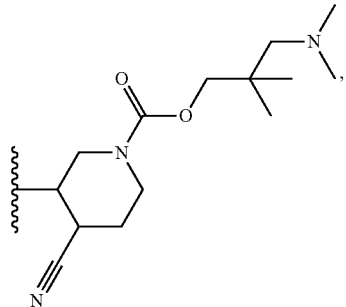,
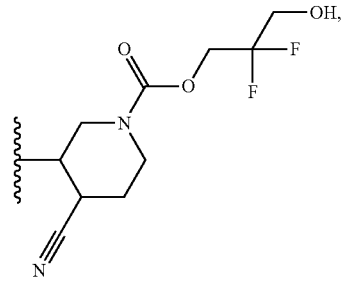,
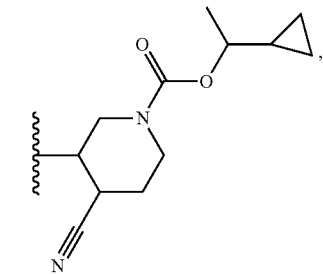,
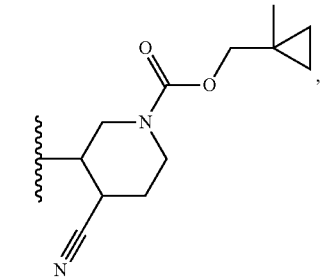,
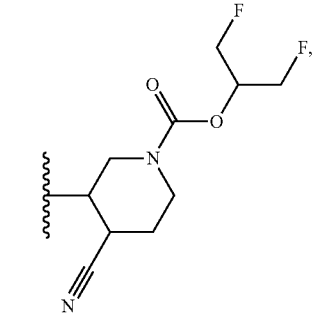,

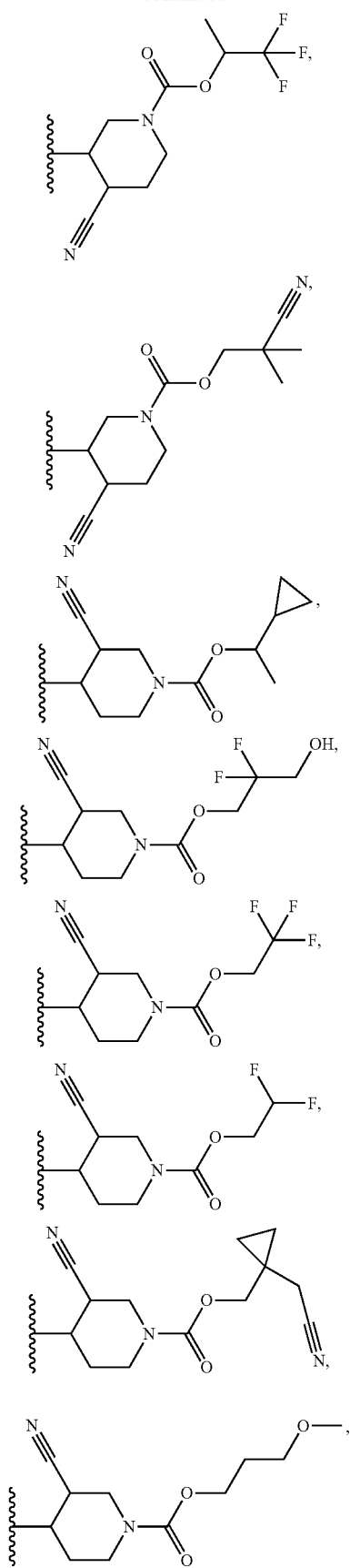
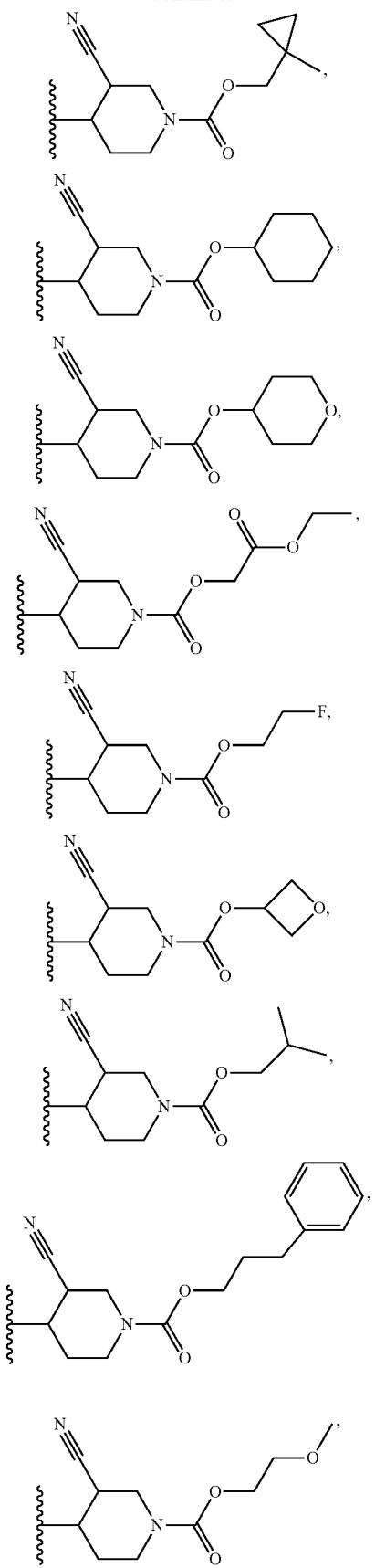

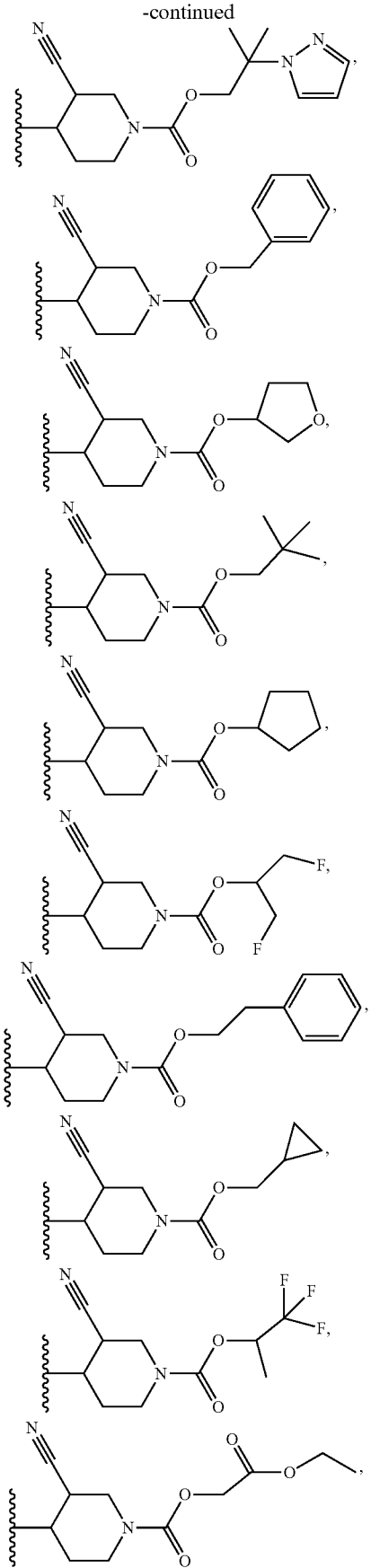
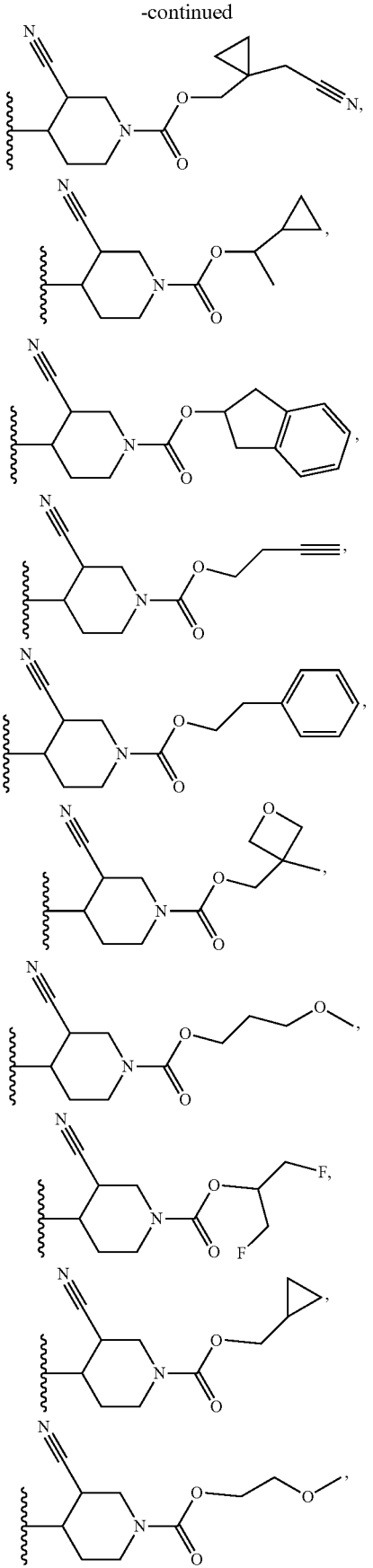

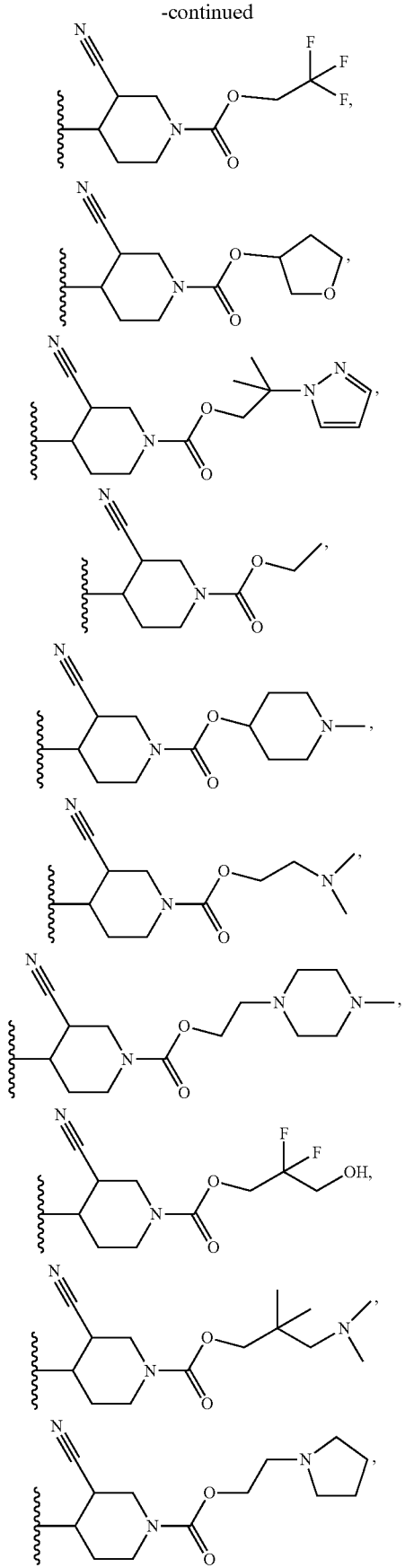
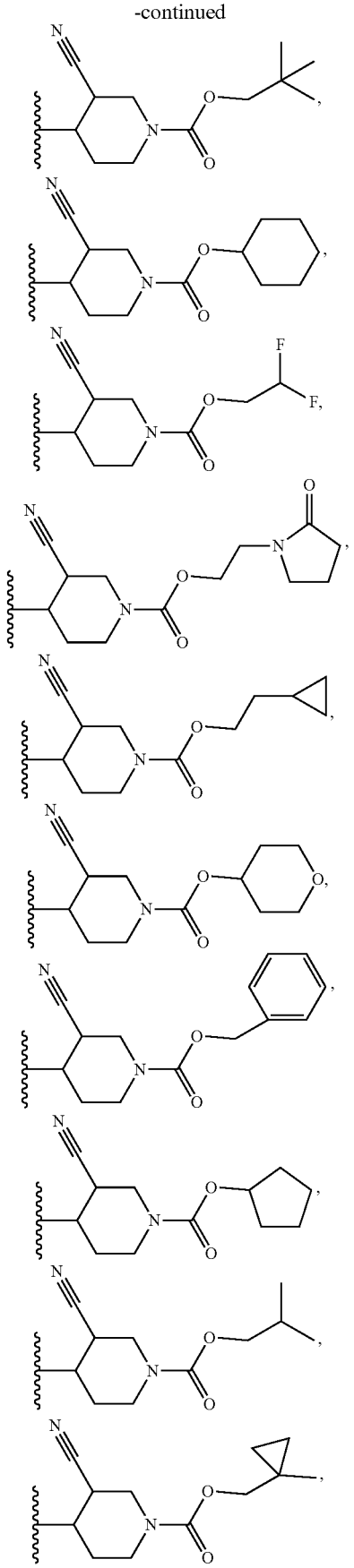

-continued
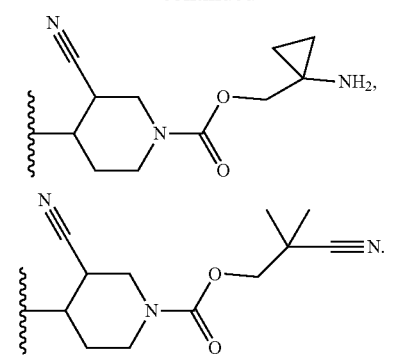
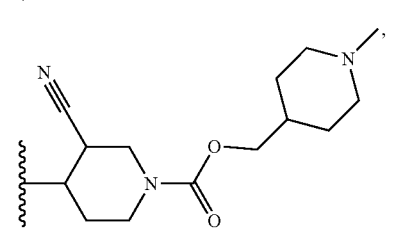
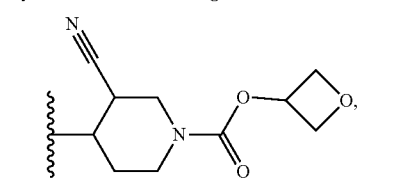
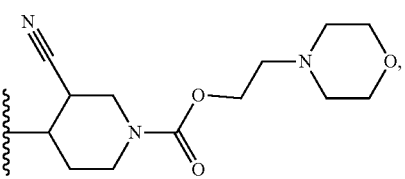
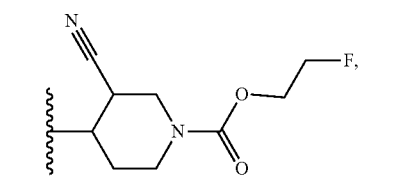
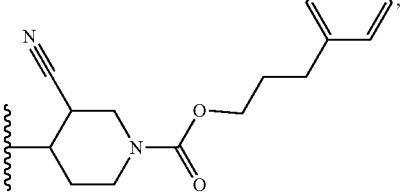
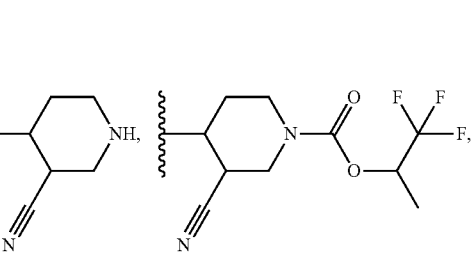
-continued
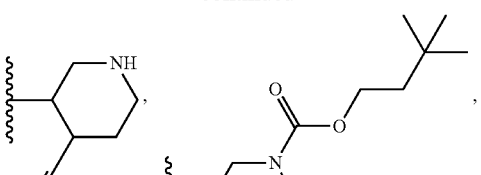
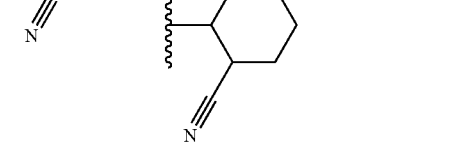
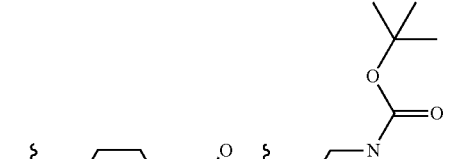
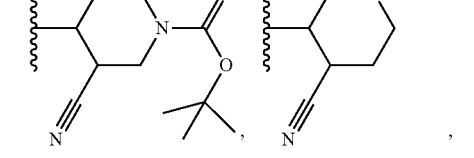
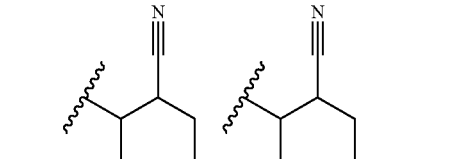
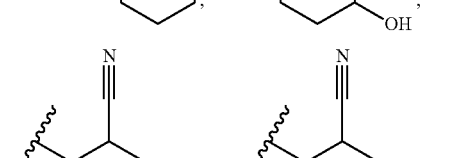
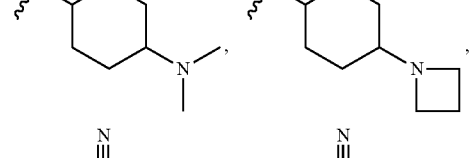
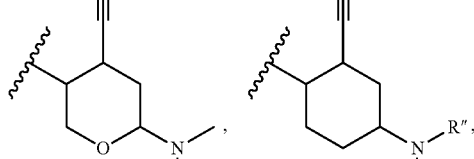
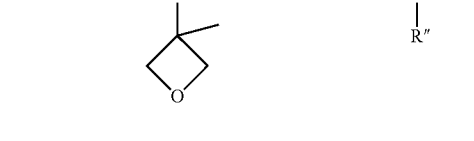
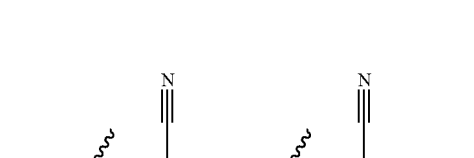
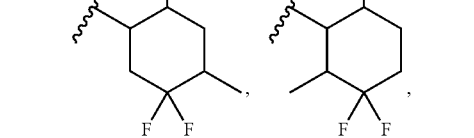

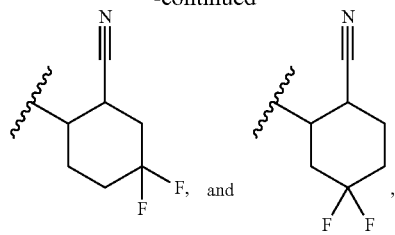

or a stereoisomer thereof, wherein each R" is independently selected from hydrogen, $C_{1-4}$alkyl, and $CH_2$(oxy) $C_{1-4}$alkyl; and $R^4$, $R^{4a}$, and $R^{4b}$ are independently selected from hydrogen and $C_{1-4}$alkyl.

According to one embodiment, R in the compound of formula (III) is selected from the group consisting of

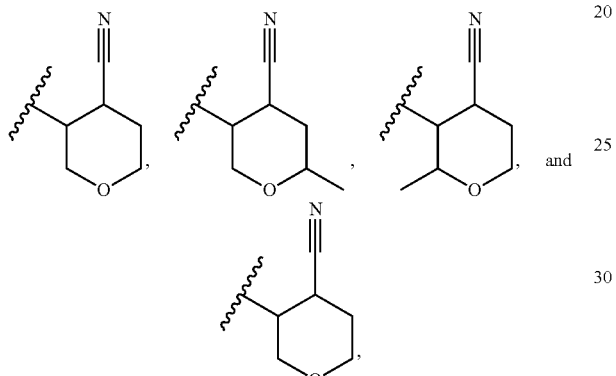

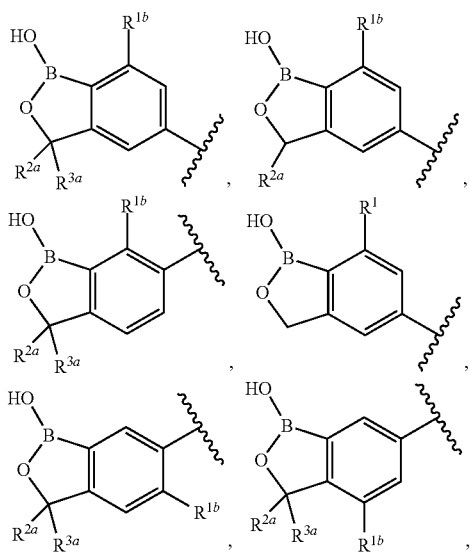

or an enantiomer thereof.

In one embodiment of the compound of formula (III), $R^4$, $R^{4a}$ and $R^{4b}$ are each hydrogen.

In one embodiment of the compound of formula (III), $R^4$, $R^{4a}$ and $R^{4b}$ are each hydrogen.

In one embodiment of the compound of formula (III) as described herein, A is preferably selected from

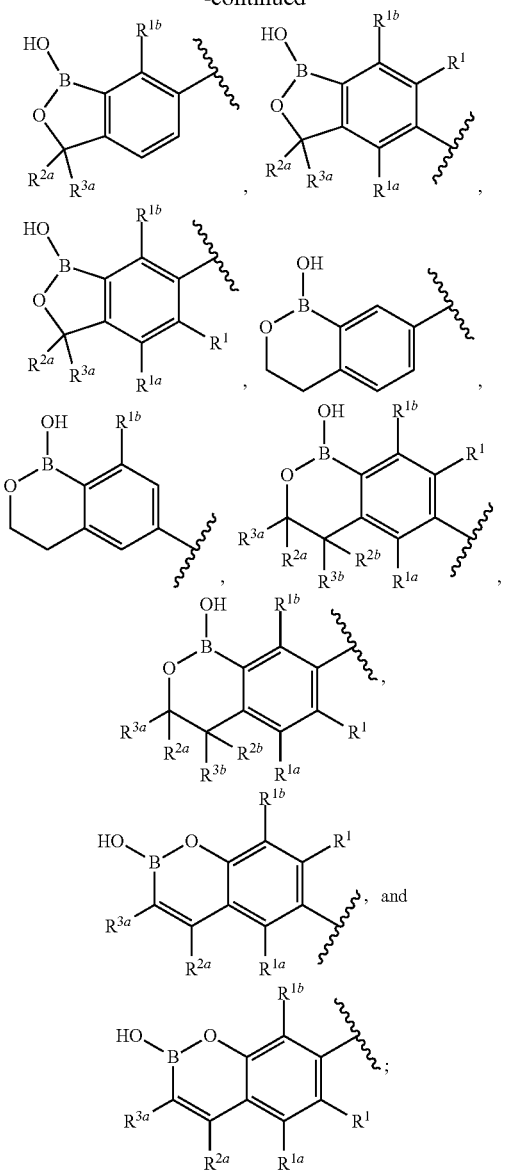

wherein:
$R^1$, $R^{1a}$ and $R^{1b}$ are independently selected from the group consisting of hydrogen, halogen, $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, partially or fully halogenated cyclopropyl, $O(C_1$-$C_3$ alkyl), and $O(C_1$-$C_3$ haloalkyl);

$R^{2a}$ and $R^{3a}$ are independently selected from the group consisting of hydrogen, halogen, $C_1$-$C_3$ alkyl, $C_2$-$C_3$ alkenyl, $C_2$-$C_3$ alkynyl, or $R^{3a}$ together with $R^{3a}$ form cyclopropyl, cyclobutyl, oxetane, or cyclobutanone, wherein each of $R^{2a}$ and $R^{3a}$ is independently unsubstituted or substituted with one or more of halogen, hydroxy, amino, alkyl- or di(alkyl) amino, alkyl, cycloalkyl, haloalkyl, alkenyl, haloalkenyl, alkynyl, haloalkynyl, alkoxy, haloalkoxy, alkylthio, haloalkylthio, $R^7S(O)$—, $R^7S(O)_2$—, $R^7C(O)$—, $R^7R^8NC(O)$—, $R^7OC(O)$—, $R^7C(O)O$—, $R^7C(O)NR^8$—, —CN or —$NO_2$;

$R^{2b}$ and $R^{3b}$ are independently selected from the group consisting of: hydrogen, $C_1$-$C_3$ alkyl, $C_2$-$C_3$ alkenyl, $C_2$-$C_3$ alkynyl, or $R^{2b}$ together with $R^{3b}$ form cyclopropyl, cyclobutyl, oxetane, or cyclobutanone, wherein each of $R^{2b}$ and $R^{3b}$ is independently unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R^7S(O)$—, $R^7S(O)_2$—, $R^7C(O)$—, $R^7R^8NC(O)$—, $R^7OC(O)$—, $R^7C(O)O$—, $R^7C(O)NR^8$—, —CN or —NO$_2$; and $R^7$ and $R^8$ are independently hydrogen, alkyl, haloalkyl, thioalkyl, alkylthioalkyl, hydroxyalkyl, alkoxy-alkyl, alkenyl, haloalkenyl, alkynyl or haloalkynyl.

In yet another embodiment of the compound of formula (III), A is preferably selected from

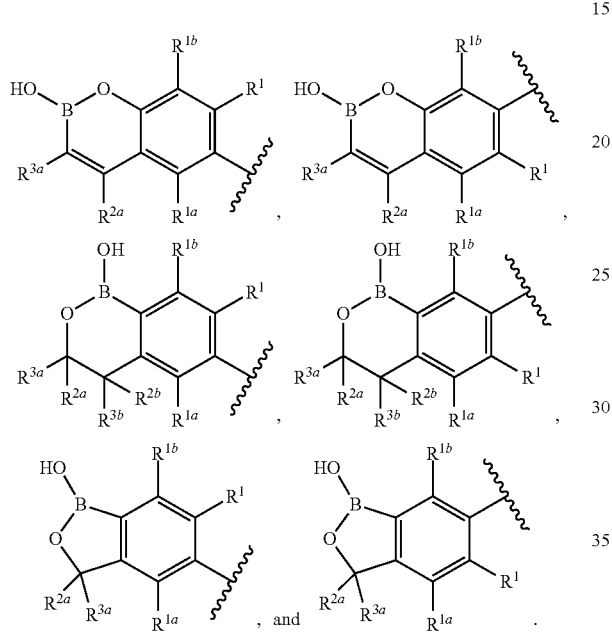

, and

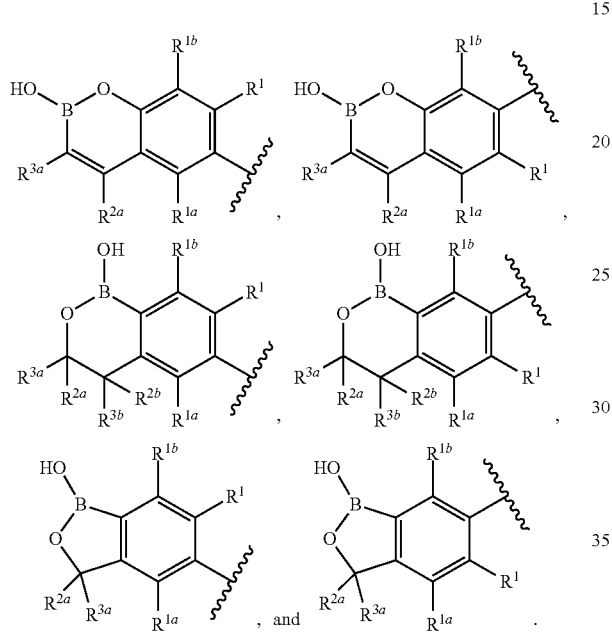

.

In one embodiment of the compound of formula (III) as described herein, $R^{2a}$, $R^{3a}$, $R^{2b}$, and $R^{3b}$ are independently selected from the group consisting of hydrogen, halogen, and C$_1$-C$_3$ alkyl. In one embodiment, $R^1$, $R^{1a}$, and $R^{1b}$ are independently selected from the group consisting of hydrogen, halogen, and C$_1$-C$_3$ alkyl. In one embodiment, $R^1$, $R^{1a}$, and $R^{1b}$ are independently selected from the group consisting of hydrogen and fluorine when $R^1$, $R^{1a}$ and/or $R^{1b}$ is ortho relative to the position where A is attached to nitrogen.

In one embodiment the compound according to the invention is selected from the group consisting of the following:

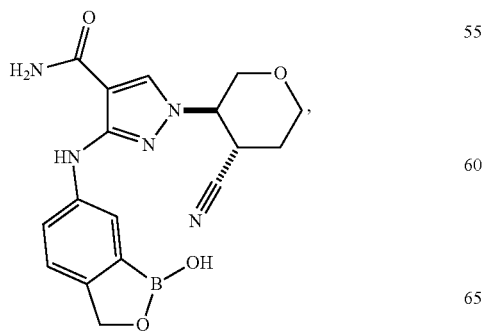

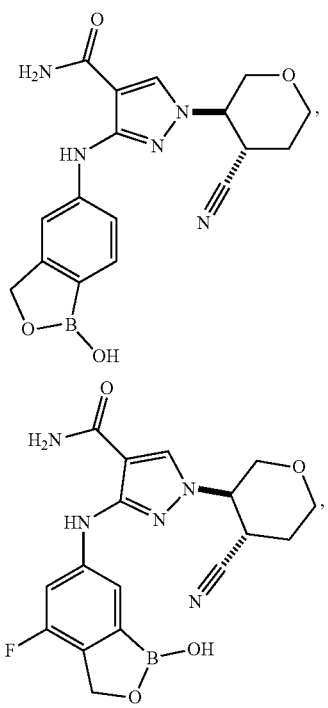

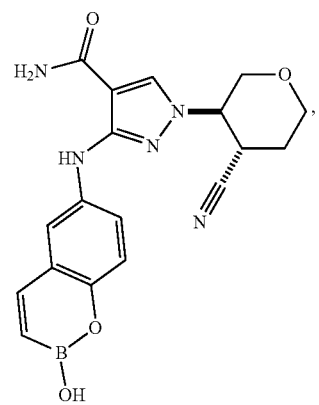

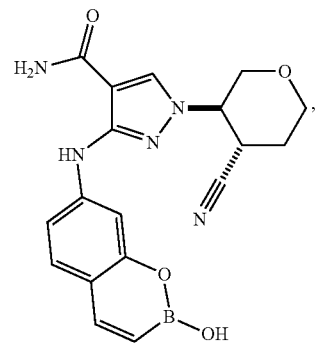

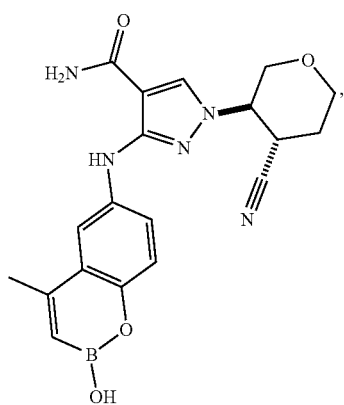
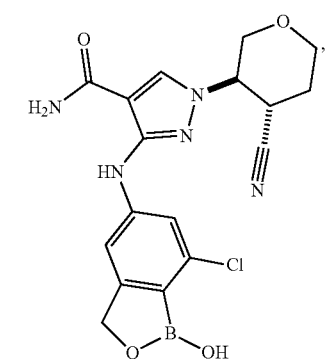
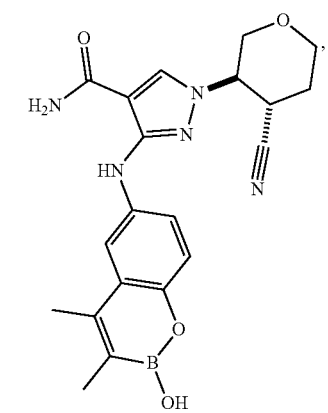
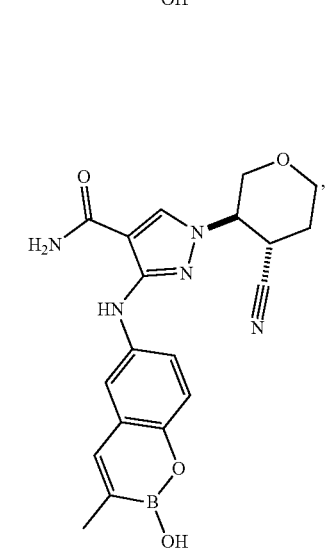
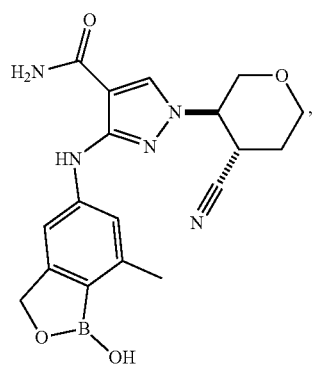
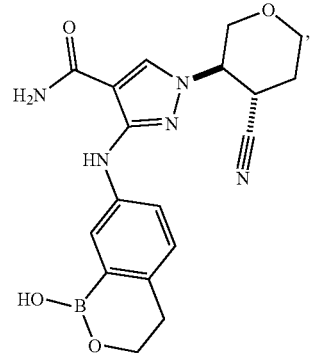
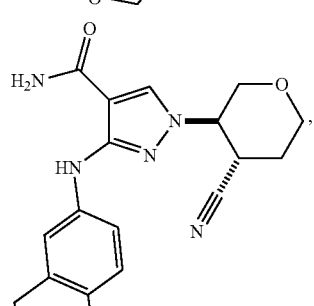
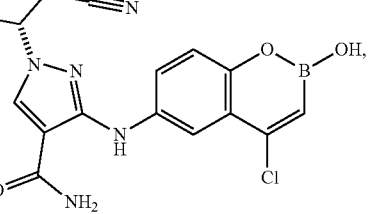
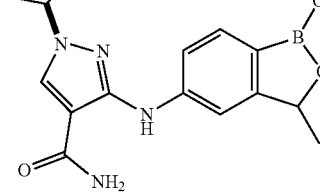

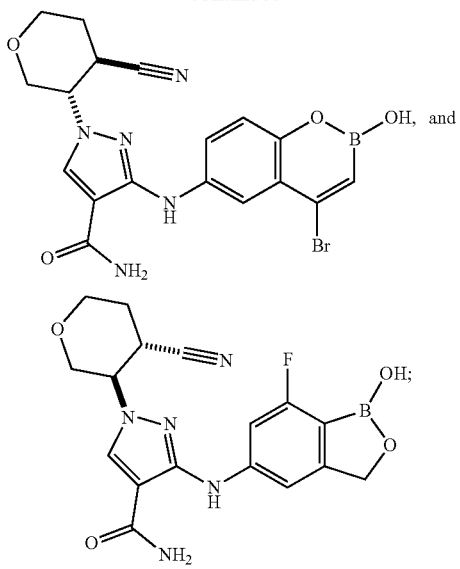

In one embodiment, the present invention provides for a compound of formula (IV), (IVa), or (IVb), or a pharmaceutically acceptable salt or a stereoisomer or a tautomer thereof:

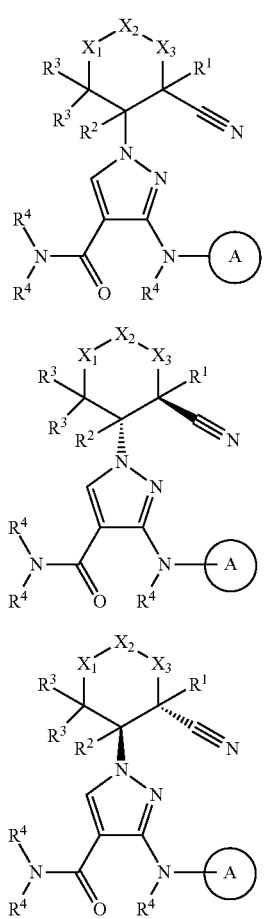

wherein:
$X_1$ is selected from the group consisting of —O—, —N($R^6$)—, and —C($R^7$)($R^8$)—;
$X_2$ is selected from the group consisting of —O—, —N($R^6$)—, and —C($R^7$)($R^8$)—, or
$X_2$ comprises a bond between $X_1$ and $X_3$;
$X_3$ is selected from the group consisting of —O—, —N($R^6$)—, and —C($R^7$)($R^8$)—, except $X_1$ and $X_2$ cannot both be —O—, and $X_2$ and $X_3$ cannot both be —O—;
$R^1$ is selected from the group consisting of hydrogen, halogen (when $X_3$ is —C($R^7$)($R^8$)), hydroxy, $C_{1-6}$ alkyl, $C_{3-7}$ cycloalkyl, $C_{1-6}$ alkyl(oxy), and $C_{3-7}$ cycloalkyl(oxy), wherein the last four members of the of the above-mentioned $R^1$ group may optionally be substituted independently of one another with one or more halogen;
$R^2$ is selected from the group consisting of hydrogen, $C_{1-6}$ alkyl, $C_{3-7}$ cycloalkyl, $C_{1-6}$ alkyl(oxy), and $C_{3-7}$ cycloalkyl(oxy), wherein the last four members of the above-mentioned $R^2$ group may optionally be substituted independently of one another with one or more halogen;
each $R^3$ is independently selected from the group consisting of hydrogen, halogen (when $X_1$ is —C($R^7$)($R^8$)), $C_{1-6}$ alkyl, $C_{3-7}$ cycloalkyl, $C_{1-6}$ alkyl(oxy), and $C_{3-7}$ cycloalkyl(oxy), wherein the last four members of the above-mentioned $R^3$ group may optionally be substituted independently of one another with one or more halogen;
each $R^4$ is independently selected from the group consisting of hydrogen, $C_{1-6}$ alkyl, $C_{3-7}$ cycloalkyl, $C_{1-6}$ alkyl(oxy), and $C_{3-7}$ cycloalkyl(oxy), wherein the above-mentioned members of each $R^4$ group, except hydrogen, may optionally be substituted independently of one another with one or more halogen;
A is selected from the group consisting of benzo[c][1,2]oxaborol-1(3H)-ol, 3,4-dihydro-1Hbenzo[c][1,2]oxaborinin-1-ol, and 2H-benzo[e][1,2]oxaborinin-2-ol, or a derivative thereof, such as a moiety selected from any one of $A_1$-$A_6$:

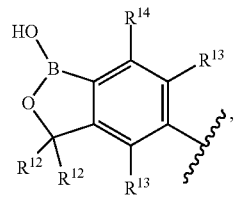

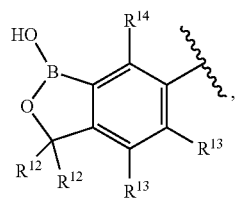

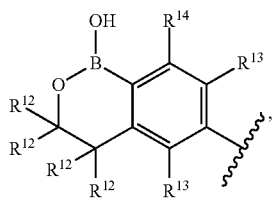

-continued

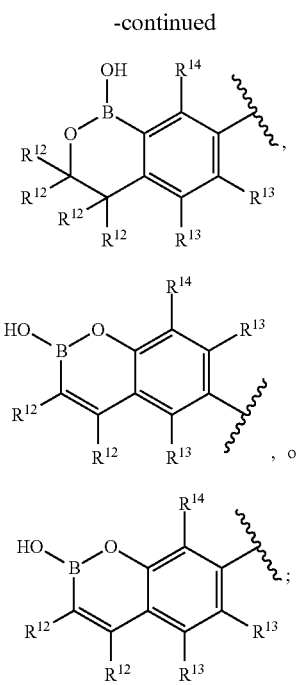

R⁶ is selected from the group consisting of hydrogen, $C_{1-6}$ alkyl, $C_{3-7}$ cycloalkyl, $C_{1-6}$ alkyl(oxy), $C_{3-7}$ cycloalkyl(oxy), —COO—$C_{1-6}$alkyl, —COO—$C_{3-7}$-cycloalkyl, —($C_{1-3}$-alkyl)-($C_{3-6}$-cycloalkyl), —($C_{2-3}$-alky(oxy)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl), wherein the above-mentioned members of the R⁶ group, except hydrogen, may optionally be substituted independently of one another by one or more substituents selected from the group consisting of $C_{1-6}$ alkyl and halogen, except halogen may not be adjacent to a heteroatom;

R⁷ and R⁸ are independently selected from the group consisting of hydrogen, halogen, hydroxy, —N(R⁹)(R¹⁰), —O(R¹¹), $C_{1-6}$ alkyl, $C_{3-7}$ cycloalkyl, $C_{1-6}$ alkyl(oxy), $C_{3-7}$ cycloalkyl(oxy), —COO—$C_{1-6}$ alkyl, —COO—$C_{3-7}$-cycloalkyl, —($C_{1-3}$-alkyl)-($C_{3-6}$-cycloalkyl), —($C_{2-3}$-alkyl(oxy)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl), wherein the last fifteen members of the above-mentioned R⁷ and R⁸ groups may optionally be substituted independently of one another by one or more substituents selected from the group consisting of halogen and hydroxy, and wherein R⁷ and R⁸ may be linked together to form a ring;

R⁹ and R¹⁰ are independently selected from the group consisting of hydrogen, $C_{1-6}$ alkyl, $C_{3-7}$ cycloalkyl, $C_{1-6}$ alkyl(oxy), $C_{3-7}$ cycloalkyl(oxy), —COO—$C_{1-6}$ alkyl, —COO—$C_{3-7}$-cycloalkyl, —($C_{1-3}$-alkyl)-($C_{3-6}$-cycloalkyl), —($C_{2-3}$-alkyoxyl)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl); wherein the last fourteen members of the above-mentioned R⁹ and R¹⁰ groups may optionally be substituted independently of one another by one or more halogen, or R⁹ and R¹⁰ may be linked together to form a ring;

R¹¹ is selected from the group consisting of hydrogen, $C_{1-6}$ alkyl, $C_{3-7}$ cycloalkyl, $C_{1-6}$ alkyl(oxy), $C_{3-7}$cycloalkyl(oxy), —COO—$C_{1-6}$ alkyl, —COO—$C_{3-7}$-cycloalkyl, —($C_{1-3}$-alkyl)-($C_{3-6}$-cycloalkyl), —($C_{2-3}$-alkyoxyl)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl), wherein the last thirteen members of the above-mentioned R¹¹ group may optionally be substituted independently of one another by one or more substituents selected from the group consisting of halogen and hydroxy, except that said optional substitution may not be geminal;

each R¹² is independently selected from the group consisting of hydrogen, halogen, $C_{1-6}$ alkyl, $C_{3-7}$ cycloalkyl, 4-7-membered heterocycloalkyl, $C_{1-6}$ alkyl(oxy), and $C_{3-7}$ cycloalkyl(oxy), wherein the last four members of the above-mentioned R¹² group may optionally be substituted independently of one another by one or more substituents selected from the group consisting of halogen and hydroxy, except when R¹² is adjacent to oxygen, R¹² is not halogen, and two adjacent R¹² may be connected to provide a fused cycloalkyl, such as cyclopropyl; and R¹³ and R¹⁴ are independently selected from the group consisting of hydrogen, halogen, cyano, $C_{1-6}$alkyl, $C_{3-7}$ cycloalkyl, $C_{1-6}$ alkyl(oxy), $C_{3-7}$ cycloalkyl(oxy), —($C_{1-3}$-alkyl)-($C_{3-6}$-cycloalkyl), —($C_{2-3}$-alkyl(oxy)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), —N—(R⁶)(R⁶), —SO₂—(R⁶), —SO₂—(R⁶)(R⁶), —S(O)—(R⁶), and —S—(R⁶), wherein the last fourteen members of the above-mentioned R¹³ and R¹⁴ groups may optionally be substituted independently of one another by one or more substituents selected from the group consisting of halogen and hydroxy.

In one embodiment of the compound of formula (IV), (IVa), and (IVb) as described herein $X_1$ is selected from the group consisting of —O—, —N(R⁶)—, and —C(R⁷)(R⁸)—;

$X_2$ is selected from the group consisting of —O—, —N(R⁶)—, and —C(R⁷)(R⁸)—, or $X_2$ comprises a bond between $X_1$ and $X_3$;

$X_3$ is —C(R⁷)(R⁸)—, except $X_1$ and $X_2$ cannot both be —O—;

R¹ is selected from the group consisting of hydrogen, $C_{1-6}$ alkyl, and $C_{3-7}$ cycloalkyl, wherein the last two members of the above-mentioned group may optionally be substituted independently of one another with one or more halogen;

R² is selected from the group consisting of hydrogen, $C_{1-6}$ alkyl, and $C_{3-7}$ cycloalkyl, wherein the last two members of the above-mentioned R²group may optionally be substituted independently of one another with one or more halogen;

each R³ is independently selected from the group consisting of hydrogen, $C_{1-6}$ alkyl, and $C_{3-7}$ cycloalkyl, wherein the last two members of the above-mentioned R³ group may optionally be substituted independently of one another with one or more halogen;

each R⁴ is independently selected from the group consisting of hydrogen, $C_{1-6}$ alkyl, and $C_{3-7}$ cycloalkyl, wherein the last two members of the above-mentioned $R^4$ group may optionally be substituted independently of one another with one or more halogen;

A is selected from the group consisting of benzo[c][1,2]oxaborol-1(3H)-ol, 3,4-dihydro-1Hbenzo[c][1,2]oxaborinin-1-ol, and 2H-benzo[e][1,2]oxaborinin-2-ol, or a derivative thereof, such as a moiety selected from any one of $A_1$-$A_6$:

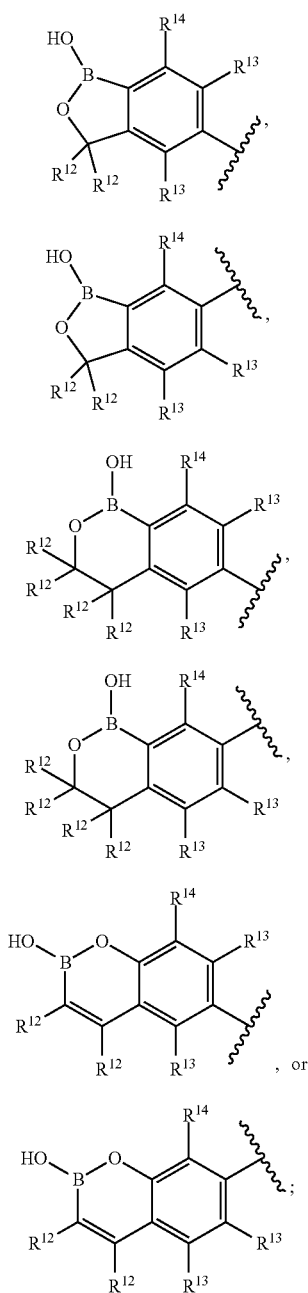

$R^6$ is selected from the group consisting of hydrogen, $C_{1-6}$ alkyl, $C_{3-7}$ cycloalkyl, $C_{1-6}$ alkyl(oxy), $C_{3-7}$ cycloalkyl(oxy), —COO—$C_{1-6}$ alkyl, —COO—$C_{3-7}$-cycloalkyl, —($C_{1-3}$-alkyl)-($C_{3-6}$-cycloalkyl), —($C_{2-3}$-alky(oxy)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl), wherein the above-mentioned members of the $R^6$ group, except hydrogen, may optionally be substituted independently of one another by one or more substituents selected from the group consisting of $C_{1-6}$ alkyl and halogen, except halogen may not be adjacent to a heteroatom;

$R^7$ and $R^8$ are independently selected from the group consisting of hydrogen, —$C_{1-6}$ alkyl, $C_{3-7}$ cycloalkyl, $C_{1-6}$ alkyl(oxy), and $C_{3-7}$ cycloalkyl(oxy), wherein the last four members of the above-mentioned $R^7$ and $R^8$ groups may optionally be substituted independently of one another by one or more substituents selected from the group consisting of halogen and hydroxy, and $R^7$ and $R^8$ may be linked together to form a ring;

$R^9$ and $R^{10}$ are independently selected from the group consisting of hydrogen, $C_{1-6}$ alkyl, $C_{3-7}$ cycloalkyl, $C_{1-6}$ alkyl(oxy), $C_{3-7}$ cycloalkyl(oxy), —COO—$C_{1-6}$ alkyl, —COO—$C_{3-7}$-cycloalkyl, —($C_{1-3}$-alkyl)-($C_{3-6}$-cycloalkyl), —($C_{2-3}$-alkyoxyl)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl); wherein the last fourteen members of the above-mentioned $R^9$ and $R^{10}$ groups may optionally be substituted independently of one another by one or more halogen, or $R^9$ and $R^{10}$ may be linked together to form a ring;

$R^{11}$ is selected from the group consisting of hydrogen, $C_{1-6}$ alkyl, $C_{3-7}$ cycloalkyl, $C_{1-6}$ alkyl(oxy), $C_{3-7}$ cycloalkyl(oxy), —COO—$C_{1-6}$ alkyl, —COO—$C_{3-7}$-cycloalkyl, —($C_{1-3}$-alkyl)-($C_{3-6}$-cycloalkyl), —($C_{2-3}$-alkyoxyl)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl), wherein the last thirteen members of the above-mentioned $R^{11}$ group may optionally be substituted independently of one another by one or more substituents selected from the group consisting of halogen and hydroxy, except that said optional substitution may not be geminal;

each $R^{12}$ is independently selected from the group consisting of hydrogen, halogen, $C_{1-6}$ alkyl, $C_{3-7}$ cycloalkyl, 4-7-membered heterocycloalkyl, $C_{1-6}$ alkyl(oxy), and $C_{3-7}$ cycloalkyl(oxy), wherein the last four members of the above-mentioned $R^{12}$ group may optionally be substituted independently of one another by one or more substituents selected from the group consisting of halogen and hydroxy, except when $R^{12}$ is adjacent to oxygen, $R^{12}$ is not halogen, and two adjacent $R^{12}$ may be connected to provide a fused cycloalkyl, such as cyclopropyl;

each $R^{13}$ is independently selected from the group consisting of hydrogen, halogen, and $C_{1-6}$ alkyl; and each $R^{14}$ is independently selected from the group consisting of hydrogen, halogen, cyano, $C_{1-6}$ alkyl, $C_{3-7}$ cycloalkyl, $C_{1-6}$ alkyl(oxy), $C_{3-7}$ cycloalkyl(oxy), —($C_{1-3}$-alkyl)-($C_{3-6}$-cycloalkyl), —($C_{2-3}$-alkyl(oxy)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), —N—($R^6$)($R^6$), —$SO_2$—($R^6$), —$SO_2$—($R^6$)($R^6$), —S(O)—($R^6$), and —S—($R^6$), wherein the last fourteen members of the above-mentioned $R^{14}$ group may optionally be substituted independently of one another by one or more substituents selected from the group consisting of halogen and hydroxy.

In one embodiment of the compound of formula (IV), (IVa), and (IV)b as described herein X$_1$ is selected from the group consisting of —O—, —N(R$^6$)—, and —C(R$^7$)(R$^8$)—;

X$_2$ is selected from the group consisting of —O— and —C(R$^7$)(R$^8$)—, except X$_1$ and X$_2$ may not both be —O—, or X$_2$ comprises a bond between X$_1$ and X$_3$;

X$_3$ is —C(R$^7$)(R$^8$)—;

R$^1$ is selected from the group consisting of hydrogen and C$_{1-6}$ alkyl;

R$^2$ is selected from the group consisting of hydrogen and C$_{1-6}$ alkyl;

each R$^3$ is independently selected from the group consisting of hydrogen and C$_{1-6}$ alkyl;

each R$^4$ is independently selected from the group consisting of hydrogen and C$_{1-6}$ alkyl;

A is selected from the group consisting of benzo[c][1,2]oxaborol-1(3H)-ol, 3,4-dihydro-1Hbenzo[c][1,2]oxaborinin-1-ol, and 2H-benzo[e][1,2]oxaborinin-2-ol, or a derivative thereof, such as a moiety selected from any one of A$_1$-A$_6$:

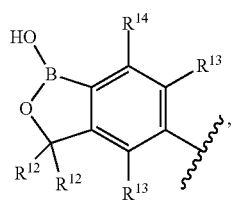

A$_1$

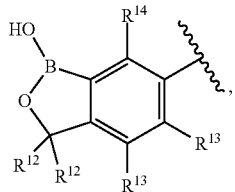

A$_2$

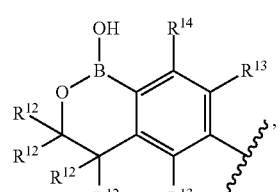

A$_3$

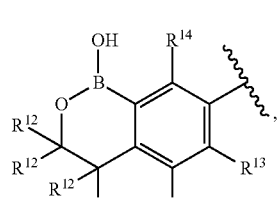

A$_4$

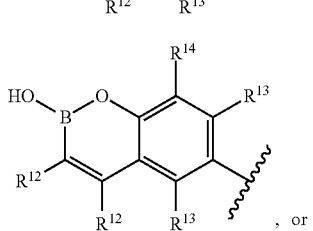

A$_5$

, or

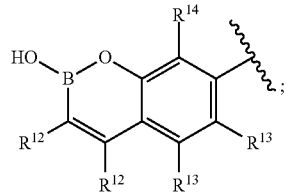

A$_6$

;

R$^6$ is selected from the group consisting of hydrogen, C$_{1-6}$ alkyl, C$_{3-7}$ cycloalkyl, C$_{1-6}$ alkyl(oxy), C$_{3-7}$ cycloalkyl(oxy), —COO—C$_{1-6}$ alkyl, —COO—C$_{3-7}$-cycloalkyl, —(C$_{1-3}$-alkyl)-(C$_{3-6}$-cycloalkyl), —(C$_{2-3}$-alky(oxy)-(C$_{2-6}$-alkyl), —(C$_{2-3}$-alkyl(oxy)-(C$_{3-6}$-cycloalkyl), 4-7-membered heterocycloalkyl, —(C$_{1-3}$-alkyl)-(4-7-membered heterocycloalkyl), -heteroaryl, and —(C$_{1-3}$-alkyl)-(heteroaryl), wherein the above-mentioned members of the R$^6$ group, except hydrogen, may optionally be substituted independently of one another by one or more substituents selected from the group consisting of C$_{1-6}$ alkyl and halogen, except halogen may not be adjacent to a heteroatom;

R$^7$ and R$^8$ are independently selected from the group consisting of hydrogen and C$_{1-6}$ alkyl, wherein the C$_{1-6}$ alkyl may optionally be substituted with one or more of halogen;

R$^9$ and R$^{10}$ are independently selected from the group consisting of hydrogen, C$_{1-6}$ alkyl, C$_{3-7}$ cycloalkyl, C$_{1-6}$ alkyl(oxy), C$_{3-7}$ cycloalkyl(oxy), —COO—C$_{1-6}$ alkyl, —COO—C$_{3-7}$-cycloalkyl, —(C$_{1-3}$-alkyl)-(C$_{3-6}$-cycloalkyl), —(C$_{2-3}$-alkyoxyl)-(C$_{2-6}$-alkyl), —(C$_{2-3}$-alkyl(oxy)-(C$_{3-6}$-cycloalkyl), 4-7-membered heterocycloalkyl, —(C$_{1-3}$-alkyl)-(4-7-membered heterocycloalkyl), -heteroaryl, and —(C$_{1-3}$-alkyl)-(heteroaryl); wherein the last fourteen members of the above-mentioned R$^9$ and R$^{10}$ groups may optionally be substituted independently of one another by one or more halogen, or R$^9$ and R$^{10}$ may be linked together to form a ring;

R$^{11}$ is selected from the group consisting of hydrogen, C$_{1-6}$ alkyl, C$_{3-7}$ cycloalkyl, C$_{1-6}$ alkyl(oxy), C$_{3-7}$cycloalkyl(oxy), —COO—C$_{1-6}$ alkyl, —COO—C$_{3-7}$-cycloalkyl, —(C$_{1-3}$-alkyl)-(C$_{3-6}$-cycloalkyl), —(C$_{2-3}$-alkyoxyl)-(C$_{2-6}$-alkyl), —(C$_{2-3}$-alkyl(oxy)-(C$_{3-6}$-cycloalkyl), 4-7-membered heterocycloalkyl, —(C$_{1-3}$-alkyl)-(4-7-membered heterocycloalkyl), -heteroaryl, and —(C$_{1-3}$-alkyl)-(heteroaryl), wherein the last thirteen members of the above-mentioned R$^{11}$ group may optionally be substituted independently of one another by one or more substituents selected from the group consisting of halogen and hydroxy, except that said optional substitution may not be geminal;

each R$^{12}$ is independently selected from the group consisting of hydrogen, halogen, C$_{1-6}$ alkyl, C$_{3-7}$ cycloalkyl, 4-7-membered heterocycloalkyl, C$_{1-6}$ alkyl(oxy), and C$_{3-7}$ cycloalkyl(oxy), wherein the last four members of the above-mentioned R$^{12}$ group may optionally be substituted independently of one another by one or more substituents selected from the group consisting of halogen and hydroxy, except when R$^{12}$ is adjacent to oxygen, R$^{12}$ is not halogen, and two adjacent R$^{12}$ may be connected to provide a fused cycloalkyl, such as cyclopropyl;

$R^{13}$ is hydrogen; and each $R^{14}$ is independently selected from the group consisting of hydrogen, halogen, cyano, $C_{1-6}$ alkyl, $C_{3-7}$ cycloalkyl, $C_{1-6}$ alkyl(oxy), $C_{3-7}$ cycloalkyl(oxy), —($C_{1-3}$-alkyl)-($C_{3-6}$-cycloalkyl), —($C_{2-3}$-alkyl(oxy)-($C_{2-6}$-alkyl), and 4-7-membered heterocycloalkyl, wherein the last seven members of the above-mentioned $R^{14}$ group may optionally be substituted independently of one another by one or more substituents selected from the group consisting of halogen and hydroxy.

In yet another embodiment of the compound of formula (IV), (IVa), and (IVb) as described herein $X_1$ is selected from the group consisting of —O—, —N($R^6$)—, and —C($R^7$)($R^8$)—;

$X_2$ is selected from the group consisting of —O— and —C($R^7$)($R^8$)—, except $X_1$ and $X_2$ may not both be —O—, or $X_2$ comprises a bond between $X_1$ and $X_3$;

$X_3$ is —C($R^7$)($R^8$)—;

$R^1$ is selected from the group consisting of hydrogen and $C_{1-6}$ alkyl;

$R^2$ is selected from the group consisting of hydrogen and $C_{1-6}$ alkyl;

each $R^3$ is independently selected from the group consisting of hydrogen and $C_{1-6}$ alkyl;

each $R^4$ is independently selected from the group consisting of hydrogen and $C_{1-6}$ alkyl;

A is selected from the group consisting of benzo[c][1,2]oxaborol-1(3H)-ol, 3,4-dihydro-1Hbenzo[c][1,2]oxaborinin-1-ol, and 2H-benzo[e][1,2]oxaborinin-2-ol, or a derivative thereof, such as a moiety selected from any one of $A_1$-$A_6$:

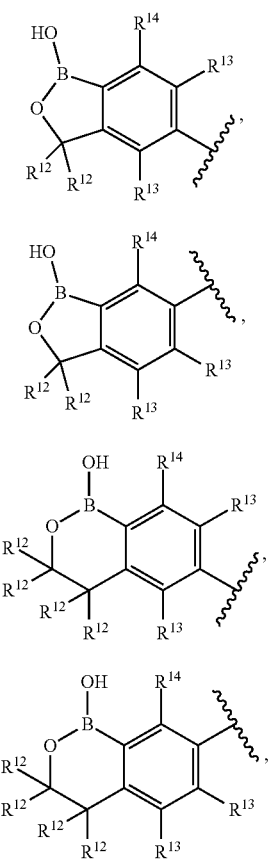

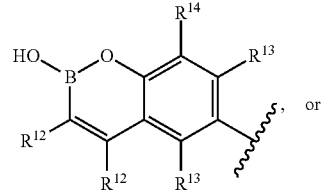

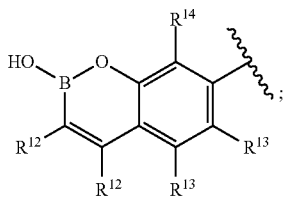

$R^6$ is selected from the group consisting of hydrogen, $C_{1-6}$ alkyl, $C_{3-7}$ cycloalkyl, $C_{1-6}$ alkyl(oxy), $C_{3-7}$ cycloalkyl (oxy), —COO—$C_{1-6}$ alkyl, —COO—$C_{3-7}$-cycloalkyl, —($C_{1-3}$-alkyl)-($C_{3-6}$-cycloalkyl), —($C_{2-3}$-alky(oxy)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl), wherein the above-mentioned members of the $R^6$ group, except hydrogen, may optionally be substituted independently of one another by one or more substituents selected from the group consisting of $C_{1-6}$ alkyl and halogen, except halogen may not be adjacent to a heteroatom;

$R^7$ and $R^8$ are independently selected from the group consisting of hydrogen and $C_{1-6}$ alkyl, wherein the $C_{1-6}$ alkyl may optionally be substituted with one or more of halogen;

$R^9$ and $R^{10}$ are independently selected from the group consisting of hydrogen, $C_{1-6}$ alkyl, $C_{3-7}$ cycloalkyl, $C_{1-6}$ alkyl(oxy), $C_{3-7}$ cycloalkyl(oxy), —COO—$C_{1-6}$ alkyl, —COO—$C_{3-7}$-cycloalkyl, —($C_{1-3}$-alkyl)-($C_{3-6}$-cycloalkyl), —($C_{2-3}$-alkyoxyl)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl); wherein the last fourteen members of the above-mentioned $R^9$ and $R^{10}$ groups may optionally be substituted independently of one another by one or more halogen, or $R^9$ and $R^{10}$ may be linked together to form a ring;

$R^{11}$ is selected from the group consisting of hydrogen, $C_{1-6}$ alkyl, $C_{3-7}$ cycloalkyl, $C_{1-6}$ alkyl(oxy), $C_{3-7}$cycloalkyl(oxy), —COO—$C_{1-6}$ alkyl, —COO—$C_{3-7}$-cycloalkyl, —($C_{1-3}$-alkyl)-($C_{3-6}$-cycloalkyl), —($C_{2-3}$-alkyoxyl)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl), wherein the last thirteen members of the above-mentioned $R^{11}$ group may optionally be substituted independently of one another by one or more substituents selected from the group consisting of halogen and hydroxy, except that said optional substitution may not be geminal;

each $R^{12}$ is independently selected from the group consisting of hydrogen, halogen, $C_{1-6}$ alkyl, $C_{3-7}$ cycloalkyl, 4-7-membered heterocycloalkyl, $C_{1-6}$ alkyl(oxy), and $C_{3-7}$ cycloalkyl(oxy), wherein the last four members of the above-mentioned $R^{12}$ group may optionally be substituted independently of one another by one or more substituents selected from the group consisting of halogen and hydroxy, except when $R^{12}$ is adjacent to oxygen, $R^{12}$ is not halogen, and two adjacent $R^{12}$ may be connected to provide a fused cycloalkyl, such as cyclopropyl;

$R^{13}$ is hydrogen; and each $R^{14}$ is independently selected from the group consisting of hydrogen, halogen, cyano, $C_{1-6}$ alkyl, $C_{3-7}$ cycloalkyl, $C_{1-6}$ alkyl(oxy), $C_{3-7}$ cycloalkyl(oxy), —($C_{1-3}$-alkyl)-($C_{3-6}$-cycloalkyl), —($C_{2-3}$-alkyl(oxy)-($C_{2-6}$-alkyl), and 4-7-membered heterocycloalkyl, wherein the last seven members of the above-mentioned $R^{14}$ group may optionally be substituted independently of one another by one or more substituents selected from the group consisting of halogen and hydroxy.

In one embodiment of the compound of formula (IV), (IVa), and (IV)b as described herein $X_1$ is selected from the group consisting of —O—, —N($R^6$)—, and —C($R^7$)($R^8$)—;

$X_2$ is —C($R^7$)($R^8$)—;

$X_3$ is —C($R^7$)($R^8$)—;

$R^1$, $R^2$, $R^3$, and $R^4$ are hydrogen;

A is selected from the group consisting of benzo[c][1,2]oxaborol-1(3H)-ol, 3,4-dihydro-1Hbenzo[c][1,2]oxaborinin-1-ol, and 2H-benzo[e][1,2]oxaborinin-2-ol, or a derivative thereof, such as a moiety selected from any one of $A_1$-$A_6$:

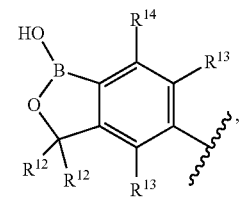
$A_1$

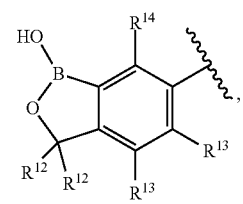
$A_2$

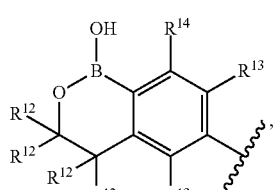
$A_3$

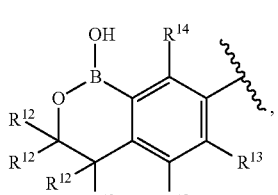
$A_4$

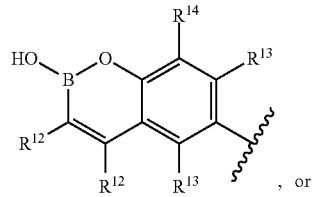
$A_5$

, or

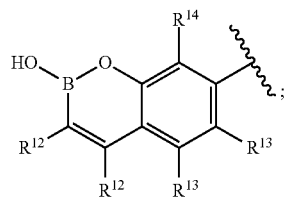
$A_6$
;

$R^6$ is selected from the group consisting of hydrogen, $C_{1-6}$ alkyl, $C_{3-7}$ cycloalkyl, $C_{1-6}$ alkyl(oxy), $C_{3-7}$ cycloalkyl (oxy), —COO—$C_{1-6}$alkyl, —COO—$C_{3-7}$-cycloalkyl, —($C_{1-3}$-alkyl)-($C_{3-6}$-cycloalkyl), —($C_{2-3}$-alky(oxy)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl), wherein the above-mentioned members of the $R^6$ group, except hydrogen, may optionally be substituted independently of one another by one or more substituents selected from the group consisting of $C_{1-6}$ alkyl and halogen, except halogen may not be adjacent to a heteroatom;

$R^7$ and $R^8$ are independently selected from the group consisting of hydrogen and $C_{1-6}$ alkyl, wherein $C_{1-6}$ alkyl may optionally be substituted with one or more of halogen;

$R^9$ and $R^{10}$ are independently selected from the group consisting of hydrogen, $C_{1-6}$ alkyl, $C_{3-7}$ cycloalkyl, $C_{1-6}$ alkyl(oxy), $C_{3-7}$ cycloalkyl(oxy), —COO—$C_{1-6}$ alkyl, —COO—$C_{3-7}$-cycloalkyl, —($C_{1-3}$-alkyl)-($C_{3-6}$-cycloalkyl), —($C_{2-3}$-alkyoxyl)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl); wherein the last fourteen members of the above-mentioned $R^9$ and $R^{10}$ groups may optionally be substituted independently of one another by one or more halogen, or $R^9$ and $R^{10}$ may be linked together to form a ring;

$R^{11}$ is selected from the group consisting of hydrogen, $C_{1-6}$ alkyl, $C_{3-7}$ cycloalkyl, $C_{1-6}$ alkyl(oxy), $C_{3-7}$ cycloalkyl(oxy), —COO—$C_{1-6}$ alkyl, —COO—$C_{3-7}$-cycloalkyl, —($C_{1-3}$-alkyl)-($C_{3-6}$-cycloalkyl), —($C_{2-3}$-alkyoxyl)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl), wherein the last thirteen members of the above-mentioned $R^{11}$ group may optionally be substituted independently of one another by one or more substituents selected from the group consisting of halogen and hydroxy, except that said optional substitution may not be geminal;

each $R^{12}$ is independently selected from the group consisting of hydrogen, halogen, $C_{1-6}$ alkyl, and $C_{3-7}$ cycloalkyl, wherein the last two substituents may optionally be substituted independently of one another by one or more halogen;

$R^{13}$ is hydrogen; and each $R^{14}$ is independently selected from the group consisting of hydrogen, halogen, cyano, $C_{1-6}$ alkyl, $C_{3-7}$ cycloalkyl, and $C_{1-6}$ alkyl(oxy), wherein the last three members of the above-mentioned $R^{14}$ group may optionally be substituted independently of one another by one or more halogen.

In one embodiment of the compound of formula (IV), (IVa), and (IVb) as described herein $X_1$ is selected from the group consisting of —O—, —N($R^6$)—, and —C($R^7$)($R^8$)—;

$X_2$ is —C($R^7$)($R^8$)—;

$X_3$ is —C($R^7$)($R^8$)—;

$R^1$, $R^2$, $R^3$, and $R^4$ are hydrogen;

A is selected from the group consisting of benzo[c][1,2]oxaborol-1(3H)-ol, 3,4-dihydro-1Hbenzo[c][1,2]oxaborinin-1-ol, and 2H-benzo[e][1,2]oxaborinin-2-ol, or a derivative thereof, such as a moiety selected from any one of $A_1$-$A_6$:

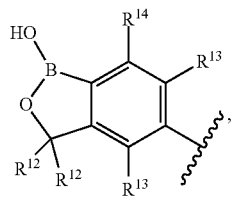
$A_1$

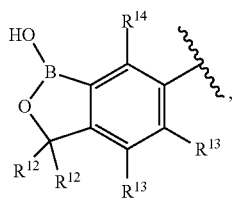
$A_2$

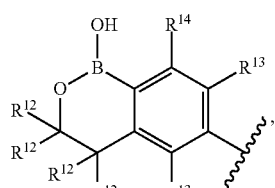
$A_3$

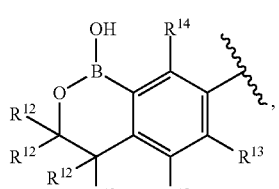
$A_4$

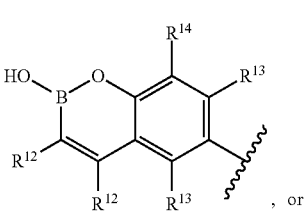
$A_5$

, or

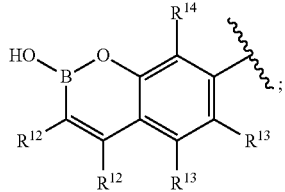
$A_6$

;

$R^6$ is selected from the group consisting of hydrogen, $C_{1-6}$ alkyl, $C_{3-7}$ cycloalkyl, $C_{1-6}$ alkyl(oxy), $C_{3-7}$ cycloalkyl(oxy), —COO—$C_{1-6}$ alkyl, —COO—$C_{3-7}$-cycloalkyl, —($C_{1-3}$-alkyl)-($C_{3-6}$-cycloalkyl), —($C_{2-3}$-alky(oxy)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl), wherein the above-mentioned members of the $R^6$ group, except hydrogen, may optionally be substituted independently of one another by one or more substituents selected from the group consisting of $C_{1-6}$ alkyl and halogen, except halogen may not be adjacent to a heteroatom;

$R^7$ and $R^8$ are independently selected from the group consisting of hydrogen and $C_{1-6}$ alkyl, wherein $C_{1-6}$ alkyl may optionally be substituted with one or more of halogen;

$R^9$ and $R^{10}$ are independently selected from the group consisting of hydrogen, $C_{1-6}$ alkyl, $C_{3-7}$ cycloalkyl, $C_{1-6}$ alkyl(oxy), $C_{3-7}$ cycloalkyl(oxy), —COO—$C_{1-6}$ alkyl, —COO—$C_{3-7}$-cycloalkyl, —($C_{1-3}$-alkyl)-($C_{3-6}$-cycloalkyl), —($C_{2-3}$-alkyoxyl)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl); wherein the last fourteen members of the above-mentioned $R^9$ and $R^{10}$ groups may optionally be substituted independently of one another by one or more halogen, or $R^9$ and $R^{10}$ may be linked together to form a ring;

$R^{11}$ is selected from the group consisting of hydrogen, $C_{1-6}$ alkyl, $C_{3-7}$ cycloalkyl, $C_{1-6}$ alkyl(oxy), $C_{3-7}$ cycloalkyl(oxy), —COO—$C_{1-6}$ alkyl, —COO—$C_{3-7}$-cycloalkyl, —($C_{1-3}$-alkyl)-($C_{3-6}$-cycloalkyl), —($C_{2-3}$-alkyoxyl)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl), wherein the last thirteen members of the above-mentioned $R^{11}$ group may optionally be substituted independently of one another by one or more substituents selected from the group consisting of halogen and hydroxy, except that said optional substitution may not be geminal;

each $R^{12}$ is independently selected from the group consisting of hydrogen, halogen, $C_{1-6}$ alkyl, and $C_{3-7}$ cycloalkyl, wherein the last two substituents may optionally be substituted independently of one another by one or more halogen;

$R^{13}$ is hydrogen; and each $R^{14}$ is independently selected from the group consisting of hydrogen, halogen, cyano, $C_{1-6}$ alkyl, $C_{3-7}$ cycloalkyl, and $C_{1-6}$ alkyl(oxy), wherein the last three members of the above-mentioned $R^{14}$ group may optionally be substituted independently of one another by one or more halogen.

In one embodiment of the compound of formula (IV), (IVa), and (IV)b as described herein $X_1$ is selected from the group consisting of —O—, —N($R^6$)—, and —C($R^7$)($R^8$)—;

$X_2$ is —C($R^7$)($R^8$)—;

$X_3$ is —C($R^7$)($R^8$)—;

$R^1$, $R^2$, $R^3$, and $R^4$ are hydrogen;

A is selected from the group consisting of benzo[c][1,2]oxaborol-1(3H)-ol, 3,4-dihydro-1Hbenzo[c][1,2]oxaborinin-1-ol, and 2H-benzo[e][1,2]oxaborinin-2-ol, or a derivative thereof, such as a moiety selected from any one of $A_1$-$A_6$:

$R^7$ and $R^8$ are independently selected from the group consisting of hydrogen and $C_{1-6}$ alkyl, wherein $C_{1-6}$ alkyl may optionally be substituted with one or more of halogen;

$R^9$ and $R^{10}$ are independently selected from the group consisting of hydrogen, $C_{1-6}$ alkyl, $C_{3-7}$ cycloalkyl, $C_{1-6}$ alkyl(oxy), $C_{3-7}$ cycloalkyl(oxy), —COO—$C_{1-6}$ alkyl, —COO—$C_{3-7}$-cycloalkyl, —($C_{1-3}$-alkyl)-($C_{3-6}$-cycloalkyl), —($C_{2-3}$-alkyoxyl)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl); wherein the last fourteen members of the above-mentioned $R^9$ and $R^{10}$ groups may optionally be substituted independently of one another by one or more halogen, or $R^9$ and $R^{10}$ may be linked together to form a ring;

$R^{11}$ is selected from the group consisting of hydrogen, $C_{1-6}$ alkyl, $C_{3-7}$ cycloalkyl, $C_{1-6}$ alkyl(oxy), $C_{3-7}$ cycloalkyl(oxy), —COO—$C_{1-6}$alkyl, —COO—$C_{3-7}$-cycloalkyl, —($C_{1-3}$-alkyl)-($C_{3-6}$-cycloalkyl), —($C_{2-3}$-alkyoxyl)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl), wherein the last thirteen members of the above-mentioned $R^{11}$ group may optionally be substituted independently of one another by one or more substituents selected from the group consisting of halogen and hydroxy, except that said optional substitution may not be geminal;

each $R^{12}$ is independently selected from the group consisting of hydrogen, halogen, $C_{1-6}$ alkyl, and $C_{3-7}$ cycloalkyl, wherein the last two substituents may optionally be substituted independently of one another by one or more halogen;

$R^{13}$ is hydrogen; and each $R^{14}$ is independently selected from the group consisting of hydrogen, halogen, cyano, $C_{1-6}$ alkyl, $C_{3-7}$ cycloalkyl, and $C_{1-6}$ alkyl(oxy), wherein the last three members of the above-mentioned $R^{14}$ group may optionally be substituted independently of one another by one or more halogen.

In one embodiment the compound according to the invention is a compound selected from the group consisting of Examples 1-57 as shown below:

| Example Number | Structure |
|---|---|
| 1 | 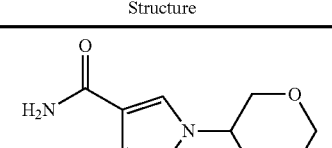 |

| Example Number | Structure |
|---|---|
| 2 | 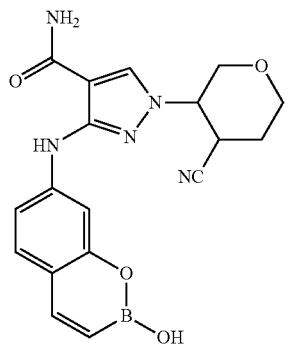 [SMILES: N#CC1CCOCC1n1cc(C(N)=O)c(Nc2ccc3c(c2)OB(O)C=C3)n1] |
| 3 | 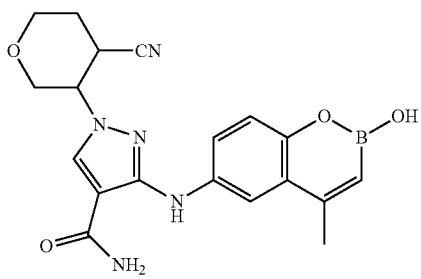 |
| 4 | 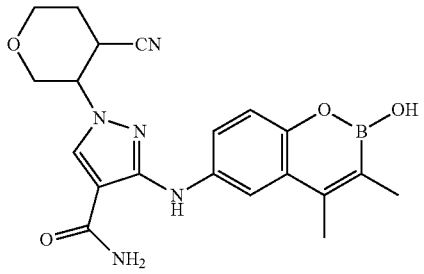 |
| 5 | 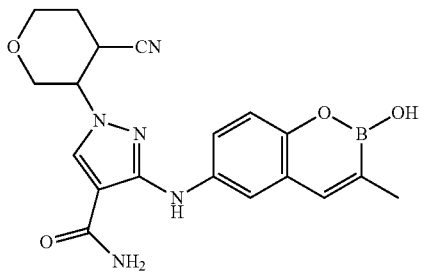 [SMILES: CC1=Cc2cc(Nc3nn(C4COCCC4C#N)cc3C(N)=O)ccc2OB1O] |
| 6 | 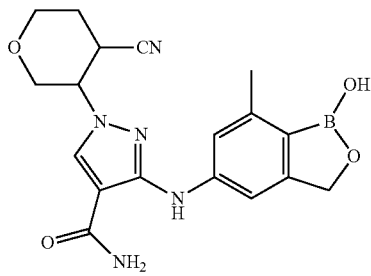 |
| Example Number | Structure |
|---|---|
| 7 | 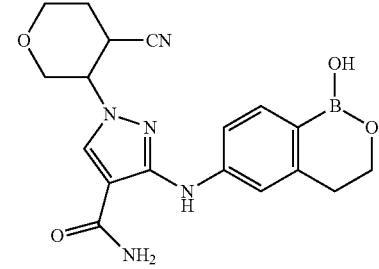 [SMILES: N#CC1CCOCC1n1cc(C(N)=O)c(Nc2ccc3c(c2)CCOB3O)n1] |
| 8 | 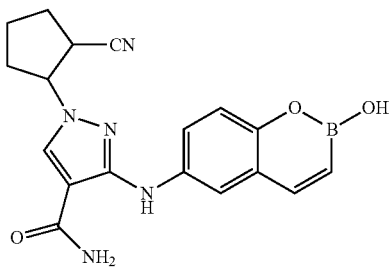 [SMILES: N#CC1CCCC1n1cc(C(N)=O)c(Nc2ccc3c(c2)C=CB(O)O3)n1] |
| 9 | 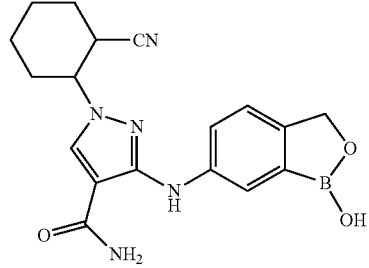 [SMILES: N#CC1CCCCC1n1cc(C(N)=O)c(Nc2ccc3c(c2)B(O)OC3)n1] |
| 10 | 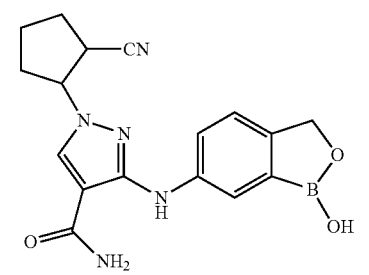 [SMILES: N#CC1CCCC1n1cc(C(N)=O)c(Nc2ccc3c(c2)B(O)OC3)n1] |
| 11 | 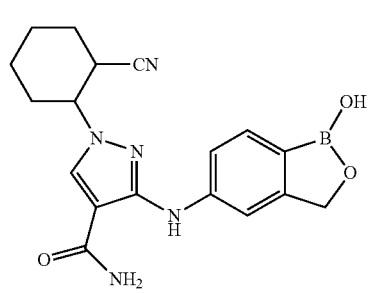 [SMILES: N#CC1CCCCC1n1cc(C(N)=O)c(Nc2ccc3c(c2)COB3O)n1] |

| Example Number | Structure |
|---|---|
| 12 | 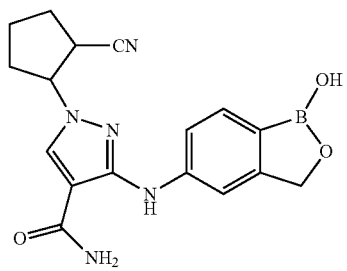 [SMILES: N#CC1CCCC1n1cc(C(N)=O)c(Nc2ccc3c(c2)COB3O)n1] |
| 13 | 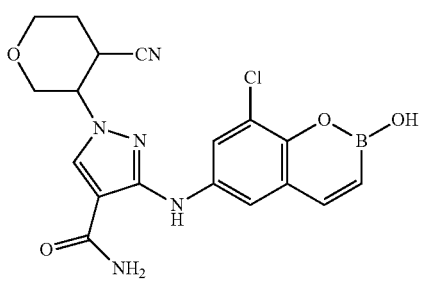 |
| 14 | 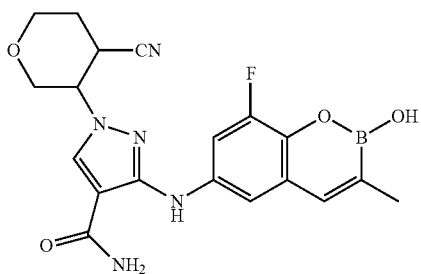 |
| 15 | 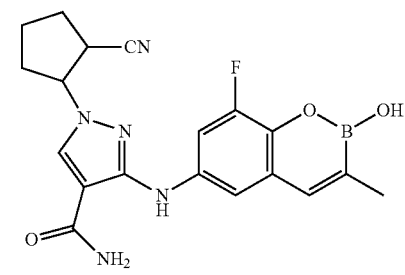 |
| 16 | 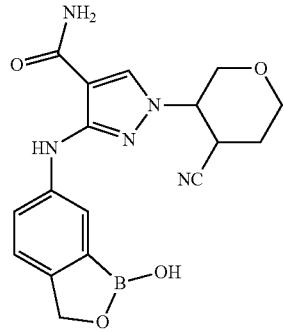 [SMILES: N#CC1CCOCC1n1cc(C(N)=O)c(Nc2ccc3c(c2)B(O)OC3)n1] |
| Example Number | Structure |
|---|---|
| 17 | 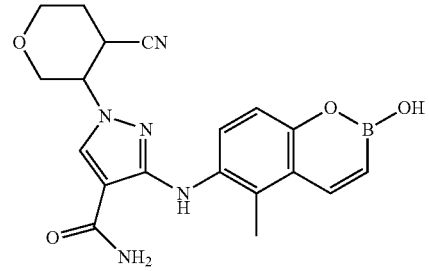 |
| 18 | 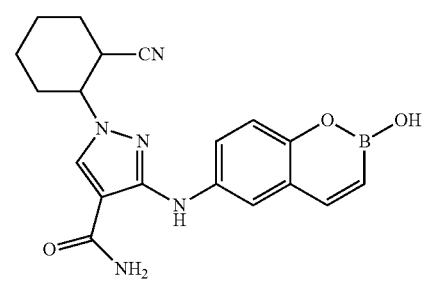 [SMILES: N#CC1CCCCC1n1cc(C(N)=O)c(Nc2ccc3c(c2)C=CB(O)O3)n1] |
| 19 | 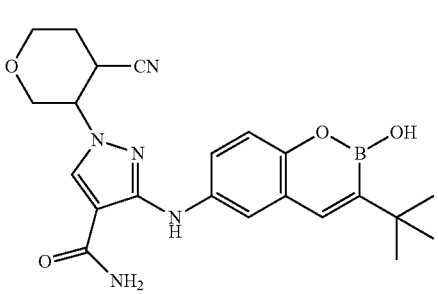 [SMILES: CC(C)(C)C1=Cc2cc(Nc3nn(C4COCCC4C#N)cc3C(N)=O)ccc2OB1O] |
| 20 | 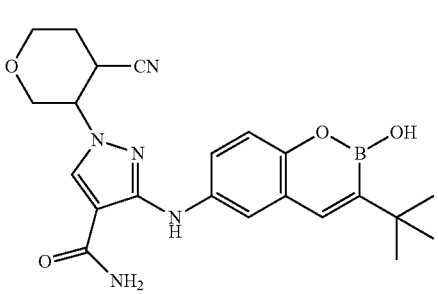 [SMILES: CC(C)(C)C1=Cc2cc(Nc3nn(C4COCCC4C#N)cc3C(N)=O)ccc2OB1O] |
| 21 | 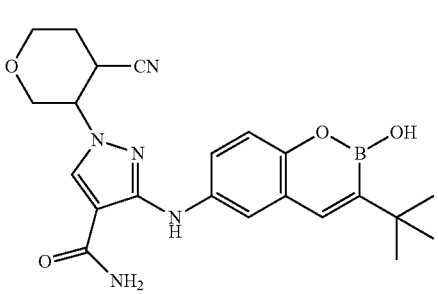 [SMILES: CC(C)(C)C1=Cc2cc(Nc3nn(C4COCCC4C#N)cc3C(N)=O)ccc2OB1O] |

-continued
| Example Number | Structure |
|---|---|
| 22 | 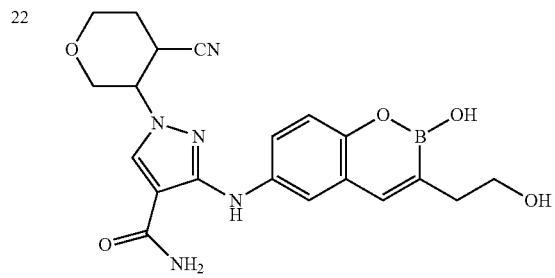 |
| 23 | 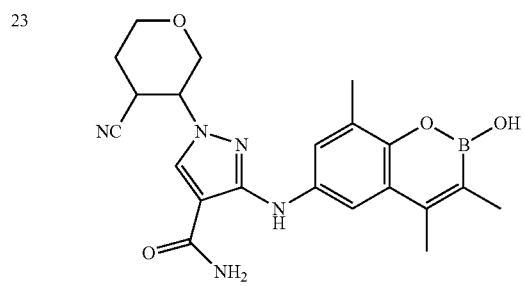 |
| 24 | 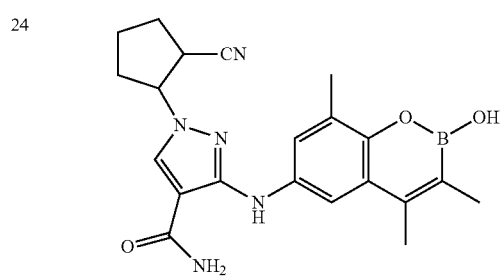 |
| 25 | 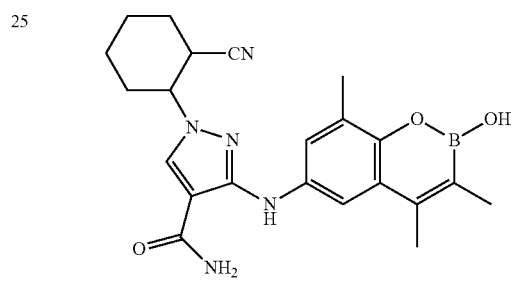 |
| 26 | 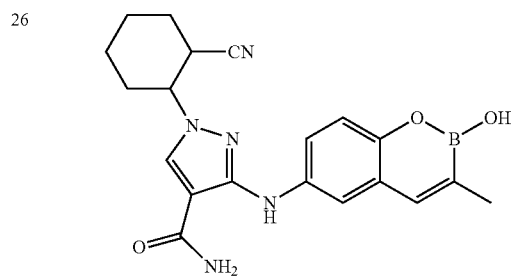 |
-continued
| Example Number | Structure |
|---|---|
| 27 | 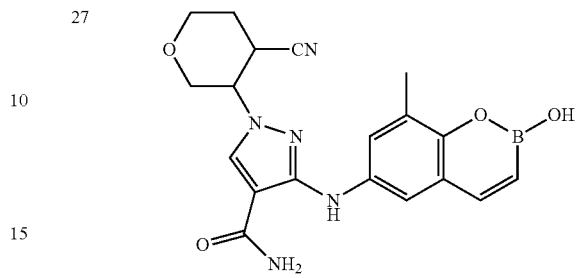 |
| 28 | 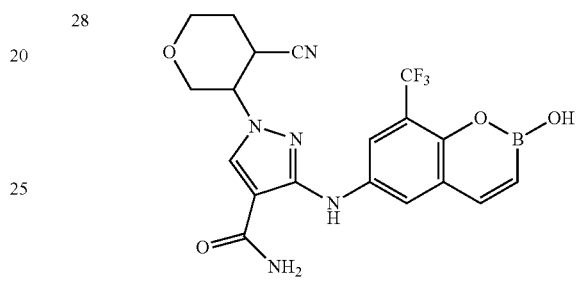 |
| 29 | 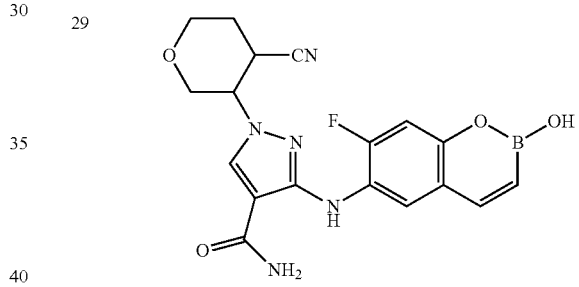 |
| 30 | 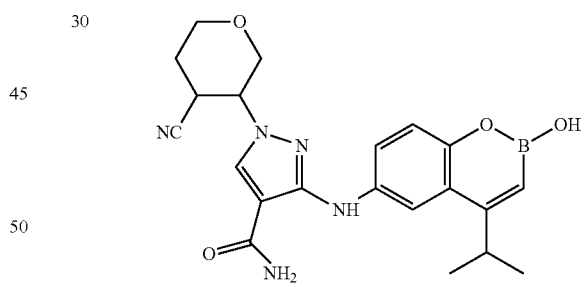 |
| 31 | 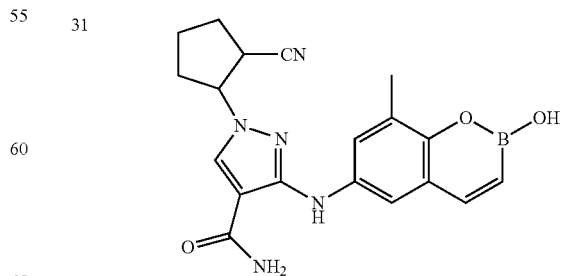 |

| Example Number | Structure |
|---|---|
| 32 | 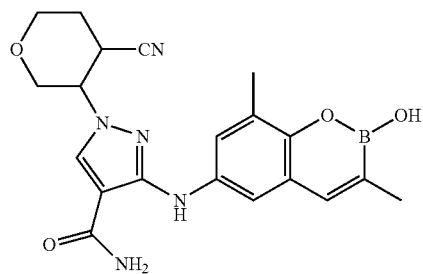 |
| 33 | 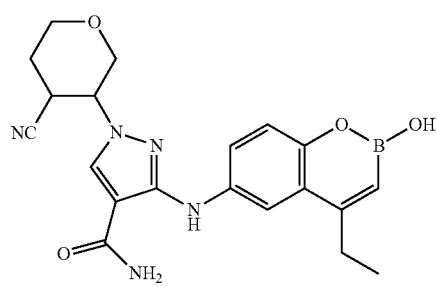 [SMILES: CCC1=CB(O)Oc2ccc(Nc3nn(C4COCCC4C#N)cc3C(N)=O)cc21] |
| 34 | 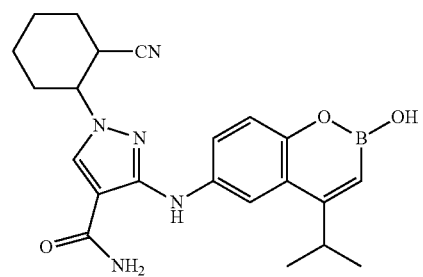 [SMILES: CC(C)C1=CB(O)Oc2ccc(Nc3nn(C4CCCCC4C#N)cc3C(N)=O)cc21] |
| 35 | 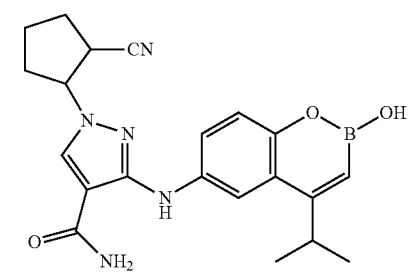 [SMILES: CC(C)C1=CB(O)Oc2ccc(Nc3nn(C4CCCC4C#N)cc3C(N)=O)cc21] |
| 36 | 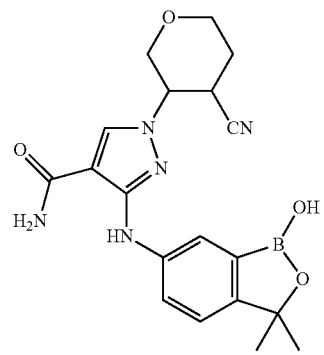 [SMILES: CC1(C)OB(O)c2cc(Nc3nn(C4COCCC4C#N)cc3C(N)=O)ccc21] |
| Example Number | Structure |
|---|---|
| 37 | 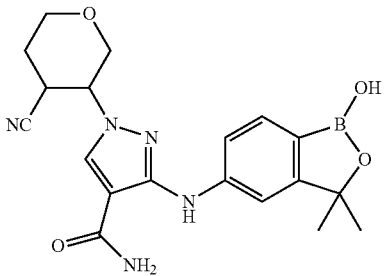 [SMILES: CC1(C)OB(O)c2ccc(Nc3nn(C4COCCC4C#N)cc3C(N)=O)cc21] |
| 38 | 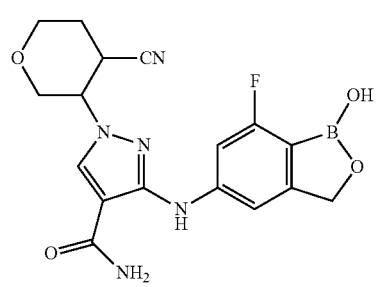 |
| 39 | 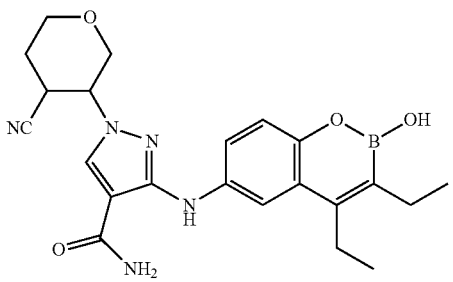 [SMILES: CCC1=C(CC)c2cc(Nc3nn(C4COCCC4C#N)cc3C(N)=O)ccc2OB1O] |
| 40 | 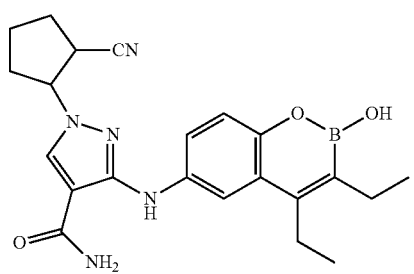 [SMILES: CCC1=C(CC)c2cc(Nc3nn(C4CCCC4C#N)cc3C(N)=O)ccc2OB1O] |
| 41 | 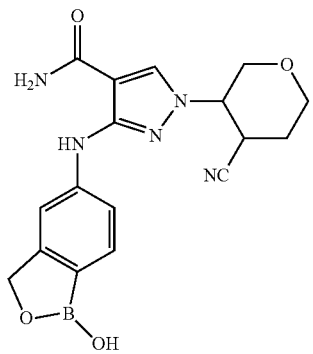 [SMILES: N#CC1CCOCC1n1cc(C(N)=O)c(Nc2ccc3c(c2)COB3O)n1] |

-continued

| Example Number | Structure |
|---|---|
| 42 | (structure) |
| 43 | (structure) |
| 44 | (structure) |
| 45 | (structure) |
| 46 | (structure) |
| 47 | (structure) |
| 48 | (structure) |
| 49 | (structure) |
| 50 | (structure) |
| 51 | (structure) |

| Example Number | Structure |
|---|---|
| 52 | 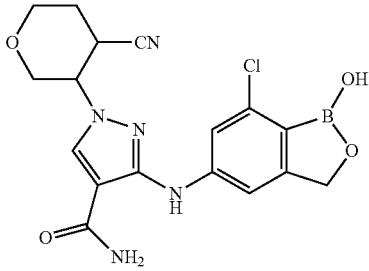 |
| 53 | 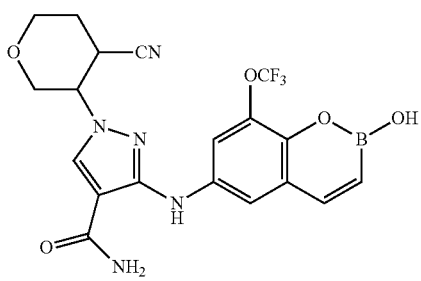 [SMILES: N#CC1CCOCC1n1cc(C(N)=O)c(Nc2cc3c(c(OC(F)(F)F)c2)OB(O)C=C3)n1] |
| 54 | 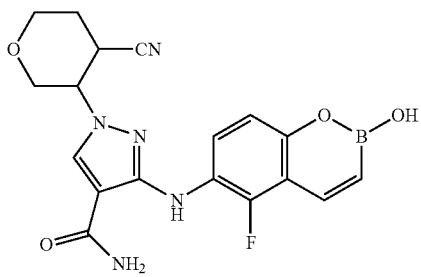 |
| 55 | 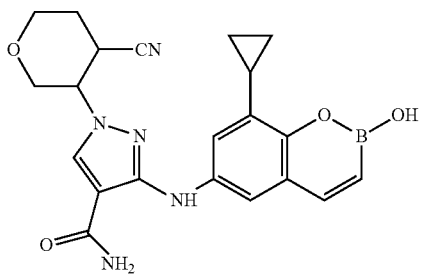 |
| 56 | 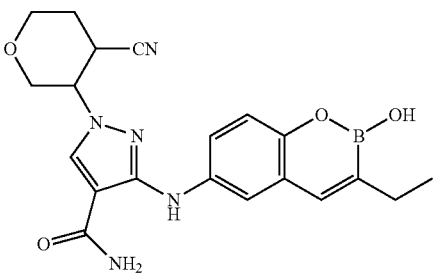 [SMILES: CCC1=Cc2cc(Nc3nn(C4COCCC4C#N)cc3C(N)=O)ccc2OB1O] |

| Example Number | Structure |
|---|---|
| 57 | 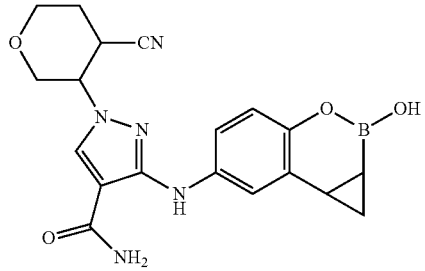 [SMILES: N#CC1CCOCC1n1cc(C(N)=O)c(Nc2ccc3c(c2)C2CC2B(O)O3)n1] |

In one embodiment, the compound according to the invention is selected from the group consisting of Examples 1-57 and has trans relative stereochemistry as represented in formula (IVa) and (IVb):

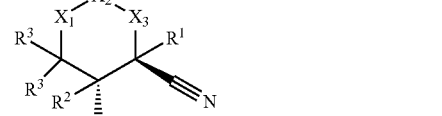
(IVa)

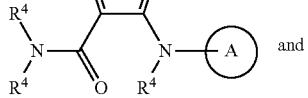 and

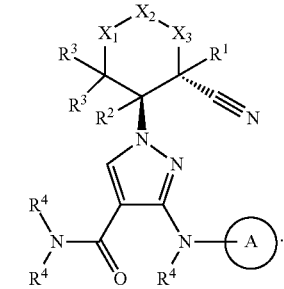
(IVb)

In one embodiment, the compound according to the invention is selected from the group consisting of Examples 1-57 and has trans relative stereochemistry as represented in formula (IVb).

Definitions

Terms used herein will have their customary meaning in the art unless specified otherwise. The organic moieties mentioned in the definitions of the variables of the compound of formula (I), formula II, formula (III), formula (IV), (IVa), and (IVb) are—like the term halogen—collective terms for individual listings of the individual group members. The prefix Cn-Cm (or Cn-m) indicates, in each case, the possible number of carbon atoms in the group.

The term "animal" as used herein includes all mammals, birds and fish and also includes all vertebrate animals. Animals include, but are not limited to, cats, dogs, cattle, chickens, cows, deer, goats, horses, llamas, pigs, sheep and yaks. It also includes an individual animal in all stages of development, including embryonic and fetal stages. In some embodiments, the animal will be a non-human animal.

By the term "enriched" is meant when the weight:weight ratio is at least approximately 1.05 or higher in favor of the enantiomer that displays significant in vitro and in vivo activity (the eutomer).

In one embodiment, the compounds of the instant invention are selective JAK1 inhibitors relative to JAK2. The determination of relative selectivity for a given compound of JAK1 inhibition is defined as the relative ratio of the (JAK2 $IC_{50}$ value/JAK1 $IC_{50}$ value) In one embodiment, for a given compound, the relative ratio of the (JAK2 $IC_{50}$ value/JAK1 $IC_{50}$ value) is at least 2. In yet another embodiment, for a given compound, the relative ratios of the JAK2 $IC_{50}$ value/JAK1 $IC_{50}$ value) is at least 5. In another embodiment, the relative ratios of the JAK2 $IC_{50}$/JAK1 $IC_{50}$ are preferably at least 10 In one embodiment the ratios of the JAK2 $IC_{50}$/JAK1 $IC_{50}$ are greater than 10.

The term "treatment" or "treating" includes alleviating, ameliorating, relieving or otherwise reducing the signs and symptoms associated with a disease or disorder.

"Therapeutically effective amount" means that amount of a drug or pharmaceutical agent that will elicit the biological or medical response of a tissue, a system, animal or human that is being sought by a researcher, veterinarian, medical doctor or other clinician.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, formula II, formula (III), formula (IV), (IVa), and (IVb) or a mixture thereof, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent.

When referring to the compounds disclosed herein, the following terms have the following meanings unless indicated otherwise. The following definitions are meant to clarify, but not limit, the terms defined. If a particular term used herein is not specifically defined, such term should not be considered indefinite. Rather, terms are used within their accepted meanings.

As used herein, "alkyl" refers to monovalent saturated aliphatic hydrocarbon groups having from 1 to 20 carbon atoms, preferably 1-8 carbon atoms, preferably 1-6 carbon atoms. The hydrocarbon chain may be either straight-chained or branched. Illustrative alkyl groups include methyl, ethyl, n-propyl, iso-propyl, n-butyl, iso-butyl, and tert-butyl. Similarly, an "alkenyl" group refers to an alkyl group having one or more double bonds present in the chain, and an "alkynyl" group refers to an alkyl group having one or more triple bonds present in the chain.

As used herein "halogen" or "halo" refers to a halogen. In some embodiments, the halogen is preferably Br, Cl, or F.

As used herein, "haloalkyl" refers to monovalent saturated aliphatic hydrocarbon groups having from 1 to 20 carbon atoms, preferably 1-8 carbon atoms, preferably 1-6 carbon atoms, wherein at least one hydrogen atom is substituted by a halogen, including but not limited to perhalo groups where all hydrogen atoms are replaced with halogen atoms. The haloalkyl chain can be either straight-chained or branched. Illustrative alkyl groups include trifluoromethyl, trifluoroethyl, trifluoropropyl, trifluorobutyl, and pentafluoroethyl. Similarly, a "haloalkenyl" group refers to a haloalkyl group having one or more double bonds present in the chain, and a "haloalkynyl" group refers to a haloalkyl group having one or more triple bonds present in the chain.

Moreover, an "alkylene" linker group refers to a divalent alkyl group, namely $(CH_2)_x$, where x is 1 to 20, preferably 1 to 8, preferably 1 to 6, and more preferably 1 to 3.

As used herein, "hydroxyalkyl" refers to an alkyl group as herein defined substituted with one or more —OH group. Similarly, a "hydroxyalkenyl" group refers to a haloalkyl group having one or more double bonds present in the chain, and a "hydroxyalkynyl" group refers to a haloalkyl group having one or more triple bonds present in the chain.

As used herein, "aryl" refers to a substituted or unsubstituted carbocyclic aromatic ring system, either pendent or fused, such as phenyl, naphthyl, anthracenyl, phenanthryl, tetrahydronaphthyl, indane, or biphenyl. A preferred aryl group is phenyl.

As used herein, "cycloalkyl" refers to an unsaturated or partially saturated hydrocarbon ring, containing from 3 to 15 ring atoms. Illustrative cycloalkyl groups include cyclopropyl, cyclobutyl, cyclopentyl, cyclohexyl, as well as partially saturated versions thereof, such as cyclohexenyl, and cyclohexadienyl. Moreover, bridged rings, such as adamantane, are included within the definition of "cycloalkyl."

As used herein, the term "heterocyclyl" refers to an unsaturated or partially saturated hydrocarbon ring, containing from 3 to 15 ring atoms, wherein one or more carbon atom is replaced with a heteroatom selected from O, N, S, or Si, where each N, S, or Si may be oxidized, and where each N may be quarternized. A heterocyclyl group may be attached to the remainder of the molecule through a heteroatom. Heterocyclyl does not include heteroaryl.

As used herein, the term "heteroaryl" or "heteroaromatic" refers to aromatic ring groups having 5 to 14 ring atoms selected from carbon and at least one (typically 1-4, more typically 1 or 2) heteroatom (e.g., oxygen, nitrogen, sulfur, or silicon). They include monocyclic rings and polycyclic rings in which a monocyclic heteroaromatic ring is fused to one or more other carbocyclic aromatic or heteroaromatic rings. Examples of monocyclic heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), triazolyl (e.g., 2-triazolyl, 5-triazolyl), tetrazolyl (e.g., tetrazolyl) and thienyl (e.g., 2-thienyl, 3-thienyl. Examples of monocyclic six-membered nitrogen-containing heteroaryl groups include pyrimidinyl, pyridinyl and pyridazinyl. Examples of polycyclic aromatic heteroaryl groups include carbazolyl, benzimidazolyl, benzothienyl, benzofuranyl, indolyl, quinolinyl, benzotriazolyl, benzothiazolyl, benzoxazolyl, benzimidazolyl, isoquinolinyl, indolyl, isoindolyl, acridinyl, or benzisoxazolyl.

The terms "arylalkyl," "heteroarylalkyl," and "heterocyclylalkyl" refers to those radicals in which an aryl, heteroaryl, or heterocyclyl group is linked through an alkyl group. Examples includes benzyl, phenethyl, pyridylmethyl, and the like. The terms also include alkyl linking groups in which a carbon atom, for example, a methylene group, has been replaced by, for example, an oxygen atom. Examples include phenoxymethyl, pyrid-2-yloxymethyl, 3-(naphth-1-yloxy)propyl, and the like. Similarly, the term "benzyl" as used herein is a radical in which a phenyl group is attached to a $CH_2$ group, thus, a $CH_2Ph$ group. Benzyl groups may be substituted or unsubstituted. The term substituted benzyl refers to radicals in which the phenyl group or $CH_2$ contains one or more substituents. In one embodiment, the phenyl group may have 1 to 5 substituents, or in another embodiment 2 to 3 substituents.

As used herein "optionally substituted" refers to a substitution of a hydrogen atom, which would otherwise be present for the substituent. When discussing ring systems, the optional substitution is typically with 1, 2, or 3 substituents replacing the normally-present hydrogen. When referencing straight and branched moieties, however, the number of substitutions may be more, occurring wherever hydrogen is present. The substitutions may be the same or different.

Illustrative substituents, which with multiple substituents can be the same or different, include halogen, haloalkyl, R', OR', OH, SH, SR', $NO_2$, CN, C(O)R', C(O)(alkyl substituted with one or more of halogen, haloalkyl, $NH_2$, OH, SH, CN, and $NO_2$), C(O)OR', OC(O)R', CON(R')$_2$, OC(O)N(R')$_2$, $NH_2$, NHR', N(R')$_2$, NHCOR', NHCOH, NHCONH$_2$, NHCONHR', NHCON(R')$_2$, NRCOR', NRCOH, NHCO$_2$H, NHCO$_2$R', NHC(S)NH$_2$, NHC(S)NHR', NHC(S)N(R')$_2$, CO$_2$R', CO$_2$H, CHO, CONH$_2$, CONHR', CON(R')$_2$, S(O)$_2$H, S(O)$_2$R', SO$_2$NH$_2$, S(O)H, S(O)R', SO$_2$NHR', SO$_2$N(R')$_2$, NHS(O)$_2$H, NR'S(O)$_2$H, NHS(O)$_2$R', NR'S(O)$_2$R', Si(R')$_3$, where each of the preceding may be linked through a divalent alkylene linker, $(CH_2)_x$, where x is 1, 2, or 3. In embodiments where a saturated carbon atom is optionally substituted with one or more substituent groups, the substituents may be the same or different and also include =O, =S, =NNHR', =NNH$_2$, =NN(R')$_2$, =N—OR', =N—OH, =NNHCOR', =NNHCOH, =NNHCO$_2$R', =NNHCO$_2$H, =NNHSO$_2$R', =NNHSO$_2$H, =N—CN, =NH, or =NR'. For each of the preceding, each may be linked through an alkylene linker, $(CH_2)_x$, where x is 1, 2, or 3, Each occurrence of R' is the same or different and, in some embodiments, represents hydrogen, alkyl, alkenyl, alkynyl, cycloalkyl, aryl, heterocyclyl, or heteroaryl, or, in some embodiments, when two R' are each attached to a nitrogen atom, they may form a saturated or unsaturated heterocyclic ring containing from 4 to 6 ring atoms.

As used herein, the phrase veterinary or veterinarily, or pharmaceutical or pharmaceutically acceptable salt refers to any salt of a compound disclosed herein which retains its biological properties and which is not toxic or otherwise undesirable for veterinary or pharmaceutical use. The general use of the terms pharmaceutical or pharmaceutically is intended to reach either veterinary or veterinarily, as well. The terms may be used interchangeably as context allows.

Such salts may be derived from a variety of organic and inorganic counter-ions known in the art. Such salts include acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid, and like acids.

Salts further include, by way of example only, salts of non-toxic organic or inorganic acids, such as halides, such as, chloride and bromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like.

Examples of inorganic bases that may be used to form base addition salts include, but are not limited to, metal hydroxides, such as lithium hydroxide, sodium hydroxide, and potassium hydroxide; metal amides, such as lithium amide and sodium amide; metal carbonates, such as lithium carbonate, sodium carbonate, and potassium carbonate; and ammonium bases such as ammonium hydroxide and ammonium carbonate.

Examples of organic bases that may be used to form base addition salts include, but are not limited to, metal alkoxides, such as lithium, sodium, and potassium alkoxides including lithium methoxide, sodium methoxide, potassium methoxide, lithium ethoxide, sodium ethoxide, potassium ethoxide, and potassium tert-butoxide; quaternary ammonium hydroxides, such as choline hydroxide; and amines including, but not limited to, aliphatic amines (i.e., alkylamines, alkenylamines, alkynylamines, and alicyclic amines), heterocyclic amines, arylamines, heteroarylamines, basic amino acids, amino sugars, and polyamines.

The base may be a quaternary ammonium hydroxide, wherein one or more of the alkyl groups of the quaternary ammonium ion are optionally substituted with one or more suitable substituents. Preferably, at least one alkyl group is substituted with one or more hydroxyl groups. Non-limiting examples of quaternary ammonium hydroxides that may be used in accordance with the present invention include choline hydroxide, trimethylethylammonium hydroxide, tetramethylammonium hydroxide, and is preferably choline hydroxide. An alkylamine base may be substituted or unsubstituted. Non-limiting examples of unsubstituted alkylamine bases that may be used in accordance with the present invention include methylamine, ethylamine, diethylamine, and triethylamine. A substituted alkylamine base may be substituted with one or more hydroxyl groups, and preferably one to three hydroxyl groups. Non-limiting examples of substituted alkylamine bases that may be used in accordance with the present invention include 2-(diethylamino)ethanol, N,N-dimethylethanolamine (deanol), tromethamine, ethanolamine, and diolamine.

Stereoisomers and Polymorphic Forms

In certain cases, the depicted substituents may contribute to optical isomers and/or stereoisomerism. Compounds having the same molecular formula but differing in the nature or sequence of bonding of their atoms or in the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers". When a compound has an asymmetric center, for example when it is bonded to four different groups, a pair of enantiomers is possible. A molecule with at least one stereocenter may be characterized by the absolute configuration of its asymmetric center and is designated (R) or (S) according to the rules of Cahn and Prelog (Cahn et al., 1966, *Angew. Chem.* 78: 413-447, *Angew. Chem., Int. Ed. Engl.* 5: 385-414 (errata: *Angew. Chem., Int. Ed. Engl.* 5:511); Prelog and Helmchen, 1982, *Angew. Chem.* 94: 614-631, *Angew. Chem. Internal. Ed. Eng.* 21: 567-583; Mata and Lobo, 1993, *Tetrahedron: Asymmetry* 4: 657-668) or may be characterized by the manner in which the molecule rotates the plane of polarized light and is designated dextrorotatory or levorotatory (namely, as (+)- or (−)-isomers, respectively). A chiral compound may exist as either an individual enantiomer or as a mixture thereof. A mixture containing equal proportions of enantiomers is called a "racemic mixture".

In certain embodiments, the compounds disclosed herein may possess one or more asymmetric centers, and such compounds may therefore be produced as a racemic mixture, an enantiomerically enriched mixture, or as an individual enantiomer. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art.

In certain embodiments, the compounds disclosed herein are "stereochemically pure". A stereochemically pure compound has a level of stereochemical purity that would be recognized as "pure" by those of skill in the art. Of course, this level of purity may be less than 100%. In certain embodiments, "stereochemically pure" designates a compound that is substantially free, i.e. at least about 85% or more, of alternate isomers. In particular embodiments, the compound is at least about 85%, about 90%, about 91%, about 92%, about 93%, about 94%, about 95%, about 96%, about 97%, about 98%, about 99%, about 99.5% or about 99.9% free of other isomers.

In addition, the compounds disclosed herein ('active agents') may exist as hydrates or solvates, in which a certain stoichiometric amount of water or a solvent is associated with the molecule in the crystalline form. The compositions of the invention may include hydrates and solvates of the active agents. In some embodiments, the compositions of the invention may include up to 15% (w/w), up to 20% (w/w), or up to 30% (w/w) of a particular solid form.

As used herein, the terms "subject" and "patient" may be used interchangeably herein. In one embodiment, the subject is a human. In one embodiment, the subject is a companion animal such as a dog or cat. In a further embodiment, the subject is an animal such as a sheep, cow, horse, goat, fish, pig, or domestic fowl (e.g., chicken, turkey, duck, or goose). In another embodiment, the subject is a primate such as a monkey such as a cynomolgous monkey or a chimpanzee.

In addition, a pharmaceutically acceptable prodrug of the compound represented by the formula (I), formula (II), and formula (III) is also included in the present invention. The pharmaceutically acceptable prodrug refers to a compound having a group which may be converted into an amino group, a hydroxyl group, a carboxyl group, or the like, by solvolysis or under a physiological condition. Examples of the groups forming the prodrug include those as described in Prog. Med., 5, 2157-2161 (1985) or "Pharmaceutical Research and Development" (Hirokawa Publishing Company, 1990), vol. 7, Drug Design, 163-198. The term prodrug is used throughout the specification to describe any pharmaceutically acceptable form of a compound which, upon administration to a patient, provides the active compound. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that may be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound.

The present invention includes all pharmaceutically acceptable isotopically-labelled compounds of the invention wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labelled compounds of the invention, such as those incorporating a radioactive isotope, may be useful in drug or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, may be useful in Positron Emission Topography (PET) studies for examining substrate receptor occupancy. Isotopically-labeled compounds of the invention may generally be prepared by conventional techniques known to those skilled in the art or by processes analogous to those described in the accompanying Examples using an appropriate isotopically-labeled reagent in place of the non-labeled reagent previously employed. In one aspect, the invention provides a process for preparing a compound of any embodiment of formula (I), formula (II), formula (III), formula (IV), formula (IVa) and formula (IVb) as described herein.

Compositions and Methods of Administration

The compounds of formula (I), formula (II), formula (III), formula (IV), formula (IVa) and formula (IVb) used in the methods disclosed herein may be administered in certain embodiments using veterinary or pharmaceutical compositions including at least one compound of formula (I), formula (II), formula (IV), formula (IVa) and formula (IVb), if appropriate in the salt form, either used alone or in the form of a combination with one or more compatible and veterinary or pharmaceutically acceptable carriers, such as diluents or adjuvants, or with another agent. There are provided compositions which comprise a derivative of a compound of formula (I), formula (II), formula (III), formula (IV), formula (IVa) and formula (IVb) or a salt thereof, and an acceptable excipient, carrier or diluent. The composition may also be in a variety of forms which include, but are not limited to, oral formulations, injectable formulations, and topical, dermal or subdermal formulations. The particular route selected by the practitioner depends upon factors such as the physicochemical properties of the pharmaceutical or therapeutic agent, the condition of the host and economics.

In one aspect, the invention provides for a method for treating a patient having a disease or disorder susceptible to modulation of JAK comprising administering a therapeutically effective amount of a compound as described herein, including any embodiment of a compound according formula (I), (II), (III), (IV), (IVa), or (IVb).

In one embodiment, the invention provides a method of treating a patient having a disease or disorder that can be ameliorated by the selective inhibition of a Janus kinase JAK 1 relative to JAK 2.

In one embodiment, the invention provides for a method of treating a patient having a disease or disorder with a therapeutically effective amount of a compound which is an embodiment of formula (I), formula (II), formula (III), formula (IV), formula (IVa) and formula (IVb), wherein the disease or disorder is one or more of atopic dermatitis, flea allergy dermatitis, eczema, pruritus, psoriasis, psoriatic arthritis, Bechet's disease, *Pityriasis rubra* pilaris, alopecia areata, discoid lupus erythematosus, vitiligo, palmoplantar pustulosis, mucocutaneous disease erythema multiforme, mycosis fungoides, graft-versus-host disease, cutaneous lupus, rheumatoid arthritis (RA), arthritis, ulcerative colitis, Crohn's disease, inflammatory bowel disease (IBD), transplant rejection, systemic lupus erythematosus (SLE), dermatomyositis, Sjogren's syndrome, dry eye disease, secondary hypereosinophilic syndrome (HES), allergy, allergic dermatitis, asthma, vasculitis, multiple sclerosis, diabetic nephropathy, cardiovascular disease, artherosclerosis, and cancer.

In one embodiment, the invention provides a method of treating a patient as described above, wherein the disease or disorder is one or more of atopic dermatitis, flea allergy dermatitis psoriasis, and rheumatoid arthritis.

According to one embodiment, the invention provides for a method of treating a patient having a disease or disorder susceptible to modulating of JAK and comprising administering an amount of a compound according to the invention in an amount to perturb an immune regulatory pathway in a cell. In one such embodiment, the perturbation results in an effect on the JAK-STAT pathway.

In one aspect, the invention provides a method of inhibiting JAK in a mammalian cell comprising contacting the mammalian cell with a compound according to any embodiment of formula (I), (II), and (III), (IV), (IVa), or (IVb). In certain embodiments, the mammalian cell is a cell from a subject having an inflammatory condition.

In one aspect, the invention provides for a composition comprising a compound according to any embodiment of formula (I), formula (II), formula (III), formula (IV), formula (IVa) and formula (IVb) and a pharmaceutically or veterinary acceptable carrier.

The composition may be in a form suitable for oral use, for example, as dietary supplements, troches, lozenges, chewables, tablets, hard or soft capsules, emulsions, aqueous or oily suspensions, aqueous or oily solutions, dispersible powders or granules, syrups, or elixirs. Compositions intended for oral use may be prepared according to any method known in the art for the manufacture of veterinary or pharmaceutical compositions and such compositions may contain one or more agents selected from the group consisting of sweetening agents, bittering agents, flavoring agents, coloring agents and preserving agents in order to provide elegant and palatable preparations. In certain cases, it is convenient and efficient to administer veterinary medicines orally by placing the therapeutic agent in a solid or liquid matrix that is suitable for oral delivery. These methods include chewable drug-delivery formulations. The problem associated with administering oral formulations to animals is that the therapeutic agent often provides an unpleasant taste, aroma, or texture, which causes the animals to reject the composition. This is further exacerbated by compositions that are hard and difficult to swallow.

Oral veterinary compositions in the form of soft chewable compositions ("soft chews"), or chewable tablets that are palatable are usually convenient to administer to certain animals, particularly cats and dogs, and may be used effectively to dose veterinary medicine to these animals. However, many oral compositions comprising active agents with a bitter or unpleasant taste are not well accepted by cats and dogs. Furthermore, when the bioavailability of an active agent from an oral dosage form is not sufficient or is variable, the required exposure of the animal to the active ingredient may not be sufficient to provide the desired efficacy. Problems such as these often lead to low or suboptimal efficacy and control of parasites.

Chewable dosage forms for drug delivery are well known to pharmaceutical technology. It is known in the pharmaceutical industry that the act of chewing increases the surface area of the available active ingredient and may increase the rate of absorption by the digestive tract. Chewable systems are also advantageous where it is desirable to make an active ingredient available topically to the mouth or throat areas for both local effects and/or systemic absorption. Further, chewable dosage forms are also utilized to ease drug administration in pediatric and geriatric patients. Examples of chewable dosage forms may be found in U.S. Pat. Nos. 6,387,381; 4,284,652; 4,327,076; 4,935,243; 6,270,790; 6,060,078; 4,609,543; and, 5,753,255, all incorporated herein by reference.

Palatability and "mouth feel" are important characteristics to be considered in providing a dosage form, or matrix, for an active pharmaceutical or medicinal. Unfortunately, many pharmaceuticals and other active ingredients have a bitter or otherwise unpalatable taste, or an unacceptable mouth feel, due to the grittiness or chalkiness of the compound, or both. These characteristics make it difficult to incorporate such active ingredients into the current state of the art for chewable dosage forms because the objectionable taste and/or mouth feel make it less likely to obtain compliance by the user. Oral veterinary dosage forms that are not palatable to the animal treated result in low acceptance of the medicament by the animal and a low level of compliance. Thus, there is a need for improved oral veterinary dosage forms that are palatable and well accepted by the treated animal.

Another challenge with oral veterinary compositions, particularly soft chewable compositions, is that the release and dissolution of the active agent from the composition after it is ingested by the animal can be variable and incomplete. This leads to variability in the amount of the drug that is absorbed from the digestive tract of the animal.

U.S. Pat. No. 7,955,632 (incorporated herein by reference) describes palatable, edible soft chewable medication vehicles for the delivery of pharmaceutically acceptable active ingredients to an animal and processes of making the same.

Furthermore, US 2004/0037869 A1, US 2004/0151759 A1, WO 2005/062782 and WO 2004/016252 to Cleverly et al. (incorporated herein by reference) describe chewable veterinary formulations and tablets that contain at least one pharmaceutical active agent, and WO 2009/02451A2 and US 2011/0059988 to Heckeroth et al. describe various compositions for oral administration to animals (all incorporated herein by reference).

Traditionally, in veterinary formulations, palatability had been achieved by the inclusion of animal byproducts or flavors derived from animal sources into the formulation. For example, it is customary to include excipients, such as chicken powder, liver powder, beef, ham, fish, or rawhide-derived products in dog chews to make the chew attractive and palatable to the dog. See, e.g., U.S. Pat. Nos. 6,086,940; 6,093,441; 6,159,516; 6,110,521; 5,827,565; 6,093,427, all to Axelrod et al. (all incorporated herein by reference).

Exceptionally palatable soft chewable oral veterinary compositions that provide high bioavailability of active agent are described in U.S. Pat. Nos. 9,259,417; 9,233,100; 9,931,320; 10,596,156; all to Soll et al. (all incorporated herein by reference).

Lozenges are solid compositions containing one or more active ingredients intended to dissolve or disintegrate slowly in the oral cavity by passive incubation in the oral cavity, or actively by sucking or chewing. They may be used for systemic effect if the drug is absorbed through the buccal or esophageal lining or is swallowed. In particular, soft lozenges may be chewed or allowed to dissolve slowly in the mouth. These dosage forms have the advantage of being flavored and thus easy to administer to both human and animal patients; have formulas that are easy to change and may be patient specific; may deliver accurate amounts of the active ingredient to the oral cavity and digestive system; and allow for the drug to remain in contact with the oral or esophageal cavity for an extended period of time.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example, peanut oil, liquid paraffin, or olive oil.

The compositions may also be in the form of oil-in-water or water-in-oil emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and preservatives.

In one embodiment of the formulation, the composition is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids. Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously. In one embodiment of the oily phase, the oily phase may be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example, $C_8$-$C_{10}$ caprylic/capric triglyceride. In another embodiment, the oily phase will represent a % v/v range selected from the group consisting of about 2 to about 15%; about 7 to about 10%; and about 8 to about 9% v/v of the microemulsion. The aqueous phase includes, for example, water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion. Surfactants for the microemulsion include diethylene glycol monoethyl ether, dipropylene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol. Some compounds are common to the three components discussed above, for example, aqueous phase, surfactant and cosurfactant. However, it is well within the skill level of the practitioner to use different compounds for each component of the same formulation. In one embodiment, for example, for the amount of surfactant/cosurfactant, the cosurfactant to surfactant ratio may be from about 1/10 to about 1/2. In another embodiment for the amount of cosurfactant, there will be from about 25 to about 75% v/v of surfactant and from about 10 to about 55% v/v of cosurfactant in the microemulsion.

Oily suspensions may be formulated by suspending the active ingredient in a vegetable oil, for example, atachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an antioxidant such as ascorbic acid, or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxypropylmethylcellulose, sodium alginate, polvinylpyrrolidone, gum tragacanth and gum acacia; dispersing or wetting agents may be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example, polyethylene sorbitan monooleate. The aqueous suspensions may also contain one or more preservatives, for example, ethyl, or n-propyl, p-hydroxybenzoate, one or more coloring agents, one or more flavoring agents, and one or more sweetening agents and/or bittering agents, such as those set forth herein.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and coloring agent(s).

The compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. Preservatives, such as phenol or benzyl alcohol, may be used.

In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

Topical, dermal and subdermal formulations may include emulsions, creams, ointments, gels or pastes.

Organic solvents that may be used in the invention include but are not limited to: acetyltributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol and diethyl phthalate, or a mixture of at least two of these solvents.

As vehicle or diluent, compositions of the present invention may include plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$-$C_{12}$) triglycerides.

Dosage forms may contain from about 0.5 mg to about 5 g of an active agent.

In one embodiment of the invention, the active agent is present in the formulation at a concentration of about 0.05 to 10% weight/volume.

A compound of formula (I), formula (II), formula (III), formula (IV), formula (IVa) and formula (IVb) may be employed as such or in the form of their preparations or formulations as combinations.

A compound of formula (I), formula (II), formula (III), formula (IV), formula (IVa) and formula (IVb) according to the invention may be combined with one or more agents having the same sphere of activity, for example, to increase activity, or with substances having another sphere of activity, for example, to broaden the range of activity. As an example, a combination of a compound of formula (I) (or of a compound of formula (I), formula (II), formula (IV), formula (IVa) and formula (IVb)) with one or more of an additional JAK inhibitor or a JAK/Signal Transducer and Activator of Transcription (JAK/STAT) modulator may offer therapeutic advantage. Examples of JAK inhibitors that may be useful as combination agents include Baricitinib, Ruxolitinib, Filgotinib, CYT387, Upadacitinib, Fedratinib, Peficitinib, Lestaurtinib, Pacritinib, Oclacitinib, Cerdulatinib, and Tofacitinib.

The compounds of formula (I), formula (II) or formula (III) according to the invention may be combined with one or more additional active agents. Further additional active agents which may be used in the methods provided herein in combination with a compound of formula (I), (II) or (III) include, but are not limited to, disease-modifying anti-rheumatic drugs (DMARDs such as cyclosporine A and methotrexate), anti-inflammatory agents such as nonsteroidal anti-inflammatory drugs (NSAIDs), immunosuppressants, mycophenolate mofetil, biologic agents, TNF-α inhibitors (such as etanercept), Cox-2 inhibitors (such as firocoxib), and analgesics. These agents may include but are not limited to cyclosporin A, e.g. Sandimmune® or Neoral®, rapamycin, FK-506 (tacrolimus), leflunomide, deoxyspergualin, mycophenolate, e.g., Cellcept®, azathioprine, e.g. Imuran®, daclizumab, e.g. Zenapax®, OKT3, e.g. Orthocolone®, AtGam, aspirin, acetaminophen, ibuprofen, naproxen, piroxicam, and anti-inflammatory steroids, e.g. prednisolone or dexamethasone.

In some embodiments, the second active agents may include, but are not limited to, anti-inflammatories such as NSAIDs including, but not limited to, diclofenac (e.g., ARTHROTEC®), diflunisal (e.g., DOLOBID®), etodolac (e.g., LODINE®), fenoprofen (e.g., NALFON®), ibuprofen (e.g., ADVIL®, CHILDREN'S ADVIL/MOTRIN®, MEDIPREN®, MOTRIN®, NUPRIN®, or PEDIACARE FEVER®), indomethacin (e.g., ARTHREXIN®), ketoprofen (e.g., ORUVAIL®), ketorolac (e.g., TORADOL®), fosfomycin tromethamine (e.g., MONURAL®), meclofenamate (e.g., MECLOMEN®), nabumetone (e.g., RELAFEN®), naproxen (e.g., ANAPROX®, ANAPROX® DS, EC-NAPROSYN®, NAPRELAN® or NAPROSYN®), oxaprozin (e.g., DAY PRO®), piroxicam (e.g., FELDENE®), sulindac (e.g., CLINORIL®), and tolmetin (e.g., TOLECTIN® DS or TOLECTIN®).

In other embodiments, the second active agents may include, but are not limited to, disease-modifying antirheumatic drugs (e.g., DMARDs) or immnunosuppressants such as, but not limited to, methotrexate (e.g., RHEUMA- TREX®), sulfasalazine (e.g., AZULFIDINE®), and cyclosporine (e.g., SANDIMMUNE® or NEROAL®; and including cyclosporine A).

In other embodiments, the second active agents may include, but are not limited to, mycophenolate mofetil (e.g., CellCept®), an immunosuppressive agent widely used in organ transplantation and gaining favor in treating autoimmune and inflammatory skin disorders.

In further embodiments, the second active agents may include, but are not limited to, biologic agents such as etanercept (e.g., ENBREL®), infliximab (e.g., REMICADE®) and adalimumab (e.g., HUMIRA®).

In further embodiments of interest, the second active agents may include, but are not limited to Cox-2 inhibitors such as celecoxib (e.g., CELEBREX®), firocoxib (e.g. PREVICOX®), valdecoxib (e.g., BEXTRA®) and meloxicam (e.g., MOBIC®, METACAM®).

In further embodiments, the second active agents may include veterinary therapeutic agents that are well-known in the art (see e.g. Plumb's Veterinary Drug Handbook, 5th Edition, ed. Donald C. Plumb, Blackwell Publishing, (2005) or The Merck Veterinary Manual, 9th Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide, clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium. calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, *Propionibacterium acnes* injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/l-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, and zonisamide and mixtures thereof.

These one or more additional active agents may be administered as part of the same or separate dosage forms, via the same or different routes of administration, and on the same or different administration schedules according to standard pharmaceutical practice known to one skilled in the art.

The pharmaceutical preparation comprising the compounds of formula (I), (II), (III), (IVa), (IVb), and (IV) for delivery to a human or other mammal, is preferably in unit dosage form, in which the preparation is subdivided into unit doses containing an appropriate quantity of the active component. The unit dosage form may be a packaged preparation containing discrete quantities of the preparation, such as packaged tablets, capsules, and powders in vials or ampoules. Also, the unit dosage form may be a capsule, tablet or lozenge itself, or it may be an appropriate number of any of these in packaged form.

The quantity of active component in a unit dose preparation may be varied or adjusted from about 0.1 mg to about 1000 mg, according to the particular application and the potency of the active component. The composition may, if desired, also contain other compatible therapeutic agents.

In therapeutic use for the treatment or alleviation of inflammation, auto-immune diseases, and cancer in a human or other mammal, the compounds utilized in the method of treatment are administered at an initial dosage of about 0.1 mg/kg to about 100 mg/kg per interval, about 0.1 mg/kg to about 50.0 mg/kg per interval, about 0.1 mg/kg to about 10.0 mg/kg per interval, about 0.1 mg/kg to about 5.0 mg/kg per interval, about 0.1 mg/kg to about 2.5 mg/kg per interval, about 0.1 mg/kg to about 2.0 mg/kg per interval, about 0.1 mg/kg to about 1.0 mg/kg per interval, about 0.4 mg/kg to about 1.0 mg/kg per interval, or about 0.4 mg/kg to about 0.6 mg/kg per interval. Preferred intervals may be daily, weekly, monthly, quarterly, semi-annually, or annually. The dosages may be varied depending on the requirements of the patient, for example, the size of the human or mammal being treated, the severity of the condition being treated, the route of administration, and the potency of the compound(s) being used. Determination of the proper dosage and route of administration for a particular situation is within the skill of the practitioner. Generally, the treatment will be initiated with smaller dosages, which are less than the optimum dose of the compound, which may be increased in small increments until the optimum effect under the particular circumstances of the condition is reached. For convenience, the total daily dosage may be divided and administered in portions during the day if desired.

In therapeutic use, the compounds of formula (I), (II), (III), (IVa), (IVb), and (IV) are useful in manufacture of a medicament for a method of the treating any indication where inhibition of JAK would be desirable, including but not limited to cancer, neuroinflammation, inflammatory airway diseases, ankylosing spondylitis, inflammatory bowel diseases, rheumatoid arthritis, psoriasis, and atopic dermatitis. In one or more embodiments, one or more of a compound of formula (I), (II), (III), (IVa), (IVb), and (IV) is useful in the treatment of one or more of atopic dermatitis, psoriasis, psoriatic arthritis, Bechet's disease, *Pityriasis rubra* pilaris, alopecia areata, discoid lupus erythematosus, vitiligo, palmoplantar pustulosis, mucocutaneous disease erythema multiforme, mycosis fungoides, graft-versus-host disease, cutaneous lupus, rheumatoid arthritis (RA), arthritis, ulcerative colitis, Crohn's disease, inflammatory bowel disease (IBD), transplant rejection, systemic lupus erythematosus (SLE), dermatomyositis, Sjogren's syndrome, dry eye disease, secondary hypereosinophilic syndrome (HES), allergy, asthma, vasculitis, multiple sclerosis, diabetic nephropathy, cardiovascular disease, artherosclerosis, and cancer. One route of administration may be oral. One route of administration may be topical.

In one aspect, the invention of the present disclosure provides for a method of treating one or more diseases or disorders of inflammation, auto-immune dysfunction, and cancer comprising administering to a subject in need thereof an effective amount of a compound that is an embodiment herein of formula (I), (II), (III), (IV), (IVa) or (IVb).

In one embodiment, the invention of the present disclosure provides a method of treating atopic dermatitis, flea allergy dermatitis, psoriasis, or rheumatoid arthritis comprising administering to a subject in need thereof an effective amount of a compound that is an embodiment of formula (I), (II), (III), (IV), (IVa) or (IVb). In one embodiment, the compound is administered orally; in one embodiment, the compound is administered parenterally; in one embodiment, the compound is administered topically.

In one embodiment, the invention of the present disclosure provides for a method for treating one or more diseases or disorders of inflammation, auto-immune dysfunction, and cancer comprising administering to a subject in need thereof an effective amount of a compound according to any embodiment herein of formula (I), (II), (III), (IV), (IVa) or (IVb) wherein the subject is a mammal.

In one embodiment, the invention of the present disclosure provides for method for treating one or more diseases or disorders of inflammation, auto-immune dysfunction, and cancer comprising administering to a subject in need thereof an effective amount of a compound according to any embodiment herein of formula (I), (II), (III), (IV), (IVa) or (IVb) wherein the subject is selected from one or more of livestock mammals, domestic mammals, and companion animals. In one embodiment, the mammal is one or more of humans, cattle, sheep, goats, llamas, alpacas, pigs, horses, donkeys, dogs, and cats. In one embodiment, the mammal is a human, a dog, or a cat.

In one aspect, the invention of the present disclosure provides a compound for use in medicine, wherein the compound is an embodiment of formula (I), (II), (III), (IV), (IVa), or (IVb) herein.

In another aspect, the invention of the present disclosure provides for use of a compound according to any embodiment herein of any of formula (I), (II) (III), (IV), (IVa), and (IVb) for the manufacture of a medicament for the treatment of one or more diseases or disorder of inflammation, auto-immune dysfunction, and cancer.

In one embodiment, the invention of the present disclosure provides for use of a compound according to any embodiment herein of formula (I), (II), (III) (IV), (IVa), or (IVb) for the manufacture of a medicament for the treatment of a disease or disorder that can be ameliorated by the selective inhibition of a Janus kinase JAK 1 relative to JAK 2. In one embodiment, the disease or disorder is atopic dermatitis, flea allergy dermatitis, psoriasis, or rheumatoid arthritis.

In one aspect, the invention provides for use of a compound according to an embodiment of formula (I), (II), (III), (IV), (IVa) or (IVb) herein and a second active agent in the manufacture of a medicament for the treatment of a disease or a disorder that can be ameliorated by the selective inhibition of a Janus kinase JAK 1 relative to JAK 2.

In one aspect, the invention provides for use of a compound according to an embodiment of formula (I), (II), and (III), (IV), (IVa), or (IVb) herein for the treatment of one or more diseases or disorders of inflammation, auto-immune dysfunction, and cancer. In one embodiment, the disease or disorder is atopic dermatitis, flea allergy dermatitis, psoriasis, or rheumatoid arthritis.

The present invention explicitly encompasses compounds described herein, including salt forms thereof, and salt forms thereof. The present invention also encompasses those compounds presented herein, including stereoisomers thereof. The compounds encompassed by the present invention include, in some embodiments, compounds selected from Compound Lists 1 and 2 as described herein.

Compound List 1

| Structure | IUPAC Name |
|---|---|
| $C_{17}H_{18}BN_5O_4$<br>Example 16 herein | 1-(trans-4-cyanotetrahydro-2H-pyran-3-yl)-3-((1-hydroxy-1,3-dihydrobenzo[c][1,2]oxaborol-6-yl)amino)-1H-pyrazole-4-carboxamide |
| $C_{17}H_{18}BN_5O_4$<br>Example 41 herein | 1-(trans-4-cyanotetrahydro-2H-pyran-3-yl)-3-((1-hydroxy-1,3-dihydrobenzo[c][1,2]oxaborol-5-yl)amino)-1H-pyrazole-4-carboxamide |

-continued

| Structure | IUPAC Name |
|---|---|
| C₁₇H₁₇BFN₅O₄<br>Example 1 herein | 1-(trans-4-cyanotetrahydro-2H-pyran-3-yl)-3-((4-fluoro-1-hydroxy-1,3-dihydrobenzo[c][1,2]oxaborol-6-yl)amino)-1H-pyrazole-4-carboxamide |
| C₁₈H₁₈BFN₅O₄<br>Example 51 herein | 1-(trans-4-cyanotetrahydro-2H-pyran-3-yl)-3-((2-hydroxy-2H-benzo[e][1,2]oxaborinin-6-yl)amino)-1H-pyrazole-4-carboxamide |
| C₁₈H₁₈BN₅O₄<br>Example 2 herein | 1-(trans-4-cyanotetrahydro-2H-pyran-3-yl)-3-((2-hydroxy-2H-benzo[e][1,2]oxaborinin-7-yl)amino)-1H-pyrazole-4-carboxamide |

| Structure | IUPAC Name |
|---|---|
| C₁₉H₂₀BN₅O₄<br>Example 3 herein | 1-(trans-4-cyanotetrahydro-2H-pyran-3-yl)-3-((2-hydroxy-4-methyl-2H-benzo[e][1,2]oxaborinin-6-yl)amino)-1H-pyrazole-4-carboxamide |
| C₁₇H₁₇BClN₅O₄<br>Example 52 herein | 3-((7-chloro-1-hydroxy-1,3-dihydrobenzo[e][1,2]oxaborol-5-yl)amino)-1-(trans-4-cyanotetrahydro-2H-pyran-3-yl)-1H-pyrazole-4-carboxamide |
| C₂₀H₂₂BN₅O₄<br>Example 4 herein | 1-(trans-4-cyanotetrahydro-2H-pyran-3-yl)-3-((2-hydroxy-3,4-dimethyl-2H-benzo[c][1,2]oxaborinin-6-yl)amino)-1H-pyrazole-4-carboxamide |

| Structure | IUPAC Name |
|---|---|
| C₁₉H₂₀BN₅O₄<br>Example 5 herein | 1-(trans-4-cyanotetrahydro-2H-pyran-3-yl)-3-((2-hydroxy-3-methyl-2H-benzo[e][1,2]oxaborinin-6-yl)amino)-1H-pyrazole-4-carboxamide |
| C₁₈H₂₀BN₅O₄<br>Example 6 herein | 1-(trans-4-cyanotetrahydro-2H-pyran-3-yl)-3-((1-hydroxy-7-methyl-1,3-dihydrobenzo[c][1,2]oxaborol-5-yl)amino)-1H-pyrazole-4-carboxamide |
| C₁₈H₂₀BN₅O₄<br>Example 42 herein | 1-(trans-4-cyanotetrahydro-2H-pyran-3-yl)-3-((1-hydroxy-3,4-dihydro-1H-benzo[c][1,2]oxaborinin-7-yl)amino)-1H-pyrazole-4-carboxamide |

-continued

| Structure | IUPAC Name |
|---|---|
| 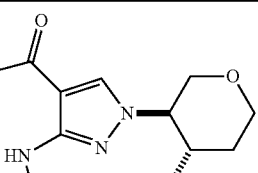<br>$C_{18}H_{20}BN_5O_4$<br>Example 7 herein | 1-(trans-4-cyanotetrahydro-2H-pyran-3-yl)-3-((1-hydroxy-3,4-dihydro-1H-benzo[c][1,2]oxaborinin-6-yl)amino)-1H-pyrazole-4-carboxamide |

Compound List 2

Example 43 herein

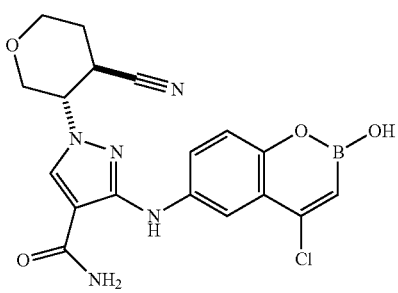

Prophetic Example

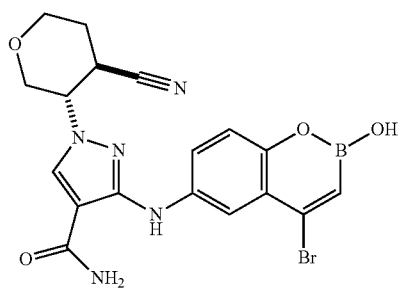

Prophetic Example

Example 38 herein

A composition comprising a therapeutically acceptable amount of any of the compounds described herein is within the scope of the invention. The composition may further comprise a pharmaceutically or veterinary acceptable excipient, diluent, carrier, or mixture thereof. Such a composition may be administered to a subject in need thereof to treat or control a disease or disorder mediated, in whole or in part, directly or indirectly, by JAK. The composition may further comprise an additional active agent, as described herein.

EXAMPLES

Experimental Procedures

The following examples provide a more detailed description of the process conditions for preparing compounds of the present invention. It is to be understood, however, that the invention, as fully described herein and as recited in the claims, is not intended to be limited by the details of the following schemes or modes of preparation.

Certain abbreviations may be used in describing the examples of the present disclosure. The abbreviations are believed to be used consistently within commonly accepted use of those skilled in the art.

Chemistry Examples

In the following schemes, general substituent groups are represented with assignments that may not align with the formulae of the present disclosure. The following schemes provide a key for such substituent groups that should be followed for the schemes and not applied to the formulae of the present disclosure.

Synthetic Examples

Following the general and specific synthetic teaching of the present disclosure, the compounds listed have been synthesized and characterized as set forth herein:

Preparation of Intermediate A

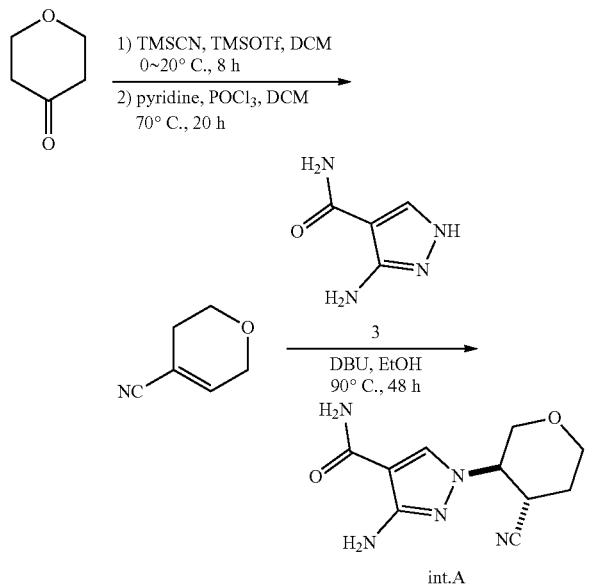

Preparation of 3,6-dihydro-2H-pyran-4-carbonitrile

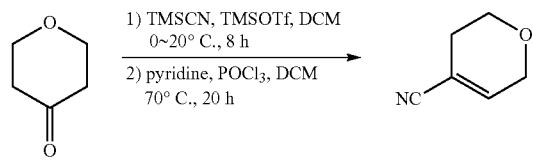 [SMILES: O=C1CCOCC1 ; N#CC1=CCOCC1]

To a mixture of TMSCN (142 g, 1.44 mol, 180 mL, 1.2 eq) in DCM (600 mL) was added tetrahydropyran-4-one (120 g, 1.20 mol, 100 mL, 1 eq) and TMSOTf (13.3 g, 59.9 mmol, 9.0 mL, 0.05 eq) dropwise at 0° C. and stirred at 20° C. for 8 h. Then added pyridine (979 g, 12.3 mol, 10.3 eq), followed by POCl$_3$ (551 g, 3.60 mol, 3 eq) dropwise. The resulting mixture was heated and stirred at 70° C. for 20 h under N$_2$ atmosphere. TLC showed the reaction was completed. The reaction mixture was poured into 5 L of ice water and adjusted pH to 7 by HCl (2 N). The black solid was filtered out. The filtrate was extracted with EtOAc (2 L×2). The combined organic layers were washed with brine (2 L×2), dried over Na$_2$SO$_4$, filtered and concentrated under reduced pressure to give a residue. The residue was purified by column chromatography (SiO$_2$, Petroleum ether/Ethyl acetate=15/1 to 5/1) to give 3,6-dihydro-2H-pyran-4-carbonitrile (100 g, 76.4% yield) as red oil. $^1$H NMR (CDCl$_3$, 400 MHz) δ 6.66-6.63 (m, 1H), 4.26 (q, J=2.8 Hz, 2H), 3.82 (t, J=5.6 Hz, 2H), 2.38-2.33 (m, 2H).

Preparation of 3-amino-1-[(trans)-4-cyanotetrahydro-2H-pyran-3-yl]pyrazole-4-carboxamide

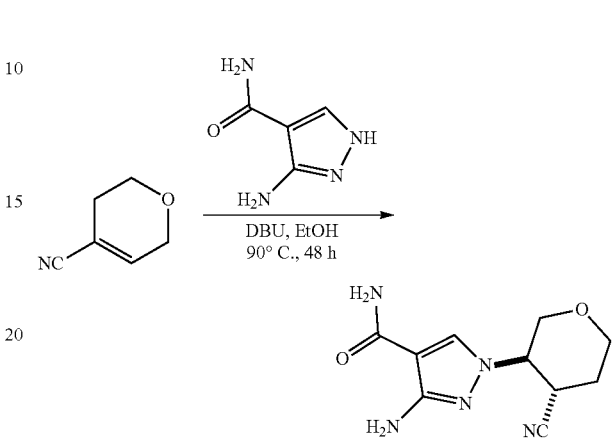

To a mixture of 3-amino-1H-pyrazole-4-carboxamide (15.0 g, 118 mmol, 1 eq) and 3,6-dihydro-2H-pyran-4-carbonitrile (26.0 g, 237 mmol, 2 eq) in ethanol (600 mL) was added DBU (41.7 g, 273 mmol, 41.2 mL, 2.3 eq) dropwise at 20° C. The resulting mixture was heated and stirred at 90° C. for 48 h under N$_2$ atmosphere. LCMS showed the reaction was completed and desired MS observed. The reaction mixture was concentrated in vacuum to give a residue. The residue was purified by column chromatography (SiO$_2$, Ethyl acetate/MeOH=1/0 to 20/1) to give 3-amino-1-(4-cyanotetrahydro-2H-pyran-3-yl) pyrazole-4-carboxamide (5.4 g, 19.3% yield) as a white solid.

$^1$H NMR (DMSO-d$_6$, 400 MHz) δ 8.04 (s, 1H), 7.36 (br s, 1H), 6.83 (br s, 1H), 5.50 (s, 2H), 4.39-4.33 (m, 1H), 3.94-3.89 (m, 2H), 3.56-3.37 (m, 2H), 3.38-3.32 (m, 1H), 2.12-2.09 (m, 1H), 1.95-1.91 (m, 1H).

Preparation of Intermediate D1

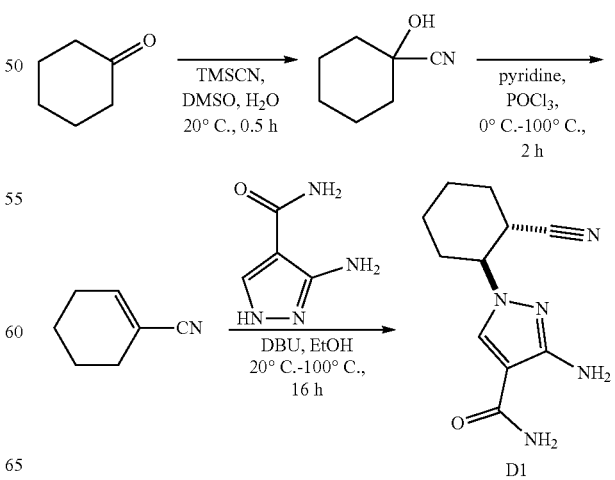

Preparation of 1-hydroxycyclohexanecarbonitrile

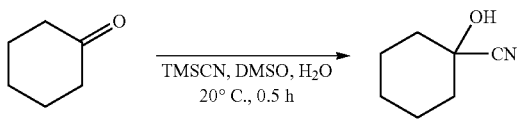

To a mixture of cyclohexanone (968 mmol, 100 mL, 1 eq) in DMSO (950 mL) and H₂O (175 mL) was added TMSCN (1.26 mol, 157.4 mL, 1.3 eq) drop-wise at 20° C. under N₂. The mixture was stirred at 20° C. for 0.5 h. TLC showed the reaction was completed. The mixture was poured into ice-water (w/w=1/1) (2 L) and stirred for 10 min. The aqueous phase was extracted with ethyl acetate (500 mL×3). The combined organic phase was washed with brine (300 mL×2), dried with anhydrous Na₂SO₄, filtered and concentrated in vacuum to give a residue. The residue was purified by column chromatography (SiO₂, Petroleum ether/Ethyl acetate=10/1 to 4/1) to give 1-hydroxycyclohexanecarbonitrile (100 g, 82.5% yield) as a yellow oil.

Preparation of cyclohexene-1-carbonitrile

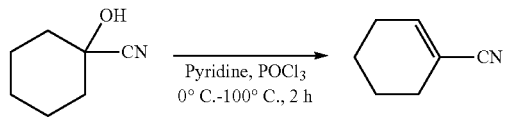 [SMILES: N#CC1(O)CCCCC1 ; N#CC1=CCCCC1]

To a mixture of 1-hydroxycyclohexanecarbonitrile (50.0 g, 399 mmol, 1 eq) in pyridine (6.39 mol, 516 mL, 16 eq) was added POCl₃ (799 mmol, 74.2 mL, 2 eq) drop-wise at 0° C. under N₂. The mixture was heated to 100° C. and stirred for 2 h. TLC showed the reaction was completed. The mixture was poured into ice-water (w/w=1/1) (2.5 L) and stirred for 10 min. The aqueous phase was extracted with ethyl acetate (1 L×3). The combined organic phase was washed with brine (1 L×2), dried with anhydrous Na₂SO₄, filtered and concentrated in vacuum to give a residue. The residue was purified by column chromatography (SiO₂, Petroleum ether/Ethyl acetate=10/1 to 5/1) to give cyclohexene-1-carbonitrile (29.0 g, 67.7% yield) as a yellow oil. ¹H NMR (CDCl3-d₆, 400 MHz) δ 6.62-6.59 (m, 1H), 2.20-2.16 (m, 4H), 1.67-1.63 (m, 4H).

Preparation of 3-amino-1-((trans)-2-cyanocyclohexyl)-1H-pyrazole-4-carboxamide

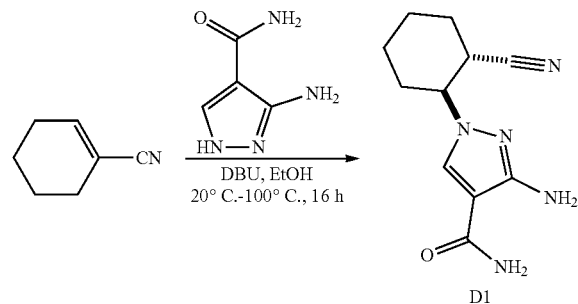

To a mixture of cyclohexene-1-carbonitrile (11.2 g, 104 mmol, 2.2 eq) and 3-amino-1H-pyrazole-4-carboxamide (6.0 g, 47.5 mmol, 1 eq) in EtOH (100 mL) was added DBU (114 mmol, 17.2 mL, 2.4 eq) drop-wise at 20° C. under N₂. LCMS showed the reaction was completed and desired MS observed. The mixture was heated to 100° C. and stirred for 16 h. The reaction mixture was concentrated in vacuum to give a residue. The residue was purified by column chromatography (SiO₂, Ethyl acetate/methanol=1/0 to 10/1) to give 3-amino-1-((trans)-2-cyanocyclohexyl)-1H-pyrazole-4-carboxamide (3.0 g, 27.0% yield) as a white solid. ¹H NMR (DMSO-hd 6, 400 MHz) δ 7.99 (s, 1H), 7.31 (br s, 1H), 6.79 (br s, 1H), 5.44 (s, 2H), 4.20-4.13 (m, 1H), 3.15-3.08 (m, 1H), 2.15-2.12 (m, 1H), 1.89-1.86 (m, 1H), 1.77-1.65 (m, 4H), 1.43-1.26 (m, 2H).

Preparation of Intermediate D2

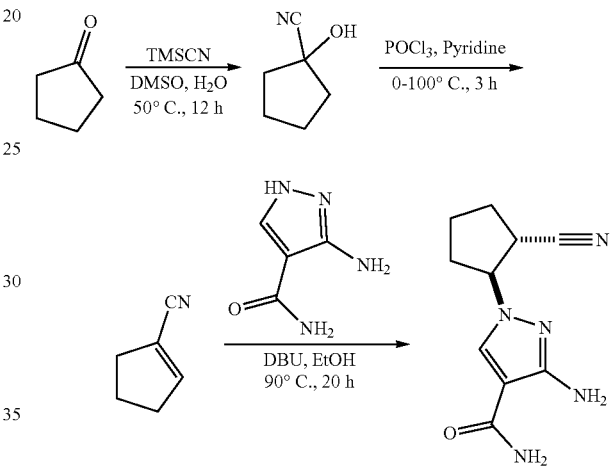

Preparation of 1-hydroxycyclopentanecarbonitrile

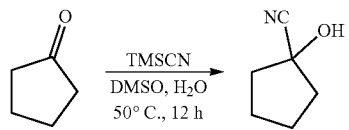 [SMILES: "TMSCN" ; O=C1CCCC1 ; N#CC1(O)CCCC1]

To a mixture of cyclopentanone (83.0 g, 986 mmol, 87.3 mL, 1 eq) in DMSO (800 mL) and H₂O (160 mL) was added dropwise TMSCN (127 g, 1.28 mol, 160 mL, 1.3 eq) at 0° C. The mixture was heated and stirred at 50° C. for 12 h. TLC showed the reaction was completed. The reaction was poured into ice: H₂O=(1:1, 500 mL) and extracted with EtOAc (500 mL×3). The combined organic layers were washed with brine (500 mL×2), dried over anhydrous Na₂SO₄, filtered and concentrated under reduced pressure to give a residue. The residue was purified by flash silica gel chromatography (ISCO®; 330 g SepaFlash® Silica Flash Column, Eluent of 0~10% Ethyl acetate/Petroleum ether gradient @ 150 mL/min) to give 1-hydroxycyclopentanecarbonitrile (50.0 g, 45.5% yield) as colorless oil. 1H NMR (CDCl₃, 400 MHz) δ 3.56-3.40 (m, 1H), 2.18-2.05 (m, 4H), 1.97-1.79 (m, 4H).

Preparation of cyclopentene-1-carbonitrile

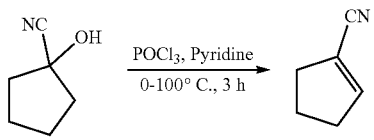

To a mixture of 1-hydroxycyclopentanecarbonitrile (50.0 g, 449 mmol, 1 eq) in pyridine (500 mL) was added dropwise POCl₃ (137 g, 899 mmol, 83.6 mL, 2 eq) at 0° C. under N₂. The mixture was heated and stirred at 100° C. for 3 h. TLC showed the reaction was completed. The reaction was poured into ice: H₂O=(1:1, 1000 mL) and extracted with EtOAc (500 mL×3). The combined organic layers were washed with brine (500 mL×2), dried over anhydrous Na₂SO₄, filtered and concentrated under reduced pressure to give a residue. The residue was purified by flash silica gel chromatography (ISCO®; 330 g SepaFlash® Silica Flash Column, Eluent of 0-5% Ethyl acetate/Petroleum ether gradient @ 150 mL/min) to give cyclopentene-1-carbonitrile (18.0 g, 42.9% yield) as yellow oil. 1H NMR (CDCl₃, 400 MHz) δ 6.66 (q, J=2.0 Hz, 1H), 2.61-2.52 (m, 4H), 2.04-1.98 (m, 2H).

Preparation of Rac-3-amino-1-(2-cyanocyclopentyl)pyrazole-4-carboxamide

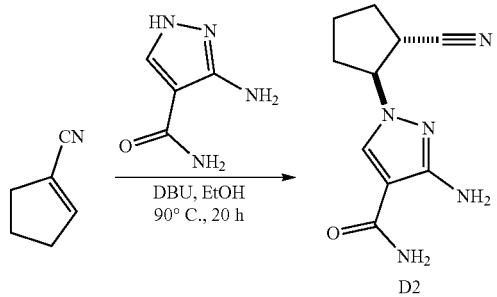

To a mixture of cyclopentene-1-carbonitrile (7.38 g, 71.3 mmol, 90% purity, 1.5 eq) and 3-amino-1H-pyrazole-4-carboxamide (6.00 g, 47.5 mmol, 1 eq) in EtOH (100 mL) was added DBU (14.4 g, 95.1 mmol, 14.3 mL, 2 eq) in one portion at 20° C. The mixture was heated and stirred at 90° C. for 20 h. TLC showed the reaction was completed. The reaction mixture was concentrated under reduced pressure to give a residue. The residue was purified by flash silica gel chromatography (ISCO®; 220 g SepaFlash® Silica Flash Column, Eluent of 0~10% MeOH/Ethyl Acetate gradient @ 150 mL/min) to give 3-amino-1-(trans-2-cyanocyclopentyl)pyrazole-4-carboxamide (6.00 g, 57.5% yield) as a white solid. 1H NMR (DMSO-hd 6, 400 MHz) δ 8.03 (s, 1H), 7.30 (br s, 1H), 6.79 (br s, 1H), 5.49 (s, 2H), 4.71 (q, J=8.0 Hz, 1H), 3.26 (q, J=8.8 Hz, 1H), 2.26-2.09 (m, 2H), 1.96-1.72 (m, 4H).

Examples

1. Preparation of 1-[trans-4-cyanotetrahydro-2H-pyran-3-yl]-3-[(4-fluoro-1-hydroxy-3H-2,1-benzoxaborol-6-yl)amino]pyrazole-4-carboxamide

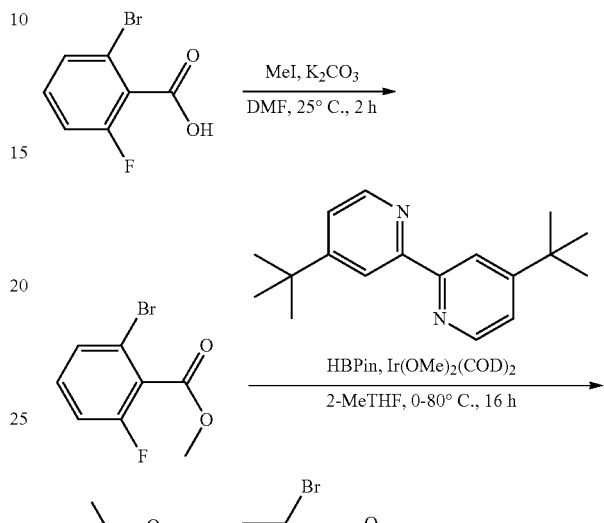

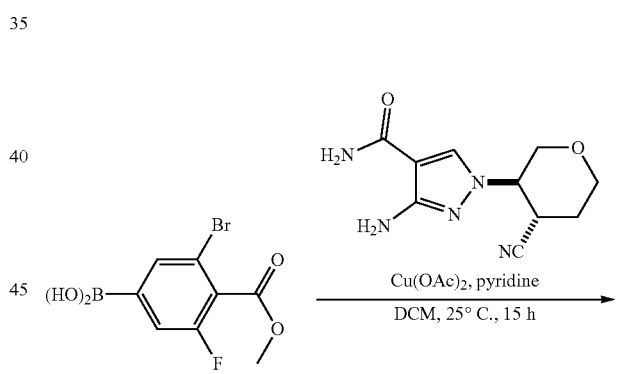

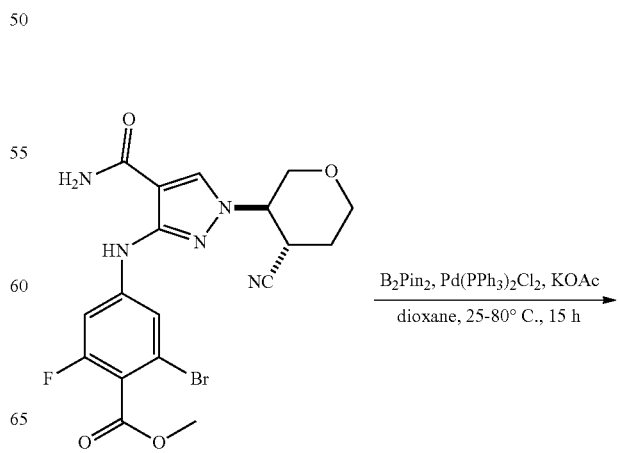

-continued

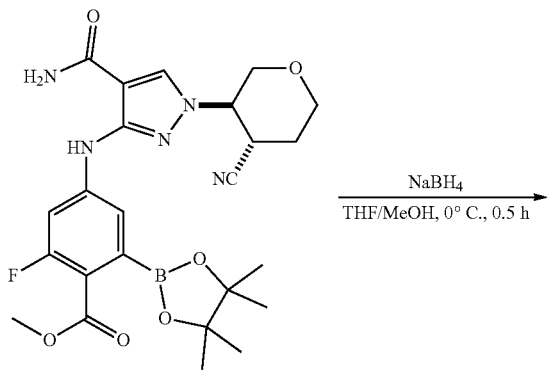

1.1 Preparation of methyl 2-bromo-6-fluoro-benzoate

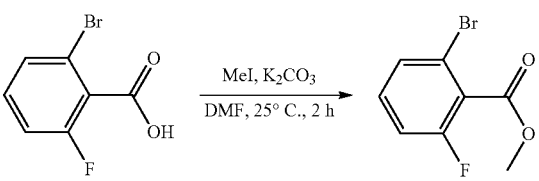

To a mixture of 2-bromo-6-fluoro-benzoic acid (15.00 g, 68.5 mmol, 1 eq) and K₂CO₃ (9.47 g, 68.5 mmol, 1 eq) in DMF (100 mL) was added iodomethane (14.58 g, 102 mmol, 6.4 mL, 1.5 eq) dropwise at 25° C. under N₂, the resulting mixture was stirred at 25° C. for 2 h. H₂O (150 mL) was added into the above reaction mixture, which was extracted with PE (50 mL×3). The combined organic layers were washed by brine (50 mL×2), dried over Na₂SO₄, filtered and concentrated in vacuo to give a residue. The residue was purified by flash silica gel chromatography (ISCO®; 120 g SepaFlash® Silica Flash Column, Eluent of 5-6% Ethyl acetate/Petroleum ether gradient @120 mL/min) to give methyl 2-bromo-6-fluoro-benzoate (12.00 g, 51.5 mmol, 75.18% yield) as colorless oil. 1H NMR (CDCl₃, 400 MHz) δ 7.36 (d, J=8.0 Hz, 1H), 7.25 (dd, J=8.0, 6.4 Hz, 1H), 7.06 (t, J=8.0 Hz, 1H), 3.95 (s, 3H).

1.2 Preparation of methyl 2-bromo-6-fluoro-4-(4,4,5,5-tetramethyl-1,3,2-diaxaborolan-2-yl) benzoate

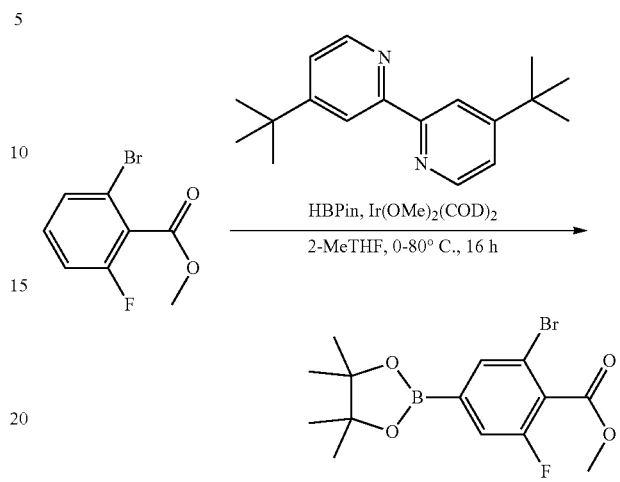

To a mixture of methyl 2-bromo-6-fluoro-benzoate (4.00 g, 17.2 mmol, 1 eq), Ir(OMe)₂(COD)₂ (228 mg, 343 μmol, 0.02 eq) and 4-tert-butyl-2-(4-tert-butyl-2-pyridyl)pyridine (138 mg, 515 μmol, 0.03 eq) in 2-MeTHF (30 mL) was added 4,4,5,5-tetramethyl-1,3,2-dioxaborolane (3.30 g, 25.8 mmol, 3.74 mL, 1.5 eq) dropwise at 0° C. under N₂ atmosphere, the resulting mixture was stirred at 80° C. for 16 h. The reaction mixture was filtered, and the filtrate was concentrated in vacuo to give a residue. The residue was purified by flash silica gel chromatography (ISCO®; 40 g SepaFlash® Silica Flash Column, Eluent of 0~10% Ethyl acetate/Petroleum ether gradient @100 mL/min) to give methyl 2-bromo-6-fluoro-4-(4,4,5,5-tetramethyl-1,3,2-dioxaborolan-2-yl)benzoate (2.80 g, 5.46 mmol, 31.81% yield, 70% purity) as colorless oil. 1H NMR (CDCl₃, 400 MHz) δ 7.80 (s, 1H), 7.48 (d, J=8.8 Hz, 1H), 3.98 (s, 3H), 1.35 (s, 12H).

1.3 Preparation of (3-bromo-5-fluoro-4-methoxycarbonyl-phenyl)boronic acid

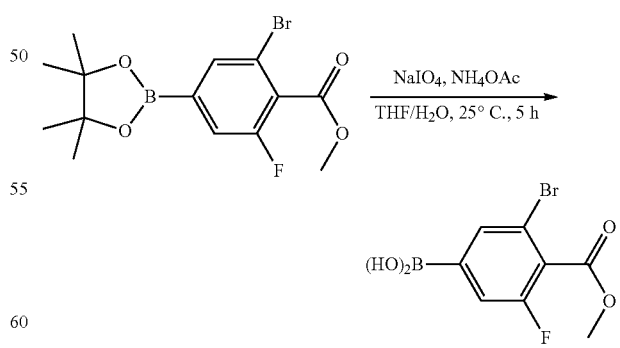

To a mixture of methyl 2-bromo-6-fluoro-4-(4,4,5,5-tetramethyl-1,3,2-dioxaborolan-2-yl) benzoate (2.80 g, 5.46 mmol, 70% purity, 1 eq) in THF (15 mL) and H₂O (20 mL) was added NaIO₄ (4.67 g, 21.8 mmol, 1.21 mL, 4 eq) and ammonium acetate (1.68 g, 21.8 mmol, 4 eq) in one portion

1.4 Preparation of methyl 2-bromo-4-[[4-carbamoyl-1-[trans-4-cyanotetrahydro-2H-pyran-3-yl]pyrazol-3-yl]amino]-6-fluoro-benzoate

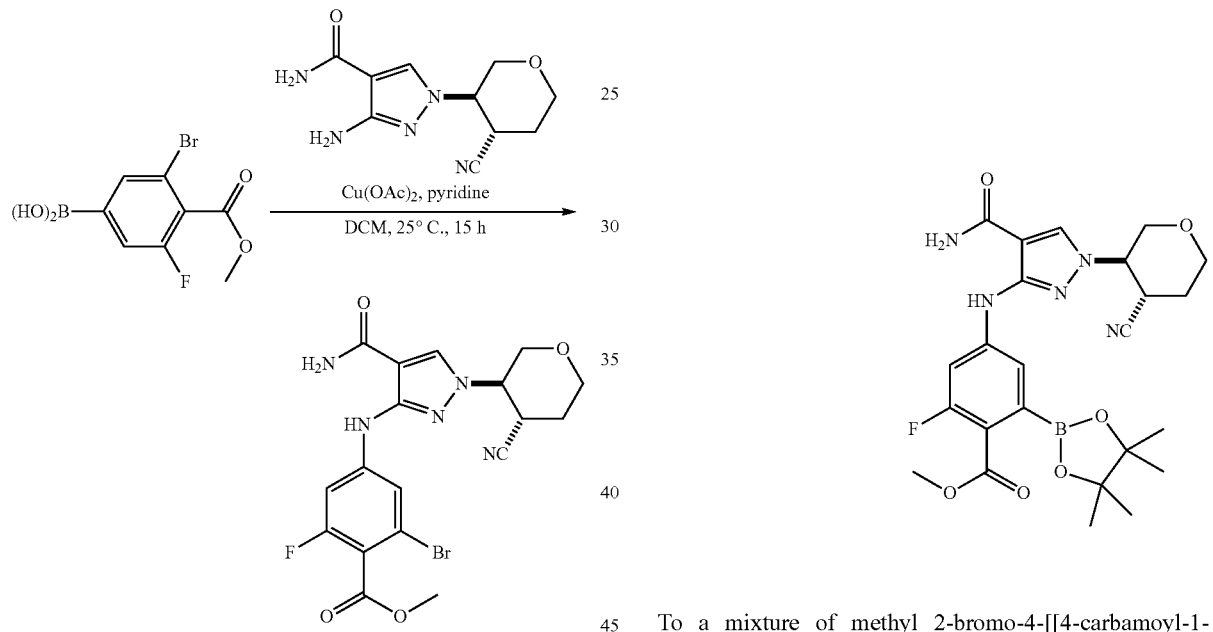

To a mixture of (3-bromo-5-fluoro-4-methoxycarbonyl-phenyl)boronic acid (565 mg, 2.04 mmol, 1.2 eq) and 3-amino-1-[trans-4-cyanotetrahydro-2H-pyran-3-yl]pyrazole-4-carboxamide (400 mg, 1.70 mmol, 1 eq) in DCM (50 mL) was added pyridine (673 mg, 8.50 mmol, 5 eq) and Cu(OAc)₂ (772 mg, 4.25 mmol, 2.5 eq) in one portion at 25° C. under N₂ atmosphere, the resulting mixture was stirred at 25° C. for 15 h. Then the reaction mixture was filtered, the filtrate was concentrated in vacuo to give a residue. The residue was purified by flash silica gel chromatography (ISCO®; 20 g SepaFlash® Silica Flash Column, Eluent of 75-85% Ethyl acetate/Petroleum ether gradient @ 90 mL/min) to give methyl 2-bromo-4-[[4-carbamoyl-1-[trans-4-cyanotetrahydro-2H-pyran-3-yl]pyrazol-3-yl]amino]-6-fluoro-benzoate (200 mg, 429 µmol, 12.61% yield) as a white solid. ¹H NMR (DMSO-hd 6, 400 MHz) δ 9.60 (s, 1H), 8.36 (s, 1H), 7.81 (br s, 1H), 7.69-7.65 (m, 2H), 7.31 (br s, 1H), 4.66-4.61 (m, 1H), 4.08-4.06 (m, 1H), 4.05-4.03 (m, 1H), 3.85 (s, 3H), 3.68-3.65 (m, 2H), 3.49-3.48 (m, 1H), 2.17-2.14 (m, 1H), 2.00-1.90 (m, 1H).

1.5 Preparation of methyl 4-[[4-carbamoyl-1-[trans-4-cyanotetrahydro-2H-pyran-3-yl] pyrazol-3-yl]amino]-2-fluoro-6-(4,4,5,5-tetramethyl-1,3,2-dioxaborolan-2-yl)benzoate

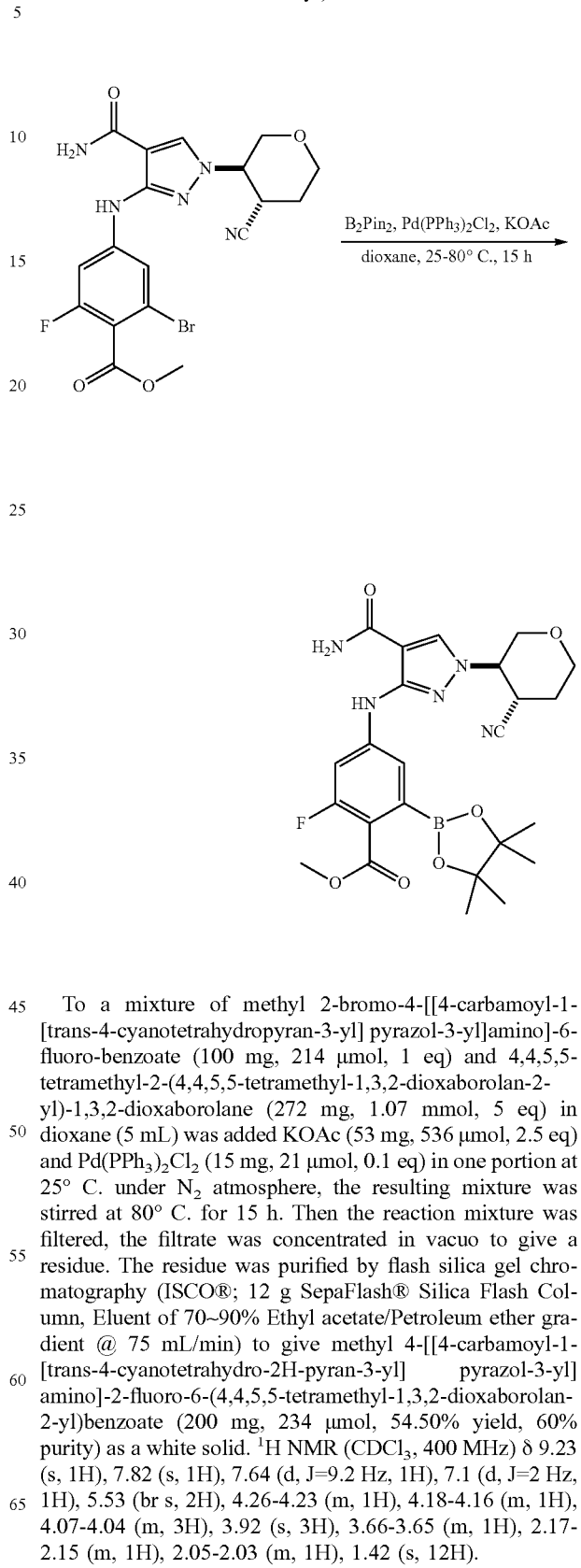

To a mixture of methyl 2-bromo-4-[[4-carbamoyl-1-[trans-4-cyanotetrahydropyran-3-yl] pyrazol-3-yl]amino]-6-fluoro-benzoate (100 mg, 214 µmol, 1 eq) and 4,4,5,5-tetramethyl-2-(4,4,5,5-tetramethyl-1,3,2-dioxaborolan-2-yl)-1,3,2-dioxaborolane (272 mg, 1.07 mmol, 5 eq) in dioxane (5 mL) was added KOAc (53 mg, 536 µmol, 2.5 eq) and Pd(PPh₃)₂Cl₂ (15 mg, 21 µmol, 0.1 eq) in one portion at 25° C. under N₂ atmosphere, the resulting mixture was stirred at 80° C. for 15 h. Then the reaction mixture was filtered, the filtrate was concentrated in vacuo to give a residue. The residue was purified by flash silica gel chromatography (ISCO®; 12 g SepaFlash® Silica Flash Column, Eluent of 70~90% Ethyl acetate/Petroleum ether gradient @ 75 mL/min) to give methyl 4-[[4-carbamoyl-1-[trans-4-cyanotetrahydro-2H-pyran-3-yl] pyrazol-3-yl] amino]-2-fluoro-6-(4,4,5,5-tetramethyl-1,3,2-dioxaborolan-2-yl)benzoate (200 mg, 234 µmol, 54.50% yield, 60% purity) as a white solid. ¹H NMR (CDCl₃, 400 MHz) δ 9.23 (s, 1H), 7.82 (s, 1H), 7.64 (d, J=9.2 Hz, 1H), 7.1 (d, J=2 Hz, 1H), 5.53 (br s, 2H), 4.26-4.23 (m, 1H), 4.18-4.16 (m, 1H), 4.07-4.04 (m, 3H), 3.92 (s, 3H), 3.66-3.65 (m, 1H), 2.17-2.15 (m, 1H), 2.05-2.03 (m, 1H), 1.42 (s, 12H).

--- at 25° C. under N₂ atmosphere, the resulting mixture was stirred at 25° C. for 5 h. H₂O (10 mL) was added into the above mixture, the resulting mixture was extracted with EtOAc (10 mL×2). The combined organic layers were washed by brine (10 mL×2), dried over Na₂SO₄, filtered and concentrated in vacuo to give a residue. The residue was purified by flash silica gel chromatography (ISCO®; 40 g SepaFlash® Silica Flash Column, Eluent of 5-15% Ethyl acetate/Petroleum ether gradient @ 90 mL/min) to give (3-bromo-5-fluoro-4-methoxycarbonyl-phenyl)boronic acid (1.20 g, 4.33 mmol, 79.39% yield) as a white solid. 1H NMR (DMSO-hd 6, 400 MHz) δ 8.58 (s, 2H), 7.89 (s, 1H), 7.64 (d, J=9.6 Hz, 1H), 3.91 (m, 3H).

1.6 Preparation of 1-[trans-4-cyanotetrahydro-2H-pyran-3-yl]-3-[(4-fluoro-1-hydroxy-3H-2,1-benzoxaborol-6-yl)amino]pyrazole-4-carboxamide

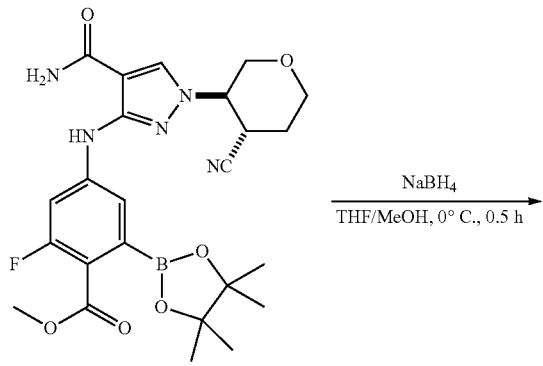

To a mixture of methyl 4-[[4-carbamoyl-1-[trans-4-cyanotetrahydropyran-3-yl]pyrazol-3-yl]amino]-2-fluoro-6-(4,4,5,5-tetramethyl-1,3,2-dioxaborolan-2-yl)benzoate (200 mg, 234 μmol, 60% purity, 1 eq) in THF (1 mL) and MeOH (0.1 mL) was added NaBH$_4$ (44 mg, 1.17 mmol, 5 eq) in portions at 0° C. under N$_2$ atmosphere, the resulting mixture was stirred at 0° C. for 0.5 h. The reaction was quenched with addition of H$_2$O (3 mL) at 0° C., pH of the resulting mixture was adjusted to 2-3 with 2N HCl, the mixture was extracted with EtOAc (5 mL×4). The combined organic layers were washed by brine (3 mL×2), dried over Na$_2$SO$_4$, filtered and concentrated in vacuo to give a residue. The residue was purified by prep-HPLC (column: Welch Xtimate C18 100*25 mm*3 um; mobile phase: [water (0.05% HCl)-ACN]; B %: 5%-35%, 8 min) to give 1-[trans-4-cyanotetrahydropyran-3-yl]-3-[(4-fluoro-1-hydroxy-3H-2,1-benzoxaborol-6-yl)amino]pyrazole-4-carboxamide (35.6 mg, 89 μmol, 38.25% yield, 96.75% purity) as a white solid. $^1$H NMR (DMSO-hd 6, 400 MHz) δ 9.42 (s, 1H), 9.32 (s, 1H), 8.32 (s, 1H), 7.76 (br s, 1H), 7.71 (d, J=12.4 Hz, 1H), 7.44 (s, 1H), 7.25 (br s, 1H), 5.01 (s, 2H), 4.60 (dd, J=12.0, 4.4 Hz, 1H), 4.06-4.02 (m, 1H), 3.91-3.89 (m, 1H), 3.72-3.67 (m, 2H), 3.52-3.48 (m, 1H), 2.18-2.15 (m, 1H), 2.01-1.97 (m, 1H). MS (ESI): mass calculated for C$_{17}$H$_{17}$BFN$_5$O$_4$, 385.14, m/z found 386.2 [M+H]$^+$. Purity by HPLC: 96.75% (220 nm), 99.38% (254 nm).

2. Preparation of 1-[trans-4-cyanotetrahydro-2H-pyran-3-yl]-3-[(2-hydroxy-1,2-benzoxaborinin-7-yl)amino]pyrazole-4-carboxamide

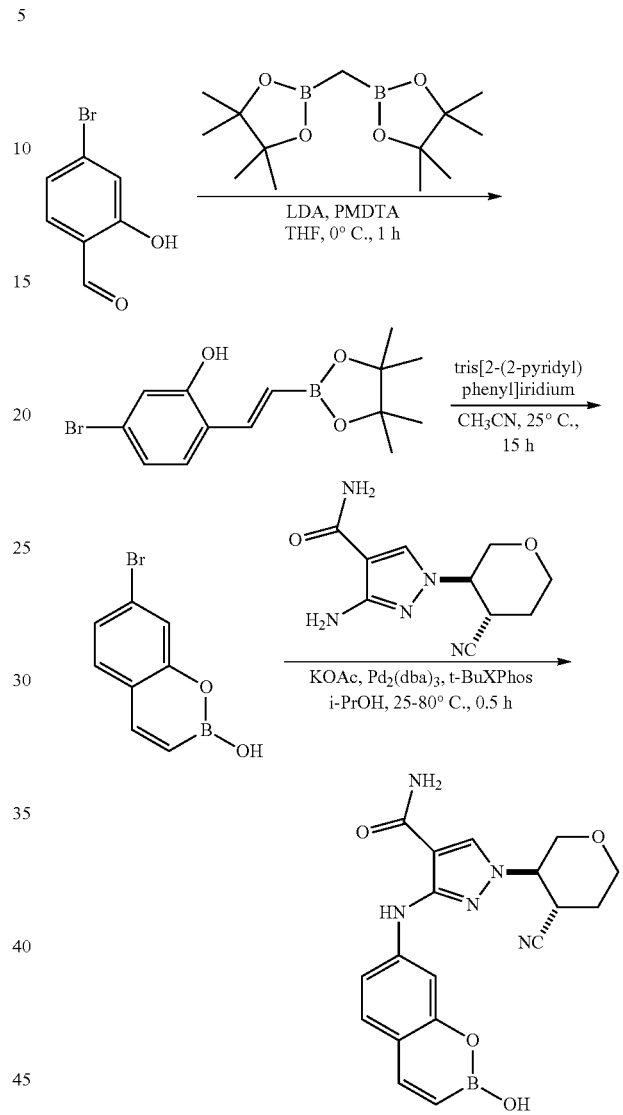

2.1 Preparation of (E)-5-bromo-2-(2-(4,4,5,5-tetramethyl-1,3,2-diaxaborolan-2-yl)vinyl) phenol

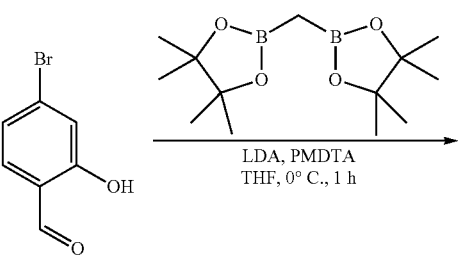

-continued

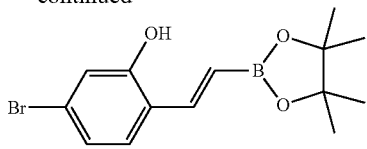

To a mixture of LDA (2 M, 37.3 mL, 3 eq) in THF (50 mL) was added 4,4,5,5-tetramethyl-2-[(4,4,5,5-tetramethyl-1,3,2-dioxaborolan-2-yl)methyl]-1,3,2-dioxaborolane (20.00 g, 74.6 mmol, 3 eq) and N'-[2-(dimethylamino)ethyl]-N,N,N'-trimethyl-ethane-1,2-diamine (8.62 g, 49.7 mmol, 10.4 mL, 2 eq) dropwise at 0° C. under $N_2$ atmosphere, the resulting mixture was stirred at 0° C. for 20 min. To the above mixture was then added a solution of 4-bromo-2-hydroxy-benzaldehyde (5.00 g, 24.8 mmol, 1 eq) in THF (50 mL) at 0° C., and the resulting mixture was stirred for 1 h at 0° C. The reaction was quenched with sat. aq $NH_4Cl$ (100 mL), extracted with EtOAc (50 mL×2). The combined organic layers were washed by brine (100 mL×2), dried over $Na_2SO_4$, filtered and concentrated in vacuo to give a residue. The residue was purified by flash silica gel chromatography (ISCO®; 80 g SepaFlash® Silica Flash Column, Eluent of 10-15% Ethyl acetate/Petroleum ether gradient @100 mL/min) to give (E)-5-bromo-2-(2-(4,4,5,5-tetramethyl-1,3,2-dioxaborolan-2-yl)vinyl)phenol (5.00 g, 15.38 mmol, 61.85% yield) as yellow oil. $^1$H NMR (CDCl$_3$, 400 MHz) δ 7.56 (d, J=18.4 Hz, 1H), 7.33 (d, J=8.4 Hz, 1H), 7.05 (d, J=8.4 Hz, 1H), 7.00 (s, 1H), 6.16 (d, J=18.4 Hz, 1H), 5.49 (br d, 1H), 1.29 (s, 12H).

2.2 Preparation of 7-bromo-2-hydroxy-1,2-benzoxaborinine

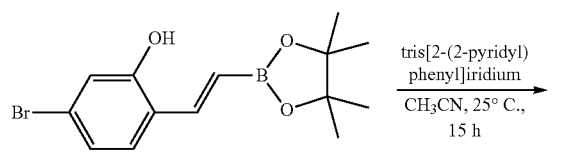

To a mixture of 5-bromo-2-[(Z)-2-(4,4,5,5-tetramethyl-1,3,2-dioxaborolan-2-yl)vinyl]phenol (500 mg, 1.54 mmol, 1 eq) in CH$_3$CN (10 mL) was added tris[2-(2-pyridyl)phenyl]iridium (10 mg, 15 μmol, 0.01 eq) in one portion at 25° C. under $N_2$ atmosphere, the resulting mixture was stirred and irradiated using 34W blue LED lamps for 15 h. The mixture was filtered, and the filtrate was concentrated in vacuo to give a residue. The residue was purified by prep-HPLC (column: Waters Xbridge Prep OBD C18 150*40 mm*10 um; mobile phase: [water (10 mM NH$_4$HCO$_3$)-ACN]; B %: 30%-60%, 8 min) to give 7-bromo-2-hydroxy-1,2-benzoxaborinine (240 mg, 1.07 mmol, 23.13% yield) as a white solid. $^1$H NMR (DMSO-hd 6, 400 MHz) δ 9.17 (s, 1H), 7.78 (d, J=12.0 Hz, 1H), 7.47 (d, J=8.0 Hz, 1H), 7.45 (d, J=2.0 Hz, 1H), 7.33 (dd, J=8, 2 Hz, 1H), 6.17 (d, J=12.0 Hz, 1H).

2.3 Preparation of 1-[rans-4-cyanotetrahydro-2H-pyran-3-yl]-3-[(2-hydroxy-1,2-benzoxaborinin-7-yl)amino]pyrazole-4-carboxamide

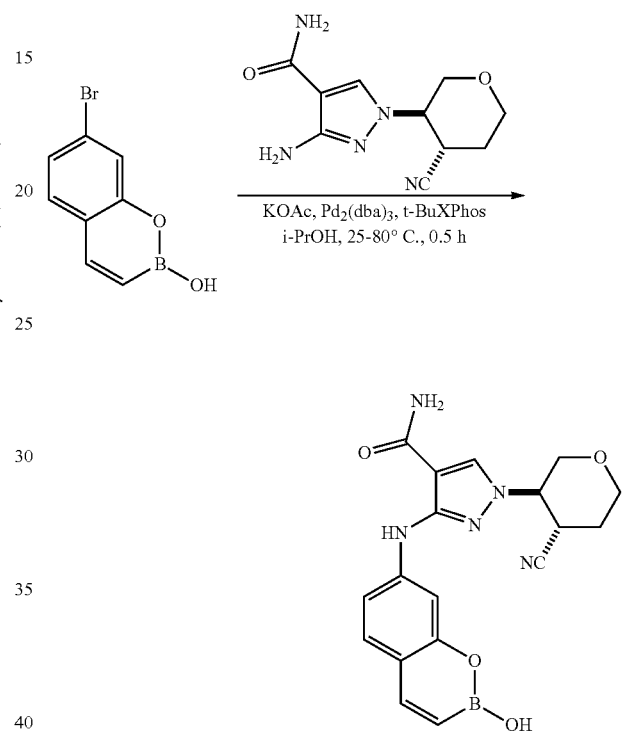

To a mixture of 3-amino-1-[trans-4-cyanotetrahydropyran-3-yl]pyrazole-4-carboxamide (276 mg, 1.17 mmol, 1.1 eq) and 7-bromo-2-hydroxy-1,2-benzoxaborinine (240 mg, 1.07 mmol, 1 eq) in i-PrOH (4 mL) was added AcOK (157 mg, 1.60 mmol, 1.5 eq), Pd$_2$(dba)$_3$ (49 mg, 53 μmol, 0.05 eq) and t-BuXPhos (45 mg, 107 μmol, 0.1 eq) in one portion at 25° C. under $N_2$ atmosphere, the resulting mixture was stirred at 80° C. for 0.5 h. The mixture was filtered, and the filtrate was concentrated in vacuo to give a residue. The residue was purified by prep-HPLC (column: Welch Xtimate C18 100*25 mm*3 um; mobile phase: [water (0.05% HCl)-ACN]; B %:10%-40%, 8 min) to give 1-[trans-4-cyanotetrahydro-2H-pyran-3-yl]-3-[(2-hydroxy-1,2-benzoxaborinin-7-yl)amino] pyrazole-4-carboxamide (150.9 mg, 398 μmol, 37.28% yield, 95.11% purity) as a white solid. $^1$HNMR (DMSO-hd 6, 400 MHz) δ 9.42 (s, 1H), 8.80 (s, 1H), 8.33 (s, 1H), 7.77 (br s, 1H), 7.69 (d, J=11.6 Hz, 1H), 7.54 (d, J=2.0 Hz, 1H), 7.35 (d, J=8.4 Hz, 1H), 7.24 (br s, 1H), 7.11 (d, J=8.4, 2.0 Hz, 1H), 5.87 (d, J=11.6 Hz, 1H), 4.63-4.58 (m, 1H), 4.08-4.04 (m, 1H), 3.92-3.90 (m, 1H), 3.71-3.65 (m, 2H), 3.52-3.50 (m, 1H), 2.19-2.17 (m, 1H), 2.02-1.99 (m, 1H). MS (ESI): mass calculated for $C_{18}H_{18}BN_5O_4$, 379.15, m/z found 380.2[M+H]$^+$. Purity by HPLC: 95.11% (220 nm), 98.39% (254 nm).

3. Preparation of 1-[trans-4-cyanotetrahydro-2H-pyran-3-yl]-3-[(2-hydroxy-4-methyl-1,2-benzoxaborinin-6-yl)amino]pyrazole-4-carboxamide

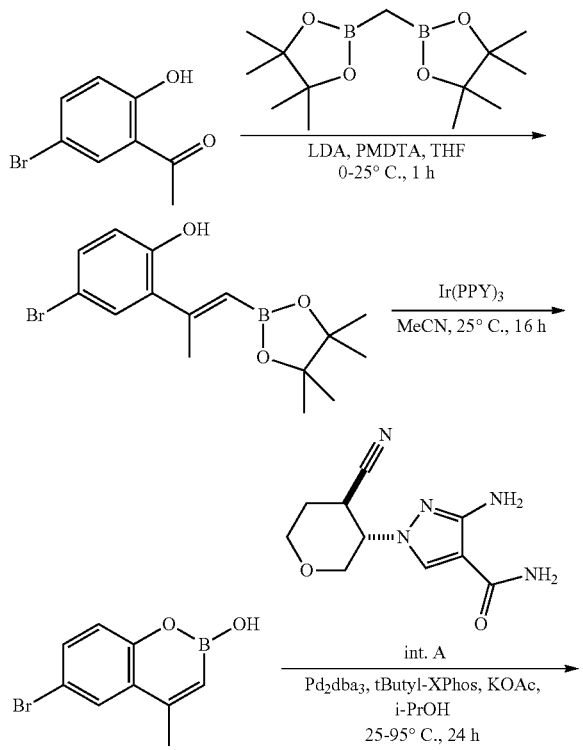

3.1 Preparation of 4-bromo-2-[(E)-1-methyl-2-(4,4,5,5-tetramethyl-1,3,2-dioxaborolan-2-yl)vinyl] phenol

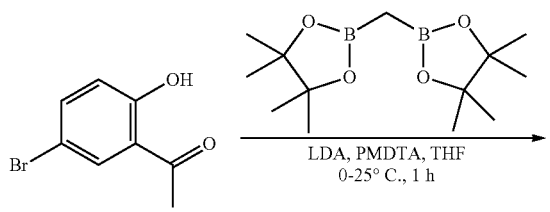

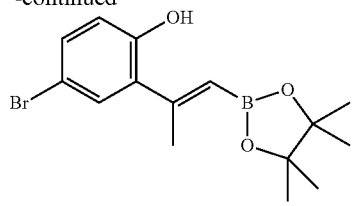

To a mixture of LDA (2 M, 25.6 mL, 2.2 eq) in THF (40 mL) was added N'-[2-(dimethylamino)ethyl]-N,N,N'-trimethyl-ethane-1,2-diamine (8.06 g, 46.5 mmol, 9.7 mL, 2 eq) and a solution of 4,4,5,5-tetramethyl-2-[(4,4,5,5-tetramethyl-1,3,2-dioxaborolan-2-yl) methyl]-1,3,2-dioxaborolane (12.4 g, 46.5 mmol, 2 eq) in THF (30 mL) at 0° C. under $N_2$. The reaction was stirred at 0° C. for 20 min. Then added a solution of 1-(5-bromo-2-hydroxy-phenyl)ethanone (5.0 g, 23.3 mmol, 1 eq) in THF (30 mL) at 0° C. The reaction mixture was stirred at 25° C. for another 40 min. TLC showed the reaction was completed. The mixture was quenched with sat. aq. $NH_4Cl$ (100 mL), adjusted pH to 6 with 2 N HCl and then extracted with EtOAc (50 mL×3). The combined organic layers were washed with brine (80 mL×2), dried over $Na_2SO_4$, filtered and concentrated under reduced pressure to get the residue. The residue was purified by flash silica gel chromatography (ISCO®; 80 g SepaFlash® Silica Flash Column, Eluent of 0-15% Ethylacetate/Petroleum ether gradient @ 100 mL/min) to give 4-bromo-2-[(E)-1-methyl-2-(4,4,5,5-tetramethyl-1,3,2-dioxaborolan-2-yl)vinyl]phenol (5 g, 80% purity) as yellow oil.

3.2 Preparation of 6-bromo-2-hydroxy-4-methyl-1,2-benzoxaborinine

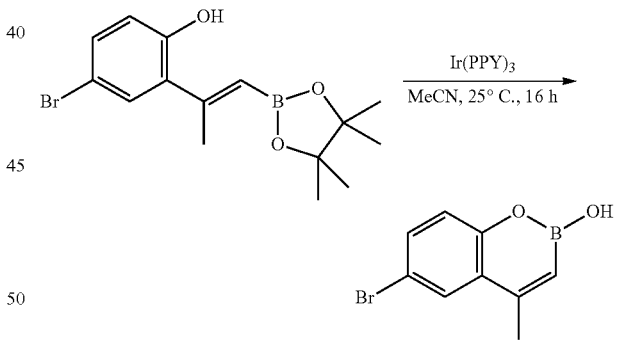

To a mixture of 4-bromo-2-[(E)-1-methyl-2-(4,4,5,5-tetramethyl-1,3,2-dioxaborolan-2-yl)vinyl]phenol (2.50 g, 5.9 mmol, 80% purity, 1 eq) in $CH_3CN$ (30 mL) was added tris[2-(2-pyridyl)phenyl]iridium (39 mg, 59 umol, 0.01 eq) in one portion at 25° C. under $N_2$. The reaction was stirred and irradiated using 34W blue LED lamps for 16 h. LCMS showed the reaction was completed and desired MS observed. 2 parallel reactions were combined for work up. The mixture was concentrated under reduced pressure to give the residue. The residue was purified by flash silica gel chromatography (ISCO®; 40 g SepaFlash® Silica Flash Column, Eluent of 0-15% Ethyl acetate/Petroleum ether gradient @ 100 mL/min) to give 6-bromo-2-hydroxy-4-methyl-1,2-benzoxaborinine (2.50 g) as a yellow solid. $^1H$ NMR (CDCl₃, 400 MHz) δ 8.95 (s, 1H), 7.74 (d, J=2.4 Hz, 1H), 7.55 (dd, J=2.4, 8.4 Hz, 1H), 7.18 (d, J=8.8 Hz, 1H), 5.99 (s, 1H), 2.35 (s, 3H).

3.3 Preparation of 1-[trans-4-cyanotetrahydro-2H-pyran-3-yl]-3-[(2-hydroxy-4-methyl-1,2-benzoxaborinin-6-yl)amino]pyrazole-4-carboxamide

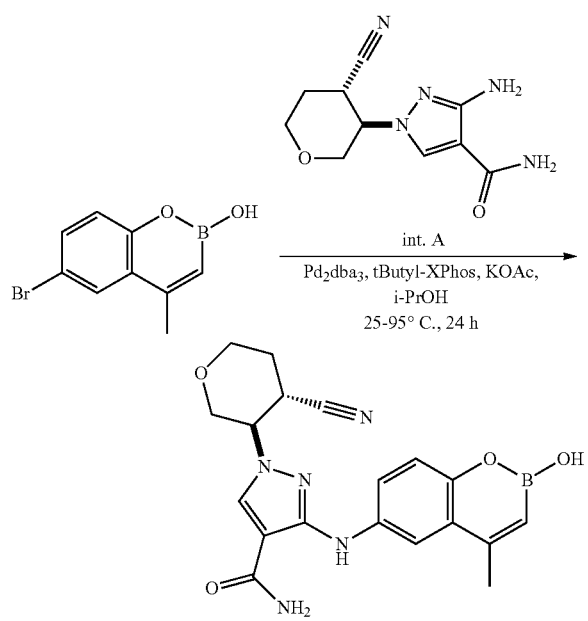

A mixture of 6-bromo-2-hydroxy-4-methyl-1,2-benzoxaborinine (500 mg, 2.1 mmol, 1 eq) and 3-amino-1-(trans-4-cyanotetrahydro-2H-pyran-3-yl)pyrazole-4-carboxamide (542 mg, 2.3 mmol, 1.1 eq) in i-PrOH (10 mL) was added Pd₂(dba)₃ (19 mg, 21 umol, 0.01 eq), t-Bu Xphos (178 mg, 419 umol, 0.2 eq) and KOAc (411 mg, 4.2 mmol, 2 eq) at 25° C. under N₂. Then reaction was stirred at 95° C. for 24 h. LCMS showed the reaction was completed and desired MS observed. 4 parallel reactions were combined for work up. The reaction mixture was filtered and concentrated in vacuum to give a residue. The residue was quenched with H₂O (60 mL), adjusted pH to 6 with 2H HCl at 0° C., and then extracted with EtOAc (30 mL×3). The combined organic layers were washed with brine (40 mL×3), dried over Na₂SO₄, filtered and concentrated under reduced pressure to give a residue. The residue was purified by flash silica gel chromatography (ISCO®; 20 g SepaFlash® Silica Flash Column, Eluent of 0~100% Ethyl acetate/Petroleum ether gradient @ 50 mL/min) to give 1-(trans-4-cyanotetrahydro-2H-pyran-3-yl)-3-[(2-hydroxy-1,2-benzoxaborinin-6-yl)amino]pyrazole-4-carboxamide (800 mg) as an off-white solid. The product was separated by SFC (column: DAICEL CHIRALPAK AD (250 mm*30 mm, 10 um); mobile phase: [Neu-ETOH]; B %: 53%-53%, 5 min) to give 1-[trans-4-cyanotetrahydro-2H-pyran-3-yl]-3-[(2-hydroxy-4-methyl-1,2-benzoxaborinin-6-yl)amino]pyrazole-4-carboxamide (stereoisomer one) (365.7 mg, 96.7% purity, 99.3% ee, first peak, Rt=1.330 min) as an off-white solid. ¹H NMR (DMSO-d₆, 400 MHz) δ 9.06 (s, 1H), 8.63 (s, 1H), 8.29 (s, 1H), 7.93 (d, J=2.8 Hz, 1H), 7.69 (br s, 1H), 7.50 (dd, J=2.8, 8.8 Hz, 1H), 7.12 (d, J=8.8 Hz, 2H), 5.93 (s, 1H), 4.60-4.54 (m, 1H), 4.06 (dd, J=4.4, 11.6 Hz, 1H), 3.95-3.92 (m, 1H), 3.72-3.65 (m, 2H), 3.46-3.33 (m, 1H), 2.40 (s, 3H), 2.18-2.14 (m, 1H), 2.01-1.96 (m, 1H). MS (ESI): mass calculated for C₁₉H₂₀BN₅O₄ 393.16; m/z found 392.1 [M−H]⁻. HPLC: 96.72% (220 nm), 99.74% (254 nm). and 1-[trans-4-cyanotetrahydropyran-3-yl]-3-[(2-hydroxy-4-methyl-1,2-benzoxaborinin-6-yl)amino]pyrazole-4-carboxamide (stereoisomer two) (365.4 mg, 98.0% purity, 99.4% ee, second peak, Rt=1.548) as an off-white solid. ¹H NMR (DMSO-d₆, 400 MHz) δ 9.06 (s, 1H), 8.63 (s, 1H), 8.29 (s, 1H), 7.93 (d, J=2.8 Hz, 1H), 7.69 (br s, 1H), 7.50 (dd, J=2.8, 8.8 Hz, 1H), 7.17-7.11 (m, 2H), 5.93 (s, 1H), 4.58-4.53 (m, 1H), 4.06 (dd, J=4.4, 11.2 Hz, 1H), 3.95-3.92 (m, 1H), 3.72-3.65 (m, 2H), 3.46-3.33 (m, 1H), 2.41 (s, 3H), 2.18-2.15 (m, 1H), 2.01-1.93 (m, 1H). MS (ESI): mass calculated for C₁₉H₂₀BN₅O₄ 393.16, m/z found 392.1 [M−H]⁻. HPLC: 98.00% (220 nm), 99.88% (254 nm).

4. Preparation of 1-(trans-4-cyanotetrahydro-2H-pyran-3-yl)-3-((2-hydroxy-3,4-dimethyl-2H-benzo[e][1,2]oxaborinin-6-yl)amino)-1H-pyrazole-4-carboxamide

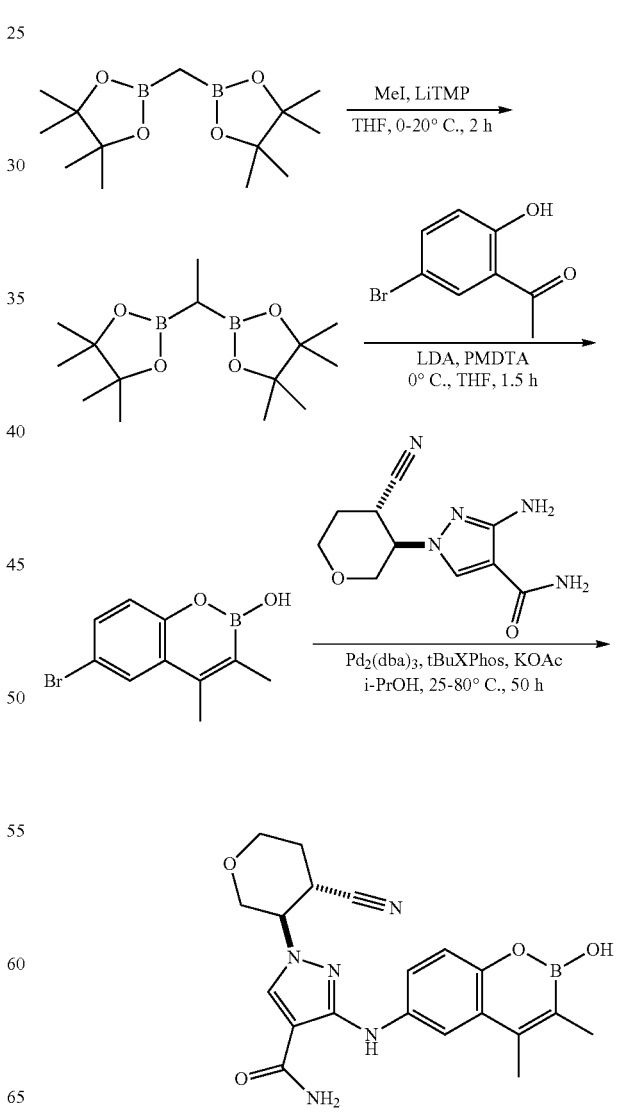

4.1 Preparation of 4,4,5,5-tetramethyl-2-[1-(4,4,5,5-tetramethyl-1,3,2-diaxaborolan-2-yl) ethyl]-1,3,2-dioxaborolane

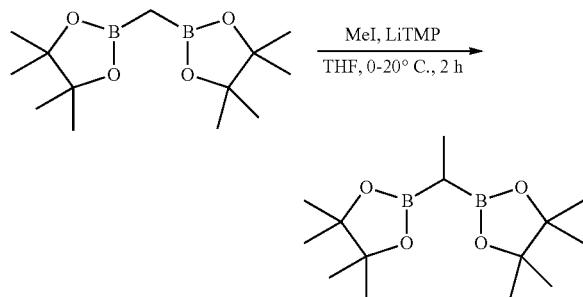

To a mixture of 2,2,6,6-tetramethylpiperidine (2.90 g, 20.5 mmol, 3.5 mL, 1.1 eq) in THF (30 mL) was added n-BuLi (2.5 M, 8.2 mL, 1.1 eq) dropwise at 0° C. under N₂ atmosphere, the resulting mixture was stirred at 0° C. for 30 min. Then a solution of 4,4,5,5-tetramethyl-2-[(4,4,5,5-tetramethyl-1,3,2-dioxaborolan-2-yl)methyl]-1,3,2-dioxaborolane (5.00 g, 18.66 mmol, 1 eq) in THF (30 mL) was added to the above mixture dropwise at 0° C., the reaction mixture was stirred for 30 min at 0° C. MeI (2.91 g, 20.5 mmol, 13 mL, 1.1 eq) was added dropwise to reaction mixture at 0° C., the resulting mixture was stirred for 30 min at 20° C. The mixture was poured into sat. aq NH₄Cl (50 mL), and stirred for 5 min. The aqueous phase was extracted with ethyl acetate (30 mL×3). The combined organic phase was washed with brine (30 mL×2), dried with anhydrous Na₂SO₄, filtered and concentrated in vacuo to give a residue. The residue was purified by flash silica gel chromatography (ISCO®; 80 g SepaFlash® Silica Flash Column, Eluent of 5-12% Ethyl acetate/Petroleum ether gradient @ 120 mL/min) to give 4,4,5,5-tetramethyl-2-[1-(4,4,5,5-tetramethyl-1,3,2-dioxaborolan-2-yl)ethyl]-1,3,2-dioxaborolane (3.60 g, 12.77 mmol, 68.42% yield) as colorless oil. 1H NMR (CDCl₃, 400 MHz) δ 1.22 (s, 24H), 1.05 (d, J=7.2 Hz, 3H), 0.74 (q, J=7.2 Hz, 1H).

4.2 Preparation of 6-bromo-2-hydroxy-3,4-dimethyl-1,2-benzoxaborinine

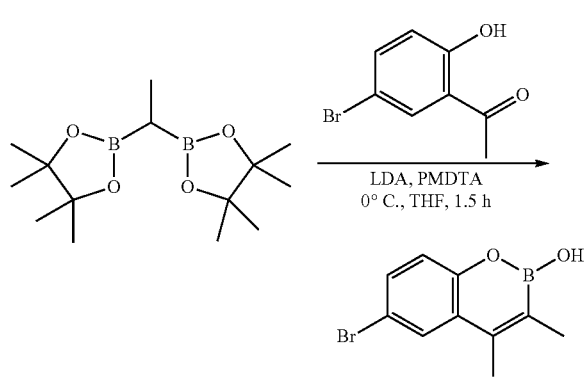

To a mixture of 4,4,5,5-tetramethyl-2-[1-(4,4,5,5-tetramethyl-1,3,2-dioxaborolan-2-yl)ethyl]-1,3,2-dioxaborolane (2.62 g, 9.30 mmol, 2 eq) and LDA (2 M, 4.70 mL, 2 eq) in THF (15 mL) was added N'-[2-(dimethylamino)ethyl]-N,N,N'-trimethyl-ethane-1,2-diamine (1.21 g, 6.98 mmol, 1.5 mL, 1.5 eq) dropwise at 0° C. under N₂ atmosphere, the resulting mixture was stirred for 30 min at 0° C. To the above mixture was added a solution of 1-(5-bromo-2-hydroxy-phenyl) ethanone (1 g, 4.65 mmol, 1 eq) in THF (5 mL) dropwise at 0° C., the resulting mixture was stirred for 1 h at 0° C. The mixture was poured into sat. aq. NH₄Cl (10 mL), the pH of the resulting mixture was adjusted to 5-6 with HCl (2N) at 0° C. The mixture was extracted with EtOAc (10 mL×2), the combined organic layers were washed by brine (10 mL×2), dried over Na₂SO₄, filtered and concentrated in vacuo to give a residue. The residue was purified by flash silica gel chromatography (ISCO®; 80 g SepaFlash® Silica Flash Column, Eluent of 5-7% Ethyl acetate/Petroleum ether gradient @ 100 mL/min) to give 6-bromo-2-hydroxy-3,4-dimethyl-1,2-benzoxaborinine (500 mg, 1.91 mmol, 41.04% yield, 96.53% purity) as a white solid. ¹H NMR (DMSO-hd 6, 400 MHz) δ 8.89 (s, 1H), 7.74 (d, J=2.4 Hz, 1H), 7.47 (dd, J=8.8, 2.4 Hz, 1H), 7.14 (d, J=8.8 Hz, 1H), 2.23 (s, 3H), 1.97 (s, 3H). MS (ESI): mass calculated for C₁₀H₁₀BBrO₂, 252.00, m/z found 251.1 [M−H]⁻. Purity by HPLC: 96.53% (220 nm), 99.57% (254 nm).

4.3 Preparation of 1-(trans-4-cyanotetrahydro-2H-pyran-3-yl)-3-((2-hydroxy-3,4-dimethyl-2H-benzo[e][1,2]oxaborinin-6-yl)amino)-1H-pyrazole-4-carboxamide

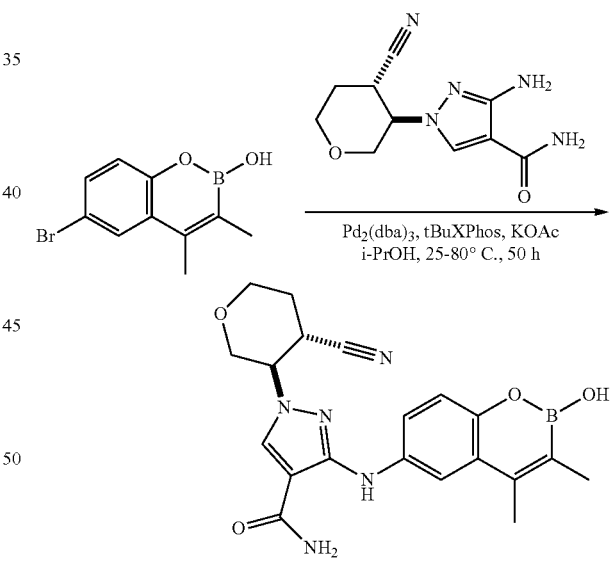

To a mixture of 6-bromo-2-hydroxy-3,4-dimethyl-1,2-benzoxaborinine (130 mg, 514 μmol, 1 eq) and 3-amino-1-(trans-4-cyanotetrahydropyran-3-yl)pyrazole-4-carboxamide (145 mg, 617 μmol, 1.2 eq) in i-PrOH (3 mL) was added Pd₂(dba)₃ (24 mg, 26 μmol, 0.05 eq), t-Bu Xphos (22 mg, 51 μmol, 0.1 eq) and KOAc (76 mg, 771 μmol, 1.5 eq) in one portion at 25° C. under N₂ atmosphere, the resulting mixture was stirred at 80° C. for 50 h. To the above mixture was added H₂O (0.1 mL) at 25° C., the resulting mixture was concentrated in vacuo to give a residue. The residue was purified by prep-HPLC (column: Waters Xbridge BEH C18 100*30 mm*10 um; mobile phase: [water (10 mM NH$_4$HCO$_3$)-ACN]; B %: 25%-55%, 10 min) to give 1-(trans-4-cyanotetrahydro-2H-pyran-3-yl)-3-((2-hydroxy-3,4-dimethyl-2H-benzo[e][1,2]oxaborinin-6-yl)amino)-1H-pyrazole-4-carboxamide (96 mg, 228.64 μmol, 14.83% yield, 96.99% purity) as a yellow solid. $^1$H NMR (DMSO-hd 6, 400 MHz) δ 9.04 (s, 1H), 8.56 (s, 1H), 8.29 (s, 1H), 7.94 (d, J=2.8 Hz, 1H), 7.69 (br s, 1H), 7.42 (dd, J=8.4, 2.8 Hz, 1H), 7.15 (br s, 1H), 7.08 (d, J=8.4 Hz, 1H), 4.58-4.55 (m, 1H), 4.08-4.04 (m, 1H), 3.97-3.94 (m, 1H), 3.72-3.67 (m, 2H), 3.46-3.40 (m, 1H), 2.32 (s, 3H), 2.29-2.25 (m, 1H), 2.05-1.99 (m, 1H), 1.98 (s, 3H). MS (ESI): mass calculated for C$_{20}$H$_{22}$BN$_5$O$_4$, 407.18, m/z found 408.2[M+H]$^+$. Purity by HPLC: 96.99% (220 nm), 98.08% (254 nm).

5. Preparation of 1-(trans-4-cyanotetrahydro-2H-pyran-3-yl)-3-((2-hydroxy-3-methyl-2H-benzo[e][1,2]oxaborinin-6-yl)amino)-1H-pyrazole-4-carboxamide

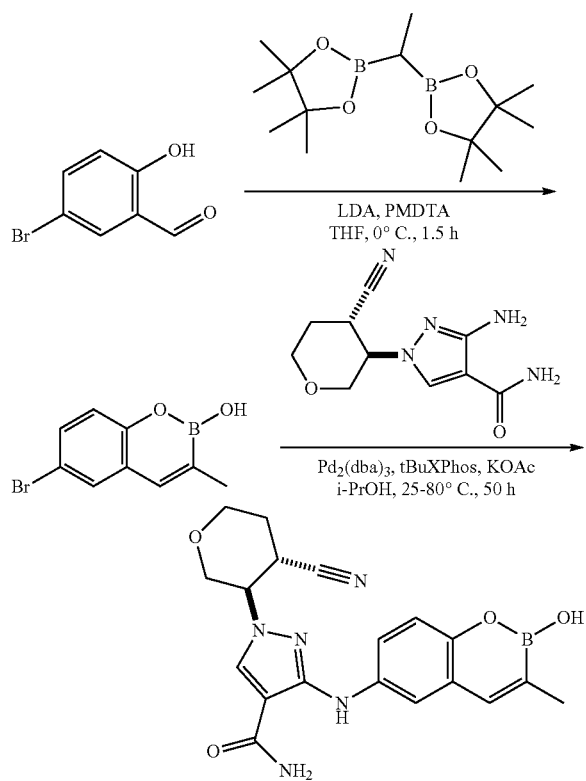

5.1 Preparation of 6-bromo-2-hydroxy-3-methyl-1,2-benzoxaborinine

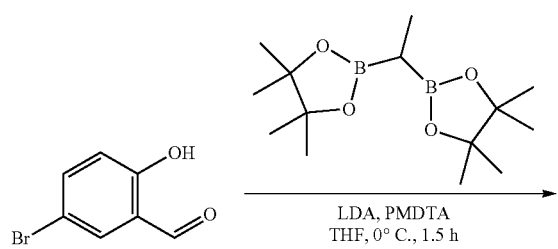

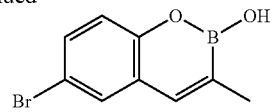

To a mixture of LDA (2 M, 12.4 mL, 2 eq) in THF (15 mL) was added 4,4,5,5-tetramethyl-2-[1-(4,4,5,5-tetramethyl-1,3,2-dioxaborolan-2-yl)ethyl]-1,3,2-dioxaborolane (5.96 g, 21.1 mmol, 1.7 eq) and N'-[2-(dimethylamino)ethyl]-N,N,N'-trimethyl-ethane-1,2-diamine (3.23 g, 18.66 mmol, 3.9 mL, 1.5 eq) dropwise at 0° C. under N$_2$ atmosphere, the resulting mixture was stirred at 0° C. for 20 min. Then 5-bromo-2-hydroxy-benzaldehyde (2.5 g, 12.44 mmol, 1 eq) in THF (10 mL) was added into the mixture above, the reaction mixture was stirred at 0° C. for additional 1 h. The reaction was quenched with sat. aq NH$_4$Cl (20 mL), extracted with EtOAc (20 mL×2). The combined organic layers were washed with brine (10 mL×2), dried over Na$_2$SO$_4$, filtered and concentrated in vacuo to give a residue, which was purified by prep-HPLC (column: Phenomenex Gemini-NX 80*40 mm*3 um; mobile phase: [water (10 mM NH$_4$HCO$_3$)-ACN]; B %: 25%-55%, 8 min) to give 6-bromo-2-hydroxy-3-methyl-1,2-benzoxaborinine (600 mg, 2.48 mmol, 19.97% yield, 98.86% purity) as a white solid. $^1$H NMR (DMSO-hd 6, 400 MHz) δ 9.09 (s, 1H), 7.65 (d, J=2.4 Hz, 1H), 7.45-7.42 (m, 2H), 7.14 (d, J=8.8 Hz, 1H), 2.01 (s, 3H). MS (ESI): mass calculated for C$_9$H$_8$BBrO$_2$, 237.98, m/z found 237.1[M–H]$^-$. Purity by HPLC: 98.86% (220 nm), 99.14%(254 nm).

5.2 Preparation of 1-(trans-4-cyanotetrahydro-2H-pyran-3-yl)-3-((2-hydroxy-3-methyl-2H-benzo[e][1,2]oxaborinin-6-yl)amino)-1H-pyrazole-4-carboxamide

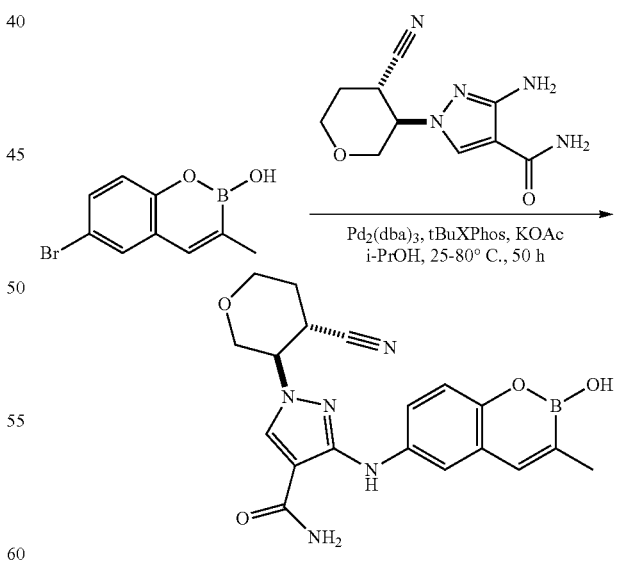

To a mixture of 6-bromo-2-hydroxy-3-methyl-1,2-benzoxaborinine (400 mg, 1.00 mmol, 1 eq) and 3-amino-1-(trans-4-cyanotetrahydropyran-3-yl)pyrazole-4-carboxamide (282 mg, 1.20 mmol, 1.2 eq) in i-PrOH (10 mL) was added Pd$_2$(dba)$_3$ (45.8 mg, 50.0 μmol, 0.05 eq), AcOK (147 mg, 1.50 mmol, 1.5 eq) and t-Bu Xphos (42.5 mg, 100 μmol, 0.1 eq) in one portion at 25° C. under N₂ atmosphere, the resulting mixture was stirred at 80° C. for 50 h. The reaction mixture was poured into H₂O (0.2 mL), filtered and concentrated in vacuo to give a residue, which was purified by prep-HPLC (column: Welch Xtimate C18 100*25 mm*3 um; mobile phase: [water (0.05% HCl)-ACN]; B %: 30%-50%, 8 min) to give 1-(trans-4-cyanotetrahydro-2H-pyran-3-yl)-3-((2-hydroxy-3-methyl-2H-benzo[e][1,2]oxaborinin-6-yl)amino)-1H-pyrazole-4-carboxamide (50.1 mg, 121 μmol, 12.1% yield, 94.9% purity) as an off-white solid. ¹H NMR (DMSO-hd 6, 400 MHz) δ 9.06 (s, 1H), 8.76 (s, 1H), 8.28 (s, 1H), 7.65 (br s, 1H), 7.60 (d, J=2.8 Hz, 1H), 7.48 (s, 1H), 7.46 (dd, J=8.8, 2.8 Hz, 1H), 7.13 (br s, 1H), 7.08 (d, J=8.8 Hz, 1H), 4.57-4.54 (m, 1H), 4.03 (dd, J=11.2, 4.4 Hz, 1H), 3.92-3.87 (m, 1H), 3.72-3.67 (m, 2H), 3.52-3.49 (m, 1H), 2.17-2.14 (m, 1H), 2.07 (s, 3H), 2.06-1.97 (m, 1H). MS (ESI): mass calculated for $C_{19}H_{20}BN_5O_4$, 393.16, m/z found 392.1[M−H]. Purity by HPLC: 94.87% (220 nm), 99.83% (254 nm).

6. Preparation of 1-(trans-4-cyanotetrahydro-2H-pyran-3-yl)-3-[(1-hydroxy-7-methyl-3H-2,1-benzoxaborol-5-yl)amino]pyrazole-4-carboxamide

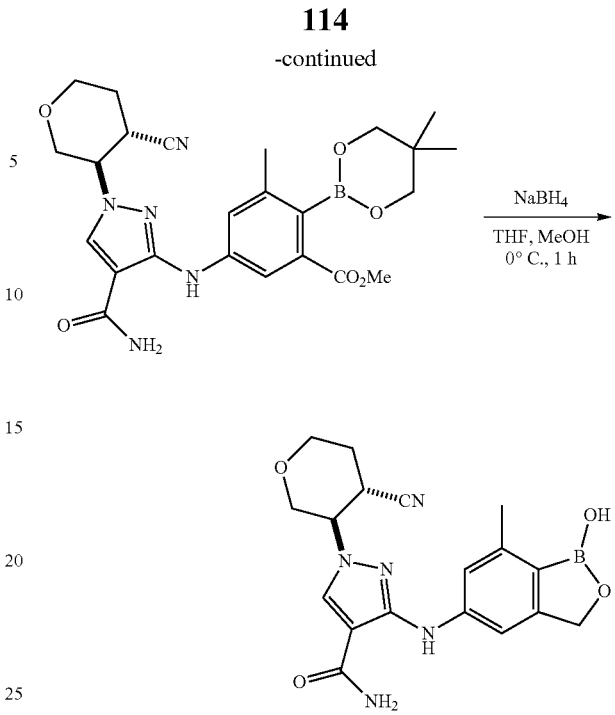

6.1 Preparation of methyl 2-bromo-3-methyl-5-(4,4,5,5-tetramethyl-1,3,2-diaxaborolan-2-yl)benzoate

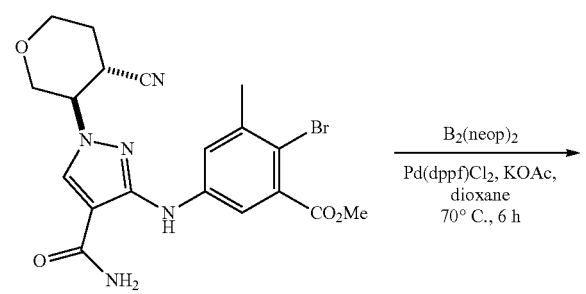

To a mixture of methyl 2-bromo-3-methyl-benzoate (1.00 g, 4.37 mmol, 1 eq) and 4,4,5,5-tetramethyl-1,3,2-dioxaborolane (3.35 g, 26.19 mmol, 3.80 mL, 6 eq) in 2-MeTHF (30 mL) was added 4-tert-butyl-2-(4-tert-butyl-2-pyridyl)pyridine (117 mg, 436 μmol, 0.1 eq) and Ir(OMe)₂(COD)₂ (58 mg, 87.5 μmol, 0.02 eq) dropwise at 20° C., the resulting mixture was stirred at 90° C. for 72 h under N₂ atmosphere. The combined reaction mixture was concentrated in vacuo to give a residue, which was purified by column chromatography (SiO₂, Petroleum ether/Ethyl acetate=O/1 to 10/1) to give methyl 2-bromo-3-methyl-5-(4,4,5,5-tetramethyl-1,3,2-dioxaborolan-2-yl)benzoate (1.27 g, 3.57 mmol, 81.73% yield) as yellow oil. ¹H NMR (CDCl₃, 400 MHz) δ 7.87 (s, 1H), 7.76 (s, 1H), 3.93 (s, 3H), 2.47 (s, 3H), 1.35 (s, 12H).

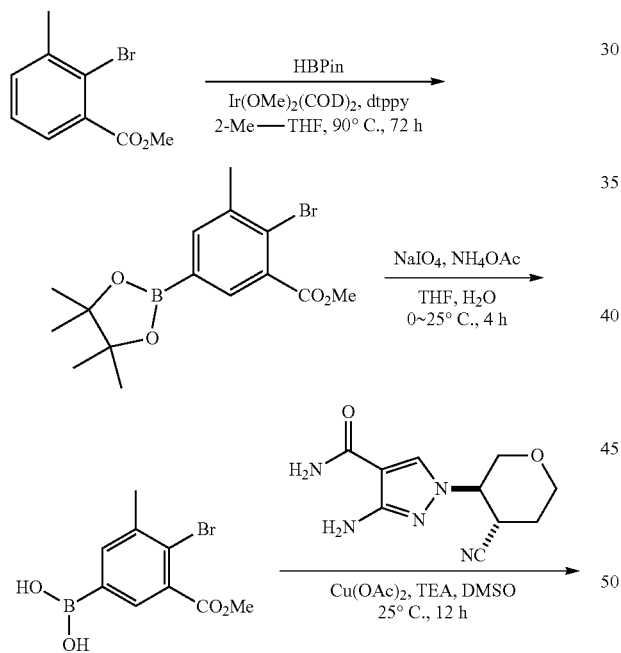

6.2 Preparation of (4-bromo-3-methoxycarbonyl-5-methyl-phenyl)boronic acid

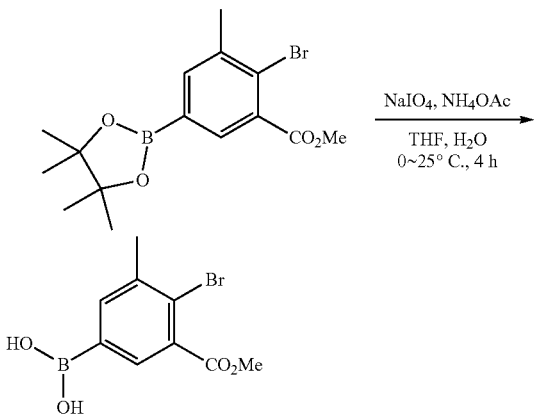

To a mixture of methyl 2-bromo-3-methyl-5-(4,4,5,5-tetramethyl-1,3,2-dioxaborolan-2-yl) benzoate (3.80 g, 10.70 mmol, 1 eq) in H$_2$O (20 mL) and THF (20 mL) was added NaIO$_4$ (9.16 g, 42.81 mmol, 2.37 mL, 4 eq) and NH$_4$OAc (3.30 g, 42.81 mmol, 4 eq) in small portions at 0° C., the resulting mixture was stirred at 25° C. for 4 h under N$_2$ atmosphere. Then the reaction mixture was partitioned between EtOAc (20 mL) and H$_2$O (20 mL). The organic phase was separated, washed with brine (20 mL×2), dried over Na$_2$SO$_4$, filtered and concentrated in vacuo to give a residue, which was purified by column chromatography (SiO$_2$, Petroleum ether/Ethyl acetate=1/0 to 2/1) to give (4-bromo-3-methoxycarbonyl-5-methyl-phenyl)boronic acid (2.4 g, 8.79 mmol, 82.17% yield) as yellow solid. $^1$H NMR (DMSO-hd 6, 400 MHz) δ 8.29 (s, 2H), 7.86 (s, 1H), 7.83 (s, 1H), 3.85 (s, 3H), 2.40 (s, 3H).

6.3 Preparation of methyl 2-bromo-5-((4-carbamoyl-1-(trans-4-cyanotetrahydro-2H-pyran-3-yl)-1H-pyrazol-3-yl)amino)-3-methylbenzoate

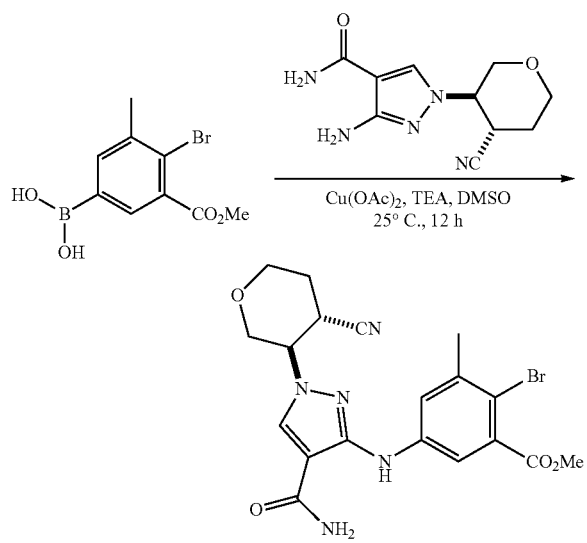

To a mixture of 3-amino-1-(trans-4-cyanotetrahydropyran-3-yl)pyrazole-4-carboxamide (1.00 g, 4.25 mmol, 1 eq) and (4-bromo-3-methoxycarbonyl-5-methyl-phenyl)boronic acid (1.16 g, 4.25 mmol, 1 eq) in DMSO (20 mL) was added TEA (2.15 g, 21.25 mmol, 2.96 mL, 5 eq), Cu(OAc)$_2$ (155 mg, 851 µmol, 0.2 eq) and 4 Å molecular sieve (500 mg, 4.25 mmol, 1 eq) at 25° C., the resulting mixture was stirred at 25° C. for 12 h under O$_2$ atmosphere. The reaction mixture was poured into sat. NH$_4$Cl (20 mL), the resulting precipitates were removed by filtration, the filtrate was extracted with DCM (20 mL×3). The combined organic layers were washed with brine (20 mL×2), dried over Na$_2$SO$_4$, filtered and concentrated in vacuo to give a residue, which was purified by column chromatography (SiO$_2$, Petroleum ether/Ethyl acetate=10/1 to 1/2) to give methyl 2-bromo-5-((4-carbamoyl-1-(trans-4-cyanotetrahydro-2H-pyran-3-yl)-1H-pyrazol-3-yl)amino)-3-methylbenzoate (840 mg, 1.82 mmol, 42.74% yield) as a yellow solid. $^1$H NMR (DMSO-d$_6$, 400 MHz) δ 9.29 (s, 1H), 8.32 (s, 1H), 7.78 (d, J=2.4 Hz, 1H), 7.76 (br s, 1H), 7.67 (d, J=2.4 Hz, 1H), 7.25 (br s, 1H), 4.62-4.59 (m, 1H), 4.09-4.06 (m, 1H), 3.97-3.94 (m, 1H), 3.86 (s, 3H), 3.68-3.62 (m, 2H), 3.49-3.45 (m, 1H), 2.39 (s, 3H), 2.20-2.16 (m, 1H), 2.06-1.96 (m, 1H).

6.4 Preparation of methyl 5-[[4-carbamoyl-1-(trans-4-cyanotetrahydro-2H-pyran-3-yl)pyrazol-3-yl]amino]-2-(5,5-dimethyl-1,3,2-dioxaborinan-2-yl)-3-methyl-benzoate

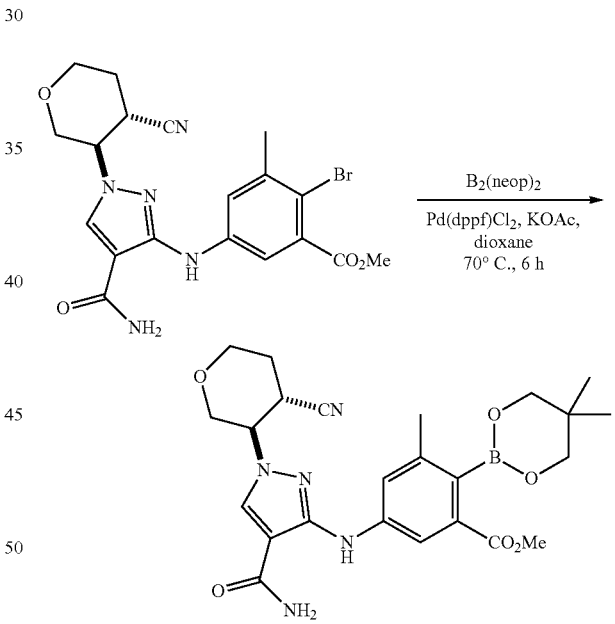

A mixture of 2-(5,5-dimethyl-1,3,2-dioxaborinan-2-yl)-5,5-dimethyl-1,3,2-dioxaborinane (157 mg, 693 µmol, 2 eq), methyl 2-bromo-5-((4-carbamoyl-1-(trans-4-cyanotetrahydro-2H-pyran-3-yl)-1H-pyrazol-3-yl)amino)-3-methylbenzoate (160 mg, 346.10 µmol, 1 eq), KOAc (51 mg, 519 µmol, 1.5 eq) and Pd(dppf)C12 (13 mg, 18 µmol, 0.05 eq) in dioxane (10 mL) was degassed and purged with N$_2$ for 3 times, the resulting mixture was stirred at 70° C. for 6 h under N$_2$ atmosphere. The reaction mixture was filtered, the filtrate was concentrated in vacuo to give a residue, which was purified by column chromatography (SiO$_2$, Petroleum ether/Ethyl acetate=10/1 to 1/1) to give methyl 5-[[4-carbamoyl-1-(trans-4-cyanotetrahydro-2H-pyran-3-yl) pyrazol-3-yl]amino]-2-(5,5-dimethyl-1,3,2-dioxaborinan-2-yl)-3-methyl-benzoate (600 mg, 1.21 mmol, 70.00% yield) as a yellow solid. $^1$H NMR (DMSO-d$_6$, 400 MHz) δ 9.23 (s, 1H), 8.32 (s, 1H), 7.97 (d, J=2.0 Hz, 1H), 7.74 (br s, 1H), 7.49 (d, J=2.0 Hz, 1H), 7.23 (br s, 1H), 4.60-4.57 (m, 1H), 4.10-4.06 (m, 1H), 3.96-3.93 (m, 1H), 3.87 (s, 3H), 3.68 (s, 4H), 3.66-3.62 (m, 2H), 3.52-3.48 (m, 1H), 2.35 (s, 3H), 2.20-2.17 (m, 1H), 2.06-1.96 (m, 1H), 1.06 (s, 6H).

6.5 Preparation of 1-[trans-4-cyanotetrahydropyran-3-yl]-3-[(1-hydroxy-7-methyl-3H-2,1-benzoxaborol-5-yl)amino]pyrazole-4-carboxamide

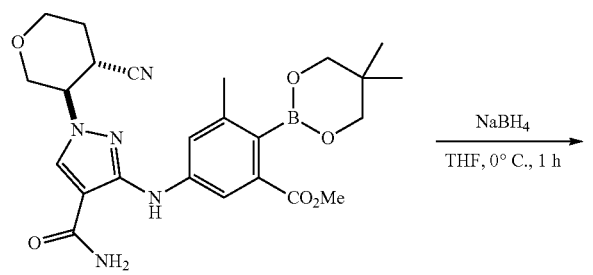

To a mixture of methyl 5-[[4-carbamoyl-1-[trans-4-cyanotetrahydropyran-3-yl]pyrazol-3-yl]amino]-2-(5,5-dimethyl-1,3,2-dioxaborinan-2-yl)-3-methyl-benzoate (1.00 g, 2.02 mmol, 1 eq) in THF (20 mL) was added NaBH$_4$ (382 mg, 10.1 mmol, 5 eq) in portions at 0° C. under N$_2$. The mixture was stirred at 0° C. for 1 h. LCMS showed the reaction was completed and desired MS observed. 2 parallel reactions were combined for work up. The mixture was added H$_2$O (15 mL), adjusted pH=5 with HCl (2N) and extracted with EtOAc (10 mL×2). The combined organic layers were washed by brine (10 mL×2), dried over Na$_2$SO$_4$, filtered and concentrated under reduced pressure to get a residue. The residue was purified by prep-HPLC (column: Phenomenex luna C18 (250*70 mm, 15 um); mobile phase: [water (0.04% HCl)-ACN]; B %: 17%-47%, 20 min) to give 1-(trans-4-cyanotetrahydropyran-3-yl)-3-[(1-hydroxy-7-methyl-3H-2,1-benzoxaborol-5-yl)amino]pyrazole-4-carboxamide (543 mg, 34.0% yield, 96.4% purity). The product (543 mg, 96.4% purity) was purified by SFC (column: DAICEL CHIRALPAK IG (250 mm*30 mm, 10 um); mobile phase: [Neu-IPA]; B %: 40%-40%, 6 min) to give 1-[trans-4-cyanotetrahydropyran-3-yl]-3-[(1-hydroxy-7-methyl-3H-2,1-benzoxaborol-5-yl) amino] pyrazole-4-carboxamide (stereoisomer one) (243 mg, 99.6% purity, 99.4% ee, first peak, Rt=2.153 min) as a white solid. $^1$H NMR (DMSO-d$_6$, 400 MHz) δ 9.33 (s, 1H), 8.59 (s, 1H), 8.31 (s, 1H), 7.73 (br s, 1H), 7.46 (s, 1H), 7.21 (br s, 1H), 7.07 (s, 1H), 4.90 (s, 2H), 4.58-4.55 (m, 1H), 4.07-4.02 (m, 1H), 3.92-3.87 (m, 1H). 3.71-3.64 (m, 2H), 3.52-3.48 (m, 1H), 2.40 (s, 3H), 2.18-2.14 (m, 1H), 2.02-1.97 (m, 1H), MS (ESI): mass calculated for C$_{18}$H$_{20}$BN$_5$O$_4$ 381.16, m/z found 382.3 [M+H]$^+$. HPLC: 99.65% (220 nm), 100% (254 nm). and 1-[trans-4-cyano tetrahydropyran-3-yl]-3-[(1-hydroxy-7-methyl-3H-2,1-benzoxaborol-5-yl)amino]pyrazole-4-carboxamide (stereoisomer two) (233 mg, 99.4% purity, 97.1% ee, second peak, Rt=2.533 min) as a white solid. $^1$H NMR (DMSO-hd 6, 400 MHz) δ 9.33 (s, 1H), 8.60 (s, 1H), 8.30 (s, 1H), 7.73 (br s, 1H), 7.46 (s, 1H), 7.21 (br s, 1H), 7.07 (s, 1H), 4.90 (s, 2H), 4.58-4.55 (m, 1H), 4.07-4.02 (m, 1H), 3.92-3.87 (m, 1H). 3.71-3.64 (m, 2H), 3.52-3.48 (m, 1H), 2.40 (s, 3H), 2.18-2.14 (m, 1H), 2.02-1.97 (m, 1H), MS (ESI): mass calculated for C$_{18}$H$_{20}$BN$_5$O$_4$ 381.16, m/z found 382.2 [M+H]$^+$. HPLC: 99.43% (220 nm), 100% (254 nm).

7. Preparation of 1-(trans-4-cyanotetrahydro-2H-pyran-3-yl)-3-((1-hydroxy-3,4-dihydro-1H-benzo[c][1,2]oxaborinin-6-yl)amino)-1H-pyrazole-4-carboxamide

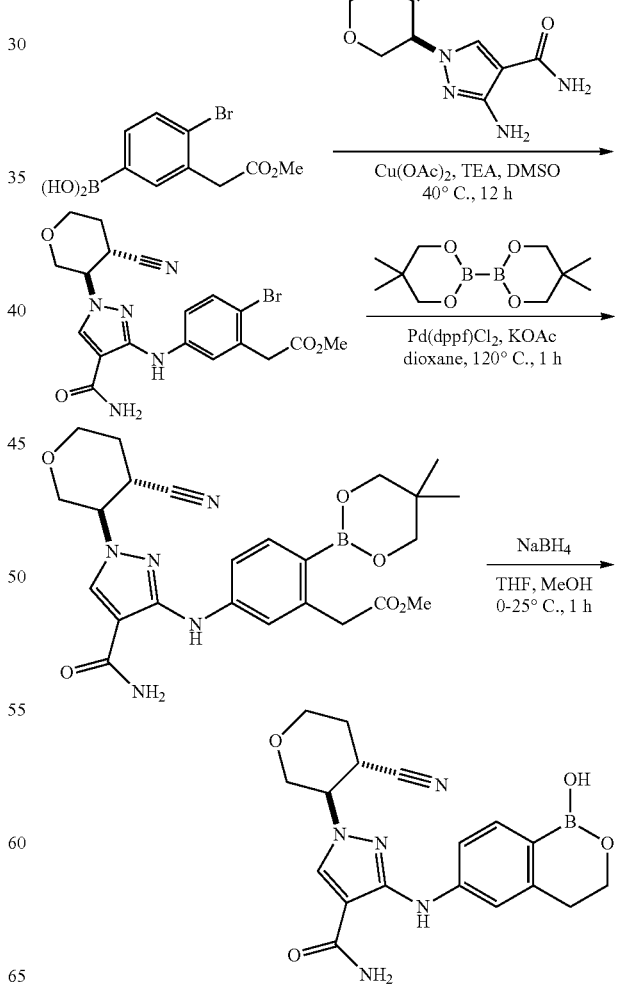

7.1 Preparation of methyl 2-(2-bromo-5-((4-carbamoyl-1-(trans-4-cyanotetrahydro-2H-pyran-3 yl)-1H-pyrazol-3 yl)amino)phenyl)acetate

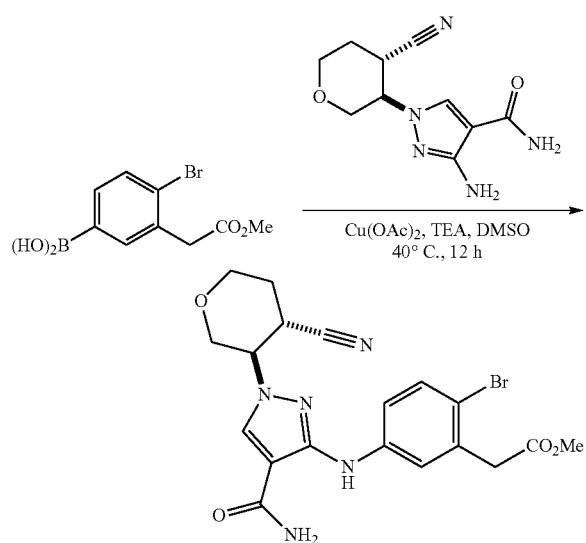

To a solution of 3-amino-1-(trans-4-cyanotetrahydro-2H-pyrazol-3-yl)-1H-pyrazole-4-carboxamide (948 mg, 4.03 mmol, 1.1 eq) in DMSO (15 mL) was added Cu(OAc)₂ (1.66 g, 9.16 mmol, 2.5 eq), [4-bromo-3-(2-methoxy-2-oxo-ethyl)phenyl]boronic acid (1 g, 3.66 mmol, 1 eq) and TEA (1.85 g, 18.3 mmol, 2.6 mL, 5 eq) at 25° C., the resulting mixture was stirred at 40° C. for 12 h under O₂ atmosphere. The reaction mixture was cooled to r.t., filtered with celite, the filtrate was diluted with H₂O (20 mL), extracted with EtOAc (10 mL×3). The combined organic layers were washed with brine (20 mL), dried over Na₂SO₄, filtered and concentrated in vacuo to give a residue. The residue was purified by flash silica gel chromatography (ISCO®; 12 g SepaFlash® Silica Flash Column, Eluent of 0~50% Ethyl acetate/Petroleum ether gradient @ 50 mL/min) to give methyl 2-(2-bromo-5-((4-carbamoyl-1-(trans-4-cyanotetrahydro-2H-pyran-3-yl)-1H-pyrazol-3-yl)amino)phenyl)acetate (1.20 g, 2.60 mmol, 70.83% yield) as a yellow solid. ¹H NMR (DMSO-d₆, 400 MHz) δ 9.25 (s, 1H), 8.31 (s, 1H), 7.75 (s, 1H), 7.54-7.50 (m, 1H), 7.76-7.43 (m, 2H), 7.25 (s, 1H), 4.59-4.56 (m, 1H), 4.03-4.02 (m, 2H), 3.79-3.78 (m, 1H), 3.70 (s, 2H), 3.69-3.68 (m, 1H), 3.66 (s, 3H), 3.63-3.62 (m, 1H), 2.14-2.08 (m, 1H), 1.99-1.98 (m, 1H).

7.2 Preparation of methyl 2-(S-((4-carbamoyl-1-(trans-4-cyanotetrahydro-2H-pyran-3-yl)-1H-pyrazol-3-yl)amino)-2-(5,5-dimethyl-1,3,2-dioxaborinan-2-yl)phenyl)acetate

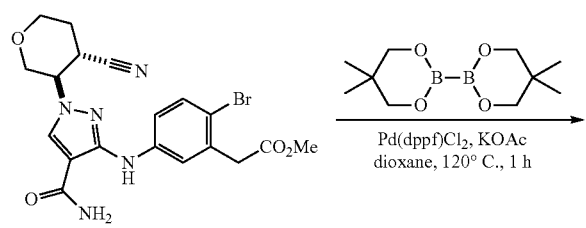

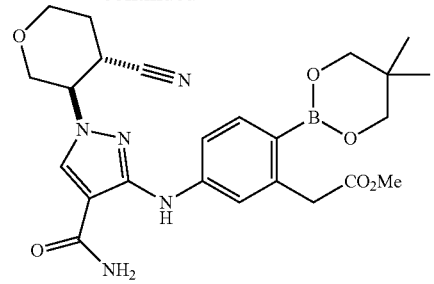

A mixture of 2-(5,5-dimethyl-1,3,2-dioxaborinan-2-yl)-5,5-dimethyl-1,3,2-dioxaborinane (855 mg, 3.79 mmol, 2.5 eq), methyl 2-(2-bromo-5-((4-carbamoyl-1-(trans-4-cyanotetrahydro-2H-pyran-3-yl)-1H-pyrazol-3-yl)amino)phenyl)acetate (700 mg, 1.51 mmol, 1 eq), KOAc (372 mg, 3.79 mmol, 2.5 eq) and Pd(PPh₃)₂Cl₂ (106 mg, 151 μmol, 0.1 eq) in dioxane (20 mL) was degassed and purged with N₂ for 3 times, the resulting mixture was stirred at 120° C. for 1 h under N₂ atmosphere. The reaction mixture was filtered, the filtrate was concentrated in vacuo to give a residue. The crude product was triturated with MTBE (5 mL) at 25° C. for 10 min to give methyl 2-(5-((4-carbamoyl-1-(trans-4-cyanotetrahydro-2H-pyran-3-yl)-1H-pyrazol-3-yl)amino)-2-(5,5-dimethyl-1,3,2-dioxaborinan-2-yl)phenyl)acetate (500 mg, crude) as a brown solid, which was used directly without further purification.

7.3 Preparation of 1-(trans-4-cyanotetrahydro-2H-pyran-3-yl)-3-((1-hydroxy-3,4-dihydro-1H-benzo[c][1,2]oxaborinin-6-yl)amino)-1H-pyrazole-4-carboxamide

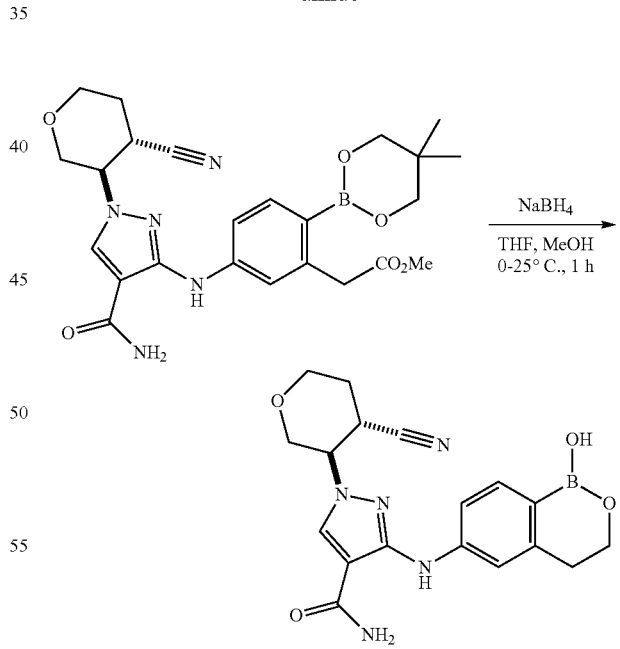

To a solution of methyl 2-(5-((4-carbamoyl-1-(trans-4-cyanotetrahydro-2H-pyran-3-yl)-1H-pyrazol-3-yl)amino)-2-(5,5-dimethyl-1,3,2-dioxaborinan-2-yl)phenyl)acetate (500 mg, 1.01 mmol, 1 eq) in THF (5 mL) and MeOH (1 mL) was added NaBH₄ (191 mg, 5.05 mmol, 5 eq) in portions at 0° C., the resulting mixture was stirred at 25° C. for 1 h. The reaction was quenched with 2N HCl, partitioned between H₂O (10 mL) and EtOAc (10 mL), and the aqueous layer was extracted with EtOAc (10 mL×2). The combined organic phase was washed with brine (10 mL×3), dried with anhydrous Na₂SO₄, filtered and concentrated in vacuo to give a residue. The residue was purified by Prep-HPLC (column: Phenomenex luna C18 80*40 mm*3 um; mobile phase: [water (0.04% HCl)-ACN]; B %: 15%-35%, 7 min) to give 1-(trans-4-cyanotetrahydro-2H-pyran-3-yl)-3-((1-hydroxy-3,4-dihydro-1H-benzo[c][1,2]oxaborinin-6-yl)amino)-1H-pyrazole-4-carboxamide (58 mg, 152.15 μmol, 15.07% yield) as a white solid. ¹H NMR (DMSO-hd 6, 400 MHz) δ 9.31 (s, 1H), 8.31 (s, 1H), 8.16 (s, 1H), 7.72 (s, 1H), 7.58 (d, J=8.4 Hz, 1H), 7.36 (dd, J=1.6, 8.0 Hz, 1H), 7.33 (s, 1H), 7.21 (s, 1H), 4.61-4.55 (m, 1H), 4.06-4.02 (m, 3H), 3.93-3.90 (m, 1H), 3.71-3.65 (m, 2H), 3.52-3.46 (m, 1H), 2.86-2.81 (m, 2H), 2.18-2.14 (m, 1H), 2.04-1.93 (m, 1H). MS (ESI): mass calculated for $C_{18}H_{20}BN_5O_4$, 381.16, m/z found 382.2 [M+H]⁺. Purity by HPLC: 93.88% (220 nm), 92.24 (254 nm).

8. Preparation of 1-(trans-2-cyanocyclopentyl)-3-[(2-hydroxy-1,2-benzoxaborinin-6-yl)amino]pyrazole-4-carboxamide

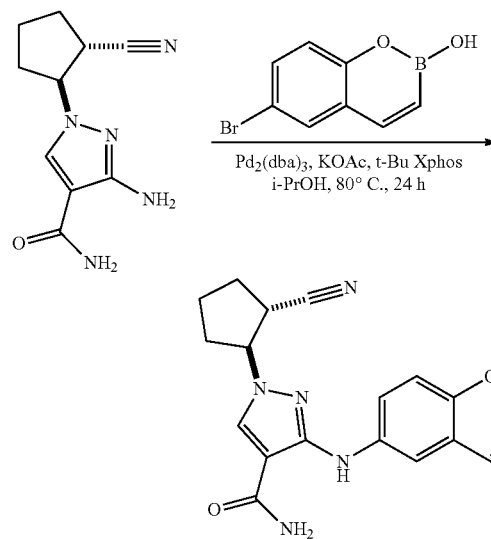

To a mixture of 3-amino-1-(2-cyanocyclopentyl)pyrazole-4-carboxamide (130 mg, 533 umol, 90% purity, 1.2 eq) and 6-bromo-2-hydroxy-1,2-benzoxaborinine (100 mg, 444 umol, 1 eq) in i-PrOH (2 mL) was added Pd₂(dba)₃ (20 mg, 22.2 umol, 0.05 eq), KOAc (65 mg, 667 umol, 1.5 eq) and t-Bu Xphos (19 mg, 44.4 umol, 0.1 eq) in one portion at 20° C. under N₂. The mixture was heated to 80° C. and stirred for 24 h. LCMS showed the reaction was completed and desired MS observed. The reaction mixture was quenched with H₂O (0.5 mL), filtered and concentrated under reduced pressure to give a residue. The residue was purified by prep-HPLC (column: Waters Xbridge BEH C18 100*30 mm*10 um; mobile phase: [water (10 mM NH₄HCO₃)-ACN]; B %: 15/0-45%, 8 min) to give 1-(trans-2-cyano cyclopentyl)-3-[(2-hydroxy-1,2-benzoxaborinin-6-yl)amino]pyrazole-4-carboxamide (74 mg, 22.9% yield, 95.0% purity) as a white solid. ¹H NMR (DMSO-hd 6, 400 MHz) δ 9.06 (s, 1H), 8.79 (s, 1H), 8.27 (s, 1H), 7.79 (d, J=2.8 Hz, 1H), 7.76 (d, J=11.6 Hz, 1H), 7.61 (br s, 1H), 7.49 (dd, J=2.8, 8.8 Hz, 1H), 7.20-7.10 (m, 2H), 6.10 (d, J=12.0 Hz, 1H), 4.87 (q, J=8.0 Hz, 1H), 3.42 (q, J=8.8 Hz, 1H), 2.35-2.29 (m, 1H), 2.26-2.19 (m, 1H), 2.12-2.03 (m, 1H), 2.01-1.84 (m, 3H). MS (ESI): mass calculated for $C_{18}H_{18}BN_5O_3$, 363.15, m/z found 362.2 [M−H]⁻. HPLC: 95.09% (220 nm), 99.68% (254 nm).

9. Preparation of 1-(trans-2-cyanocyclohexyl)-3-[(1-hydroxy-3H-2,1-benzoxaborol-6-yl)amino]pyrazole-4-carboxamide

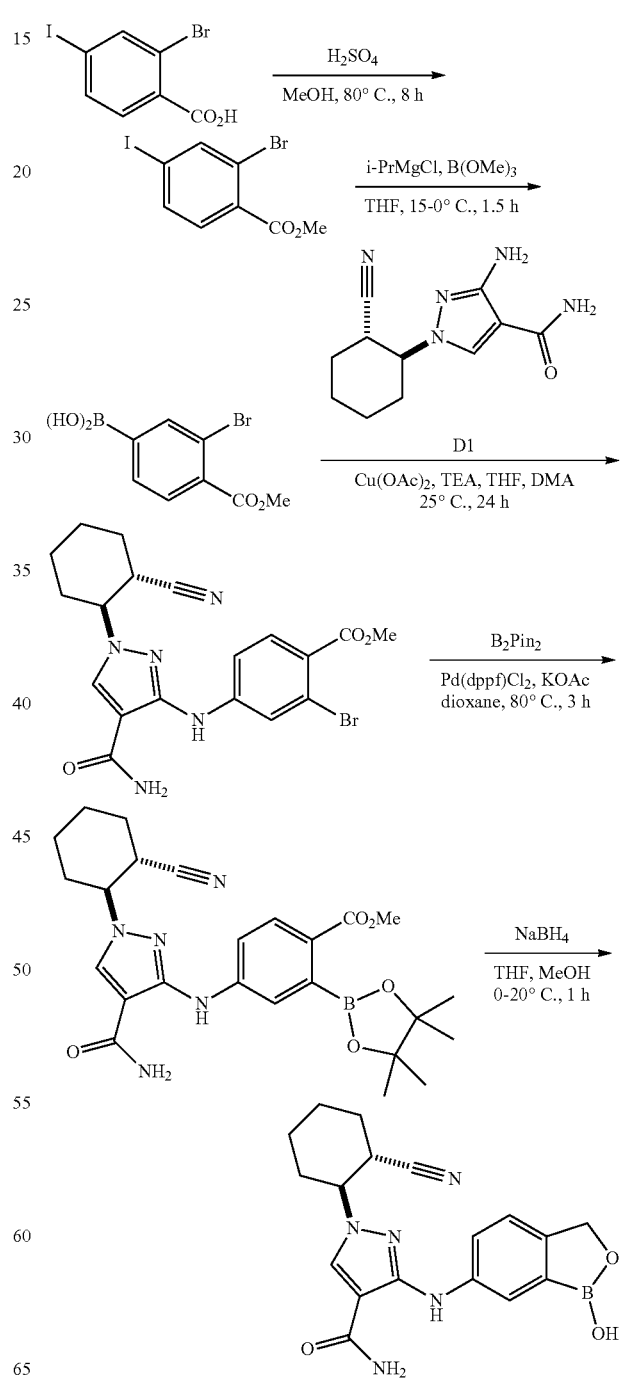

9.1 Preparation of methyl 2-bromo-4-iodo-benzoate

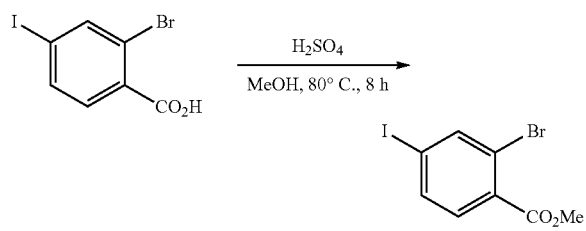

To a mixture of 2-bromo-4-iodo-benzoic acid (5.00 g, 15.3 mmol, 1 eq) in MeOH (100 mL) was added $H_2SO_4$ (7.65 g, 76.5 mmol, 4.2 mL, 98% purity, 5 eq) in one portion at 20° C. The mixture was heated to 80° C. and stirred at 80° C. for 8 h. TLC showed the reaction was completed. The reaction mixture was concentrated under reduced pressure to give a residue. The residue was poured into ice $H_2O$ (50 mL) and adjusted pH=7 by addition of sat·aq. $Na_2CO_3$. The mixture was extracted with EtOAc (40 mL×3). The combined organic layers were washed with brine (40 mL×2), dried over anhydrous $Na_2SO_4$, filtered and concentrated under reduced pressure to give methyl 2-bromo-4-iodo-benzoate (5.00 g, 95.9% yield) as a brown solid. 1H NMR ($CDCl_3$, 400 MHz) δ 8.06 (d, J=1.6 Hz, 1H), 7.71 (dd, J=1.6, 8.0 Hz, 1H), 7.53 (d, J=8.4 Hz, 1H), 3.93 (s, 3H).

9.2 Preparation of (3-bromo-4-methoxycarbonyl-phenyl)boronic acid

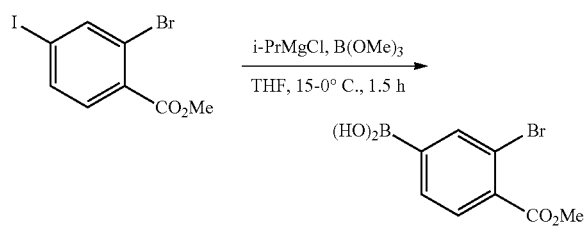

To a mixture of 2-[2-(dimethylamino)ethoxy]-N,N-dimethyl-ethanamine (4.51 g, 28.2 mmol, 1.2 eq) in THF (80 mL) was added i-PrMgCl (2 M, 14.1 mL, 1.2 eq) drop-wise at 15° C. under $N_2$. The mixture was stirred for 0.5 h at 15° C. Methyl 2-bromo-4-iodo-benzoate (8.00 g, 23.5 mmol, 1 eq) was added drop-wise to the reaction mixture and the resulting mixture was stirred at 25° C. for 10 min. Then $B(OMe)_3$ (4.88 g, 46.9 mmol, 5.3 mL, 2 eq) was added drop-wise at 0° C. and stirred for 1 h. LCMS showed the reaction was completed and desired MS observed. The reaction mixture was quenched with sat·aq. $NH_4Cl$ (80 mL) at 0° C. and adjusted pH=5 with HCl (2 N). Then the mixture was extracted with EtOAc (80 mL×4). The combined organic layers were washed with brine (80 mL×3), dried over $Na_2SO_4$, filtered and concentrated under reduced pressure to give a residue. The residue was purified by flash silica gel chromatography (ISCO®; 120 g SepaFlash® Silica Flash Column, Eluent of 0-100% Ethyl acetate/Petroleum ether gradient @ 100 mL/min) to give (3-bromo-4-methoxycarbonyl-phenyl)boronic acid (3.50 g, 57.6% yield) as a white solid. 1H NMR (DMSO-hd 6, 400 MHz) δ 8.04 (s, 1H), 7.80 (dd, J=0.8, 7.6 Hz, 1H), 7.69 (d, J=7.6 Hz, 1H), 3.83 (s, 3H).

9.3 Preparation of methyl 2-bromo-4-[[4-carbamoyl-1-(trans-2-cyanocyclohexyl)pyrazol-3-yl]amino]benzoate

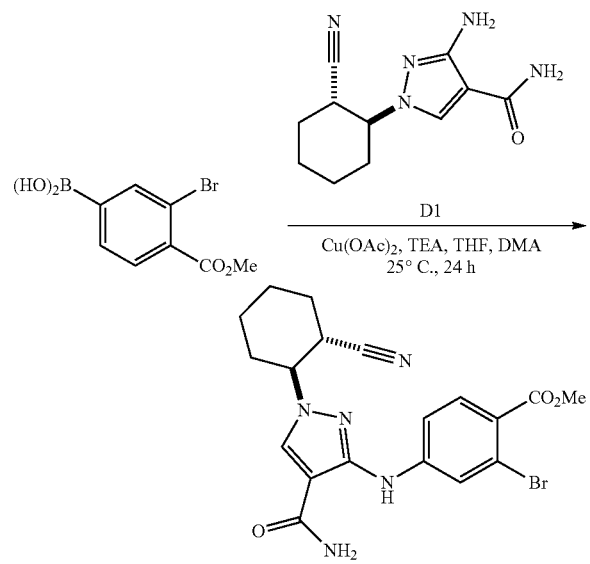

To a mixture of (3-bromo-4-methoxycarbonyl-phenyl)boronic acid (800 mg, 3.09 mmol, 1 eq) and 3-amino-1-(2-cyanocyclohexyl)pyrazole-4-carboxamide (865 mg, 3.71 mmol, 1.2 eq) in THF (20 mL) and DMA (5 mL) was added TEA (1.56 g, 15.4 mmol, 2.15 mL, 5 eq), $Cu(OAc)_2$ (1.40 g, 7.73 mmol, 2.5 eq) and 4 A molecular sieve (1.5 g) in one portion at 25° C. under $O_2$. The mixture was stirred at 25° C. for 24 h. LCMS showed the reaction was completed and desired MS observed. The reaction mixture was filtered and the filtrate was concentrated under reduced pressure to give a residue. The residue was purified by flash silica gel chromatography (ISCO®; 40 g SepaFlash® Silica Flash Column, Eluent of 0~100% Ethyl acetate/Petroleum ether gradient @ 50 mL/min) to give methyl 2-bromo-4-[[4-carbamoyl-1-(trans-2-cyanocyclohexyl)pyrazol-3-yl]amino]benzoate (600 mg, 43.5% yield) as yellow oil. 1H NMR (DMSO-hd 6, 400 MHz) δ 11.95 (br s, 1H), 9.58 (s, 1H), 8.30 (s, 1H), 7.99 (d, J=2.0 Hz, 1H), 7.80 (d, J=8.8 Hz, 1H), 7.77 (br s, 1H), 7.58 (dd, J=2.4, 8.8 Hz, 1H), 7.28 (br s, 1H), 4.44 (dt, J=4.4, 11.2 Hz, 1H), 3.80 (s, 3H), 3.26-3.20 (m, 1H), 2.20-2.17 (m, 1H), 1.86-1.73 (m, 5H), 1.49-1.27 (m, 2H).

9.4 Preparation of methyl 4-[[4-carbamoyl-1-(trans-2-cyanocyclohexyl)pyrazol-3-yl]amino]-2-(4,4,5,5-tetramethyl-1,3,2-dioxaborolan-2-yl)benzoate

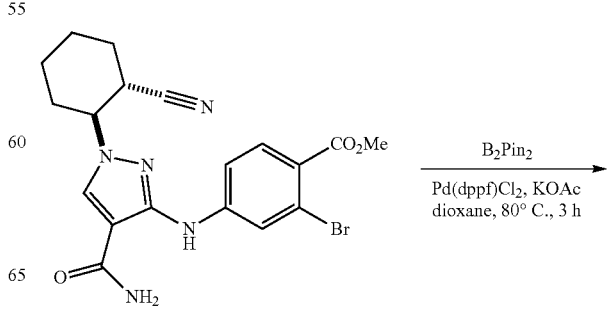

-continued

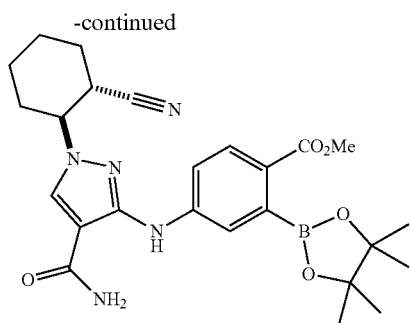

To a mixture of methyl 2-bromo-4-[[4-carbamoyl-1-(trans-2-cyanocyclohexyl)pyrazol-3-yl]amino] benzoate (430 mg, 963 umol, 1 eq) and 4,4,5,5-tetramethyl-2-(4,4,5,5-tetramethyl-1,3,2-dioxaborolan-2-yl)-1,3,2-dioxaborolane (489 mg, 1.93 mmol, 2 eq) in dioxane (5 mL) was added KOAc (284 mg, 2.89 mmol, 3 eq) and Pd(dppf)Cl2 (35 mg, 48.1 umol, 0.05 eq) in one portion at 25° C. under $N_2$. The mixture was stirred at 80° C. for 3 h. LCMS showed the reaction was completed and desired MS observed. The reaction mixture was filtered and the filtrate was concentrated under reduced pressure to give a residue. The residue was purified by flash silica gel chromatography (ISCO®; 40 g SepaFlash® Silica Flash Column, Eluent of 0~100% Ethyl acetate/Petroleum ether gradient @ 50 mL/min) to give methyl 4-[[4-carbamoyl-1-(trans-2-cyanocyclohexyl)pyrazol-3-yl]amino]-2-(4,4,5,5-tetramethyl-1,3,2-dioxaborolan-2-yl)benzoate (300 mg, 63.1% yield) as a yellow solid. 1H NMR (DMSO-hd 6, 400 MHz) δ 9.52 (s, 1H), 8.28 (s, 1H), 7.87 (d, J=8.8 Hz, 1H), 7.80 (d, J=8.8 Hz, 1H), 7.76 (br d, J=2.0 Hz, 1H), 7.62 (d, J=8.8 Hz, 1H), 7.48 (dd, J=2.0, 8.4 Hz, 1H), 7.25 (br s, 1H), 4.43 (dt, J=4.0, 11.2 Hz, 1H), 3.80 (s, 3H), 3.27-3.17 (m, 1H), 2.17 (br d, J=11.6 Hz, 1H), 1.87-1.69 (m, 5H), 1.51-1.23 (m, 14H).

9.5 Preparation of 1-(trans-2-cyanocyclohexyl)-3-[(1-hydroxy-3H-2,1-benzoxaborol-6-yl) amino]pyrazole-4-carboxamide

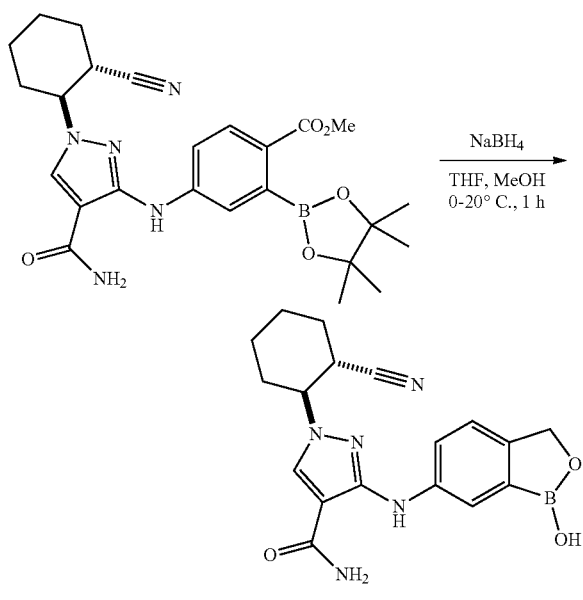

To a mixture of methyl 4-[[4-carbamoyl-1-(2-cyanocyclohexyl)pyrazol-3-yl]amino]-2-(4,4,5,5-tetramethyl-1,3,2-dioxaborolan-2-yl)benzoate (300 mg, 608 umol, 1 eq) in THF (10 mL) and MeOH (0.5 mL) was added NaBH4 (69 mg, 1.82 mmol, 3 eq) in portions at 0° C. The mixture was stirred at 25° C. for 1 h. LCMS showed the reaction was completed and desired MS observed. The reaction mixture was added water (10 mL) at 0° C. The resulting mixture was adjusted pH to 5 with HCl (2 N) and stirred for 10 min at 0° C. The solution was diluted with EtOAc (5 mL) and extracted with EtOAc (10 mL×3). The combined organic layers were washed with brine (15 mL×2), dried over $Na_2SO_4$, filtered and concentrated under reduced pressure to give a residue. The residue was purified by prep-HPLC (column: Welch Xtimate C18 100*25 mm*3 um; mobile phase: [water (0.04% HCl)-ACN]; B %: 10%-40%, 8 min) to give 1-(trans-2-cyanocyclohexyl)-3-[(1-hydroxy-3H-2,1-benzoxaborol-6-yl) amino]pyrazole-4-carboxamide (133 mg, 60.1% yield, 100% purity) as a white solid. 1H NMR (DMSO-hd 6, 400 MHz) δ 9.23 (s, 1H), 9.09 (s, 1H), 8.23 (s, 1H), 7.75-7.70 (m, 1H), 7.73-7.70 (m, 1H), 7.67 (br s, 1H), 7.29 (d, J=8.4 Hz, 1H), 7.16 (br s, 1H), 4.92 (s, 2H), 4.38 (dt, J=3.6, 10.8 Hz, 1H), 3.30-3.27 (m, 1H), 2.19 (br d, J=10.0 Hz, 1H), 2.00-1.97 (m, 1H), 1.90-1.70 (m, 4H), 1.52-1.29 (m, 2H). MS (ESI): mass calculated for $C_{18}H_{20}BN_5O_3$, 365.17, m/z found 366.2 [M+H]+. HPLC: 100.00% (220 nm), 100.00 (254 nm).

10. Preparation of 1-(trans-2-cyanocyclopentyl)-3-[(1-hydroxy-3H-2,1-benzoxaborol-6-yl)amino]pyrazole-4-carboxamide

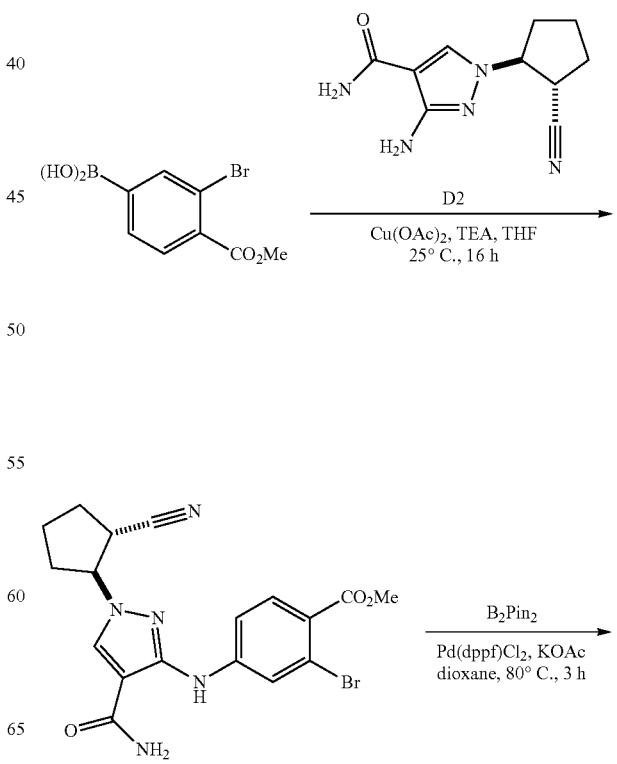

-continued

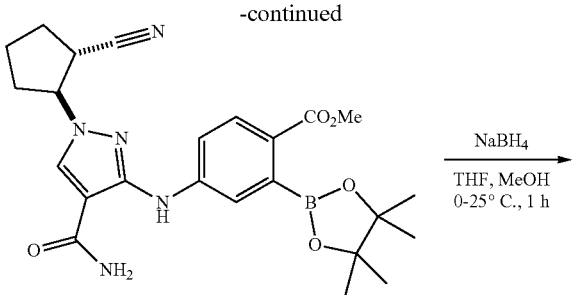

10.1 Preparation of methyl 2-bromo-4-[[4-carbamoyl-1-(trans-2-cyanocyclopentyl)pyrazol-3-yl]amino]benzoate

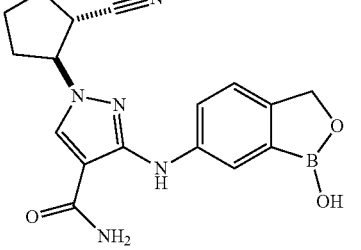

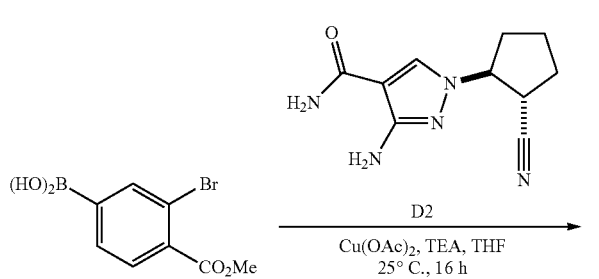

To a mixture of (3-bromo-4-methoxycarbonyl-phenyl) boronic acid (600 mg, 2.32 mmol, 1 eq) and 3-amino-1-(trans-2-cyanocyclopentyl)pyrazole-4-carboxamide (509 mg, 2.32 mmol, 1 eq) in THF (10 mL) was added TEA (1.17 g, 11.6 mmol, 1.6 mL, 5 eq), Cu(OAc)$_2$ (1.05 g, 5.80 mmol, 2.5 eq) and 4 Å molecular sieve (1 g) at 25° C. under O$_2$. The mixture was stirred at 25° C. for 16 h. LCMS showed the reaction was completed and desired MS observed. The reaction mixture was filtered and the filtrate was concentrated under reduced pressure to give a residue. The residue was purified by flash silica gel chromatography (ISCO®; 40 g SepaFlash® Silica Flash Column, Eluent of 0-100% Ethyl acetate/Petroleum ether gradient @ 50 mL/min) to give methyl 2-bromo-4-[[4-carbamoyl-1-(trans-2-cyanocyclopentyl)pyrazol-3-yl]amino]benzoate (0.36 g, 35.9% yield) as a yellow solid. 1H NMR (DMSO-hd 6, 400 MHz) δ 9.57 (s, 1H), 8.34 (s, 1H), 8.06 (d, J=2.0 Hz, 1H), 7.79 (d, J=8.8 Hz, 1H), 7.73 (br s, 1H), 7.54 (dd, J=2.0, 8.4 Hz, 1H), 7.28 (br s, 1H), 4.96 (q, J=8.0 Hz, 1H), 3.79 (s, 3H), 3.43-3.35 (m, 1H), 2.33-2.21 (m, 2H), 2.14-2.05 (m, 1H), 1.98-1.87 (m, 5H).

10.2 Preparation of methyl 4-[[4-carbamoyl-1-(trans-2-cyanocyclopentyl)pyrazol-3-yl]amino]-2-(4,4,5,5-tetramethyl-1,3,2-dioxaborolan-2-yl)benzoate

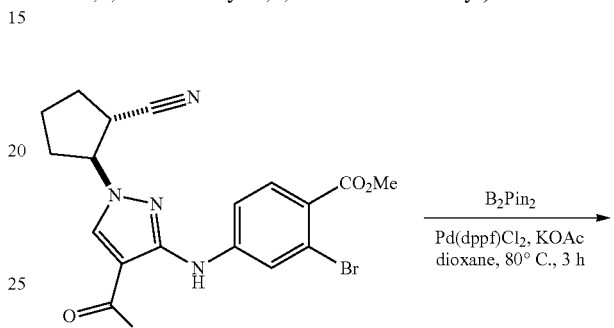

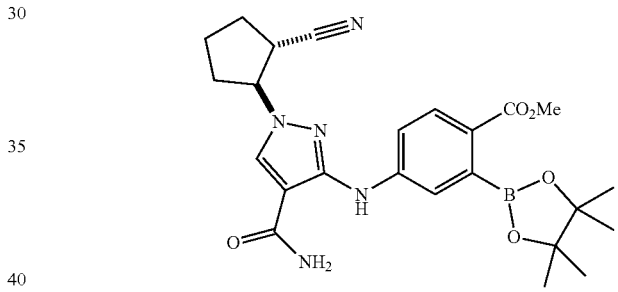

To a mixture of methyl 2-bromo-4-[[4-carbamoyl-1-(trans-2-cyanocyclopentyl)pyrazol-3-yl]amino]benzoate (360 mg, 832 umol, 1 eq) and 4,4,5,5-tetramethyl-2-(4,4,5,5-tetramethyl-1,3,2-dioxaborolan-2-yl)-1,3,2-dioxaborolane (B$_2$Pin$_2$, 423 mg, 1.67 mmol, 2 eq) in dioxane (5 mL) was added KOAc (246 mg, 2.50 mmol, 3 eq) and Pd(dppf)C12 (31 mg, 41.6 umol, 0.05 eq) in one portion at 20° C. under N$_2$. The mixture was heated to 80° C. and stirred at 80° C. for 3 h. LCMS showed the reaction was completed and desired MS observed. The reaction mixture was filtered and the filtrate was concentrated under reduced pressure to give a residue. The residue was purified by flash silica gel chromatography (ISCO®; 40 g SepaFlash® Silica Flash Column, Eluent of 0~100% Ethyl acetate/Petroleum ether gradient @ 50 mL/min) to give methyl4-[[4-carbamoyl-1-(trans-2-cyanocyclopentyl)pyrazol-3-yl]amino]-2-(4,4,5,5-tetramethyl-1,3,2-dioxaborolan-2-yl)benzoate (0.3 g, 75.1% yield) as a yellow solid. 1H NMR (DMSO-hd 6, 400 MHz) δ 9.55 (d, J=14.8 Hz, 1H), 8.32 (d, J=0.8 Hz, 1H), 7.86 (d, J=8.8 Hz, 1H), 7.80 (d, J=8.8 Hz, 0.5H), 7.72 (br s, 0.5H), 7.68 (d, J=2.0 Hz, 0.5H), 7.64-7.62 (m, 1H), 7.52 (dd, J=2.0, 8.4 Hz, 0.5H), 7.25 (br s, 1H), 4.99-4.92 (m, 1H), 3.79 (d, J=1.6 Hz, 3H), 3.46-3.38 (m, 1H), 2.31-2.23 (m, 2H), 2.14-2.05 (m, 1H), 1.97-1.82 (m, 3H), 1.33 (s, 6H).

10.3 Preparation of 1-(trans-2-cyanocyclopentyl)-3-[(1-hydroxy-3H-2,1-benzoxaborol-6-yl)amino] pyrazole-4-carboxamide

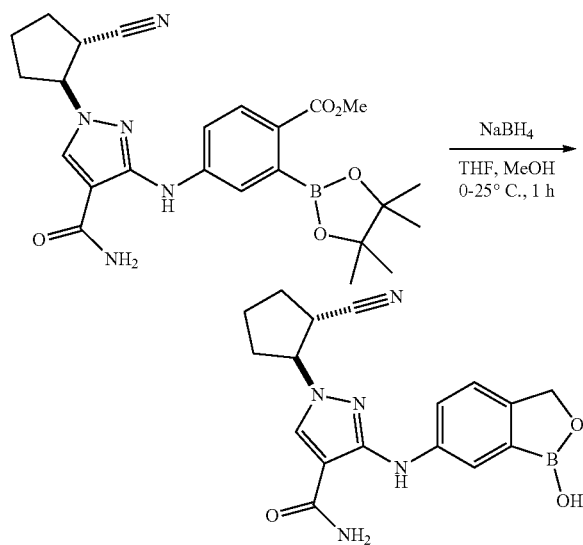

To a mixture of methyl 4-[[4-carbamoyl-1-(trans-2-cyanocyclopentyl)pyrazol-3-yl]amino]-2-(4,4,5,5-tetramethyl-1,3,2-dioxaborolan-2-yl)benzoate (300 mg, 625 umol, 1 eq) in THF (10 mL) and MeOH (0.5 mL) was added NaBH$_4$ (72 mg, 1.88 mmol, 3 eq) in portions at 0° C. The reaction was allowed to warm to 25° C. and stirred at 25° C. for 1 h. LCMS showed the reaction was completed and desired MS observed. The reaction mixture was quenched with H$_2$O (10 mL) at 0° C., adjusted pH to 5 with HCl (2 N) and stirred for 10 min at 0° C. The mixture was extracted with EtOAc (10 mL×3). The combined organic layers were washed with brine (15 mL×2), dried over Na$_2$SO$_4$, filtered and concentrated under reduced pressure to give a residue. The residue was purified by prep-HPLC (column: Welch Xtimate C18 100*25 mm*3 um; mobile phase: [water (0.04% HCl)-ACN]; B %: 10%-40%, 8 min) to give 1-(trans-2-cyanocyclopentyl)-3-[(1-hydroxy-3H-2,1-benzoxaborol-6-yl) amino] pyrazole-4-carboxamide (73.6 mg, 33.5% yield, 100% purity) as a white solid. 1H NMR (DMSO-hd 6, 400 MHz) δ 9.21 (s, 1H), 9.04 (s, 1H), 8.28 (s, 1H), 7.75-7.71 (m, 2H), 7.64 (br s, 1H), 7.29 (d, J=8.0 Hz, 1H), 7.16 (br s, 1H), 4.92 (s, 2H), 4.91-4.87 (m, 1H), 3.47-3.40 (m, 1H), 2.32-2.28 (m, 1H), 2.25-2.17 (m, 1H), 2.14-2.04 (m, 1H), 2.01-1.84 (m, 3H). MS (ESI): mass calculated for C$_{17}$H$_{18}$BN$_5$O$_3$, 351.15, m/z found 352.2 [M+H]$^+$. HPLC: 100.00% (220 nm), 100.00 (254 nm).

11. Preparation of 1-(trans-2-cyanocyclohexyl)-3-((1-hydroxy-1,3-dihydrobenzo[c][1,2] oxaborol-5-yl)amino)-1H-pyrazole-4-carboxamide

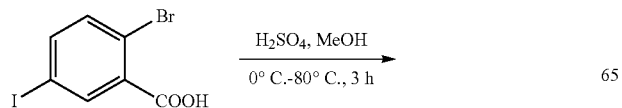

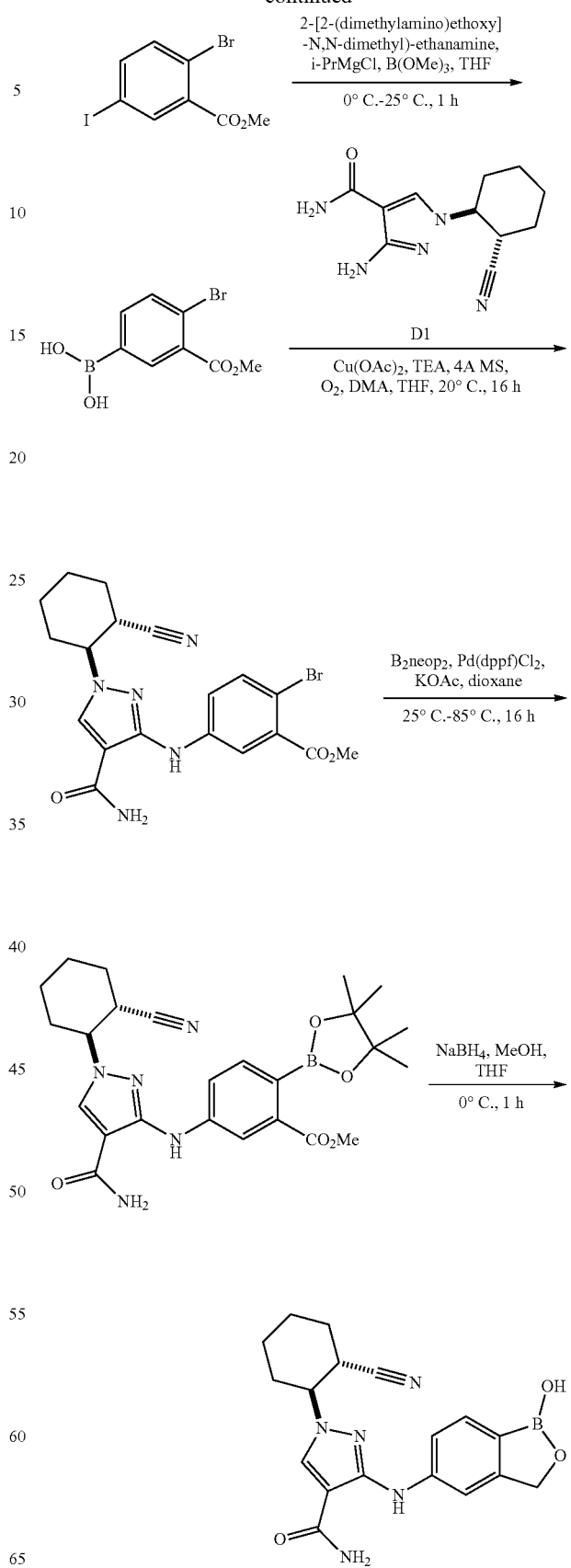

11.1 Preparation of methyl 2-bromo-5-iodo-benzoate 1

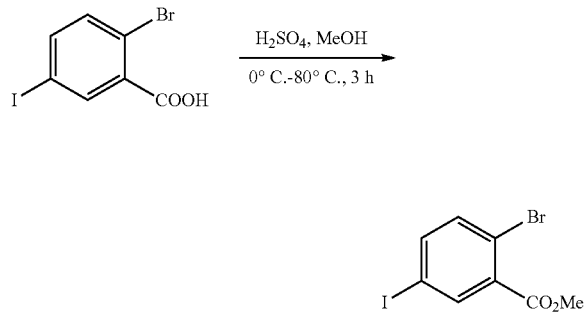

To a solution of 2-bromo-5-iodo-benzoic acid (10.0 g, 30.5 mmol, 1 eq) in MeOH (150 mL) was added drop-wise a solution of $H_2SO_4$ (4.89 mL, 91.7 mmol, 3 eq) at 0° C. over a period of 5 mins under $N_2$. The reaction was heated and stirred at 80° C. for 3 h. TLC showed the reaction was completed. The reaction mixture was adjusted pH to 7 with sat·aq. $Na_2CO_3$ (100 mL) at 0° C., and extracted with ethyl acetate (100 mL×3). The combined organic phase was washed with brine (100 mL×2), dried with anhydrous $Na_2SO_4$, filtered and concentrated in vacuum to give a residue. The residue was purified by column chromatography ($SiO_2$, Petroleum ether/Ethyl acetate=10/1 to 5/1) to give methyl 2-bromo-5-iodo-benzoate (10.0 g, 95.8% yield) as a yellow solid. $^1$H NMR (CDCl$_3$-d$_6$, 400 MHz) δ 8.10 (s, 1H), 7.63 (dd, J=8.4 Hz, 2.0 Hz, 1H), 7.38 (d, J=8.4 Hz, 1H), 3.94 (s, 3H).

11.2 Preparation of (4-bromo-3-methoxycarbonyl-phenyl)boronic acid

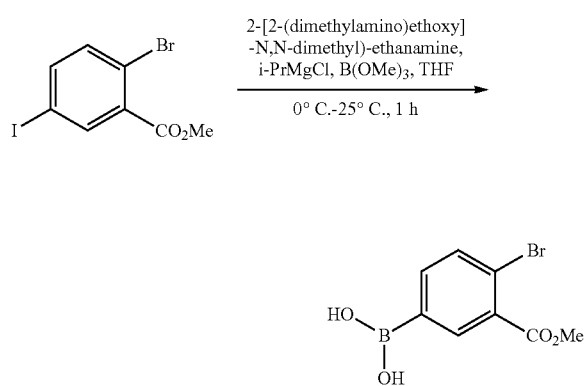

To a solution of 2-[2-(dimethylamino)ethoxy]-N,N-dimethyl-ethanamine (2.82 g, 17.6 mmol, 1.2 eq) in THF (60 mL) was added i-PrMgCl (2 M, 8.80 mL, 1.2 eq) at 15° C. The mixture was stirred at 15° C. for 20 min. Then methyl 2-bromo-5-iodo-benzoate (5.00 g, 14.6 mmol, 1 eq) was added drop-wise to the reaction mixture at 15° C. The resulting mixture was allowed to warm to 25° C. and continue stirred at 25° C. for 10 min. Trimethyl borate (3.31 mL, 29.3 mmol, 2 eq) was added drop-wise at 0° C. The reaction mixture was stirred at 0° C. for 1 h. TLC showed the reaction was completed. The reaction mixture was quenched by addition of sat. aq. $NH_4Cl$ (100 mL) at 0° C., then extracted with ethyl acetate (40 mL×3). The combined organic layers were washed with brine (90 mL×3), dried over $Na_2SO_4$, filtered and concentrated under reduced pressure to give a residue. The residue was purified by column chromatography ($SiO_2$, Petroleum ether/Ethyl acetate=1/1 to 0/1) to give (4-bromo-3-methoxycarbonyl-phenyl)boronic acid (2.00 g, 52.6% yield) as a yellow solid. $^1$H NMR (DMSO-hd 6, 400 MHz) δ 8.35 (s, 1H), 8.14-8.13 (m, 1H), 7.90-7.87 (m, 1H), 7.77-7.73 (m, 1H), 3.89-3.86 (m, 3H).

11.3 Preparation of methyl2-bromo-5-((4-carbamoyl-1-(trans-2-cyanocyclohexyl)-1H-pyrazol-3-yl)amino)benzoate

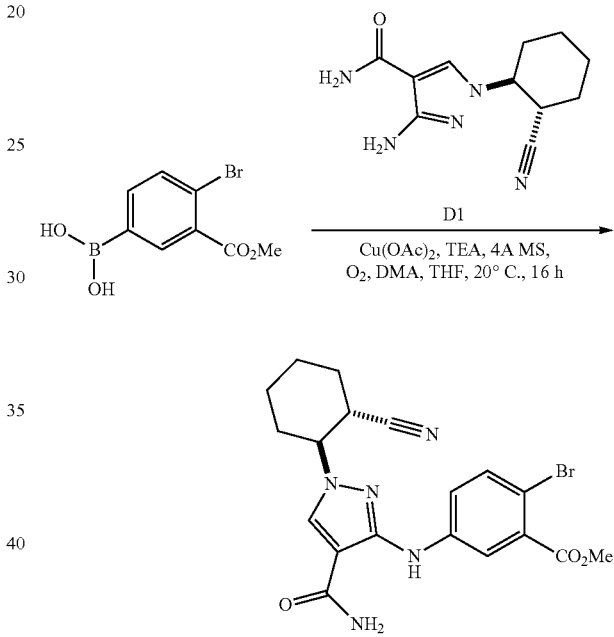

To a mixture of 3-amino-1-((1S,2S)-2-cyanocyclohexyl)-1H-pyrazole-4-carboxamide (793 mg, 3.40 mmol, 1.1 eq) and (4-bromo-3-methoxycarbonyl-phenyl)boronic acid (800 mg, 3.09 mmol, 1 eq) in THF (30 mL) and DMA (5 mL) was added Cu(OAc)$_2$ (1.40 g, 7.73 mmol, 2.5 eq), 4 A molecular sieve (1.5 g) and TEA (1.56 g, 15.4 mmol, 2.15 mL, 5 eq) in one portion at 20° C. under 02. The mixture was stirred at 20° C. for 16 h. LCMS showed the reaction was completed and desired MS observed. The reaction mixture was filtered and the filtrate was concentrated under reduced pressure to give a residue. The residue was purified by column chromatography ($SiO_2$, Ethyl acetate/Methanol=1/0 to 5/1) to give methyl 2-bromo-5-((4-carbamoyl-1-(trans-2-cyanocyclohexyl)-1H-pyrazol-3-yl)amino)benzoate (1.2 g, 87.0% yield) as a yellow solid. $^1$H NMR (DMSO-hd 6, 400 MHz) δ 12.50 (s, 1H), 9.89 (s, 1H), 8.14 (s, 1H), 8.55 (d, J=2.8 Hz, 1H), 8.25 (dd, J=8.8 Hz, 3.2 Hz, 1H), 8.11 (d, J=8.8 Hz, 1H), 7.77 (br s, 1H), 4.99-4.93 (m, 1H), 4.40 (s, 3H), 3.82-3.74 (m, 1H), 2.72-2.65 (m, 1H), 2.57-2.53 (m, 1H), 2.39-2.26 (m, 4H), 2.00-1.99 (m, 1H), 1.87-1.86 (m, 1H).

11.4 Preparation of methyl 5-((4-carbamoyl-1-(trans-2-cyanocyclohexyl)-1H-pyrazol-3-yl) amino)-2-(4,4,5,5-tetramethyl-1,3,2-dioxaborolan-2-yl)benzoate

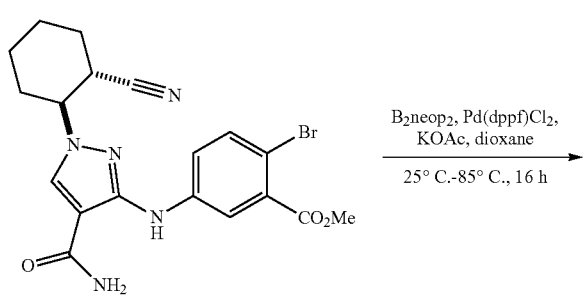

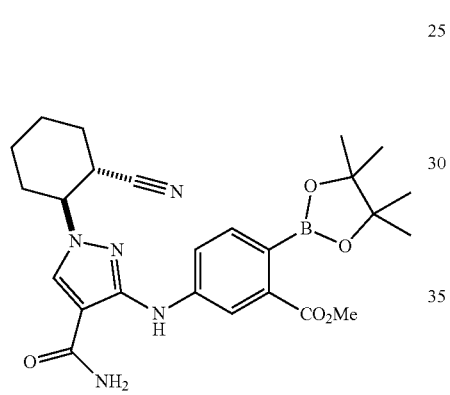

To a mixture of methyl 2-bromo-5-((4-carbamoyl-1-((1S, 2S)-2-cyanocyclohexyl)-1H-pyrazol-3-yl)amino)benzoate (1.0 g, 1.34 mmol, 60% purity, 1 eq) in dioxane (20 mL) was added KOAc (395 mg, 4.03 mmol, 3 eq), Pd(dppf)Cl2 (98.3 mg, 135 umol, 0.1 eq) and 4,4,4',4',5,5,5',5'-octamethyl-2,2'-bi(1,3,2-dioxaborolane) (853 mg, 3.36 mmol, 2.5 eq) in one portion at 25° C. under N$_2$, then the mixture was heated to 85° C. and stirred for 16 h. LCMS showed the reaction was completed and desired MS observed. The reaction mixture was filtered and the filtrate was concentrated in vacuum to give a residue. The residue was purified by column chromatography (SiO$_2$, Ethyl acetate/Methanol=1/0 to 10/1) to give methyl 5-((4-carbamoyl-1-(trans-2-cyanocyclohexyl)-1H-pyrazol-3-yl)amino)-2-(4,4,5,5-tetramethyl-1,3,2-dioxaborolan-2-yl)benzoate (500 mg, crude) as brown oil. $^1$H NMR (DMSO-hd 6, 400 MHz) δ 9.37 (s, 1H), 8.27 (s, 1H), 7.97 (d, J=2.4 Hz, 1H), 7.77 (dd, J=8.4 Hz, 2.4 Hz, 1H), 7.71 (br s, 1H), 7.40 (d, J=8.0 Hz, 1H), 7.22 (br s, 1H), 4.45-4.38 (m, 1H), 3.82 (s, 3H), 3.27-3.20 (m, 1H), 2.21-2.17 (m, 1H), 2.03-1.98 (m, 1H), 1.96 (m, 12H), 1.83-1.72 (m, 4H), 1.49-1.32 (m, 2H).

11.5 Preparation of 1-(trans-2-cyanocyclohexyl)-3-((1-hydroxy-1,3-dihydrobenzo[c][1,2]oxaborol-5-yl) amino)-1H-pyrazole-4-carboxamide

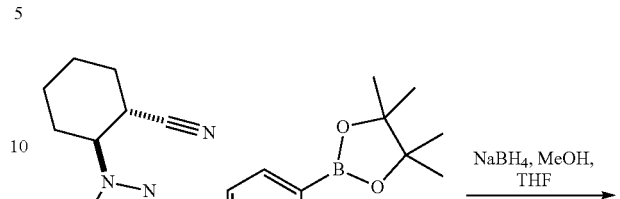

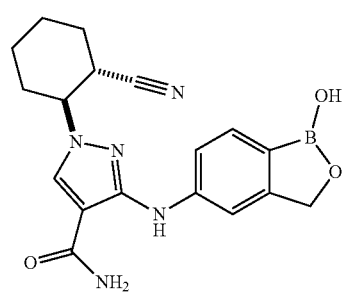

To a mixture of methyl 5-((4-carbamoyl-1-((1S,2S)-2-cyanocyclohexyl)-1H-pyrazol-3-yl) amino)-2-(4,4,5,5-tetramethyl-1,3,2-dioxaborolan-2-yl)benzoate (500 mg, 1.01 mmol, 1 eq) in THF (10 mL) was added MeOH (12.3 mmol, 0.5 mL, 12.1 eq) and NaBH$_4$ (115 mg, 3.04 mmol, 3 eq) in portions at 0° C. under N$_2$. The mixture was stirred at 0° C. for 1 h. LCMS showed the reaction was completed and desired MS observed. The mixture was poured into ice-water (w/w=1/1) (20 mL). The reaction mixture was adjusted pH to 4-5 with HCl (2 N) at 0° C. The aqueous phase was extracted with ethyl acetate (10 mL×3). The combined organic phases was washed with brine (10 mL), dried with anhydrous Na$_2$SO$_4$, filtered and concentrated in vacuum to give a residue. The residue was purified by prep-HPLC (column: Phenomenex luna C18 80*40 mm*3 um; mobile phase: [water (0.04% HCl)-ACN]; B %: 27%-45%, 7 min) to give 1-(trans-2-cyanocyclohexyl)-3-((1-hydroxy-1,3-dihydrobenzo [c][1,2]oxaborol-5-yl)amino)-1H-pyrazole-4-carboxamide (107 mg, 28.8% yield, 99.7% purity) as a white solid. $^1$H NMR (DMSO-hd 6, 400 MHz) δ 9.39 (s, 1H), 8.88 (s, 1H), 8.26 (s, 1H), 7.70 (br s, 1H), 7.60-7.57 (m, 2H), 7.38 (d, J=8.0 Hz, 1H), 7.19 (br s, 1H), 4.93 (s, 2H), 4.43-4.36 (m, 1H), 3.30-3.24 (m, 1H), 2.19-1.98 (m, 2H), 1.85-1.72 (m, 4H), 1.45-1.36 (m, 2H). MS (ESI): mass calculated for C$_{18}$H$_{20}$BN$_5$O$_3$ 365.17, m/z found 366.2 [M+H]$^+$. HPLC: 99.79% (220 nm), 100% (254 nm).

12. Preparation of 1-(trans-2-cyanocyclopentyl)-3-((1-hydroxy-1,3-dihydrobenzo[c][1,2]oxaborol-5-yl)amino)-1H-pyrazole-4-carboxamide

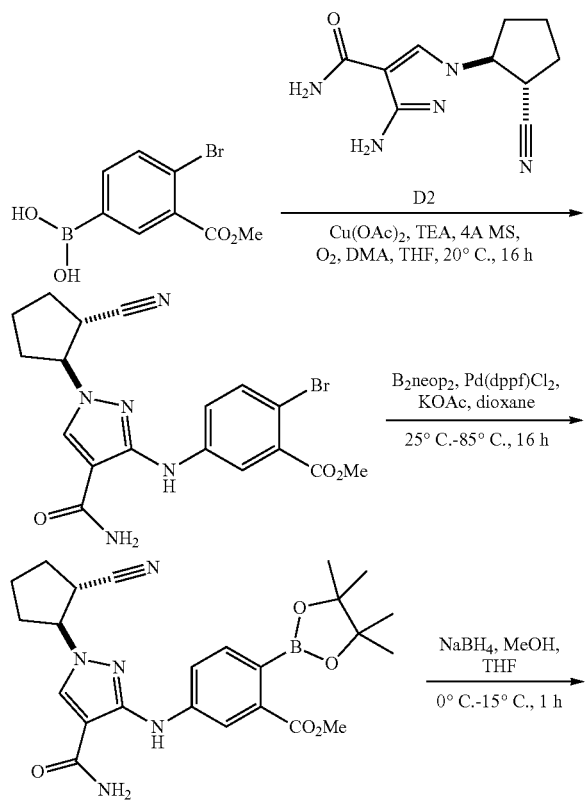

12.1 Preparation of methyl 2-bromo-5-((4-carbamoyl-1-(trans-2-cyanocyclopentyl)-1H-pyrazol-3-yl)amino)benzoate

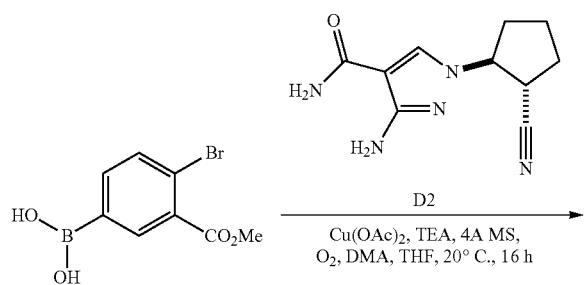

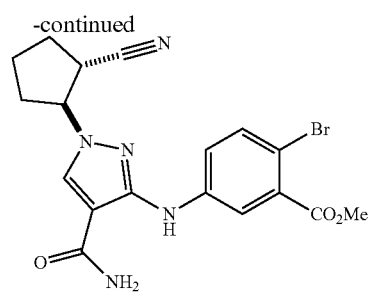

To a mixture of 3-amino-1-(trans-2-cyanocyclopentyl)-1H-pyrazole-4-carboxamide (700 mg, 3.19 mmol, 1 eq) and (4-bromo-3-methoxycarbonyl-phenyl)boronic acid (826 mg, 3.19 mmol, 1 eq) in THF (50 mL) was added Cu(OAc)$_2$ (1.45 g, 7.98 mmol, 2.5 eq), 4 A molecular sieve (1.5 g) and TEA (15.9 mmol, 2.22 mL, 5 eq) in one portion at 20° C. under O$_2$. The mixture was stirred at 20° C. for 16 h. The reaction mixture was filtered and the filtrate was concentrated under reduced pressure to give a residue. The residue was purified by column chromatography (SiO$_2$, Ethyl acetate/Methanol=1/0 to 10/1) to give methyl 2-bromo-5-((4-carbamoyl-1-(trans-2-cyanocyclopentyl)-1H-pyrazol-3-yl)amino)benzoate (600 mg, 1.39 mmol, 43.4% yield) as a yellow solid. $^1$H NMR (DMSO-d$_6$, 400 MHz) δ 9.34 (s, 1H), 8.31 (s, 1H), 8.12 (d, J=2.8 Hz, 1H), 7.67 (br s, 1H), 7.62-7.58 (m, 3.2 Hz, 1H), 7.56-7.53 (m, 1H), 7.21 (br s, 1H), 4.97-4.90 (m, 1H), 3.84 (s, 3H), 3.41-3.34 (m, 1H), 2.32-2.23 (m, 2H), 2.07-1.96 (m, 1H), 1.94-1.92 (m, 1H), 1.92-1.88 (m, 2H).

12.2 Preparation of methyl 5-((4-carbamoyl-1-(trans-2-cyanocyclopentyl)-1H-pyrazol-3-yl)amino)-2-(4,4,5,5-tetramethyl-1,3,2-dioxaborolan-2-yl)benzoate

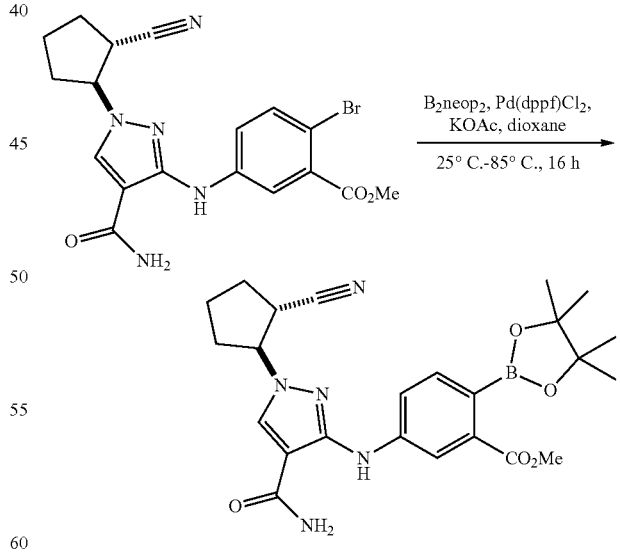

To a mixture of methyl 2-bromo-5-((4-carbamoyl-1-(trans-2-cyanocyclopentyl)-1H-pyrazol-3-yl)amino)benzoate (500 mg, 1.16 mmol, 1 eq) in dioxane (10 mL) was added KOAc (340 mg, 3.47 mmol, 3 eq), Pd(dppf)Cl2 (84.6 mg, 115 umol, 0.1 eq) and 4,4,4',4',5,5,5',5'-octamethyl-2,2'-bi(1,3,2-dioxaborolane) (734 mg, 2.89 mmol, 2.5 eq) in one portion at 25° C. under N$_2$. The mixture was heated to 85° C. and stirred for 16 h. The reaction mixture was filtered and the filtrate was concentrated in vacuum. The residue was purified by prep-TLC (SiO$_2$, Ethyl acetate/Methanol=1/0 to 10/1) to give methyl 5-((4-carbamoyl-1-(trans-2-cyanocyclopentyl)-1H-pyrazol-3-yl)amino)-2-(4,4,5,5-tetramethyl-1,3,2-dioxaborolan-2-yl)benzoate (500 mg, 90.1% yield) as a brown solid.

12.3 Preparation of 1-(trans-2-cyanocyclopentyl)-3-((1-hydroxy-1,3-dihydrobenzo[c][1,2]oxaborol-5-yl)amino)-1H-pyrazole-4-carboxamide

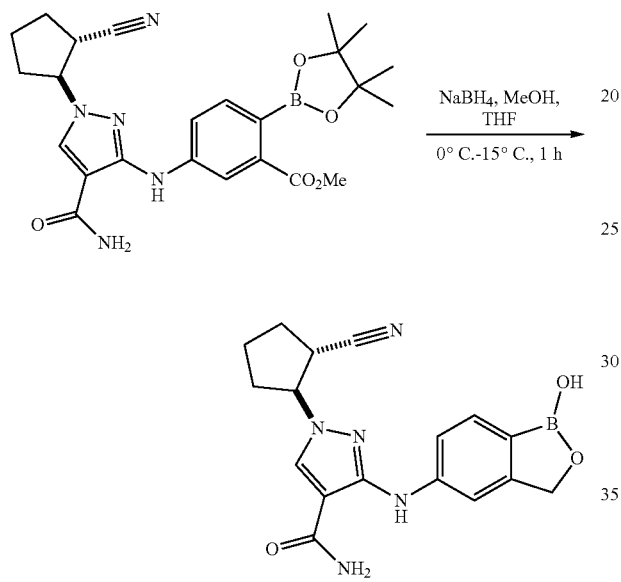

To a mixture of methyl 5-((4-carbamoyl-1-(trans-2-cyanocyclopentyl)-1H-pyrazol-3-yl) amino)-2-(4,4,5,5-tetramethyl-1,3,2-dioxaborolan-2-yl)benzoate (500 mg, 1.04 mmol, 1 eq) in THF (10 mL) was added MeOH (12.3 mmol, 0.5 mL, 11.8 eq) and NaBH$_4$ (119 mg, 3.13 mmol, 3 eq) in portions at 0° C. under N$_2$. The mixture was stirred at 15° C. for 1 h. LCMS showed the reaction was completed and desired MS observed. The mixture was poured into ice-water (w/w=1/1) (20 mL) and the aqueous phase was adjusted pH to 5-6 with HCl (2N). The aqueous phase was extracted with ethyl acetate (10 mL×3). The combined organic phases was washed with brine (10 mL), dried with anhydrous Na$_2$SO$_4$, filtered and concentrated in vacuum to give a residue. The residue was purified by prep-HPLC (column: Phenomenex luna C18 80*40 mm*3 um; mobile phase: [water (0.04% HCl)-ACN]; B %: 25%-43%, 7 min) to give 1-(trans-2-cyanocyclopentyl)-3-((1-hydroxy-1,3-dihydrobenzo[c] [1,2]oxaborol-5-yl)amino)-1H-pyrazole-4-carboxamide (119 mg, 31.7% yield, 97.0% purity) as a white solid. $^1$H NMR (DMSO-hd 6, 400 MHz) δ 9.37 (s, 1H), 8.88 (s, 1H), 8.30 (s, 1H), 7.66 (s, 2H), 7.58 (d, J=8.0 Hz, 1H), 7.35 (d, J=8.0 Hz, 1H), 7.19 (br s, 0.5H), 4.93-4.86 (m, 3H), 3.43-3.36 (m, 1H), 2.31-2.21 (m, 2H), 2.09-1.87 (m, 4H). MS (ESI): mass calculated for C$_{17}$H$_{18}$BN$_5$O$_3$ 351.15, m/z found 352.1 [M+H]$^+$. HPLC: 97.07% (220 nm), 100% (254 nm).

13. Preparation of 3-((8-chloro-2-hydroxy-2H-benzo[e][1,2]oxaborinin-6-yl)amino)-1-(trans-4-cyanotetrahydro-2H-pyran-3-yl)-1H-pyrazole-4-carboxamide

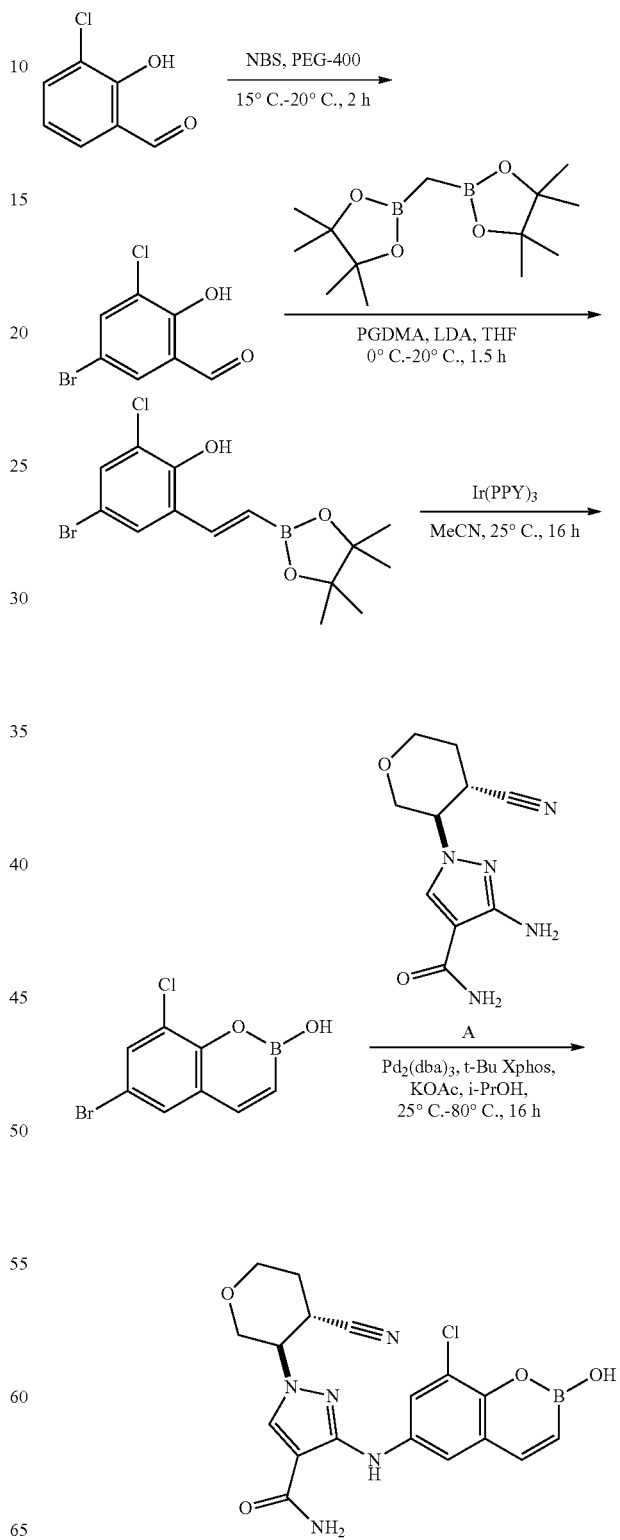

13.1 Preparation of 5-bromo-3-chloro-2-hydroxy-benzaldehyde

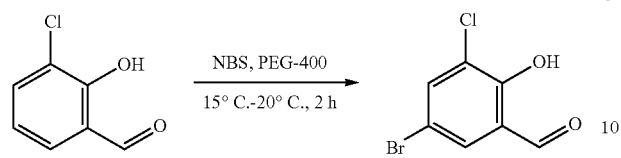

To a mixture of 3-chloro-2-hydroxy-benzaldehyde (4.50 g, 28.7 mmol, 1 eq) in PEG-400 (70 mL) was added NBS (5.37 g, 30.2 mmol, 1.05 eq) in portions at 15° C. The mixture was stirred at 20° C. for 2 h. TLC showed the reaction was completed. The mixture was poured into ice-water (w/w=1/1) (100 mL). The aqueous phase was extracted with ethyl acetate (50 mL×3). The combined organic phase was washed with brine (50 mL), dried with anhydrous $Na_2SO_4$, filtered and concentrated in vacuum to give a residue. The residue was purified by column chromatography ($SiO_2$, Petroleum ether/Ethyl acetate=10/1 to 5/1) to give 5-bromo-3-chloro-2-hydroxy-benzaldehyde (5.50 g, 81.2% yield) as a white solid. $^1$H NMR (DMSO-hd 6, 400 MHz) δ 11.20 (s, 1H), 10.11 (s, 1H), 7.98 (s, 1H), 7.83 (s, 1H).

13.2 Preparation of 4-bromo-2-chloro-6-[(E)-2-(4,4,5,5-tetramethyl-1,3,2-dioxaborolan-2-yl) vinyl]phenol

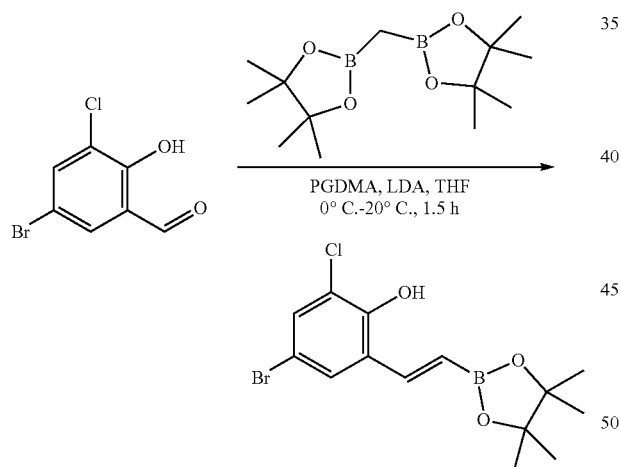

To a solution of LDA (2 M, 10.6 mL, 2.5 eq) in THF (10 mL) was added N'-[2-(dimethylamino)ethyl]-N,N,N'-trimethyl-ethane-1,2-diamine (3.68 g, 21.2 mmol, 4.43 mL, 2.5 eq) drop-wise at 0° C. Then, added 4,4,5,5-tetramethyl-2-[(4,4,5,5-tetramethyl-1,3,2-dioxaborolan-2-yl)methyl]-1,3,2-dioxaborolane (4.55 g, 16.7 mmol, 2 eq) in THF (5 mL) at 0° C. After addition, the mixture was stirred at 0° C. for 30 min, and then to this was added 5-bromo-3-chloro-2-hydroxy-benzaldehyde (2.00 g, 8.49 mmol, 1 eq) in THF (5 mL) at 0° C. The reaction was allowed to warm to 20° C. and stirred at 20° C. for 1 h. TLC showed the reaction was completed. The mixture was poured into sat. aq. $NH_4Cl$ (50 mL). The aqueous phase was extracted with ethyl acetate (20 mL×3). The combined organic phase was washed with brine (10 mL×2), dried with anhydrous $Na_2SO_4$, filtered and concentrated in vacuum to give a residue. The residue was purified by column chromatography ($SiO_2$, Petroleum ether/Ethyl acetate=10/1 to 5/1) to give 4-bromo-2-chloro-6-[(E)-2-(4,4,5,5-tetramethyl-1,3,2-dioxaborolan-2-yl)vinyl]phenol (2 g, 5.56 mmol, 65.5% yield) as yellow oil.

13.3 Preparation of 6-bromo-8-chloro-2-hydroxy-1,2-benzoxaborinine

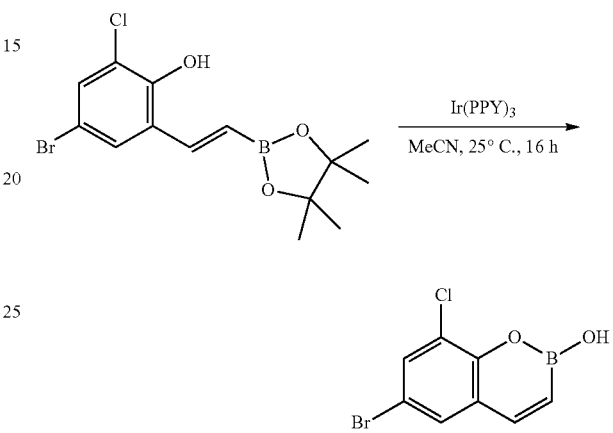

To a mixture of 4-bromo-2-chloro-6-[(E)-2-(4,4,5,5-tetramethyl-1,3,2-dioxaborolan-2-yl) vinyl]phenol (1.0 g, 2.78 mmol, 1 eq) in $CH_3CN$ (11 mL) was added tris[2-(2-pyridyl)phenyl]iridium (18.2 mg, 27.8 umol, 0.01 eq) in one portion at 25° C. under $N_2$. The reaction was stirred and irradiated using 34 W blue LED lamps for 16 h. TLC showed the reaction was completed. The mixture was filtered and concentrated to give the residue. The residue was purified by column chromatography ($SiO_2$, Petroleum ether/Ethyl acetate=5/1 to 4/1) to give 6-bromo-8-chloro-2-hydroxy-1,2-benzoxaborinine (225 mg, 31.1% yield) as a white solid.

$^1$H NMR (DMSO-hd 6, 400 MHz) δ 9.45 (s, 1H), 7.81-7.77 (m, 3H), 6.27 (d, J=11.6 Hz, 1H). MS (ESI): mass calculated for $C_8H_5BBrClO_2$ 257.93, m/z found 257.0 [M−H]$^−$. HPLC: 98.95% (220 nm), 97.82% (254 nm).

13.4 Preparation of 3-[(8-chloro-2-hydroxy-1,2-benzoxaborinin-6-yl)amino]-1-[trans-4-cyanotetrahydr-2H-opyran-3-yl]pyrazole-4-carboxamide

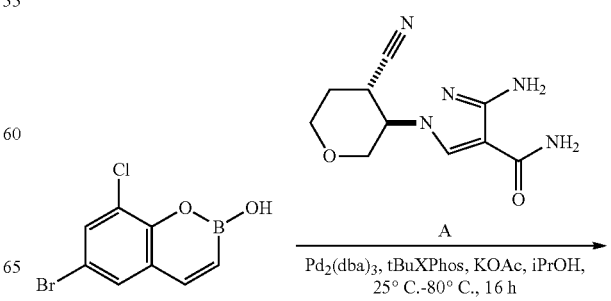

141
-continued

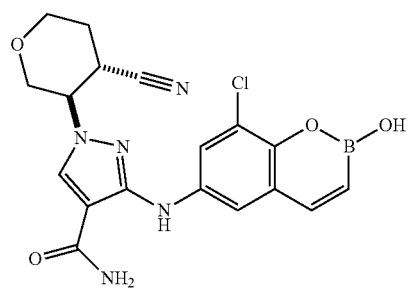

To a mixture of 6-bromo-8-chloro-2-hydroxy-1,2-benzoxaborinine (500 mg, 1.93 mmol, 1 eq) and 3-amino-1-(trans-4-cyanotetrahydro-2H-pyran-3-yl)-1H-pyrazole-4-carboxamide (454 mg, 1.93 mmol, 1 eq) in i-PrOH (20 mL) was added $Pd_2(dba)_3$ (177 mg, 193 umol, 0.1 eq), t-Bu Xphos (164 mg, 386 umol, 0.2 eq) and KOAc (379 mg, 3.86 mmol, 2 eq) in one portion at 25° C. The mixture was heated and stirred at 80° C. for 16 h. LCMS showed the reaction was completed and desired MS observed. 2 parallel reactions were combined for work up. The reaction mixture was filtered, and the filtrate was concentrated under reduced pressure to give a residue. The residue was purified by prep-HPLC (column: Phenomenex luna C18 (250*70 mm, 15 um); mobile phase: [water (HCl)-ACN]; B %: 14%-44%, 20 min) to give 3-[(8-chloro-2-hydroxy-1,2-benzoxaborinin-6-yl) amino]-1-[trans-4-cyanotetrahydro-2H-pyran-3-yl]pyrazole-4-carboxamide (590 mg) and then separated by SFC (column: DAICEL CHIRALPAK IC (250 mm*30 mm, 10 um); mobile phase: [Neu-IPA]; B %: 50/6-50%/6.10 min). to give 3-[(8-chloro-2-hydroxy-1,2-benzoxaborinin-6-yl) amino]-1-[trans-4-cyanotetrahydro-2H-pyran-3-yl]pyrazole-4-carboxamide (stereoisomer one) (197.5 mg, 24.7% yield, 97.1% purity, 100% ee, first peak, Rt=1.262 min) as a white solid. $^1$H NMR (DMSO-$d_6$, 400 MHz) δ 9.17 (s, 1H), 9.14 (s, 1H), 8.32 (s, 1H), 7.84 (d, J=10.4 Hz, 1H), 7.80 (d, J=2.8 Hz, 1H), 7.74 (br s, 0.5H), 7.68 (d, J=2.8 Hz, 1H), 7.22 (br s, 0.5H), 6.20 (d, J=12.0 Hz, 1H), 4.62-4.58 (m, 1H), 4.09-4.04 (m, 1H), 3.95-3.91 (m, 1H), 3.72-3.69 (m, 2H), 3.67-3.50 (m, 1H), 2.20-2.15 (m, 1H), 2.03-1.99 (m, 1H). MS (ESI): mass calculated for $C_{18}H_{17}BClN_5O_4$ 413.11, m/z found 414.2 [M+H]$^+$. HPLC: 97.10% (220 nm), 99.78% (254 nm). and 3-[(8-chloro-2-hydroxy-1,2-benzoxaborinin-6-yl)amino]-1-[trans-4-cyanotetrahydro-2H-pyran-3-yl]pyrazole-4-carboxamide (stereoisomer two) (176 mg, 22.0% yield, 98.1% purity, 99.2% ee, second peak, Rt=1.431 min) as a white solid. $^1$H NMR (DMSO-hd 6, 400 MHz) δ 9.17 (s, 1H), 9.14 (s, 1H), 8.32 (s, 1H), 7.84 (d, J=10.4 Hz, 1H), 7.80 (d, J=2.8 Hz, 1H), 7.74 (br s, 0.5H), 7.68 (d, J=2.8 Hz, 1H), 7.22 (br s, 0.5H), 6.20 (d, J=12.0 Hz, 1H), 4.62-4.56 (m, 1H), 4.09-4.04 (m, 1H), 3.95-3.92 (m, 1H), 3.72-3.66 (m, 2H), 3.51-3.50 (m, 1H), 2.20-2.16 (m, 1H), 2.03-1.98 (m, 1H). MS (ESI): mass calculated for $C_{18}H_{17}BClN_5O_4$ 413.11, m/z found 414.1 [M+H]$^+$. HPLC: 98.18%(220 nm), 99.83%(254 nm).

142

14. Preparation of 1-(trans-4-cyanotetrahydro-2H-pyran-3-yl)-3-[(8-fluoro-2-hydroxy-3-methyl-1,2-benzoxaborinin-6-yl)amino]pyrazole-4-carboxamide

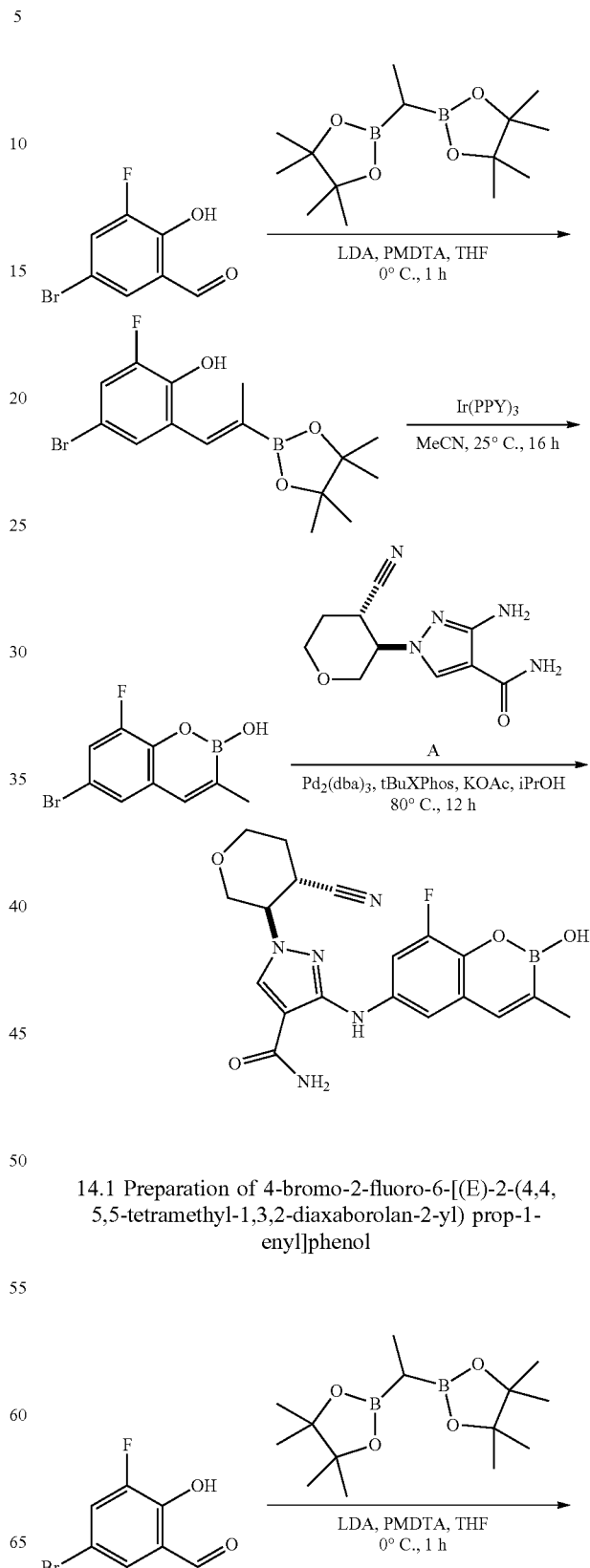

14.1 Preparation of 4-bromo-2-fluoro-6-[(E)-2-(4,4,5,5-tetramethyl-1,3,2-diaxaborolan-2-yl) prop-1-enyl]phenol

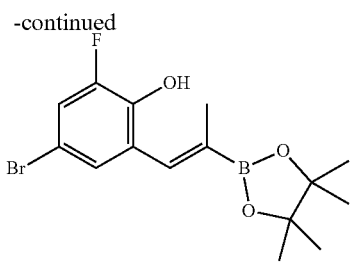

To a solution of LDA (2 M, 6.85 mL, 3 eq) in THF (5 mL) was added dropwise N'-[2-(dimethylamino)ethyl]-N,N,N'-trimethyl-ethane-1,2-diamine (PMDTA, 1.58 g, 9.13 mmol, 1.9 mL, 2 eq) and 4,4,5,5-tetramethyl-2-[1-(4,4,5,5-tetramethyl-1,3,2-dioxaborolan-2-yl) ethyl]-1,3,2-dioxaborolane (3.22 g, 11.4 mmol, 2.5 eq) at 0° C. under $N_2$. The mixture was stirred at 0° C. for 30 min. A solution of 5-bromo-3-fluoro-2-hydroxy-benzaldehyde (1.00 g, 4.57 mmol, 1 eq) in THF (5 mL) was added dropwise to the reaction at 0° C. The reaction mixture was stirred for 0.5 h at 20° C. TLC showed the reaction was completed. The reaction mixture was added water (30 mL) at 0° C., and then the resulting mixture was adjusted pH to 5 with HCl (2 N). The solution was diluted with EtOAc (10 mL) and extracted with EtOAc (20 mL×3). The combined organic layers were washed with brine (30 mL×2), dried over $Na_2SO_4$, filtered and concentrated under reduced pressure to give a residue. The residue was purified by flash silica gel chromatography (ISCO®; 40 g SepaFlash® Silica Flash Column, Eluent of 0~10% Ethyl acetate/Petroleum ether gradient @50 mL/min) to give 4-bromo-2-fluoro-6-[(E)-2-(4,4,5,5-tetramethyl-1,3,2-dioxaborolan-2-yl)prop-1-enyl]phenol (1.1 g, 67.5% yield) as a yellow solid. 1H NMR (DMSO-hd 6, 400 MHz) S 10.01 (s, 1H), 7.40 (dd, J=2.4, 10.4 Hz, 1H), 7.19 (s, 1H), 7.15 (d, J=1.6 Hz, 1H), 1.80 (s, 3H), 1.25 (s, 12H).

14.2 Preparation of 6-bromo-8-fluoro-2-hydroxy-3-methyl-1,2-benzoxaborinine

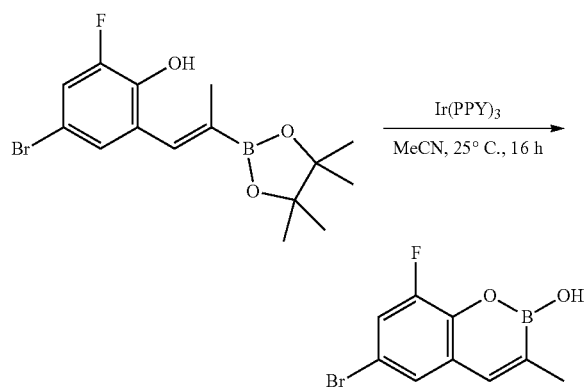

To a mixture of 4-bromo-2-fluoro-6-[(E)-2-(4,4,5,5-tetramethyl-1,3,2-dioxaborolan-2-yl) prop-1-enyl]phenol (600 mg, 1.68 mmol, 1 eq) in $CH_3CN$ (7 mL) was added tris[2-(2-pyridyl)phenyl]iridium (Ir(PPY)$_3$, 11.00 mg, 16.8 umol, 0.01 eq) in one portion at 25° C. under $N_2$. The reaction mixture was stirred at 25° C. and irradiated using 34W blue LED lamps for 16 hrs. LCMS showed the reaction was completed and desired MS observed. The reaction mixture was concentrated under reduced pressure to give a residue. The residue was purified by flash silica gel chromatography (ISCO®; 20 g SepaFlash® Silica Flash Column, Eluent of 0~10% Ethyl acetate/Petroleum ether gradient @ 50 mL/min) to give 6-bromo-8-fluoro-2-hydroxy-3-methyl-1,2-benzoxaborinine (350 mg, 81.1% yield, 99.3% purity) as a white solid. 1H NMR (DMSO-d$_6$, 400 MHz) δ 9.39 (s, 1H), 7.56-7.53 (m, 1H), 7.52 (s, 1H), 7.47 (s, 1H), 2.02 (s, 3H). MS (ESI): mass calculated for $C_9H_7BBrFO_2$, 255.97, m/z found 255.0 [M–H]⁻. HPLC: 99.33% (220 nm), 99.43 (254 nm).

14.3 Preparation of 1-(trans-4-cyanotetrahydro-2H-pyran-3-yl)-3-[(8-fluoro-2-hydroxy-3-methyl-1,2-benzoxaborinin-6-yl)amino]pyrazole-4-carboxamide

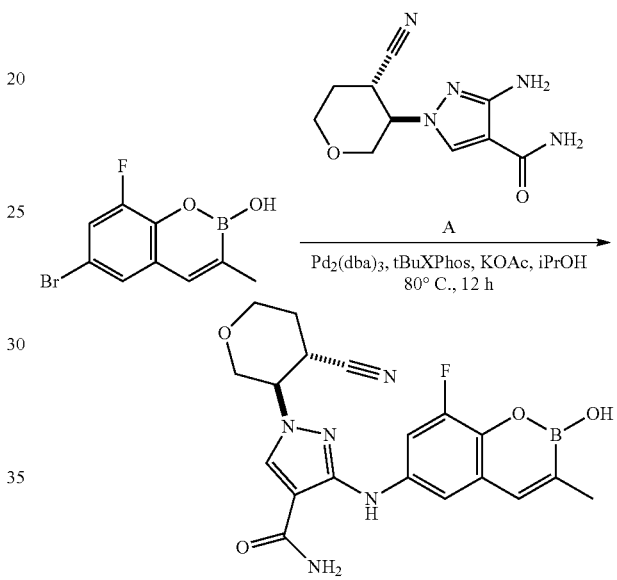

To a mixture of 6-bromo-8-fluoro-2-hydroxy-3-methyl-1,2-benzoxaborinine (500 mg, 1.95 mmol, 1 eq) and 3-amino-1-(trans-4-cyanotetrahydropyran-3-yl)pyrazole-4-carboxamide (550 mg, 2.34 mmol, 1.2 eq) in i-PrOH (10 mL) was added KOAc (478 mg, 4.87 mmol, 2.5 eq), t-Bu Xphos (165 mg, 389 umol, 0.2 eq) and Pd$_2$(dba)$_3$ (178 mg, 195 umol, 0.1 eq) in one portion at 20° C. under $N_2$. The mixture was heated and stirred at 80° C. for 12 h. LCMS showed the reaction was completed and desired MS observed. 5 parallel reactions were combined for work up. The reaction mixture was filtered and concentrated under reduced pressure. The residue was purified by prep-HPLC (column: Phenomenex luna C18 250 mm*100 mm*10 um; mobile phase: [water (HCl)-ACN]; B %: 0%-12%, 20 min) to give 1-(trans-4-cyanotetrahydro-2H-pyran-3-yl)-3-[(8-fluoro-2-hydroxy-3-methyl-1,2-benzoxaborinin-6-yl)amino]pyrazole-4-carboxamide (510 mg, 12.7% yield) as a yellow solid. 1H NMR (DMSO-hd 6, 400 MHz) δ 9.15 (s, 1H), 9.10 (br s, 1H), 8.30 (s, 1H), 7.72 (br s, 1H), 7.61 (dd, J=2.4, 13.6 Hz, 1H), 7.49 (s, 1H), 7.30 (d, J=1.2 Hz, 1H), 7.20 (br s, 1H), 4.57 (dt, J=4.4, 10.4 Hz, 1H), 4.04 (dd, J=4.4, 11.2 Hz, 1H), 3.91 (d, J=10.4 Hz, 1H), 3.74-3.66 (m, 2H), 3.54-3.48 (m, 1H), 2.17 (br d, J=9.6 Hz, 1H), 2.02 (d, J=1.2 Hz, 3H), 2.00-1.95 (m, 1H). further separated by SFC (column: Phenomenex-Cellulose-2 (250 mm*30 mm, 10 um); mobile phase: [Neu-MeOH]; B %: 45%-45%, 8 min) to give 1-[trans-4-cyanotetrahydro-2H-pyran-3-yl]-3-[(8-fluoro-2-hydroxy-3- methyl-1,2-benzoxaborinin-6-yl)amino]pyrazole-4-carboxamide (stereoisomer one) (232 mg, 97.1% purity, 99.5% ee, first peak, Rt=1.458 min) as a white solid. $^1$H NMR (DMSO-hd 6, 400 MHz) δ 9.15 (s, 1H), 9.11 (s, 1H), 8.29 (s, 1H), 7.74 (br s 1H), 7.61 (dd, J=13.6 Hz, 2.8 Hz, 1H), 7.49 (s, 1H), 7.31 (s, 1H), 7.20 (br s, 1H), 4.57 (td, J=14.4 Hz, 1H), 4.03 (dd, J=11.2 Hz, 4.4 Hz, 1H), 3.95-3.88 (m, 1H) 3.73-3.65 (m, 2H), 3.55-3.49 (m, 1H), 2.20-2.13 (m, 1H), 2.02 (s, 3H), 2.00-1.93 (m, 1H). MS (ESI): mass calculated for $C_{19}H_{19}BFN_5O_4$ 411.15; m/z found 412.2 [M+H]$^+$. HPLC: 97.17% (220 nm), 99.28% (254 nm). and 1-[trans-4-cyanotetrahydro-2H-pyran-3-yl]-3-[(8-fluoro-2-hydroxy-3-methyl-1,2-benzoxaborinin-6-yl)amino]pyrazole-4-carboxamide (stereoisomer two) (160 mg, 97.4% purity, 96.0% ee, second peak, Rt=1.646 min) as a white solid. $^1$H NMR (DMSO-hd 6, 400 MHz) δ 9.15 (s, 1H), 9.11 (s, 1H), 8.29 (s, 1H), 7.74 (br s 1H), 7.61 (d, J=13.2 Hz, 1H), 7.49 (s, 1H), 7.31 (s, 1H), 7.20 (br s, 1H), 4.64-4.51 (m, 1H), 4.08-4.00 (m, 1H), 3.96-3.87 (m, 1H) 3.75-3.63 (m, 2H), 3.54-3.48 (m, 1H), 2.19-2.12 (m, 1H), 2.02 (s, 3H), 1.99-1.90 (m, 1H). MS (ESI): mass calculated for $C_{19}H_{19}BFN_5O_4$ 411.15; m/z found 412.2 [M+H]$^+$. HPLC: 97.45% (220 nm), 98.86% (254 nm).

15. Preparation of 1-(trans-2-cyanocyclopentyl)-3-[(8-fluoro-2-hydroxy-3-methyl-1,2-benzoxaborinin-6-yl)amino]pyrazole-4-carboxamide To a mixture of 6-bromo-8-fluoro-2-hydroxy-3-methyl-1,2-benzoxaborinine (100 mg, 389 umol, 1 eq) and 3-amino-1-(trans-2-cyanocyclopentyl)pyrazole-4-carboxamide (103 mg, 467 umol, 1.2 eq) in i-PrOH (5 mL) was added KOAc (96 mg, 973 umol, 2.5 eq), t-Bu Xphos (33 mg, 77.9 umol, 0.2 eq) and Pd$_2$(dba)$_3$ (36 mg, 38.9 umol, 0.1 eq) in one portion at 20° C. under N$_2$. The mixture was heated and stirred at 80° C. for 12 h. LCMS showed the reaction was completed and desired MS observed.

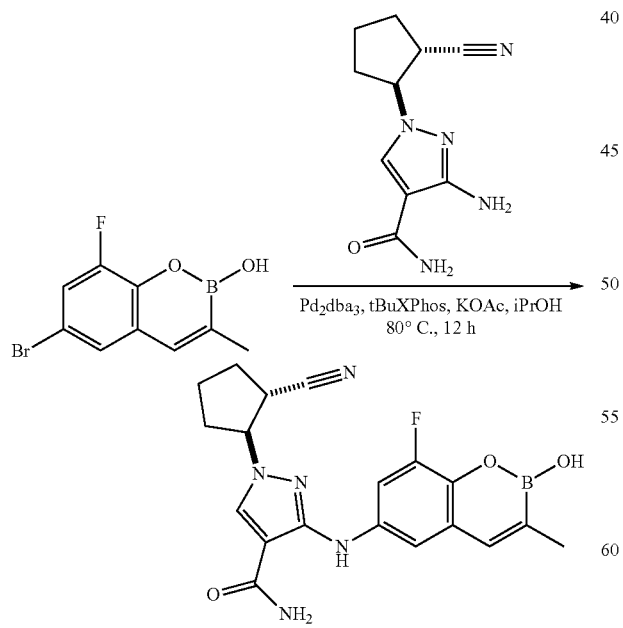

The reaction mixture was filtered and concentrated under reduced pressure to give a residue. The residue was purified by prep-HPLC (column: Phenomenex Gemini-NX 80*40 mm*3 um; mobile phase: [water (10 mM NH$_4$HCO$_3$)-ACN]; B %: 15%-45%, 8 min) to give 1-(trans-2-cyanocyclopentyl)-3-[(8-fluoro-2-hydroxy-3-methyl-1,2-benzoxaborinin-6-yl)amino]pyrazole-4-carboxamide (18.5 mg, 12.0% yield, 91.9% purity) as a yellow solid. 1H NMR (DMSO-hd 6, 400 MHz) δ 9.12 (s, 1H), 9.09 (s, 1H), 8.29 (s, 1H), 7.62 (dd, J=2.4, 13.2 Hz, 2H), 7.45 (s, 1H), 7.34 (d, J=1.2 Hz, 1H), 7.15 (s, 1H), 4.88 (q, J=8.0 Hz, 1H), 3.43-3.36 (m, 1H), 2.35-2.29 (m, 1H), 2.27-2.19 (m, 1H), 2.12-2.05 (m, 1H), 2.01 (s, 3H), 1.97-1.84 (m, 3H). MS (ESI): mass calculated for $C_{19}H_{19}BFN_5O_3$, 395.16, m/z found 396.2 [M+H]$^+$. HPLC: 91.94% (220 nm), 97.67% (254 nm).

16. Preparation of 1-(trans-4-cyanotetrahydro-2H-pyran-3-yl)-3-((1-hydroxy-1,3-dihydrobenzo[c][1,2]oxaborol-6-yl)amino)-1H-pyrazole-4-carboxamide

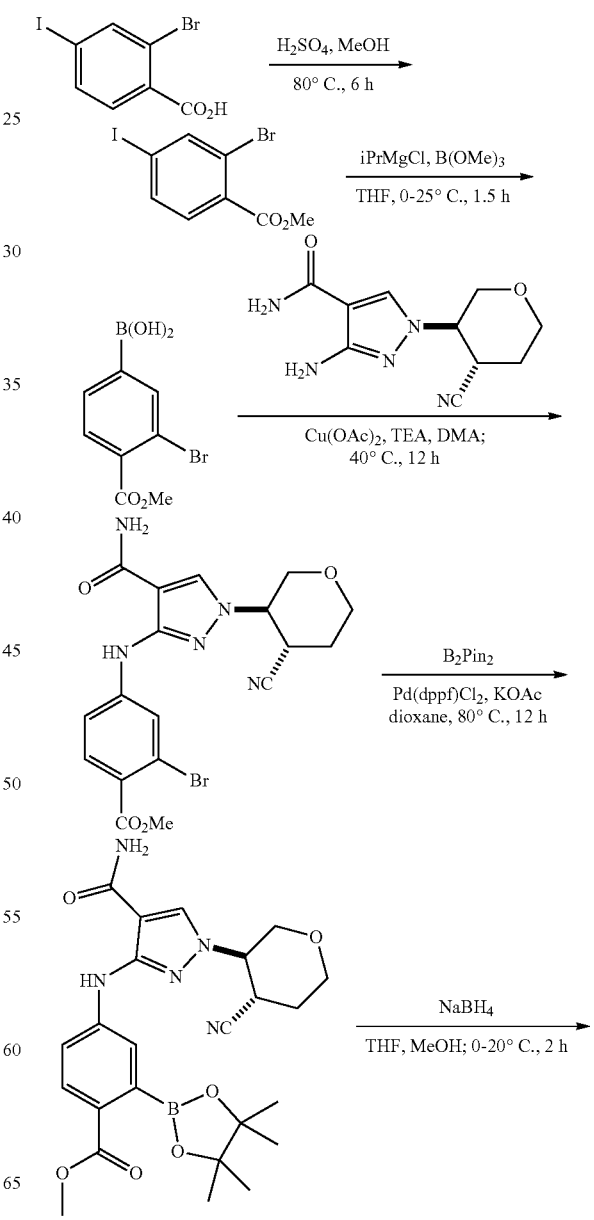

-continued

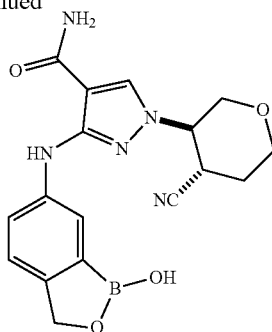

16.1 Preparation of methyl 2-bromo-4-iodo-benzoate

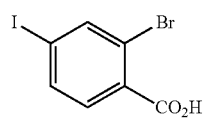

To a solution of 2-bromo-4-iodo-benzoic acid (25.0 g, 76.5 mmol, 1 eq) in MeOH (250 mL) was added H$_2$SO$_4$ (38.2 g, 382 mmol, 20.8 mL, 98% purity, 5 eq) in one portion at 20° C. The mixture was heated to 80° C. and stirred at 80° C. for 6 h. TLC showed the reaction was completed. The reaction mixture was concentrated under reduced pressure to give a residue. The residue was poured into ice-water (200 mL), adjusted pH=7 by sat·aq·Na$_2$CO$_3$ and then extracted with EtOAc (200 mL×3). The combined organic layers were washed with brine (200 mL×2), dried over anhydrous Na$_2$SO$_4$, filtered and concentrated under reduced pressure to give methyl 2-bromo-4-iodo-benzoate (24.5 g, 93.9% yield) as a yellow solid. 1H NMR (CDCl$_3$, 400 MHz) δ 8.06 (s, 1H), 7.71 (dd, J=1.6, 8.4 Hz, 1H), 7.52 (d, J=8.0 Hz, 1H), 3.93 (s, 3H).

16.2 Preparation of (3-bromo-4-methoxycarbonyl-phenyl)boronic acid

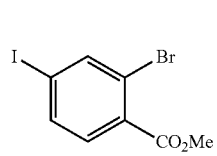

To a mixture of 2-[2-(dimethylamino)ethoxy]-N,N-dimethyl-ethanamine (5.64 g, 35.2 mmol, 1.2 eq) in THF (100 mL) was added i-PrMgCl (2 M, 17.6 mL, 1.2 eq) at 15° C. under N$_2$. The resulting mixture was stirred for 0.5 h at 15° C. Methyl 2-bromo-4-iodo-benzoate (10.0 g, 29.3 mmol, 1 eq) was added dropwise to the reaction mixture, and the mixture was stirred at 25° C. for 10 min. B(OMe)$_3$ (6.10 g, 58.6 mmol, 6.6 mL, 2 eq) was added to the reaction mixture dropwise at 0° C. and stirred for 1 h. LCMS showed the reaction was completed and desired MS observed. The reaction was quenched by addition of sat. aq. NH$_4$Cl (100 mL) at 0° C., adjusted pH=5 by HCl (2N) and extracted with EtOAc (30 mL×3). The combined organic layers were washed with brine (100 mL×3), dried over Na$_2$SO$_4$, filtered and concentrated under reduced pressure to give a residue. The residue was purified by flash silica gel chromatography (ISCO®; 120 g SepaFlash® Silica Flash Column, Eluent of 0-25% Ethyl acetate/Petroleum ether gradient @ 50 mL/min) to give (3-bromo-4-methoxy carbonyl-phenyl)boronic acid (5.00 g, 65.8% yield) as a yellow solid. 1H NMR (DMSO-hd 6, 400 MHz) δ 8.04 (s, 1H), 7.81 (d, J=7.6 Hz, 1H), 7.69 (d, J=7.6 Hz, 1H), 3.83 (s, 3H).

16.3 Preparation of methyl 2-bromo-4-((4-carbamoyl-1-(trans-4-cyanotetrahydro-2H-pyran-3-yl)-1H-pyrazol-3-yl)amino)benzoate

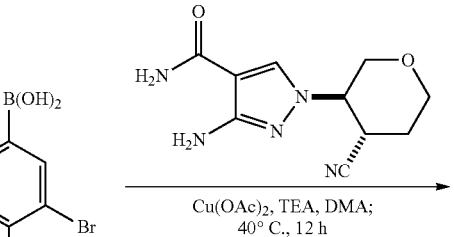

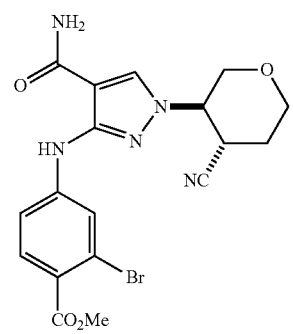

To a solution of (3-bromo-4-methoxycarbonyl-phenyl)boronic acid (1.00 g, 3.86 mmol, 1 eq) in DMA (15 mL) was added 3-amino-1-(trans-4-cyanotetrahydropyran-3-yl)pyrazole-4-carboxamide (817 mg, 3.47 mmol, 0.9 eq), Cu(OAc)$_2$ (1.75 g, 9.65 mmol, 2.5 eq), 4 A molecular sieve (1 g, 1.00 eq) and TEA (1.95 g, 19.3 mmol, 2.7 mL, 5 eq) at 25° C. The mixture was heated to 40° C. and stirred at 40° C. for 12 h. TLC showed the reaction was completed. 4 parallel reactions were combined for work up. The reaction mixture was filtered. The filtrate was quenched by addition H$_2$O (40 mL), then extracted with EtOAc (40 mL×3). The combined organic layers were washed with brine (40 mL×3), dried over Na$_2$SO$_4$, filtered and concentrated under reduced pressure to give a residue. The residue was purified by flash silica gel chromatography (ISCO®; 120 g SepaFlash® Silica Flash Column, Eluent of 0~60% Ethyl acetate/Petroleum ether gradient @ 100 mL/min) to give methyl-2-bromo-4-[[4-carbamoyl-1-(trans-4-cyanotetrahydropyran-3-yl)pyrazol-3-yl]amino]benzoate (4 g, 57.8% yield) as a white solid. 1H NMR (DMSO-hd 6, 400 MHz) δ 9.60 (s, 1H), 8.36 (s, 1H), 7.94 (d, J=2.0 Hz, 1H), 7.81 (d, J=8.8 Hz, 2H), 7.61 (dd, J=2.0, 8.8 Hz, 1H), 7.30 (s, 1H), 4.67-4.58 (m, 1H), 4.08-3.98 (m, 3H), 3.92 (br d, J=10.8 Hz, 1H), 3.70-3.61 (m, 2H), 3.50-3.45 (m, 1H), 2.17 (br d, J=10.0 Hz, 1H), 1.99 (s, 3H), 1.57-1.48 (m, 2H).

16.4 Preparation of methyl 4-((4-carbamoyl-1-(trans-4-cyanotetrahydro-2H-pyran-3-yl)-1H-pyrazol-3-yl)amino)-2-(4,4,5,5-tetramethyl-1,3,2-dioxaborolan-2-yl)benzoate

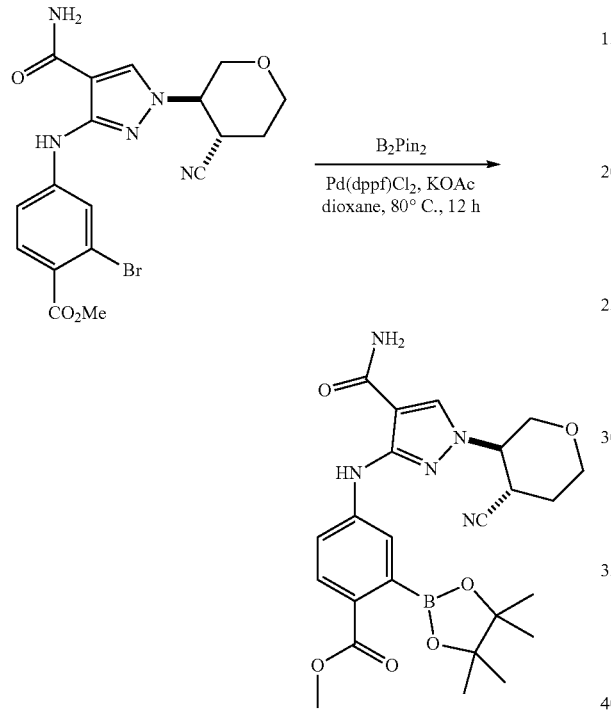

A mixture of methyl 2-bromo-4-[[4-carbamoyl-1-(trans-4-cyanotetrahydro-2H-pyran-3-yl)pyrazol-3-yl]amino]benzoate (1.00 g, 2.23 mmol, 1 eq), 4,4,5,5-tetramethyl-2-(4,4,5,5-tetramethyl-1,3,2-dioxaborolan-2-yl)-1,3,2-dioxaborolane (1.13 g, 4.46 mmol, 2 eq), KOAc (656 mg, 6.69 mmol, 3 eq) and Pd(dppf)Cl2 (81.6 mg, 111 umol, 0.05 eq) in dioxane (20 mL) was degassed and purged with $N_2$ for 3 times. The mixture was heated and stirred at 80° C. for 12 h under $N_2$ atmosphere. LCMS showed the reaction was completed and desired MS observed. 4 parallel reactions were combined for work up. The reaction mixture was filtered and the filtrate was concentrated under reduced pressure to give a residue. The residue was purified by flash silica gel chromatography (ISCO®; 120 g SepaFlash® Silica Flash Column, Eluent of 0~70% Ethyl acetate/Petroleum ether gradient @ 100 mL/min) to give methyl 4-((4-carbamoyl-1-(trans-4-cyanotetrahydro-2H-pyran-3-yl)-1H-pyrazol-3-yl)amino)-2-(4,4,5,5-tetramethyl-1,3,2-dioxaborolan-2-yl)benzoate (3.00 g, 67.8% yield) as a white solid. 1H-NMR (DMSO-hd 6, 400 MHz) δ 9.54 (s, 1H), 8.34 (s, 1H), 7.83-7.80 (m, 2H), 7.66 (s, 1H), 7.55-7.53 (m, 1H), 7.33-7.32 (m, 1H), 4.64-4.61 (m, 1H), 4.08-4.05 (m, 2H), 4.03-4.01 (m, 1H), 3.92-3.90 (m, 1H), 3.79 (s, 3H), 3.68-3.61 (m, 2H), 3.42-3.40 (m, 1H), 2.16-2.14 (m, 1H), 1.34 (s, 12H).

16.5 Preparation of 1-(trans-4-cyanotetrahydro-2H-pyran-3-yl)-3-((1-hydroxy-1,3-dihydrobenzo[c][1,2]oxaborol-6-yl)amino)-1H-pyrazole-4-carboxamide

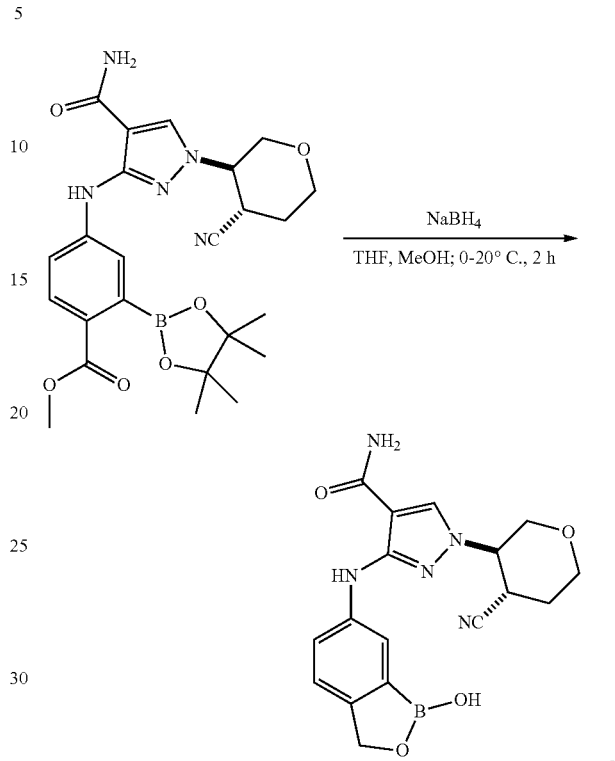

To a solution of methyl 4-[[4-carbamoyl-1-(trans-4-cyanotetrahydro-2H-pyran-3-yl)pyrazol-3-yl] amino]-2-(4,4,5,5-tetramethyl-1,3,2-dioxaborolan-2-yl)benzoate (3.00 g, 6.06 mmol, 1 eq) in THF (30 mL) was added NaBH4 (1.49 g, 39.4 mmol, 6.5 eq) in portions at 0° C. The mixture was stirred at 20° C. for 2 h. LCMS showed the reaction was completed and desired MS observed. The reaction was poured into ice-water (30 mL), adjusted pH=6 by HCl (2N) and extracted with EtOAc (30 mL×3). The combined organic layers were washed with brine (30 mL×2), dried over anhydrous $Na_2SO_4$, filtered and concentrated under reduced pressure to give a residue. The residue was purified by prep-HPLC (column: Phenomenex luna C18 (250*70 mm, 15 um); mobile phase: [water (0.05% HCl)-ACN]; B %: 10%-40%, 30 min) to give 1-(trans-4-cyanotetrahydro-2H-pyran-3-yl)-3-((1-hydroxy-1,3-dihydrobenzo[c][1,2] oxaborol-6-yl)amino)-1H-pyrazole-4-carboxamide (600 mg, yield 30%, purity 99.8%) as a white solid, which was further separated by SFC (column: DAICEL CHIRALPAK IC (250 mm*30 mm, 10 um); mobile phase: [Neu-IPA]; B %: 50%-50%, 9 min) to give 1-(trans-4-cyanotetrahydro-2H-pyran-3-yl)-3-((1-hydroxy-1,3-dihydrobenzo[c][1,2] oxaborol-6-yl)amino)-1H-pyrazole-4-carboxamide (stereoisomer one) (243 mg, 97.5% purity, 100% ee, first peak, Rt=2.279 min) as a white solid 1H NMR (DMSO-hd 6, 400 MHz) δ 9.25 (s, 1H), 9.11 (s, 1H), 8.30 (s, 1H), 7.74 (s, 1H), 7.69 (dd, J=2.0, 8.0 Hz, 2H), 7.30 (d, J=8.0 Hz, 1H), 7.20 (br s, 1H), 4.93 (s, 2H), 4.59-4.55 (m, 1H), 4.03 (dd, J=4.0, 11.2 Hz, 1H), 3.92 (br d, J=10.8 Hz, 1H), 3.74-3.66 (m, 2H), 3.52-3.47 (m, 1H), 2.16 (br d, J=10.0 Hz, 1H), 2.04-1.94 (m, 1H). MS (ESI): mass calculated for $C_{17}H_{18}MBN_5O_4$, 367.15, m/z found 368.2 [M+H]+. HPLC: 97.53% (220 nm), 99.74 (254 nm). and 1-(trans-4-cyanotetrahydro-2H-pyran-3-yl)-3-((1-hydroxy-1,3-dihydrobenzo[c][1,2]oxaborol-6-yl)amino)-1H-pyrazole-4-carboxamide (stereoisomer two) (239 mg, 99.4% purity, 100% ee, second peak, Rt=2.804 min) as a white solid. 1H NMR (DMSO-$d_6$, 400 MHz) δ 9.25 (s, 1H), 9.11 (s, 1H), 8.30 (s, 1H), 7.74 (d, J=1.6 Hz, 1H), 7.69 (dd, J=2.4, 8.4 Hz, 2H), 7.30 (d, J=8.0 Hz, 1H), 7.20 (br s, 1H), 4.93 (s, 2H), 4.60-4.54 (m, 1H), 4.03 (dd, J=4.0, 11.2 Hz, 1H), 3.92 (br d, J=10.4 Hz, 1H), 3.74-3.67 (m, 2H), 3.50-3.45 (m, 1H), 2.16 (br d, J=10.0 Hz, 1H), 2.04-1.97 (m, 1H). MS (ESI): mass calculated for $C_{17}H_{18}MBN_5O_4$, 367.15, m/z found 368.2 [M+H]$^+$. HPLC: 99.47% (220 nm), 100.00% (254 nm).

17. Preparation of 1-(trans-4-cyanotetrahydro-2H-pyran-3-yl)-3-((2-hydroxy-5-methyl-2H-benzo[e][1,2]oxaborinin-6-yl)amino)-1H-pyrazole-4-carboxamide

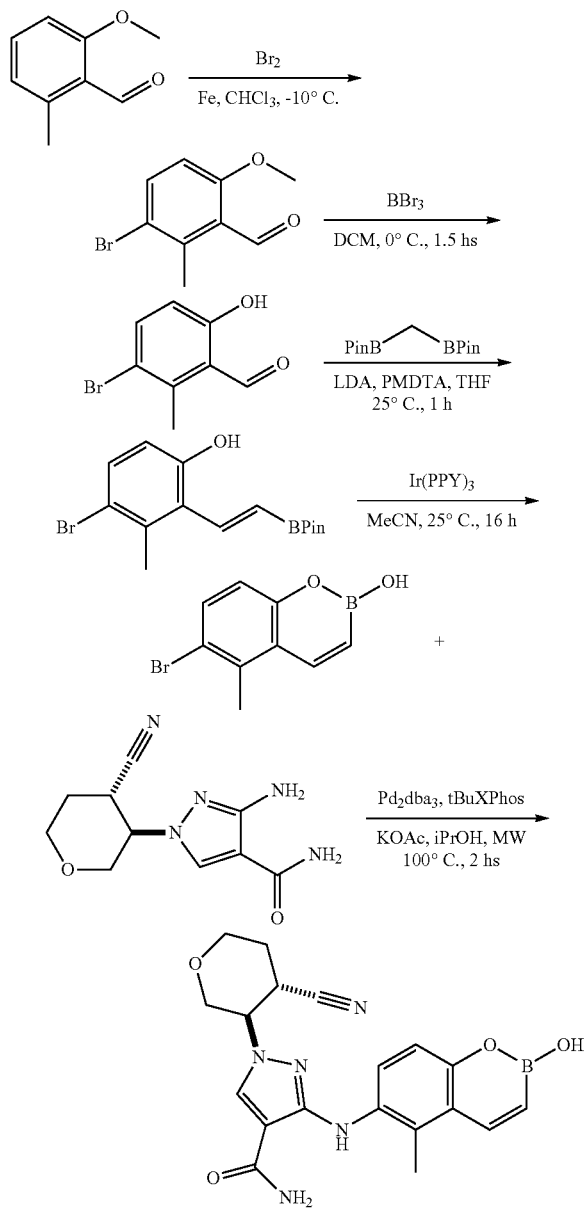

17.1 Preparation of 3-bromo-6-methoxy-2-methylbenzaldehyde

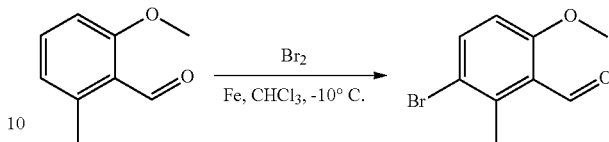

To a solution of 2-methoxy-6-methylbenzaldehyde (8 g, 53 mmol, 1 eq) in chloroform (150 mL) was added Fe (150 mg, 2.69 mmol, 0.05 eq) in one portion at −10° C. After addition, the mixture was stirred at −10° C. for 10 mins, and then a solution of bromine (1.3 g, 8.0 mmol, 1.2 eq) in DCM (3 mL) was added drop-wise at −10° C. in 10 minutes. The resulting mixture was stirred at −10° C. for 1 hour. TLC showed the reaction was completed. Then the result solution was poured into water (250 mL). The organic layer was washed with sodium thiosulfate solution (2×250 mL), water (250 mL) and brine solution (250 mL). The organic layer was dried over sodium sulfate and concentrated under reduced pressure to give light yellow solid which was used in next step directly without purification. 3-bromo-6-methoxy-2-methylbenzaldehyde (12 g, 52.4 mmol) was obtained as light-yellow solid. 1H NMR (400 MHz, CDCl$_3$) δ 7.67 (d, J=9.2 Hz, 1H), 6.76 (d, J=8.8 Hz, 1H), 3.90 (s, 3H), 2.65 (s, 3H).

17.2 Preparation of 3-bromo-6-hydroxy-2-methylbenzaldehyde

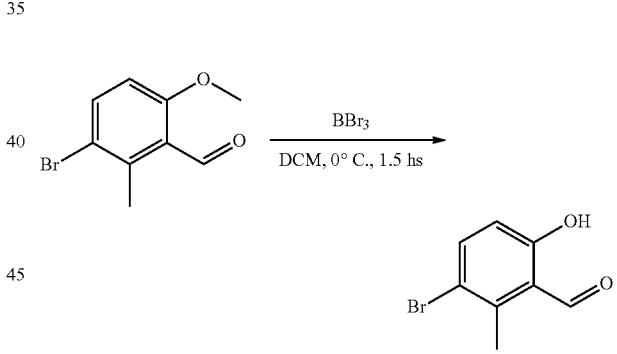

A solution of boron tribromide (13.1 g, 52.4 mmol, 5.1 mL, 1 eq) in dichloromethane (5 ml) was added to a stirred solution of 3-bromo-6-methoxy-2-methyl-benzaldehyde (12 g, 52.4 mmol, 1 eq) in DCM (150 mL) under nitrogen at 0° C. The reaction mixture was stirred for 1.5 hours at 0° C. TLC showed the reaction was completed. Water (400 mL) was added cautiously at 0° C. and the mixture was continue stirred for 15 min. TLC showed the reaction was completed. The organic layer was washed with sodium bicarbonate aqueous (200 mL), water (200 mL) and brine (200 mL), then the organic layer was dried over sodium sulfate and concentrated under reduced pressure to give the crude product as brown solid which was purified by silica gel column chromatography (Petroleum ether/Ethyl acetate=100:1 to 50:1) to afford 3-bromo-6-hydroxy-2-methyl-benzaldehyde (11 g, 97.6% yield) as yellow solid. $^1$H NMR (400 MHz, CDCl$_3$) δ 12.07 (s, 1H), 10.37 (s, 1H), 7.64 (d, J=8.8 Hz, 1H), 6.75 (d, J=8.8 Hz, 1H), 2.69 (s, 3H).

17.3 Preparation of (E)-4-bromo-3-methyl-2-(2-(4,4,5,5-tetramethyl-1,3,2-dioxaborolan-2-yl)vinyl)phenol

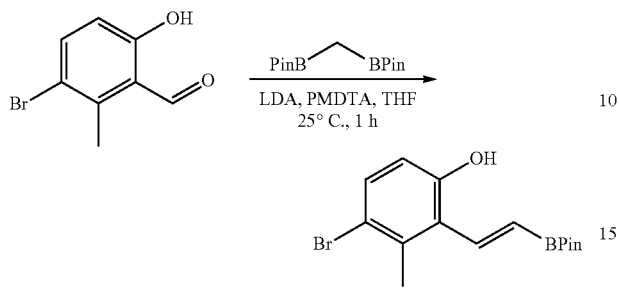

To a solution of N'-[2-(dimethylamino)ethyl]-N,N,N'-trimethylethane-1,2-diamine (PMDTA, 4.8 g, 28 mmol, 5.8 mL, 2 eq) in THF (20 mL) was added LDA (2 M, 17.5 mL, 2.5 eq) and a solution of 4,4,5,5-tetramethyl-2-[(4,4,5,5-tetramethyl-1,3,2-dioxaborolan-2-yl)methyl]-1,3,2-dioxaborolane (B1, 7.5 g, 27.9 mmol, 2 eq) in THF (10 mL) at 0° C. under N$_2$. The mixture was stirred at 0° C. for 20 min. Then to this reaction was added drop-wise a solution of 3-bromo-6-hydroxy-2-methyl-benzaldehyde (3 g, 13.9 mmol, 1 eq) in THF (6 mL) at 25° C. The mixture was stirred at 25° C. for 40 min. LCMS showed the reaction was completed and desired MS observed. NH$_4$Cl aqueous (30 mL) was added to the reaction solution and adjusted the pH=5-6 with HCl (2N) at 0° C. The suspension was extracted with EtOAc (50 mL×2). The combined organic layers were washed by brine (50 mL×2), dried over Na$_2$SO$_4$, filtered and concentrated under reduced pressure to get yellow gum which was purified by flash silica gel chromatography (ISCO®; 80 g SepaFlash® Silica Flash Column, Eluent of 5-7% Ethyl acetate/Petroleum ether gradient @ 100 mL/min) to give 4-bromo-3-methyl-2-[(E)-2-(4,4,5,5-tetramethyl-1,3,2-dioxaborolan-2-yl)vinyl]phenol (1.56 g, 33% yield) as yellow gum. $^1$H NMR (400 MHz, DMSO-d6) δ 9.87 (s, 1H), 7.38-7.27 (m, 2H), 6.69 (d, J=8.4 Hz, 1H), 5.93 (d, J=14.4 Hz, 1H), 2.34 (s, 3H), 1.24 (s, 12H).

17.4 Preparation of 6-bromo-5-methyl-2H-benzo[e][1,2]oxaborinin-2-ol

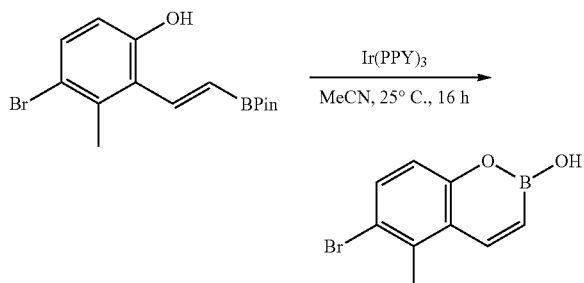

To a mixture of 4-bromo-3-methyl-2-[(E)-2-(4,4,5,5-tetramethyl-1,3,2-dioxaborolan-2-yl)vinyl]phenol (2 g, 5.90 mmol, 1 eq) in McCN (20 mL) was added tris[2-(2-pyridyl)phenyl]iridium (Ir(PPY)$_3$, 193 mg, 295 umol, 0.05 eq) in one portion at 25° C. under N$_2$. The reaction mixture was stirred at 25° C. and irradiated using 34W blue LED lamps for 16 hrs. TLC showed the reaction was completed. The reaction mixture was concentrated to give yellow solid which was purified by silica gel chromatography (Petroleum ether/Ethyl acetate=1/1) to afford 6-bromo-2-hydroxy-5-methyl-1,2-benzoxaborinine (0.9 g, 64% yield) as a yellow solid. $^1$H NMR (400 MHz, DMSO-d6) δ 9.07 (br s, 1H), 8.09 (d, J=12.4 Hz, 1H), 7.58 (d, J=8.8 Hz, 1H), 7.04 (d, J=8.8 Hz, 1H), 6.21 (d, J=12.0 Hz, 1H), 2.54 (s, 3H).

17.5 Preparation of 1-(trans-4-cyanotetrahydro-2H-pyran-3-yl)-3-((2-hydroxy-5-methyl-2H-benzo[e][1,2]oxaborinin-6-yl)amino)-1H-pyrazole-4-carboxamide

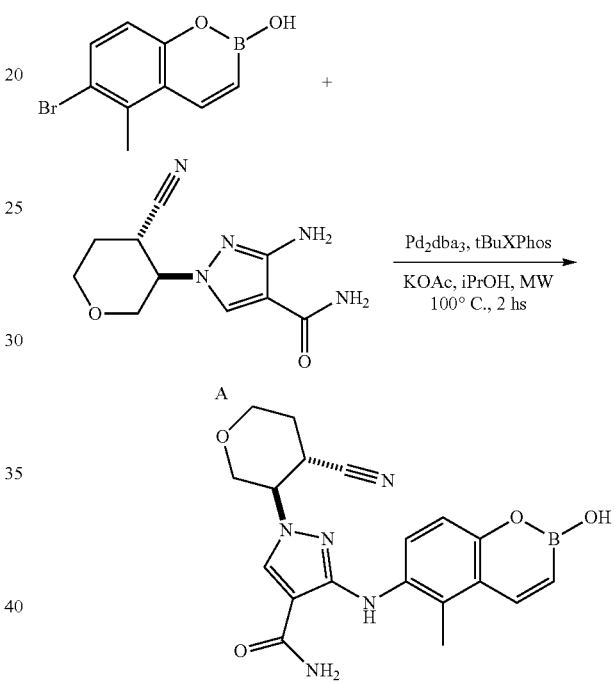

To a mixture of 6-bromo-2-hydroxy-5-methyl-1,2-benzoxaborinine (1.5 g, 6.3 mmol, 1 eq) and 3-amino-1-[trans-4-cyanotetrahydropyran-3-yl]pyrazole-4-carboxamide (1.48 g, 6.3 mmol, 1 eq) in propan-2-ol (20 mL) added Pd$_2$(dba)$_3$ (280 mg, 314 umol, 0.05 eq), di-tert-butyl-[2-(2,4,6-triisopropylphenyl)phenyl]phosphine (260 mg, 630 umol, 0.1 eq) and KOAc (1.23 g, 12.5 mmol, 2 eq) at 20° C. under N$_2$. The mixture was stirred at 100° C. for 2 h under microwave. LCMS showed the reaction was completed and desired MS observed. The mixture was cooled to 25° C., and EtOAc (40 mL) was added to the result mixture. The mixture filtered and the solution was concentrated under reduced pressure to get yellow gum which was purified by silica gel column chromatography (Petroleum ether/Ethyl acetate=1:1) to afford crude product. Then the crude product was further purified by Prep-HPLC (column: Phenomenex luna C18 (250*70 mm, 10 um); mobile phase: [water (HCl)-ACN]; B %: 15%-45%, 25 min) to give desired product (0.95 g) as a white solid. $^1$H NMR (400 MHz, DMSO-d6) δ 9.26 (s, 1H), 8.78 (s, 1H), 8.30 (s, 1H), 8.27 (d, J=8.8 Hz, 1H), 8.17 (d, J=12.4 Hz, 1H), 7.75 (br s, 1H), 7.17 (br s, 1H), 7.08 (d, J=9.2 Hz, 1H), 6.15 (d, J=12.4 Hz, 1H), 4.62-4.49 (m, 1H), 4.06-3.97 (m, 1H), 3.94-3.86 (m, 1H), 3.72-3.60 (m, 2H), 3.53-3.44 (m, 1H), 2.39 (s, 3H), 2.20-2.10 (m, 1H), 2.04-1.90 (m, 1H). MS (ESI): mass calculated for $C_{19}H_{20}BN_5O_4$, 393.16, m/z found 394.2[M+H]+. HPLC: 99.57% (220 nm), 99.24% (254 nm). 845 mg was further separated by SFC (column: REGIS(S,S)WHELK-O1 (250 mm*25 mm, 10 um); mobile phase: [Neu-IPA]; B %: 50%-50%, 9 min) to give two isomers: 1-[trans-4-cyanotetrahydro-2H-pyran-3-yl]-3-[(2-hydroxy-5-methyl-1,2-benzoxaborinin-6-yl) amino]pyrazole-4-carboxamide (stereoisomer one)(374.3 mg, 15.1% yield, 100% ee, first peak, Rt=1.329 min) as a white solid; $^1$H NMR (400 MHz, DMSO-d6) δ 9.25 (s, 1H), 8.79 (s, 1H), 8.30 (s, 1H), 8.27 (d, J=8.8 Hz, 1H), 8.17 (d, J=12.4 Hz, 1H), 7.75 (br s, 1H), 7.17 (br s, 1H), 7.08 (d, J=8.8 Hz, 1H), 6.15 (d, J=12.0 Hz, 1H), 4.62-4.49 (m, 1H), 4.06-3.97 (m, 1H), 3.94-3.86 (m, 1H), 3.72-3.60 (m, 2H), 3.53-3.44 (m, 1H), 2.39 (s, 3H), 2.20-2.10 (m, 1H), 2.04-1.90 (m, 1H). MS (ESI): mass calculated for $C_{19}H_{20}BN_5O_4$, 393.16, m/z found 394.2[M+H]+. HPLC: 99.90% (220 nm), 100% (254 nm) and 1-[trans-4-cyanotetrahydropyran-3-yl]-3-[(2-hydroxy-5-methyl-1,2-benzoxaborinin-6-yl)amino] pyrazole-4-carboxamide (stereoisomer two) (280 mg, 11.1% yield, 99.44% ee, second peak, Rt=1.543 min) (BN-203940-02) as a white solid. $^1$H NMR (400 MHz, DMSO-d6) δ 9.21 (s, 1H), 8.75 (s, 1H), 8.26 (s, 1H), 8.23 (d, J=9.2 Hz, 1H), 8.13 (d, J=12.4 Hz, 1H), 7.71 (br s, 1H), 7.12 (br s, 1H), 7.04 (d, J=8.8 Hz, 1H), 6.12 (d, J=12.4 Hz, 1H), 4.62-4.49 (m, 1H), 4.06-3.97 (m, 1H), 3.94-3.86 (m, 1H), 3.72-3.60 (m, 2H), 3.53-3.44 (m, 1H), 2.35 (s, 3H), 2.20-2.10 (m, 1H), 2.04-1.90 (m, 1H). MS (ESI): mass calculated for $C_{19}H_{20}BN_5O_4$, 393.16, m/z found 394.2[M+H]+. HPLC: 99.95% (220 nm), 99.93% (254 nm).

18. Preparation of 1-(trans-2-cyanocyclohexyl)-3-[(2-hydroxy-1,2-benzoxaborinin-6-yl)amino]pyrazole-4-carboxamide

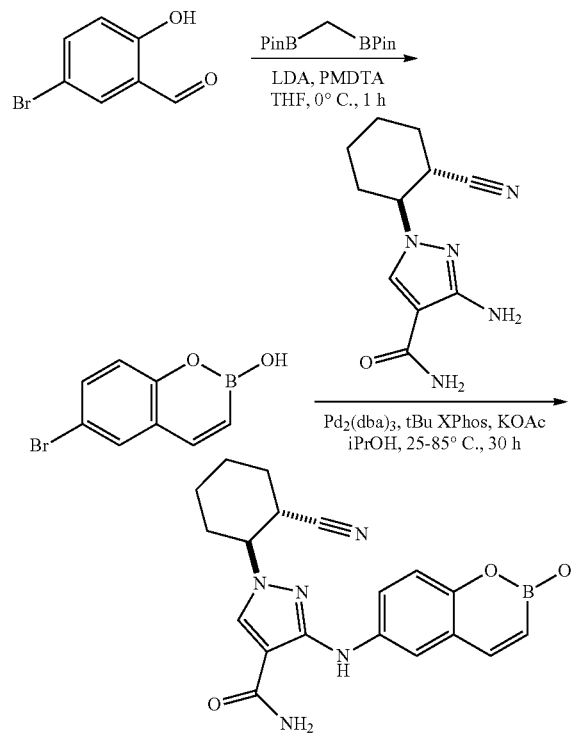

18.1 Preparation of 6-bromo-2-hydroxy-1,2-benzoxaborinine

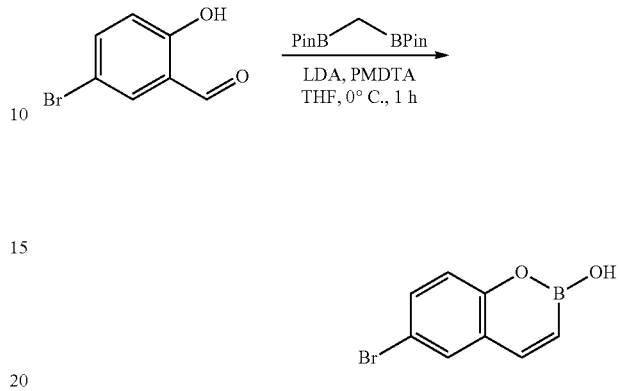

To a solution of LDA (2 M, 18.7 mL, 2.5 eq) in THF (50 mL) was added 4,4,5,5-tetramethyl-2-[(4,4,5,5-tetramethyl-1,3,2-dioxaborolan-2-yl)methyl]-1,3,2-dioxaborolane (10.0 g, 37.3 mmol, 2.5 eq) and N'-[2-(dimethylamino)ethyl]-N,N,N'-trimethyl-ethane-1,2-diamine (PMDTA, 7.76 g, 44.8 mmol, 9.4 mL, 3 eq) dropwise at 0° C. under $N_2$. The mixture was stirred at 0° C. for 20 min. To the resulting mixture was added a solution of 5-bromo-2-hydroxy-benzaldehyde (3.00 g, 14.9 mmol, 1 eq) in THF (10 mL) dropwise at 0° C. The mixture was continue stirred for 1 h at 0° C. LCMS showed the reaction was completed and desired MS observed. The mixture was quenched by addition of sat. aq. $NH_4Cl$ (30 mL) and extracted with EtOAc (30 mL×2). The combined organic layers were washed by brine (30 mL×2), dried over $Na_2SO_4$, filtered and concentrated under reduced pressure to get a residue. The residue was purified by flash silica gel chromatography (ISCO®; 40 g SepaFlash® Silica Flash Column, Eluent of 20~40% Ethyl acetate/Petroleum ether gradient @ 75 mL/min) to get 6-bromo-2-hydroxy-1,2-benzoxaborinine (500 mg, 14.9% yield) as a white solid. $^1$H NMR (CDCl$_3$, 400 MHz) δ 7.69 (d, J=12.0 Hz, 1H), 7.55 (d, J=2.4 Hz, 1H), 7.46 (dd, J=8.8, 2.4 Hz, 1H), 7.14 (d, J=8.8 Hz, 1H), 6.28 (d, J=12.0 Hz, 1H).

18.2 Preparation of 1-(trans-2-cyanocyclohexyl)-3-[(2-hydroxy-1,2-benzoxaborinin-6-yl)amino]pyrazole-4-carboxamide

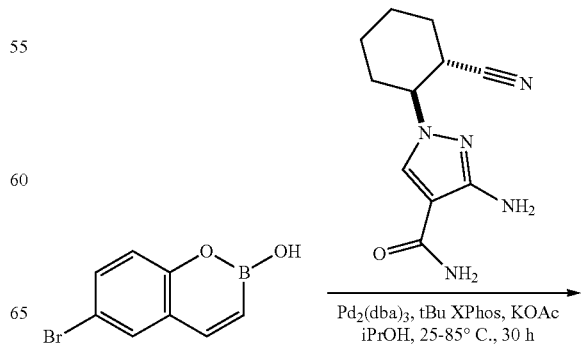

-continued

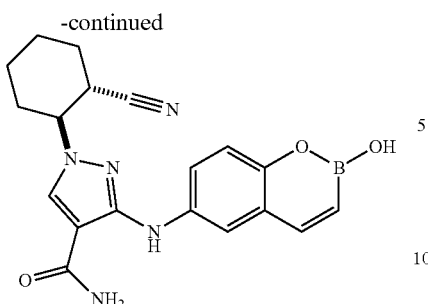

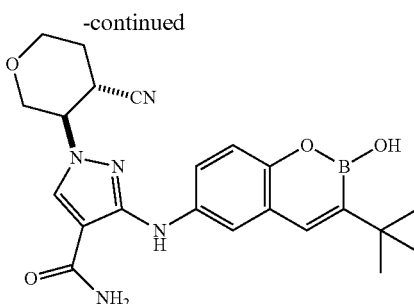

To a mixture of 3-amino-1-(trans-2-cyanocyclohexyl)pyrazole-4-carboxamide (143 mg, 611 umol, 1.1 eq) and 6-bromo-2-hydroxy-1,2-benzoxaborinine (125 mg, 556 umol, 1 eq) in i-PrOH (10 mL) was added AcOK (82 mg, 834 umol, 1.5 eq), Pd$_2$(dba)$_3$ (26 mg, 27.8 umol, 0.05 eq) and t-Bu Xphos (24 mg, 55.6 umol, 0.1 eq) in one portion at 25° C. under N$_2$. The mixture was heated to 85° C. and stirred at 85° C. for 30 h. LCMS showed the reaction was completed and desired MS observed. The mixture was added H$_2$O (0.1 mL) at 25° C., filtered and the filtrate was concentrated under reduced pressure to give a residue. The residue was purified by prep-HPLC (column: Phenomenex Gemini-NX 80*40 mm*3 um; mobile phase: [water (10 mM NH$_4$HCO$_3$)-ACN]; B %: 15%-45%, 8 min) to get 1-(trans-2-cyanocyclohexyl)-3-[(2-hydroxy-1,2-benzoxaborinin-6-yl)amino]pyrazole-4-carboxamide (34.9 mg, 90.8% purity) as an off-white solid. $^1$H NMR (DMSO-d$_6$, 400 MHz) δ 9.07 (s, 1H), 8.80 (s, 1H), 8.23 (s, 1H), 7.79 (d, J=12.0 Hz, 1H), 7.68 (d, J=2.8 Hz, 1H), 7.5 (br s, 1H), 7.57 (dd, J=8.8, 2.8 Hz, 1H), 7.14-7.11 (m, 2H), 6.10 (d, J=12.0 Hz, 1H), 4.39-4.33 (m, 1H), 3.32-3.29 (m, 1H), 2.21-2.18 (m, 1H), 1.98-1.96 (m, 1H), 1.84-1.71 (m, 4H), 1.45-1.37 (m, 2H). MS (ESI): mass calculated for C$_{19}$H$_{20}$BN$_5$O$_3$ 377.17, m/z found 378.2 [M+H]$^+$. HPLC: 90.87% (220 nm), 96.68% (254 nm).

19. Preparation of 3-[(3-tert-butyl-2-hydroxy-1,2-benzoxaborinin-6-yl)amino]-1-(trans-4-cyanotetrahydro-2H-pyran-3-yl)pyrazole-4-carboxamide

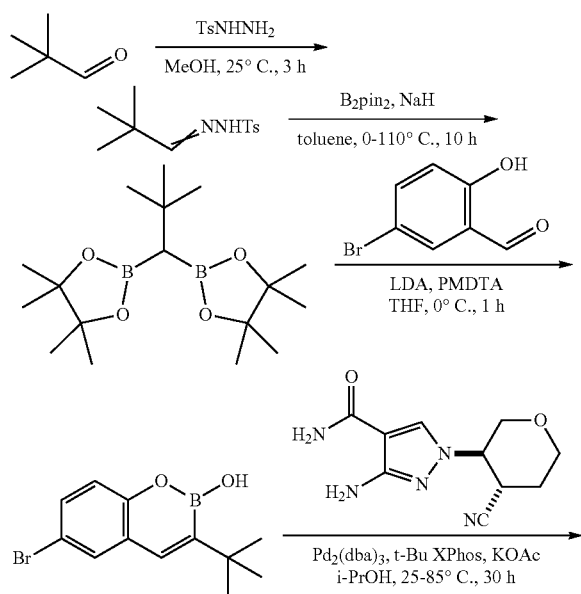

19.1 Preparation of N-(2,2-dimethylpropylideneamino)-4-methyl-benzenesulfonamide

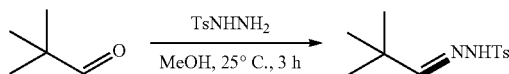

To a mixture of 2,2-dimethylpropanal (10.0 g, 116 mmol, 12.8 mL, 1 eq) in MeOH (100 mL) was added 4-methyl-benzenesulfonohydrazide (21.6 g, 116 mmol, 1 eq) in one portion at 25° C. under N$_2$. The mixture was stirred at 25° C. for 3 h. TLC showed the reaction was completed. The mixture was concentrated under reduced pressure to give N-(2,2-dimethylpropylideneamino)-4-methyl-benzenesulfonamide (20.0 g, crude) as a white solid.

19.2 Preparation of 2-[2,2-dimethyl-1-(4,4,5,5-tetramethyl-1,3,2-dioxaborolan-2-yl)propyl]-4,4,5,5-tetramethyl-1,3,2-dioxaborolane

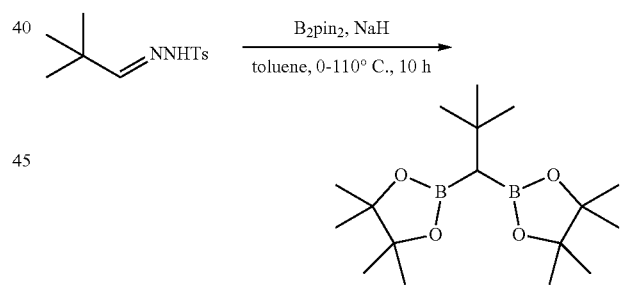

To a mixture of N-[2,2-dimethylpropylideneamino]-4-methyl-benzenesulfonamide (10.0 g, 39.3 mmol, 1 eq) in toluene (250 mL) was added NaH (1.89 g, 47.2 mmol, 60% purity, 1.2 eq) in portions at 0° C. under N$_2$. The reaction was allowed to warm to 25° C. and stirred at 25° C. for 0.5 h. To the reaction mixture was added 4,4,5,5-tetramethyl-2-(4,4,5,5-tetramethyl-1,3,2-dioxaborolan-2-yl)-1,3,2-dioxaborolane (11.9 g, 47.2 mmol, 1.2 eq) at 25° C. The resulting mixture was heated to 110° C. and stirred at 110° C. for 9.5 h. TLC showed the reaction was completed. The mixture was quenched with H$_2$O (100 mL) at 0° C. and extracted with EtOAc (100 mL×2). The combined organic layers were washed by brine (100 mL×2), dried over Na$_2$SO$_4$, filtered and concentrated under reduced pressure to get a residue. The residue was purified by flash silica gel chromatography (ISCO®; 120 g SepaFlash® Silica Flash Column, Eluent of 10-20/Ethyl acetate/Petroleum ether gradient @ 120 mL/min) to get 2-[2,2-dimethyl-1-(4,4,5,5-tetramethyl-1,3,2-dioxaborolan-2-yl)propyl]-4,4,5,5-tetramethyl-1,3,2-dioxaborolane (8.20 g, 64.4% yield) as colorless oil. $^1$H NMR (CDCl$_3$, 400 MHz) δ 1.24 (s, 12H), 1.23 (s, 12H), 1.07 (s, 9H), 0.78 (s, 1H).

19.3 Preparation of 6-bromo-3-tert-butyl-2-hydroxy-1,2-benzoxaborinine

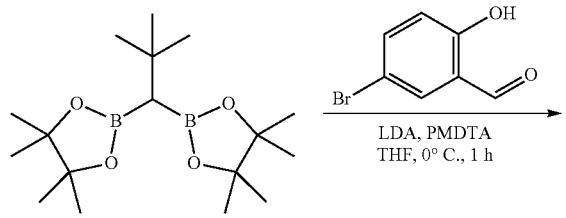

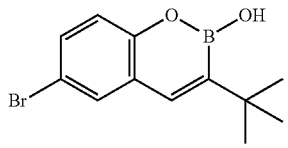

To a mixture of LDA (2 M, 2.5 mL, 2 eq) in THF (10 mL) was added 2-[2,2-dimethyl-1-(4,4,5,5-tetramethyl-1,3,2-dioxaborolan-2-yl)propyl]-4,4,5,5-tetramethyl-1,3,2-dioxaborolane (1.61 g, 4.97 mmol, 2 eq) and N'-[2-(dimethylamino)ethyl]-N,N,N'-trimethyl-ethane-1,2-diamine (PMDTA, 1.08 g, 6.22 mmol, 1.3 mL, 2.5 eq) dropwise at 0° C. under N$_2$. The mixture was stirred at 0° C. for 0.5 h. Then added a solution of 5-bromo-2-hydroxy-benzaldehyde (500 mg, 2.49 mmol, 1 eq) in THF (10 mL) at 0° C. The resulting mixture was stirred at 0° C. for 0.5 h. LCMS showed the reaction was completed and desired MS observed. The mixture was quenched by addition of sat. aq. NH$_4$Cl (30 mL) and extracted with EtOAc (20 mL×2). The combined organic layers were washed by brine (30 mL×2), dried over Na$_2$SO$_4$, filtered and concentrated under reduced pressure to get a residue. The residue was purified by flash silica gel chromatography (ISCO®; 20 g SepaFlash® Silica Flash Column, Eluent of 20-25% Ethyl acetate/Petroleum ether gradient @ 60 mL/min) to get the crude product. The crude product was triturated by Petroleum ether (3 mL) and filtered to give 6-bromo-3-tert-butyl-2-hydroxy-1,2-benzoxaborinine (200 mg, 99.2% purity) as a white solid. $^1$H NMR (DMSO-d$_6$, 400 MHz) δ 9.14 (s, 1H), 7.74 (d, J=2.4 Hz, 1H), 7.47-7.43 (m, 2H), 7.12 (d, J=8.8 Hz, 1H), 1.24 (s, 9H). MS (ESI): mass calculated for C$_{12}$H$_{14}$BBrO$_2$ 280.03; m/z found 279.1 [M−H]$^−$. HPLC: 99.26% (220 nm), 100% (254 nm).

19.4 Preparation of 3-[(3-tert-butyl-2-hydroxy-1,2-benzoxaborinin-6-yl)amino]-1-(trans-4-cyanotetrahydro-2H-pyran-3-yl)pyrazole-4-carboxamide

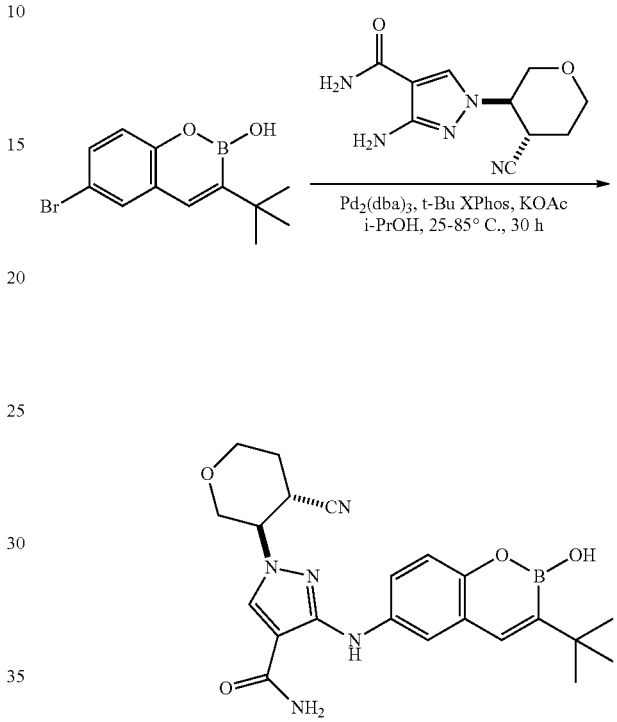

To a mixture of 3-amino-1-(4-cyanotetrahydropyran-3-yl)pyrazole-4-carboxamide (201 mg, 854 umol, 1.2 eq) and 6-bromo-3-tert-butyl-2-hydroxy-1,2-benzoxaborinine (200 mg, 712 umol, 1 eq) in i-PrOH (10 mL) was added AcOK (105 mg, 1.07 mmol, 1.5 eq), Pd$_2$(dba)$_3$ (33 mg, 35.6 umol, 0.05 eq) and t-Bu Xphos (30 mg, 71 umol, 0.1 eq) in one portion at 25° C. under N$_2$. The mixture was heated to 85° C. and stirred at 85° C. for 30 h. LCMS showed the reaction was completed and desired MS observed. The mixture was quenched with H$_2$O (0.1 mL), filtered and concentrated under reduced pressure to get a residue. The residue was purified by prep-HPLC (column: Waters Xbridge BEH C18 100*30 mm*10 um; mobile phase: [water (10 mM NH$_4$HCO$_3$)-ACN]; B %: 20/6-50%/6.10 min) to get 3-[(3-tert-butyl-2-hydroxy-1,2-benzoxaborinin-6-yl)amino]-1-(trans-4-cyanotetrahydro-2H-pyran-3-yl)pyrazole-4-carboxamide (85 mg, 99.5% purity) as a yellow solid. 1H-NMR (DMSO-hd 6, 400 MHz) δ 9.07 (s, 1H), 8.83 (s, 1H), 8.28 (s, 1H), 7.68 (br s, 1H), 7.60-7.58 (m, 1H), 7.57-7.54 (m, 1H), 7.42 (s, 1H), 7.12 (br s, 1H), 7.08 (d, J=7.6 Hz, 1H), 4.59-4.53 (m, 1H), 4.07-4.02 (m, 1H), 3.93-3.90 (m, 1H), 3.72-3.66 (m, 2H), 3.50-3.48 (m, 1H), 2.16-2.14 (m, 1H), 2.01-1.99 (m, 1H), 1.25 (s, 9H). MS (ESI): mass calculated for C$_{22}$H$_{26}$BN$_5$O$_4$ 435.21; m/z found 436.3 [M+H]$^+$. HPLC: 99.51% (220 nm), 98.07% (254 nm).

20. Preparation of 3-[(3-tert-butyl-2-hydroxy-1,2-benzoxaborinin-6-yl)amino]-1-(trans-2-cyanocyclopentyl)pyrazole-4-carboxamide

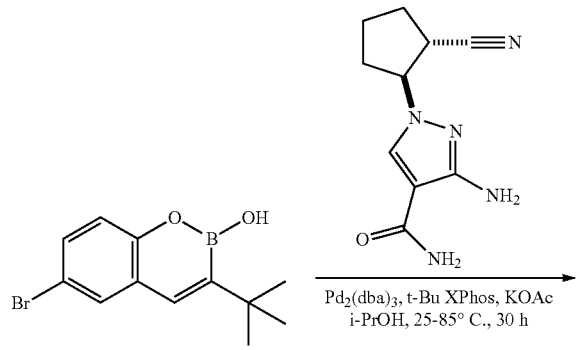

To a mixture of 3-amino-1-(trans-2-cyanocyclopentyl) pyrazole-4-carboxamide (93.6 mg, 427 umol, 1.2 eq) and 6-bromo-3-tert-butyl-2-hydroxy-1,2-benzoxaborinine (100 mg, 355 umol, 1 eq) in i-PrOH (5 mL) was added AcOK (52.4 mg, 533 umol, 1.5 eq), Pd$_2$(dba)$_3$ (16.3 mg, 17.8 umol, 0.05 eq) and t-Bu Xphos (15.1 mg, 35.6 umol, 0.1 eq) in one portion at 25° C. under N$_2$. The mixture was heated and stirred at 85° C. for 30 h. LCMS showed the reaction was completed and desired MS observed. The mixture was quenched with H$_2$O (0.3 mL), filtered and concentrated under reduced pressure to get a residue. The residue was purified by prep-HPLC (column: Waters Xbridge BEH C18 100*30 mm*10 um; mobile phase: [water (10 mM NH$_4$HCO$_3$)-ACN]; B %: 25%-55%, 10 min) to get 3-[(3-tert-butyl-2-hydroxy-1,2-benzoxaborinin-6-yl)amino]-1-(trans-2-cyanocyclopentyl)pyrazole-4-carboxamide (34.6 mg, 22.7% yield, 98.2% purity) as a yellow solid. 1H-NMR (DMSO-hd 6, 400 MHz) δ 9.03 (s, 1H), 8.81 (s, 1H), 8.27 (s, 1H), 7.77 (s, 1H), 7.60-7.58 (br s, 1H), 7.46-7.43 (m, 2H), 7.13-7.10 (br s, 1H), 7.06 (d, J=8.4 Hz, 1H), 4.89-4.83 (m, 1H), 3.39-3.31 (m, 1H), 2.30-2.28 (m, 2H), 2.07-1.88 (m, 4H), 1.24 (s, 9H).

21. Preparation of 3-[(3-tert-butyl-2-hydroxy-1,2-benzoxaborinin-6-yl)amino]-1-(trans-2-cyanocyclohexyl)pyrazole-4-carboxamide

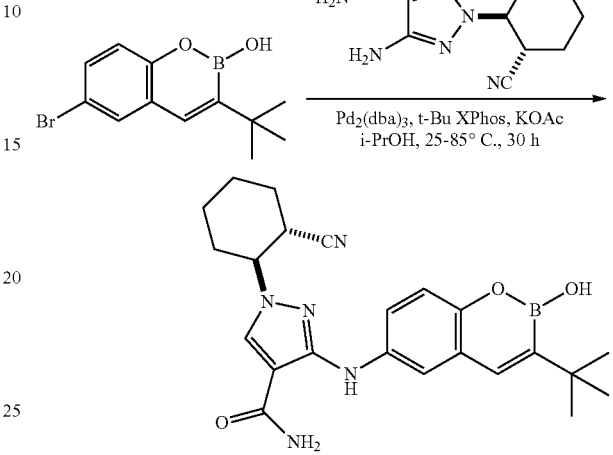

To a mixture of 3-amino-1-(2-cyanocyclohexyl)pyrazole-4-carboxamide (149 mg, 640 umol, 1.2 eq) and 6-bromo-3-tert-butyl-2-hydroxy-1,2-benzoxaborinine (150 mg, 533 umol, 1 eq) in i-PrOH (10 mL) was added AcOK (78.6 mg, 800 umol, 1.5 eq), Pd$_2$(dba)$_3$ (24.5 mg, 26.7 umol, 0.05 eq) and t-Bu Xphos (22.7 mg, 53.4 umol, 0.1 eq) in one portion at 25° C. under N$_2$. The mixture was heated and stirred at 85° C. for 30 h. LCMS showed the reaction was completed and desired MS observed. The mixture was quenched with H$_2$O (0.1 mL), filtered and the filtrate was concentrated under reduced pressure to get a residue. The residue was purified by prep-HPLC (column: Waters Xbridge BEH C18 100*30 mm*10 um; mobile phase: [water (10 mM NH$_4$HCO$_3$)-ACN]; B %: 35%-65%, 10 min) to give 3-[(3-tert-butyl-2-hydroxy-1,2-benzoxaborinin-6-yl)amino]-1-(2-cyanocyclohexyl)pyrazole-4-carboxamide (55.9 mg, 23.9% yield, 99.1% purity) as a yellow solid. 1H-NMR (DMSO-hd 6, 400 MHz) δ 9.05 (s, 1H), 8.82 (s, 1H), 8.23 (s, 1H), 7.68 (br s, 1H), 7.61 (dd, J=8.8, 2.8 Hz, 1H), 7.54 (d, J=2.8 Hz, 1H), 7.41 (s, 1H), 7.12 (br s, 1H), 7.08 (d, J=8.8 Hz, 1H), 4.38-4.35 (m, 1H), 3.28-3.27 (m, 1H), 2.23-2.18 (m, 1H), 2.09-2.06 (m, 1H), 1.83-1.71 (m, 4H), 1.51-1.48 (m, 1H), 1.36-1.31 (m, 1H), 1.25 (s, 9H). MS (ESI): mass calculated for C$_{23}$H$_{28}$BN$_5$O$_3$ 433.23; m/z found 432.3 [M−H]$^-$. HPLC: 99.19% (220 nm), 99.85% (254 nm).

22. 1-[rans-4-cyanoaxan-3-yl]-3-{[2-hydroxy-3-(2-hydroxyethyl)-2H-1,2-benzoxaborinin-6-yl]amino}-1H-pyrazole-4-carboxamide

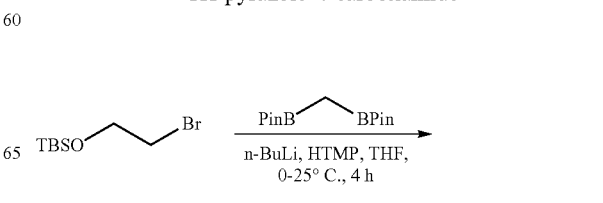

-continued

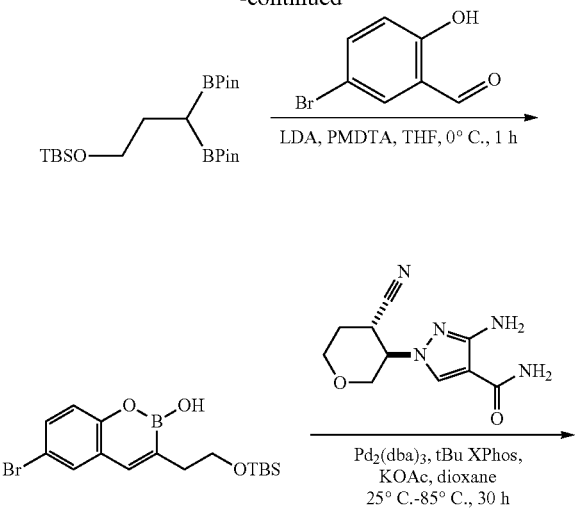

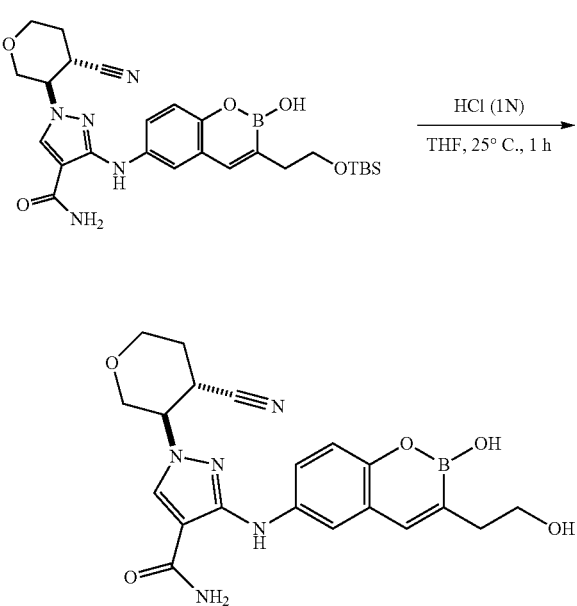

22.1 Preparation of 3,3-bis(4,4,5,5-tetramethyl-1,3,2-dioxaborolan-2-yl)propoxy-tert-butyl-dimethyl-silane

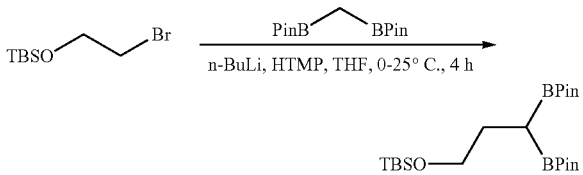

To a mixture of 2,2,6,6-tetramethylpiperidine (HTMP, 2.90 g, 20.5 mmol, 3.48 mL, 1.1 eq) in THF (60 mL) was added n-BuLi (2.5 M, 8.21 mL, 1.1 eq) dropwise at 0° C. under $N_2$. The mixture was stirred at 0° C. for 30 min. To the reaction mixture was added a solution of 4,4,5,5-tetramethyl-2-[(4,4,5,5-tetramethyl-1,3,2-dioxaborolan-2-yl)methyl]-1,3,2-dioxaborolane (5.00 g, 18.6 mmol, 1 eq) in THF (30 mL) dropwise at 0° C. The reaction mixture was stirred for 30 min at 0° C. Then a solution of 2-bromoethoxy-tert-butyl-dimethyl-silane (11.1 g, 46.6 mmol, 2.5 eq) in THF (30 mL) was added dropwise to the above mixture at 0° C. The resulting reaction mixture was stirred for 3 h at 20° C. TLC showed the reaction was completed. The mixture was poured into sat. aq. $NH_4Cl$ (50 mL) and extracted with ethyl acetate (30 mL×3). The combined organic phase was washed with brine (30 mL×2), dried over $Na_2SO_4$, filtered and concentrated in vacuum to give a residue. The residue was purified by flash silica gel chromatography (ISCO®; 80 g SepaFlash® Silica Flash Column, Eluent of 5~10% Ethyl acetate/Petroleum ether gradient @ 100 mL/min) to give 3,3-bis(4,4,5,5-tetramethyl-1,3,2-dioxaborolan-2-yl)propoxy-tert-butyl-dimethyl-silane (4.7 g, 59.0% yield) as colorless oil. $^1$H NMR (CDCl$_3$, 400 MHz) δ 3.55 (t, J=7.2 Hz, 2H), 1.82-1.77 (m, 2H), 1.22 (s, 24H), 0.91 (s, 9H), 0.87 (t, J=6.8 Hz, 1H), 0.04 (s, 6H).

22.2 Preparation of 2-(6-bromo-2-hydroxy-1,2-benzoxaborinin-3-yl)ethoxy-tert-butyl-dimethyl-silane To a mixture of LDA (2 M, 5.47 mL, 2.2 eq) in THF (20 mL) was added 3,3-bis(4,4,5,5-tetramethyl-1,3,2-dioxaborolan-2-yl)propoxy-tert-butyl-dimethyl-silane (4.67 g, 10.9 mmol, 2.2 eq) and N'-[2-(dimethylamino)ethyl]-N,N,N'-trimethyl-ethane-1,2-diamine (2.16 g, 12.4 mmol, 2.60 mL, 2.5 eq) dropwise at 0° C. under $N_2$. The mixture was stirred at 0° C. for 30 min, and then to the mixture was added a solution of 5-bromo-2-hydroxy-benzaldehyde (1.00 g, 4.97 mmol, 1 eq) in THF (20 mL). The resulting mixture was stirred for 0.5 h at 0° C. LCMS showed the reaction was completed and desired MS observed. The mixture was quenched with sat. aq. $NH_4Cl$ (50 mL) and extracted with EtOAc (50 mL×2). The combined organic layers were washed by brine (30 mL×2), dried over $Na_2SO_4$, filtered and concentrated under reduced pressure to get a residue. The residue was purified by flash silica gel chromatography (ISCO®; 40 g SepaFlash® Silica Flash Column, Eluent of 15-25% Ethyl acetate/Petroleum ether gradient @ 75 mL/min) to give 2-(6-bromo-2-hydroxy-1,2-benzoxaborinin-3-yl)ethoxy-tert-butyl-dimethyl-silane (2.00 g, 31.4% yield, 30% purity) as colorless oil.

$^1$H NMR (DMSO-d$_6$, 400 MHz) δ 9.07 (s, 1H), 7.66 (d, J=2.4 Hz, 1H), 7.47-7.45 (m, 2H), 7.14 (d, J=8.8 Hz, 1H), 3.75 (t, J=7.2 Hz, 2H), 2.66-2.65 (m, 2H), 0.85 (s, 9H), 0.01 (s, 6H).

22.3 Preparation of 3-[[3-[2-[tert-butyl(dimethyl)silyl]oxyethyl]-2-hydroxy-1,2-benzoxaborinin-6-yl]amino]-1-[trans-4-cyanotetrahydro-2H-pyran-3-yl]pyrazole-4-carboxamide

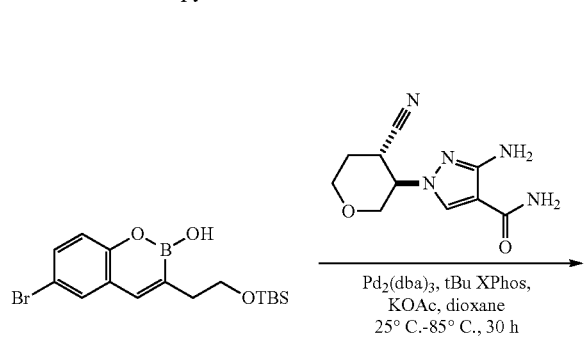

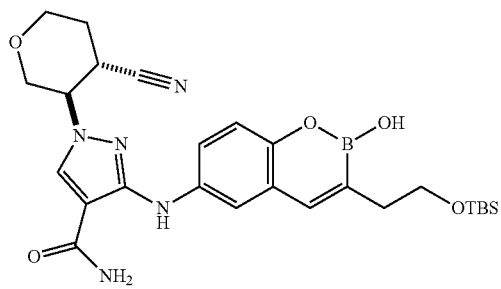

To a mixture of 3-amino-1-(trans-4-cyanotetrahydropyran-3-yl)pyrazole-4-carboxamide (235 mg, 1.00 mmol, 1.2 eq) and 2-(6-bromo-2-hydroxy-1,2-benzoxaborinin-3-yl)ethoxy-tert-butyl-dimethyl-silane (800 mg, 835 umol, 40/a purity, 1 eq) in i-PrOH (10 mL) was added AcOK (122 mg, 1.25 mmol, 1.5 eq), Pd$_2$(dba)$_3$ (38.2 mg, 41.8 umol, 0.05 eq) and t-Bu Xphos (35.5 mg, 83.5 umol, 0.1 eq) in one portion at 25° C. under N$_2$. The mixture was stirred at 85° C. for 30 h. LCMS showed the reaction was completed and desired MS observed. The mixture was added H$_2$O (0.5 mL), filtered and the filtrate was concentrated under reduced pressure to get a residue. The residue was purified by flash silica gel chromatography (ISCO®; 20 g SepaFlash® Silica Flash Column, Eluent of 70-85% Ethyl acetate/Petroleum ether gradient @ 60 mL/min) to give 3-[[3-[2-[tert-butyl(dimethyl)silyl]oxyethyl]-2-hydroxy-1,2-benzoxaborinin-6-yl]amino]-1-(trans-4-cyano tetrahydropyran-3-yl]pyrazole-4-carboxamide (200 mg, 22.2% yield) as a white solid. $^1$H NMR (DMSO-hd 6, 400 MHz) δ 9.08 (s, 1H), 8.76 (s, 1H), 8.30 (s, 1H), 7.72 (br s, 1H), 7.64 (d, J=2.8 Hz, 1H), 7.51 (s, 1H), 7.48 (dd, J=8.8, 2.8 Hz, 1H), 7.17 (br s, 1H), 7.11 (d, J=8.8 Hz, 1H), 4.59-4.56 (m, 1H), 4.07-4.03 (m, 1H), 4.01-3.98 (m, 1H), 3.78-3.76 (m, 2H), 3.75-3.73 (m, 2H), 3.58-3.55 (m, 1H), 2.58-2.56 (m, 2H), 2.23-2.19 (m, 1H), 2.01-1.98 (m, 1H), 0.85 (s, 9H), 0.02 (s, 6H).

22.4 Preparation of 1-[trans-4-cyanooxan-3-yl]-3-{[2-hydroxy-3-(2-hydroxyethyl)-2H-1,2-benzoxaborinin-6-yl]amino}-1H-pyrazole-4-carboxamide

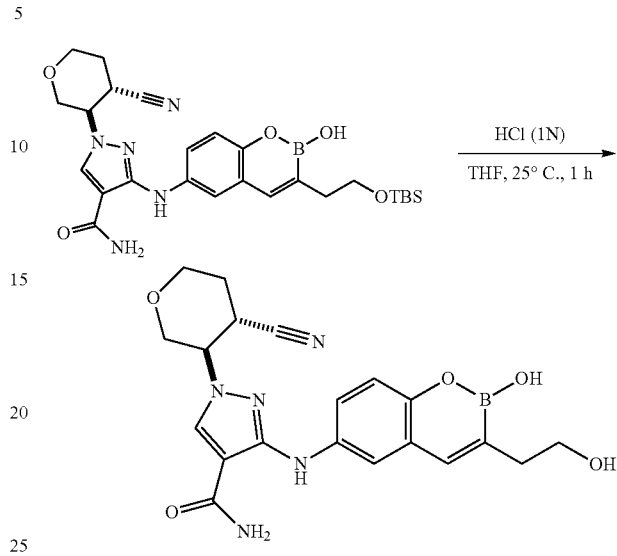

To a mixture of 3-[[3-[2-[tert-butyl(dimethyl)silyl]oxyethyl]-2-hydroxy-1,2-benzoxaborinin-6-yl]amino]-1-[trans-4-cyanotetrahydropyran-3-yl]pyrazole-4-carboxamide (100 mg, 186 umol, 1 eq) in THF (1 mL) was added HCl (1 M, 1.12 mL, 6 eq) in one portion at 25° C. under N$_2$. The mixture was stirred at 25° C. for 1 h. LCMS showed the reaction was completed and desired MS observed. The mixture was concentrated under reduced pressure to give a residue. The residue was purified by prep-HPLC (column: Waters Xbridge BEH C18 100*30 mm*10 um; mobile phase: [water (10 mM NH$_4$HCO$_3$)-ACN]; B %: 5%-35%, 10 min) to give 1-[trans-4-cyanooxan-3-yl]-3-{[2-hydroxy-3-(2-hydroxyethyl)-2H-1,2-benzoxaborinin-6-yl]amino}-1H-pyrazole-4-carboxamide (65 mg, 39.3% yield, 95.3% purity) as a white solid. $^1$H NMR (DMSO-hd 6, 400 MHz) 9.07 (s, 1H), 8.79 (s, 1H), 8.28 (s, 1H), 7.71 (br s, 1H), 7.61 (d, J=2.4 Hz, 1H), 7.49-7.45 (m, 2H), 7.15 (br s, 1H), 7.09 (d, J=8.8 Hz, 1H), 4.68 (t, J=5.2 Hz, 1H), 4.56-4.54 (m, 1H), 4.05-4.03 (m, 1H), 3.95-3.89 (m, 1H), 3.73-3.70 (m, 2H), 3.60-3.55 (m, 3H), 2.56-2.53 (m, 2H), 2.18-2.15 (m, 1H), 2.01-1.99 (m, 1H). MS (ESI): mass calculated for C$_{20}$H$_{22}$BN$_5$O$_5$ 423.17; m/z found 422.2 [M−H]$^-$. HPLC: 95.37% (220 nm), 97.68% (254 nm).

23. Preparation of 1-(trans-4-cyanotetrahydropyran-3-yl)-3-[(2-hydroxy-3,4,8-trimethyl-1,2-benzoxaborinin-6-yl)amino]pyrazole-4-carboxamide

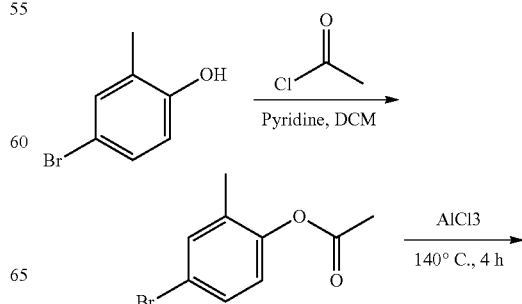

23.1 Preparation of (4-bromo-2-methyl-phenyl) acetate

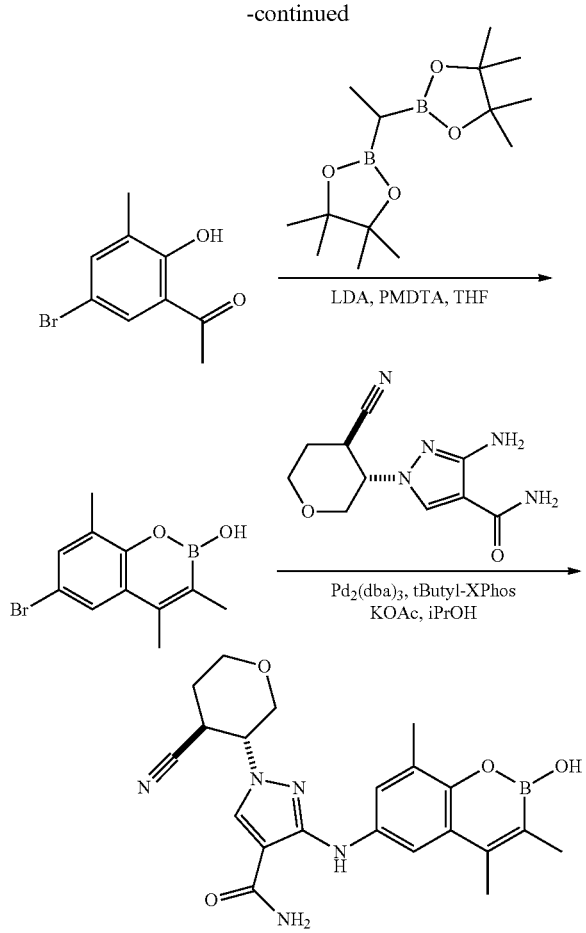

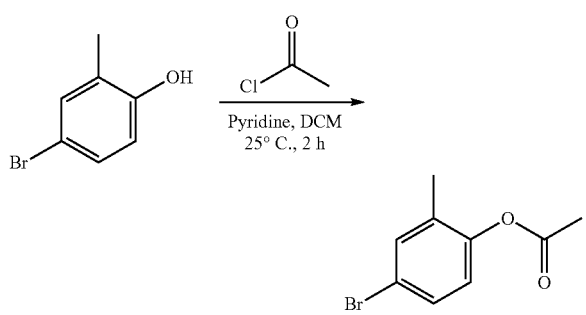

To a solution of 4-bromo-2-methyl-phenol (3.00 g, 16 mmol, 1 eq) and pyridine (2.50 g, 32.1 mmol, 2.6 mL, 2 eq) in DCM (20 mL) was dropwise added acetyl chloride (1.26 g, 16 mmol, 1.1 mL, 1 eq) at 0° C. The resulting mixture was stirred at 25° C. for 2 h. TLC showed the reaction was completed. The reaction mixture was concentrated under reduced pressure to remove DCM. The reaction was quenched with H$_2$O (30 mL), adjust pH=6 with 2N HCl and extracted with EtOAc (10 mL×3). The combined organic layers were washed with brine (20 mL), dried over with Na$_2$SO$_4$, filtered and concentrated under reduced pressure to give (4-bromo-2-methyl-phenyl) acetate (3.30 g, 89.8% yield) as yellow liquid. 1H NMR (CDCl$_3$, 400 MHz) δ 7.39 (d, J=2.4 Hz, 1H), 7.35-7.29 (m, 1H), 6.90 (d, J=8.4 Hz, 1H), 2.33 (s, 3H), 2.17 (s, 3H).

23.2 Preparation of 1-(5-bromo-2-hydroxy-3-methyl-phenyl)ethanone

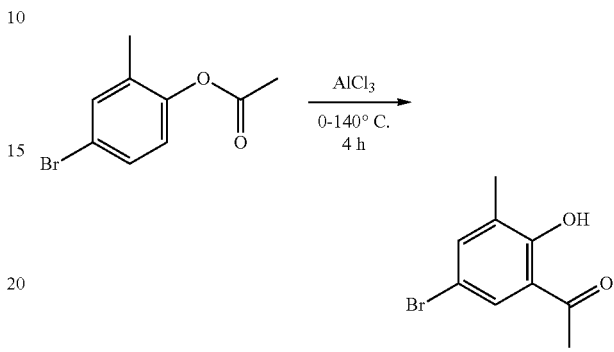

To a solution of (4-bromo-2-methyl-phenyl) acetate (3.30 g, 14.4 mmol, 3.4 mL, 1 eq) was added AClCl$_3$ (4.80 g, 36.0 mmol, 2.5 eq) at 0° C. After addition, the resulting mixture was heated and stirred at 140° C. for 4 h. TLC showed the reaction was completed. The reaction mixture was quenched by addition H$_2$O (100 mL) at 0° C. and then extracted with DCM (100 mL×3). The combined organic layers were washed with brine (200 mL), dried over with Na$_2$SO$_4$, filtered and concentrated under reduced pressure to give a residue. The residue was purified by flash silica gel chromatography (ISCO®; 120 g SepaFlash® Silica Flash Column, Eluent of 0~10% Ethyl acetate/Petroleum ether gradient @ 100 mL/min) to give 1-(5-bromo-2-hydroxy-3-methyl-phenyl)ethanone (3.00 g, 90.9% yield) as a yellow solid. 1H NMR (CDCl$_3$, 400 MHz) δ 12.48 (s, 1H), 7.69 (d, J=2.3 Hz, 1H), 7.46-7.44 (m, 1H), 2.62 (s, 3H), 2.25 (s, 3H).

23.3 Preparation of 6-bromo-2-hydroxy-3,4,8-trimethyl-1,2-benzoxaborinine

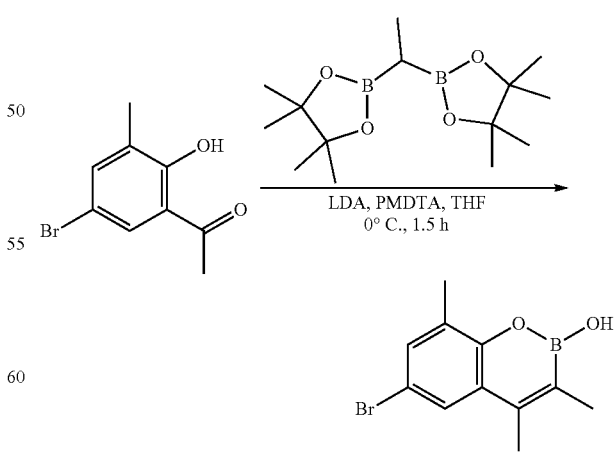

To a solution of LDA (2 M, 6.6 mL, 3 eq) in THF (10 mL) was dropwise added N'-[2-(dimethylamino)ethyl]-N,N,N'-trimethyl-ethane-1,2-diamine (1.51 g, 8.7 mmol, 1.8 mL, 2 eq) and 4,4,5,5-tetramethyl-2-[1-(4,4,5,5-tetramethyl-1,3,2-dioxaborolan-2-yl)ethyl]-1,3,2-dioxaborolane (2.46 g, 8.7 mmol, 2 eq) at 0° C. After addition, the mixture was stirred at 0° C. for 30 min and then 1-(5-bromo-2-hydroxy-3-methyl-phenyl)ethanone (1.00 g, 4.4 mmol, 1 eq) in THF (3 mL) was added dropwise at 0° C. The resulting mixture was stirred at 0° C. for another 1 h. LCMS showed the reaction was completed and desired MS observed. The reaction mixture was quenched by sat. NH$_4$Cl (50 mL), adjust pH=7 with 1N HCl and extracted with EtOAc (20 mL×3). The combined organic layers were washed with brine (50 mL), dried over Na$_2$SO$_4$, filtered and concentrated under reduced pressure to give a residue. The residue was purified by flash silica gel chromatography (ISCO®; 40 g SepaFlash® Silica Flash Column, Eluent of 0~30% Ethyl acetate/Petroleum ether gradient @ 100 mL/min) to give crude product. Then the crude product was triturated with Petroleum ether (10 mL) at 25° C. for 10 min to give 6-bromo-2-hydroxy-3,4,8-trimethyl-1,2-benzoxaborinine (0.7 g, 60.0% yield) was as a yellow solid. 1H NMR (DMSO-d$^6$, 400 MHz) δ 8.81 (s, 1H), 7.56 (d, J=2.4 Hz, 1H), 7.40 (d, J=2.0 Hz, 1H), 2.33 (s, 3H), 2.21 (s, 3H), 1.97 (s, 3H). MS (ESI): mass calculated for C$_{11}$H$_{12}$BBrO$_2$, 266.01, m/z found 266.9 [M−H]$^-$. HPLC: 98.91% (220 nm), 99.83% (254 nm).

23.4 Preparation of 1-(trans-4-cyanotetrahydropyran-3-yl)-3-[(2-hydroxy-3,4,8-trimethyl-1,2-benzoxaborinin-6-yl)amino]pyrazole-4-carboxamide

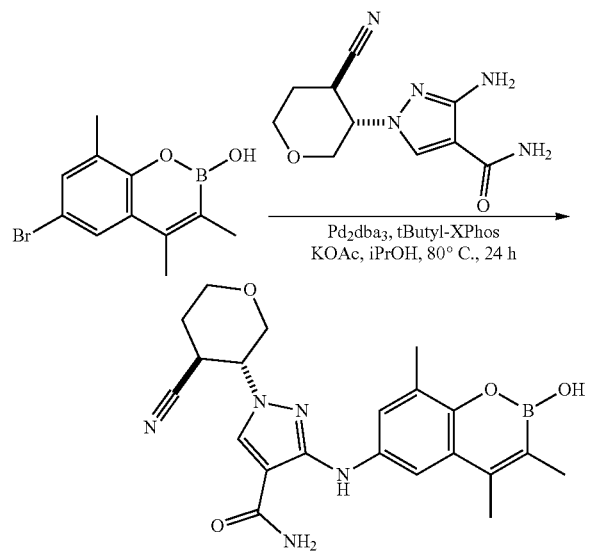

To a solution of 3-amino-1-(trans-4-cyanotetrahydro-2H-pyran-3-yl)pyrazole-4-carboxamide (264 mg, 1.12 mmol, 1.5 eq) in i-PrOH (5 mL) was added KOAc (147 mg, 1.5 mmol, 2 eq), 6-bromo-2-hydroxy-3,4,8-trimethyl-1,2-benzoxaborinine (200 mg, 749 umol, 1 eq), Pd$_2$(dba)$_3$ (69 mg, 75 umol, 0.1 eq) and t-Bu Xphos (64 mg, 150 umol, 0.2 eq) under N$_2$. The resulting mixture was heated and stirred at 80° C. for 48 h. LCMS showed the reaction was completed and desired MS observed. 9 parallel reactions were combined for work up. The reaction mixture was filtered and the filtrate was concentrated under reduced pressure to give a residue. The residue was purified by prep-HPLC (column: Welch Xtimate C18 250*70 mm #10 um; mobile phase: [water (10 mM NH$_4$HCO$_3$)-ACN]; B %: 30%-60%, 20 min) to give 1-(trans-4-cyanotetrahydro-2H-pyran-3-yl)-3-[(2-hydroxy-3,4,8-trimethyl-1,2-benzoxaborinin-6-yl) amino]pyrazole-4-carboxamide (550 mg, yield 19.3%, purity 97%) as a yellow solid, 1H NMR (DMSO-hd 6, 400 MHz) δ 8.97 (s, 1H), 8.47 (s, 1H), 8.28 (s, 1H), 7.91 (d, J=2.4 Hz, 1H), 7.69 (s, 1H), 7.2 (d, J=2.0 Hz, 1H), 7.16 (s, 1H), 4.58-4.55 (m, 1H), 4.08 (dd, J=10.8, 4 Hz, 1H), 3.94 (d, J=9.6 Hz, 1H), 3.72-3.63 (m, 2H), 3.42-3.32 (m, 1H), 2.34 (s, 3H), 2.29 (s, 3H), 2.17-2.16 (m, 1H), 2.16-1.98 (m, 4H). MS (ESI): mass calculated for C$_{21}$H$_{24}$BN$_5$O$_4$, 421.19, m/z found 420.1 [M−H]$^-$. HPLC: 95.14% (220 nm), 99.3 (254 nm). which was further separated by SFC (condition: column: DAICEL CHIRALCEL OJ (250 mm*30 mm, 10 um); mobile phase: [Neu-ETOH]; B %: 50%-50%, 5 min) to give 1-[trans-4-cyanotetrahydro-2H-pyran-3-yl]-3-[(2-hydroxy-3,4,8-trimethyl-1,2-benzoxaborinin-6-yl)amino]pyrazole-4-carboxamide (stereoisomer one) (211 mg, 7.43% yield, 100% ee, first peak, Rt=1.497 min) as a yellow solid 1H NMR (DMSO-hd 6, 400 MHz) δ 8.97 (s, 1H), 8.47 (s, 1H), 8.28 (s, 1H), 7.91 (d, J=2.4 Hz, 1H), 7.69 (s, 1H), 7.2 (d, J=2.0 Hz, 1H), 7.16 (s, 1H), 4.58-4.55 (m, 1H), 4.08 (dd, J=10.8, 4 Hz, 1H), 3.94 (d, J=9.6 Hz, 1H), 3.72-3.63 (m, 2H), 3.42-3.32 (m, 1H), 2.34 (s, 3H), 2.29 (s, 3H), 2.17-2.16 (m, 1H), 2.16-1.98 (m, 4H). MS (ESI): mass calculated for C$_{21}$H$_{24}$BN$_5$O$_4$, 421.19, m/z found 420.1 [M−H]$^-$. HPLC: 97.32% (220 nm), 99.27% (254 nm) and 1-[trans-4-cyanotetrahydro-2H-pyran-3-yl]-3-[(2-hydroxy-3,4,8-trimethyl-1,2-benzoxaborinin-6-yl) amino]pyrazole-4-carboxamide (stereoisomer two) (222.5 mg, 7.83% yield, 99.4% ee, second peak, Rt=1.650 min) as a yellow solid. 1H NMR (DMSO-hd 6, 400 MHz) δ 8.97 (s, 1H), 8.47 (s, 1H), 8.28 (s, 1H), 7.91 (d, J=2.4 Hz, 1H), 7.69 (s, 1H), 7.2 (d, J=2.0 Hz, 1H), 7.16 (s, 1H), 4.58-4.55 (m, 1H), 4.08 (dd, J=10.8, 4 Hz, 1H), 3.94 (d, J=9.6 Hz, 1H), 3.72-3.63 (m, 2H), 3.42-3.32 (m, 1H), 2.34 (s, 3H), 2.29 (s, 3H), 2.17-2.16 (m, 1H), 2.16-1.98 (m, 4H). MS (ESI): mass calculated for C$_{21}$H$_{24}$BN$_5$O$_4$, 421.19, m/z found 420.1 [M−H]$^-$. HPLC: 97.32% (220 nm), 99.27% (254 nm).

24. Preparation of 1-(trans-2-cyanocyclopentyl)-3-[(2-hydroxy-3,4,8-trimethyl-1,2-benzoxaborinin-6-yl)amino]pyrazole-4-carboxamide

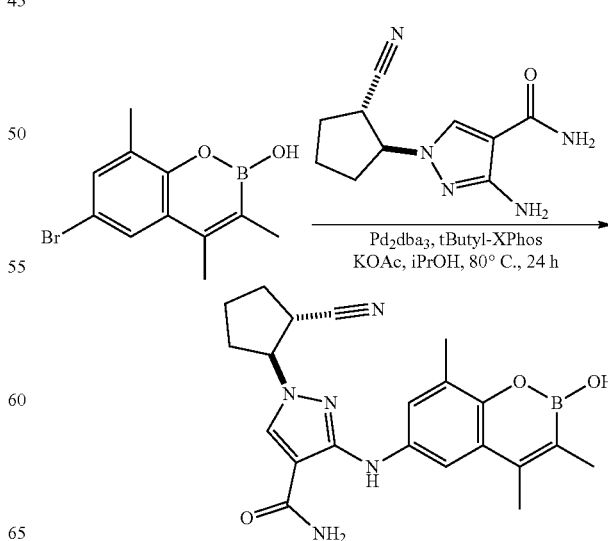

To a solution of 3-amino-1-(trans-2-cyanocyclopentyl) pyrazole-4-carboxamide (185 mg, 843 umol, 1.5 eq) in i-PrOH (3 mL) was added KOAc (110 mg, 1.12 mmol, 2 eq), 6-bromo-2-hydroxy-3,4,8-trimethyl-1,2-benzoxaborinine (150 mg, 562 umol, 1 eq), Pd$_2$(dba)$_3$ (26 mg, 28.1 umol, 0.05 eq) and t-Bu Xphos (24 mg, 56.2 umol, 0.1 eq) at 25° C. The resulting mixture was stirred at 80° C. for 24 h. LCMS showed the reaction was completed and desired MS observed. The reaction mixture was filtered, and the filtrate was concentrated under reduced pressure to give a residue. The residue was purified by prep-HPLC column: Waters Xbridge BEH C18 100*30 mm*10 um; mobile phase: [water (10 mM NH$_4$HCO$_3$)-ACN]; B %: 30%-60%, 10 min) to give 1-(trans-2-cyanocyclopentyl)-3-[(2-hydroxy-3,4,8-trimethyl-1,2-benzoxaborinin-6-yl)amino] pyrazole-4-carboxamide (20.6 mg, 9.05% yield) as a yellow solid. 1H NMR (DMSO-hd 6, 400 MHz) δ 9.98 (s, 1H), 8.46 (s, 1H), 8.27 (s, 1H), 7.88 (d, J=2.4 Hz, 1H), 7.60 (s, 1H), 7.25 (d, J=2.0 Hz, 1H), 7.11 (s, 1H), 4.92 (q, J=8.0 Hz, 1H), 3.40 (q, J=8.6 Hz, 1H), 2.33 (s, 3H), 2.31-2.27 (m, 1H), 2.27-2.20 (m, 4H), 2.17-2.06 (m, 1H), 1.97 (s, 3H), 1.94-1.85 (m, 3H) MS (ESI): mass calculated for C$_{21}$H$_{24}$BN$_5$O$_3$, 405.20, m/z found 404.1 [M–H]$^-$. HPLC: 99.37% (220 nm), 99.67% (254 nm).

25. Preparation of 1-(trans-2-cyanocyclohexyl)-3-[(2-hydroxy-3,4,8-trimethyl-1,2-benzoxaborinin-6-yl)amino]pyrazole-4-carboxamide

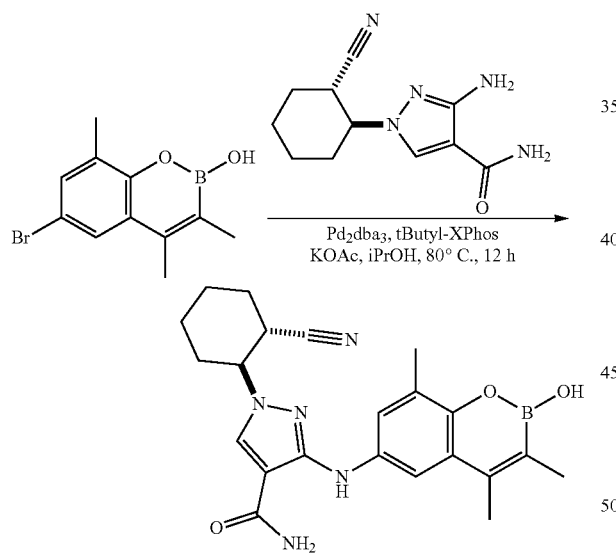

To a solution of 3-amino-1-(trans-2-cyanocyclohexyl) pyrazole-4-carboxamide (105 mg, 450 umol, 1.2 eq) in i-PrOH (5 mL) was added KOAc (74 mg, 749 umol, 2 eq), 6-bromo-2-hydroxy-3,4,8-trimethyl-1,2-benzoxaborinine (100 mg, 374 umol, 1 eq), Pd$_2$(dba)$_3$ (34 mg, 37 umol, 0.1 eq) and t-Bu Xphos (32 mg, 75 umol, 0.2 eq) at 25° C. The resulting mixture was heated and stirred at 80° C. for 12 h. LCMS showed the reaction was completed and desired MS observed. The reaction mixture was filtered, and the filtrate was concentrated under reduced pressure to give a residue. The residue was purified by prep-HPLC (column: Waters Xbridge BEH C18 100*30 mm*10 um; mobile phase: [water (10 mM NH$_4$HCO$_3$)-ACN]; B %: 30%-60%, 10 min) to give 1-(trans-2-cyanocyclohexyl)-3-[(2-hydroxy-3,4,8-trimethyl-1,2-benzoxaborinin-6-yl)amino] pyrazole-4-carboxamide (16.2 mg, 10.3% yield) as a yellow solid. 1H NMR (DMSO-hd 6, 400 MHz) δ 8.95 (s, 1H), 8.47 (s, 1H), 8.22 (s 1H), 7.94 (d, J=2.4 Hz, 1H), 7.64 (s, 1H), 7.21 (d, J=2.4 Hz, 1H), 7.11 (s, 1H), 4.42-4.33 (m, 1H), 3.32-3.24 (m, 1H), 2.33 (s, 3H), 2.27 (s, 3H), 2.22-2.15 (m, 1H), 2.05-1.99 (m, 1H), 1.97 (s, 3H), 1.91-1.69 (m, 4H), 1.52-1.40 (m, 1H), 1.34-1.30 (m, 1H). MS (ESI): mass calculated for C$_{22}$H$_{26}$BN$_5$O$_3$, 419.21, m/z found 418.2 [M–H]$^-$. HPLC: 93.91% (220 nm), 98.62% (254 nm).

26. Preparation of 1-[trans-2-cyanocyclohexyl]-3-[(2-hydroxy-3-methyl-1,2-benzoxaborinin-6-yl)amino]pyrazole-4-carboxamide

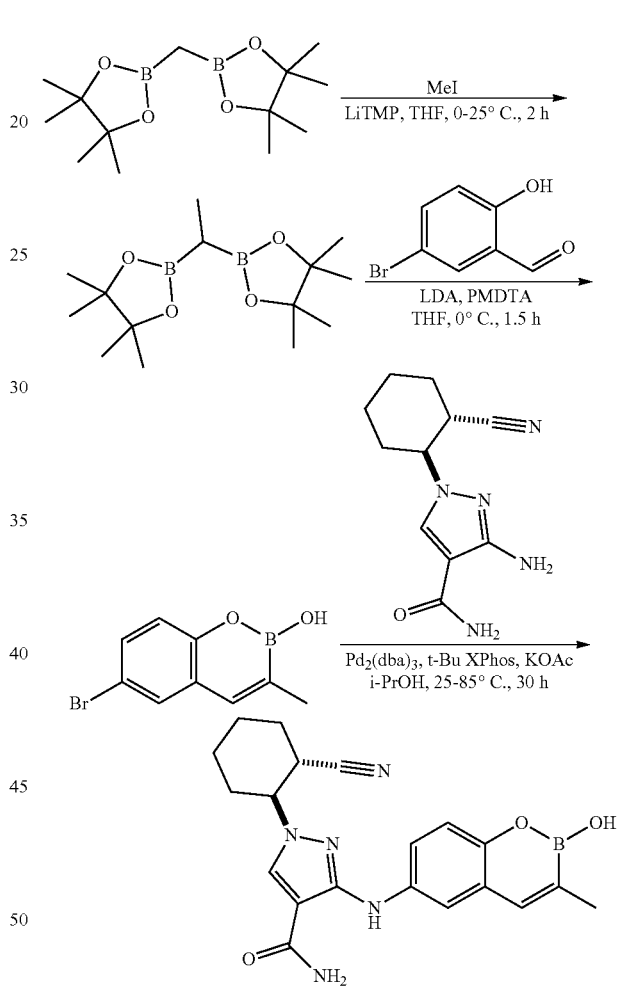

26.1 Preparation of 4,4,5,5-tetramethyl-2-[1-(4,4,5,5-tetramethyl-1,3,2-diaxaborolan-2-yl)ethyl]-1,3,2-dioxaborolane

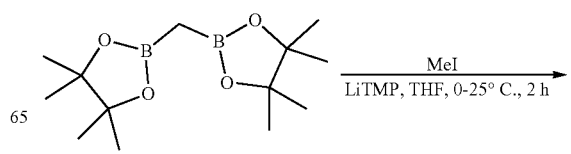

-continued

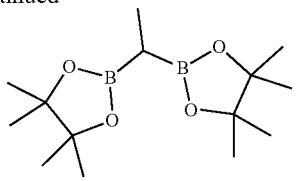

To a mixture of 2,2,6,6-tetramethylpiperidine (HTMP, 8.70 g, 61.6 mmol, 10.5 mL, 1.1 eq) in THF (100 mL) was added n-BuLi (2.5 M, 24.6 mL, 1.1 eq) drop-wise at 0° C. under $N_2$. The mixture was stirred at 0° C. for 30 min. To the reaction mixture was added a solution of 4,4,5,5-tetramethyl-2-[(4,4,5,5-tetramethyl-1,3,2-dioxaborolan-2-yl)methyl]-1,3,2-dioxaborolane (15 g, 56.0 mmol, 1 eq) in THF (50 mL) dropwise at 0° C. The reaction mixture was stirred for 30 min at 0° C. Then MeI (8.74 g, 61.6 mmol, 3.8 mL, 1.1 eq) was added dropwise to above mixture at 0° C. The resulting reaction mixture was stirred at 25° C. for 1 h. TLC showed the reaction was completed. The mixture was poured into sat. aq. $NH_4Cl$ (50 mL) and stirred for 10 min. The aqueous phase was extracted with ethyl acetate (50 mL×3). The combined organic phase was washed with brine (30 mL×2), dried over $Na_2SO_4$, filtered and concentrated in vacuum to give a residue. The residue was purified by flash silica gel chromatography (ISCO®; 120 g SepaFlash® Silica Flash Column, Eluent of 5-15% Ethyl acetate/Petroleum ether gradient @ 120 mL/min) to get 4,4,5,5-tetramethyl-2-[1-(4,4,5,5-tetramethyl-1,3,2-dioxaborolan-2-yl)ethyl]-1,3,2-dioxaborolane (10.0 g, 63.3% yield) as colorless oil. H NMR (CDCl$_3$, 400 MHz) δ 1.24 (s, 24H), 1.05 (d, J=7.2 Hz, 3H), 0.73-0.70 (m, 1H).

26.2 Preparation of 6-bromo-2-hydroxy-3-methyl-1,2-benzoxaborinine

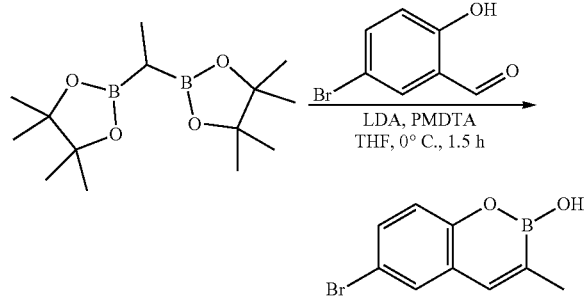

To a mixture of LDA (2 M, 16.4 mL, 2.2 eq) in THF (50 mL) was added 4,4,5,5-tetramethyl-2-[1-(4,4,5,5-tetramethyl-1,3,2-dioxaborolan-2-yl)ethyl]-1,3,2-dioxaborolane (8.42 g, 29.8 mmol, 2 eq) and N'-[2-(dimethylamino)ethyl]-N,N,N'-trimethyl-ethane-1,2-diamine (PMDTA, 5.17 g, 29.8 mmol, 6.2 mL, 2 eq) dropwise at 0° C. under $N_2$. The mixture was stirred at 0° C. for 30 min. To the reaction mixture was added a solution of 5-bromo-2-hydroxy-benzaldehyde (3.00 g, 14.9 mmol, 1 eq) in THF (10 mL) at 0° C. The resulting mixture was stirred at 0° C. for 1 h. LCMS showed the reaction was completed and desired MS observed. The mixture was quenched by addition of sat. aq. $NH_4Cl$ (50 mL) and extracted with EtOAc (30 mL×2). The combined organic layers were washed by brine (50 mL×2), dried over $Na_2SO_4$, filtered and concentrated under reduced pressure to get a residue. The residue was purified by flash silica gel chromatography (ISCO®; 80 g SepaFlash® Silica Flash Column, Eluent of 30-40% Ethyl acetate/Petroleum ether gradient @100 mL/min) to get 6-bromo-2-hydroxy-3-methyl-1,2-benzoxaborinine (400 mg, 11.2% yield) as a white solid. $^1$H NMR (DMSO-hd 6, 400 MHz) δ 9.08 (s, 1H), 7.65 (d, J=2.4 Hz, 1H), 7.46-7.43 (m, 2H), 7.14 (d, J=8.4 Hz, 1H), 2.01 (s, 3H).

26.3 Preparation of 1-[trans-2-cyanocyclohexyl]-3-[(2-hydroxy-3-methyl-1,2-benzoxaborinin-6-yl)amino]pyrazole-4-carboxamide

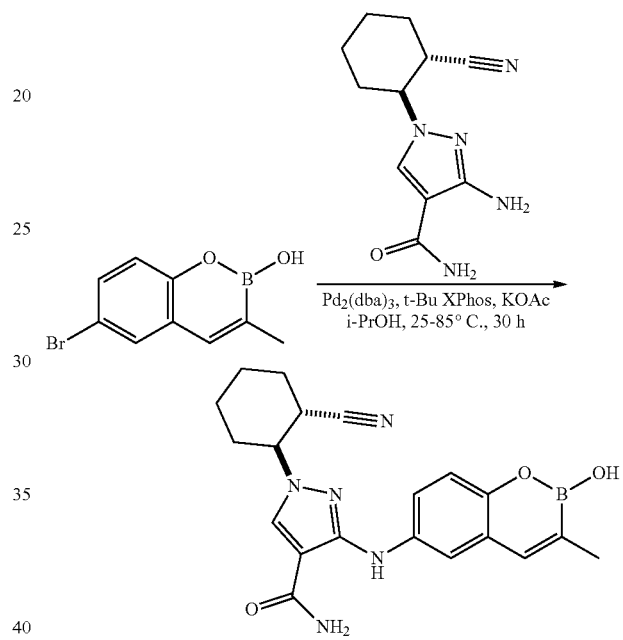

To a mixture of 3-amino-1-(trans-2-cyanocyclohexyl)pyrazole-4-carboxamide (100 mg, 429 umol, 1 eq) and 6-bromo-2-hydroxy-3-methyl-1,2-benzoxaborinine (102 mg, 429 umol, 1 eq) in i-PrOH (10 mL) was added AcOK (63 mg, 643 umol, 1.5 eq), Pd$_2$(dba)$_3$ (20 mg, 21 umol, 0.05 eq) and t-Bu Xphos (18 mg, 43 umol, 0.1 eq) in one portion at 25° C. under $N_2$. The mixture was heated to 85° C. and stirred at 85° C. for 30 h. LCMS showed the reaction was completed and desired MS observed. The mixture was quenched with $H_2O$ (0.5 mL), filtered and concentrated under reduced pressure to get a residue. The residue was purified by prep-HPLC (column: Waters Xbridge BEH C18 100*30 mm*10 um; mobile phase: [water (NH$_4$HCO$_3$)-ACN]; B %: 25%-55%, 10 min) to get 1-[trans-2-cyanocyclohexyl]-3-[(2-hydroxy-3-methyl-1,2-benzoxaborinin-6-yl)amino]pyrazole-4-carboxamide (42.2 mg, 24.2% yield, 96.3% purity) as a gray solid. $^1$H NMR (DMSO-hd 6, 400 MHz) δ 9.04 (s, 1H), 8.76 (s, 1H), 8.22 (s, 1H), 7.65 (br s, 1H), 7.59 (d, J=2.8 Hz, 1H), 7.49-7.45 (m, 2H), 7.11 (br s, 1H), 7.08 (d, J=7.2 Hz, 1H), 4.39-4.32 (m, 1H), 3.31-3.28 (m, 1H), 2.21-2.19 (m, 1H), 2.01 (s, 3H), 1.99-1.96 (m, 1H), 1.83-1.69 (m, 4H), 1.44-1.37 (m, 2H). MS (ESI): mass calculated for C$_{20}$H$_{22}$BN$_5$O$_3$ 391.18; m/z found 392.2 [M+H]$^+$. HPLC: 96.33% (220 nm), 98.83% (254 nm).

27. Preparation of 1-[trans-4-cyanotetrahydro-2H-pyran-3-yl]-3-[(2-hydroxy-8-methyl-1,2-benzoxaborinin-6-yl)amino]pyrazole-4-carboxamide

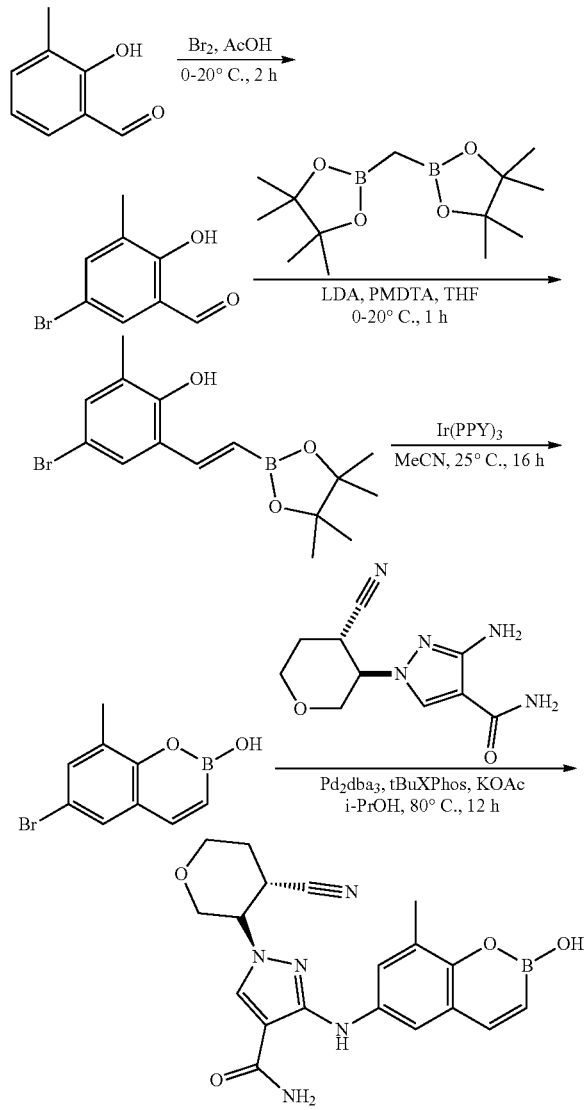

27.1 Preparation of 5-bromo-2-hydroxy-3-methyl-benzaldehyde

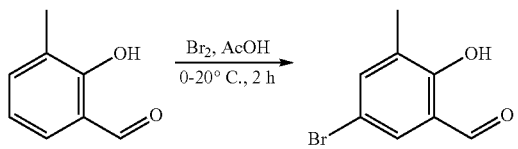

To a mixture of 2-hydroxy-3-methyl-benzaldehyde (25.0 g, 183 mmol, 1 eq) in AcOH (200 mL) was added dropwise $Br_2$ (33.7 g, 211 mmol, 10.8 mL, 1.15 eq) at 0° C. The mixture was stirred at 20° C. for 2 h. LCMS showed the reaction was completed and desired MS observed. The reaction mixture was quenched by addition $H_2O$ (250 mL) at 0° C. and the resulting suspension was filtered. The filter cake was dissolved in EtOAc (200 mL). Then the organic layer was washed with sat·aq·$Na_2SO_3$ (150 mL×3), dried over $Na_2SO_4$, filtered and concentrated under reduced pressure to give 5-bromo-2-hydroxy-3-methyl-benzaldehyde (20.0 g, 50.6% yield) as a yellow solid. 1H NMR ($CDCl_3$, 400 MHz) δ 11.18 (s, 1H), 9.80 (s, 1H), 7.49 (d, J=2.0 Hz, 2H), 2.25 (s, 3H).

27.2 Preparation of 4-bromo-2-methyl-6-[(E)-2-(4,4,5,5-tetramethyl-1,3,2-dioxaborolan-2-yl) vinyl]phenol

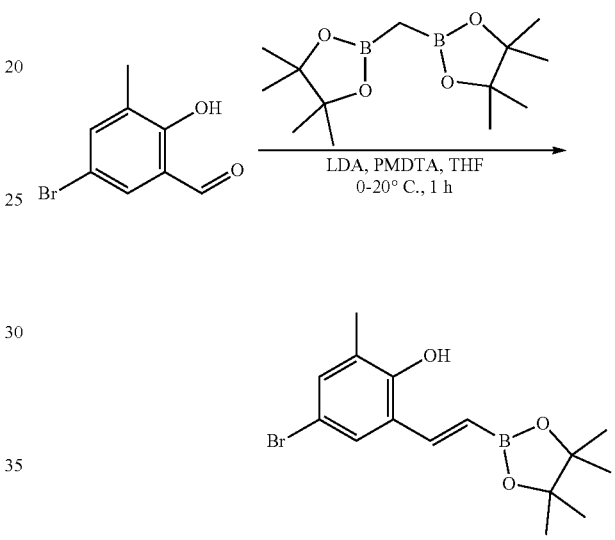

To a mixture of LDA (2 M, 62.78 mL, 3 eq) in THF (30 mL) was added dropwise N'-[2-(dimethylamino)ethyl]-N,N,N'-trimethyl-ethane-1,2-diamine (14.5 g, 83.7 mmol, 2 eq) and 4,4,5,5-tetramethyl-2-[(4,4,5,5-tetramethyl-1,3,2-dioxaborolan-2-yl) methyl]-1,3,2-dioxaborolane (28.0 g, 104 mmol, 2.5 eq) at 0° C. under $N_2$. The mixture was stirred at 0° C. for 30 min. And then a solution of 5-bromo-2-hydroxy-3-methyl-benzaldehyde (9 g, 41.8 mmol, 2.65 mL, 1 eq) in THF (30 mL) was added dropwise to the reaction mixture at 0° C. and stirred at 20° C. for 30 min. TLC showed the reaction was completed. The reaction mixture was added $H_2O$ (100 mL) at 0° C., adjusted pH to 5 with HCl (2 N) and stirred for 10 min at 0° C. The solution was and extracted with EtOAc (100 mL×3). The combined organic layers were washed with brine (100 mL×2), dried over $Na_2SO_4$, filtered and concentrated under reduced pressure to give a residue. The residue was purified by flash silica gel chromatography (ISCO®; 120 g SepaFlash® Silica Flash Column, Eluent of 0-5% Ethyl acetate/Petroleum ether gradient @ 100 mL/min) to give 4-bromo-2-methyl-6-[(E)-2-(4,4,5,5-tetramethyl-1,3,2-dioxaborolan-2-yl)vinyl]phenol (15.0 g, crude) as yellow oil. 1H NMR (DMSO-hd 6, 400 MHz) δ 9.01 (s, 1H), 7.76 (s, 1H), 7.61 (d, J=18.8 Hz, 1H), 7.58-7.45 (m, 2H), 7.25 (d, J=2.4 Hz, 1H), 6.04 (d, J=18.4 Hz, 1H), 2.17 (s, 3H), 1.24 (s, 12H).

273 Preparation of 6-bromo-2-hydroxy-8-methyl-1,2-benzoxaborinine

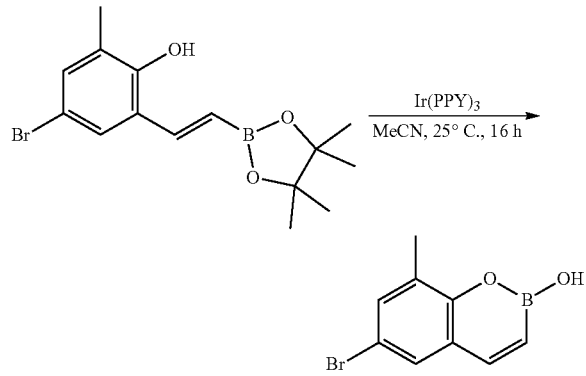

To a mixture of 4-bromo-2-methyl-6-[(E)-2-(4,4,5,5-tetramethyl-1,3,2-dioxaborolan-2-yl) vinyl]phenol (5.00 g, 14.7 mmol, 1 eq) in MCCN (30 mL) was added tris[2-(2-pyridyl)phenyl]iridium (97 mg, 147 umol, 0.01 eq) in one portion at 20° C. under $N_2$. The reaction was stirred and irradiated using 34W blue LED lamps for 16 h. TLC showed the reaction was completed. The reaction mixture was filtered and the cake was washed with EtOAc (20 mL×2). And then the filter cake was dried in vacuo to afford 6-bromo-2-hydroxy-8-methyl-1,2-benzoxaborinine (3.00 g, 28.3% yield) as a yellow solid. 1H NMR (DMSO-hd 6, 400 MHz) δ 9.09 (s, 1H), 7.74 (d, J=11.6 Hz, 1H), 7.56 (d, J=2.4 Hz, 1H), 7.44 (d, J=2.0 Hz, 1H), 6.17 (d, J=12.0 Hz, 1H), 2.33 (s, 3H).

27.4 Preparation of 1-[trans-4-cyanotetrahydro-2H-pyran-3-yl]-3-[(2-hydroxy-8-methyl-1,2-benzoxaborinin-6-yl)amino]pyrazole-4-carboxamide

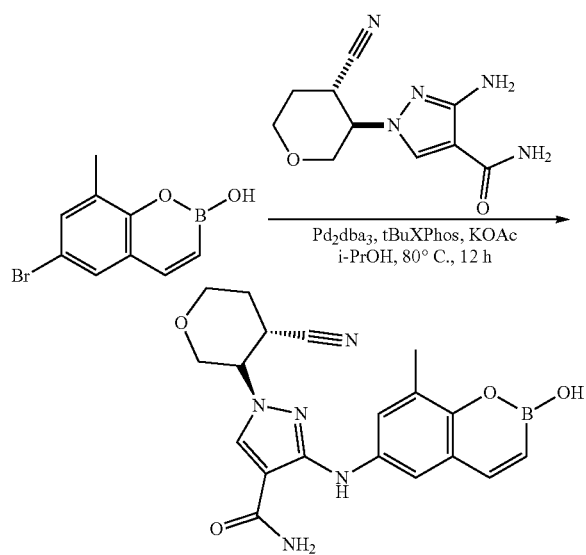

To a mixture of 6-bromo-2-hydroxy-8-methyl-1,2-benzoxaborinine (500 mg, 2.09 mmol, 1 eq) and 3-amino-1-[trans-4-cyanotetrahydropyran-3-yl]pyrazole-4-carboxamide (591 mg, 2.51 mmol, 1.2 eq) in i-PrOH (10 mL) was added $Pd_2(dba)_3$ (192 mg, 209 umol, 0.1 eq), ditert-butyl-[2-(2,4,6-triisopropylphenyl)phenyl]phosphine (178 mg, 418 umol, 0.2 eq) and potassium acetate (514 mg, 5.23 mmol, 2.5 eq) in one portion at 20° C. under $N_2$. The mixture was heated and stirred at 80° C. for 12 h. LCMS showed the reaction was completed and desired MS observed. 4 parallel reactions were combined for work up. The reaction mixture was filtered and the filtrate was concentrated under reduced pressure to give a residue. The residue was purified by prep-HPLC (column: Phenomenex C18 250*70 mm 10u; mobile phase: [water($NH_4HCO_3$)-ACN]; B %: 25%-50% to give 1-[trans-4-cyanotetrahydro-2H-pyran-3-yl]-3-[(2-hydroxy-8-methyl-1,2-benzoxaborinin-6-yl)amino]pyrazole-4-carboxamide (1.00 g, yield 28%, purity 95.1%) as a white solid, which was further separated by SFC (condition: column: DAICEL CHIRALPAK IC (250 mm*30 mm, 10 um); mobile phase: [Neu-MeOH]; B %: 40%-40%, 10 min) to give 1-[trans-4-cyanotetrahydropyran-3-yl]-3-[(2-hydroxy-8-methyl-1,2-benzoxaborinin-6-yl)amino]pyrazole-4-carboxamide (stereoisomer one) (237 mg, 7.20% yield, 98.6% purity, 99.7% ee, first peak, Rt=1.381 min). 1H NMR (DMSO-hd 6, 400 MHz) δ 9.01 (s, 1H), 8.77 (s, 1H), 8.28 (s, 1H), 7.80 (d, J=12.0 Hz, 1H), 7.69 (s, 1H), 7.64 (d, J=2.4 Hz, 1H), 7.30 (d, J=2.4 Hz, 1H), 7.16 (s, 1H), 6.10 (d, J=12.0 Hz, 1H), 4.55-4.52 (m, 1H), 4.08-4.05 (m, 1H), 4.03-4.02 (m, 2H), 3.72-3.70 (m, 1H), 3.50 (t, J=2.0 Hz, 1H), 2.34 (s, 3H), 2.16-2.15 (m, 1H), 2.07-1.98 (m, 1H), MS (ESI): mass calculated for $C_9H_{20}BN_5O_4$, 393.16, m/z found 394.2 [M+H]$^+$. HPLC: 98.66% (220 nm), 99.73% (254 nm) and 1-[trans-4-cyanotetrahydropyran-3-yl]-3-[(2-hydroxy-8-methyl-1,2-benzoxaborinin-6-yl)amino]pyrazole-4-carboxamide (stereoisomer two) (225 mg, 6.83% yield, 97.4% purity, 99.6% ee, second peak, Rt=1.517 min) as a white solid. 1H NMR (DMSO-hd 6, 400 MHz) δ 9.01 (s, 1H), 8.78 (s, 1H), 8.28 (s, 1H), 7.80 (d, J=12.0 Hz, 1H), 7.69 (s, 1H), 7.64 (d, J=2.4 Hz, 1H), 7.30 (d, J=2.4 Hz, 1H), 7.16 (s, 1H), 6.10 (d, J=12.0 Hz, 1H), 4.55-4.53 (m, 1H), 4.03-4.02 (m, 1H), 3.72-3.70 (m, 1H), 3.69-3.66 (m, 2H), 3.50 (t, J=2.0 Hz, 1H), 2.34 (s, 3H), 2.16-2.15 (m, 1H), 2.07-1.98 (m, 1H), MS (ESI): mass calculated for $C_{19}H_{20}BN_5O_4$, 393.16, m/z found 394.2 [M+H]$^+$. HPLC: 97.42% (220 nm), 99.22% (254 nm).

28. 1-[trans-4-cyanotetrahydro-2H-pyran-3-yl]-3-[[2-hydroxy-8-(trifluoromethyl)-1,2-benzoxaborinin-6-yl]amino]pyrazole-4-carboxamide

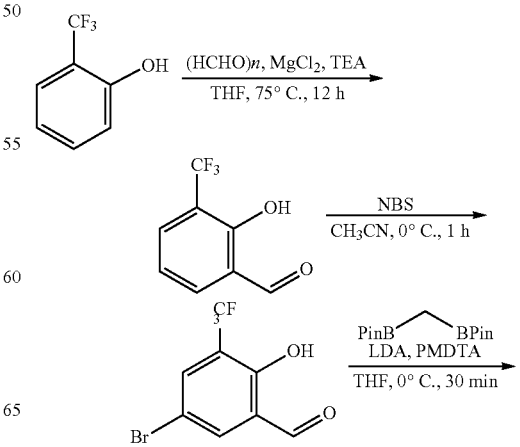

-continued

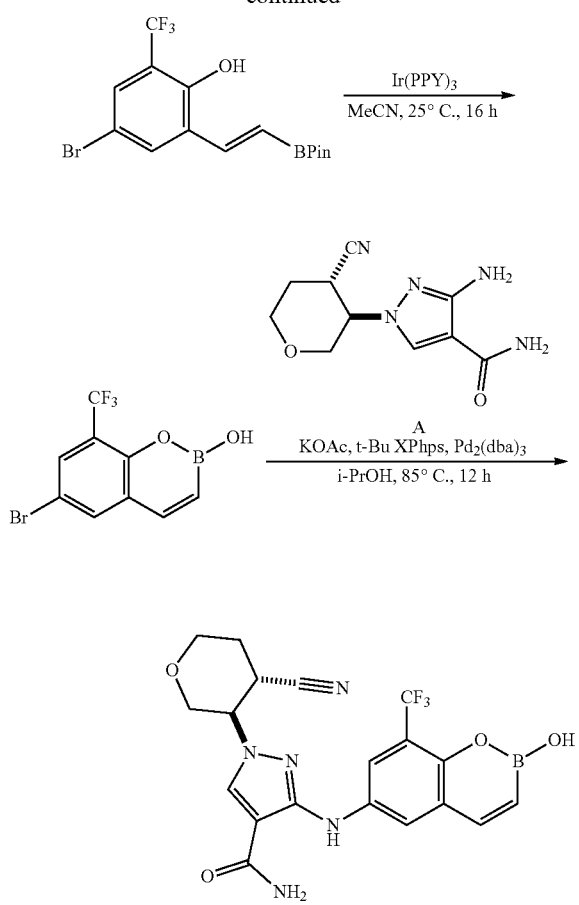

28.1 Preparation of 2-hydroxy-3-(trifluoromethyl)benzaldehyde

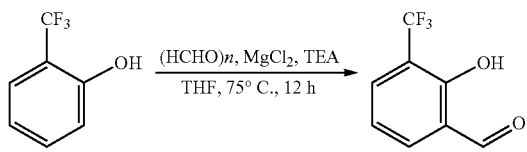 [SMILES: Oc1ccccc1C(F)(F)F ; O=Cc1cccc(C(F)(F)F)c1O]

To a solution of 2-(trifluoromethyl)phenol (14 g, 86.3 mmol, 1 eq) in THF (300 mL) was added paraformaldehyde (20.7 g, 690 mmol, 8 eq), MgCl$_2$ (12.3 g, 129 mmol, 1.5 eq) and TEA (30.5 g, 302 mmol, 3.5 eq). The mixture was heated and stirred at 75° C. for 12 h. TLC showed the reaction was completed. The reaction mixture was quenched by addition H$_2$O (200 mL) at 0° C., and extracted with EtOAc (50 mL×3). The combined organic layers were washed with brine (50 mL×3), dried over Na$_2$SO$_4$, filtered and concentrated under reduced pressure to give a residue. The residue was purified by column chromatography (SiO$_2$, Petroleum ether/Ethyl acetate=20/1 to 5/1) to give 2-hydroxy-3-(trifluoromethyl)benzaldehyde (10.7 g, 65.1% yield) as yellow oil. $^1$H NMR (CDCl$_3$, 400 MHz) δ 11.74 (s, 1H), 9.97 (s, 1H), 7.84 (d, J=8.0 Hz, 1H), 7.78 (d, J=7.6 Hz, 1H), 7.13 (t, J=7.6 Hz, 1H).

28.2 Preparation of 5-bromo-2-hydroxy-3-(trifluoromethyl)benzaldehyde

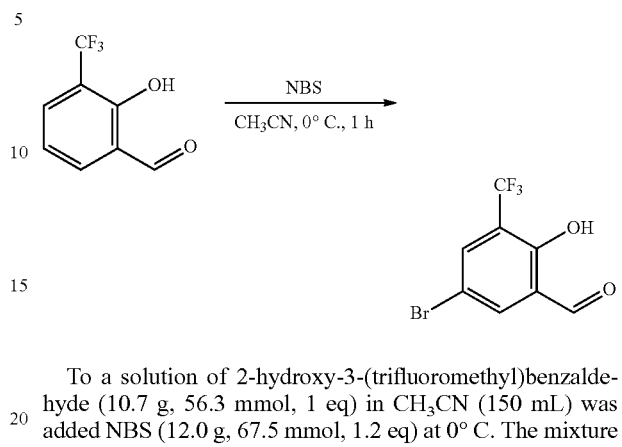

To a solution of 2-hydroxy-3-(trifluoromethyl)benzaldehyde (10.7 g, 56.3 mmol, 1 eq) in CH$_3$CN (150 mL) was added NBS (12.0 g, 67.5 mmol, 1.2 eq) at 0° C. The mixture was stirred at 0° C. for 1 h. TLC showed the reaction was completed. The reaction mixture was quenched by addition H$_2$O (100 mL) at 0° C., and extracted with EtOAc (50 mL×3). The combined organic layers were washed with brine (50 mL×3), dried over Na$_2$SO$_4$, filtered and concentrated under reduced pressure to give a residue. The residue was purified by column chromatography (SiO$_2$, Petroleum ether/Ethyl acetate=1/0 to 10/1) to give 5-bromo-2-hydroxy-3-(trifluoromethyl)benzaldehyde (10 g, 66.0% yield) as brown oil. $^1$H NMR (CDCl$_3$, 400 MHz) δ 11.63 (s, 1H), 9.91 (s, 1H), 7.93 (d, J=2.4 Hz, 1H), 7.89 (d, J=2.4 Hz, 1H).

28.3 Preparation of 4-bromo-2-[(E)-2-(4,4,5,5-tetramethyl-1,3,2-diaxaborolan-2-yl)vinyl]-6-(trifluoromethyl)phenol

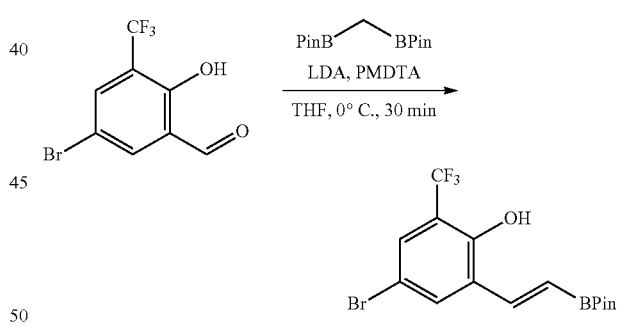

To a solution of LDA (2 M, 40.9 mL, 2.2 eq) in THF (50 mL) was added dropwise N'-[2-(dimethylamino)ethyl]-N,N,N'-trimethyl-ethane-1,2-diamine (12.8 g, 74.3 mmol, 15.5 mL, 2 eq) and 4,4,5,5-tetramethyl-2-[(4,4,5,5-tetramethyl-1,3,2-dioxaborolan-2-yl)methyl]-1,3,2-dioxaborolane (19.9 g, 74.3 mmol, 2 eq) at 0° C. The mixture was stirred at 0° C. for 20 min, and then a solution of 5-bromo-2-hydroxy-3-(trifluoromethyl)benzaldehyde (10 g, 37.1 mmol, 1 eq) in THF (50 mL) was added dropwise at 0° C. The resulting mixture was continue stirred at 0° C. for 10 min. LCMS showed the reaction was completed and desired MS observed. The reaction mixture was quenched by addition H$_2$O (70 mL), and extracted with EtOAc (50 mL×3). The combined organic layers were washed with brine (50 mL×3), dried over Na$_2$SO$_4$, filtered and concentrated under reduced pressure to give a residue. The residue was purified by column chromatography (SiO$_2$, Petroleum ether/Ethyl acetate=1/0 to 3/1) to give 4-bromo-2-[(E)-2-(4,4,5,5-tetramethyl-1,3,2-dioxaborolan-2-yl)vinyl]-6-(trifluoromethyl)phenol (11.5 g, 78.7% yield) as yellow oil.

28.4 Preparation of 6-bromo-2-hydroxy-8-(trifluoromethyl)-1,2-benzoxaborinine

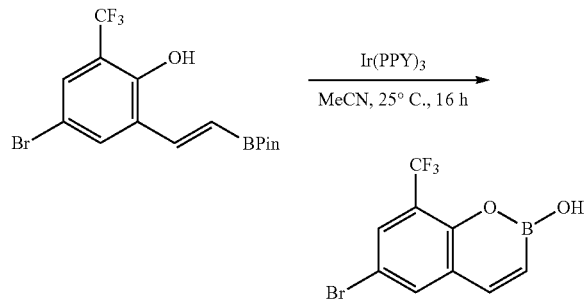

To a solution of 4-bromo-2-[(E)-2-(4,4,5,5-tetramethyl-1,3,2-dioxaborolan-2-yl)vinyl]-6-(trifluoromethyl)phenol (5.65 g, 14.4 mmol, 1 eq) in CH$_3$CN (20 mL) was added tris[2-(2-pyridyl)phenyl]iridium (94 mg, 143 umol, 0.01 eq). The reaction was stirred and irradiated using 34 W blue LED lamps at 25° C. for 16 h. TLC showed the reaction was completed. The reaction mixture was filtered and concentrated under reduced pressure to give a residue. The residue was purified by column chromatography (SiO$_2$, Petroleum ether/Ethyl acetate=10/1 to 1/1) to give 6-bromo-2-hydroxy-8-(trifluoromethyl)-1,2-benzoxaborinine (4.4 g, 52.2% yield) as yellow oil.

$^1$H NMR (CDCl$_3$, 400 MHz) δ 7.75 (s, 1H), 7.72 (d, J=2.0 Hz, 1H), 7.70 (s, 1H), 7.67 (s, 1H), 6.40 (d, J=12.0 Hz, 1H).

28.5 Preparation of 1-[trans-4-cyanotetrahydro-2H-pyran-3-yl]-3-[[2-hydroxy-8-(trifluoromethyl)-1,2-benzoxaborinin-6-yl]amino]pyrazole-4-carboxamide

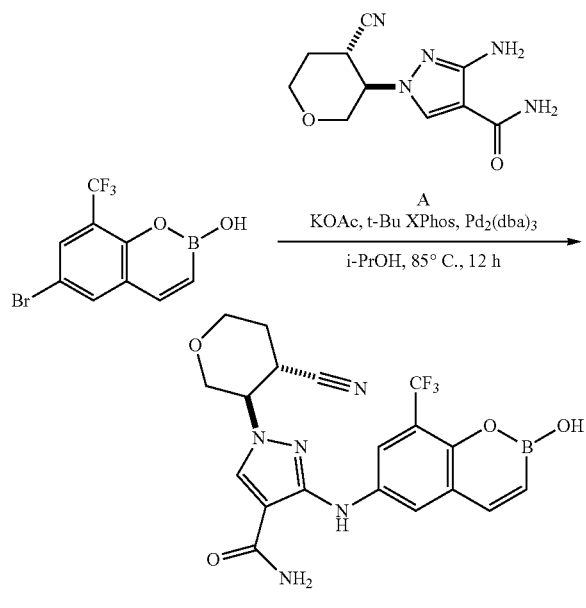

A mixture of 6-bromo-2-hydroxy-8-(trifluoromethyl)-1,2-benzoxaborinine (1 g, 3.41 mmol, 1 eq), 3-amino-1-(trans-4-cyanotetrahydropyran-3-yl)pyrazole-4-carboxamide (803 mg, 3.41 mmol, 1 eq), KOAc (503 mg, 5.12 mmol, 1.5 eq), t-Bu XPhos (72 mg, 170 umol, 0.05 eq) and Pd$_2$(dba)$_3$ (313 mg, 341 umol, 0.1 eq) in i-PrOH (15 mL) was degassed and purged with N$_2$ for 3 times. Then mixture was heated and stirred at 85° C. for 12 h under N$_2$. The reaction mixture was filtered and concentrated under reduced pressure to give a residue. The residue was purified by prep-HPLC (column: Phenomenex Luna 80×30 mm×3 um; mobile phase: [water (HCl)-ACN]; B %: 20/0-50%, 8 min) to give 1-(trans-4-cyanotetrahydro-2H-pyran-3-yl)-3-[[2-hydroxy-8-(trifluoromethyl)-1,2-benzoxaborinin-6-yl]amino]pyrazole-4-carboxamide (580 mg, 97.5% purity) as a white solid. $^1$H NMR (DMSO-hd 6, 400 MHz) δ 9.25 (s, 1H), 9.19 (s, 1H), 8.32 (s, 1H), 7.99 (dd, J=2.4, 14.0 Hz, 2H), 7.88 (d, J=12.0 Hz, 1H), 7.74 (s, 1H), 7.22 (s, 1H), 6.23 (d, J=11.6 Hz, 1H), 4.60 (td, J=4.8, 10.4 Hz, 1H), 4.07 (dd, J=4.4, 11.2 Hz, 1H), 3.93 (d, J=12.0 Hz, 1H), 3.71-3.60 (m, 2H), 3.46 (t, J=12.0 Hz, 1H), 2.18 (d, J=10.0 Hz, 1H), 2.05-1.94 (m, 1H). MS (ESI): mass calculated for C$_{19}$H$_{17}$BF$_3$NSO$_4$ 447.13; m/z found 446.1 [M−H]$^-$. HPLC: 97.56% (220 nm), 99.92% (254 nm). The product (543 mg) was further separated by SFC (column: DAICEL CHIRALPAK IC (250 mm×30 mm, 10 um); mobile phase: [Neu-IPA]; B %: 36/0-36%, 7 min) to give 1-[trans-4-cyanotetrahydro-2H-pyran-3-yl]-3-[[2-hydroxy-8-(trifluoromethyl)-1,2-benzoxaborinin-6-yl]amino]pyrazole-4-carboxamide (stereoisomer one) (206.8 mg, 13.5% yield, 97.6% purity, 100% ee, first peak, Rt=1.083 min) as an off-white solid. $^1$H NMR (DMSO-hd 6, 400 MHz) δ 9.26 (s, 2H), 8.33 (s, 1H), 8.00 (dd, J=2.0, 13.6 Hz, 2H), 7.89 (d, J=12.0 Hz, 1H), 7.75 (s, 1H), 7.24 (s, 1H), 6.24 (d, J=12.0 Hz, 1H), 4.60 (td, J=4.4, 10.0 Hz, 1H), 4.08 (dd, J=4.4, 11.2 Hz, 1H), 3.94 (d, J=11.2 Hz, 1H), 3.72-3.61 (m, 2H), 3.47 (t, J=11.2 Hz, 1H), 2.18 (d, J=10.4 Hz, 1H), 2.06-1.94 (m, 1H). MS (ESI): mass calculated for C$_{19}$H$_{17}$BF$_3$NSO$_4$ 447.13; m/z found 446.0 [M−H]$^-$. HPLC: 97.66% (220 nm), 99.26% (254 nm). and 1-[trans-4-cyanotetrahydro-2H-pyran-3-yl]-3-[[2-hydroxy-8-(trifluoromethyl)-1,2-benzoxaborinin-6-yl]amino]pyrazole-4-carboxamide (stereoisomer two) (204 mg, 13.3% yield, 97.2% purity, 100% ee, second peak, Rt=1.205 min) as a white solid. $^1$H NMR (DMSO-hd 6, 400 MHz) δ 9.26 (s, 2H), 8.33 (s, 1H), 8.00 (dd, J=2.8, 14.0 Hz, 2H), 7.89 (d, J=12.0 Hz, 1H), 7.76 (s, 1H), 7.23 (s, 1H), 6.24 (d, J=12.0 Hz, 1H), 4.60 (td, J=4.4, 10.0 Hz, 1H), 4.08 (dd, J=4.4, 11.2 Hz, 1H), 3.94 (d, J=10.4 Hz, 1H), 3.72-3.60 (m, 2H), 3.49 (t, J=11.6 Hz, 1H), 2.18 (d, J=9.6 Hz, 1H), 2.06-1.94 (m, 1H). MS (ESI): mass calculated for C$_{19}$H$_{17}$BF$_3$NSO$_4$ 447.13; m/z found 446.1 [M−H]$^-$. HPLC: 97.26% (220 nm), 99.42% (254 nm).

29. 1-(trans-4-cyanotetrahydro-2H-pyran-3-yl)-3-[(7-fluoro-2-hydroxy-1,2-benzoxaborinin-6-yl)amino]pyrazole-4-carboxamide

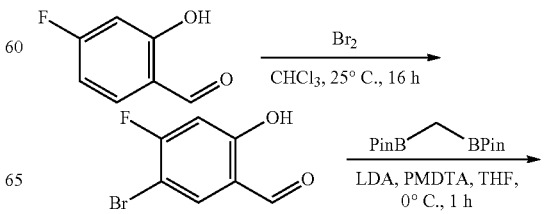

-continued

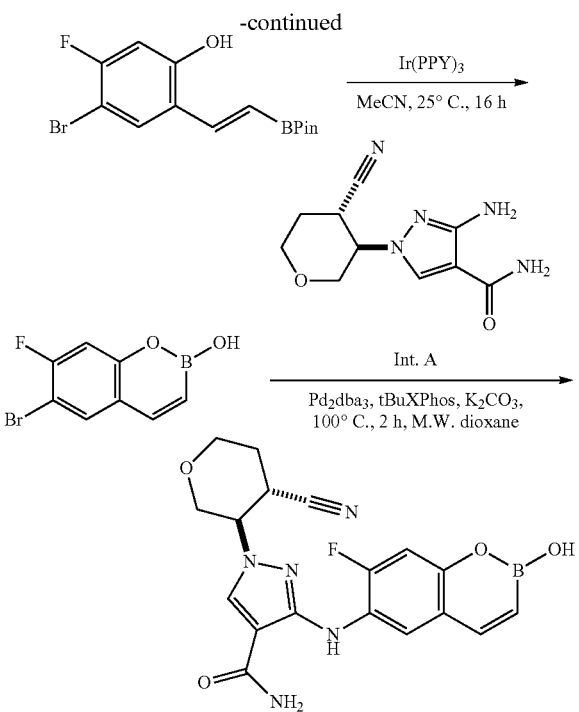

29.1 Preparation of
5-bromo-4-fluoro-2-hydroxybenzaldehyde

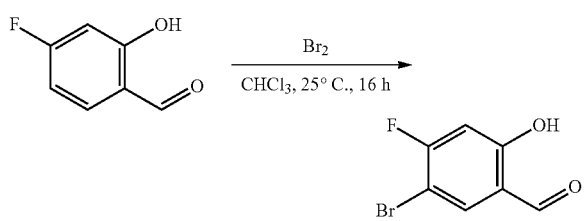

To a solution of 4-fluoro-2-hydroxy-benzaldehyde (1 g, 7.14 mmol, 1 eq) in CH$_3$Cl (10 mL) was added Br$_2$ (1.1 g, 6.78 mmol, 0.95 eq) dropwise at 0° C. The reaction was allowed to warm to 25° C. and stirred at 25° C. for 16 h. TLC showed the reaction was completed. The reaction mixture was quenched with H$_2$O (20 mL) and extracted with EtOAc (10 mL×3). The combined organic layers were washed with brine (10 mL), dried over anhydrous Na$_2$SO$_4$, filtered and concentrated under reduced pressure to give a residue. The residue was purified by silica gel column chromatography (Petroleum ether:EtOAc=100:1 to 10:1) to give 5-bromo-4-fluoro-2-hydroxy-benzaldehyde (1 g, 63.9% yield) as a yellow solid.

29.2 Preparation of (E)-4-bromo-5-fluoro-2-(2-(4,4,5,5-tetramethyl-1,3,2-diaxaborolan-2-yl)vinyl)phenol

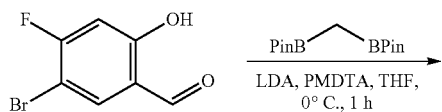

-continued

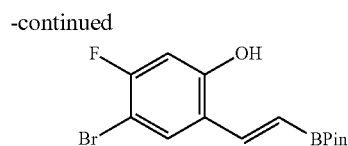

To a mixture of LDA (2 M, 22.8 mL, 2.5 eq) in THF (5 mL) was added N'-[2-(dimethylamino)ethyl]-N,N,N'-trimethyl-ethane-1,2-diamine (7.9 g, 45.6 mmol, 2 eq) and a solution of 4,4,5,5-tetramethyl-2-[(4,4,5,5-tetramethyl-1,3,2-dioxaborolan-2-yl)methyl]-1,3,2-dioxaborolane (9.80 g, 36.5 mmol, 2 eq) in THF (5 mL) at 0° C. under N$_2$. The mixture was stirred at 0° C. for 20 min. Then dropwise added a solution of 5-bromo-4-fluoro-2-hydroxy-benzaldehyde (4 g, 18.3 mmol, 1 eq) in THF (5 mL) at 25° C. The reaction was continue stirred at 25° C. for 40 min. TLC showed the reaction was completed. The reaction mixture was quenched with aq·NH$_4$Cl (100 mL) and extracted with EtOAc (50 mL×3). The combined organic layers were washed with brine (50 mL), dried over anhydrous Na$_2$SO$_4$, filtered and concentrated under reduced pressure to give a residue. The residue was purified by silica gel column chromatography (Petroleum ether:EtOAc=100:1 to 5:1) to give 4-bromo-5-fluoro-2-[(E)-2-(4,4,5,5-tetramethyl-1,3,2-dioxaborolan-2-yl)vinyl]phenol (5 g, 79.8% yield) as a yellow solid. MS: (M+1):174.1

29.3 Preparation of 6-bromo-7-fluoro-2H-benzo[e][1,2]oxaborinin-2-ol

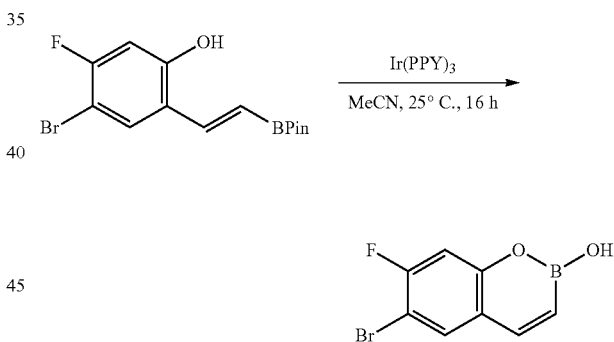

To a mixture of 4-bromo-5-fluoro-2-[(E)-2-(4,4,5,5-tetramethyl-1,3,2-dioxaborolan-2-yl) vinyl]phenol (3 g, 8.75 mmol, 1 eq) in MeCN (20 mL) was added tris[2-(2-pyridyl) phenyl]iridium (Ir(PPY)$_3$, 143 mg, 218 umol, 0.025 eq) in one portion at 25° C. under N$_2$. The reaction was stirred and irradiated using 34W blue LED lamps for 16 h. TLC showed the reaction was completed. 3 parallel reactions were combined for work up. The reaction mixture was filtered and the filter cake was washed with MCCN (5 mL) and dried in vacuum to give a residue (1 g). The residue was purified by silica gel column chromatography (Petroleum ether:EtOAc=100:1 to 1:1) to give (1.5 g, 70.6% yield) as a yellow solid.

29.4 Preparation of 1-(trans-4-cyanotetrahydro-2H-pyran-3-yl)-3-((7-fluoro-2-hydroxy-2H-benzo[e][1,2]oxaborinin-6-yl)amino)-1H-pyrazole-4-carboxamide

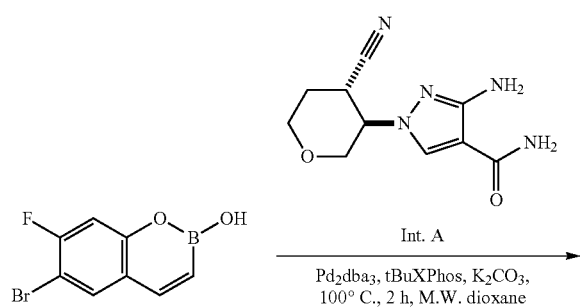

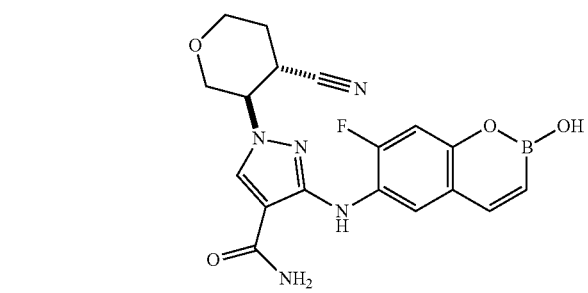

A mixture of 6-bromo-7-fluoro-2-hydroxy-1,2-benzoxaborinine (155 mg, 638 umol, 1.5 eq), 3-amino-1-(trans-4-cyanotetrahydro-2H-pyran-3-yl)pyrazole-4-carboxamide (100 mg, 425 umol, 1 eq), Pd$_2$(dba)$_3$ (38.9 mg, 42.5 umol, 0.1 eq), t-Bu Xphos (36.0 mg, 85.0 umol, 0.2 eq) and K$_2$CO$_3$ (117 mg, 850 umol, 2 eq) in i-PrOH (5 mL) was degassed and purged with N$_2$ for 3 times. The mixture was heated and stirred at 100° C. for 2 h under N$_2$ atmosphere. LCMS showed the reaction was completed and desired MS observed. The reaction mixture was quenched with H$_2$O (20 mL) and extracted with EtOAc (10 mL×3). The combined organic layers were washed with brine (10 mL), dried over anhydrous Na$_2$SO$_4$, filtered and concentrated under reduced pressure to give a residue. The residue was purified by prep-HPLC (column: Phenomenex luna C18 80*40 mm*3 um; mobile phase: [water (HCl)-ACN]; B %: 20%-40%, 7 min) to give 1-(trans-4-cyanotetrahydro-2H-pyran-3-yl)-3-[(7-fluoro-2-hydroxy-1,2-benzoxaborinin-6-yl)amino]pyrazole-4-carboxamide (67.2 mg, 39.8% yield) as an off-white solid. $^1$H NMR (DMSO-hd 6, 400 MHz) δ=9.35 (d, J=2.4 Hz, 1H), 8.93 (br d, J=16.8 Hz, 1H), 8.38 (d, J=9.6 Hz, 1H), 8.32 (s, 1H), 7.89 (d, J=12.0 Hz, 1H), 7.83-7.69 (m, 1H), 7.19 (d, J=12.4 Hz, 2H), 6.09 (d, J=12.0 Hz, 1H), 4.59 (dt, J=4.4, 10.2 Hz, 1H), 4.05 (dd, J=4.4, 11.2 Hz, 1H), 3.97-3.89 (m, 1H), 3.84-3.66 (m, 2H), 3.57-3.49 (m, 1H), 2.17 (br d, J=9.6 Hz, 1H), 2.05-1.94 (m, 1H). MS (ESI): mass calculated for C$_{18}$H$_{17}$BFN$_5$O$_4$, 397.14, m/z found 396.1[M–H]$^-$. HPLC: 100.00% (220 nm), 99.88% (254 nm).

30. Preparation of 1-[trans-4-cyanotetrahydro-2H-pyran-3-yl]-3-[(2-hydroxy-4-isopropyl-1,2-benzoxaborinin-6-yl)amino]pyrazole-4-carboxamide

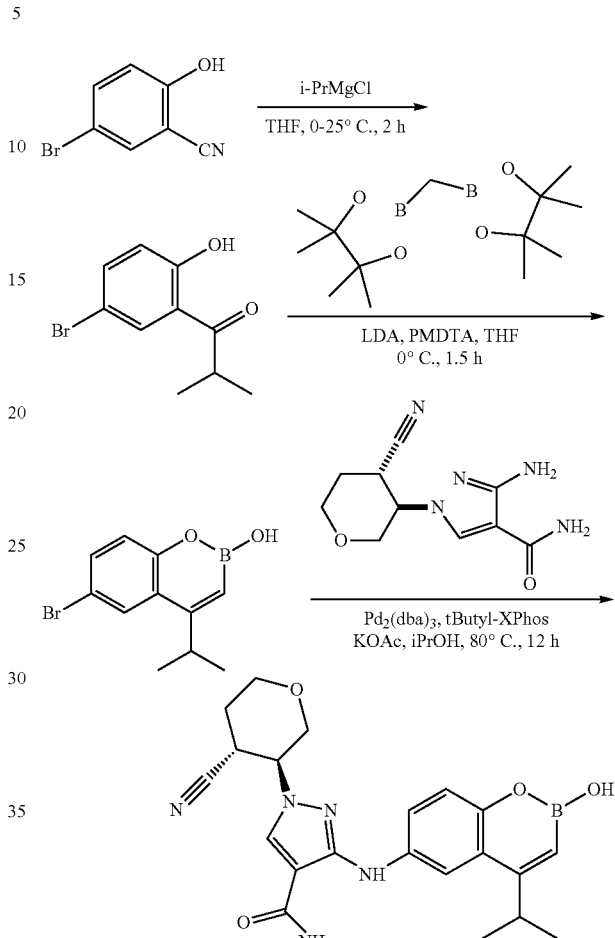

30.1 Preparation of 1-(5-bromo-2-hydroxy-phenyl)-2-methyl-propan-1-one

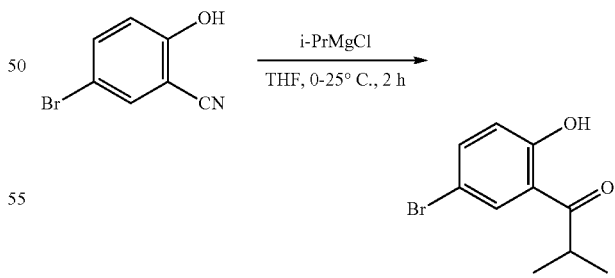

To a solution of 5-bromo-2-hydroxy-benzonitrile (10 g, 50.5 mmol, 6.7 mL, 1 eq) in THF (200 mL) was added i-PrMgCl (2 M, 75.7 mL, 3 eq) at 0° C. The reaction was allowed to warm to 25° C. and stirred at 25° C. for 2 h. LCMS showed the reaction was completed and desired MS observed. The reaction mixture was quenched by H$_2$O (100 mL) at 0° C., and then extracted with EtOAc (80 mL×3). The combined organic layers were washed with brine (50 mL), dried over Na$_2$SO$_4$, filtered and concentrated under reduced pressure to give a residue. The residue was purified by column chromatography (Petroleum ether/Ethyl acetate=10/1 to 3/1) to give 1-(5-bromo-2-hydroxy-phenyl)-2-methyl-propan-1-one (10 g, 81.4% yield) as a white solid.

30.2 Preparation of 6-bromo-2-hydroxy-4-isopropyl-1,2-benzoxaborinine

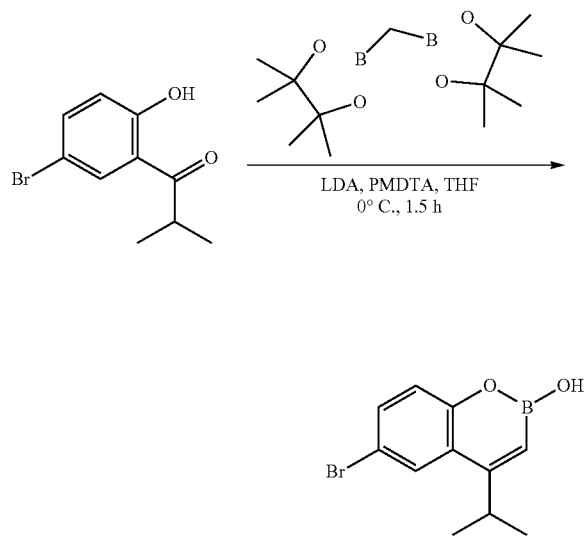

To a solution of LDA (2 M, 15.4 mL, 5 eq) in THF (20 mL) was added dropwise N'-[2-(dimethylamino)ethyl]-N,N,N'-trimethyl-ethane-1,2-diamine (PMDTA, 4.28 g, 24.7 mmol, 5.2 mL, 4 eq) and 4,4,5,5-tetramethyl-2-[(4,4,5,5-tetramethyl-1,3,2-dioxaborolan-2-yl)methyl]-1,3,2-dioxaborolane (6.61 g, 24.7 mmol, 4 eq) at 0° C. The mixture was stirred at 0° C. for 30 min. Then a solution of 1-(5-bromo-2-hydroxy-phenyl)-2-methyl-propan-1-one (1.50 g, 6.2 mmol, 1 eq) in THF (10 mL) was added dropwise at 0° C. The reaction was continue stirred at 0° C. for 1 h. LCMS showed the reaction was completed and desired MS observed. The reaction mixture was quenched by sat. aq. NH$_4$Cl (100 mL), and adjusted pH=7 with 1N HCl, then extracted with EtOAc (50 mL×3). The combined organic layers were washed with brine (100 mL), dried over with Na$_2$SO$_4$, filtered and concentrated under reduced pressure to give a residue. The residue was purified by flash silica gel chromatography (ISCO®; 40 g SepaFlash® Silica Flash Column, Eluent of 0~30/Ethyl acetate/Petroleum ether gradient @ 100 mL/min) to give crude product. The crude product was triturated with Petroleum ether (10 mL) at 25° C. for 10 min to give 6-bromo-2-hydroxy-4-isopropyl-1,2-benzoxaborinine (0.9 g, 3.37 mmol, 54.6% yield) as off-white solid. 1H NMR (DMSO-d$^6$, 400 MHz) δ 8.96 (s, 1H), 7.84 (d, J=2.3 Hz, 1H), 7.55 (dd, J=2.4, 8.8 Hz, 1H), 7.84 (d, J=8.8 Hz, 1H), 6.03 (s, 1H), 3.26-3.23 (m, 1H), 1.19 (d, J=6.8 Hz, 6H) MS (ESI): mass calculated for C$_{11}$H$_{12}$BBrO$_2$, 266.01, m/z found 265.1 [M−H]$^−$. HPLC: 99.71% (220 nm), 99.70 (254 nm).

30.3 Preparation of 1-[trans-4-cyanotetrahydropyran-3-yl]-3-[(2-hydroxy-4-isopropyl-1,2-benzoxaborinin-6-yl)amino]pyrazole-4-carboxamide

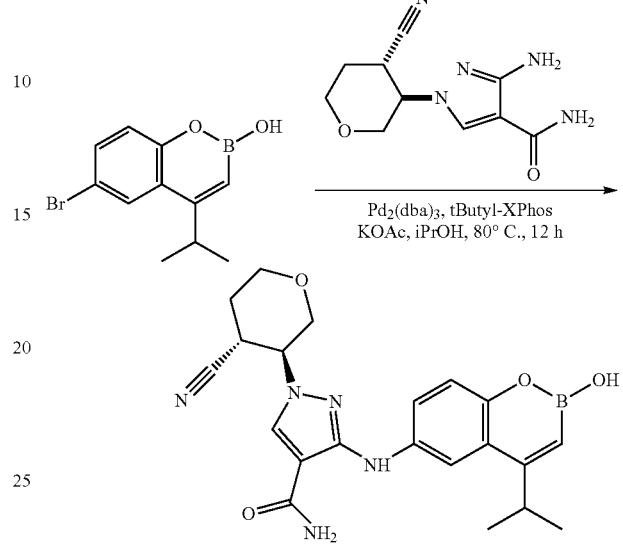

To a solution of 6-bromo-2-hydroxy-4-isopropyl-1,2-benzoxaborinine (0.5 g, 1.87 mmol, 1 eq), 3-amino-1-(trans-4-cyanotetrahydropyran-3-yl)pyrazole-4-carboxamide (396 mg, 1.69 mmol, 0.9 eq), t-Bu Xphos (159 mg, 374 umol, 0.2 eq), Pd$_2$(dba)$_3$ (171 mg, 187 umol, 0.1 eq) and KOAc (367 mg, 3.75 mmol, 2 eq) in i-PrOH (10 mL) was degassed and purged with N$_2$ for 3 times. Then the mixture was heated and stirred at 80° C. for 12 h under N$_2$ atmosphere. LCMS showed the reaction was completed and desired MS observed. 3 parallel reactions were combined for work up. The reaction mixture was filtered and the filtrate was concentrated under reduced pressure to give a residue. The residue was purified by column chromatography (SiO$_2$, Petroleum ether/Ethyl acetate=1/1 to 0/1) to give desired compound (980 mg, yield 59%, purity 94.9%) as a white solid, which was further separated by SFC (condition: column: DAICEL CHIRALPAK IC (250 mm*30 mm, 10 um); mobile phase: [Neu-MeOH]; B %: 50%-50%, 5 min) to give 1-[trans-4-cyanotetrahydro-2H-pyran-3-yl]-3-[(2-hydroxy-4-isopropyl-1,2-benzoxaborinin-6-yl)amino]pyrazole-4-carboxamide (stereoisomer one) (404.6 mg, 51.2% yield, 99.5% ee, first peak, Rt=1.288 min) 1H NMR (DMSO-d$^6$, 400 MHz) δ 9.08 (s, 1H), 8.64 (s, 1H), 8.29 (s, 1H), 8.22-8.21 (m, 1H) 7.72 (s, 1H), 7.37-7.34 (m, 1H), 7.16-7.12 (m, 2H), 5.97 (s, 1H), 4.59-4.56 (m, 1H), 4.09-4.06 (m, 1H), 3.72-3.69 (m, 1H), 3.60-3.56 (m, 1H), 3.49-3.42 (m, 1H), 3.42-3.36 (m, 1H), 3.30-3.28 (m, 1H), 2.21-2.19 (m, 1H), 2.03-1.99 (m, 1H), 1.28 (t, J=6.8 Hz, 6H). MS (ESI): mass calculated for C$_{21}$H$_{24}$BN$_5$O$_4$, 421.19, m/z found 422.2 [M+H]$^+$. HPLC: 97.80% (220 nm), 99.26% (254 nm). and 1-[trans-4-cyanotetrahydro-2H-pyran-3-yl]-3-[(2-hydroxy-4-isopropyl-1,2-benzoxaborinin-6-yl)amino]pyrazole-4-carboxamide (stereoisomer two) (427.1 mg, 54.1% yield, 97.4% purity, 99.2% ee, second peak, Rt=1.401 min) as a white solid. 1H NMR (DMSO-d$^6$, 400 MHz) δ 9.08 (s, 1H), 8.65 (s, 1H), 8.30 (s, 1H), 8.22-8.21 (m, 1H) 7.72 (s, 1H), 7.37-7.34 (m, 1H), 7.16-7.12 (m, 2H), 5.97 (s, 1H), 4.59-4.56 (m, 1H), 4.09-4.06 (m, 1H), 3.72-3.69 (m, 1H), 3.60-3.56 (m, 1H), 3.49-3.42 (m, 1H), 3.42-3.36 (m, 1H), 3.30-3.28 (m, 1H), 2.21-2.19 (m, 1H), 2.03-1.99 (m, 1H), 1.28 (t, J=6.8 Hz, 6H) MS (ESI): mass calculated for $C_{21}H_{24}BN_5O_4$, 421.19, m/z found 422.3 [M+H]$^+$. HPLC: 97.82% (220 nm), 99.31% (254 nm).

31. Preparation of 1-(trans-2-cyanocyclopentyl)-3-[(2-hydroxy-8-methyl-1,2-benzoxaborinin-6-yl)amino]pyrazole-4-carboxamide

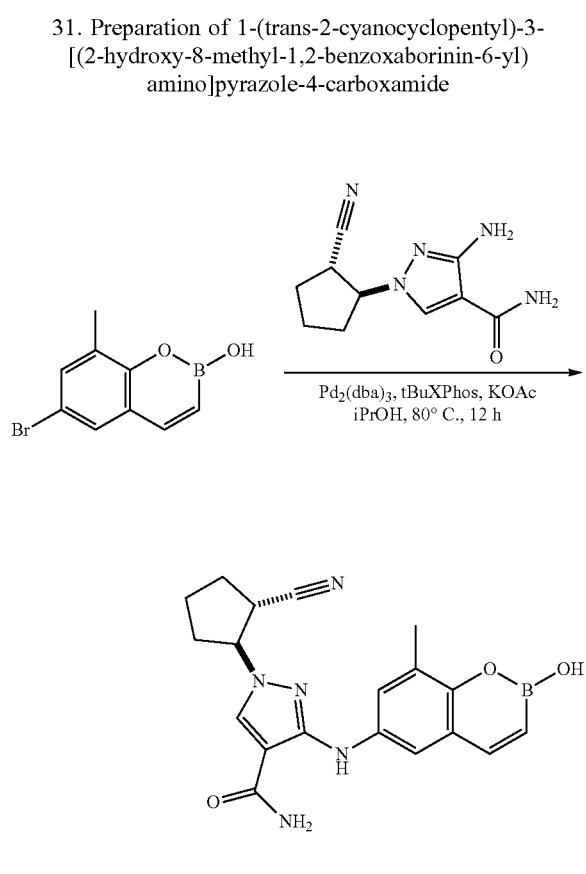

A mixture of 6-bromo-2-hydroxy-8-methyl-1,2-benzoxaborinine (100 mg, 418 umol, 1 eq), 3-amino-1-(2-cyanocyclopentyl)pyrazole-4-carboxamide (110 mg, 502 umol, 1.2 eq), t-Bu Xphos (36 mg, 83 umol, 0.2 eq), Pd$_2$(dba)$_3$ (77 mg, 83 umol, 0.2 eq) and KOAc (82.1 mg, 837 umol, 2 eq) in i-PrOH (6 mL) was degassed and purged with N$_2$ for 3 times, and then the mixture was heated to 80° C. and stirred at 80° C. for 12 h under N$_2$ atmosphere. LCMS showed the reaction was completed and desired MS observed. The reaction mixture was filtered and the filtrate was concentrated under reduced pressure. The residue was purified by prep-HPLC (column: Phenomenex Gemini-NX C18 75*30 mm*3 um; mobile phase: [water (10 mM NH$_4$HCO$_3$)-ACN]; B %: 25%-45%, 8 min) to give 1-(trans-2-cyanocyclopentyl)-3-[(2-hydroxy-8-methyl-1,2-benzoxaborinin-6-yl)amino]pyrazole-4-carboxamide (18 mg, 11.4% yield) as a white solid. 1H NMR (DMSO-hd 6, 400 MHz) δ 8.99 (s, 1H), 8.76 (s, 1H), 8.27 (s, 1H), 7.74 (d, J=12.0 Hz, 1H), 7.67 (d, J=2.8 Hz, 1H), 7.59 (brs, 1H), 7.36 (s, 1H), 7.13 (brs, 1H), 6.08 (d, J=11.6 Hz, 1H), 4.87 (q, J=8.0 Hz, 1H), 3.41-3.33 (m, 1H), 2.31 (s, 3H), 2.26-2.24 (m, 1H), 2.18-2.13 (m, 1H), 1.95-1.84 (m, 4H) MS (ESI): mass calculated for $C_{19}H_{20}BN_5O_3$, 377.17, m/z found 378.2 [M+H]$^+$. HPLC: 92.03% (220 nm), 97.51% (254 nm).

32. Preparation of 1-[trans-4-cyanotetrahydro-2H-pyran-3-yl]-3-[(2-hydroxy-3,8-dimethyl-1,2-benzoxaborinin-6-yl)amino]pyrazole-4-carboxamide

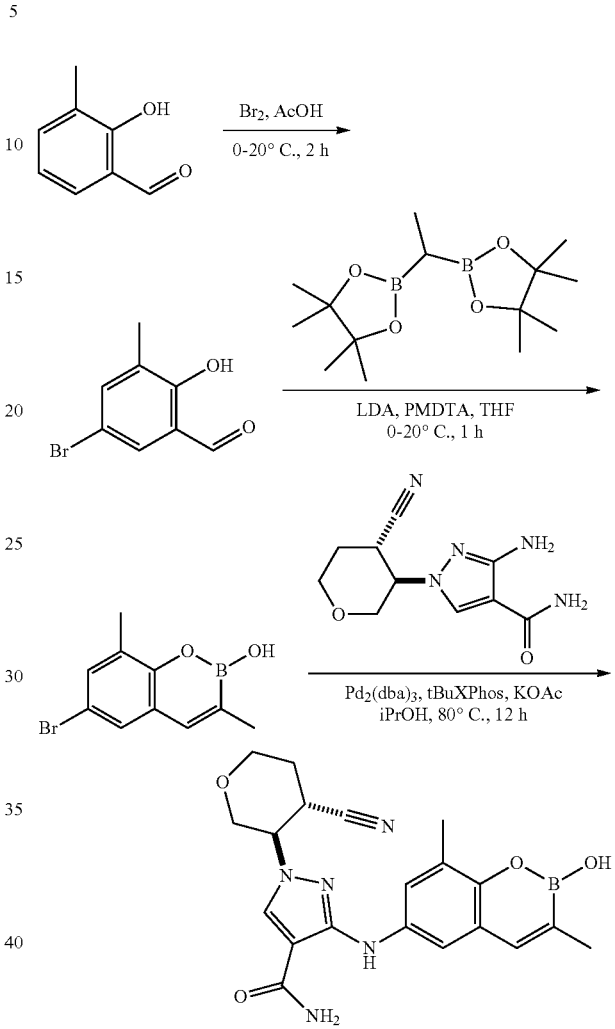

32.1 Preparation of 5-bromo-2-hydroxy-3-methyl-benzaldehyde

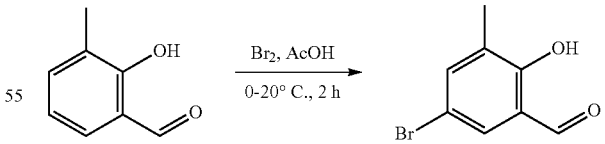

To a mixture of 2-hydroxy-3-methyl-benzaldehyde (10 g, 73.4 mmol, 1 eq) in AcOH (300 mL) was added Br$_2$ (13.5 g, 84.5 mmol, 1.15 eq) at 25° C. under N$_2$. The mixture was stirred at 25° C. for 2 h. TLC showed the reaction was completed. The reaction mixture was quenched by addition H$_2$O (100 mL), then solid was precipitate out. The precipitate was filtered to give 5-bromo-2-hydroxy-3-methyl-benzaldehyde (10 g, 63.3% yield) as a white solid.

32.2 Preparation of 6-bromo-2-hydroxy-3,8-dimethyl-1,2-benzoxaborinine

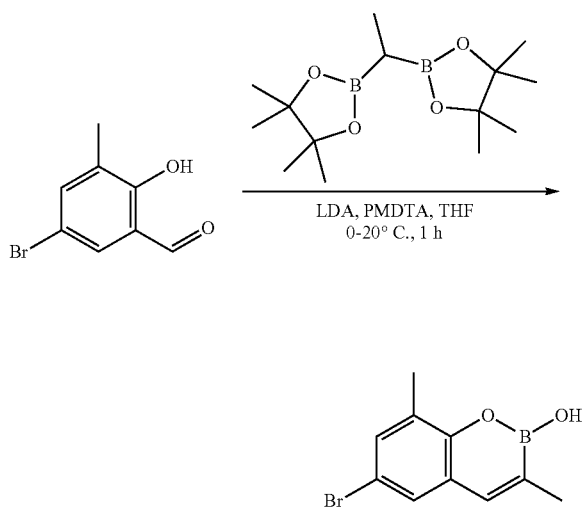

To a mixture of LDA (2 M, 5.1 mL, 2.2 eq) in THF (30 mL) was added N'-[2-(dimethylamino)ethyl]-N,N,N'-trimethyl-ethane-1,2-diamine (PMDTA, 1.6 g, 9.30 mmol, 1.94 mL, 2 eq) and a solution of 4,4,5,5-tetramethyl-2-[1-(4,4,5,5-tetramethyl-1,3,2-dioxaborolan-2-yl)ethyl]-1,3,2-dioxaborolane (2.9 g, 10.2 mmol, 2.2 eq) in THF (30 mL) at 0° C. for 30 min. Then added 5-bromo-2-hydroxy-3-methyl-benzaldehyde (1 g, 4.65 mmol, 1 eq) at 0° C. under $N_2$. The reaction was allowed to warm to 20° C. and stirred at 20° C. for 1 h. LCMS showed the reaction was completed and desired MS observed. The reaction mixture was quenched by sat. aq. $NH_4Cl$ (50 mL), extracted with EtOAc (30 mL×3). The combined organic layers were washed with brine (20 mL×2), dried over $Na_2SO_4$, filtered and concentrated under reduced pressure to give a residue. The residue was purified by column chromatography ($SiO_2$, Petroleum ether/Ethyl acetate=10/1 to 5/1) to give 6-bromo-2-hydroxy-3,8-dimethyl-1,2-benzoxaborinine (0.55 g, 46.7% yield) as a white solid. 1H NMR (DMSO-hd 6, 400 MHz) δ 9.03 (s, 1H), 7.48 (s, 1H), 7.43 (s, 1H), 7.37 (s, 1H), 2.33 (s, 3H), 2.02 (s, 3H).

32.3 Preparation of 1-[trans-4-cyanotetrahydro-2H-pyran-3-yl]-3-[(2-hydroxy-3,8-dimethyl-1,2-benzoxaborinin-6-yl)amino]pyrazole-4-carboxamide

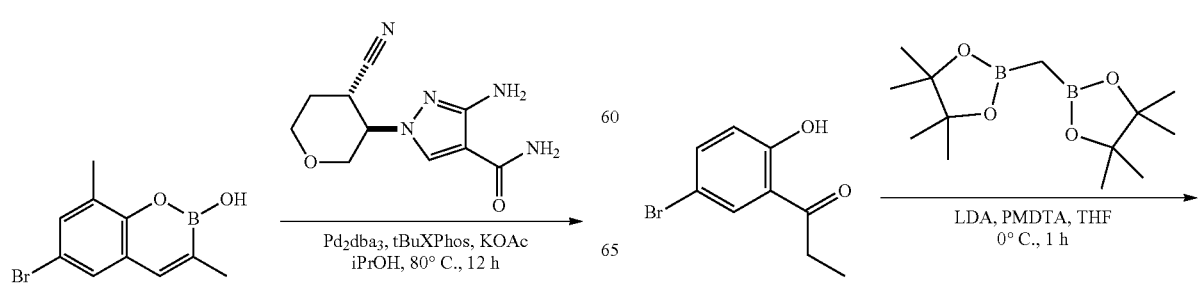

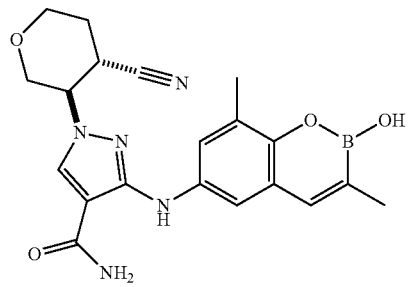

To a mixture of 6-bromo-2-hydroxy-3,8-dimethyl-1,2-benzoxaborinine (0.2 g, 790 umol, 1 eq) and 3-amino-1-[trans-4-cyanotetrahydro-2H-pyran-3-yl]pyrazole-4-carboxamide (223 mg, 949 umol, 1.2 eq) in i-PrOH (8 mL) was added $Pd_2(dba)_3$ (36 mg, 39.5 umol, 0.05 eq), KOAc (116 mg, 1.19 mmol, 1.5 eq) and t-Bu XPhos (34 mg, 79.0 umol, 0.1 eq) at 25° C. under $N_2$. The mixture was heated to 80° C. and stirred for 12 hrs. LCMS showed the reaction was completed and desired MS observed. The reaction mixture was filtered and concentrated under reduced pressure to give a residue. The residue was purified by column chromatography ($SiO_2$, Petroleum ether/Ethyl acetate=10/1 to 0/1) to give 1-[trans-4-cyanotetrahydro-2H-pyran-3-yl]-3-[(2-hydroxy-3,8-dimethyl-1,2-benzoxaborinin-6-yl)amino]pyrazole-4-carboxamide (42 mg, 13.0% yield) as a white solid. 1H NMR (DMSO-hd 6, 400 MHz) δ 8.99 (s, 1H), 8.67 (s, 1H), 8.28 (s, 1H), 7.68 (br s, 1H), 7.55 (s, 1H), 7.47 (s, 1H), 7.21 (s, 1H), 7.14 (br s, 1H), 4.57-4.53 (m, 1H), 4.06-4.03 (m, 1H), 3.94-3.92 (m, 2H), 3.73-3.67 (m, 1H), 3.52 (t, J=10.2 Hz, 1H), 2.34 (s, 3H), 2.19-2.16 (m, 1H), 2.03 (s, 3H), 2.01-1.98 (m, 1H). MS (ESI): mass calculated for $C_{20}H_{22}BN_5O_4$, 407.18, m/z found 406.2 [M−H]⁻. HPLC: 94.85% (220 nm), 99.02% (254 nm).

33. Preparation of 1-(trans-4-cyanotetrahydro-2H-pyran-3-yl)-3-[(4-ethyl-2-hydroxy-1,2-benzoxaborinin-6-yl)amino]pyrazole-4-carboxamide

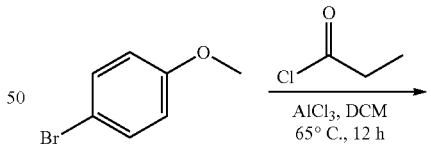

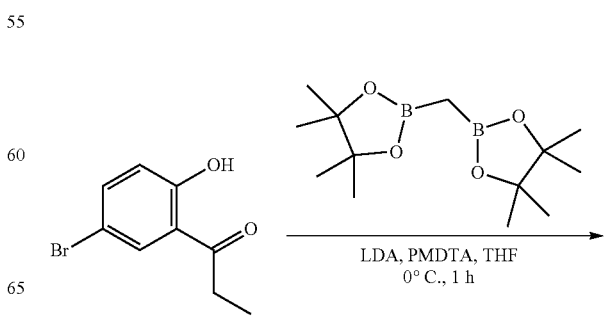

-continued

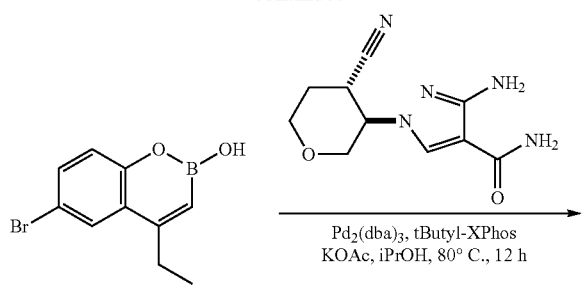

Pd₂(dba)₃, tButyl-XPhos
KOAc, iPrOH, 80° C., 12 h

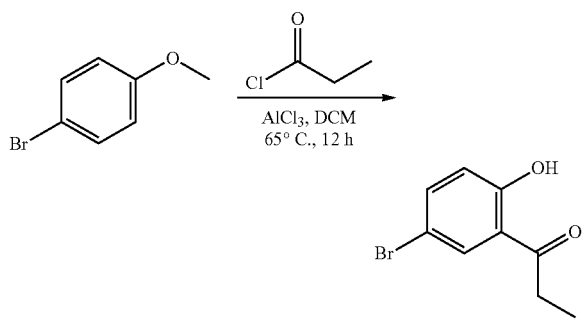

33.1 Preparation of 1-(5-bromo-2-hydroxy-phenyl)propan-1-one

AlCl₃, DCM
65° C., 12 h

To a solution of propanoyl chloride (4.95 g, 53.4 mmol, 4.95 mL, 2 eq) in DCM (50 mL) was added AClCl₃ (14.3 g, 107 mmol, 4 eq) at 0° C. After addition, the mixture was stirred at 0° C. for 30 min, and then 1-bromo-4-methoxy-benzene (5.00 g, 26.7 mmol, 1 eq) was added at 0° C. The resulting mixture was heated and stirred at 65° C. for 12 h. TLC showed the reaction was completed. The reaction mixture was quenched by addition H₂O (100 mL) at 0° C., and then extracted with DCM (50 mL×3). The combined organic layers were washed with brine (50 mL), dried over Na₂SO₄, filtered and concentrated under reduced pressure to give a residue. The residue was purified by flash silica gel chromatography (ISCO®; 20 g SepaFlash® Silica Flash Column, Eluent of 0~10% Ethyl acetate/Petroleum ether gradient @ 100 mL/min) to give 1-(5-bromo-2-hydroxy-phenyl)propan-1-one (5.00 g, 81.6% yield) as a yellow solid. 1H NMR (CDCl₃, 400 MHz) δ=12.26 (s, 1H), 7.88 (s, 1H), 7.54 (dd, J=2.0, 8.9 Hz, 1H), 6.90 (d, J=8.9 Hz, 1H), 3.03 (q, J=7.2 Hz, 2H), 1.25 (t, J=7.2 Hz, 3H).

33.2 Preparation of 6-bromo-4-ethyl-2-hydroxy-1,2-benzoxaborinine

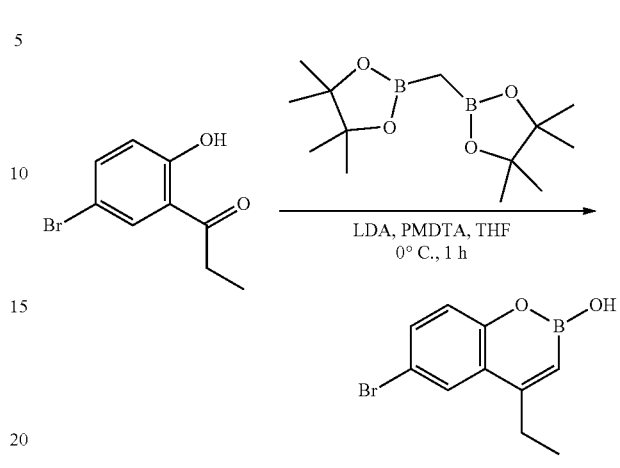

LDA, PMDTA, THF
0° C., 1 h

To a solution of LDA (2 M, 21.8 mL, 5 eq) in THF (30 mL) was dropwise added N'-[2-(dimethylamino)ethyl]-N,N,N'-trimethyl-ethane-1,2-diamine (PMDTA, 6.05 g, 34.9 mmol, 7.29 mL, 4 eq) and 4,4,5,5-tetramethyl-2-[(4,4,5,5-tetramethyl-1,3,2-dioxaborolan-2-yl)methyl]-1,3,2-dioxaborolane (9.36 g, 34.9 mmol, 4 eq) at 0° C. After addition, the mixture was stirred at 0° C. for 30 min, and then 1-(5-bromo-2-hydroxy-phenyl)propan-1-one (2 g, 8.73 mmol, 1 eq) in THF (10 mL) was added dropwise at 0° C. The resulting mixture was continue stirred at 0° C. for 1 h. LCMS showed the reaction was completed and desired MS observed. The reaction mixture was quenched by addition of NH₄Cl (100 mL), adjust pH=7 with 1N HCl and extracted with EtOAc (50 mL×3). The combined organic layers were washed with brine (100 mL), dried over with Na₂SO₄, filtered and concentrated under reduced pressure to give a residue. The residue was purified by flash silica gel chromatography (ISCO®; 40 g SepaFlash® Silica Flash Column, Eluent of 0~30% Ethyl acetate/Petroleum ether gradient @ 100 mL/min) to give crude product. The crude product was triturated with Petroleum ether (10 mL) at 25° C. for 10 min to give 6-bromo-4-ethyl-2-hydroxy-1,2-benzoxaborinine (0.8 g, 36.2% yield) as a white solid. 1H NMR (DMSO-d⁶, 400 MHz) δ=8.96 (s, 1H), 7.78 (d, J=2.4 Hz, 1H), 7.54 (dd, J=2.0, 8.9 Hz, 1H), 7.19 (d, J=8.4 Hz, 1H), 5.99 (s, 1H), 2.70 (q, J=7.2 Hz, 2H), 1.19 (t, J=7.3 Hz, 3H).

33.3 Preparation of 1-(trans-4-cyanotetrahydropyran-3-yl)-3-[(4-ethyl-2-hydroxy-1,2-benzoxaborinin-6-yl)amino]pyrazole-4-carboxamide

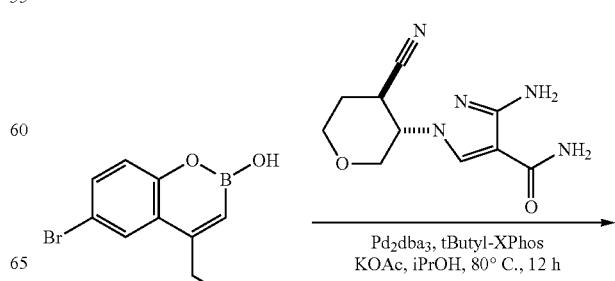

Pd₂dba₃, tButyl-XPhos
KOAc, iPrOH, 80° C., 12 h

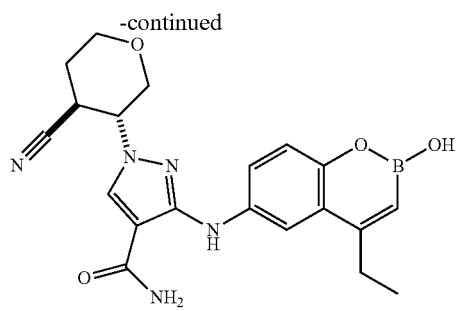

To a solution of 3-amino-1-(trans-4-cyanotetrahydropyran-3-yl)pyrazole-4-carboxamide (279 mg, 1.19 mmol, 1.5 eq) in i-PrOH (5 mL) was added KOAc (155 mg, 1.58 mmol, 2 eq), 6-bromo-4-ethyl-2-hydroxy-1,2-benzoxaborinine (200 mg, 791 umol, 1 eq), Pd$_2$(dba)$_3$ (36.0 mg, 39.5 umol, 0.05 eq) and t-Bu Xphos (33.1 mg, 79.0 umol, 0.1 eq) at 25° C. The resulting mixture was stirred at 80° C. for 12 h. LCMS showed the reaction was completed and desired MS observed. The reaction mixture was filtered, and the filtrate was concentrated under reduced pressure to give a residue. The residue was purified by prep-HPLC (column: Waters Xbridge BEH C18 100*30 mm*10 um; mobile phase: [water (10 mM NH$_4$HCO$_3$)-ACN]; B %: 15%-45%, 10 min) to give 1-(trans-4-cyanotetrahydropyran-3-yl)-3-[(4-ethyl-2-hydroxy-1,2-benzoxaborinin-6-yl)amino] pyrazole-4-carboxamide (100.2 mg, 15.5% yield) as a yellow solid. 1H NMR (DMSO-d$^6$, 400 MHz) δ=9.08 (s, 1H), 8.64 (s, 1H), 8.29 (s, 1H), 8.09 (s, 1H), 7.72 (s, 1H), 7.41 (d, J=6.9 Hz, 1H), 7.19-7.12 (m, 2H), 5.93 (s, 1H), 4.59-4.56 (m, 1H), 4.08-4.05 (m, 1H), 3.97-3.94 (m, 1H), 3.72-3.62 (m, 2H), 3.41-3.42 (m, 1H), 2.81-2.76 (m, 2H), 2.20-2.17 (m, 1H), 2.01-1.99 (m, 1H), 1.27 (t, J=7.2 Hz, 3H) MS (ESI): mass calculated for C$_{20}$H$_{22}$BN$_5$O$_4$, 407.18, m/z found 406.2 [M−H]$^-$. HPLC: 99.34% (220 nm), 99.51% (254 nm).

34. Preparation of 1-(trans-2-cyanocyclohexyl)-3-[(2-hydroxy-4-isopropyl-1,2-benzoxaborinin-6-yl)amino]pyrazole-4-carboxamide

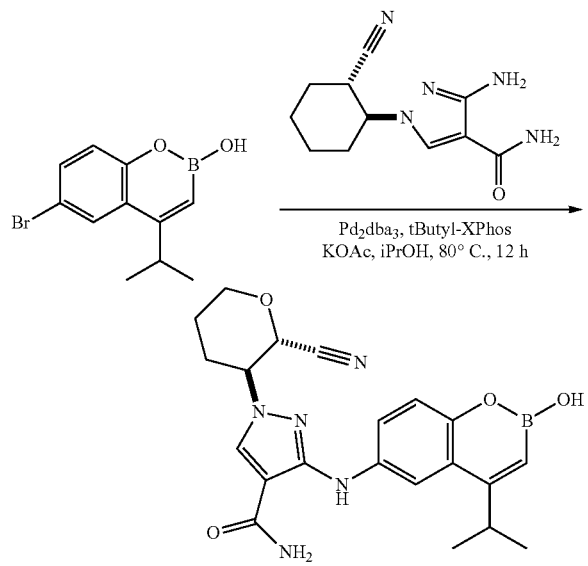

To a solution of 3-amino-1-(trans-2-cyanocyclohexyl)pyrazole-4-carboxamide (157 mg, 674 umol, 1.5 eq) in i-PrOH (5 mL) was added KOAc (88 mg, 899 umol, 2 eq), 6-bromo-2-hydroxy-4-isopropyl-1,2-benzoxaborinine (120 mg, 450 umol, 1 eq), Pd$_2$(dba)$_3$ (21 mg, 22.5 umol, 0.05 eq) and t-Bu Xphos (19 mg, 45 umol, 0.1 eq) at 25° C. under N$_2$. The resulting mixture was heated and stirred at 80° C. for 12 h. LCMS showed the reaction was completed and desired MS observed. The reaction mixture was filtered, and the filtrate was concentrated under reduced pressure to give a residue. The residue was purified by prep-HPLC (column: Waters Xbridge BEH C18 100*30 mm*10 um; mobile phase: [water (10 mM NH$_4$HCO$_3$)-ACN]; B %: 30%-60%, 10 min) to give 1-(trans-2-cyanocyclohexyl)-3-[(2-hydroxy-4-isopropyl-1,2-benzoxaborinin-6-yl)amino]pyrazole-4-carboxamide (17.3 mg, 9.18% yield) as a yellow solid. 1H NMR (DMSO-d$^6$, 400 MHz) δ 9.05 (s, 1H), 8.63 (s, 1H), 8.32-8.27 (m, 1H), 8.23 (s, 1H), 7.72-7.61 (m, 1H), 7.37-7.29 (m, 1H), 7.16-7.09 (m, 1H), 5.96 (s, 1H), 4.47-4.28 (m, 1H), 3.29-3.17 (m, 2H), 2.26-2.17 (m, 1H), 2.07-1.97 (m, 1H), 1.97-1.61 (m, 5H), 1.55-1.38 (m, 1H), 1.27 (t, J=7.0 Hz, 6H). MS (ESI): mass calculated for C$_{22}$H$_{26}$BN$_5$O$_3$, 419.21, m/z found 418.3 [M−H]$^-$. HPLC: 97.39% (220 nm), 99.89% (254 nm).

35. Preparation of 1-(trans-2-cyanocyclopentyl)-3-[(2-hydroxy-4-isopropyl-1,2-benzoxaborinin-6-yl)amino]pyrazole-4-carboxamide

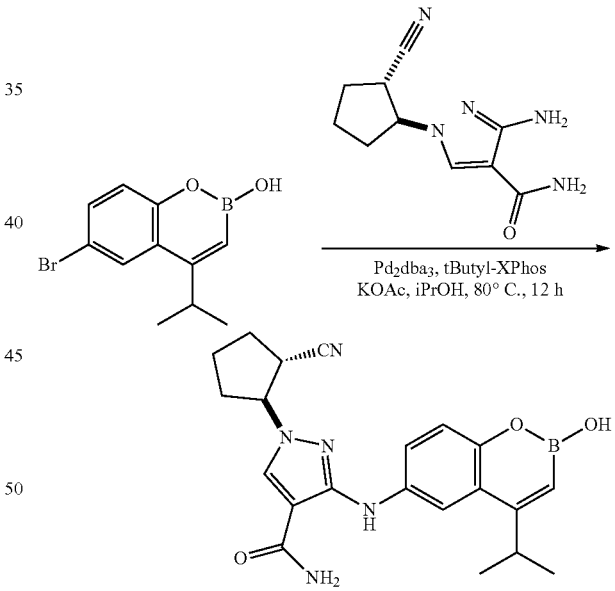

To a solution of 3-amino-1-(trans-2-cyanocyclopentyl)pyrazole-4-carboxamide (148 mg, 674 umol, 1.5 eq) in i-PrOH (3 mL) was added KOAc (88 mg, 899 umol, 2 eq), 6-bromo-2-hydroxy-4-isopropyl-1,2-benzoxaborinine (120 mg, 450 umol, 1 eq), Pd$_2$(dba)$_3$ (21 mg, 22.5 umol, 0.05 eq) and t-Bu Xphos (19 mg, 45 umol, 0.1 eq) at 25° C. under N$_2$. The resulting mixture was heated and stirred at 80° C. for 12 h. LCMS showed the reaction was completed and desired MS observed. The reaction mixture was filtered, and the filtrate was concentrated under reduced pressure to give a residue. The residue was purified by prep-HPLC (column: Waters Xbridge BEH C18 100*30 mm*10 um; mobile phase: [water (10 mM NH₄HCO₃)-ACN]; B %: 30%-60%, 1 min) to give 1-(trans-2-cyanocyclopentyl)-3-[(2-hydroxy-4-isopropyl-1,2-benzoxaborinin-6-yl)amino]pyrazole-4-carboxamide (30.2 mg, 16.5% yield) as a white solid. 1H NMR (DMSO-d₆, 400 MHz) δ 9.09 (s, 1H), 9.63 (s, 1H), 8.28 (s, 1H), 8.28-8.27 (m, 1H), 7.63 (s, 1H), 7.33-7.29 (m, 1H), 7.12 (d, J=8.8 Hz, 2H), 5.96 (s, 1H), 4.97-4.91 (m, 1H), 3.41-3.32 (m, 1H), 3.29-3.26 (m, 1H), 2.23-2.14 (m, 2H), 2.16-2.14 (m, 1H), 1.93-1.92 (m, 1H) 1.90-1.88 (m, 2H), 1.24 (t, J=6.6 Hz, 6H) MS (ESI): mass calculated for C₂₁H₂₄BN₅O₃, 405.20, m/z found 404.2 [M−H]⁻. HPLC: 92.21% (220 nm), 99.38% (254 nm).

36. Preparation of 1-[trans-4-cyanotetrahydro-2H-pyran-3-yl]-3-[(1-hydroxy-3,3-dimethyl-2,1-benzoxaborol-6-yl)amino]pyrazole-4-carboxamide

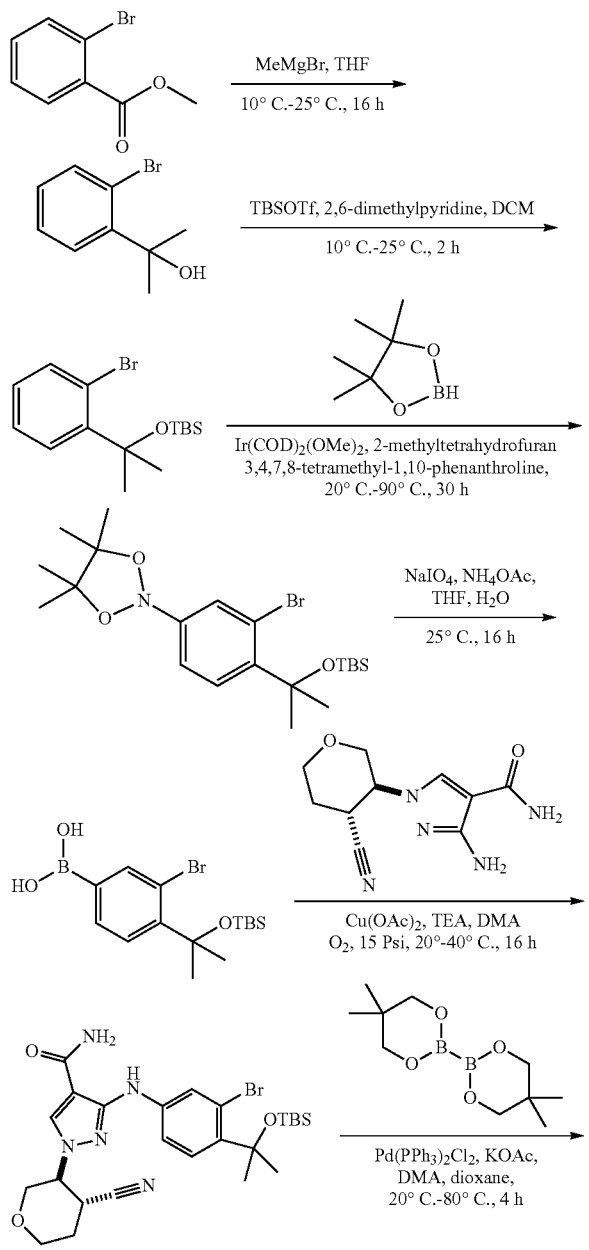

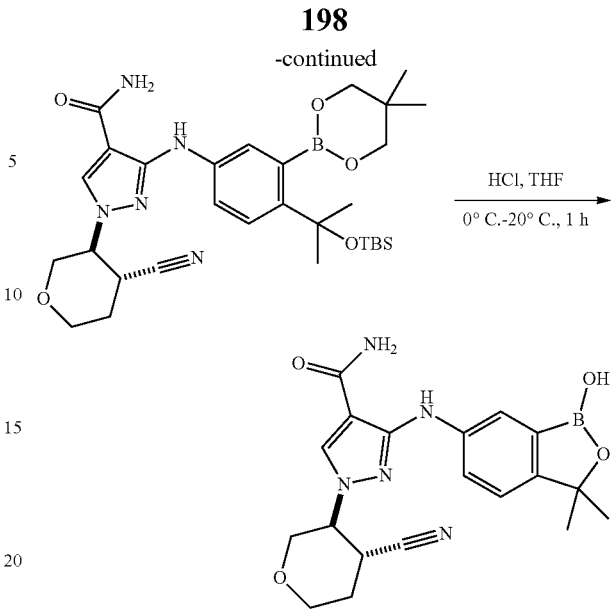

36.1 Preparation of 2-(2-bromophenyl)propan-2-ol

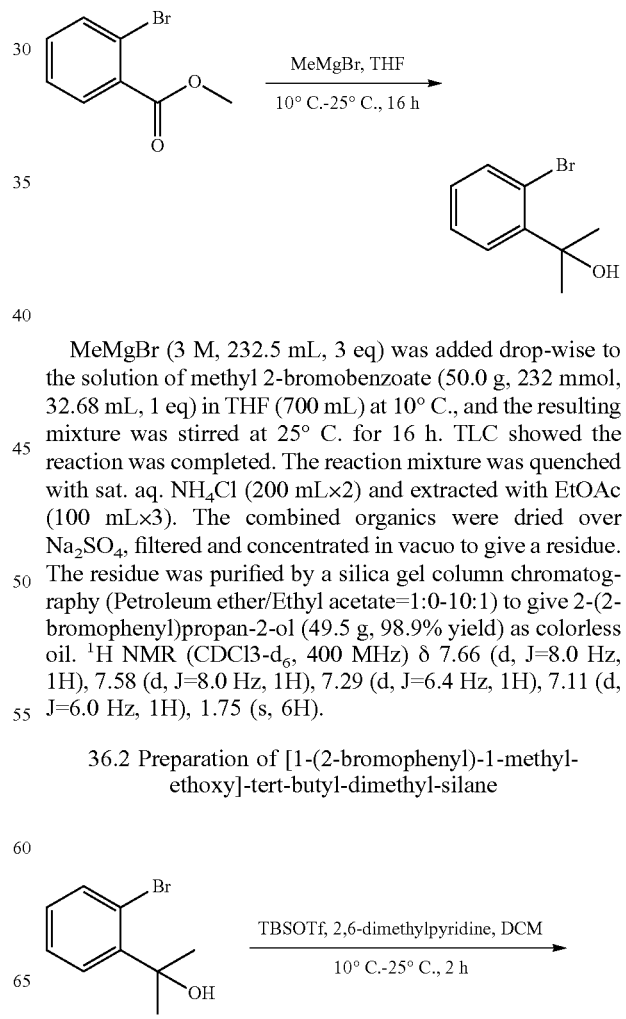

MeMgBr (3 M, 232.5 mL, 3 eq) was added drop-wise to the solution of methyl 2-bromobenzoate (50.0 g, 232 mmol, 32.68 mL, 1 eq) in THF (700 mL) at 10° C., and the resulting mixture was stirred at 25° C. for 16 h. TLC showed the reaction was completed. The reaction mixture was quenched with sat. aq. NH₄Cl (200 mL×2) and extracted with EtOAc (100 mL×3). The combined organics were dried over Na₂SO₄, filtered and concentrated in vacuo to give a residue. The residue was purified by a silica gel column chromatography (Petroleum ether/Ethyl acetate=1:0-10:1) to give 2-(2-bromophenyl)propan-2-ol (49.5 g, 98.9% yield) as colorless oil. ¹H NMR (CDCl3-d₆, 400 MHz) δ 7.66 (d, J=8.0 Hz, 1H), 7.58 (d, J=8.0 Hz, 1H), 7.29 (d, J=6.4 Hz, 1H), 7.11 (d, J=6.0 Hz, 1H), 1.75 (s, 6H).

36.2 Preparation of [1-(2-bromophenyl)-1-methyl-ethoxy]-tert-butyl-dimethyl-silane -continued

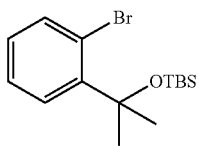

To a solution of 2-(2-bromophenyl)propan-2-ol (30.0 g, 139 mmol, 1 eq) and 2,6-dimethylpyridine (279 mmol, 32.49 mL, 2 eq) in DCM (300 mL) was added [tert-butyl(dimethyl)silyl]trifluoromethanesulfonate (209 mmol, 48.1 mL, 1.5 eq) drop-wise at 10° C. The mixture was allowed to warm to 25° C. stirred at 25° C. for 2 h. TLC showed the reaction was completed. The mixture was poured into ice-water (w/w=1/1) (500 mL) and stirred for 10 min. The aqueous phase was extracted with DCM (500 mL×3). The combined organic phase was washed with brine (500 mL×2), dried with anhydrous $Na_2SO_4$, filtered and concentrated in vacuum to give a residue. The residue was purified by column chromatography ($SiO_2$, Petroleum ether/Ethyl acetate=10/1 to 5/1) to give [1-(2-bromophenyl)-1-methyl-ethoxy]-tert-butyl-dimethyl-silane (39.0 g, 84.9% yield) as a yellow oil. $^1$H NMR (CDCl3-$d_6$, 400 MHz) δ 7.91 (d, J=8.0 Hz, 1H), 7.57 (d, J=8.0 Hz, 1H), 7.28 (t, J=6.8 Hz, 1H), 7.07 (t, J=2.0 Hz, 1H), 1.80 (s, 6H), 0.99 (s, 9H), 0.18 (s, 6H).

36.3 Preparation of [1-[2-bromo-4-(4,4,5,5-tetramethyl-1,3,2-dioxaborolan-2-yl)phenyl]-1-methyl-ethoxy]-tert-butyl-dimethyl-silane and [1-[2-bromo-5-(4,4,5,5-tetramethyl-1,3,2-diaxaborolan-2-yl)phenyl]-1-methyl-ethoxy]-tert-butyl-dimethyl-silane

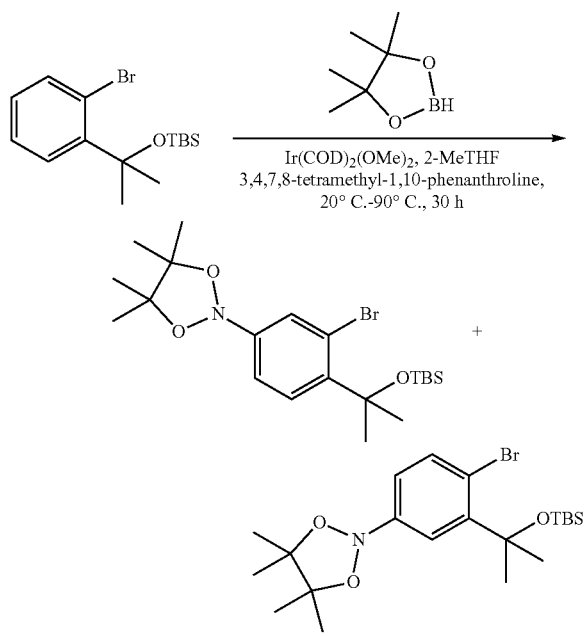

To a mixture of [1-(2-bromophenyl)-1-methyl-ethoxy]-tert-butyl-dimethyl-silane (8.0 g, 24.3 mmol, 1 eq), Ir(COD)$_2$(OMe)$_2$ (644 mg, 971 umol, 0.04 eq) and 3,4,7,8-tetramethyl-1,10-phenanthroline (574 mg, 2.43 mmol, 0.1 eq) in 2-methyltetrahydrofuran (80 mL) was added 4,4,5,5-tetramethyl-1,3,2-dioxaborolane (194 mmol, 28.2 mL, 8 eq) drop-wise under $N_2$. The mixture was heated to 90° C. and stirred for 30 h. TLC showed the reaction was completed. 3 parallel reactions were combined for work up. The mixture was poured into ice-water (w/w=1/1) (250 mL) and stirred for 10 min. The aqueous phase was extracted with ethyl acetate (200 mL×3). The combined organic phase was washed with brine (150 mL×2), dried with anhydrous $Na_2SO_4$, filtered and concentrated in vacuum to give a residue. The residue was purified by column chromatography ($SiO_2$, Petroleum ether/Ethyl acetate=5/1 to 3/1) to give [1-[2-bromo-4-(4,4,5,5-tetramethyl-1,3,2-dioxaborolan-2-yl)phenyl]-1-methyl-ethoxy]-tert-butyl-dimethyl-silane and [1-[2-bromo-5-(4,4,5,5-tetramethyl-1,3,2-dioxaborolan-2-yl)phenyl]-1-methyl-ethoxy]-tert-butyl-dimethyl-silane (36 g, mixture) as a yellow solid. $^1$H NMR (CDCl3-$d_6$, 400 MHz) δ 7.99 (s, 1H), 7.92 (d, J=7.6 Hz, 1H), 7.73 (d, J=7.6 Hz, 1H), 1.78 (s, 6H), 1.34 (s, 12H), 0.97 (s, 9H), 0.16 (s, 6H).

36.4 Preparation of (3-bromo-4-(2-((tert-butyldimethylsilyl)oxy)propan-2-yl)phenyl)boronic acid and (4-bromo-3-(2-((tert-butyldimethylsilyl)oxy)propan-2-yl)phenyl)boronic acid

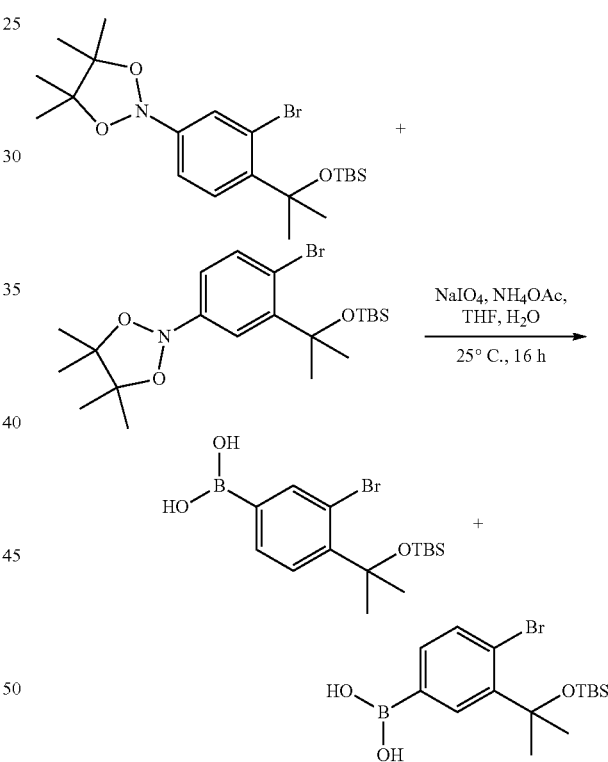

To a solution of [1-[2-bromo-4-(4,4,5,5-tetramethyl-1,3,2-dioxaborolan-2-yl)phenyl]-1-methyl-ethoxy]-tert-butyl-dimethyl-silane (24.0 g, 52.7 mmol, 1 eq) in THF (250 mL) and H$_2$O (100 mL) was added NaIO$_4$ (33.8 g, 158 mmol, 3 eq) and NH$_4$OAc (12.2 g, 158 mmol, 3 eq) at 25° C. The mixture was stirred at 25° C. for 16 h. TLC showed the reaction was completed. The mixture was poured into ice-water (w/w=1/1) (300 mL) and stirred for 10 min. The aqueous phase was extracted with ethyl acetate (200 mL×3). The combined organic phase was washed with brine (200 mL×2), dried with anhydrous Na$_2$SO$_4$, filtered and concentrated in vacuum to give a residue. The residue was purified by column chromatography (SiO$_2$, Petroleum ether/Ethyl acetate=5/1 to 3/1) to give crude product. Then the crude product was triturated with Petroleum ether (100 mL) at 20° C. for 10 min to give [3-bromo-4-[1-[tert-butyl(dimethyl) silyl]oxy-1-methyl-ethyl]phenyl]boronic acid (Compound 5, 5.0 g, 25.4% yield) as a white solid. And (4-bromo-3-(2-((tert-butyldimethylsilyl)oxy)propan-2-yl)phenyl)boronic acid (Compound 5A, 12 g, crude) as brown oil. ¹H NMR (DMSO-hd 6, 400 MHz) δ 8.17 (s, 2H), 7.94 (s, 1H), 7.74-7.67 (m, 2H), 1.69 (s, 6H), 0.90 (s, 9H), 0.09 (s, 6H). ¹H NMR (DMSO-hd 6, 400 MHz) δ 8.19 (s, 1H), 8.07 (s, 2H), 7.57-7.51 (m, 2H), 1.73 (s, 6H), 0.92 (s, 9H), 0.10 (s, 6H).

36.5 Preparation of 3-[3-bromo-4-[1-[tert-butyl(dimethyl)silyl]oxy-1-methyl-ethyl]anilino]-1-(trans 4-cyanotetrahydro-2H-pyran-3-yl)pyrazole-4-carboxamide

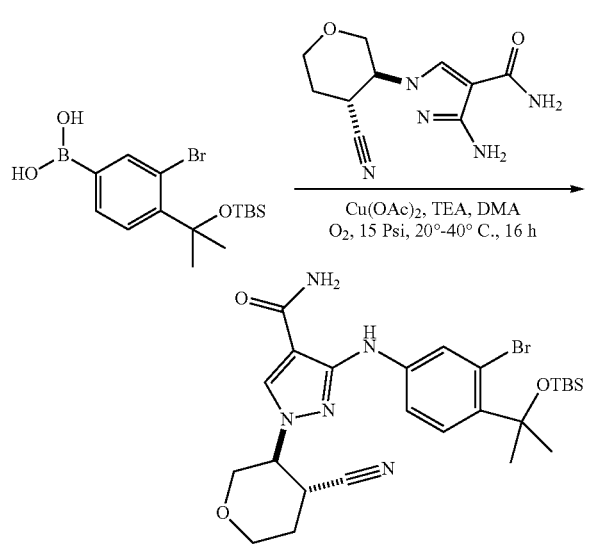

To a mixture of 3-amino-1-(trans-4-cyanotetrahydropyran-3-yl)pyrazole-4-carboxamide (1.0 g, 4.25 mmol, 1 eq) and [3-bromo-4-[1-[tert-butyl(dimethyl)silyl]oxy-1-methyl-ethyl]phenyl]boronic acid (1.90 g, 5.10 mmol, 1.2 eq) in DMA (20 mL) was added 4 A molecular sieve (7 g), TEA (2.96 mL, 21.2 mmol, 5 eq) and Cu(OAc)₂ (1.93 g, 10.6 mmol, 2.5 eq) in one portion at 25° C. under O₂. The mixture was stirred at 40° C. for 16 h. LCMS showed the reaction was completed and desired MS observed. 4 parallel reactions were combined for work up. The reaction mixture was filtered. The filtrate was added H₂O (200 mL) at 20° C. and extracted with ethyl acetate (80 mL×4). The combined organic layers were washed with brine (60 mL×3), dried over Na₂SO₄, filtered and concentrated under reduced pressure to give a residue. The residue was purified by column chromatography (SiO₂, Petroleum ether/Ethyl acetate=1/1 to 0/1) to give 3-[3-bromo-4-[1-[tert-butyl(dimethyl)silyl]oxy-1-methyl-ethyl]anilino]-1-(trans-4-cyanotetrahydro-2H-pyran-3-yl)pyrazole-4-carboxamide (5.00 g, 52.2% yield) as a yellow solid. ¹H NMR (DMSO-d₆, 400 MHz) δ 9.20 (s, 1H), 8.31 (s, 1H), 7.84 (d, J=2.0 Hz, 1H), 7.74 (br s, 1H), 7.61 (d, J=8.8 Hz, 1H), 7.47-7.44 (m, 1H), 7.22 (br s, 1H), 4.61-4.57 (m, 1H), 4.06-4.04 (m, 1H), 3.93-3.90 (m, 1H), 3.65-3.62 (m, 1H), 3.61-3.45 (m, 1H), 2.18-2.14 (m, 1H), 2.04-1.99 (m, 2H), 1.71 (s, 6H), 0.92 (s, 9H), 0.10 (s, 6H).

36.6 Preparation of 3-[4-[1-[tert-butyl(dimethyl)silyl]oxy-1-methyl-ethyl]-3-(5,5-dimethyl-1,3,2-dioxaborinan-2-yl)anilino]-1-(trans-4-cyanotetrahydro-2H-pyran-3-yl)pyrazole-4-carboxamide

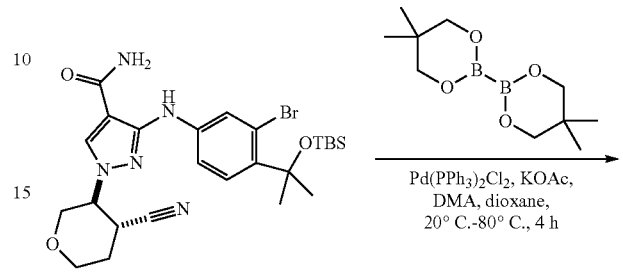

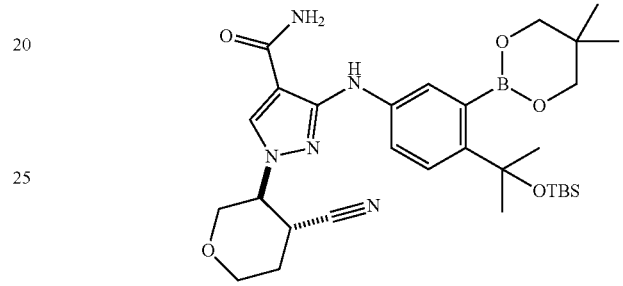

To a mixture of 3-[3-bromo-4-[1-[tert-butyl(dimethyl)silyl]oxy-1-methyl-ethyl]anilino]-1-(4-cyanotetrahydropyran-3-yl)pyrazole-4-carboxamide (500 mg, 889 umol, 1 eq) in DMA (1 mL) and dioxane (10 mL) was added Pd(PPh₃)₂Cl₂ (62.4 mg, 88.9 umol, 0.1 eq), KOAc (262 mg, 2.67 mmol, 3 eq) and 2-(5,5-dimethyl-1,3,2-dioxaborinan-2-yl)-5,5-dimethyl-1,3,2-dioxaborinane (1.00 g, 4.44 mmol, 5 eq) in one portion at 20° C. under N₂. The mixture was stirred at 80° C. for 4 h. 5 parallel reactions were combined for work up. The mixture was filtered and the filtrate was concentrated in vacuum to give a residue. The residue was purified by column chromatography (SiO₂, Petroleum ether/Ethyl acetate=1/1 to 0/1) to give 3-[4-[1-[tert-butyl(dimethyl)silyl]oxy-1-methyl-ethyl]-3-(5,5-dimethyl-1,3,2-dioxaborinan-2-yl)anilino]-1-(4-cyanotetrahydropyran-3-yl)pyrazole-4-carboxamide (2.5 g, crude) as brown oil.

36.7 Preparation of 1-[trans-4-cyanotetrahydro-2H-pyran-3-yl]-3-[(1-hydroxy-3,3-dimethyl-2,1-benzoxaborol-6-yl)amino]pyrazole-4-carboxamide

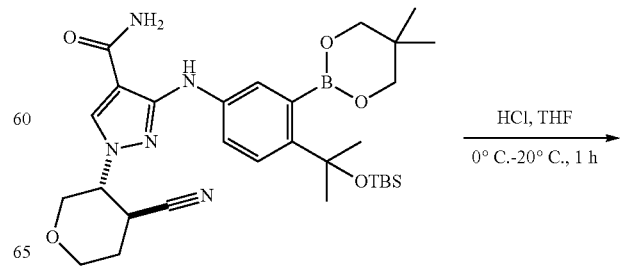

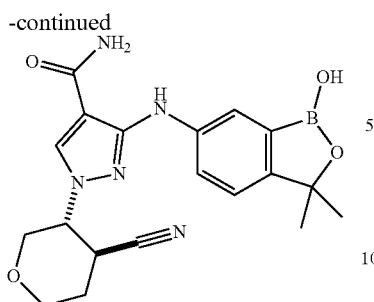

To a mixture of 3-[4-[1-[tert-butyl(dimethyl)silyl]oxy-1-methyl-ethyl]-3-(5,5-dimethyl-1,3,2-dioxaborinan-2-yl)anilino]-1-(trans-4-cyanotetrahydro-2H-pyran-3-yl)pyrazole-4-carboxamide (2.0 g, 3.36 mmol, 1 eq) in THF (20 mL) was added HCl (6 N, 2.80 mL, 5 eq) drop-wise at 0° C. under $N_2$. The mixture was stirred at 20° C. for 1 h. The mixture was poured into ice-water (w/w=1/1) (10 mL) and stirred for 10 min. The aqueous phase was extracted with ethyl acetate (10 mL×4). The combined organic phase was washed with brine (10 mL×2), dried with anhydrous $Na_2SO_4$, filtered and concentrated in vacuum to give a residue. The residue was purified by prep-HPLC (column: Phenomenex luna c18 250 mm*100 mm*10 um; mobile phase: [water (0.05% HCl)-ACN]; B %: 15%-45%, 25 min) to give 1-[trans-4-cyanotetrahydro-2H-pyran-3-yl]-3-[(1-hydroxy-3,3-dimethyl-2,1-benzoxaborol-6-yl)amino]pyrazole-4-carboxamide (580 mg), which was separated by SFC (column: DAICEL CHIRALPAK IC (250 mm*30 mm, 10 um); mobile phase: [Neu-IPA]; B %: 35%-35%, 10 min) to give 1-[trans-4-cyanotetrahydro-2H-pyran-3-yl]-3-[(1-hydroxy-3,3-dimethyl-2,1-benzoxaborol-6-yl)amino]pyrazole-4-carboxamide (stereoisomer one) (215.2 mg, 16.2% yield, 98.1% purity, 100% ee, first peak, Rt=2.860 min) as a white solid. $^1$H NMR (DMSO-hd 6, 400 MHz) δ 9.20 (s, 1H), 8.94 (s, 1H), 8.30 (s, 1H), 7.73-7.68 (m, 2H), 7.64 (s, 1H), 7.28 (d, J=8.0 Hz, 1H), 7.19 (br s, 1H), 4.59-4.55 (m, 1H), 4.06-4.02 (m, 1H), 3.95-3.91 (m, 1H), 3.73-3.67 (m, 2H), 3.49-3.48 (m, 1H), 2.19-2.14 (m, 1H), 2.02-1.98 (m, 1H), 1.43 (s, 6H). MS (ESI): mass calculated for $C_{19}H_{22}BN_5O_4$ 395.18, m/z found 396.2 $[M+H]^+$. HPLC: 98.12% (220 nm), 98.23% (254 nm). and 1-[trans-4-cyanotetrahydro-2H-pyran-3-yl]-3-[(1-hydroxy-3,3-dimethyl-2,1-benzoxa borol-6-yl)amino]pyrazole-4-carboxamide (stereoisomer two) (215.4 mg, 16.2% yield, 100% purity, 100% ee, second peak, Rt=3.633 min) as a white solid. $^1$H NMR (DMSO-hd 6, 400 MHz) δ 9.20 (s, 1H), 8.94 (s, 1H), 8.30 (s, 1H), 7.71-7.68 (m, 2H), 7.64 (s, 1H), 7.30 (d, J=8.4 Hz, 1H), 7.18 (br s, 1H), 4.57-4.55 (m, 1H), 4.06-4.02 (m, 1H), 3.95-3.91 (m, 1H), 3.73-3.67 (m, 2H), 3.49-3.45 (m, 1H), 2.18-2.14 (m, 1H), 2.01-1.98 (m, 1H), 1.43 (s, 6H). MS (ESI): mass calculated for $C_{19}H_{22}BN_5O_4$ 395.18, m/z found 396.2 $[M+H]^+$. HPLC: 100% (220 nm), 100% (254 nm).

37. Preparation of 1-(trans-4-cyanotetrahydro-2H-pyran-3-yl)-3-[(1-hydroxy-3,3-dimethyl-2,1-benzoxaborol-6-yl)amino]pyrazole-4-carboxamide

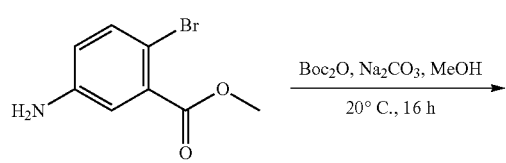

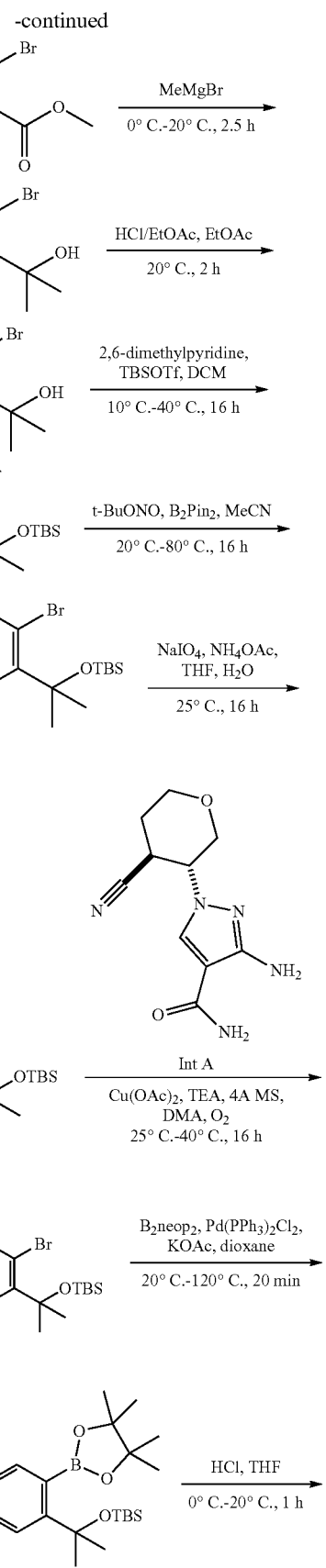

-continued

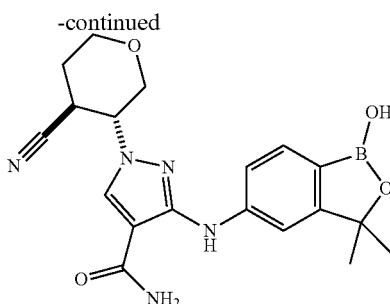

37.1 Preparation of methyl 2-bromo-5-(tert-butoxycarbonylamino)benzoate

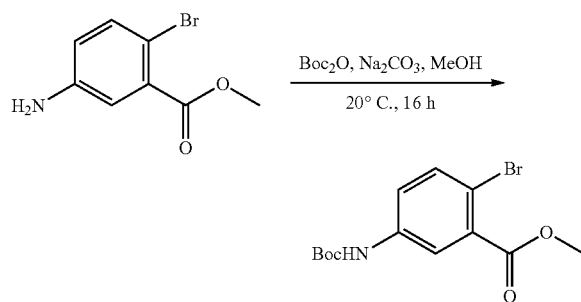

To a mixture of methyl 5-amino-2-bromo-benzoate (10.0 g, 43.4 mmol, 1 eq) in MeOH (90 mL) was added Boc$_2$O (20.8 g, 95.6 mmol, 2.2 eq) and Na$_2$CO$_3$ (13.8 g, 130 mmol, 3 eq) at 20° C. The mixture was stirred at 20° C. for 16 h. TLC showed the reaction was completed. The reaction was removed methanol under reduced pressure to give a residue. The residue was added H$_2$O (150 L) and extracted with ethyl acetate (50 mL×3). The combined organic layers were washed with brine (40 mL×3), dried over Na$_2$SO$_4$, filtered and concentrated under reduced pressure to give a residue. The residue was purified by column chromatography (SiO$_2$, Petroleum ether/Ethyl acetate=10/1 to 5/1) to give methyl 2-bromo-5-(tert-butoxycarbonylamino)benzoate (11.0 g, 76.6% yield) as a white solid. $^1$H NMR (CDCl$_3$-d$_6$, 400 MHz) δ 7.84 (d, J=2.8 Hz, 1H), 7.55 (d, J=8.8 Hz, 1H), 7.40 (dd, J=8.8 Hz, 2.8 Hz, 1H), 6.60 (s, 1H), 3.92 (s, 3H), 1.52 (s, 9H).

37.2 Preparation of tert-butyl N-[4-bromo-3-(1-hydroxy-1-methyl-ethyl)phenyl]carbamate

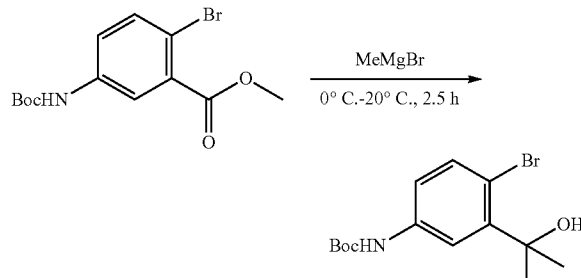

To a solution of MeMgBr (3 M, 72.6 mL, 6 eq) was added methyl 2-bromo-5-(tert-butoxycarbonylamino)benzoate (12.0 g, 36.3 mmol, 1 eq) dropwise at 0° C. was allowed to warm to 20° C. and stirred at 20° C. for 2 h. TLC showed the reaction was completed. The reaction mixture was poured into sat aq·NH$_4$Cl (300 mL) and extracted with ethyl acetate (150 mL×3). The combined organic layers were washed with brine (100 mL×2), dried over Na$_2$SO$_4$, filtered and concentrated under reduced pressure to give tert-butyl N-[4-bromo-3-(1-hydroxy-1-methyl-ethyl)phenyl]carbamate (20.0 g, 60.5 mmol, 83.3% yield) as a white solid. $^1$H NMR (CDCl$_3$-d$_6$, 400 MHz) δ 7.61 (d, J=2.8 Hz, 1H), 7.48 (d, J=8.4 Hz, 1H), 7.25 (br s, 1H), 6.48 (br s, 1H), 2.67 (s, 1H), 1.74 (s, 6H), 1.52 (s, 9H).

37.3 Preparation of 2-(5-amino-2-bromo-phenyl)propan-2-ol

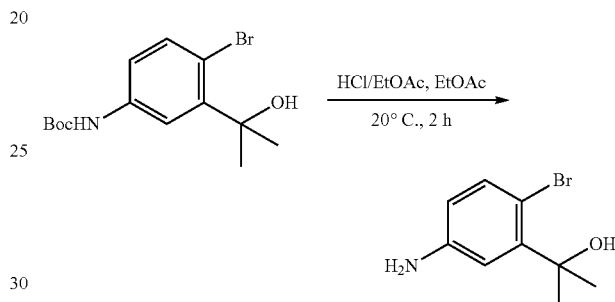

To a mixture of tert-butyl N-[4-bromo-3-(1-hydroxy-1-methyl-ethyl)phenyl]carbamate (20.0 g, 60.5 mmol, 1 eq) in EtOAc (100 mL) was added HCl/EtOAc (4 M, 151 mL, 10 eq) in one portion at 20° C. under N$_2$, the mixture was stirred at 20° C. for 2 h. TLC showed the reaction was completed. The reaction mixture was added water (200 mL) at 0° C. and then adjusted to pH=4 with solid Na$_2$CO$_3$. Then the mixture was extracted with ethyl acetate (150 mL×3). The combined organic layers were washed with brine (40 mL×2), dried over Na$_2$SO$_4$, filtered and concentrated under reduced pressure to give a residue to give 2-(5-amino-2-bromo-phenyl)propan-2-ol (13.0 g, 93.2% yield) as an off-white solid.

37.4 Preparation of 4-bromo-3-[1-[tert-butyl(dimethyl)silyl]oxy-1-methyl-ethyl]aniline

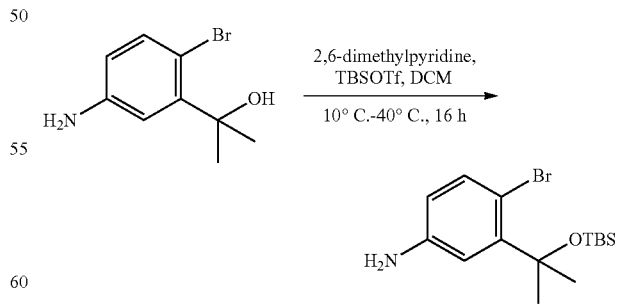

To a solution of 2-(5-amino-2-bromo-phenyl)propan-2-ol (13.0 g, 56.5 mmol, 1 eq) and 2,6-dimethylpyridine (19.7 mL, 169 mmol, 3 eq) in DCM (130 mL) was added [tert-butyl(dimethyl)silyl] trifluoromethanesulfonate (25.9 mL, 113 mmol, 2 eq) drop-wise at 10° C. The mixture was stirred at 40° C. for 16 h. The reaction mixture was quenched by addition H$_2$O (30 mL) and extracted with dichloromethane (150 mL×2). The combined organic phase was washed with brine (150 mL), dried with anhydrous Na$_2$SO$_4$, filtered and concentrated in vacuum to give a residue. The residue was purified by column chromatography (SiO$_2$, Petroleum ether/Ethyl acetate=10/1 to 5/1) to give 4-bromo-3-[1-[tert-butyl(dimethyl)silyl] oxy-1-methyl-ethyl]aniline (10.0 g, 51.4% yield) as yellow oil. $^1$H NMR (CDCl3-d$_6$, 400 MHz) δ 7.30 (s, 1H), 7.29 (d, J=4.4 Hz, 1H), 6.41 (dd, J=8.4 Hz, 2.8 Hz, 1H), 3.65 (br s, 1H), 1.75 (s, 6H), 0.98 (s, 9H), 0.17 (s, 6H).

37.5 Preparation of [1-[2-bromo-5-(4,4,5,5-tetramethyl-1,3,2-dioxaborolan-2-yl)phenyl]-1-methyl-ethoxy]-tert-butyl-dimethyl-silane

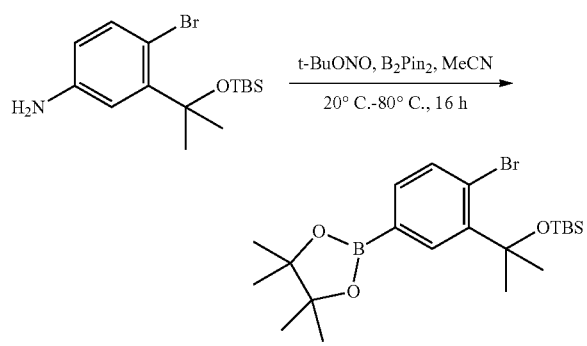

To a mixture of 4-bromo-3-[1-[tert-butyl(dimethyl)silyl]oxy-1-methyl-ethyl]aniline (10.0 g, 29.0 mmol, 1 eq) in MCCN (100 mL) was added t-BuONO (8.98 g, 87.1 mmol, 3 eq) and 4,4,5,5-tetramethyl-2-(4,4,5,5-tetramethyl-1,3,2-dioxaborolan-2-yl)-1,3,2-dioxaborolane (22.1 g, 87.1 mmol, 3 eq) at 20° C. The mixture was heated and stirred at 80° C. for 16 h. LCMS showed the reaction was completed and desired MS observed. The mixture was concentrated in vacuum to give a residue. The residue was purified by column chromatography (SiO$_2$, Petroleum ether/Ethyl acetate=10/1 to 5/1) to give [1-[2-bromo-5-(4,4,5,5-tetramethyl-1,3,2-dioxaborolan-2-yl)phenyl]-1-methyl-ethoxy]-tert-butyl-dimethyl-silane (6.00 g, 45.3% yield) as yellow oil. $^1$H NMR (CDCl3-d6, 400 MHz) δ 8.41 (s, 1H), 7.56 (d, J=7.6 Hz, 1H), 7.45 (d, J=7.6 Hz, 1H), 1.79 (s, 6H), 1.33 (s, 12H), 1.02 (s, 9H), 0.18 (s, 6H).

37.6 Preparation of [4-bromo-3-[1-[tert-butyl(dimethyl)silyl]oxy-1-methyl-ethyl]phenyl] boronic acid

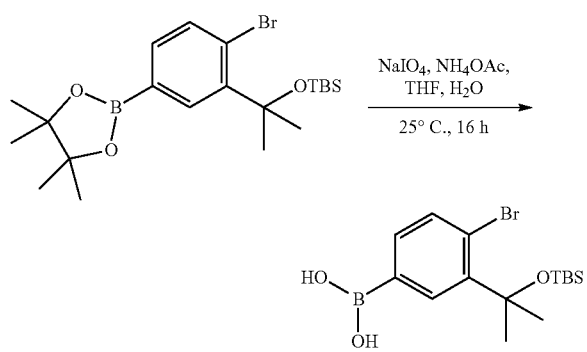

To a solution of [1-[2-bromo-5-(4,4,5,5-tetramethyl-1,3,2-dioxaborolan-2-yl)phenyl]-1-methyl-ethoxy]-tert-butyl-dimethyl-silane (5.00 g, 10.9 mmol, 1 eq) in THF (50 mL) and H$_2$O (20 mL) was added NaIO$_4$ (7.05 g, 32.9 mmol, 3 eq) and NH$_4$OAc (2.54 g, 32.9 mmol, 3 eq) at 25° C. The mixture was stirred at 25° C. for 16 h. LCMS showed the reaction was completed and desired MS observed. The mixture was poured into ice-water (w/w=1/1) (40 mL) and stirred for 10 min. The aqueous phase was extracted with ethyl acetate (50 mL×3). The combined organic phase was washed with brine (40 mL×2), dried with anhydrous Na$_2$SO$_4$, filtered and concentrated in vacuum to give a residue. The residue was separated by column chromatography (SiO$_2$, Petroleum ether/Ethyl acetate=5/1 to 3/1) to give [4-bromo-3-[1-[tert-butyl(dimethyl)silyl]oxy-1-methyl-ethyl]phenyl]boronic acid (4.0 g, 97.6% yield) as a white solid. $^1$H NMR (DMSO-hd 6, 400 MHz) S 8.19 (s, 1H), 8.06 (s, 2H), 7.57-7.51 (m, 2H), 1.73 (s, 6H), 0.92 (s, 9H), 0.10 (s, 6H).

37.7 Preparation of 3-[4-bromo-3-[1-[tert-butyl(dimethyl)silyl]oxy-1-methyl-ethyl]anilino]-1-(trans-4-cyanotetrahydro-2H-pyran-3-yl)pyrazole-4-carboxamide

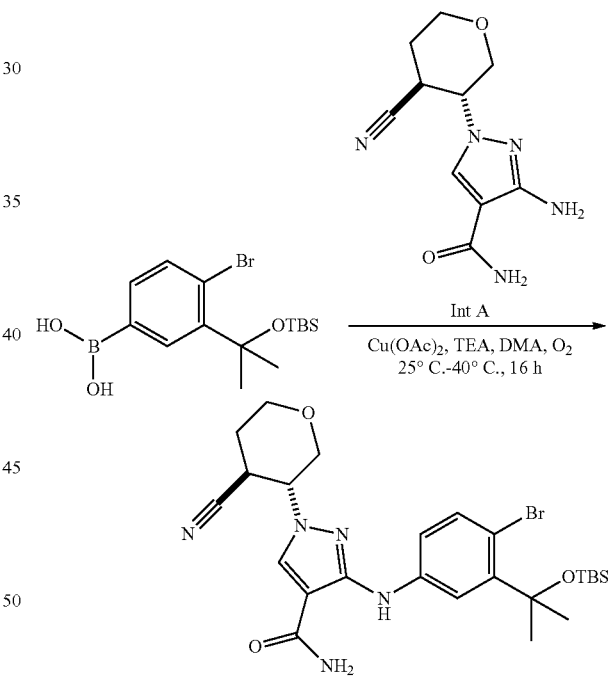

To a mixture of 3-amino-1-(trans-4-cyanotetrahydropyran-3-yl)pyrazole-4-carboxamide (600 mg, 2.55 mmol, 1 eq) and [4-bromo-3-[1-[tert-butyl(dimethyl)silyl]oxy-1-methyl-ethyl]phenyl]boronic acid (951 mg, 2.55 mmol, 1 eq) in DMA (15 mL) was added 4 A molecular sieve (1.3 g), TEA (1.29 g, 12.7 mmol, 1.78 mL, 5 eq) and Cu(OAc)$_2$ (1.16 g, 6.38 mmol, 2.5 eq) in one portion at 25° C. under O$_2$. The mixture was heated and stirred at 40° C. for 16 h. LCMS showed the reaction was completed and desired MS observed. 2 parallel reactions were combined for work up. The reaction mixture was filtered. The filtrate was added H$_2$O (70 mL) at 20° C. and extracted with ethyl acetate (30 mL×3). The combined organic layers were washed with brine (30 mL×2), dried over Na$_2$SO$_4$, filtered and concentrated under reduced pressure to give a residue. The residue was purified by column chromatography (SiO$_2$, Petroleum ether/Ethyl acetate=3/1 to 1/1) to give 3-[4-bromo-3-[1-[tert-butyl(dimethyl)silyl]oxy-1-methyl-ethyl]anilino]-1-(4-cyanotetrahydro-2H-pyran-3-yl)pyrazole-4-carboxamide (1.60 g, 55.7% yield) as a yellow solid. $^1$H NMR (DMSO-d$_6$, 400 MHz) δ 9.38 (s, 1H), 8.30 (s, 1H), 7.75 (br s, 1H), 7.67-7.61 (m, 2H), 7.46 (d, J=8.4 Hz, 1H), 7.27 (br s, 1H), 4.61-4.55 (m, 1H), 4.05-4.03 (m, 1H), 4.02-4.01 (m, 1H), 3.70-3.63 (m, 2H), 3.45-3.42 (m, 1H), 2.18-2.13 (m, 1H), 2.00-1.95 (m, 1H), 1.74 (s, 1H), 0.95 (s, 1H), 0.13 (s, 6H).

37.8 Preparation of 3-[3-[1-[tert-butyl(dimethyl)silyl]oxy-1-methyl-ethyl]-4-(5,5-dimethyl-1,3,2-dioxaborinan-2-yl)anilino]-1-(trans-4-cyanotetrahydro-2H-pyran-3-yl)pyrazole-4-carboxamide

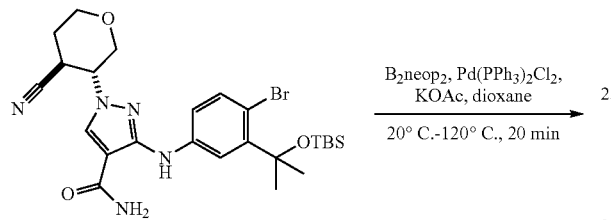

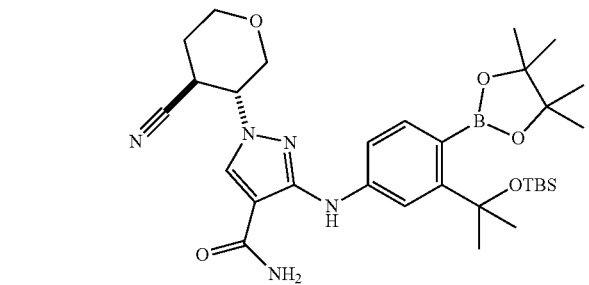

To a mixture of 3-[4-bromo-3-[1-[tert-butyl(dimethyl)silyl]oxy-1-methyl-ethyl]anilino]-1-(trans-4-cyanotetrahydropyran-3-yl)pyrazole-4-carboxamide (100 mg, 177 umol, 1 eq) in dioxane (4 mL) was added KOAc (43.6 mg, 444 umol, 2.5 eq), Pd(PPh$_3$)$_2$Cl$_2$ (12.4 mg, 17.7 umol, 0.1 eq) and 2-(5,5-dimethyl-1,3,2-dioxaborinan-2-yl)-5,5-dimethyl-1,3,2-dioxaborinane (481 mg, 2.13 mmol, 12 eq) in one portion at 20° C. under N$_2$. The mixture was heated and stirred at 120° C. for 20 min. LCMS showed the reaction was completed and desired MS observed. 13 parallel reactions were combined for work up. The mixture was filtered and the filtrate was concentrated in vacuum to give a residue. The residue was purified by column chromatography (SiO$_2$, Petroleum ether/Ethyl acetate=3/1 to 1/1) to give 3-[3-[1-[tert-butyl(dimethyl)silyl]oxy-1-methyl-ethyl]-4-(5,5-dimethyl-1,3,2-dioxaborinan-2-yl)anilino]-1-(trans-4-cyanotetrahydropyran-3-yl)pyrazole-4-carboxamide (2.3 g, crude) as brown oil.

37.9 Preparation of 1-(trans-4-cyanotetrahydro-2H-pyran-3-yl)-3-[(1-hydroxy-3,3-dimethyl-2,1-benzoxaborol-6-yl)amino]pyrazole-4-carboxamide

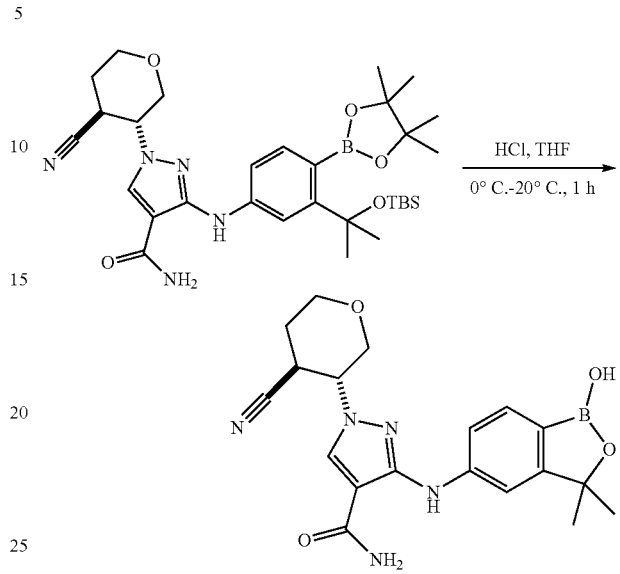

To a mixture of 3-[4-[1-[tert-butyl(dimethyl)silyl]oxy-1-methyl-ethyl]-3-(5,5-dimethyl-1,3,2-dioxaborinan-2-yl)anilino]-1-(trans-4-cyanotetrahydro-2H-pyran-3-yl)pyrazole-4-carboxamide (2.0 g, 3.36 mmol, 1 eq) in THF (20 mL) was added HCl (4 N, 4.20 mL, 5 eq) drop-wise at 0° C. under N$_2$. The reaction was allowed to warm to 20° C. and stirred at 20° C. for 1 h. The mixture was poured into ice-water (w/w=1/1)(40 mL) and stirred for 10 min. The aqueous phase was extracted with ethyl acetate (20 mL×4). The combined organic phase was washed with brine (20 mL), dried with anhydrous Na$_2$SO$_4$, filtered and concentrated in vacuum to give a residue. The residue was purified by prep-HPLC (column: Phenomenex luna C18 250*50 mm*10 um; mobile phase: [water (HCl)-ACN]; B %: 20%-50%, 10 min) to give 1-(4-cyanotetrahydropyran-3-yl)-3-[(1-hydroxy-3,3-dimethyl-2,1-benzoxaborol-6-yl)amino]pyrazole-4-carboxamide (182.7 mg, 13.7% yield) as a white solid. $^1$H NMR (DMSO-hd 6, 400 MHz) δ 9.34 (s, 1H), 8.74 (s, 1H), 8.31 (s, 1H), 7.74 (br s, 1H), 7.55-7.52 (m, 1H), 7.48-7.46 (m, 2H), 7.21 (br s, 1H), 4.61-4.56 (m, 1H), 4.08-4.03 (m, 1H), 3.91-3.90 (m, 1H), 3.68-3.63 (m, 2H), 3.48-3.47 (m, 1H), 2.20-2.15 (m, 1H), 2.01-1.97 (m, 1H), 1.44 (s, 6H). MS (ESI): mass calculated for C$_{19}$H$_{22}$BN$_5$O$_4$ 395.18, m/z found 396.2 [M+H]$^+$. HPLC: 96.62% (220 nm), 92.95% (254 nm).

38. Preparation of 1-[trans-4-cyanotetrahydro-2H-pyran-3-yl]-3-[(7-fluoro-1-hydroxy-3H-2,1-benzoxaborol-5-yl)amino]pyrazole-4-carboxamide

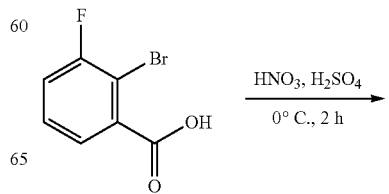

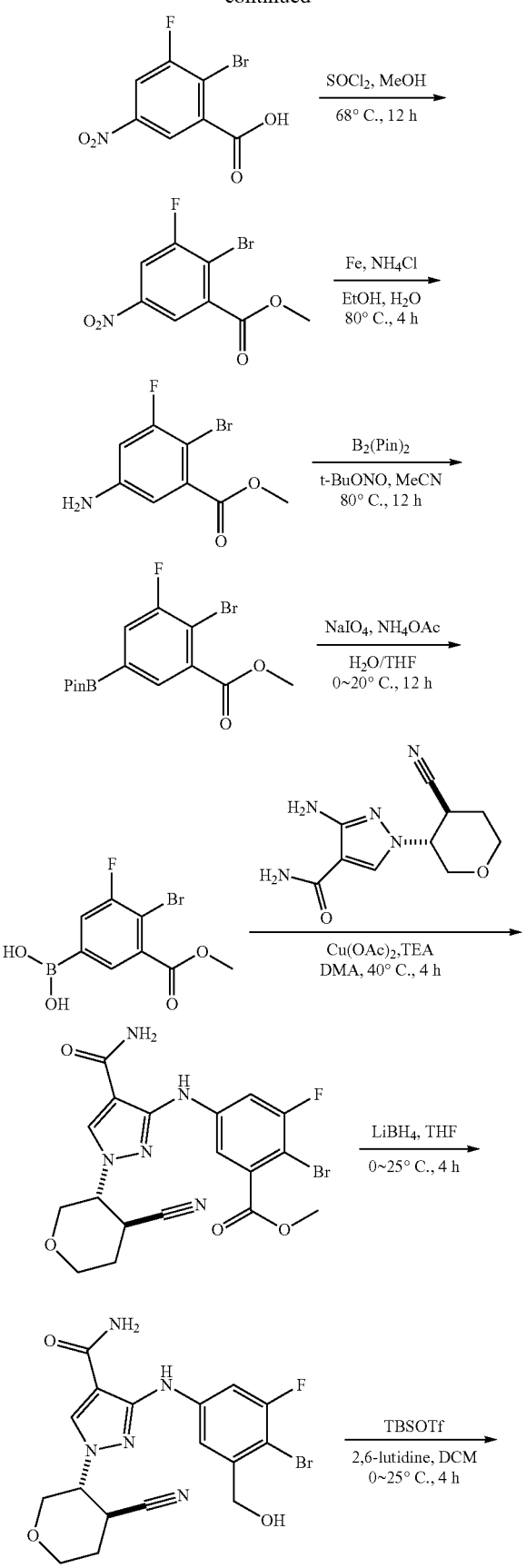

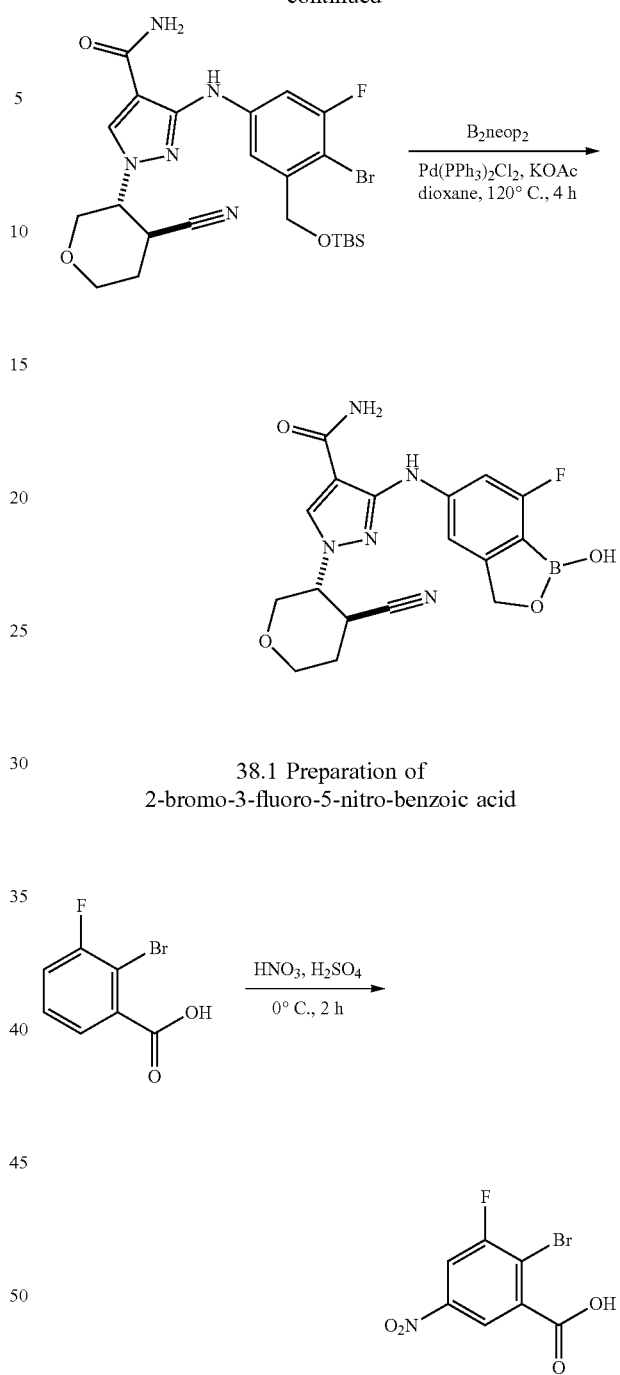

38.1 Preparation of 2-bromo-3-fluoro-5-nitro-benzoic acid

To a mixture of 2-bromo-3-fluoro-benzoic acid (100 g, 456 mmol, 4.07 mL, 1 eq) in $H_2SO_4$ (300 mL) was added Fuming Nitric Acid (50.4 g, 800 mmol, 1.75 eq) dropwise at 0° C. The mixture was stirred at 0° C. for 2 h. TLC showed the reaction was completed. The reaction mixture was poured into ice water (1500 mL) and some white solid formed. The result mixture was filtered. The filter cake was washed with water (300 mL×10) and dried in vacuum to give 2-bromo-3-fluoro-5-nitro-benzoic acid (35.0 g, 14.5% yield) as an off-white solid. $^1$H NMR (CDCl$_3$, 400 MHz) δ 8.69 (dd, J=2.4 Hz, 1.2 Hz, 1H), 8.19 (dd, J=7.6 Hz, 2.8 Hz, 1H).

38.2 Preparation of methyl 2-bromo-3-fluoro-5-nitro-benzoate

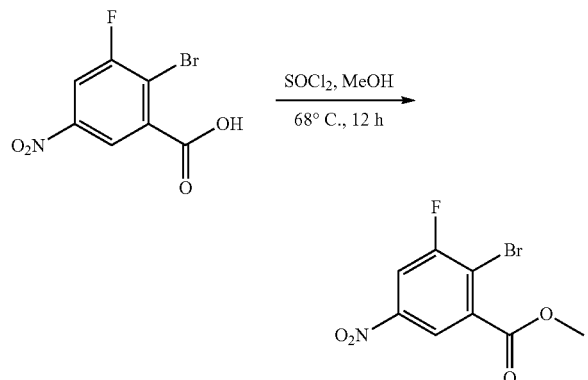

To a mixture of 2-bromo-3-fluoro-5-nitro-benzoic acid (15.0 g, 57 mmol, 1 eq) in MeOH (100 mL) was added SOCl$_2$ (7.5 g, 64 mmol, 1.1 eq) dropwise at 0° C. The mixture was heated and stirred at 68° C. for 12 h. TLC showed the reaction was completed. The mixture was concentrated in vacuum to remove MeOH. The residue was poured into ice water (150 mL) and some white solid formed. The solid was filtered and the filter cake was washed with water (100 mL×3) and dried in vacuum to give methyl 2-bromo-3-fluoro-5-nitro-benzoate (27.6 g, 87.3% yield) as an off-white solid. $^1$H NMR (CDCl$_3$, 400 MHz) δ 8.69 (dd, J=2.4 Hz, 1.2 Hz, 1H), 8.19 (dd, J=7.6 Hz, 2.4 Hz, 1H), 4.02 (s, 3H).

38.3 Preparation of methyl 5-amino-2-bromo-3-fluoro-benzoate

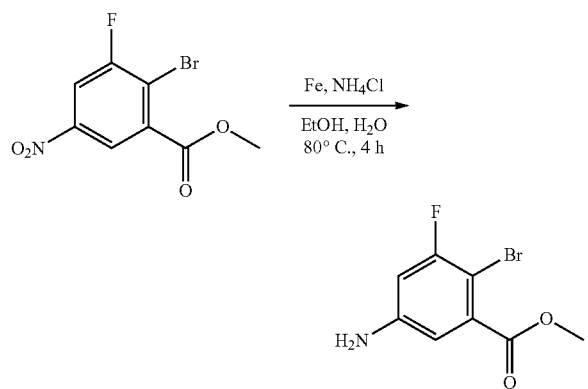

To a mixture of methyl 2-bromo-3-fluoro-5-nitro-benzoate (25.0 g, 90 mmol, 1 eq) in H$_2$O (150 mL) and EtOH (150 mL) was added Fe powder (25.2 g, 450 mmol, 5 eq) and NH$_4$Cl (29.0 g, 542 mmol, 6 eq) in portions at 20° C. The mixture was heated and stirred at 80° C. for 4 h. TLC showed the reaction was completed. The reaction mixture was filter and the filtrate was concentrated under reduced pressure to give a residue. The residue was diluted with H$_2$O (50 mL) and extracted with EtOAc (100 mL×2). The combined organic layers were washed with brine (100 mL×2), dried over Na$_2$SO$_4$, filtered and concentrated under reduced pressure to give methyl 5-amino-2-bromo-3-fluoro-benzoate (18.6 g, 83.3% yield) as a yellow solid. $^1$H NMR (CDCl$_3$, 400 MHz) δ 6.88 (dd, J=2.8 Hz, 1.2 Hz, 1H), 6.56 (dd, J=10.0 Hz, 2.8 Hz, 1H), 3.96 (br s, 2H), 3.91 (s, 3H).

38.4 Preparation of methyl 2-bromo-3-fluoro-5-(4,4,5,5-tetramethyl-1,3,2-dioxaborolan-2-yl) benzoate

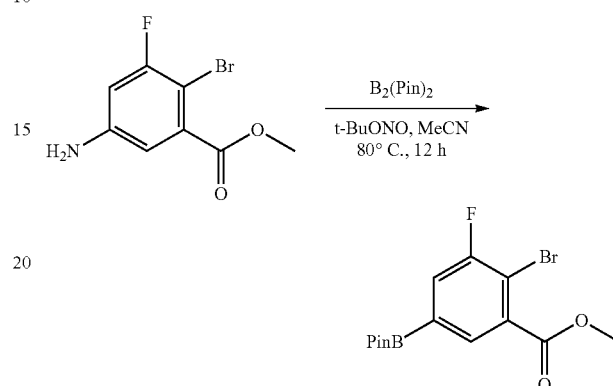

To a mixture of methyl 5-amino-2-bromo-3-fluoro-benzoate (9.0 g, 36 mmol, 1 eq) in McCN (250 mL) was added t-BuONO (9.4 g, 91 mmol, 2.5 eq) and 4,4,5,5-tetramethyl-2-(4,4,5,5-tetramethyl-1,3,2-dioxaborolan-2-yl)-1,3,2-dioxaborolane (16.6 g, 66 mmol, 1.8 eq) in portions at 20° C. The mixture was heated and stirred at 80° C. for 12 h. The resulting mixture was concentrated in vacuum to give a residue. The residue was purified by column chromatography (SiO$_2$, Petroleum ether/Ethyl acetate=20/1 to 10/1) to give methyl 2-bromo-3-fluoro-5-(4,4,5,5-tetramethyl-1,3,2-dioxaborolan-2-yl)benzoate (9 g, 51.8% yield, 75% purity) as a yellow solid. $^1$H NMR (CDCl$_3$, 400 MHz) δ 7.95 (s, 1H), 7.62 (d, J=8.4 Hz, 1H), 3.93 (s, 3H), 1.31 (s, 12H).

38.5 Preparation of (4-bromo-3-fluoro-5-methoxycarbonyl-phenyl)boronic acid

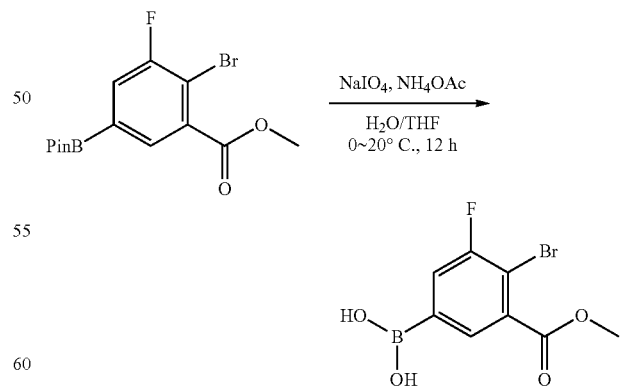

To a mixture of methyl 2-bromo-3-fluoro-5-(4,4,5,5-tetramethyl-1,3,2-dioxaborolan-2-yl)benzoate (9.0 g, 18.8 mmol, 75% purity, 1 eq) in H$_2$O (250 mL) and THF (150 mL) was added NaIO$_4$ (40.2 g, 188 mmol, 10 eq) and NH$_4$OAc (14.5 g, 188 mmol, 10 eq) in portions at 0° C. The

38.6 Preparation of methyl 2-bromo-5-[[4-carbamoyl-1-(trans-4-cyanotetrahydro-2H-pyran-3-yl) pyrazol-3-yl]amino]-3-fluoro-benzoate

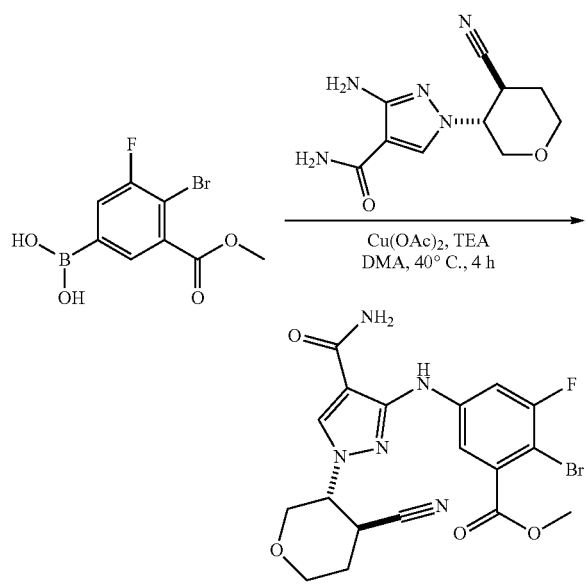

A mixture of 3-amino-1-(trans-4-cyanotetrahydro-2H-pyran-3-yl)pyrazole-4-carboxamide (1.0 g, 4.3 mmol, 1.2 eq) and (4-bromo-3-fluoro-5-methoxycarbonyl-phenyl)boronic acid (1.0 g, 3.6 mmol, 1 eq) in DMA (15 mL) was added TEA (2.5 mL, 5 eq), Cu(OAc)$_2$ (131 mg, 722 umol, 0.2 eq) and 4 A molecular sieve (500 mg) at 25° C. The resulting mixture was heated and stirred at 40° C. for 4 h under air atmosphere. LCMS showed the reaction was completed and desired MS observed. 4 parallel reactions were combined for work up. The reaction mixture was quenched with sat. aq. NH$_4$Cl (30 mL) and extracted with EtOAc (30 mL). The organic phase was washed with brine (30 mL), dried over Na$_2$SO$_4$, filtered and concentrated under reduced pressure to give a residue. The residue was purified by column chromatography (SiO$_2$, Petroleum ether/Ethyl acetate=10/1 to 0/1) to give methyl 2-bromo-5-[[4-carbamoyl-1-(trans-4-cyanotetrahydro-2H-pyran-3-yl)pyrazol-3-yl]amino]-3-fluoro-benzoate (3.5 g, 51.9% yield) as a yellow solid. 1H NMR (DMSO-hd 6, 400 MHz) δ 9.53 (s, 1H), 8.34 (s, 1H), 7.92 (dd, J=11.2 Hz, 2.4 Hz, 1H), 7.81 (br s, 1H), 7.75 (s, 1H), 7.30 (br s, 1H), 4.65-4.61 (m, 1H), 4.08-4.03 (m, 1H), 3.92-3.89 (m, 1H), 3.88 (s, 3H), 3.69-3.63 (m, 2H), 3.50-3.46 (m, 1H), 2.18-2.15 (m, 1H), 2.01-1.98 (m, 1H).

38.7 Preparation of 3-[4-bromo-3-fluoro-5-(hydroxymethyl)anilino]-1-(trans-4-cyanotetrahydro-2H-pyran-3-yl)pyrazole-4-carboxamide

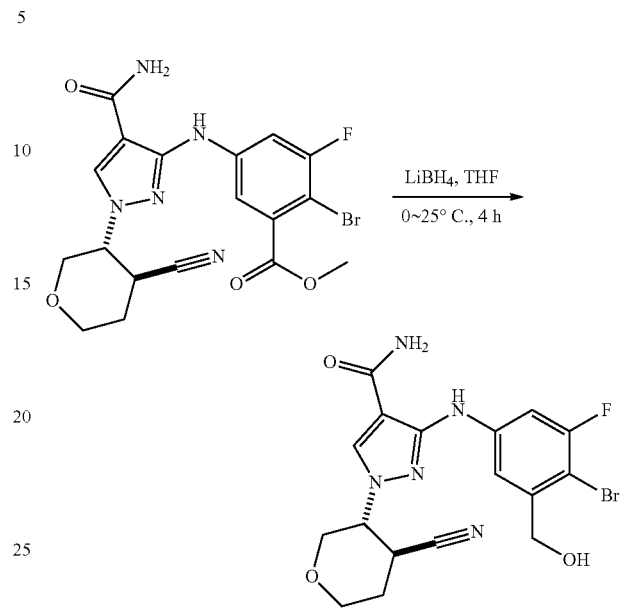

To a mixture of methyl 2-bromo-5-[[4-carbamoyl-1-(trans-4-cyanotetrahydro-2H-pyran-3-yl)pyrazol-3-yl]amino]-3-fluoro-benzoate (4.00 g, 8.58 mmol, 1 eq) in THF (50 mL) was added LiBH4 (1.12 g, 51.4 mmol, 6 eq) at 0° C. The resulting mixture was stirred at 25° C. for 4 h under N$_2$ atmosphere. LCMS showed the reaction was completed and desired MS observed. The reaction mixture was quenched by sat. aq. NH$_4$Cl (50 mL) at 0° C., and then extracted with EtOAc (30 mL×4). The combined organic layers were washed with brine (50 mL), dried over Na$_2$SO$_4$, filtered and concentrated under reduced pressure to give 3-[4-bromo-3-fluoro-5-(hydroxymethyl)anilino]-1-(4-cyanotetrahydro-2H-pyran-3-yl)pyrazole-4-carboxamide (3.5 g, 80% purity) as a white solid. 1H NMR (DMSO-hd 6, 400 MHz) δ 9.46 (s, 1H), 8.33 (s, 1H), 7.80 (br s, 1H), 7.70 (dd, J=11.2 Hz, 2.4 Hz, 1H), 7.29 (br s, 1H), 7.28 (s, 1H), 5.53 (s, 1H), 4.64-4.60 (m, 1H), 4.50 (s, 2H), 4.07-4.02 (m, 1H), 3.94-3.89 (m, 1H), 3.70-3.65 (m, 2H), 3.50-3.46 (m, 1H), 2.17-2.14 (m, 1H), 2.01-1.98 (m, 1H).

38.8 Preparation of 3-[4-bromo-3-[[tert-butyl(dimethyl)silyl]oxymethyl]-5-fluoro-anilino]-1-(4-cyanotetrahydro-2H-pyran-3-yl)pyrazole-4-carboxamide

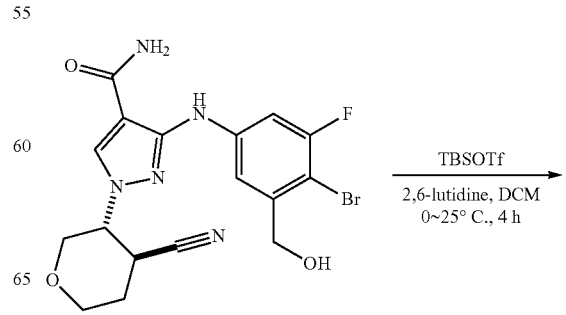

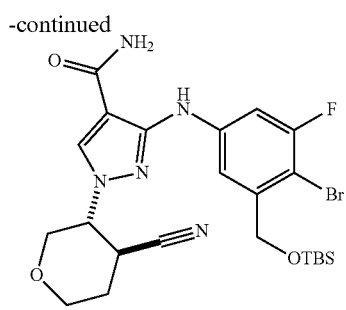

To a mixture of 3-[4-bromo-3-fluoro-5-(hydroxymethyl)anilino]-1-(trans-4-cyanotetrahydro-2H-pyran-3-yl)pyrazole-4-carboxamide (500 mg, 912 umol, 80% purity, 1 eq) in DCM (15 mL) was added 2,6-lutidine (196 mg, 1.8 mmol, 2 eq) and TBSOTf (362 mg, 1.4 mmol, 1.5 eq) at 0° C. The resulting mixture was stirred at 25° C. for 4 h under N₂ atmosphere. TLC showed the reaction was completed. 7 parallel reactions were combined for work up. The reaction mixture was concentrated under reduced pressure to give a residue. The residue was purified by column chromatography (SiO₂, Petroleum ether/Ethyl acetate=5/1 to 1/2) to give 3-[4-bromo-3-[[tert-butyl(dimethyl)silyl]oxymethyl]-5-fluoro-anilino]-1-(trans-4-cyanotetrahydro-2H-pyran-3-yl)pyrazole-4-carboxamide (2.4 g, 67.9% yield) as a yellow solid. 1H NMR (DMSO-hd 6, 400 MHz) δ 9.52 (s, 1H), 8.34 (s, 1H), 7.79 (br s, 1H), 7.67 (dd, J=11.2 Hz, 2.4 Hz, 1H), 7.27 (br s, 1H), 7.26 (s, 1H), 4.69 (s, 2H), 4.60-4.54 (m, 1H), 4.06-4.02 (m, 1H), 3.94-3.89 (m, 1H), 3.70-3.65 (m, 2H), 3.52-3.47 (m, 1H), 2.15-2.12 (m, 1H), 2.01-1.98 (m, 1H), 0.93 (s, 9H), 0.13 (s, 6H).

38.9 Preparation of 1-[trans-4-cyanotetrahydro-2H-pyran-3-yl]-3-[(7-fluoro-1-hydroxy-3H-2,1-benzoxaborol-5-yl)amino]pyrazole-4-carboxamide

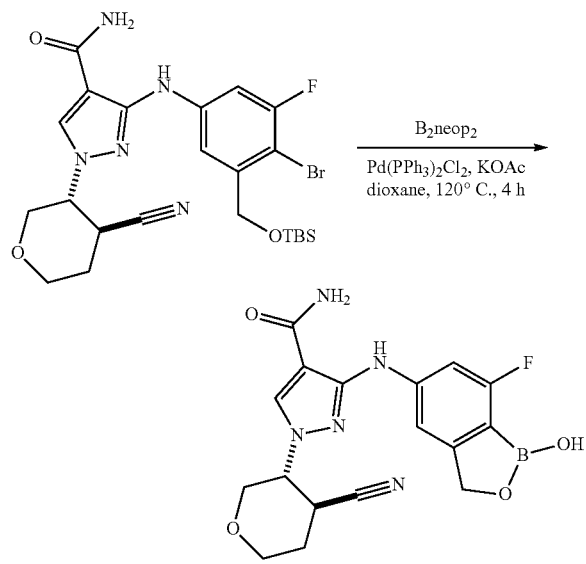

A mixture of 3-[4-bromo-3-[[tert-butyl(dimethyl)silyl]oxymethyl]-5-fluoro-anilino]-1-(trans-4-cyanotetrahydro-2H-pyran-3-yl)pyrazole-4-carboxamide (500 mg, 904 umol, 1 eq) and 4,4,5,5-tetramethyl-2-(4,4,5,5-tetramethyl-1,3,2-dioxaborolan-2-yl)-1,3,2-dioxaborolane (1.15 g, 4.52 mmol, 5 eq) in dioxane (20 mL) was added KOAc (178 mg, 1.8 mmol, 2 eq), Pd(PPh₃)₂Cl₂ (64 mg, 91 umol) at 25° C. The resulting mixture was stirred at 120° C. for 4 h under N₂ atmosphere. LCMS showed the reaction was completed and desired MS observed. 3 parallel reactions were combined for work up. The reaction mixture was filtered and the filtrate was concentrated under reduced pressure to give 1-[trans-4-cyanotetrahydro-2H-pyran-3-yl]-3-[(7-fluoro-1-hydroxy-3H-2,1-benzoxa borol-5-yl)amino]pyrazole-4-carboxamide. The residue was purified by prep-HPLC (column: Phenomenex luna C18 250*50 mm*10 um; mobile phase: [water (HCl)-ACN]; B %: 15%-40%, 10 min) and SFC separation (column: DAICEL CHIRALPAK IC (250 mm*30 mm, 10 um); mobile phase: [Neu-ETOH]; B %: 50%-50%, 9 min) to give 1-[trans-4-cyanotetrahydro-2H-pyran-3-yl]-3-[(7-fluoro-1-hydroxy-3H-2,1-benzoxa borol-5-yl)amino]pyrazole-4-carboxamide (stereoisomer one) (175 mg, 16.7% yield. 99.5% purity, 99.8 ee % first peak, Rt=1.239 min) as a white solid. 1H NMR (DMSO-hd 6, 400 MHz) δ 9.54 (s, 1H), 8.98 (s, 1H), 8.33 (s, 1H), 7.79 (br s, 1H), 7.35 (d, J=10.8 Hz 1H), 7.27 (br s, 1H), 7.25 (s, 2H), 4.94 (s, 2H), 4.63-4.59 (m, 1H), 4.06-4.02 (m, 1H), 3.93-3.89 (m, 1H), 3.70-3.64 (m, 2H), 3.52-3.47 (m, 1H), 2.17-2.12 (m, 1H), 2.03-1.97 (m, 1H). MS (ESI): mass calculated for C₁₇H₁₇BFN₅O₄, 385.14, m/z found 386.2 [M+H]⁺. HPLC: 99.57% (220 nm), 100% (254 nm). and 1-[trans-4-cyanotetrahydropyran-3-yl]-3-[(7-fluoro-1-hydroxy-3H-2,1-benzoxaborol-5-yl)amino]pyrazole-4-carboxamide (stereoisomer two) (175 mg, 16.7% yield, 96.3% purity, 98.9 ee % second peak, Rt=1.468 min) as a white solid. 1H NMR (DMSO-hd 6, 400 MHz) δ 9.53 (s, 1H), 8.98 (s, 1H), 8.33 (s, 1H), 7.79 (br s, 1H), 7.35 (d, J=10.8 Hz 1H), 7.27 (br s, 1H), 7.25 (s, 2H), 4.94 (s, 2H), 4.63-4.59 (m, 1H), 4.06-4.02 (m, 1H), 3.93-3.89 (m, 1H), 3.70-3.64 (m, 2H), 3.52-3.47 (m, 1H), 2.17-2.12 (m, 1H), 2.03-1.97 (m, 1H). MS (ESI): mass calculated for C₁₇H₁₇BFN₅O₄, 385.14, m/z found 386.2 [M+H]⁺. HPLC: 96.39% (220 nm), 98.23% (254 nm).

39. Preparation of 1-(trans-4-cyanotetrahydro-2H-pyran-3-yl)-3-[(3,4-diethyl-2-hydroxy-1,2-benzoxaborinin-6-yl)amino]pyrazole-4-carboxamid

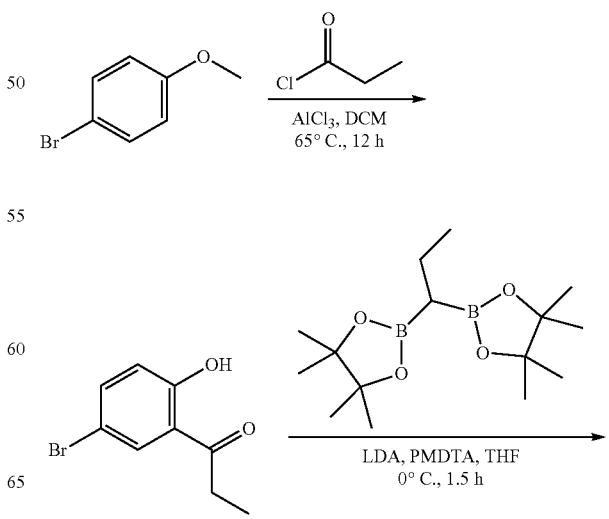

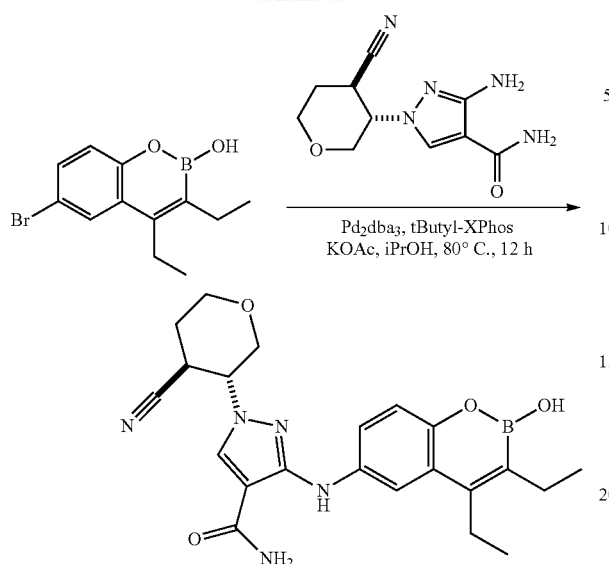

39.1 Preparation of 1-(5-bromo-2-hydroxy-phenyl)propan-1-one

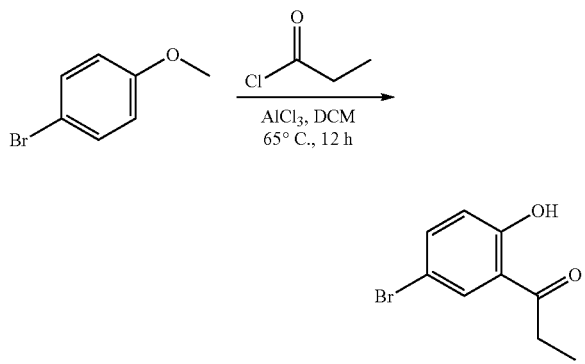

To a solution of propanoyl chloride (5.00 g, 53.5 mmol, 5 mL, 2 eq) in DCM (50 mL) was added AClCl₃ (14.3 g, 107 mmol, 4 eq) at 0° C. After addition, the mixture was stirred at 0° C. for 30 min, and then 1-bromo-4-methoxy-benzene (5.00 g, 26.7 mmol, 3.4 mL, 1 eq) was added dropwise at 0° C. The resulting mixture was heated and stirred at 65° C. for 12 h. LCMS showed the reaction was completed and desired MS observed. The reaction mixture was quenched by addition H₂O (100 mL) at 0° C. and then extracted with DCM (50 mL×3). The combined organic layers were washed with brine (50 mL), dried over with Na₂SO₄, filtered and concentrated under reduced pressure to give a residue. The residue was purified by flash silica gel chromatography (ISCO®; 20 g SepaFlash® Silica Flash Column, Eluent of 0~10% Ethyl acetate/Petroleum ether gradient @100 mL/min) to give 1-(5-bromo-2-hydroxy-phenyl)propan-1-one (5.00 g, 21.8 mmol, 81.6% yield) as a yellow solid. 1H NMR (CDCl₃, 400 MHz) δ 12.26 (s, 1H), 7.87 (d, J=2.5 Hz, 1H), 7.54 (dd, J=2.4, 8.8 Hz, 1H), 6.94-6.84 (m, 1H), 3.09-2.97 (m, 2H), 1.25 (t, J=7.2 Hz, 3H).

39.2 Preparation of 6-bromo-3,4-diethyl-2-hydroxy-1,2-benzoxaborinine

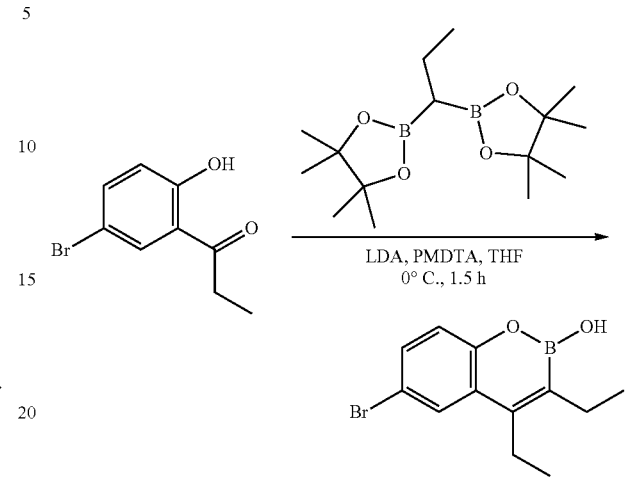

To a solution of LDA (2 M, 6.6 mL, 3 eq) in THF (10 mL) was added dropwise N'-[2-(dimethylamino)ethyl]-N,N,N'-trimethyl-ethane-1,2-diamine (1.51 g, 8.73 mmol, 1.8 mL, 2 eq) and 4,4,5,5-tetramethyl-2-[1-(4,4,5,5-tetramethyl-1,3,2-dioxaborolan-2-yl)propyl]-1,3,2-dioxaborolane (2.60 g, 8.73 mmol, 2 eq) at 0° C. After addition, the mixture was stirred at 0° C. for 30 min and then 1-(5-bromo-2-hydroxy-phenyl)propan-1-one (1.00 g, 4.4 mmol, 1 eq) in THF (5 mL) was added dropwise at 0° C. The resulting mixture was continue stirred at 0° C. for 1 h. LCMS showed the reaction was completed and desired MS observed. The reaction mixture was quenched by addition NH₄Cl (50 mL), adjust pH=7 with 1N HCl, and then extracted with EtOAc (20 mL×3). The combined organic layers were washed with brine (50 mL), dried over with Na₂SO₄, filtered and concentrated under reduced pressure to give a residue. The residue was purified by flash silica gel chromatography (ISCO®; 20 g SepaFlash® Silica Flash Column, Eluent of 0~30% Ethyl acetate/Petroleum ether gradient @ 100 mL/min) to give 6-bromo-3,4-diethyl-2-hydroxy-1,2-benzoxaborinine (1.50 g, crude) as a white solid. 1H NMR (CDCl₃, 400 MHz) δ 7.71 (d, J=2.4 Hz, 1H), 7.42-7.38 (m, 1H), 7.11-7.08 (m, 1H), 1.66-1.53 (m, 4H), 0.93 (t, J=7.3 Hz, 6H).

39.3 Preparation of 1-(trans-4-cyanotetrahydro-2H-pyran-3-yl)-3-[(3,4-diethyl-2-hydroxy-1,2-benzoxaborinin-6-yl)amino]pyrazole-4-carboxamide

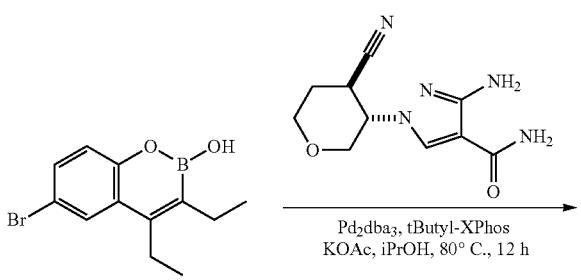

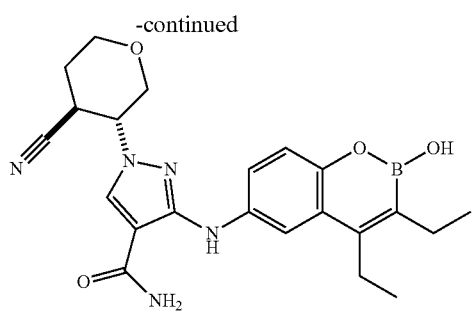

To a solution of 3-amino-1-(trans4-cyanotetrahydro-2H-pyran-3-yl)pyrazole-4-carboxamide (251 mg, 1.07 mmol, 1.5 eq) in i-PrOH (5 mL) was added KOAc (140 mg, 1.42 mmol, 2 eq), 6-bromo-3,4-diethyl-2-hydroxy-1,2-benzoxaborinine (200 mg, 712 umol, 1 eq), Pd$_2$(dba)$_3$ (65 mg, 71.2 umol, 0.1 eq) and t-BuXPhos (60 mg, 142.4 umol, 0.2 eq) at 25° C. The resulting mixture was heated and stirred at 80° C. for 12 h. LCMS showed the reaction was completed and desired MS observed. The reaction mixture was filtered and the filtrate was concentrated under reduced pressure to give a residue. The residue was purified by prep-HPLC (column: Waters Xbridge BEH C18 100*30 mm*10 um; mobile phase: [water (10 mM NH$_4$HCO$_3$)-ACN]; B %: 30%-60%, 10 min) to give 1-(trans-4-cyanotetrahydro-2H-pyran-3-yl)-3-[(3,4-diethyl-2-hydroxy-1,2-benzoxaborinin-6-yl) amino]pyrazole-4-carboxamide (43.5 mg, 14.0% yield) as a yellow solid. 1H NMR (DMSO-d$^6$, 400 MHz) δ 9.09 (s, 1H), 8.57 (s, 1H), 8.31 (s, 1H), 8.16 (d, J=2.4 Hz, 1H), 7.74 (s, 1H), 7.29-7.21 (m, 1H), 7.18 (s, 1H), 7.11-7.05 (m, 1H), 4.66-4.46 (m, 1H), 4.13-4.03 (m, 1H), 4.01-3.88 (m, 1H), 3.75-3.65 (m, 1H), 3.64-3.49 (m, 1H), 3.46-3.36 (m, 1H), 2.86-2.73 (m, 2H), 2.46-2.37 (m, 2H), 2.27-2.14 (m, 1H), 2.08-1.92 (m, 1H), 1.23 (t, J=7.5 Hz, 3H), 1.08-0.97 (m, 3H) MS (ESI): mass calculated for C$_{22}$H$_{26}$BN$_5$O$_4$, 435.21, m/z found 434.3 [M−H]$^-$. HPLC: 96.06% (220 nm), 98.04% (254 nm).

40. Preparation of 1-(trans-2-cyanocyclopentyl)-3-[(3,4-diethyl-2-hydroxy-1,2-benzoxaborinin-6-yl)amino]pyrazole-4-carboxamide

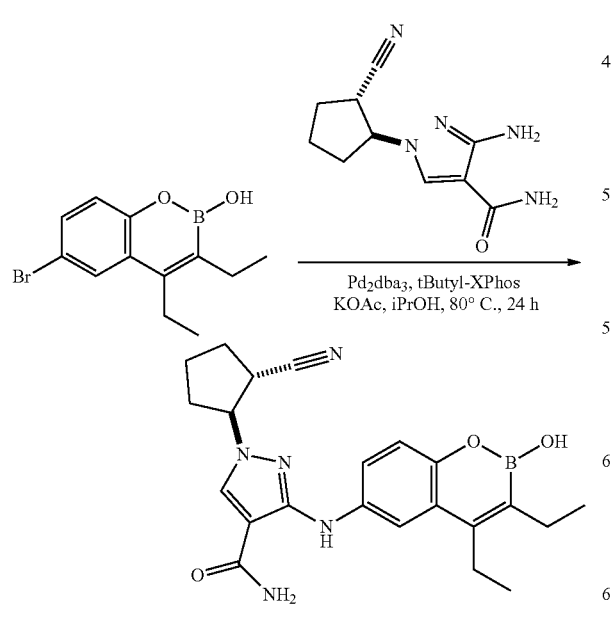

To a solution of 3-amino-1-(trans-2-cyanocyclopentyl)pyrazole-4-carboxamide (316 mg, 1.44 mmol, 1.5 eq) in i-PrOH (5 mL) was added KOAc (189 mg, 1.92 mmol, 2 eq) at 25° C., 6-bromo-3,4-diethyl-2-hydroxy-1,2-benzoxaborinine (270 mg, 961 umol, 1 eq), Pd$_2$(dba)$_3$ (88 mg, 96.1 umol, 0.1 eq) and t-Bu XPhos (82 mg, 192.2 umol, 0.2 eq) was added at 25° C. The resulting mixture was stirred at 80° C. for 24 h. LCMS showed the reaction was completed and desired MS observed. The reaction mixture was filtered and the filtrate was concentrated under reduced pressure to give a residue. The residue was purified by prep-HPLC column: column: column: Waters Xbridge BEH C18 100*30 mm*10 um; mobile phase: [water (10 mM NH$_4$HCO$_3$)-ACN]; B %: 32/6-62%, 10 min to give 1-(trans-2-cyanocyclopentyl)-3-[(3,4-diethyl-2-hydroxy-1,2-benzoxaborinin-6-yl)amino] pyrazole-4-carboxamide (63.4 mg, 15.7% yield) as a yellow solid. 1H NMR (DMSO-d$^6$, 400 MHz) δ 9.07 (s, 1H), 8.54 (s, 1H), 8.28 (s, 1H), 8.19-8.09 (m, 1H), 7.63 (s, 1H), 7.27-7.19 (m, 1H), 7.12 (s, 1H), 7.10-7.04 (m, 1H), 4.96-4.89 (m, 1H), 3.40-3.37 (m, 1H), 2.83-2.72 (m, 2H), 2.46-2.36 (m, 2H), 2.31-2.17 (m, 2H), 2.17-2.09 (m, 1H), 2.02-1.82 (m, 3H), 1.19 (t, J=7.5 Hz, 3H), 1.03 (t, J=7.5 Hz, 3H) MS (ESI): mass calculated for C22H$_{26}$BN$_5$O$_3$, 419.21, m/z found 418.2 [M−H]$^-$. HPLC: 95.76% (220 nm), 98.83 (254 nm).

41. Preparation of 1-(trans-4-cyanotetrahydro-2H-pyran-3 yl)-3-((1-hydroxy-1,3-dihydrobenzo[c][1,2]oxaborol-5-yl)amino)-1H-pyrazole-4-carboxamide

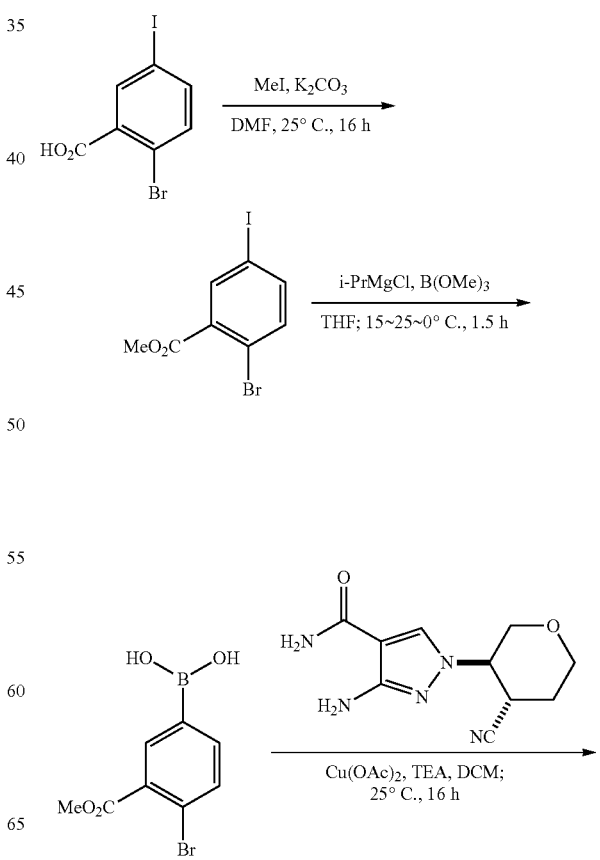

-continued

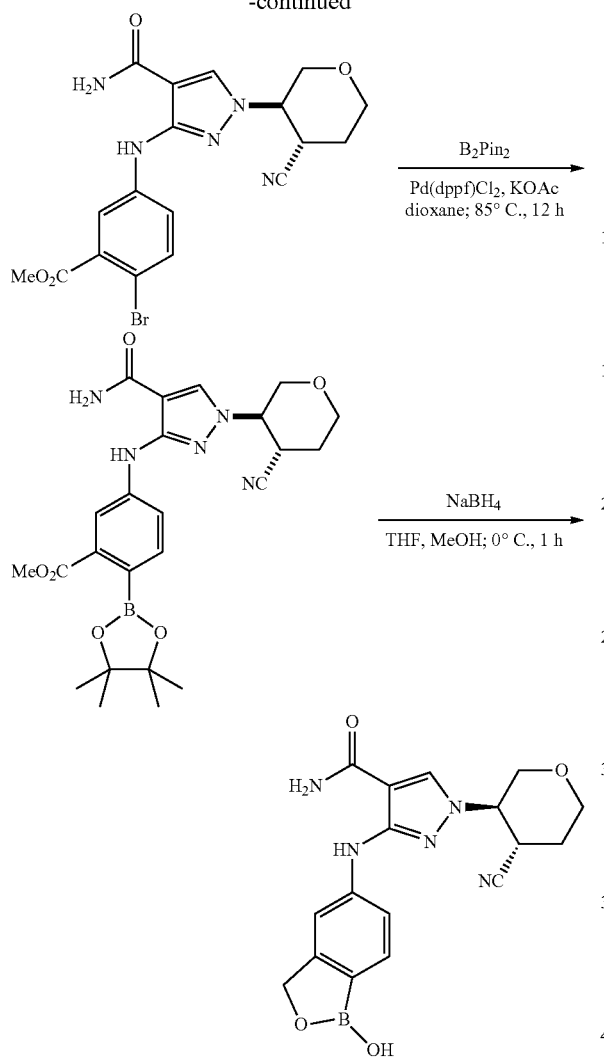

41.1 Preparation of methyl 2-bromo-5-iodo-benzoate

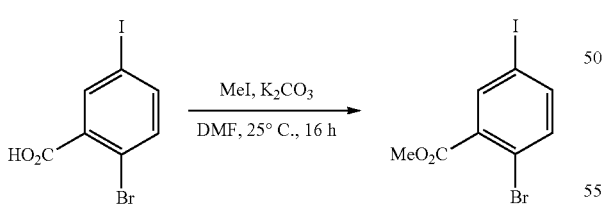

To a solution of 2-bromo-5-iodo-benzoic acid (10.0 g, 30.6 mmol, 1 eq) and K$_2$CO$_3$ (6.34 g, 45.9 mmol, 1.5 eq) in DMF (100 mL) was added MeI (5.64 g, 39.8 mmol, 1.3 eq) at 25° C. The reaction mixture was stirred at 25° C. for 16 h. TLC showed the reaction was completed. The reaction mixture was quenched by addition water (200 mL) at 0° C., then extracted with EtOAc (50 mL×3). The combined organic layers were washed with brine (100 mL×3), dried over Na$_2$SO$_4$, filtered and concentrated under reduced pressure to give methyl 2-bromo-5-iodo-benzoate (10.0 g, 95.9% yield) as brown oil. $^1$H NMR (CDCl$_3$, 400 MHz) δ 8.11 (s, 1H), 7.63 (dd, J=8.4 Hz, 2.4 Hz, 1H), 7.39 (d, J=8.4 Hz, 1H), 3.94 (s, 3H).

41.2 Preparation of (4-bromo-3-methoxycarbonyl-phenyl)boronic acid

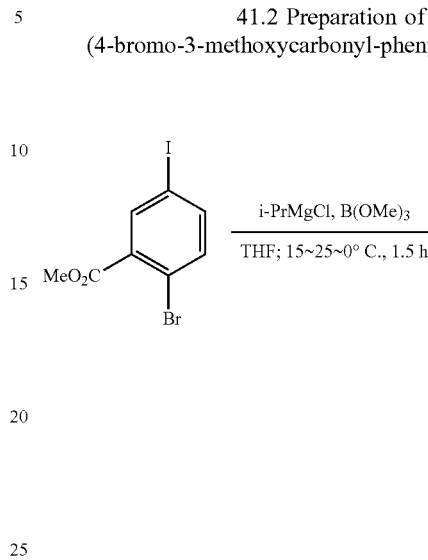

To a solution of 2-[2-(dimethylamino)ethoxy]-N,N-dimethyl-ethanamine (2.82 g, 17.6 mmol, 1.2 eq) in THF (80 mL) was added i-PrMgCl (2 M, 8.8 mL, 1.2 eq) at 15° C. The mixture was stirred at 15° C. for 20 min. Then methyl 2-bromo-5-iodo-benzoate (5.00 g, 14.7 mmol, 1 eq) was added dropwise to the reaction mixture. The resulting mixture was stirred at 25° C. for 10 min. Then the reaction was cooled to 0° C. and trimethyl borate (3.05 g, 29.3 mmol, 3.3 mL, 2 eq) was added dropwise at 0° C. The reaction mixture was continue stirred at 0° C. for 1 h. TLC showed the reaction was completed. The reaction mixture was quenched by addition of sat. aq. NH$_4$Cl (100 mL) at 0° C., then extracted with EtOAc (40 mL×3). The combined organic layers were washed with brine (90 mL×3), dried over Na$_2$SO$_4$, filtered and concentrated under reduced pressure to give a residue. The residue was purified by flash silica gel chromatography (ISCO®; 80 g SepaFlash® Silica Flash Column, Eluent of 0-25% Ethyl acetate/Petroleum ether gradient @ 75 mL/min) to give (4-bromo-3-methoxycarbonyl-phenyl)boronic acid (1.70 g, 44.8% yield) as yellow oil. $^1$H NMR (CDCl$_3$, 400 MHz) δ 8.14 (s, 1H), 7.83 (dd, J=8.0 Hz, 1.6 Hz, 1H), 7.73 (d, J=8.0 Hz, 1H), 3.86 (s, 3H).

41.3 Preparation of methyl 2-bromo-5-[[4-carbamoyl-1-[trans-4-cyanotetrahydro-2H-pyran-3-yl]pyrazol-3-yl]amino]benzoate

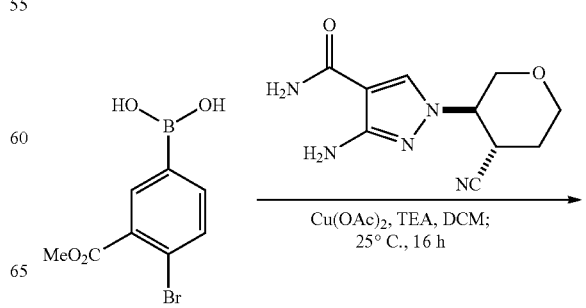

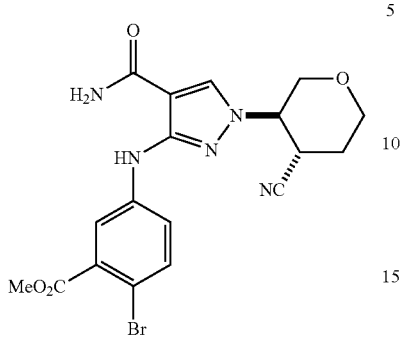

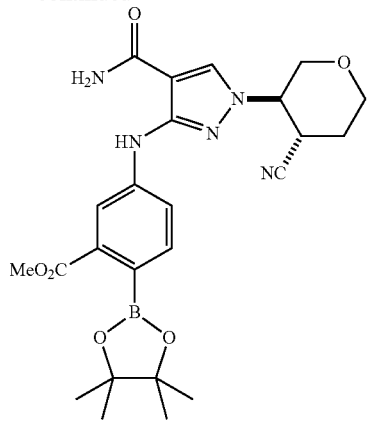

A mixture of (4-bromo-3-methoxycarbonyl-phenyl)boronic acid (1.00 g, 3.86 mmol, 1 eq), 3-amino-1-[trans-4-cyanotetrahydro-2H-pyran-3-yl]pyrazole-4-carboxamide (908 mg, 3.86 mmol, 1 eq), TEA (1.95 g, 19.3 mmol, 2.7 mL, 5 eq), Cu(OAc)$_2$ (1.75 g, 9.65 mmol, 2.5 eq) and 4 Å molecular sieve (2 g) in DCM (14 mL) was degassed and purged with 02 for 3 times. Then the mixture was stirred at 25° C. for 16 h under O$_2$ atmosphere. LCMS showed the reaction was completed and desired MS observed. The reaction mixture was filtered and filtrate was concentrated under reduced pressure to give a residue. The residue was purified by flash silica gel chromatography (ISCO®; 40 g SepaFlash® Silica Flash Column, Eluent of 0~100% Ethyl acetate/Petroleum ether gradient @ 75 mL/min) to give methyl 2-bromo-5-[[4-carbamoyl-1-[trans-4-cyanotetrahydro-2H-pyran-3-yl]pyrazol-3-yl]amino]benzoate (0.50 g, 28.9% yield) as a white solid. $^1$H NMR (DMSO-d$_6$, 400 MHz) δ 9.35 (s, 1H), 8.32 (s, 1H), 7.99 (d, J=2.8 Hz, 1H), 7.77 (br s, 1H), 7.70 (dd, J=2.8, 8.8 Hz, 1H), 7.57 (d, J=8.8 Hz, 1H), 7.25 (br s, 1H), 4.60 (dt, J=4.4, 10.0 Hz, 1H), 4.10-4.03 (m, 1H), 3.94-3.90 (m, 1H), 3.86 (s, 3H), 3.72-3.60 (m, 2H), 3.50-3.41 (m, 1H), 2.18-2.10 (m, 1H), 2.05-1.92 (m, 1H).

41.4 Preparation of methyl 5-[[4-carbamoyl-1-[rans-4-cyanotetrahydro-2H-pyran-3-yl]pyrazol-3-yl]amino]-2-(4,4,5,5-tetramethyl-1,3,2-dioxaborolan-2-yl)benzoate A mixture of methyl 2-bromo-5-[[4-carbamoyl-1-[trans-4-cyanotetrahydro-2H-pyran-3-yl]pyrazol-3-yl]amino]benzoate (250 mg, 557 umol, 1 eq), B$_2$Pin$_2$ (283 mg, 1.12 mmol, 2 eq), KOAc (164 mg, 1.67 mmol, 3 eq), Pd(dppf)C12 (20 mg, 27.9 umol, 0.05 eq) in dioxane (6 mL) was degassed and purged with N$_2$ for 3 times. Then the mixture was heated and stirred at 85° C. for 12 h under N$_2$ atmosphere. LCMS showed the reaction was completed and desired MS observed. 2 parallel reactions were combined for work up. The reaction mixture was cooled to 25° C. and filtered. The filtrate was concentrated under reduced pressure to give a residue. The residue was purified by flash silica gel chromatography (ISCO®; 40 g SepaFlash® Silica Flash Column, Eluent of 0~100% Ethyl acetate/Petroleum ether gradient @ 75 mL/min) to give methyl-5-[[4-carbamoyl-1-[trans-4-cyanotetrahydro-2H-pyran-3-yl]pyrazol-3-yl]amino]-2-(4,4,5,5-tetramethyl-1,3,2-dioxaborolan-2-yl)benzoate (0.50 g, 90.5% yield) as a white solid. $^1$H NMR (DMSO-hd 6, 400 MHz) δ 9.38 (s, 1H), 8.33 (s, 1H), 7.95 (d, J=2.4 Hz, 1H), 7.80-7.71 (m, 2H), 7.40 (d, J=8.0 Hz, 1H), 7.25 (br s, 1H), 4.60 (dt, J=4.4, 10.0 Hz, 1H), 4.10-4.04 (m, 1H), 3.95-3.90 (m, 1H), 3.83 (s, 3H), 3.70-3.58 (m, 2H), 3.51-3.41 (m, 1H), 2.19-2.15 (m, 1H), 2.06-1.97 (m, 1H), 1.30 (s, 12H).

41.5 Preparation of 1-(trans-4-cyanotetrahydro-2H-pyran-3-yl)-3-((1-hydroxy-1,3-dihydrobenzo[c][1,2]oxaborol-5-yl)amino)-1H-pyrazole-4-carboxamide

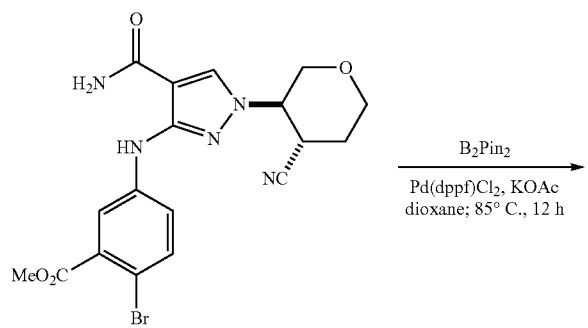

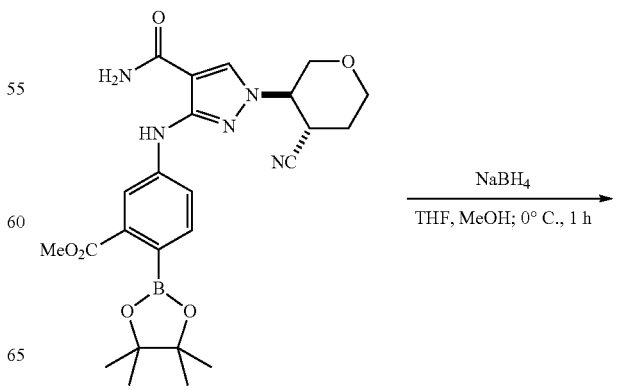

-continued

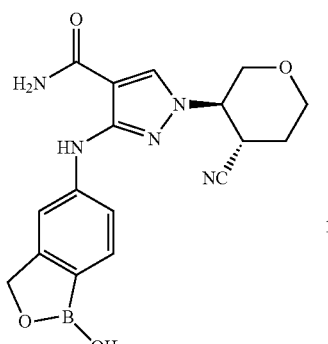

To a solution of methyl 5-[[4-carbamoyl-1-(trans-4-cyanotetrahydro-2H-pyran-3-yl)pyrazol-3-yl]amino]-2-(4,4,5,5-tetramethyl-1,3,2-dioxaborolan-2-yl)benzoate (0.85 g, 1.31 mmol, 1 eq) in MeOH (1 mL) and THF (10 mL) was added NaBH₄ (248 mg, 6.56 mmol, 5 eq) at 0° C. The mixture was stirred at 0° C. for 1 h. LCMS showed the reaction was completed and desired MS observed. The reaction mixture was quenched with water (10 mL) at 0° C., then the resulting mixture was adjusted pH to 5 with HCl (2 M) and stirred for 30 min at 0° C. The solution was diluted with EtOAc (5 mL) and extracted with EtOAc (10 mL×3). The combined organic layers were washed with brine (15 mL×2), dried over Na₂SO₄, filtered and concentrated under reduced pressure to give a residue. The residue was purified by prep-HPLC (column: Phenomenex Luna 80*30 mm*3 um; mobile phase: [water(HCl)-ACN]; B %: 5%-35%, 8 min) to give 1-(trans-4-cyanotetrahydro-2H-pyran-3-yl)-3-((1-hydroxy-1,3-dihydrobenzo[c][1,2]oxaborol-5-yl)amino)-1H-pyrazole-4-carboxamide (0.5 g, purity 95.1%) as a white solid, which was further separated by SFC (condition: column: DAICEL CHIRALPAK IC (250 mm*30 mm, 10 um); mobile phase: [Neu-IPA]; B %: 60%-60%, 12 min) to give 1-(trans-4-cyanotetrahydro-2H-pyran-3-yl)-3-((1-hydroxy-1,3-dihydrobenzo[c][1,2]oxaborol-5-yl)amino)-1H-pyrazole-4-carboxamide (stereoisomer one) (221 mg, 45.8% yield, 100% ee, first peak, Rt=2.436 min) as a white solid. ¹H NMR (DMSO-d₆, 400 MHz) δ 9.41 (s, 1H), 8.89 (br s, 1H), 8.32 (s, 1H), 7.75 (br s, 1H), 7.62-7.56 (m, 2H), 7.38 (d, J=8.0 Hz, 1H), 7.21 (br s, 1H), 4.94 (s, 2H), 4.58 (dt, J=4.4, 10.0 Hz, 1H), 4.04 (dd, J=4.0, 11.2 Hz, 1H), 3.95-3.85 (m, 1H), 3.75-3.63 (m, 2H), 3.50 (t, J=10.8 Hz, 1H), 2.16 (d, J=10.8 Hz, 1H), 2.05-1.92 (m, 1H). MS (ESI): mass calculated for C₁₇H₁₈BN₅O₄ 367.15, m/z found 368.2 [M+H]⁺. HPLC: 99.61% (220 nm), 100% (254 nm). and 1-(trans-4-cyanotetrahydro-2H-pyran-3-yl)-3-((1-hydroxy-1,3-dihydrobenzo[c][1,2]oxaborol-5-yl)amino)-1H-pyrazole-4-carboxamide (stereoisomer two) (204 mg, 42.3% yield, 100% ee, second peak, Rt=3.141 min) as a white solid.

¹H NMR (DMSO-hd 6, 400 MHz) δ 9.41 (s, 1H), 8.88 (br s, 1H), 8.32 (s, 1H), 7.75 (br s, 1H), 7.62-7.56 (m, 2H), 7.38 (d, J=8.0 Hz, 1H), 7.21 (br s, 1H), 4.94 (s, 2H), 4.58 (dt, J=4.4, 10.0 Hz, 1H), 4.04 (dd, J=4.0, 11.2 Hz, 1H), 3.95-3.85 (m, 1H), 3.75-3.63 (m, 2H), 3.50 (t, J=10.8 Hz, 1H), 2.16 (d, J=10.8 Hz, 1H), 2.05-1.92 (m, 1H). MS (ESI): mass calculated for C₁₇H₁₈BN₅O4 367.15; m/z found 368.1 [M+H]⁺. HPLC: 100% (220 nm), 100% (254 nm).

42. Preparation of 1-[trans-4-cyanotetrahydro-2H-pyran-3-yl]-3-[(1-hydroxy-3,4-dihydro-2,1-benzoxaborinin-7-yl)amino]pyrazole-4-carboxamide

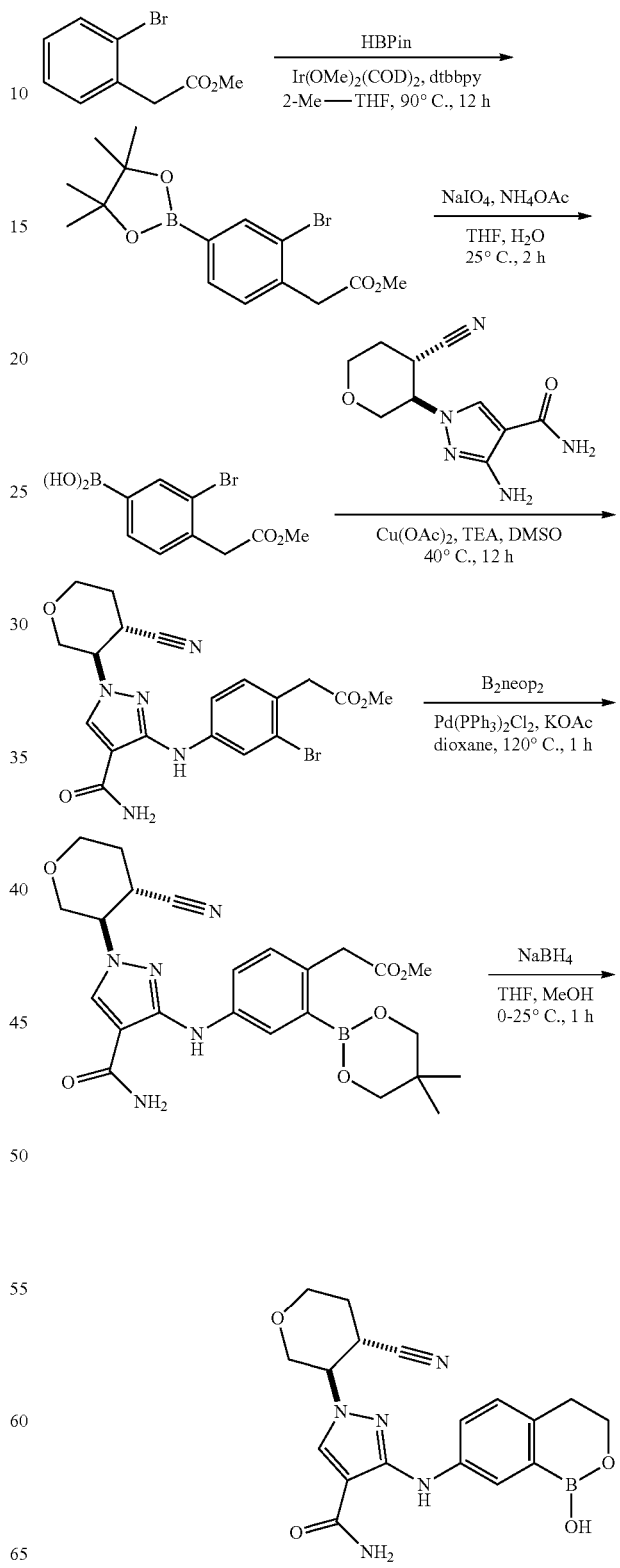

42.1 Preparation of methyl 2-[2-bromo-4-(4,4,5,5-tetramethyl-1,3,2-diaxaborolan-2-yl) phenyl]acetate

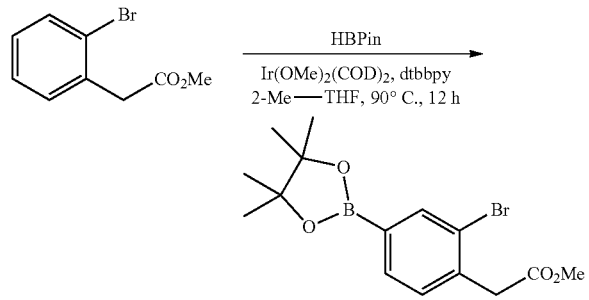

To a solution of methyl 2-(2-bromophenyl)acetate (2.00 g, 8.73 mmol, 1 eq) in 2-MeTHF (20 mL) was added 4-tert-butyl-2-(4-tert-butyl-2-pyridyl)pyridine (234 mg, 873 umol, 0.1 eq), Ir(COD)$_2$(OMe)$_2$ (289 mg, 436 umol, 0.05 eq) and 4,4,5,5-tetramethyl-1,3,2-dioxaborolane (4.50 g, 34.9 mmol, 5.1 mL, 4 eq) under N$_2$. The mixture was heated and stirred at 90° C. for 12 h under N$_2$. TLC showed the reaction was completed. 6 parallel reactions were combined for work up. The reaction mixture was concentrated under reduced pressure to give a residue. The residue was purified by flash silica gel chromatography (ISCO®; 12 g SepaFlash® Silica Flash Column, Eluent of 0~20% Ethyl acetate/Petroleum ether gradient @ 50 m/min) to give methyl 2-[2-bromo-4-(4,4,5,5-tetramethyl-1,3,2-dioxaborolan-2-yl)phenyl]acetate (totally 10 g, crude) as brown oil. $^1$H NMR (CDCl$_3$, 400 MHz) δ 8.01 (s, 0.5H), 7.71-7.69 (m, 1H), 7.60-7.55 (m, 1H), 7.29 (d, J=7.5 Hz, 0.5H), 3.82 (s, 2H), 3.71 (s, 3H), 1.34 (s, 12H).

42.2 Preparation of [3-bromo-4-(2-methoxy-2-oxo-ethyl)phenyl]boronic acid

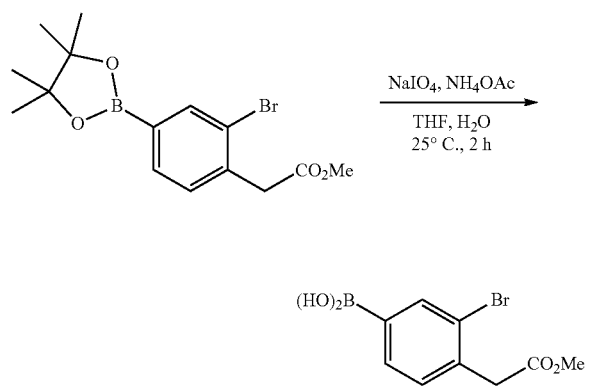

To a solution of methyl 2-[2-bromo-4-(4,4,5,5-tetramethyl-1,3,2-dioxaborolan-2-yl)phenyl]acetate (10.0 g, 28.2 mmol, 1 eq) and methyl 2-[2-bromo-5-(4,4,5,5-tetramethyl-1,3,2-dioxaborolan-2-yl)phenyl]acetate (10.0 g, 28.2 mmol, 1 eq) in THF (60 mL) and H$_2$O (30 mL) was added NaIO$_4$ (24.1 g, 113 mmol, 6.2 mL, 4 eq) and NH$_4$OAc (8.7 g, 113 mmol, 4 eq). The mixture was stirred at 25° C. for 2 h. LCMS showed the reaction was completed and desired MS observed. The reaction mixture was quenched by addition H$_2$O (200 Ml), and adjust pH=6 with 2N HCl. Then the mixture was extracted with EtOAc (100 mL×3). The combined organic layers were washed with brine (100 mL×1), dried over with Na$_2$SO$_4$, filtered and concentrated under reduced pressure to give a residue. The residue was purified by prep-HPLC (column: Waters Xbridge BEH C18 100*30 mm*10 um; mobile phase: [water (10 mM NH$_4$HCO$_3$)-ACN]; B %: 20%-50%, 10 min) to give [3-bromo-4-(2-methoxy-2-oxo-ethyl)phenyl]boronic acid (5.00 g, 21.6% yield) as a white solid. 1H NMR (DMSO-d$^5$, 400 MHz) δ 8.23 (s, 2H), 7.97 (s, 1H), 7.71 (d, J=7.5 Hz, 1H), 7.37 (d, J=7.5 Hz, 1H), 3.82 (s, 2H), 3.62 (s, 3H).

42.3 Preparation of methyl 2-[2-bromo-4-[[4-carbamoyl-1-(trans-4-cyanotetrahydro-2H-pyran-3-yl)pyrazol-3-yl]amino]phenyl]acetate

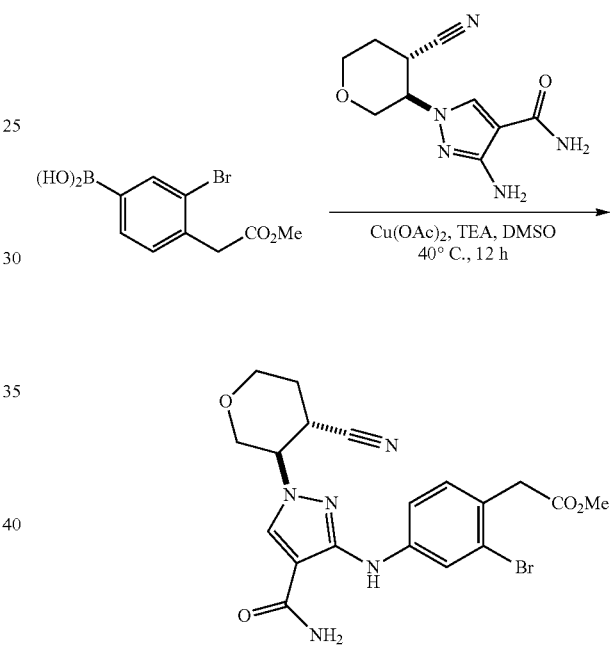

To a solution of [3-bromo-4-(2-methoxy-2-oxo-ethyl)phenyl]boronic acid (500 mg, 1.83 mmol, 1 eq) in DMSO (20 mL) was added Cu(OAc)$_2$ (832 mg, 4.58 mmol, 2.5 eq), 3-amino-1-(trans-4-cyanotetrahydro-2H-pyran-3-yl)pyrazole-4-carboxamide (517 mg, 2.2 mmol, 1.2 eq) and TEA (927 mg, 9.16 mmol, 1.28 mL, 5 eq) at 25° C. The resulting mixture was heated and stirred at 40° C. for 12 h under O$_2$ atmosphere. LCMS showed the reaction was completed and desired MS observed. 3 parallel reactions were combined for work up. The reaction mixture was filtered. The filtrate was diluted with H$_2$O (30 mL) and extracted with EtOAc (10 mL×3). The combined organic layers were washed with brine (15 mL), dried over Na$_2$SO$_4$, filtered and concentrated under reduced pressure to give a residue. The residue was purified by flash silica gel chromatography (ISCO®; 20 g SepaFlash® Silica Flash Column, Eluent of 0~50% Ethyl acetate/Petroleum ether gradient @ 50 mL/min) to give methyl 2-[2-bromo-4-[[4-carbamoyl-1-(trans-4-cyanotetrahydro-2H-pyran-3-yl)pyrazol-3-yl]amino]phenyl]acetate (1.50 g, 59.0% yield) as a yellow solid.

42.4 Preparation of methyl 2-[4-[[4-carbamoyl-1-(trans-4-cyanotetrahydro-2H-pyran-3-yl)pyrazol-3-yl]amino]-2-(5,5-dimethyl-1,3,2-dioxaborinan-2-yl)phenyl]acetate

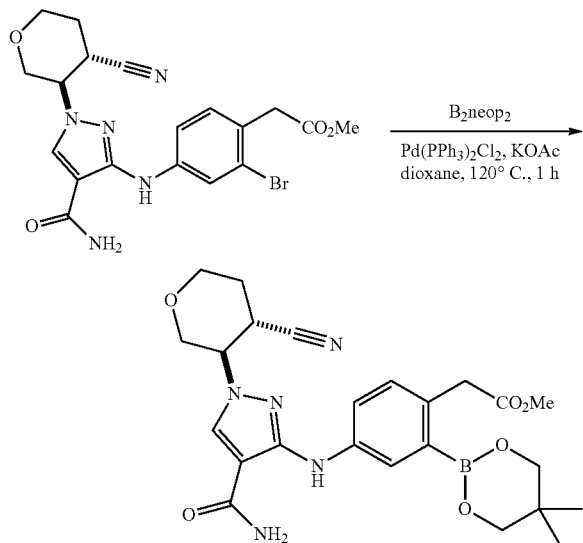

A mixture of 2-(5,5-dimethyl-1,3,2-dioxaborinan-2-yl)-5,5-dimethyl-1,3,2-dioxaborinane (611 mg, 2.70 mmol, 2.5 eq), methyl 2-[2-bromo-4-[[4-carbamoyl-1-(trans-4-cyanotetrahydro-2H-pyran-3-yl)pyrazol-3-yl]amino]phenyl]acetate (500 mg, 1.08 mmol, 1 eq), KOAc (265 mg, 2.70 mmol, 2.5 eq) and Pd(PPh$_3$)$_2$Cl$_2$ (76 mg, 108 umol, 0.1 eq) in dioxane (10 mL) was degassed and purged with N$_2$ for 3 times. Then the mixture was heated and stirred at 120° C. for 1 h under N$_2$ atmosphere. LCMS showed the reaction was completed and desired MS observed. 4 parallel reactions were combined for work up. The reaction mixture was filtered and the filtrate was concentrated under reduced pressure to give a residue. The residue was triturated with MTBE (10 mL) at 25° C. for 10 min to give methyl 2-[4-[[4-carbamoyl-1-(trans-4-cyanotetrahydro-2H-pyran-3-yl) pyrazol-3-yl]amino]-2-(5,5-dimethyl-1,3,2-dioxaborinan-2-yl)phenyl]acetate (1.30 g) as a brown solid.

42.5 Preparation of 1-[trans-4-cyanotetrahydro-2H-pyran-3-yl]-3-[(1-hydroxy-3,4-dihydro-2,1-benzoxaborinin-7-yl)amino]pyrazole-4-carboxamide

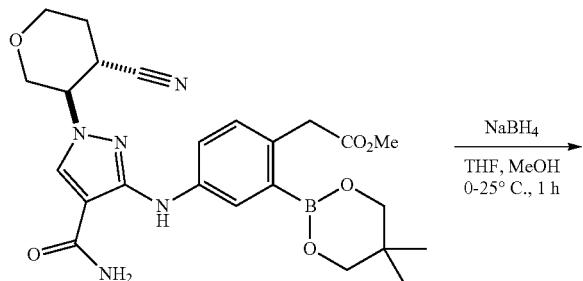

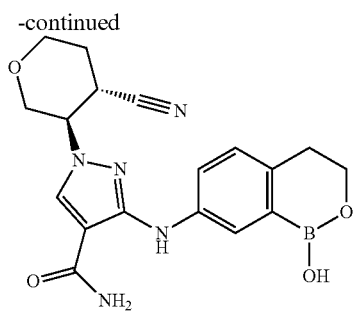

To a solution of methyl 2-[4-[[4-carbamoyl-1-(trans-4-cyanotetrahydro-2H-pyran-3-yl)pyrazol-3-yl] amino]-2-(5, 5-dimethyl-1,3,2-dioxaborinan-2-yl)phenyl]acetate (1.30 g, 2.62 mmol, 1 eq) in THF (20 mL) and MeOH (4 mL) was added NaBH$_4$ (496 mg, 13 mmol, 5 eq) at 0° C. The resulting mixture was stirred at 25° C. for 1 h. LCMS showed the reaction was completed and desired MS observed. The mixture was adjusted pH=4 with 2N HCl and stirred for 30 min. LCMS showed the reaction was completed and desired MS observed. The mixture was quenched with H$_2$O (100 mL) at 0° C. and extracted with ethyl acetate (30 mL×3). The combined organic phase was washed with brine (50 mL), dried with anhydrous Na$_2$SO$_4$, filtered and concentrated in vacuum to give the residue. The residue was purified by prep-HPLC (column: Waters Xbridge BEH C18 100*30 mm*10 um; mobile phase: [water (10 mM NH$_4$HCO$_3$)-ACN]; B %: 20%-50%, 10 min) to give 1-[trans-4-cyanotetrahydro-2H-pyran-3-yl]-3-[(1-hydroxy-3,4-dihydro-2,1-benzoxaborinin-7-yl)amino]pyrazole-4-carboxamide (640 mg, yield 93.84%, purity 98%) as a white solid, which was further separated by SFC (column: DAICEL CHIRALPAK IC (250 mm*30 mm, 10 um); mobile phase: [Neu-IPA]; B %: 40%-40%, 8 min) to give 1-[trans-4-cyanotetrahydro-2H-pyran-3-yl]-3-[(1-hydroxy-3,4-dihydro-2,1-benzoxaborinin-7-yl)amino]pyrazole-4-carboxamide (stereoisomer one) (260 mg, 25.9% yield, 100% ee, first peak, Rt=2.120 min) as a white solid. 1H NMR (DMSO-d$^6$, 400 MHz) δ=9.12 (s, 1H), 8.38 (s, 1H), 8.28 (s, 1H), 7.80 (dd, J=2.4, 8.2 Hz, 1H), 7.70 (s, 1H), 7.54 (d, J=2.4 Hz, 1H), 7.18 (s, 1H), 7.12 (d, J=8.3 Hz, 1H), 4.55 (dt, J=4.4, 10.1 Hz, 1H), 4.06-4.02 (m, 3H), 3.93-3.90 (m, 1H), 3.71-3.65 (m, 2H), 3.49-3.44 (m, 1H), 2.79 (t, J=5.8 Hz, 2H), 2.18-2.14 (m, 1H), 2.03-1.93 (m, 1H) MS (ESI): mass calculated for C$_{18}$H$_{20}$BN$_5$O$_4$, 381.16, m/z found 382.2 [M+H]$^+$. HPLC: 99.16% (220 nm), 100% (254 nm). and 1-[trans-4-cyanotetrahydro-2H-pyran-3-yl]-3-[(1-hydroxy-3,4-dihydro-2,1-benzoxaborinin-7-yl)amino]pyrazole-4-carboxamide (stereoisomer two) (262 mg, 26.1% yield, 100% ee, second peak, Rt=2.521 min) as a white solid. 1H NMR (DMSO-d$^6$, 400 MHz) δ=9.12 (s, 1H), 8.38 (s, 1H), 8.28 (s, 1H), 7.80 (dd, J=2.4, 8.2 Hz, 1H), 7.70 (s, 1H), 7.54 (d, J=2.4 Hz, 1H), 7.18 (s, 1H), 7.12 (d, J=8.3 Hz, 1H), 4.55 (dt, J=4.4, 10.1 Hz, 1H), 4.06-4.01 (m, 3H), 3.93-3.90 (m, 1H), 3.71-3.62 (m, 2H), 3.49-3.43 (m, 1H), 2.79 (t, J=5.8 Hz, 2H), 2.18-2.14 (m, 1H), 2.03-1.99 (m, 1H) MS (ESI): mass calculated for C$_{18}$H$_{20}$BN$_5$O$_4$, 381.16, m/z found 382.2 [M+H]$^+$. HPLC: 99.53% (220 nm), 99.84% (254 nm).

43. Preparation of 3-[(4-chloro-2-hydroxy-1,2-benzoxaborinin-6-yl)amino]-1-[trans-4-cyanotetrahydro-2H-pyran-3-yl]pyrazole-4-carboxamide

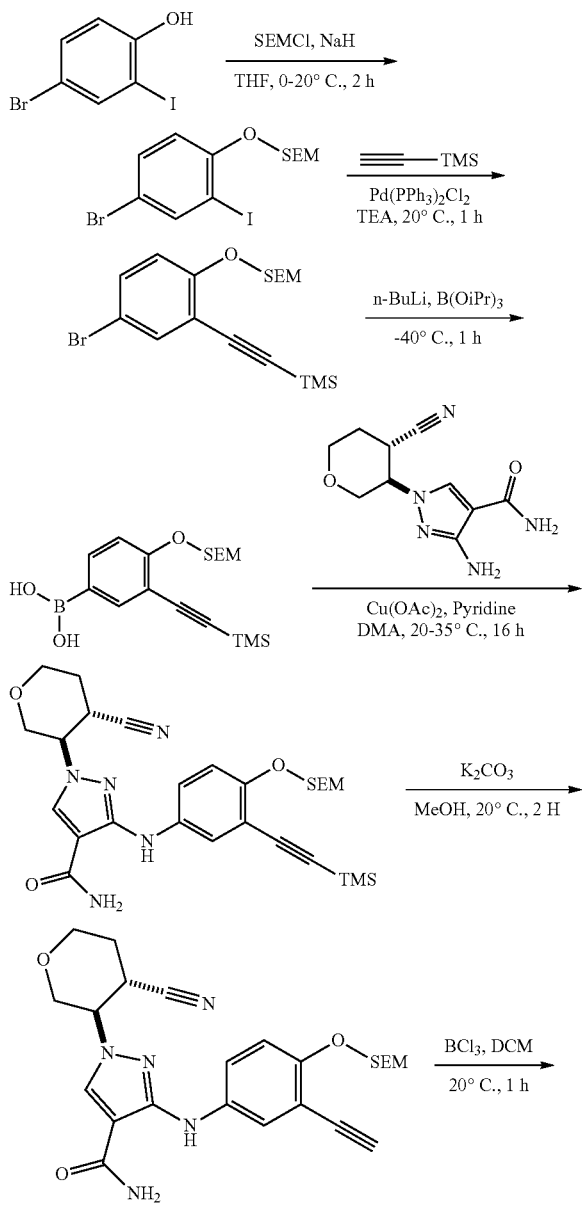

43.1 Preparation of 2-[(4-bromo-2-iodo-phenoxy)methoxy]ethyl-trimethyl-silane

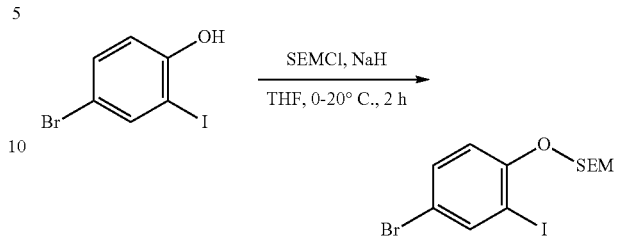

To a mixture of 4-bromo-2-iodo-phenol (20.0 g, 66.9 mmol, 1 eq) in THF (200 mL) was added NaH (4.01 g, 100 mmol, 60% purity, 1.5 eq) portion-wise at 0° C. under $N_2$. The mixture was stirred at 0° C. for 1 h. Then to this mixture was added drop-wise (2-(chloromethoxy) ethyl)trimethylsilane (73.6 mmol, 13.0 mL, 1.1 eq) at 0° C. The reaction was allowed to warm to 20° C. and stirred at 20° C. for 1 h. TLC showed the reaction was completed. The reaction mixture was poured into sat. aq. $NH_4Cl$ (200 mL) and extracted with ethyl acetate (100 mL×3). The combined organic phase was washed with brine (200 mL×2), dried with anhydrous $Na_2SO_4$, filtered and concentrated in vacuum to give a residue. The residue was purified by flash silica gel chromatography (ISCO®; 330 g SepaFlash® Silica Flash Column, Eluent of 0-25% Ethyl acetate/Petroleum ether gradient @ 100 mL/min) to give 2-[(4-bromo-2-iodo-phenoxy)methoxy] ethyl-trimethyl-silane (27.0 g, 94.0% yield) as yellow oil. $^1$H NMR (CDCl$_3$, 400 MHz) δ 7.89 (d, J=2.4 Hz, 1H), 7.39 (dd, J=8.8 Hz, 2.4 Hz, 1H), 6.97 (d, J=8.8 Hz, 1H), 5.27 (s, 2H), 3.78 (t, J=8.4 Hz, 2H), 0.95 (t, J=8.0 Hz, 2H), 0.01 (s, 9H).

43.2 Preparation of 2-[5-bromo-2-(2-trimethylsilylethoxymethoxy)phenyl]ethynyl-trimethyl-silane

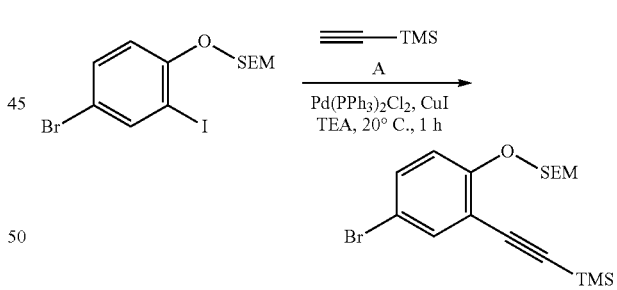

To a mixture of 2-[(4-bromo-2-iodo-phenoxy)methoxy] ethyl-trimethyl-silane (27.0 g, 62.9 mmol, 1 eq) and ethynyl (trimethyl)silane (189 mmol, 26.2 mL, 3 eq) in THF (300 mL) was added a solution of CuI (1.20 g, 6.29 mmol, 0.1 eq), Pd(PPh$_3$)$_2$Cl$_2$ (2.21 g, 3.15 mmol, 0.05 eq) and TEA (440 mmol, 61.3 mL, 7 eq) in THF (100 mL) drop-wise at 20° C. under $N_2$. The mixture was stirred at 20° C. for 1 h. LCMS showed the reaction was completed and desired MS observed. The reaction mixture was quenched with sat. aq. NH$_4$Cl (300 mL), and extracted with ethyl acetate (100 mL×3). The combined organic phase was washed with brine (150 mL×2), dried with anhydrous Na$_2$SO$_4$, filtered and concentrated in vacuum to give a residue. The residue was purified by flash silica gel chromatography (ISCO®; 330 g SepaFlash® Silica Flash Column, Eluent of 0~10% Ethyl acetate/Petroleum ether gradient @ 100 mL/min) to give 2-[5-bromo-2-(2-trimethylsilylethoxymethoxy)phenyl]ethynyl-trimethyl-silane (23.5 g, 93.5% yield) as brown oil.

$^1$H NMR (CDCl$_3$, 400 MHz) δ 7.55 (d, J=2.4 Hz, 1H), 7.34 (dd, J=9.2 Hz, 2.8 Hz, 1H), 6.99 (d, J=8.8 Hz, 1H), 5.27 (s, 2H), 3.80 (t, J=8.4 Hz, 2H), 0.96 (t, J=8.4 Hz, 2H), 0.26 (s, 9H), 0.02 (s, 9H).

43.3 Preparation of [4-(2-trimethylsilylethoxymethoxy)-3-(2-trimethylsilylethynyl)phenyl] boronic acid

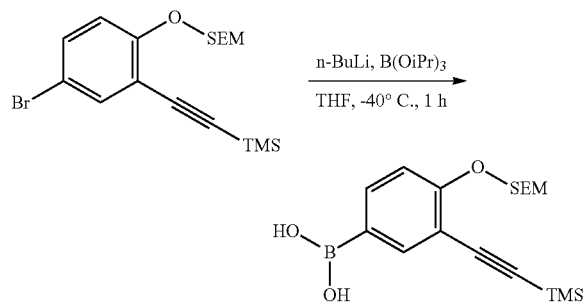

To a solution of 2-[5-bromo-2-(2-trimethylsilylethoxymethoxy)phenyl]ethynyl-trimethyl-silane (10.0 g, 25.0 mmol, 1 eq) and triisopropyl borate (30.0 mmol, 6.91 mL, 1.2 eq) in THF (100 mL) was added n-BuLi (2.5 M, 22.0 mL, 2.2 eq) at −40° C. under N$_2$. The mixture was stirred at −40° C. for 1 h. TLC showed the reaction was completed. The reaction mixture was quenched by sat. aq. NH$_4$Cl (100 mL) at 0° C., and extracted with ethyl acetate (50 mL×3). The combined organic layers were washed with brine (80 mL×3), dried over Na$_2$SO$_4$, filtered and concentrated under reduced pressure to give a residue. The residue was purified by flash silica gel chromatography (ISCO®; 80 g SepaFlash® Silica Flash Column, Eluent of 0~50% Ethyl acetate/Petroleum ether gradient @ 100 mL/min) to give [4-(2-trimethylsilylethoxymethoxy)-3-(2-trimethylsilylethynyl)phenyl] boronic acid (7.00 g, 61.3% yield, 80% purity) as a white solid. $^1$H NMR (CDCl$_3$, 400 MHz) δ 8.28 (s, 1H), 8.12 (dd, J=8.4 Hz, 1.2 Hz, 1H), 7.22 (d, J=8.4 Hz, 1H), 5.39 (s, 2H), 3.86 (t, J=8.4 Hz, 2H), 0.99 (t, J=8.4 Hz, 2H), 0.32 (s, 9H), 0.03 (s, 9H).

43.4 Preparation of 1-(trans-4-cyanotetrahydro-2H-pyran-3-yl)-3-[4-(2-trimethylsilylethoxymethoxy)-3-(2-trimethylsilylethynyl)anilino]pyrazole-4-carboxamide

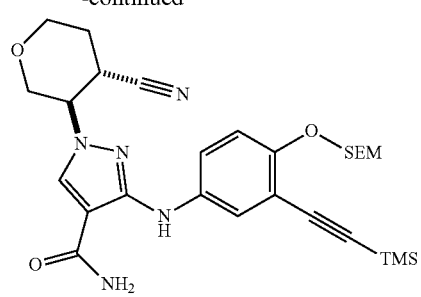

To a mixture of [4-(2-trimethylsilylethoxymethoxy)-(2-trimethylsilylethynyl)phenyl]boronic acid (4.05 g, 10.0 mmol, 90% purity, 1 eq) and 3-amino-1-(trans-4-cyanotetrahydro-2H-pyran-3-yl) pyrazole-4-carboxamide (2.52 g, 10.7 mmol, 1.07 eq) in DMA (100 mL) was added Cu(OAc)$_2$ (4.54 g, 25.0 mmol, 2.5 eq) and Pyridine (50.0 mmol, 4.04 mL, 5 eq) at 20° C. under air. The mixture was heated and stirred at 35° C. for 16 h. LCMS showed the reaction was completed and desired MS observed. 4 parallel reactions were combined for work up. The reaction mixture was filtered and the filtrate was concentrated in vacuum to give a residue. H$_2$O (100 mL) was added to the residue and then extracted with ethyl acetate (100 mL×3). The combined organic layers were washed with brine (100 mL×3), dried over Na$_2$SO$_4$, filtered and concentrated under reduced pressure to give a residue. The residue was purified by flash silica gel chromatography (ISCO®; 120 g SepaFlash® Silica Flash Column, Eluent of 0~50% Ethyl acetate/Petroleum ether gradient @ 100 mL/min) to give 1-(trans-4-cyanotetrahydro-2H-pyran-3-yl)-3-[4-(2-trimethylsilylethoxymethoxy)-3-(2-trimethylsilylethynyl)anilino]pyrazole-4-carboxamide (6 g, 54.1% yield) as a yellow solid.

$^1$H NMR (CDCl$_3$, 400 MHz) δ 8.64 (s, 1H), 7.75 (s, 1H), 7.58 (d, J=2.8 Hz, 1H), 7.48 (dd, J=9.2 Hz, 2.8 Hz, 1H), 7.05 (d, J=9.2 Hz, 1H), 5.49 (br s, 2H), 5.25 (s, 2H), 4.23-4.18 (m, 1H), 4.16-4.10 (m, 1H) 4.06-4.01 (m, 2H), 3.83 (t, J=8.4, Hz, 2H), 3.66-3.56 (m, 2H), 2.17-2.09 (m, 1H), 2.05-1.99 (m, 1H), 0.98 (t, J=8.4, Hz, 2H), 0.27 (s, 9H), 0.03 (s, 9H).

43.5 Preparation of 1-(trans-4-cyanotetrahydro-2H-pyran-3-yl)-3-[3-ethynyl-4-(2-trimethylsilylethoxymethoxy)anilino]pyrazole-4-carboxamide

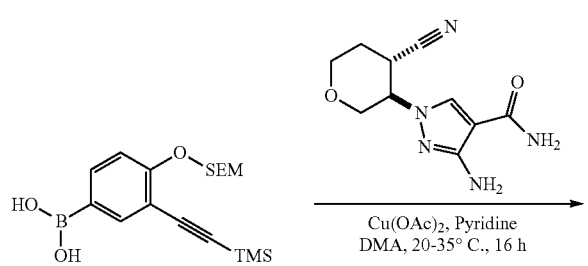

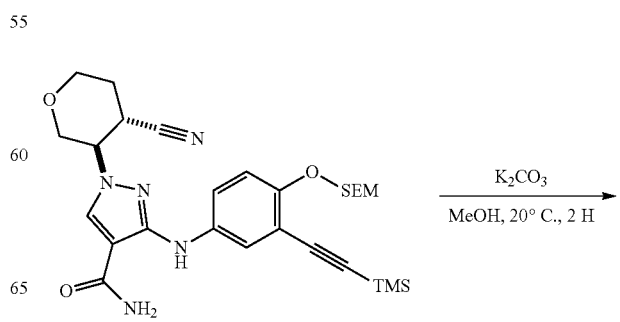

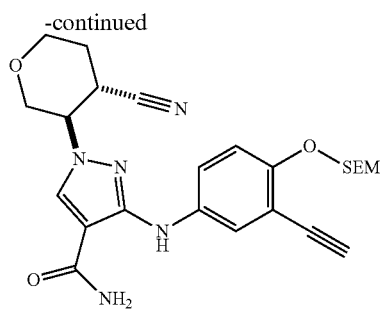

To a mixture of 1-(trans-4-cyanotetrahydro-2H-pyran-3-yl)-3-[4-(2-trimethylsilylethoxymethoxy)-3-(2-trimethylsilylethynyl)anilino]pyrazole-4-carboxamide (2.8 g, 5.06 mmol, 1 eq) in MeOH (100 mL) was added $K_2CO_3$ (489 mg, 3.54 mmol, 0.7 eq) at 20° C. The mixture was stirred at 20° C. for 2 h. LCMS showed the reaction was completed and desired MS observed. 2 parallel reactions were combined for work up. The reaction mixture was quenched with $H_2O$ (60 mL), adjusted pH to 7 with 2 N HCl at 0° C. and extracted with ethyl acetate (30 mL×3). The combined organic layers were washed with brine (35 mL×3), dried over $Na_2SO_4$, filtered and concentrated under reduced pressure to give 1-(trans-4-cyanotetrahydro-2H-pyran-3-yl)-3-[3-ethynyl-4-(2-trimethylsilylethoxymethoxy)anilino]pyrazole-4-carboxamide (4.30 g 88.2% yield) as a yellow solid. H NMR (DMSO-hd 6, 400 MHz) δ 9.02 (s, 1H), 8.28 (s, 1H), 7.73-7.66 (m, 1H), 7.56-7.52 (m, 2H), 7.18 (br s, 1H), 7.08 (d, J=8.8, Hz, 1H), 5.21 (s, 2H), 4.56 (td, J=10.4, Hz, 1H), 4.20 (s, 1H), 4.05-4.02 (m, 1H), 3.92-3.89 (m, 1H), 3.74 (t, J=8.4, Hz, 1H), 3.67-3.59 (m, 2H), 3.48-3.43 (m, 1H), 2.17-2.13 (m, 1H), 2.03-1.96 (m, 1H), 0.89 (t, J=8.0, Hz, 2H), 0.02 (s, 9H).

43.6 Preparation of chiral 3-[(4-chloro-2-hydroxy-1,2-benzoxaborinin-6-yl)amino]-1-[trans-4-cyanotetrahydr-2H-opyran-3-yl]pyrazole-4-carboxamide

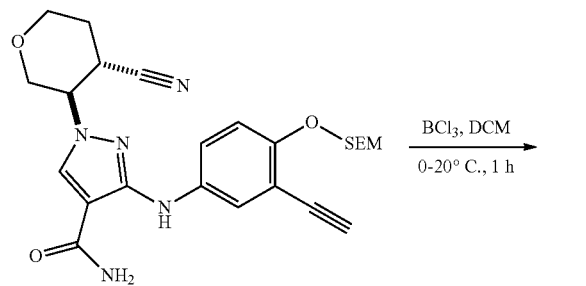

To a solution of $BCl_3$ (1 M, 10.38 mL, 10 eq) was added 1-(trans-4-cyanotetrahydro-2H-pyran-3-yl)-3-[3-ethynyl-4-(2-trimethylsilylethoxymethoxy)anilino]pyrazole-4-carboxamide (500 mg, 1.04 mmol, 1 eq) at 0° C. The reaction was allowed to warm to 20° C. and stirred at 20° C. for 1 h. LCMS showed the reaction was completed and desired MS observed. 5 parallel reactions were combined for work up. The reaction mixture was quenched by $H_2O$ (150 mL) and extracted with ethyl acetate (50 mL×3). The combined organic layers were washed with brine (30 mL×3), dried over $Na_2SO_4$, filtered and concentrated under reduced pressure to give a residue. The residue was purified by prep-HPLC (column: Phenomenex luna C18 250*50 mm*10 um; mobile phase: [water(TFA)-ACN]; B %: 25%-55%, 10 min) to give 3-[(4-chloro-2-hydroxy-1,2-benzoxaborinin-6-yl)amino]-1-(trans-4-cyanotetrahydro-2H-pyran-3-yl)pyrazole-4-carboxamide (550 mg, 25.6% yield, 99.4% purity) as an off white solid, which was further separated by SFC (column: DAICEL CHIRALPAK AD (250 mm*30 mm, 10 um); mobile phase: [Neu-ETOH]; B %: 44%-44%, 7 min) to give 3-[(4-chloro-2-hydroxy-1,2-benzoxaborinin-6-yl)amino]-1-[trans-4-cyanotetrahydro-2H-pyran-3-yl]pyrazole-4-carboxamide (stereoisomer one) (221 mg, 10.1% yield, 98.1% purity, 100% ee, first peak, Rt=1.301 min) as an off white solid. $^1$H NMR (DMSO-hd 6, 400 MHz) δ 9.17 (br s, 1H), 9.16 (s, 1H), 8.31 (br s, 1H), 8.29 (d, J=2.8 Hz, 1H), 7.71 (br s, 1H), 7.55 (dd, J=8.4 Hz, 2.8 Hz, 1H), 7.29-7.09 (m, 2H), 6.30 (s, 1H), 4.60 (td, J=10.4 Hz, 1H), 4.07 (dd, J=11.2 Hz, 4.0 Hz, 1H), 3.93 (d, J=9.2 Hz, 1H), 3.70 (t, J=10.0 Hz, 1H), 3.62 (td, J=11.2 Hz, 1H), 3.44-3.39 (m, 1H), 2.21-2.17 (m, 1H), 2.04-1.94 (m, 1H). MS (ESI): mass calculated for $C_{18}H_{17}BClN_5O_4$ 413.11, m/z found 414.1 $[M+H]^+$. HPLC: 98.14% (220 nm), 99.03% (254 nm) and 3-[(4-chloro-2-hydroxy-1,2-benzoxaborinin-6-yl)amino]-1-[trans-4-cyanotetrahydro-2H-pyran-3-yl]pyrazole-4-carboxamide (stereoisomer two) (220 mg, 10.1% yield, 99.0% purity, 100% ee, second peak, Rt=1.440 min) as an off-white solid. $^1$H NMR (DMSO-hd 6, 400 MHz) δ 9.17 (br s, 1H), 9.16 (s, 1H), 8.31 (br s, 1H), 8.29 (d, J=2.8 Hz, 1H), 7.74 (br s, 1H), 7.56 (dd, J=9.2 Hz, 2.8 Hz, 1H), 7.27-7.09 (m, 2H), 6.30 (s, 1H), 4.60 (td, J=10.0 Hz, 1H), 4.07 (dd, J=11.2 Hz, 4.4 Hz, 1H), 3.94 (d, J=11.2 Hz, 1H), 3.71 (t, J=10.4 Hz, 1H), 3.61 (td, J=14.8 Hz, 1H), 3.43-3.40 (m, 1H), 2.23-2.16 (m, 1H), 2.03-1.95 (m, 1H). MS (ESI): mass calculated for $C_{18}H_{17}BClN_5O_4$ 413.11; m/z found 414.1 $[M+H]^+$. HPLC: 99.00% (220 nm), 99.47% (254 nm).

44. Preparation of 1-[trans-4-cyanotetrahydro-2H-pyran-3-yl]-3-[(8-fluoro-2-hydroxy-1,2-benzoxaborinin-6-yl)amino]pyrazole-4-carboxamide

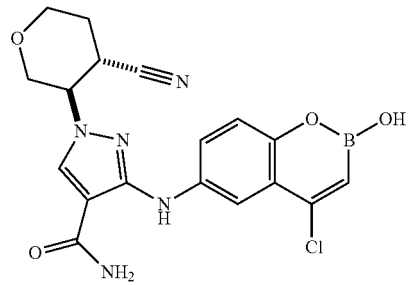
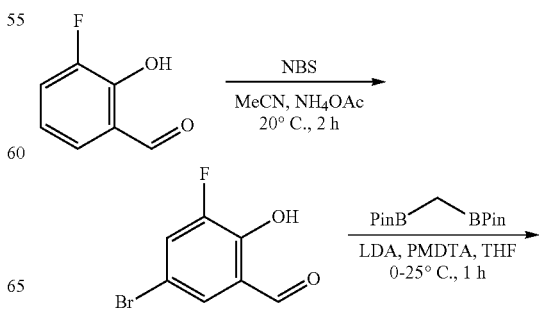

-continued

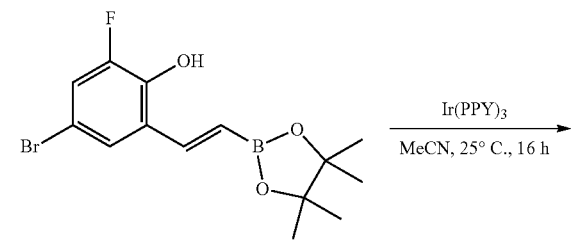

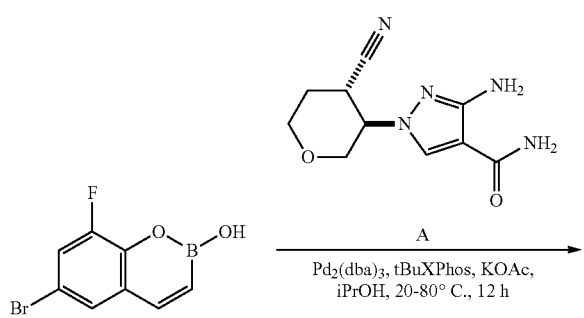

44.1 Preparation of 5-bromo-3-fluoro-2-hydroxy-benzaldehyde

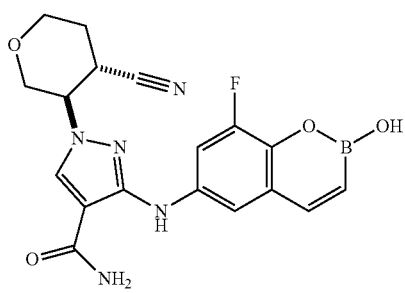

To a mixture of 3-fluoro-2-hydroxy-benzaldehyde (5.00 g, 35.7 mmol, 1 eq) in CH₃CN (80 mL) was added NH₄OAc (275 mg, 3.57 mmol, 0.1 eq) and NBS (6.99 g, 39.3 mmol, 1.1 eq) at 20° C. under N₂. The mixture was stirred at 20° C. for 2 h. TLC showed the reaction was completed. The reaction mixture was concentrated in vacuum to give a residue. The residue was purified by flash silica gel chromatography (ISCO®; 80 g SepaFlash® Silica Flash Column, Eluent of 0~10% Ethyl acetate/Petroleum ether gradient @ 75 m/min) to give 5-bromo-3-fluoro-2-hydroxy-benzaldehyde (7.05 g, 95.9% yield) as a yellow solid. ¹H NMR (CDCl₃, 400 MHz) δ 10.89 (s, 1H), 9.88 (s, 1H), 7.54-7.52 (m, 1H), 7.52-7.48 (m, 1H).

44.2 Preparation of 4-bromo-2-fluoro-6-[(E)-2-(4,4,5,5-tetramethyl-1,3,2-diaxaborolan-2-yl) vinyl]phenol

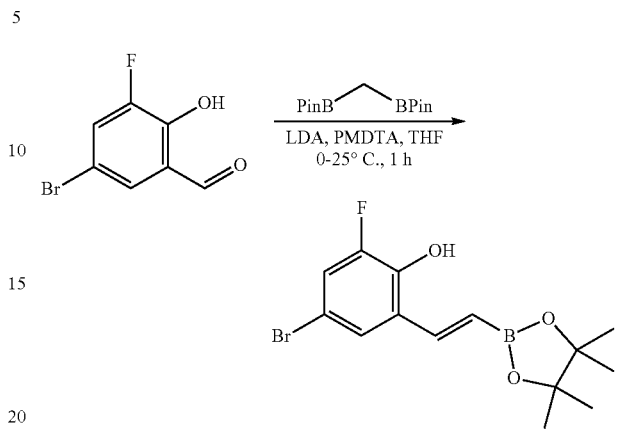

To a mixture of LDA (2 M, 28.5 mL, 2.5 eq) in THF (50 mL) was added N'-[2-(dimethylamino)ethyl]-N,N,N'-trimethyl-ethane-1,2-diamine (7.91 g, 45.7 mmol, 9.53 mL, 2 eq) and a solution of 4,4,5,5-tetramethyl-2-[(4,4,5,5-tetramethyl-1,3,2-dioxaborolan-2-yl)methyl]-1,3,2-dioxaborolane (12.2 g, 45.7 mmol, 2 eq) in THF (60 mL) at 0° C. under N₂. The mixture was stirred at 0° C. for 20 min. Then dropwise added a solution of 5-bromo-3-fluoro-2-hydroxy-benzaldehyde (5 g, 22.8 mmol, 1 eq) in THF (40 mL) at 25° C. The mixture was continue stirred at 25° C. for 40 min. LCMS showed the reaction was completed and desired MS observed. The reaction was quenched by sat aq. NH₄Cl (100 mL) and extracted with EtOAc (80 mL×3). The combined organic phase was washed with brine (100 mL×3), dried over Na₂SO₄, filtered and concentrated under reduced pressure to give a residue. The residue was purified by flash silica gel chromatography (ISCO®; 80 g SepaFlash® Silica Flash Column, Eluent of 0~10% Ethyl acetate/Petroleum ether gradient @ 75 mL/min) to give 4-bromo-2-fluoro-6-[(E)-2-(4,4,5,5-tetramethyl-1,3,2-dioxaborolan-2-yl) vinyl] phenol (8 g, 63.3% yield, 62% purity) as yellow oil.

¹H NMR (DMSO-hd 6, 400 MHz) δ 7.58 (d, J=18.8 Hz, 1H), 7.42 (s, 1H), 7.17 (dd, J=9.6 Hz, 2.4 Hz, 1H), 6.22 (d, J=18.4 Hz, 1H), 5.58 (br s, 1H) 1.32 (s, 12H).

44.3 Preparation of 6-bromo-8-fluoro-2-hydroxy-1,2-benzoxaborinine

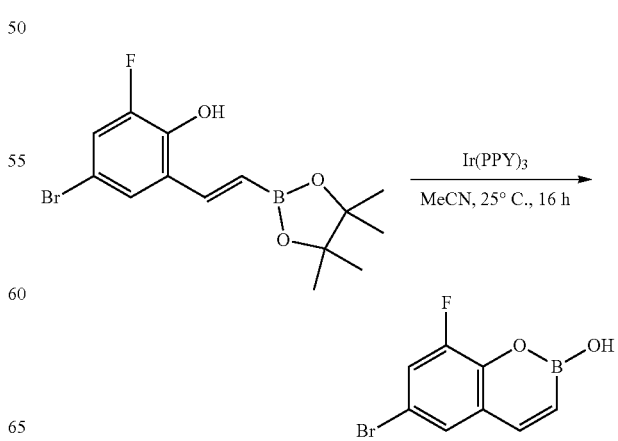

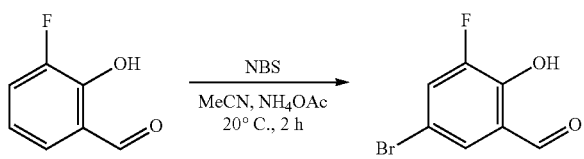 [SMILES: O=Cc1cccc(F)c1O ; "NBS" ; O=Cc1cc(Br)cc(F)c1O]

To a mixture of (E)-4-bromo-2-fluoro-6-(2-(4,4,5,5-tetramethyl-1,3,2-dioxaborolan-2-yl)vinyl)phenol (2.70 g, 4.88 mmol, 62% purity, 1 eq) in McCN (30 mL) was added tris[2-(2-pyridyl)phenyl]iridium (79.8 mg, 122 umol, 0.025 eq) in one portion at 25° C. under N₂. The reaction was stirred and irradiated using 34W blue LED lamps for 16 h. TLC showed the reaction was completed. 3 parallel reactions were combined for work up. The reaction was concentrated under reduced pressure to give a residue. The residue was purified by flash silica gel chromatography (ISCO®; 40 g SepaFlash® Silica Flash Column, Eluent of 0~20% Ethyl acetate/Petroleum ether gradient @ 75 mL/min) to give 6-bromo-8-fluoro-2-hydroxy-1,2-benzoxaborinine (4.00 g, 90.0% yield) as a yellow solid. ¹H NMR (DMSO-hd 6, 400 MHz) δ 9.42 (s, 1H), 7.79 (d, J=12.0 Hz, 1H), 7.67-7.63 (m, 2H), 6.27 (d, J=12.0 Hz, 1H).

44.4 Preparation of 1-[trans-4-cyanotetrahydro-2H-pyran-3-yl]-3-[(8-fluoro-2-hydroxy-1,2-benzoxaborinin-6-yl)amino]pyrazole-4-carboxamide

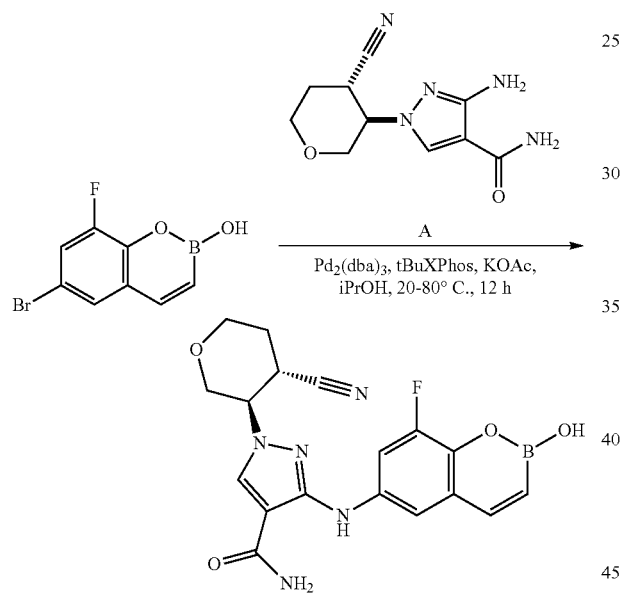

To a mixture of 3-amino-1-(trans-4-cyanotetrahydro-2H-pyran-3-yl)pyrazole-4-carboxamide (500 mg, 2.13 mmol, 1 eq) and 6-bromo-8-fluoro-2-hydroxy-1,2-benzoxaborinine (516 mg, 2.13 mmol, 1 eq) in i-PrOH (12 mL) was added t-BuXphos (162 mg, 383 umol, 0.18 eq), KOAc (417 mg, 4.25 mmol, 2 eq) and Pd₂(dba)₃ (175 mg, 191 umol, 0.09 eq) in one portion at 20° C. under N₂. The mixture was heated and stirred at 80° C. for 12 h. LCMS showed the reaction was completed and desired MS observed. 2 parallel reactions were combined for work up. The mixture was filtered and the filtrate concentrated in vacuum to give a residue. The residue was dissolved in H₂O (20 mL), adjusted pH to 7 with 2H HCl at 0° C., and then extracted with EtOAc (10 mL×3). The combined organic layers were washed with brine (10 mL×3), dried over Na₂SO₄, filtered and concentrated under reduced pressure to give a residue. The residue was triturated with DCM (20 mL) at 25° C. to give 1-(trans-4-cyanotetrahydro-2H-pyran-3-yl)-3-[(8-fluoro-2-hydroxy-1,2-benzoxaborinin-6-yl)amino]pyrazole-4-carboxamide (600 mg, 33.8% yield, 95.1% purity) as a yellow solid, which was further separated by SFC (column: DAICEL CHIRALPAK IC (250 mm*30 mm, 10 um); mobile phase: [Neu-ETOH]; B %: 35%-35%, 10 min) to give 1-[trans-4-cyanotetrahydro-2H-pyran-3-yl]-3-[(8-fluoro-2-hydroxy-1,2-benzoxaborinin-6-yl)amino]pyrazole-4-carboxamide (stereoisomer one) (200 mg, 11.5% yield, 97.1% purity, 100% ee, first peak, Rt=1.822 min) as a yellow solid. ¹H NMR (DMSO-hd 6, 400 MHz) δ 9.18 (s, 1H), 9.12 (s, 1H), 8.30 (s, 1H), 7.81 (d, J=11.6 Hz, 1H), 7.76-7.65 (m, 2H), 7.41 (s, 1H), 7.20 (br s, 1H), 6.18 (d, J=12.0 Hz, 1H), 4.57 (td, J=10.0 Hz, 1H), 4.03 (dd, J=11.2 Hz, 4.0 Hz, 1H), 3.91 (br d, J=10.4 Hz, 1H) 3.75-3.66 (m, 2H), 3.51 (t, J=11.6 Hz, 1H), 2.20-2.12 (m, 1H), 2.04-1.95 (m, 1H). MS (ESI): mass calculated for C₁₈H₁₇BFN₅O₄ 397.14, m/z found 398.2 [M+H]⁺. HPLC: 97.13% (220 nm), 98.26% (254 nm) and 1-[trans-4-cyanotetrahydro-2H-pyran-3-yl]-3-[(8-fluoro-2-hydroxy-1,2-benzoxaborinin-6-yl)amino]pyrazole-4-carboxamide (stereoisomer two) (181.7 mg, 10.5% yield, 98.0% purity, 100% ee, second peak, Rt=2.151 min) as a yellow solid. ¹H NMR (DMSO-hd 6, 400 MHz) δ 9.21 (s, 1H), 9.12 (s, 1H), 8.30 (s, 1H), 7.81 (d, J=11.2 Hz, 1H), 7.77-7.65 (m, 2H), 7.41 (s, 1H), 7.20 (br s, 1H), 6.18 (d, J=12.0 Hz, 1H), 4.57 (td, J=10.4 Hz, 1H), 4.03 (dd, J=10.8 Hz, 3.6 Hz, 1H), 3.96-3.83 (m, 1H) 3.75-3.66 (m, 2H), 3.51 (t, J=12.4 Hz, 1H), 2.20-2.15 (m, 1H), 2.04-1.95 (m, 1H). MS (ESI): mass calculated for C₁₈H₁₇BFN₅O₄ 397.14, m/z found 398.2 [M+H]⁺. HPLC: 98.00% (220 nm), 99.19% (254 nm).

45. Preparation of 1-[trans-2-cyanocyclopentyl]-3-[(8-fluoro-2-hydroxy-3-methyl-1,2-benzoxaborinin-6-yl)amino]pyrazole-4-carboxamide

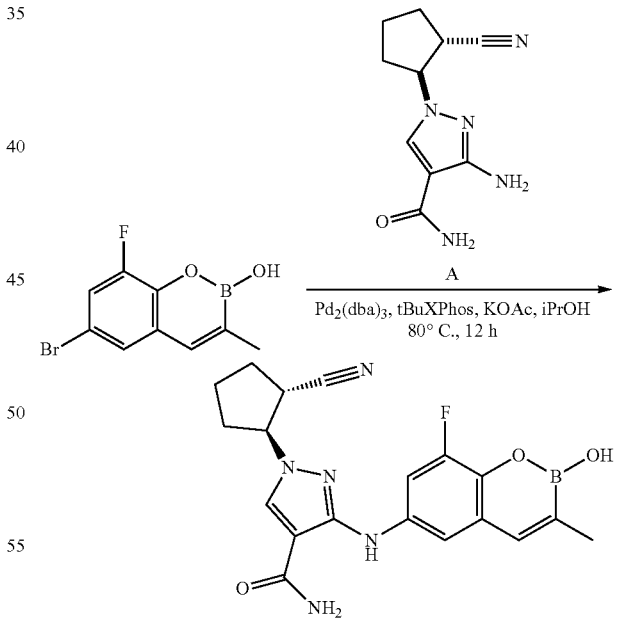

To a mixture of 6-bromo-8-fluoro-2-hydroxy-3-methyl-1,2-benzoxaborinine (500 mg, 1.95 mmol, 1 eq) and 3-amino-1-(trans-2-cyanocyclopentyl)pyrazole-4-carboxamide (513 mg, 2.34 mmol, 1.2 eq) in i-PrOH (10 mL) was added t-Bu Xphos (165 mg, 390 umol, 0.2 eq), KOAc (478 mg, 4.88 mmol, 2.5 eq) and Pd₂(dba)₃ (178 mg, 195 umol, 0.1 eq) in one portion at 20° C. under N₂. The mixture was heated to 80° C. and stirred at 80° C. for 12 h. LCMS showed the reaction was completed and desired MS observed. The reaction mixture was filtered and concentrated under reduced pressure to give a residue. The residue was purified by prep-HPLC (column: Phenomenex luna C18 (250*70 mm, 15 um); mobile phase: [water(HCl)-ACN]; B %: 25%-55%, 20 min) to give desired compound (1.00 g, yield 52%, purity 95.3%) as a white solid, which was further separated by SFC (condition: column: DAICEL CHIRALPAK IC (250 mm*30 mm, 10 um); mobile phase: [Neu-IPA]; B %: 40%-40%, 10 min) to give 1-[trans-2-cyanocyclopentyl]-3-[(8-fluoro-2-hydroxy-3-methyl-1,2-benzoxaborinin-6-yl) amino] pyrazole-4-carboxamide (stereoisomer one) (223 mg, 14.5% yield, 100% ee, first peak, Rt=2.034 min) as a white solid. 1H NMR (DMSO-hd 6, 400 MHz) δ 9.12 (s, 1H), 9.09 (s, 1H), 8.29 (s, 1H), 7.62 (dd, J=2.4, 13.2 Hz, 2H), 7.45 (s, 1H), 7.35 (d, J=1.2 Hz, 1H), 7.15 (br s, 1H), 4.88 (q, J=8.0 Hz, 1H), 3.42-3.41 (m, 1H), 2.34-2.33 (m, 1H), 2.23-2.19 (m, 1H), 2.12-2.05 (m, 1H), 1.95 (d, J=0.8 Hz, 3H), 1.97-1.89 (m, 3H). MS (ESI): mass calculated for $C_{19}H_{19}BFN_5O_3$, 395.20, m/z found 396.2 $[M+H]^+$. HPLC: 98.72% (220 nm), 99.54 (254 nm). and 1-[trans-2-cyanocyclopentyl]-3-[(8-fluoro-2-hydroxy-3-methyl-1,2-benzoxaborinin-6-yl)amino]pyrazole-4-carboxamide (stereoisomer two) (210 mg, 13.6% yield, 99.7% ee, second peak, Rt=2.291 min) as a white solid. 1H NMR (DMSO-hd 6, 400 MHz) δ 9.12 (s, 1H), 9.09 (s, 1H), 8.29 (s, 1H), 7.62 (dd, J=2.4, 13.2 Hz, 2H), 7.46 (s, 1H), 7.35 (d, J=1.2 Hz, 1H), 7.16 (br s, 1H), 4.88 (q, J=8.0 Hz, 1H), 3.42-3.40 (m, 1H), 2.34-2.33 (m, 1H), 2.27-2.19 (m, 1H), 2.12-2.01 (m, 1H), 1.95 (d, J=0.8 Hz, 3H), 1.95-1.89 (m, 3H). MS (ESI): mass calculated for $C_{19}H_{19}BFN_5O_3$, 395.20, m/z found 396.2 $[M+H]^+$. HPLC: 96.61% (220 nm), 99.33%(254 nm).

46. Preparation of 1-(trans-4-cyanotetrahydro-2H-pyran-3-yl)-3-((2-hydroxy-7-methyl-2H-benzo[e][1,2]oxaborinin-6-yl)amino)-1H-pyrazole-4-carboxamide

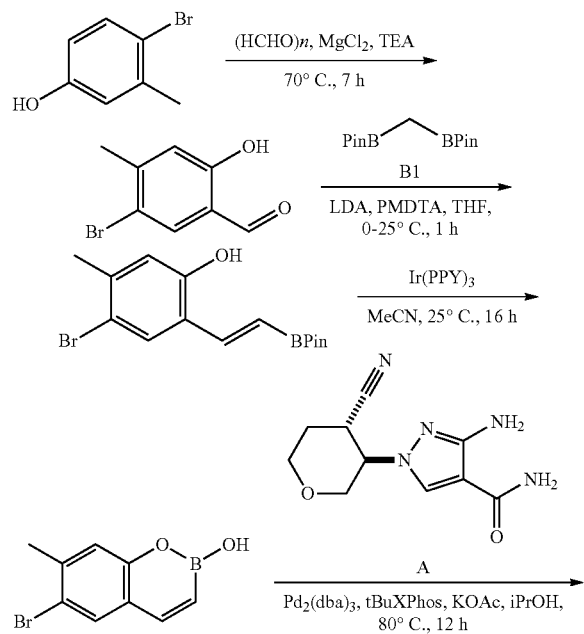

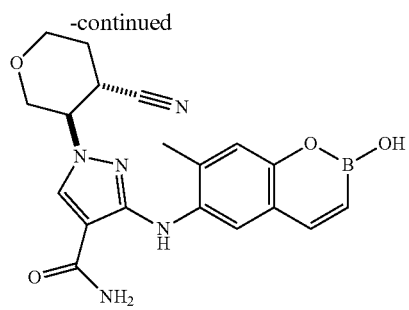

46.1 Preparation of 5-bromo-2-hydroxy-4-methylbenzaldehyde

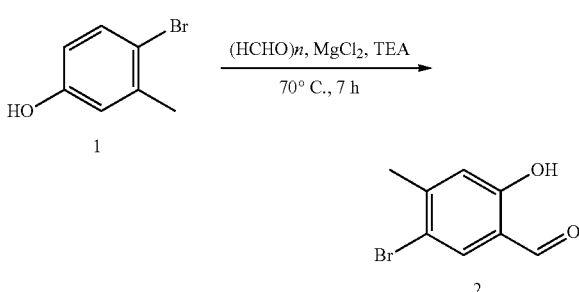

A mixture of 4-bromo-3-methyl-phenol (10 g, 53.4 mmol, 1 eq), HCHO (8.0 g, 267 mmol, 5 eq), TEA (10.8 g, 106 mmol, 2 eq) and $MgCl_2$ (7.6 g, 80.2 mmol, 1.5 eq) in MeCN (100 mL) was degassed and purged with $N_2$ for 3 times. The mixture was stirred at 70° C. for 7 hrs under $N_2$ atmosphere. TLC showed the reaction was completed. The reaction mixture was quenched with $H_2O$ (100 mL) and extracted with EtOAc (50 mL×3). The combined organic layers were washed with brine (50 mL), dried over anhydrous $Na_2SO_4$, filtered and concentrated under reduced pressure to give a residue. The residue was purified by silica gel column chromatography (Petroleum ether:EtOAc=100:1 to 10:1) to give 5-bromo-2-hydroxy-4-methyl-benzaldehyde (10 g, 86.9% yield) as a yellow solid. $^1$H NMR (400 MHz, CHLOROFORM-d) δ=10.87 (s, 1H), 9.80 (s, 1H), 7.69 (s, 1H), 6.91 (s, 1H), 2.43 (s, 3H).

46.2 Preparation of 4-bromo-5-methyl-2-(2-(4,4,5,5-tetramethyl-1,3,2-dioxaborolan-2-yl)vinyl)phenol

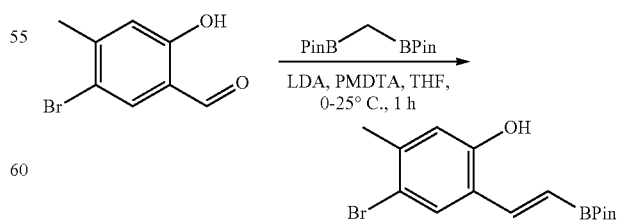

To a mixture of LDA (2 M, 45 mL, 2.5 eq) in THF (100 mL) was added N'-[2-(dimethylamino)ethyl]-N,N,N'-trimethylethane-1,2-diamine (12.5 g, 72.5 mmol, 2 eq) and a solution of 4,4,5,5-tetramethyl-2-[(4,4,5,5-tetramethyl-1,3, 2-dioxaborolan-2-yl)methyl]-1,3,2-dioxaborolane (19.4 g, 72.5 mmol, 2 eq) in THF (100 mL) at 0° C. under N₂. The mixture was stirred at 0° C. for 20 min. Then dropwise added a solution of 5-bromo-2-hydroxy-4-methyl-benzaldehyde (7.8 g, 36.2 mmol, 1 eq) in THF (100 mL) at 25° C., the mixture was stirred at 25° C. for 40 min. TLC showed the reaction was completed. The reaction mixture was diluted with aq·NH₄Cl (200 mL) and extracted with EtOAc (200 mL×3). The combined organic layers were washed with brine (500 mL), dried over anhydrous Na₂SO₄, filtered and concentrated under reduced pressure to give a residue. The residue was purified by silica gel column chromatography (Petroleum ether:EtOAc=100:1 to 10:1) to give 4-bromo-5-methyl-2-[(E)-2-(4,4,5,5-tetramethyl-1,3,2-dioxaborolan-2-yl)vinyl]phenol (5.5 g, 44.7% yield) as a yellow solid. ¹H NMR (400 MHz, CHLOROFORM-d) δ=7.59 (s, 1H), 7.55 (d, J=18.4 Hz, 1H), 6.70 (s, 1H), 6.11 (d, J=18.4 Hz, 1H), 2.31 (s, 3H), 1.31 (s, 12H).

46.3 Preparation of
6-bromo-2-hydroxy-7-methyl-1,2-benzoxaborinine

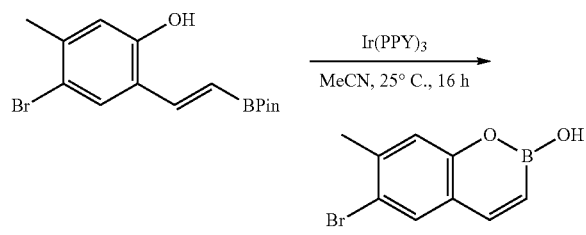

To a mixture of 4-bromo-5-methyl-2-[(E)-2-(4,4,5,5-tetramethyl-1,3,2-dioxaborolan-2-yl)vinyl]phenol (5.4 g, 15.9 mmol, 1 eq) in MCCN (20 mL) was added tris[2-(2-pyridyl)phenyl]iridium (260 mg, 0.398 mmol, 0.025 eq) in one portion at 25° C. under N₂. The reaction was stirred and irradiated using 34W blue LED lamps for 16 h. TLC showed the reaction was completed. The reaction mixture was filtered and the filter cake was washed with 5 mL of MeCN. The filter cake was dried in vacuum to give 6-bromo-2-hydroxy-7-methyl-1,2-benzoxaborinine (3.3 g, 86.7% yield) as a yellow solid.

46.4 Preparation of chiral 1-(trans-4-cyanotetrahydro-2H-pyran-3-yl)-3-((2-hydroxy-7-methyl-2H-benzo[e][1,2]oxaborinin-6-yl)amino)-1H-pyrazole-4-carboxamide

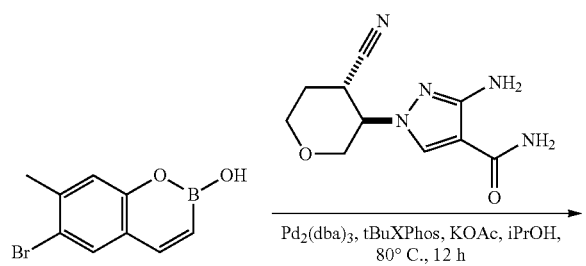

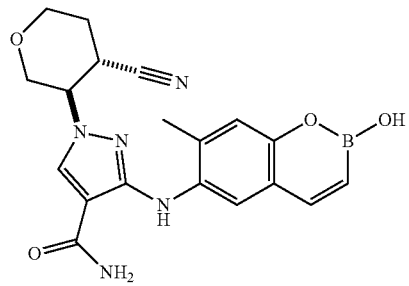

A mixture of 6-bromo-2-hydroxy-7-methyl-1,2-benzoxaborinine (3.3 g, 13.8 mmol, 1 eq), 3-amino-1-[trans-4-cyanotetrahydro-2H-pyran-3-yl]pyrazole-4-carboxamide (3.2 g, 13.8 mmol, 1 eq), KOAc (2.7 g, 27.6 mmol, 2 eq), t-Bu Xphos (1.2 g, 2.76 mmol, 0.2 eq) and Pd₂(dba)₃ (1.3 g, 1.38 mmol, 0.1 eq) in i-PrOH (50 mL) was degassed and purged with N₂ for 3 times, and then the mixture was stirred at 80° C. for 12 h under N₂ atmosphere. LCMS showed the reaction was completed and desired MS observed. The reaction mixture was quenched with H₂O (100 mL) and extracted with EtOAc (50 mL×3). The combined organic layers were washed with brine (50 mL), dried over anhydrous Na₂SO₄, filtered and concentrated under reduced pressure. The residue was purified by prep-HPLC (column: Phenomenex luna C18 (250*70 mm, 15 um); mobile phase: [water (HCl)-ACN]; B %: 15%-45%, 20 min) to give 1-(trans-4-cyanotetrahydro-2H-pyran-3-yl)-3-((2-hydroxy-7-methyl-2H-benzo[e][1,2]oxaborinin-6-yl)amino)-1H-pyrazole-4-carboxamide (600 mg, 98% purity) as a white solid. The product was further separated by SFC (column: REGIS(S,S)WHELK-O1 (250 mm*25 mm, 10 um); mobile phase: [Neu-ETOH]; B %: 55%-55%, 6 min) to give 1-(trans-4-cyanotetrahydro-2H-pyran-3-yl)-3-((2-hydroxy-7-methyl-2H-benzo[e][1,2]oxaborinin-6-yl)amino)-1H-pyrazole-4-carboxamide (stereoisomer one) (236 mg, 47.2% yield, 99.1% purity, 99.7% ee, first peak, Rt=1.513 min) as a white solid ¹H NMR (400 MHz, DMSO-d6) δ=9.22 (s, 1H), 8.73 (s, 1H), 8.28 (d, J=17.6 Hz, 2H), 7.84 (d, J=11.4 Hz, 1H), 7.79-7.66 (m, 1H), 7.16 (br d, J=1.2 Hz, 1H), 7.07 (s, 1H), 6.05 (d, J=11.4 Hz, 1H), 4.57 (dt, J=4.4, 10.2 Hz, 1H), 4.05 (dd, J=4.4, 11.2 Hz, 1H), 3.96-3.88 (m, 1H), 3.77-3.67 (m, 2H), 3.57-3.47 (m, 1H), 2.31 (s, 3H), 2.22-2.11 (m, 1H), 2.06-1.93 (m, 1H), MS (ESI): mass calculated for $C_{19}H_{20}BN_5O_4$, 393.16, m/z found 394.2[M+H]⁺. HPLC: 99.19% (220 nm), 99.51 (254 nm), and 1-(trans-4-cyanotetrahydro-2H-pyran-3-yl)-3-((2-hydroxy-7-methyl-2H-benzo[e][1,2]oxaborinin-6-yl)amino)-1H-pyrazole-4-carboxamide (stereoisomer two) (241.5 mg, 614 umol, 48.3% yield, 98.0% purity, 98.7% ee, second peak, Rt=1.683 min) as a white solid.

¹H NMR (400 MHz, DMSO-d6) δ=9.22 (s, 1H), 8.74 (s, 1H), 8.31 (s, 1H), 8.26 (s, 1H), 7.85 (d, J=12.0 Hz, 1H), 7.80-7.62 (m, 1H), 7.27-7.10 (m, 1H), 7.07 (s, 1H), 6.05 (d, J=11.8 Hz, 1H), 4.58 (dt, J=4.4, 10.2 Hz, 1H), 4.05 (dd, J=4.4, 11.2 Hz, 1H), 3.98-3.88 (m, 1H), 3.79-3.67 (m, 2H), 3.57-3.48 (m, 1H), 2.31 (s, 3H), 2.22-2.13 (m, 1H), 2.06-1.94 (m, 1H), MS (ESI): mass calculated for $C_{19}H_{20}BN_5O_4$, 393.16, m/z found 394.1[M+H]+, HPLC: 98.09% (220 nm), 98.82 (254 nm).

47. Preparation of 1-(trans-4-cyanotetrahydro-2H-pyran-3-yl)-3-((2-hydroxy-4,8-dimethyl-2H-benzo[e][1,2]oxaborinin-6-yl)amino)-1H-pyrazole-4-carboxamide

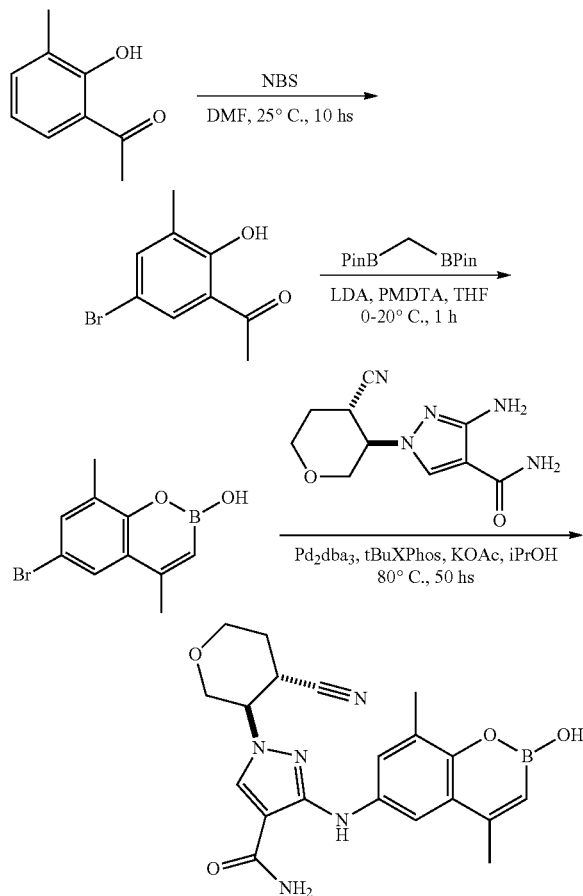

47.1 Preparation of 1-(5-bromo-2-hydroxy-3-methylphenyl)ethan-1-one

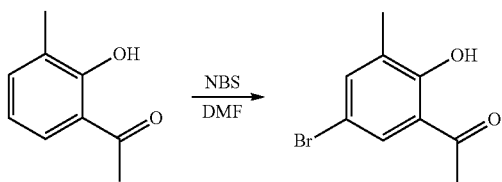

NBS (10.5 g, 59.4 mmol, 1.05 eq was added to the solution of 1-(2-hydroxy-3-methyl-phenyl)ethanone (8.5 g, 56.6 mmol, 1 eq) in DMF (20 mL) at 25° C. The result mixture was stirred at 25° C. for 10 h. TLC showed the reaction was completed. Brine (250 mL) was added to the solution, and then the mixture was extracted with EtOAc (150 mL×2). The combined organic layers were dried over Na$_2$SO$_4$ and concentrated to give yellow solid, which was purified by silica gel chromatography (Petroleum ether/Ethyl acetate=100:1 to 10:1) to give 1-(5-bromo-2-hydroxy-3-methyl-phenyl)ethanone (8 g, 61.7% yield) as light-yellow solid.

47.2 Preparation of 6-bromo-4,8-dimethyl-2H-benzo[e][1,2]oxaborinin-2-ol

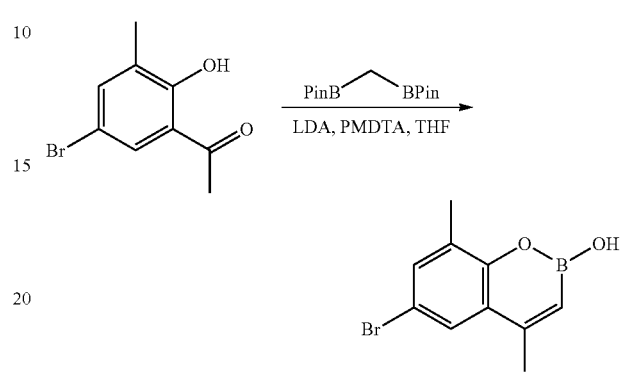

To a solution of LDA (2 M, 10.9 mL, 2.5 eq) in THF (20 mL) was added N'-[2-(dimethylamino)ethyl]-N,N,N'-trimethylethane-1,2-diamine (PMDTA, 3.03 g, 17.5 mmol, 3.65 mL, 2 eq) and a solution of 4,4,5,5-tetramethyl-2-[(4,4,5,5-tetramethyl-1,3,2-dioxaborolan-2-yl)methyl]-1,3,2-dioxaborolane (B1, 4.68 g, 17.5 mmol, 2 eq) in THF (4 mL) at 0° C. under N$_2$. The mixture was stirred at 0° C. for 20 min. Then to this was added dropwise a solution of 1-(5-bromo-2-hydroxy-3-methyl-phenyl)ethanone (2 g, 8.73 mmol, 1 eq) in THF (2 mL) at 25° C. The mixture was stirred at 25° C. for 40 min. LCMS showed the reaction was completed and desired MS observed. The mixture was quenched by sat. aq. NH$_4$Cl (50 mL) and adjusted pH=5-6 with HCl (2N) at 0° C. The suspension was extracted with EtOAc (30 mL×2). The combined organic layers were washed by brine (50 mL×2), dried over Na$_2$SO$_4$, filtered and concentrated under reduced pressure to get the residue. The residue was purified by flash silica gel chromatography (ISCO®; 80 g SepaFlash® Silica Flash Column, Eluent of 5-7% Ethyl acetate/Petroleum ether gradient @ 100 mL/min) to give 6-bromo-2-hydroxy-4,8-dimethyl-1,2-benzoxaborinine (0.5 g, 22.6% yield) as a white solid. $^1$H NMR (400 MHz, DMSO-d6) δ 8.92 (s, 1H), 7.57 (s, 1H), 7.48 (s, 1H), 5.97 (s, 1H), 2.48-2.28 (s, 6H).

47.3 Preparation of chiral 1-(trans-4-cyanotetrahydro-2H-pyran-3-yl)-3-((2-hydroxy-4,8-dimethyl-2H-benzo[e][1,2]oxaborinin-6-yl)amino)-1H-pyrazole-4-carboxamide

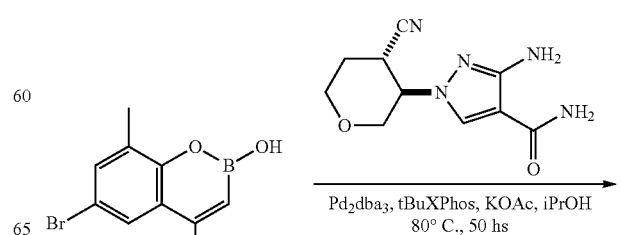

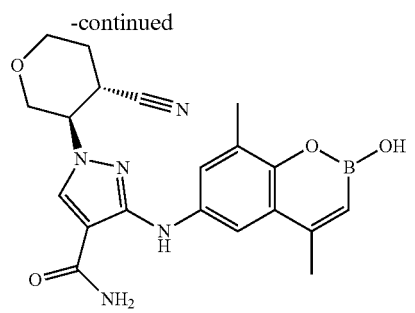

To a mixture of 6-bromo-4,8-dimethyl-2H-benzo[e][1,2]oxaborinin-2-ol (2.0 g, 7.9 mmol, 1.0 eq) and 3-amino-1-(trans-4-cyanotetrahydropyran-3-yl)pyrazole-4-carboxamide (1.86 g, 7.9 mmol, 1.0 eq) in i-PrOH (30 mL) was added Pd$_2$(dba)$_3$ (362 mg, 395 umol, 0.05 eq), t-Bu Xphos (335 mg, 790 umol, 0.1 eq) and KOAc (1.55 g, 15.8 mmol, 2.0 eq) in one portion at 25° C. under N$_2$. The mixture was heated to 80° C. and stirred at 80° C. for 50 h. LCMS showed the reaction was completed and desired MS observed. The mixture was quenched with H$_2$O (2 mL) at 25° C., filtered and concentrated under reduced pressure to get the residue. The residue was purified by as purified by silica gel column chromatography (Petroleum ether/Ethyl acetate=1:1) to afford the desired as a yellow solid, which was further separated by SFC (REGIS(S,S)WHELK-O1 (250 mm*25 mm, 10 um); mobile phase: [Neu-IPA]; B %: 50%-50%, 7 min) to give two isomers: 1-[trans-4-cyanotetrahydro-2H-pyran-3-yl]-3-[(2-hydroxy-4,8-dimethyl-1,2-benzoxaborinin-6-yl)amino]pyrazole-4-carboxamide (stereoisomer one) (257.9 mg, 27.1% yield, ee 100%, first peak, Rt=1.487 min) as a white solid $^1$H NMR (400 MHz, DMSO-d6) δ 9.06 (s, 1H), 8.66 (s, 1H), 8.35 (s, 1H), 7.96 (s, 1H), 7.76 (br s, 1H), 7.35 (s, 1H), 7.23 (br s, 1H), 5.98 (s, 1H), 4.70-4.55 (m, 1H), 4.15-4.10 (m, 1H), 4.05-3.95 (m, 1H), 3.85-3.65 (m, 2H), 3.55-3.45 (m, 1H), 2.47 (s, 3H), 2.40 (s, 3H), 2.30-2.20 (m, 1H), 2.10-1.93 (m, 1H) MS (ESI): mass calculated for C$_{20}$H$_{22}$BN$_5$O$_4$, 407.18, m/z found 408.2[M+H]$^+$. HPLC: 95.68% (220 nm), 99.77% (254 nm) and 1-[trans-4-cyanotetrahydro2H-pyran-3-yl]-3-[(2-hydroxy-4,8-dimethyl-1,2-benzoxaborinin-6-yl)amino]pyrazole-4-carboxamide (stereoisomer two) (280 mg, 29.4% yield, 99.5% ee, second peak, Rt=1.650 min) as a white solid $^1$H NMR (400 MHz, DMSO-d6) δ 9.00 (s, 1H), 8.59 (s, 1H), 8.29 (s, 1H), 7.90 (s, 1H), 7.71 (br s, 1H), 7.29 (s, 1H), 7.17 (br s, 1H), 5.93 (s, 1H), 4.65-4.50 (m, 1H), 4.10-4.05 (m, 1H), 4.00-3.90 (m, 1H), 3.80-3.60 (m, 2H), 3.50-3.40 (m, 1H), 2.41 (s, 3H), 2.35 (s, 3H), 2.25-2.15 (m, 1H), 2.05-1.90 (m, 1H). MS (ESI): mass calculated for C$_{20}$H$_{22}$BN$_5$O$_4$, 407.18, m/z found 408.2[M+H]$^+$. HPLC: 97.77% (220 nm), 97.57% (254 nm).

48. Preparation of 1-(trans-4-cyanotetrahydro-2H-pyran-3-yl)-3-((2-hydroxy-3-isopropyl-2H-benzo[e][1,2]oxaborinin-6-yl) amino)-1H-pyrazole-4-carboxamide

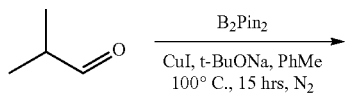

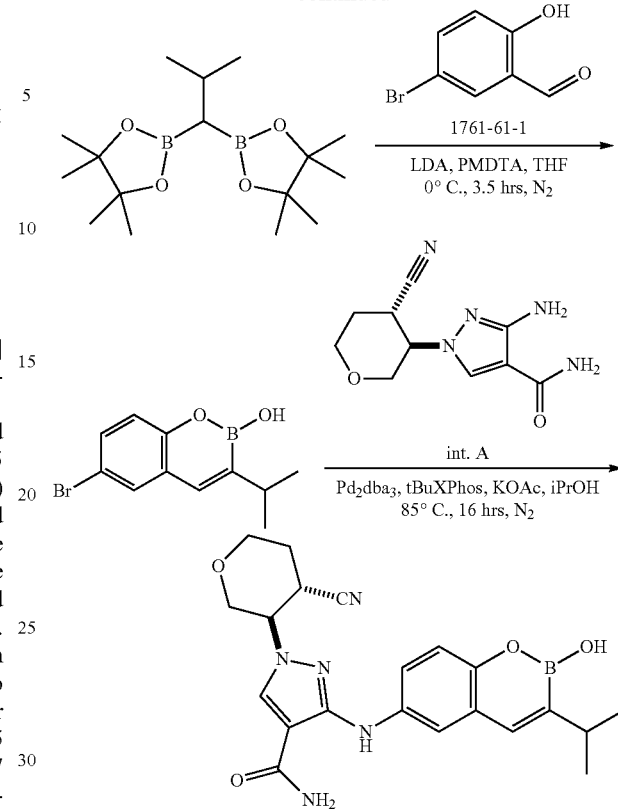

48.1 Preparation of 2,2'-(2-methylpropane-1,1-diyl) bis (4,4,5,5-tetramethyl-1,3,2-dioxaborolane)

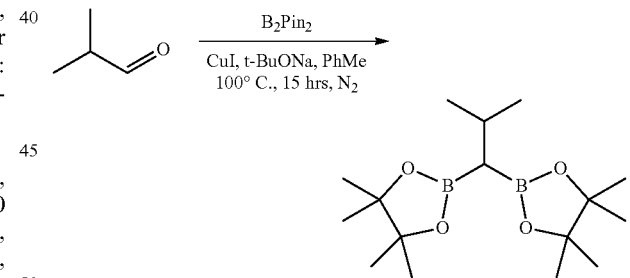

A mixture of 2-methylpropanal (0.5 g, 6.93 mmol, 632 uL, 1 eq), 4,4,5,5-tetramethyl-2-(4,4,5,5-tetramethyl-1,3,2-dioxaborolan-2-yl)-1,3,2-dioxaborolane (B$_2$Pin$_2$, 3.87 g, 15.2 mmol, 2.2 eq), CuI (132 mg, 693 umol, 0.1 eq) and t-BuONa (866 mg, 9.01 mmol, 1.3 eq) in toluene (30 mL) was degassed and purged with N$_2$ for 3 times, and then the mixture was stirred at 100° C. for 15 hours under N$_2$ atmosphere. 10 parallel reactions were combined for work up. TLC (Petroleum ether:Ethyl acetate=10:1) indicated 2-methylpropanal was consumed completely and one new spot formed. The reaction was cooled to room temperature and filtered. The filtrate was concentrated under reduced pressure to give a residue. The residue was purified by flash silica gel chromatography (ISCO®; 220 g SepaFlash® Silica Flash Column, Eluent of 0-15% Ethyl acetate/Petroleum ether gradient @ 150 mL/min) to give 2,2'-(2-methylpropane-1,1-diyl) bis(4,4,5,5-tetramethyl-1,3,2-dioxaborolane) (6 g, 34.8% yield) as colorless oil. ¹H NMR (CDCl₃, 400 MHz) δ 2.11-1.98 (m, 1H), 1.23 (d, J=3.6 Hz, 24H), 0.96 (d, J=6.8 Hz, 6H), 0.61 (br d, J=10.1 Hz, 1H).

48.2 Preparation of 6-bromo-3-isopropyl-2H-benzo[e][1,2]oxaborinin-2-ol

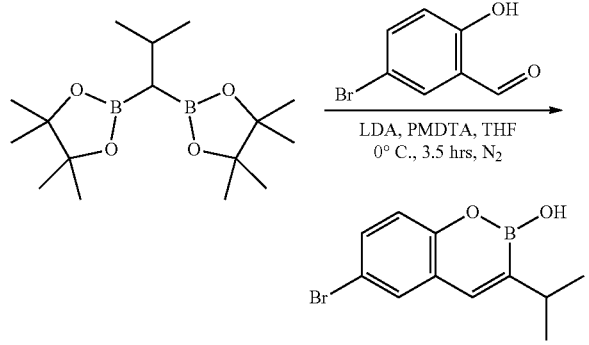

To a solution of LDA (2 M, 6.5 mL, 2 eq) in THF (10 mL) was added N'-[2-(dimethylamino)ethyl]-N,N,N'-trimethylethane-1,2-diamine (2.24 g, 12.9 mmol, 2.70 mL, 2 eq) and 2,2'-(2-methylpropane-1,1-diyl) bis(4,4,5,5-tetramethyl-1,3,2-dioxaborolane) (4 g, 12.9 mmol, 2 eq) in portions at 0° C. over a period of 10 minutes under N₂. The mixture was stirred at 0° C. for 20 minutes. Then a solution of 5-bromo-2-hydroxy-benzaldehyde (1.3 g, 6.47 mmol, 1 eq) in THF (5 mL) was added to the above mixture at 0° C., the resulting mixture was stirred at 0° C. for 3 hours. TLC (Petroleum ether:Ethyl acetate=5:1, R_f=0.6) indicated new spot formed. The reaction mixture was quenched by addition of sat. aq. NH₄Cl (30 mL) at 0° C., and then extracted with EtOAc (30 mL×3). The combined organic layers were washed with brine (30 mL×3), dried over Na₂SO₄, filtered and concentrated under reduced pressure to give a residue. The residue was purified by flash silica gel chromatography (ISCO®; 40 g SepaFlash® Silica Flash Column, Eluent of 0~10% Ethyl acetate/Petroleum ether gradient @ 60 mL/min) to give 6-bromo-3-isopropyl-2H-benzo[e][1,2] oxaborinin-2-ol (1.2 g, crude) as yellow oil. ¹H NMR (DMSO-hd 6, 400 MHz) δ 9.07 (s, 1H), 7.70 (d, J=2.4 Hz, 1H), 7.47-7.42 (m, 2H), 7.13 (d, J=8.8 Hz, 1H), 2.80-2.55 (m, 1H), 1.15 (d, J=1.6 Hz, 6H). MS (ESI): mass calculated for C₁₁H₁₂BBrO₂ 266.01; m/z found 265.0 [M–H].

48.3 Preparation of 1-(trans-4-cyanotetrahydro-2H-pyran-3-yl)-3-((2-hydroxy-3-isopropyl-2H-benzo[e][1,2] oxaborinin-6-yl) amino)-1H-pyrazole-4-carboxamide

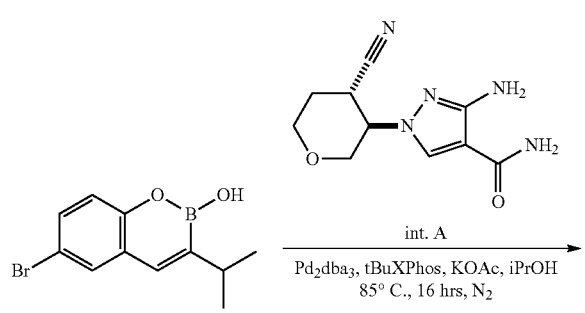

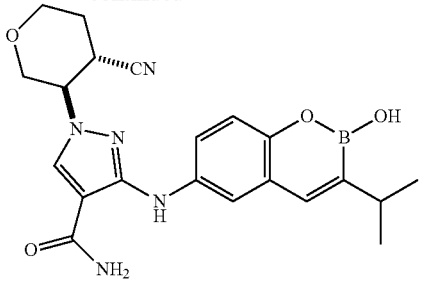

A mixture of 3-amino-1-(trans-4-cyanotetrahydro-2H-pyran-3-yl)-1H-pyrazole-4-carboxamide (0.9 g, 3.83 mmol, 1 eq), 6-bromo-3-isopropyl-2H-benzo[e] [1,2] oxaborinin-2-ol (1.12 g, 4.21 mmol, 1.1 eq), KOAc (563 mg, 5.74 mmol, 1.5 eq), Pd₂(dba)₃ (350 mg, 382 umol, 0.1 eq) and t-BuXphos (324 mg, 765.17 umol, 0.2 eq) in i-PrOH (20 mL) was degassed and purged with N₂ for 3 times, and then the mixture was stirred at 85° C. for 16 hours under N₂ atmosphere. LCMS showed the reaction was completed and desired MS observed. The reaction was cooled to room temperature and filtered. The filtrate was concentrated under reduced pressure to give a residue. The residue was purified by flash silica gel chromatography (ISCO®; 220 g SepaFlash® Silica Flash Column, Eluent of 0-15% Ethyl acetate/Petroleum ether gradient @ 150 mL/min) to give 1-(trans-4-cyanotetrahydro-2H-pyran-3-yl)-3-((2-hydroxy-3-isopropyl-2H-benzo[e] [1,2]oxaborinin-6-yl) amino)-1H-pyrazole-4-carboxamide (1.2 g, 33.8% yield, 91% purity) as yellow solid. MS (ESI): mass calculated for C₂₁H₂₄BN₅O₄ 421.19; m/z found 420.2 [M–H]⁻. 1-(trans-4-cyanotetrahydro-2H-pyran-3-yl)-3-((2-hydroxy-3-isopropyl-2H-benzo[e] [1,2] oxaborinin-6-yl) amino)-1H-pyrazole-4-carboxamide (1.2 g) was separated by SFC to give 1-(trans-4-cyanotetrahydro-2H-pyran-3-yl)-3-((2-hydroxy-3-isopropyl-2H-benzo[e] [1,2] oxaborinin-6-yl) amino)-1H-pyrazole-4-carboxamide (stereoisomer one) (454.1 mg, 36.8% yield, 97.4% purity, 100% ee, first peak, Rt=1.232 min) as a white solid. ¹H NMR (DMSO-hd 6, 400 MHz) 9.07 (s, 1H), 8.74 (s, 1H), 8.28 (s, 1H), 7.69 (br s, 1H), 7.57 (d, J=2.8 Hz, 1H), 7.52 (dd, J=2.8, 8.8 Hz, 1H), 7.44 (s, 1H), 7.16 (br s, 1H), 7.09 (d, J=8.8 Hz, 1H), 4.55 (dt, J=4.4, 10.4 Hz, 1H), 4.04 (dd, J=4.4, 11.3 Hz, 1H), 3.92 (br d, J=10.4 Hz, 1H), 3.74-3.62 (m, 2H), 3.58-3.45 (m, 1H), 2.81-2.70 (m, 1H), 2.16 (br d, J=9.6 Hz, 1H), 2.05-1.91 (m, 1H), 1.16 (d, J=6.8 Hz, 6H). MS (ESI): mass calculated for C₂₁H₂₄BN₅O₄ 421.19; m/z found 420.1 [M–H]⁻. HPLC: 97.46% (220 nm), 98.44% (254 nm). and 1-(trans-4-cyanotetrahydro-2H-pyran-3-yl)-3-((2-hydroxy-3-isopropyl-2H-benzo[e][1,2]oxaborinin-6-yl)amino)-1H-pyrazole-4-carboxamide (stereoisomer two) (446.8 mg, 36.3% yield, 97.4% purity, 100% ee, second peak, Rt=1.422 min) as an off-white solid. ¹H NMR (DMSO-hd 6, 400 MHz) δ 9.07 (s, 1H), 8.74 (s, 1H), 8.28 (s, 1H), 7.69 (br s, 1H), 7.57 (d, J=2.8 Hz, 1H), 7.52 (dd, J=2.8, 8.8 Hz, 1H), 7.44 (s, 1H), 7.17 (br s, 1H), 7.09 (d, J=8.8 Hz, 1H), 4.55 (dt, J=4.4, 10.4 Hz, 1H), 4.04 (dd, J=4.4, 11.2 Hz, 1H), 3.96-3.87 (m, 1H), 3.75-3.64 (m, 2H), 3.56-3.44 (m, 1H), 2.75 (td, J=6.8, 13.2 Hz, 1H), 2.16 (br d, J=9.6 Hz, 1H), 2.05-1.92 (m, 1H), 2.05-1.92 (m, 1H), 1.16 (d, J=6.8 Hz, 6H). MS (ESI): mass calculated for C₂₁H₂₄BN₅O₄ 421.19, m/z found 420.2 [M–H]⁻. HPLC: 97.48% (220 nm), 98.92% (254 nm).

49 Preparation of 1-(trans-2-cyanocyclohexyl)-3-[(2-hydroxy-3-isopropyl-1,2-benzoxaborinin-6-yl)amino]pyrazole-4-carboxamide

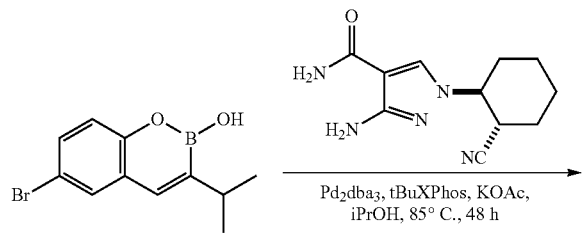

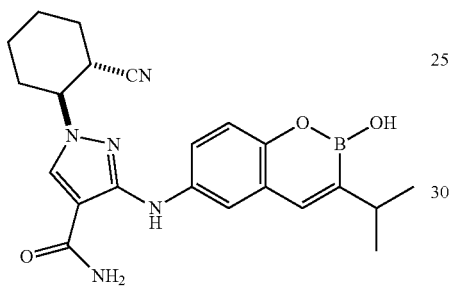

A mixture of 3-amino-1-(trans-2-cyanocyclohexyl)pyrazole-4-carboxamide (210 mg, 899 umol, 1.2 eq), 6-bromo-2-hydroxy-3-isopropyl-1,2-benzoxaborinine (200 mg, 749 umol, 1 eq), KOAc (110 mg, 1.12 mmol, 1.5 eq), $Pd_2(dba)_3$ (34 mg, 37 umol, 0.05 eq) and t-BuXphos (32 mg, 75 umol, 0.1 eq) in i-PrOH (15 mL) was degassed and purged with $N_2$ for 3 times, and then the mixture was stirred at 85° C. for 48 h under $N_2$ atmosphere. LCMS showed the reaction was completed and desired MS observed. The reaction mixture was cooled to room temperature and quenched with sat. aq. $NH_4Cl$ (0.2 mL). The resulting solution was filtered and washed with EtOH (10 mL×3). The filtrate was concentrated under reduced pressure to give a residue. The residue was purified by prep-HPLC (column: Waters Xbridge BEH C18 100*30 mm*10 um; mobile phase: [water (10 mM $NH_4HCO_3$)-ACN]; B %: 20%-50%, 10 min) to give 1-(2-cyanocyclohexyl)-3-[(2-hydroxy-3-isopropyl-1,2-benzoxaborinin-6-yl)amino] pyrazole-4-carboxamide (67.2 mg, 19.8% yield, 92.6% purity) as a yellow solid. $^1$H NMR (DMSO-$d_6$, 400 MHz) δ 9.05 (s, 1H), 8.73 (s, 1H), 8.23 (s, 1H), 7.78-7.61 (m, 1H), 7.58-7.52 (m, 2H), 7.42 (s, 1H), 7.20-7.10 (m, 1H), 7.08 (d, J=8.8 Hz, 1H), 4.36 (dt, J=3.6, 11.2 Hz, 1H), 3.30-3.24 (m, 1H), 2.80-2.70 (m, 1H), 2.18 (d, J=10.8 Hz, 1H), 2.05-1.95 (m, 1H), 1.93-1.67 (m, 4H), 1.58-1.27 (m, 2H), 1.16 (d, J=6.8 Hz, 6H). MS (ESI): mass calculated for $C_{22}H_{26}BN_5O_3$ 419.21; m/z found 418.1 [M-H]$^-$. HPLC: 92.69% (220 nm), 97.51% (254 nm).

50. Preparation of 1-(trans-2-cyanocyclopentyl)-3-[(2-hydroxy-3-isopropyl-1,2-benzoxaborinin-6-yl)amino]pyrazole-4-carboxamide

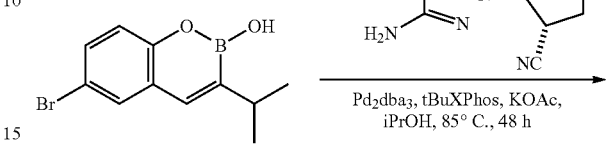

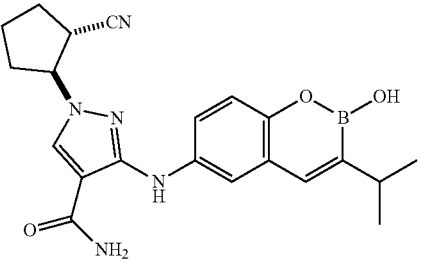

A mixture of 3-amino-1-(trans-2-cyanocyclopentyl)pyrazole-4-carboxamide (197 mg, 899 umol, 1.2 eq), 6-bromo-2-hydroxy-3-isopropyl-1,2-benzoxaborinine (200 mg, 749 umol, 1 eq), KOAc (110 mg, 1.12 mmol, 1.5 eq), $Pd_2(dba)_3$ (34 mg, 37 umol, 0.05 eq) and t-Bu Xphos (32 mg, 74.9 umol, 0.1 eq) in i-PrOH (15 mL) was degassed and purged with $N_2$ for 3 times, and then the mixture was stirred at 85° C. for 48 h under $N_2$ atmosphere. LCMS showed the reaction was completed and desired MS observed. The reaction mixture was cooled to room temperature and added sat. aq. $NH_4Cl$ (0.2 mL). The resulting solution was filtered and washed with EtOH (10 mL×3), the filtrate was concentrated under reduced pressure to give a residue. The residue was purified by prep-HPLC (column: Waters Xbridge BEH C18 100*30 mm*10 um; mobile phase: [water (10 mM $NH_4HCO_3$)-ACN]; B %: 20%-50%, 10 min) to give 1-(trans-2-cyanocyclopentyl)-3-[(2-hydroxy-3-isopropyl-1,2-benzoxaborinin-6-yl)amino]pyrazole-4-carboxamide (56.6 mg, 18.1% yield, 97.1% purity) as a yellow solid. $^1$H NMR (DMSO-$d_6$, 400 MHz) δ 9.03 (s, 1H), 8.73 (s, 1H), 8.27 (s, 1H), 7.73 (d, J=2.4 Hz, 1H), 7.60 (br s, 1H), 7.48-7.39 (m, 2H), 7.12 (br s, 1H), 7.07 (d, J=8.8 Hz, 1H), 4.90-4.83 (m, 1H), 3.47-3.37 (m, 1H), 2.81-2.70 (m, 1H), 2.33-2.20 (m, 2H), 2.13-2.04 (m, 1H), 2.00-1.85 (m, 3H), 1.15 (d, J=6.8 Hz, 6H). MS (ESI): mass calculated for $C_{21}H_{24}BN_5O3$ 405.2; m/z found 404.1 [M-H]$^-$. HPLC: 97.11% (220 nm), 98.79% (254 nm).

51. Preparation of 1-[rans-4-cyanotetrahydro-2H-pyran-3-yl]-3-[(2-hydroxy-1,2-benzoxaborinin-6-yl)amino]pyrazole-4-carboxamide

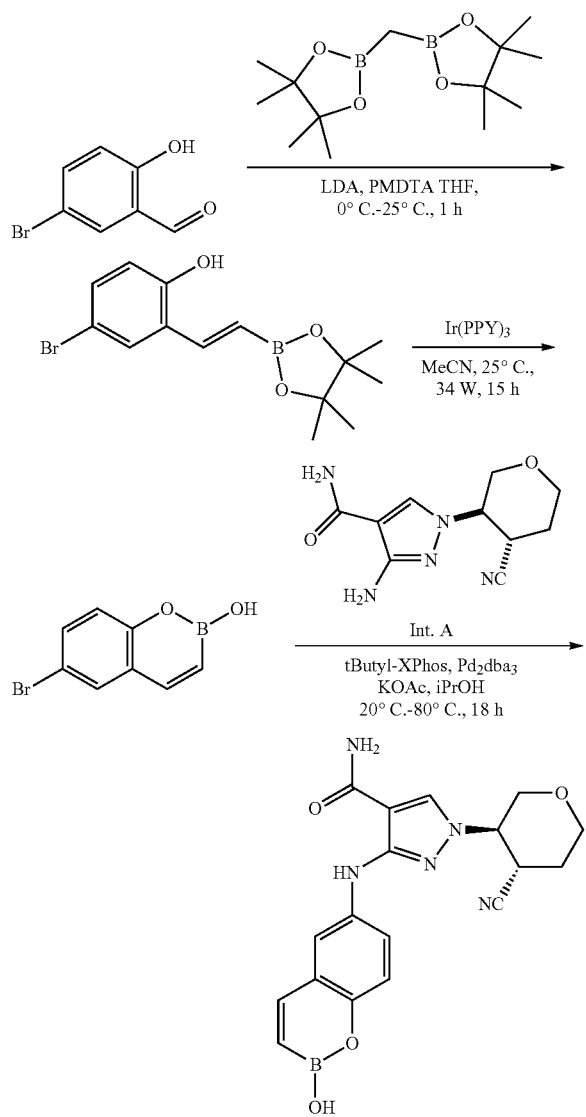

51.1 Preparation of 4-bromo-2-[(E)-2-(4,4,5,5-tetramethyl-1,3,2-dioxaborolan-2-yl) vinyl]phenol

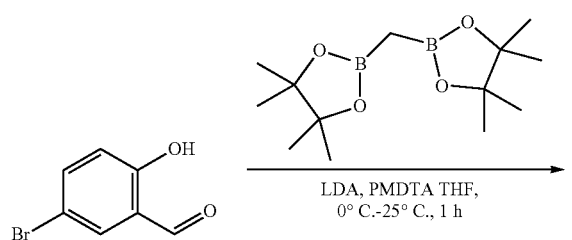

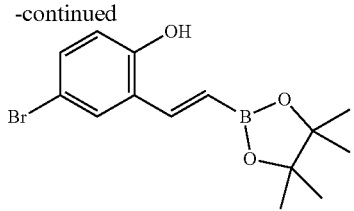

To a mixture of LDA (2 M, 27.3 mL, 2.2 eq) in THF (40 mL) was added N'-[2-(dimethylamino)ethyl]-N,N,N'-trimethyl-ethane-1,2-diamine (8.62 g, 49.8 mmol, 10.4 mL, 2 eq) and a solution of 4,4,5,5-tetramethyl-2-[(4,4,5,5-tetramethyl-1,3,2-dioxaborolan-2-yl) methyl]-1,3,2-dioxaborolane (13.3 g, 49.8 mmol, 2 eq) in THF (30 mL) at 0° C. under $N_2$. The reaction was stirred for 20 min. Then added a solution of 5-bromo-2-hydroxy-benzaldehyde (5.00 g, 24.9 mmol, 1 eq) in THF (30 mL) at 0° C. The reaction was allowed to warm to 25° C. and stirred at 25° C. for 1 h. LCMS showed the reaction was completed and desired MS observed. 2 parallel reactions were combined for work up. The mixture was quenched by sat. aq. $NH_4Cl$ (200 mL), adjusted pH to 6 with 2 N HCl and then extracted with EtOAc (80 mL×3). The combined organic layers were washed by brine (100 mL×2), dried over $Na_2SO_4$, filtered and concentrated under reduced pressure to get a residue. The residue was purified by flash silica gel chromatography (ISCO®; 220 g SepaFlash® Silica Flash Column, Eluent of 0-15% Ethyl acetate/Petroleum ether gradient @ 100 mL/min) to give 4-bromo-2-[(E)-2-(4,4,5,5-tetramethyl-1,3,2-dioxaborolan-2-yl) vinyl]phenol (12.0 g, 63.0% yield, 85% purity) as yellow oil. $^1$H NMR (CDCl$_3$, 400 MHz) δ 7.59-7.54 (m, 2H), 7.25 (dd, J=8.8 Hz, 2.8 Hz, 1H), 6.70 (d, J=8.8 Hz, 1H), 6.15 (d, J=18.8 Hz, 1H), 5.62 (br s, 1H), 1.32 (s, 12H).

51.2 Preparation of 6-bromo-2-hydroxy-1,2-benzoxaborinine

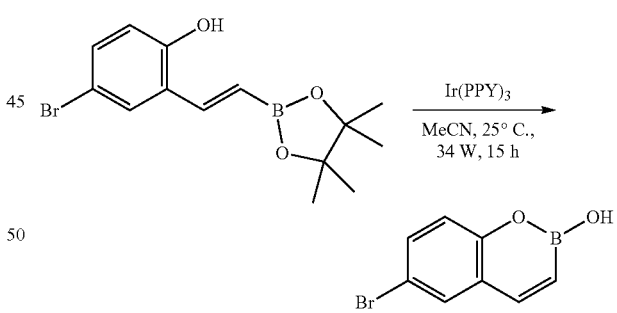

To a mixture of 4-bromo-2-[(E)-2-(4,4,5,5-tetramethyl-1,3,2-dioxaborolan-2-yl)vinyl]phenol (3 g, 7.85 mmol, 85% purity, 1 eq) in McCN (30 mL) was added tris[2-(2-pyridyl)phenyl]iridium (Ir(PPY)$_3$, 51.4 mg, 78.5 umol, 0.01 eq) in one portion at 25° C. under $N_2$. The reaction was stirred and irradiated using 34W blue LED lamps for 15 h. LCMS showed the reaction was completed and desired MS observed. The mixture was concentrated under reduced pressure to give the residue. The residue was purified by flash silica gel chromatography (ISCO®; 60 g SepaFlash® Silica Flash Column, Eluent of 0-15% Ethyl acetate/Petroleum ether gradient @ 100 mL/min) to give 6-bromo-2-hydroxy-1,2-benzoxaborinine (2.50 g, 70.8% yield) as a yellow solid. $^1$H NMR (DMSO-hd 6, 400 MHz) δ 9.14 (s, 1H), 7.79-7.75 (m, 2H), 7.53 (dd, J=8.48 Hz, 2.4 Hz, 1H), 7.19 (d, J=8.8 Hz, 1H), 6.18 (d, J=11.6 Hz, 1H).

51.3 Preparation of chiral 1-[trans-4-cyanotetrahydro-2H-pyran-3-yl]-3-[(2-hydroxy-1,2-benzoxaborinin-6-yl)amino]pyrazole-4-carboxamide

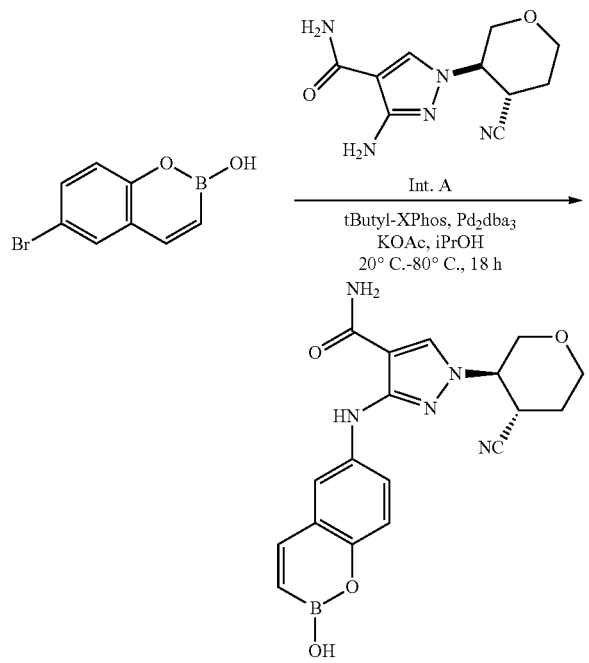

To a mixture of 3-amino-1-(trans-4-cyanotetrahydro-2H-pyran-3-yl)pyrazole-4-carboxamide (500 mg, 2.13 mmol, 1 eq) and 6-bromo-2-hydroxy-1,2-benzoxaborinine (526 mg, 2.34 mmol, 1.1 eq) in i-PrOH (10 mL) was added t-BuX-Phos (162 mg, 383 umol, 0.18 eq), KOAc (417 mg, 4.25 mmol, 2 eq) and Pd$_2$(dba)$_3$ (175 mg, 191 umol, 0.09 eq) in one portion at 20° C. under N$_2$. The mixture was heated and stirred at 80° C. for 18 h. LCMS showed the reaction was completed and desired MS observed. 4 parallel reactions were combined for work up. The mixture was filtered and filtrate was concentrated in vacuum to give a residue. The residue was dissolved with H$_2$O (60 mL) and adjusted pH to 6 with 2 N HCl at 0° C., and then extracted with EtOAc (30 mL×3). The combined organic layers were washed with brine (40 mL×3), dried over Na$_2$SO$_4$, filtered and concentrated under reduced pressure to give a residue. The residue was purified by prep-HPLC (column: Welch Xtimate C18 250*70 mm #10 um; mobile phase: [water(NH$_4$HCO$_3$)-ACN]; B %: 20%-50%, 20 min) to give 1-(trans-4-cyanotetrahydro-2H-pyran-3-yl)-3-[(2-hydroxy-1,2-benzoxaborinin-6-yl)amino]pyrazole-4-carboxamide (1.50 g, 37.2% yield) as an off-white solid. The product was further separated by SFC (column: DAICEL CHIRALPAK IC (250 mm*30 mm, 10 um); mobile phase: [Neu-IPA]; B %: 50/6-50%/6.10 min) to give 1-[trans-4-cyanotetrahydro-2H-pyran-3-yl]-3-[(2-hydroxy-1,2-benzoxaborinin-6-yl)amino] pyrazole-4-carboxamide (stereoisomer one) (435.1 mg, 13.4% yield, 99.4% purity, 100% ee, first peak, Rt=2.239 min) as an off-white solid. $^1$H NMR (DMSO-hd 6, 400 MHz) δ 9.09 (s, 1H), 8.80 (s, 1H), 8.28 (s, 1H), 7.81 (d, J=11.6 Hz, 1H), 7.75-7.63 (m, 2H), 7.54 (dd, J=8.8 Hz, 2.8 Hz, 1H), 7.23-7.12 (m, 2H), 6.11 (d, J=11.6 Hz, 1H), 4.55 (td, J=10.0 Hz, 1H), 4.03 (dd, J=11.2 Hz, 4.4 Hz, 1H), 3.95-3.90 (m, 1H) 3.75-3.66 (m, 2H), 3.54-3.48 (m, 1H), 2.20-2.12 (m, 1H), 2.04-1.95 (m, 1H). MS (ESI): mass calculated for C$_{18}$H$_{18}$BN$_5$O$_4$ 379.15; m/z found 380.1 [M+H]$^+$. HPLC: 99.40% (220 nm), 99.73% (254 nm). and 1-[trans-4-cyanotetrahydropyran-3-yl]-3-[(2-hydroxy-1,2-benzoxaborinin-6-yl)amino] pyrazole-4-carboxamide (stereoisomer two) (469.7 mg, 14.3% yield, 98.5% purity, 100% ee, second peak, Rt=2.722 min) as a yellow solid. $^1$H NMR (DMSO-hd 6, 400 MHz) δ 9.09 (s, 1H), 8.80 (s, 1H), 8.29 (s, 1H), 7.81 (d, J=12.0 Hz, 1H), 7.75-7.63 (m, 2H), 7.54 (dd, J=8.8 Hz, 2.8 Hz, 1H), 7.25-7.00 (m, 2H), 6.11 (d, J=12.0 Hz, 1H), 4.55 (td, J=14.4 Hz, 1H), 4.03 (dd, J=11.2 Hz, 4.0 Hz 1H), 3.96-3.87 (m, 1H), 3.75-3.67 (m, 1H), 3.55-3.47 (m, 1H), 2.20-2.12 (m, 1H), 2.04-1.95 (m, 1H). MS (ESI): mass calculated for C$_{18}$H$_{18}$BN$_5$O$_4$ 379.15; m/z found 380.1 [M+H]$^+$. HPLC: 98.56% (220 nm), 98.75% (254 nm).

52. Preparation of 3-((7-chloro-1-hydroxy-1,3-dihydrobenzo[c][1,2]oxaborol-5-yl)amino)-1-(trans-4-cyanotetrahydro-2H-pyran-3-yl)-1H-pyrazole-4-carboxamide

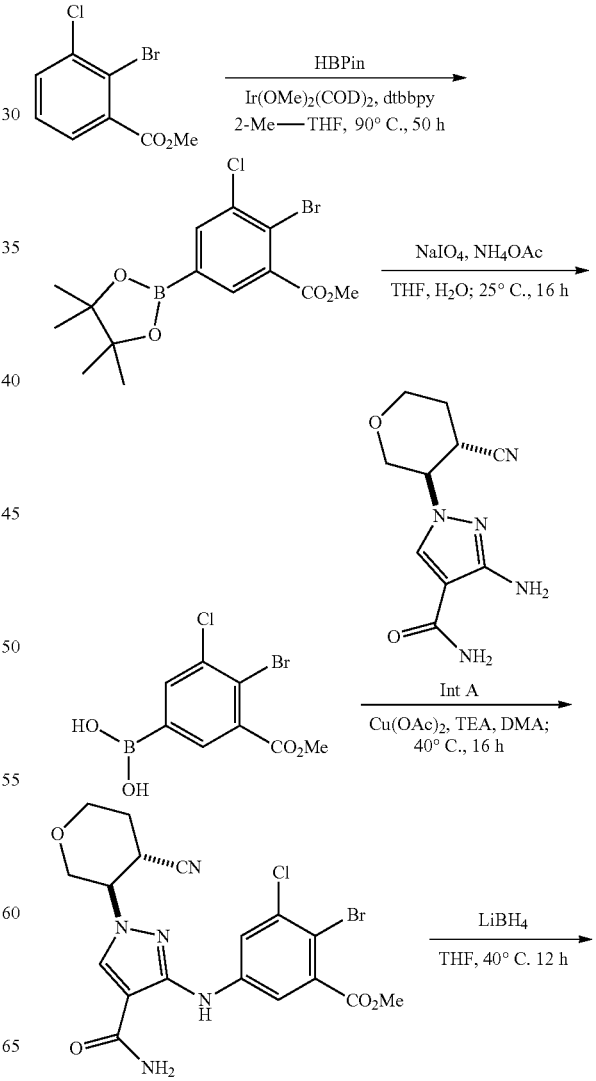

-continued

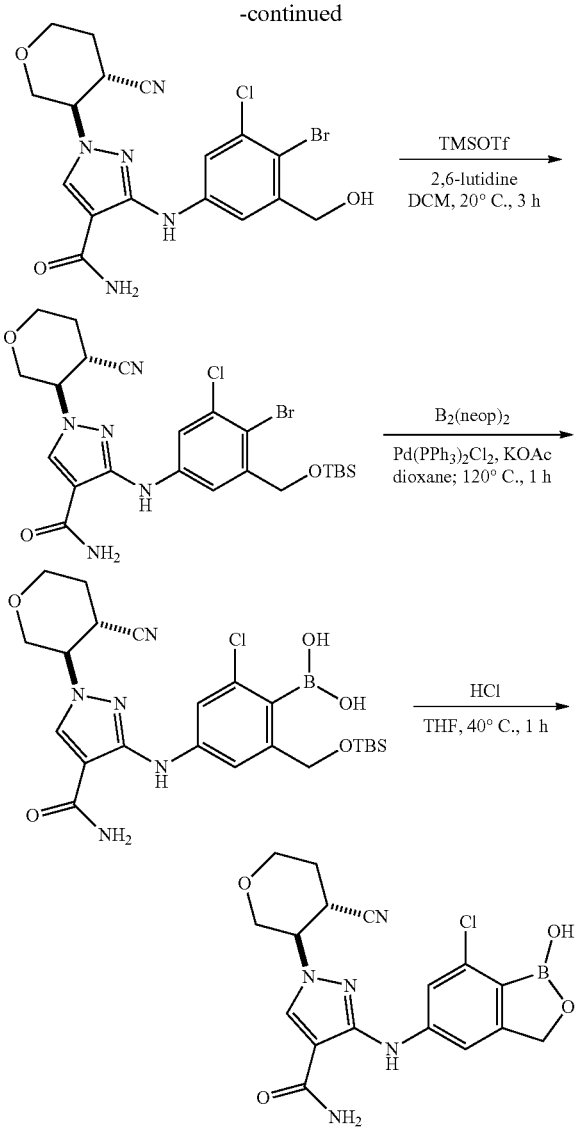

52.1 Preparation of methyl 2-bromo-3-chloro-5-(4,4,5,5-tetramethyl-1,3,2-dioxaborolan-2-yl) benzoate

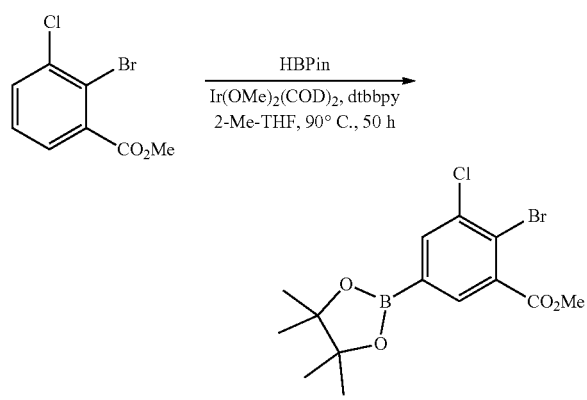

A mixture of methyl 2-bromo-3-chloro-benzoate (5 g, 20.0 mmol, 1 eq), 4,4,5,5-tetramethyl-1,3,2-dioxaborolane (10.3 g, 80.2 mmol, 11.6 mL, 4 eq), 4-tert-butyl-2-(4-tert-butyl-2-pyridyl)pyridine (dtbbpy, 538 mg, 2.00 mmol, 0.1 eq), (1Z,5Z)-cycloocta-1,5-diene;2,4-dimethyl-BLAHbicyclo[1.1.0]butane (Ir(OMe)$_2$(COD)$_2$, 531 mg, 801 umol, 0.04 eq) in 2-methyltetrahydrofuran (40 mL) was degassed and purged with N$_2$ for 3 times, and then the mixture was stirred at 90° C. for 50 h under N$_2$ atmosphere. TLC showed the reaction was completed. The reaction mixture was cooled to room temperature and filtered. The filtrate was concentrated under reduced pressure to give a residue. The residue was purified by flash silica gel chromatography (ISCO®; 330 g SepaFlash® Silica Flash Column, Eluent of 0-7% Ethyl acetate/Petroleum ether gradient @ 150 mL/min) to give methyl 2-bromo-3-chloro-5-(4,4,5,5-tetramethyl-1,3,2-dioxaborolan-2-yl) benzoate (32 g, 85.0% yield) as a yellow solid. $^1$H NMR (CDCl$_3$, 400 MHz) δ 7.97 (s, 1H), 7.93 (s, 1H), 3.94 (s, 3H), 1.35 (s, 12H).

52.2 Preparation of (4-bromo-3-chloro-5-methoxycarbonyl-phenyl)boronic acid

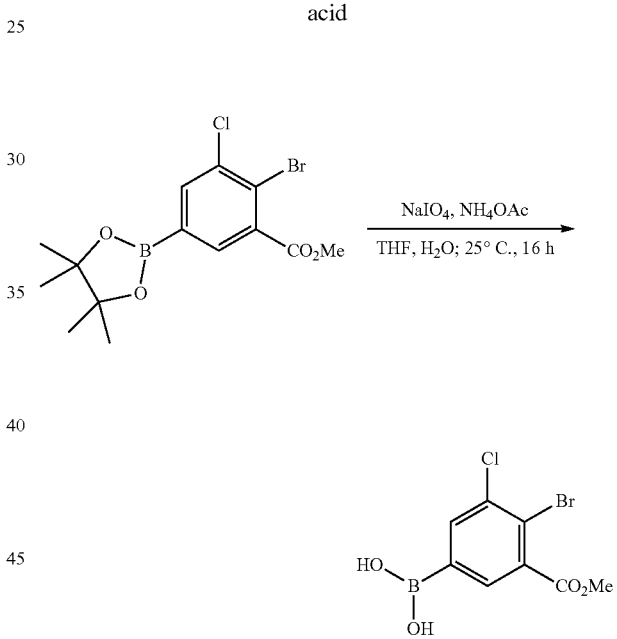

To a solution of methyl 2-bromo-3-chloro-5-(4,4,5,5-tetramethyl-1,3,2-dioxaborolan-2-yl) benzoate (11 g, 29.3 mmol, 1 eq) in THF (110 mL) and H$_2$O (55 mL) was added NaIO$_4$ (18.8 g, 87.9 mmol, 3 eq) and NH$_4$OAc (6.77 g, 87.9 mmol, 3 eq). The mixture was stirred at 25° C. for 16 h. TLC showed the reaction was completed. The reaction mixture was filtered and washed with water (30 mL×3). The filtrate was extracted with EtOAc (50 mL×3). The combined organic layers were washed with brine (150 mL×2), dried over Na$_2$SO$_4$, filtered and concentrated under reduced pressure to give a residue. The residue was triturated with a mixture of Petroleum ether (80 mL) and Ethyl acetate (15 mL) at 25° C. for 10 min to give (4-bromo-3-chloro-5-methoxycarbonyl-phenyl)boronic acid (7 g, 81.4% yield) as a white solid $^1$H NMR (DMSO-d$_6$, 400 MHz) δ 8.53 (s, 2H), 8.08 (s, 1H), 7.95 (s, 1H), 3.88 (s, 3H).

52.3 Preparation of methyl 2-bromo-5-[[4-carbamoyl-1-(trans-4-cyanotetrahydro-2H-pyran-3-yl) pyrazol-3-yl]amino]-3-chloro-benzoate

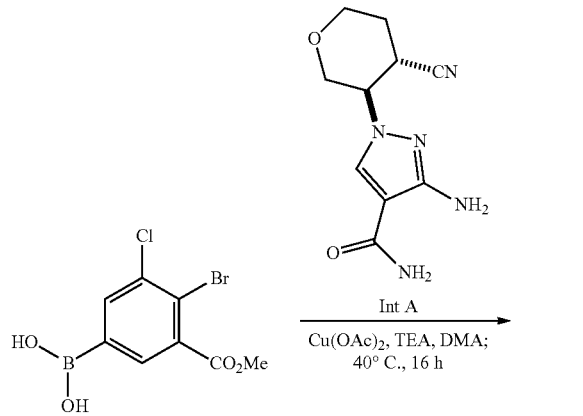

A mixture of 3-amino-1-(trans-4-cyanotetrahydropyran-3-yl)pyrazole-4-carboxamide (1 g, 4.25 mmol, 1 eq), (4-bromo-3-chloro-5-methoxycarbonyl-phenyl)boronic acid (1.37 g, 4.68 mmol, 1.1 eq), TEA (2.15 g, 21.25 mmol, 3.0 mL, 5 eq), Cu(OAc)$_2$ (1.93 g, 10.6 mmol, 2.5 eq) and 4 Å molecular sieve (2.5 g, 4.25 mmol, 1 eq) in DMA (30 mL) was stirred at 40° C. for 16 h under air. LCMS showed the reaction was completed and desired MS observed. 4 parallel reactions were combined for work up. The reaction mixture was filtered. The filtrate was added H$_2$O (300 mL) at 20° C., and then extracted with EtOAc (50 mL×3). The combined organic layers were washed with brine (50 mL×3), dried over Na$_2$SO$_4$, filtered and concentrated under reduced pressure to give a residue. The residue was purified by flash silica gel chromatography (ISCO®; 80 g SepaFlash® Silica Flash Column, Eluent of 0~100% Ethyl acetate/Petroleum ether gradient @100 mL/min) to give methyl 2-bromo-5-[[4-carbamoyl-1-(trans-4-cyanotetrahydro-2H-pyran-3-yl) pyrazol-3-yl]amino]-3-chloro-benzoate (5 g, 60.9% yield) as a yellow solid. $^1$H NMR (DMSO-d$_6$, 400 MHz) δ 9.46 (s, 1H), 8.34 (s, 1H), 8.08 (s, 1H), 7.86 (s, 1H), 7.79 (br s, 1H), 7.28 (br s, 1H), 4.63 (dt, J=4.4, 10.4 Hz, 1H), 4.10-4.05 (m, 1H), 3.95-3.90 (m, 1H), 3.87 (s, 3H), 3.67-3.55 (m, 2H), 3.50-3.40 (m, 1H), 2.20-2.10 (m, 1H), 2.05-1.95 (m, 1H).

52.4 Preparation of 3-[4-bromo-3-chloro-5-(hydroxymethyl)anilino]-1-(trans-4-cyanotetrahydro-2H-pyran-3-yl)pyrazole-4-carboxamide

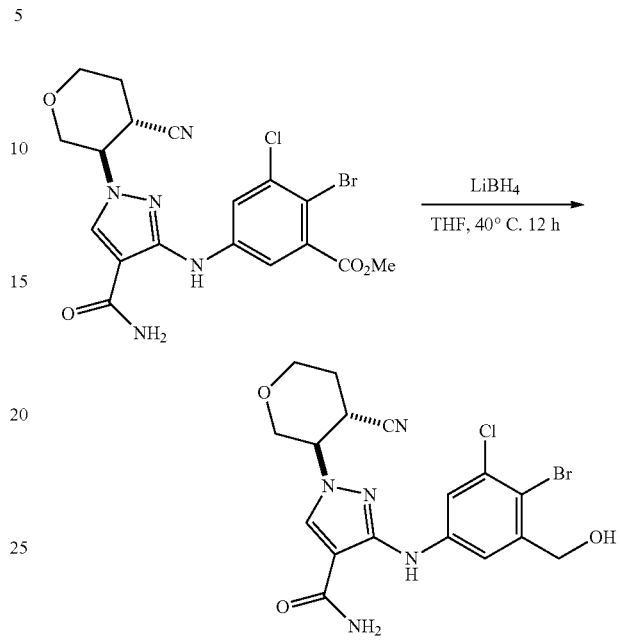

To a solution of methyl 2-bromo-5-[[4-carbamoyl-1-(4-cyanotetrahydropyran-3-yl) pyrazol-3-yl]amino]-3-chloro-benzoate (1.7 g, 3.52 mmol, 1 eq) in anhydrous THF (30 mL) was added LiBH4 (5.3 mL, 4 N, 6 eq) dropwise at 0° C. and then the mixture was heated to 40° C. and stirred at 40° C. for 12 h. TLC showed the reaction was completed. The reaction was cooled to room temperature and quenched with ice-water (50 mL) and adjust pH to 6 with HCl (1N). The resulting solution was extracted with EtOAc (30 mL×3). The combined organic layers were washed with brine (40 mL×3), dried over Na$_2$SO$_4$, filtered and concentrated under reduced pressure to give 3-[4-bromo-3-chloro-5-(hydroxymethyl)anilino]-1-(trans-4-cyanotetrahydro-2H-pyran-3-yl)pyrazole-4-carboxamide (1.4 g, crude) as a yellow solid.

52.5 Preparation of 3-[4-bromo-3-[[tert-butyl(dimethyl)silyl]oxymethyl]-5-chloro-anilino]-1-(trans-4-cyanotetrahydro-2H-pyran-3-yl)pyrazole-4-carboxamide

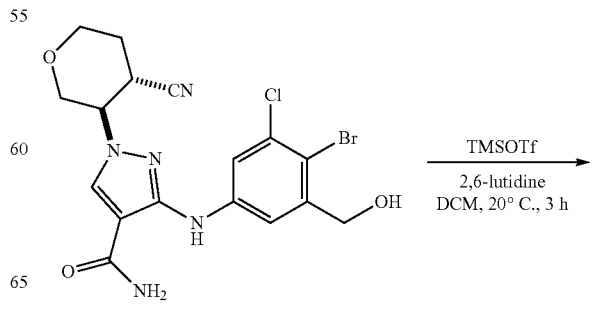

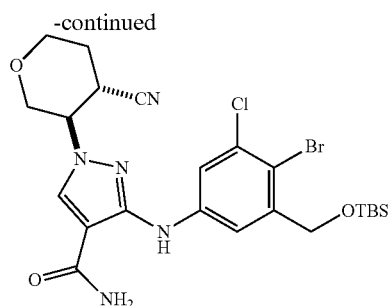

To a solution of 3-[4-bromo-3-chloro-5-(hydroxymethyl)anilino]-1-(trans-4-cyanotetrahydro-2H-pyran-3-yl)pyrazole-4-carboxamide (2 g, 4.40 mmol, 1 eq) and 2,6-dimethylpyridine (1.18 g, 11.0 mmol, 1.3 mL, 2.5 eq) in DCM (40 mL) was added TBSOTf (1.74 g, 6.60 mmol, 1.5 mL, 1.5 eq) at 0° C. The mixture was stirred at 20° C. for 3 h. The reaction mixture was quenched by addition of sat. aq. NH$_4$Cl 20 mL at 0° C., and then extracted with DCM (20 mL×3). The combined organic layers were washed with brine (10 mL×2), dried over Na$_2$SO$_4$, filtered and concentrated under reduced pressure to give a residue. The residue was purified by flash silica gel chromatography (ISCO®; 40 g SepaFlash® Silica Flash Column, Eluent of 0~100% Ethylacetate/Petroleum ether gradient @ 75 mL/min) to give 3-[4-bromo-3-[[tert-butyl(dimethyl)silyl]oxymethyl]-5-chloroanilino]-1-(trans-4-cyanotetrahydro-2H-pyran-3-yl)pyrazole-4-carboxamide (1.6 g, 63.9% yield) as a white solid. $^1$H NMR (DMSO-hd 6, 400 MHz) δ 9.47 (s, 1H), 8.34 (s, 1H), 7.84 (d, J=2.8 Hz, 1H), 7.79 (br s, 1H), 7.46 (d, J=2.4 Hz, 1H), 7.29 (br s, 1H), 4.69 (s, 2H), 4.60 (dt, J=4.4, 10.0 Hz, 1H), 4.10-4.04 (m, 1H), 3.96-3.89 (m, 1H), 3.70-3.62 (m, 1H), 3.58 (dt, J=4.0, 10.8 Hz, 1H), 3.50-3.42 (m, 1H), 2.20-2.10 (m, 1H), 2.05-1.92 (m, 2H), 0.93 (s, 9H), 0.13 (s, 6H).

52.6 Preparation of [2-[[tert-butyl(dimethyl)silyl]oxymethyl]-4-[[4-carbamoyl-1-(trans-4-cyanotetrahydro-2H-pyran-3-yl)pyrazol-3-yl]amino]-6-chlorophenyl]boronic acid

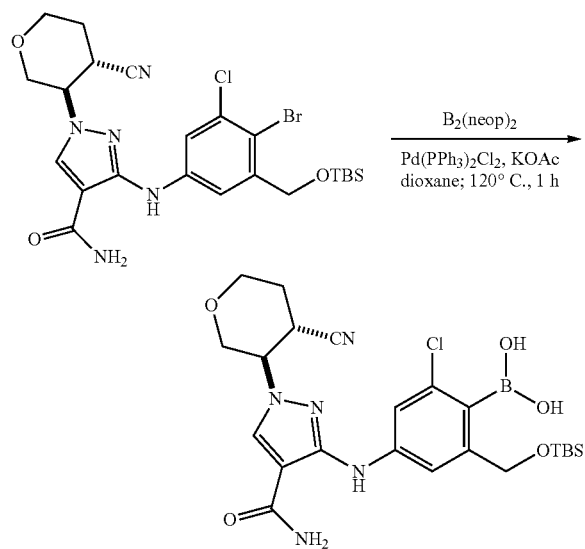

A mixture of 2-(5,5-dimethyl-1,3,2-dioxaborinan-2-yl)-5,5-dimethyl-1,3,2-dioxaborinane (595 mg, 2.64 mmol, 5 eq), 3-[4-bromo-3-[[tert-butyl(dimethyl)silyl]oxymethyl]-5-chloro-anilino]-1-(trans-4-cyanotetrahydro-2H-pyran-3-yl)pyrazole-4-carboxamide (300 mg, 527 umol, 1 eq), KOAc (155 mg, 1.58 mmol, 3 eq) and Pd(PPh$_3$)$_2$Cl$_2$ (37 mg, 52 umol, 0.1 eq) in dioxane (8 mL) was degassed and purged with N$_2$ for 3 times, and then the mixture was stirred at 120° C. for 1 h under N$_2$ atmosphere. TLC showed the reaction was completed. 5 parallel reactions were combined for work up. The reaction was cooled to room temperature and filtered. The filtrate was concentrated under reduced pressure to give a residue. The residue was purified by prep-HPLC (column: Waters Xbridge BEH C18 250*50 mm*10 um; mobile phase: [water (10 mM NH$_4$HCO$_3$)-ACN]; B %: 45%-85%, 10 min) to give [2-[[tert-butyl(dimethyl)silyl]oxymethyl]-4-[[4-carbamoyl-1-(trans-4-cyanotetrahydro-2H-pyran-3-yl)pyrazol-3-yl]amino]-6-chloro-phenyl]boronic acid (0.8 g, crude) as a yellow solid.

52.7 Preparation of chiral 3-((7-chloro-1-hydroxy-1,3-dihydrobenzo[c][1,2]oxaborol-5-yl)amino)-1-(trans-4-cyanotetrahydro-2H-pyran-3-yl)-1H-pyrazole-4-carboxamide

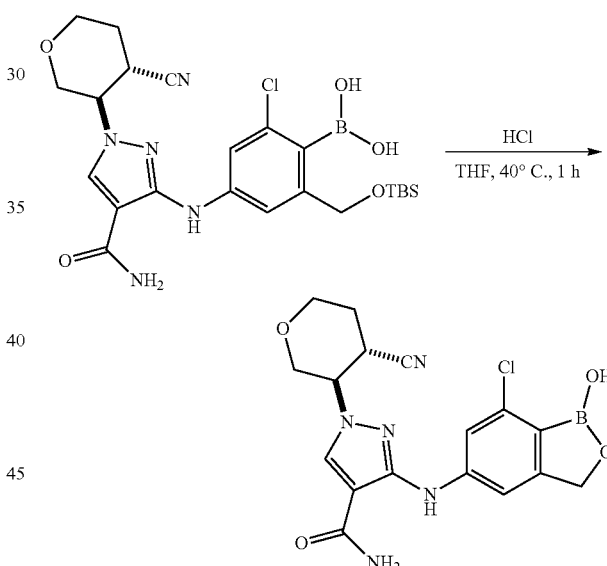

To a solution of [2-[[tert-butyl(dimethyl)silyl]oxymethyl]-4-[[4-carbamoyl-1-(trans-4-cyanotetrahydro-2H-pyran-3-yl)pyrazol-3-yl]amino]-6-chloro-phenyl]boronic acid (800 mg, 1.50 mmol, 1 eq) in THF (12 mL) was added HCl (800 uL, 6N, 3.20 eq) at 20° C. The mixture was heated and stirred at 40° C. for 1 h. LCMS showed the reaction was completed and desired MS observed. The reaction mixture was concentrated under reduced pressure to give a residue. The residue was triturated with CH$_3$CN (15 mL) at 20° C. for 10 min to give 3-((7-chloro-1-hydroxy-1,3-dihydrobenzo[c][1,2]oxaborol-5-yl)amino)-1-(trans-4-cyanotetrahydro-2H-pyran-3-yl)-1H-pyrazole-4-carboxamide (500 mg). Further separated by SFC (column: DAICEL CHIRALPAK IC (250 mm*30 mm, 10 um); mobile phase: [Neu-MeOH]; B %: 50%-50%, 10 min) to give 3-((7-chloro-1-hydroxy-1,3-dihydrobenzo[c][1,2]oxaborol-5-yl)amino)-1-(trans-4-cyanotetrahydro-2H-pyran-3-yl)-1H-pyrazole-4- carboxamide (stereoisomer one) (210 mg, 34.2% yield, 98.0% purity, 94.6% ee, first peak, Rt=1.417 min) as a white solid. ¹H NMR (DMSO-hd 6, 400 MHz) S 9.51 (s, 1H), 8.85 (s, 1H), 8.34 (s, 1H), 7.78 (br s, 1H), 7.52 (s, 1H), 7.47 (s, 1H), 7.27 (br s, 1H), 4.94 (s, 2H), 4.63-4.57 (m, 1H), 4.06 (dd, J=4.4, 11.2 Hz, 1H), 3.92 (d, J=10.8 Hz, 1H), 3.70-3.60 (m, 2H), 3.49 (t, J=10.4 Hz, 1H), 2.18-2.15 (m, 1H), 2.05-1.90 (m, 1H). MS (ESI): mass calculated for $C_{17}H_{17}BClNSO_4$ 401.11; m/z found 400.2 [M–H]⁻. HPLC: 98.08% (220 nm), 96.05% (254 nm). and 3-((7-chloro-1-hydroxy-1,3-dihydrobenzo[c][1,2]oxaborol-5-yl)amino)-1-(trans-4-cyanotetrahydro-2H-pyran-3-yl)-1H-pyrazole-4-carboxamide (stereoisomer two) (205 mg, 33.5% yield, 98.4% purity, 99.6% ee, second peak, Rt=1.597 min) as a white solid. ¹H NMR (DMSO-d₆, 400 MHz) δ 9.51 (s, 1H), 8.85 (s, 1H), 8.34 (s, 1H), 7.78 (br s, 1H), 7.52 (s, 1H), 7.47 (s, 1H), 7.26 (br s, 1H), 4.94 (s, 2H), 4.63-4.57 (m, 1H), 4.06 (dd, J=4.4, 11.2 Hz, 1H), 3.92 (d, J=10.8 Hz, 1H), 3.70-3.60 (m, 2H), 3.55-3.45 (m, 1H), 2.18-2.15 (m, 1H), 2.05-1.90 (m, 1H). MS (ESI): mass calculated for $C_{17}H_{17}BClNSO_4$ 401.11; m/z found 400.2 [M–H]⁻. HPLC: 98.48% (220 nm), 98.61% (254 nm).

53. Preparation of 1-[trans-4-cyanotetrahydro-2H-pyran-3-yl]-3-[[2-hydroxy-8-(trifluoromethoxy)-1,2-benzoxaborinin-6-yl]amino]pyrazole-4-carboxamide

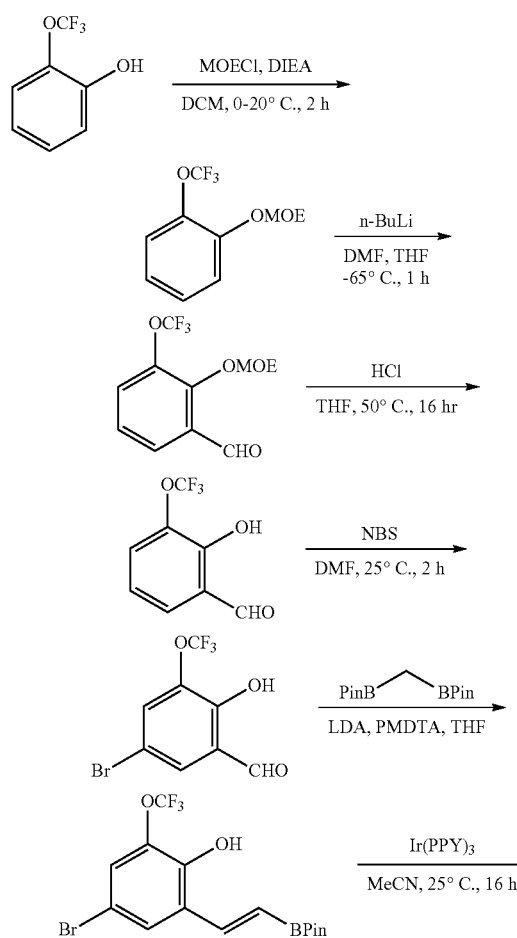

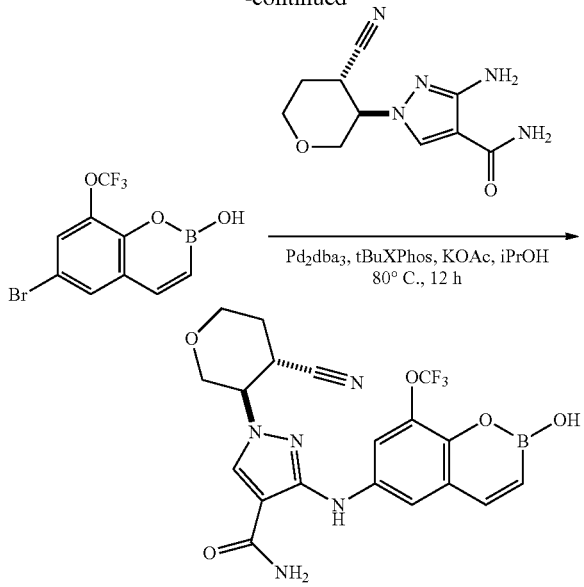

53.1 Preparation of 1-(ethoxymethoxy)-2-(trifluoromethoxy)benzene

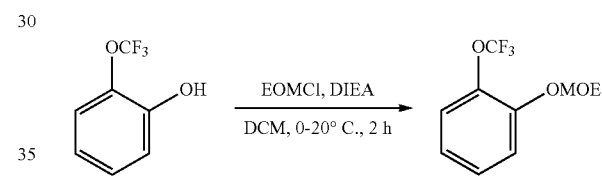

To a mixture of 2-(trifluoromethoxy)phenol (15 g, 84.2 mmol, 1 eq) and DIEA (252 mmol, 44 mL, 3 eq) in DCM (150 mL) was drop-wise added chloromethoxyethane (MOECl, 168 mmol, 15.6 mL, 2 eq) at 0° C. under N₂ atmosphere. The reaction mixture was stirred at 20° C. for 2 hours. TLC (Petroleum ether/Ethyl acetate=5/1) showed the reaction was completed. The reaction mixture was quenched by addition H₂O (20 mL) at 0° C., and then extracted with EtOAc (100 mL×3). The combined organic layers were dried over Na₂SO₄, filtered and concentrated under reduced pressure to give a residue. The residue was purified by column chromatography (SiO₂, Eluent of 0~100% Ethyl acetate/Petroleum ether gradient) to give compound 1-(ethoxymethoxy)-2-(trifluoromethoxy)benzene (19 g, 95.5% yield) as colorless oil. ¹H NMR (400 MHz, DMSO-d6) δ 7.42-7.26 (m, 3H), 7.14-6.99 (m, 1H), 5.32 (s, 2H), 3.67 (q, J=7.2 Hz, 2H), 1.12 (t, J=7.2 Hz, 3H).

53.2 Preparation of methyl 2-(ethoxymethoxy)-3-(trifluoromethoxy)benzaldehyde

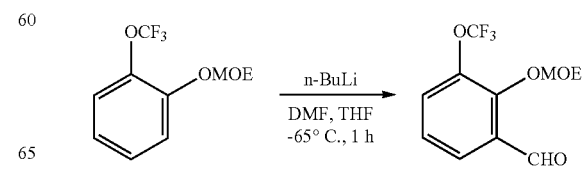

To a solution of 1-(ethoxymethoxy)-2-(trifluoromethoxy)benzene (19 g, 80.4 mmol, 1 eq) in THF (180 mL) was drop-wise added n-BuLi (2.5 M, 37 mL, 1.15 eq) at −65° C. under $N_2$ atmosphere. The reaction mixture was stirred at −65° C. for 30 min, then DMF (9.3 mL, 120 mmol, 1.5 eq) was drop-wise added to the reaction mixture and stirred for 1 h. TLC (petroleum ether:ethyl acetate=10:1) showed the reaction was completed and the starting material was consumed. The reaction mixture was warmed to the room temperature and poured into aq. $NH_4Cl$ (150 mL) and stirred for 20 min under $N_2$ atmosphere. The aqueous phase was extracted with ethyl acetate (100 mL×3). The combined organic phases were washed with brine (100 mL×2), dried with anhydrous $Na_2SO_4$, filtered and concentrated under reduce pressure to give a residue. The residue was purified by column chromatography ($SiO_2$, Eluent of 0~100% Ethyl acetate/Petroleum ether gradient) to give compound 2-(ethoxymethoxy)-3-(trifluoromethoxy)benzaldehyde (15 g, 71.5% yield) as yellow oil. $^1$H NMR (400 MHz, DMSO-d6) δ 10.25 (s, 1H), 7.79 (d, J=7.6 Hz, 2H), 7.43 (t, J=7.6 Hz, 1H), 5.25 (s, 2H), 3.78 (q, J=7.2 Hz, 2H), 1.13 (t, J=7.2 Hz, 3H).

52.3 Preparation of 2-hydroxy-3-(trifluoromethoxy)benzaldehyde

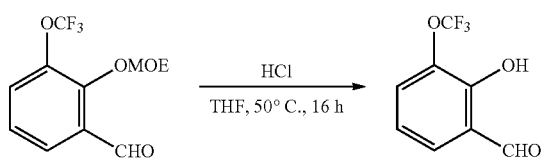

To a solution of 2-(ethoxymethoxy)-3-(trifluoromethoxy)benzaldehyde (15 g, 59.0 mmol, 1 eq) in THF (78 mL) was added HCl (4.9 mL, 12 N) in one portion at 25° C. under $N_2$ atmosphere. The reaction mixture was heated and stirred at 50° C. for 16 hours. LCMS showed the starting material was consumed completely and desired MS detected. The reaction mixture was poured into water (100 mL) and stirred for 20 min under $N_2$ atmosphere. The aqueous phase was extracted with ethyl acetate (150 mL×3). The combined organic phases were washed with brine (30 mL×2), dried with anhydrous $Na_2SO_4$, filtered and concentrated under reduce pressure to give a residue. The residue was purified by column chromatography ($SiO_2$, Eluent of 0~100% Ethyl acetate/Petroleum ether gradient) to give compound 2-hydroxy-3-(trifluoromethoxy)benzaldehyde (10 g, 82.2% yield) as a white solid. $^1$H NMR (400 MHz, DMSO-d6) δ 11.14 (s, 1H), 10.24 (s, 1H), 7.80-7.60 (m, 2H), 7.08 (t, J=8.0 Hz, 1H).

53.4 Preparation of methyl 5-bromo-2-hydroxy-3-(trifluoromethoxy)benzaldehyde

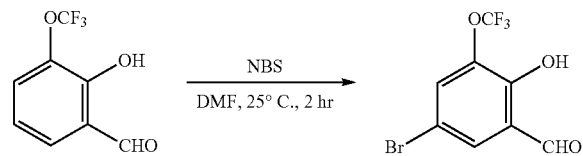 [SMILES: O=Cc1cccc(OC(F)(F)F)c1O ; "NBS" ; O=Cc1cc(Br)cc(OC(F)(F)F)c1O]

To a solution of 2-hydroxy-3-(trifluoromethoxy)benzaldehyde (3.96 g, 19.2 mmol, 1 eq) in DMF (25 mL) was added NBS (3.66 g, 20.6 mmol, 1.07 eq) in one portion at 25° C. under $N_2$ atmosphere. The reaction mixture was stirred at 25° C. for 2 hours. TLC (petroleum ether:ethyl acetate=10:1) showed the reaction was completed. The reaction mixture was poured into water (80 mL) and stirred for 20 min and extracted with ethyl acetate (100 mL×3). The combined organic phases were washed with brine (80 mL×2), dried with anhydrous $Na_2SO_4$, filtered and concentrated under reduce pressure to give a residue. The residue was purified by column chromatography ($SiO_2$, Eluent of 0~100% Ethyl acetate/Petroleum ether gradient) to give compound 5-bromo-2-hydroxy-3-(trifluoromethoxy)benzaldehyde (4.9 g, 17.1 mmol, 89.5% yield) as a white solid.

$^1$H NMR (400 MHz, DMSO-d6) δ 11.42 (s, 1H), 10.19 (s, 1H), 7.90 (dd, J=2.4, 1.2 Hz, 1H), 7.83 (d, J=2.4 Hz, 1H).

53.5 Preparation of 4-bromo-2-[(E)-2-(4,4,5,5-tetramethyl-1,3,2-diaxaborolan-2-yl)vinyl]-6-(trifluoromethoxy)phenol

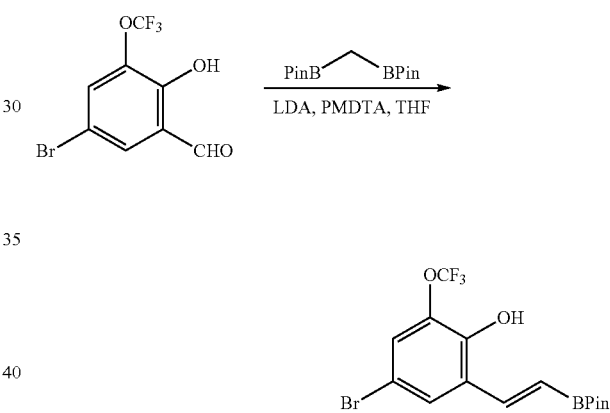

To a solution of LDA (2 M, 26.3 mL, 2.5 eq) in THF (20 mL) was added N'-[2-(dimethylamino)ethyl]-N,N,N'-trimethyl-ethane-1,2-diamine (PMDTA, 7.30 g, 42.1 mmol, 8.8 mL, 2 eq) in one portion at 0° C. under $N_2$ atmosphere. Then 4,4,5,5-tetramethyl-2-[(4,4,5,5-tetramethyl-1,3,2-dioxaborolan-2-yl)methyl]-1,3,2-dioxaborolane (14.1 g, 52.6 mmol, 2.5 eq) in THF (10 mL) was added to the reaction mixture. The reaction mixture was stirred at 0° C. for 30 min. Then 5-bromo-2-hydroxy-3-(trifluoromethoxy)benzaldehyde (6 g, 21.1 mmol, 1 eq) in THF (10 mL) was added to the reaction mixture at 0° C. under $N_2$. The reaction mixture was stirred at 25° C. for 40 min. LCMS showed the starting material was consumed completely and desired MS detected. The reaction mixture was poured into aq. $NH_4Cl$ (150 mL) and stirred for 10 min. The aqueous phase was extracted with ethyl acetate (100 mL×3). The combined organic phases were dried with anhydrous $Na_2SO_4$, filtered and concentrated under reduce pressure to give a residue. The residue was purified by column chromatography ($SiO_2$, Eluent of 5-95% Ethyl acetate/Petroleum ether gradient) to give compound 4-bromo-2-[(E)-2-(4,4,5,5-tetramethyl-1,3,2-dioxaborolan-2-yl)vinyl]-6-(trifluoromethoxy)phenol (13.2 g, crude) as yellow oil.

53.6 Preparation of 6-bromo-2-hydroxy-8-(trifluoromethoxy)-1,2-benzoxaborinine OCF$_3$OCF$_3$

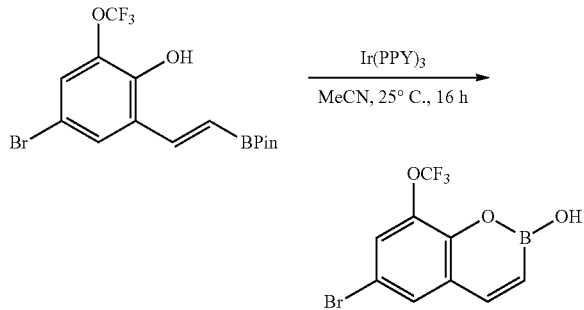

To a solution of 4-bromo-2-[(E)-2-(4,4,5,5-tetramethyl-1,3,2-dioxaborolan-2-yl)vinyl]-6-(trifluoromethoxy)phenol (1.72 g, 4.21 mmol, 1 eq) in MeCN (18 mL) was added tris[2-(2-pyridyl)phenyl]iridium (Ir(PPY)$_3$, 69 mg, 105 umol, 0.025 eq) in one portion at 25° C. under N$_2$ atmosphere. The reaction mixture was stirred at 25° C. and irradiated using 34W blue LED lamps for 16 h. TLC (petroleum ether:ethyl acetate=5:1) showed the reaction was completed. After filtration, compound 6-bromo-2-hydroxy-8-(trifluoromethoxy)-1,2-benzoxaborinine (850 mg, 65.5% yield) was obtained as a yellow solid without further purification. $^1$H NMR (400 MHz, DMSO-d6) δ 9.52 (br s, 1H), 7.86 (d, J=2.4 Hz, 1H), 7.82 (d, J=12.0 Hz, 1H), 7.72 (d, J=1.2 Hz, 1H), 6.29 (d, J=11.6 Hz, 1H).

53.7 Preparation of 1-[trans-4-cyanotetrahydro-2H-pyran-3-yl]-3-[[2-hydroxy-8-(trifluoromethoxy)-1,2-benzoxaborinin-6-yl]amino]pyrazole-4-carboxamide

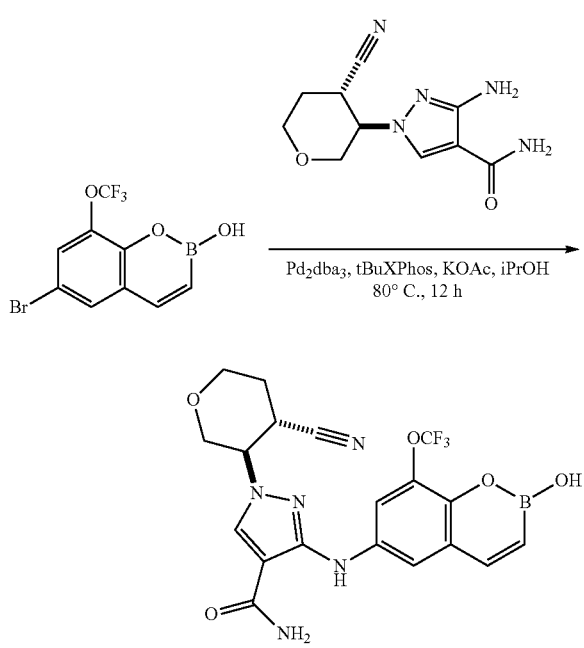

To a mixture of 6-bromo-2-hydroxy-8-(trifluoromethoxy)-1,2-benzoxaborinine (2 g, 6.48 mmol, 1 eq) and 3-amino-1-[trans-4-cyanotetrahydropyran-3-yl]pyrazole-4-carboxamide (1.52 g, 6.48 mmol, 1 eq) in i-PrOH (20 mL) was added KOAc (1.27 g, 13.0 mmol, 2 eq) in one portion at 25° C. under N$_2$. Then ditert-butyl-[2-(2,4,6-triisopropylphenyl)phenyl]phosphane (495 mg, 1.17 mmol, 0.18 eq) and Pd$_2$(dba)$_3$ (534 mg, 583 umol, 0.09 eq) was added to the reaction mixture at 25° C. under N$_2$. The system was degassed and purged with N$_2$ for 3 times and stirred at 25° C. for 5 min, then the reaction was heated to 80° C. and stirred for 12 hours. LCMS showed the reaction was completed and desired MS observed. The reaction mixture was cooled to 25° C. and poured into water (100 mL). The aqueous phase was extracted with ethyl acetate (80 mL×3). The combined organic phase was washed with brine (50 mL×2), dried over anhydrous Na$_2$SO$_4$, filtered and concentrated under reduce pressure to give a residue. The residue was purified by prep-HPLC (HCl condition: column: Phenomenex luna C18 (250*70 mm, 15 um); mobile phase: [water (HCl)-ACN]; B %: 24%-54%, 20 min) to give desired compound 1-[trans-4-cyanotetrahydropyran-3-yl]-3-[[2-hydroxy-8-(trifluoromethoxy)-1,2-benzoxaborinin-6-yl]amino]pyrazole-4-carboxamide (700 mg, yield 23.3%, purity 98.3%) as a white solid. $^1$H NMR (400 MHz, DMSO-d6) δ 9.20 (s, 2H), 8.31 (s, 1H), 7.92 (d, J=1.2 Hz, 1H), 7.84 (d, J=11.6 Hz, 1H), 7.79-7.69 (m, 1H), 7.62 (d, J=2.4 Hz, 1H), 7.30-7.14 (m, 1H), 6.21 (d, J=11.6 Hz, 1H), 4.59 (td, J=10.0, 4.4 Hz, 1H), 4.06 (dd, J=11.2, 4.4 Hz, 1H), 4.01-3.89 (m, 1H), 3.72-3.57 (m, 2H), 3.48-3.43 (m, 1H), 2.25-2.10 (m, 1H), 2.08-1.90 (m, 1H). MS (ESI): mass calculated for C$_{19}$H$_{17}$BF$_3$N$_5$O$_5$ 463.13; m/z found 464.0 [M+H]$^+$. HPLC: 98.34% (220 nm), 99.48% (254 nm). 1-[trans-4-cyanotetrahydro-2H-pyran-3-yl]-3-[[2-hydroxy-8-(trifluoromethoxy)-1,2-benzoxaborinin-6-yl]amino]pyrazole-4-carboxamide (1.08 g) was separated by SFC (condition: column: DAICEL CHIRALPAK IC (250 mm*30 mm, 10 um); mobile phase: [Neu-IPA]; B %: 33%-33%, 6 min) to give 1-[trans-4-cyanotetrahydr-2H-opyran-3-yl]-3-[[2-hydroxy-8-(trifluoromethoxy)-1,2-benzoxaborinin-6-yl]amino]pyrazole-4-carboxamide (stereoisomer one) (319 mg, 31.9% yield, 100% ee, first peak, Rt=1.074 min) as a white solid. $^1$H NMR (400 MHz, DMSO-d6) δ 9.19 (d, J=2.0 Hz, 2H), 8.31 (s, 1H), 7.92 (d, J=1.2 Hz, 1H) 7.84 (d, J=12.0 Hz, 1H), 7.75 (br d, J=5.2 Hz, 1H), 7.61 (d, J=2.8 Hz, 1H), 7.31-7.12 (m, 1H), 6.21 (d, J=11.6 Hz, 1H), 4.58 (td, J=10.0, 4.4 Hz, 1H), 4.06 (dd, J=11.2, 4.4 Hz, 1H), 3.99-3.88 (m, 1H), 3.70-3.60 (m, 3H), 2.23-2.11 (m, 1H), 2.07-1.89 (m, 1H). MS (ESI): mass calculated for C$_{19}$H$_{17}$BF$_3$N$_5$O$_5$ 463.13; m/z found 464.0 [M+H]$^+$. HPLC: 98.85% (220 nm), 99.58% (254 nm). and 1-[trans-4-cyanotetrahydr-2H-opyran-3-yl]-3-[[2-hydroxy-8-(trifluoromethoxy)-1,2-benzoxaborinin-6-yl]amino]pyrazole-4-carboxamide (stereoisomer two) (349 mg, 34.9% yield, 96.4% ee, second peak, Rt=1.184 min) as a white solid.

$^1$H NMR (400 MHz, DMSO-d6) δ 9.30-9.21 (m, 2H), 8.38 (s, 1H), 7.99 (d, J=1.2 Hz, 1H), 7.90 (d, J=12.0 Hz, 1H), 7.81 (br s, 1H), 7.68 (d, J=2.8 Hz, 1H), 7.37-7.22 (m, 1H), 6.28 (d, J=11.6 Hz, 1H), 4.65 (td, J=10.0, 4.4 Hz, 1H), 4.13 (dd, J=11.2, 4.4 Hz, 1H), 4.05-3.95 (m, 1H), 3.77-3.64 (m, 2H), 3.54-3.48 (m, 1H), 2.09-2.08 (m, 1H), 2.06-2.03 (m, 1H). MS (ESI): mass calculated for C$_{19}$H$_{17}$BF$_3$N$_5$O$_5$ 463.13; m/z found 464.0 [M+H]$^+$. HPLC: 99.21% (220 nm), 99.68% (254 nm).

54. Preparation of 1-(trans-4-cyanotetrahydro-2H-pyran-3-yl)-3-((S-fluoro-2-hydroxy-2H-benzo[e][1,2]oxaborinin-6-yl)amino)-1H-pyrazole-4-carboxamide

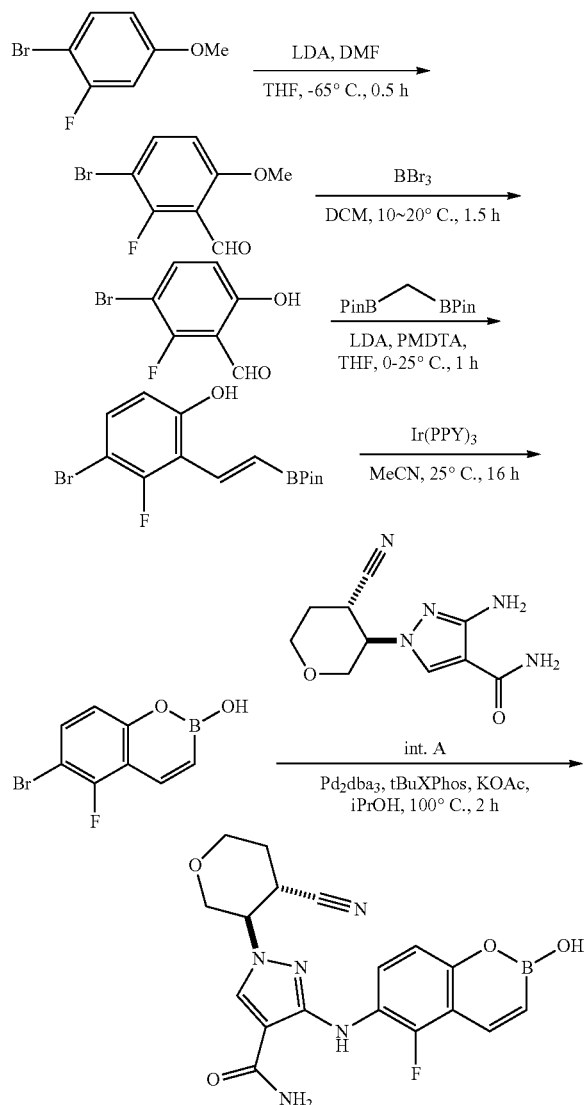

54.1 Preparation of 3-bromo-2-fluoro-6-methoxybenzaldehyde

To a solution of 1-bromo-2-fluoro-4-methoxy-benzene (4 g, 19.5 mmol, 1 eq) in THF (40 mL) was added LDA (11.7 mL, 2 M, 1.2 eq) at −65° C. The mixture was stirred −65° C. for 20 mins. Then dropwise added DMF (1.71 g, 23.4 mmol, 1.80 mL, 1.2 eq) at −65° C., The mixture was stirred at −65° C. for 10 mins. TLC showed the reaction was completed. The reaction mixture was quenched with aq. NH$_4$Cl (100 mL) and extracted with EtOAc (30 mL×3). The combined organic layers were washed with brine (50 mL), dried over anhydrous Na$_2$SO$_4$, filtered and concentrated under reduced pressure to give a residue. The residue was purified by silica gel column chromatography (PE: EtOAc=10:1 to 5:1) to give 3-bromo-2-fluoro-6-methoxy-benzaldehyde (1.8 g, 39.5% yield) as a yellow solid. $^1$H NMR (400 MHz, DMSO-d6) δ 10.24 (d, J=1.60 Hz, 1H) 7.93 (dd, J=9.00, 8.00 Hz, 1H) 7.07 (dd, J=9.20, 1.16 Hz, 1H) 3.92 (s, 3H).

54.2 Preparation of methyl 3-bromo-2-fluoro-6-hydroxybenzaldehyde

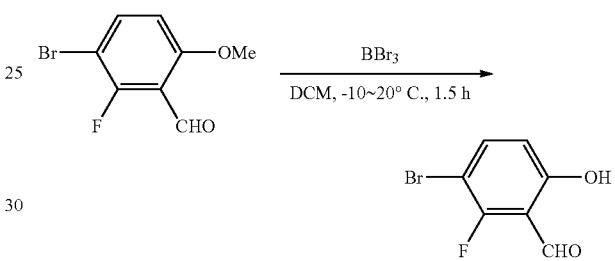

To a solution of 3-bromo-2-fluoro-6-methoxy-benzaldehyde (1.8 g, 7.72 mmol, 1 eq) in DCM (20 mL) was added BBr$_3$ (5.42 g, 21.6 mmol, 2.8 eq) at −10° C. The reaction was allowed to warm to 20° C. and stirred at 20° C. for 1.5 h. TLC showed the reaction was completed. The reaction mixture was quenched with saturated NaHCO$_3$ aqueous solution (50 mL) and extracted with EtOAc (20 mL×3). The combined organic layers were washed with brine (25 mL), dried over anhydrous Na$_2$SO$_4$, filtered and concentrated under reduced pressure to give 3-bromo-2-fluoro-6-hydroxy-benzaldehyde (1.3 g, crude) as a yellow solid used directly for next step without further purification.

$^1$H NMR (400 MHz, DMSO-d6) δ 11.35 (s, 1H) 10.22 (s, 1H) 7.78 (dd, J=8.80, 8.00 Hz, 1H) 6.82 (dd, J=9.00, 1.20 Hz, 1H).

54.3 Preparation of (E)-4-bromo-3-fluoro-2-(2-(4,4,5,5-tetramethyl-1,3,2-diaxaborolan-2-yl)vinyl)phenol

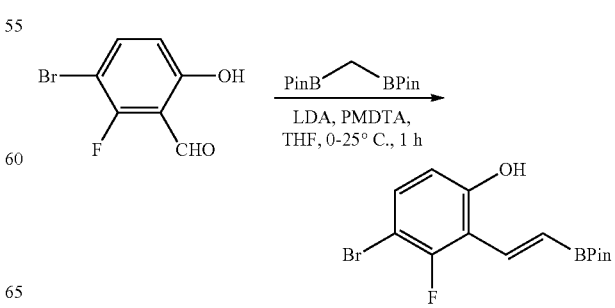

A solution of LDA (7.4 mL, 2N, 2.5 eq) in THF (13 mL) was added N'-[2-(dimethylamino)ethyl]-N,N,N'-trimethyl-ethane-1,2-diamine (2.00 g, 11.8 mmol, 2 eq) and 4,4,5,5-tetramethyl-2-[(4,4,5,5-tetramethyl-1,3,2-dioxaborolan-2-yl)methyl]-1,3,2-dioxaborolane (3.18 g, 11.8 mmol, 2 eq), and then the mixture was stirred at 0° C. for 20 mins under $N_2$ atmosphere. Then dropwise added 3-bromo-2-fluoro-6-hydroxy-benzaldehyde (1.3 g, 5.94 mmol, 1 eq) at 0° C. The reaction was allowed to warm to 25° C. and stirred at 25° C. for 40 mins under $N_2$ atmosphere. TLC showed the reaction was completed. The reaction mixture was quenched with aq·$NH_4Cl$ (50 mL) and extracted with EtOAc (20 mL×3). The combined organic layers were washed with brine (50 mL), dried over anhydrous $Na_2SO_4$, filtered and concentrated under reduced pressure to give a residue. The residue was purified by silica gel column chromatography (PE: EtOAc=100:1 to 10:1) to give 4-bromo-3-fluoro-2-[(E)-2-(4,4,5,5-tetramethyl-1,3,2-dioxaborolan-2-yl)vinyl]phenol (1.2 g, 58.9% yield) as a yellow solid.

54.4 Preparation of 6-bromo-5-fluoro-2H-benzo[e][1,2]oxaborinin-2-ol

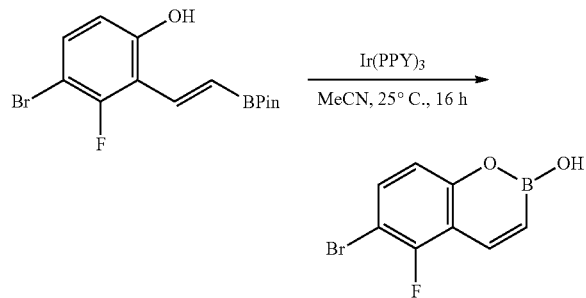

To a solution of 4-bromo-3-fluoro-2-[(E)-2-(4,4,5,5-tetramethyl-1,3,2-dioxaborolan-2-yl)vinyl]phenol (1.2 g, 3.50 mmol, 1 eq) in MCCN (15 mL) was added tris[2-(2-pyridyl)phenyl]iridium (Ir(PPY)₃, 57.2 mg, 87.4 umol, 0.025 eq). The reaction mixture was stirred at 25° C. and irradiated using 34W blue LED lamps for 16 hrs. TLC showed the reaction was completed. The reaction mixture was concentrated under reduced pressure to give 6-bromo-5-fluoro-2-hydroxy-1,2-benzoxaborinine (1.8 g, crude) used for the next step without further purification.

54.5 Preparation of 1-(trans-4-cyanotetrahydro-2H-pyran-3-yl)-3-((S-fluoro-2-hydroxy-2H-benzo[e][1,2]oxaborinin-6-yl)amino)-1H-pyrazole-4-carboxamide

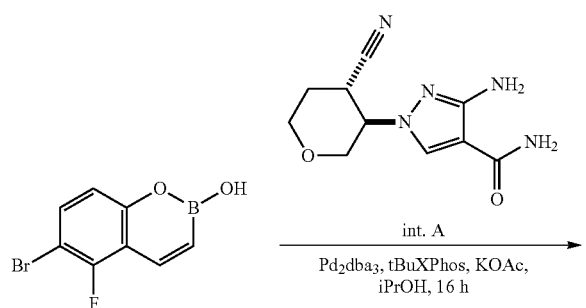

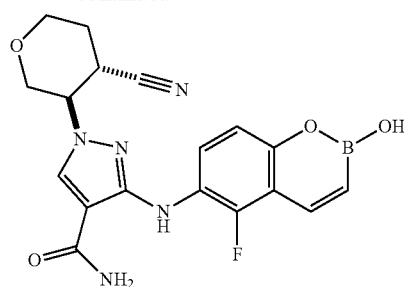

A mixture of 3-amino-1-(trans-4-cyanotetrahydropyran-3-yl)pyrazole-4-carboxamide (100 mg, 425 umol, 1 eq), 6-bromo-5-fluoro-2-hydroxy-1,2-benzoxaborinine (155 mg, 637 umol, 1.5 eq), Pd₂(dba)₃ (38.9 mg, 42.5 umol, 0.1 eq), t-Bu Xphos (36.0 mg, 85.0 umol, 0.2 eq) and $K_2CO_3$ (117 mg, 850 umol, 2 eq) in i-PrOH (5 mL) was degassed and purged with $N_2$ for 3 times, and then the mixture was stirred at 100° C. for 2 hrs under $N_2$ atmosphere. LCMS showed the reaction was completed. Then the reaction mixture was filtered and the filtrate was concentrated under reduced pressure to give a residue. The residue was quenched with $H_2O$ (10 mL) and extracted with EtOAc (5 mL×3). The combined organic layers were washed with brine (5 mL), dried over anhydrous $Na_2SO_4$, filtered and concentrated under reduced pressure to give a residue. The residue was purified by silica gel column chromatography (PE: EtOAc=5:1 to 3:1) to give 160 mg crude compound. The crude compound was further purified by prep-HPLC (HCl condition, column: Phenomenex luna C18 80*40 mm*3 um; mobile phase: [water (HCl)-ACN]; B %: 27%-42%, 7 min) to give 116 mg crude compound. The crude compound was further purified by prep-HPLC (neutral condition, column: Waters Xbridge BEH C18 100*30 mm*10 um; mobile phase: [water ($NH_4HCO_3$)-ACN]; B %: 20%-40%/6.10 min)ₓ3 to give 1-(trans-4-cyanotetrahydro-2H-pyran-3-yl)-3-[(5-fluoro-2-hydroxy-1,2-benzoxaborinin-6-yl)amino]pyrazole-4-carboxamide (60.2 mg, 35.6% yield) as a white solid. ¹H NMR (400 MHz, DMSO-d6) δ 9.38 (d, J=2.80 Hz, 1H) 9.02-9.09 (m, 1H) 8.28-8.39 (m, 2H) 7.97 (d, J=12.00 Hz, 1H) 7.77 (br s, 1H) 7.22 (br s, 1H) 7.06 (d, J=9.00 Hz, 1H) 6.23 (d, J=12.00 Hz, 1H) 4.58 (td, J=10.00, 4.38 Hz, 1H) 4.03 (dd, J=11.2, 4.38 Hz, 1H) 3.91 (br d, J=10.4 Hz, 1H) 3.64-3.77 (m, 2H) 3.46-3.55 (m, 1H) 2.15 (br d, J=9.60 Hz, 1H) 1.91-2.06 (m, 1H). MS (ESI): mass calculated for $C_{18}H_{17}BFN_5O_4$ 397.14; m/z found 396.1 [M–H]⁻. HPLC: 97.84% (220 nm), 98.55% (254 nm).

55. Preparation of 1-[trans-4-cyanotetrahydro-2H-pyran-3-yl]-3-[(8-cyclopropyl-2-hydroxy-1,2-benzoxaborinin-6-yl) amino]pyrazole-4-carboxamide

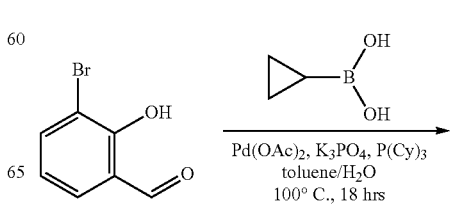

275

-continued

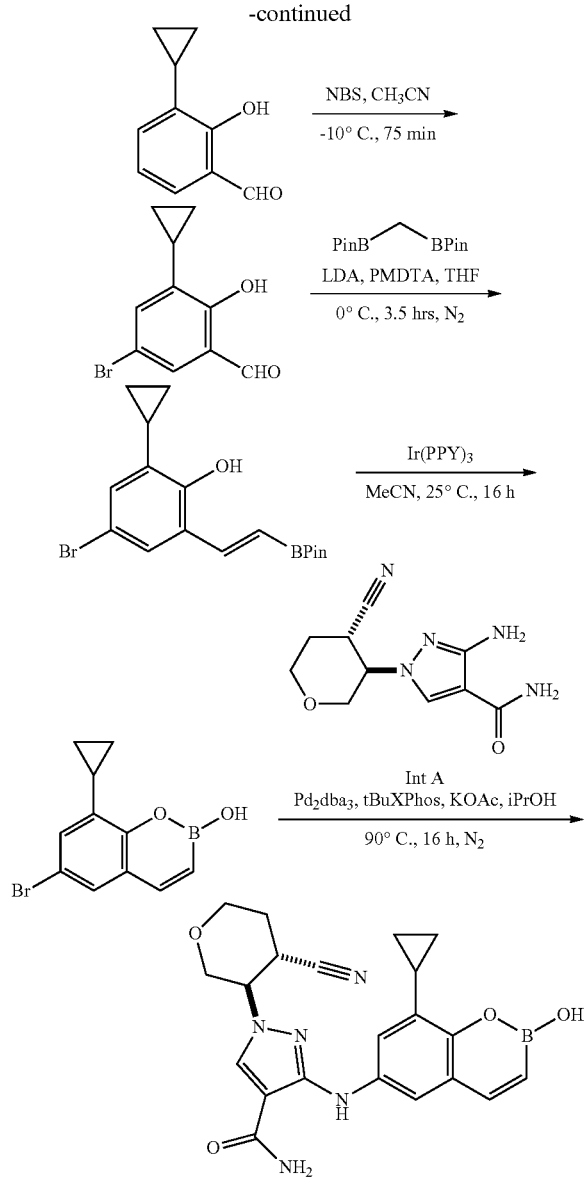

55.1 Preparation of
3-cyclopropyl-2-hydroxy-benzaldehyde

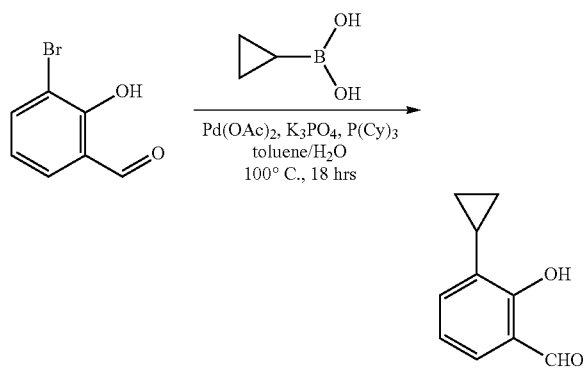

276

A mixture of cyclopropylboronic acid (1.71 g, 19.9 mmol, 2 eq), 3-bromo-2-hydroxy-benzaldehyde (2 g, 9.95 mmol, 1 eq), $K_3PO_4$ (7.39 g, 34.8 mmol, 3.5 eq), $Pd(OAc)_2$ (446 mg, 1.99 mmol, 0.2 eq) and tricyclohexylphosphane (1.12 g, 3.98 mmol, 1.29 mL, 0.4 eq) in toluene (40 mL) and $H_2O$ (10 mL) at 25° C. was degassed and purged with $N_2$ for 3 times, and then the mixture was heated and stirred at 100° C. for 18 hrs under $N_2$ atmosphere. TLC showed the reaction was completed. The reaction mixture was concentrated under reduced pressure to remove toluene, and then adjusted pH to 6 with 2N HCl. The reaction was extracted with EtOAc (50 mL×3). The combined organic layers were washed with brine 50 mL, dried over $Na_2SO_4$, filtered and concentrated under reduced pressure to give a residue. The residue was purified by flash silica gel chromatography (ISCO®; 120 g SepaFlash® Silica Flash Column, Eluent of 0~10% Ethyl acetate/Petroleum ether gradient @ 50 m/min) to give 2-hydroxy-3-(trifluoromethyl) benzaldehyde (10.7 g, 65.1% yield) as yellow oil. $^1$H NMR ($CDCl_3$, 400 MHz) δ 11.40 (s, 1H), 9.89 (s, 1H), 7.38 (dd, J=1.6, 7.6 Hz, 1H), 7.12 (dd, J=0.8, 7.2 Hz, 1H), 6.95-6.92 (m, 1H), 2.24-2.19 (m, 1H), 1.03-0.98 (m, 2H), 0.72-0.69 (m, 2H).

55.2 Preparation of
5-bromo-3-cyclopropyl-2-hydroxy-benzaldehyde

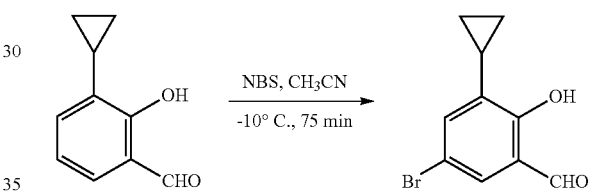

To a solution of 3-cyclopropyl-2-hydroxy-benzaldehyde (5.1 g, 31.4 mmol, 1 eq) in $CH_3CN$ (100 mL) was added 1-bromopyrrolidine-2,5-dione (6.72 g, 37.7 mmol, 1.2 eq) at −10° C. The mixture was stirred at −10° C. for 75 min. TLC showed the reaction was completed. The reaction mixture was poured into $H_2O$ (50 mL) and extracted with EtOAc (50 mL×3). The combined organic layers were washed with brine (30 mL×3), dried over $Na_2SO_4$, filtered and concentrated under reduced pressure to give a residue. The residue was purified by flash silica gel chromatography (ISCO®; 80 g SepaFlash® Silica Flash Column, Eluent of 0~10% Ethyl acetate/Petroleum ether gradient @ 50 m/min) to give 5-bromo-3-cyclopropyl-2-hydroxy-benzaldehyde (5.6 g) as a yellow solid. $^1$H NMR ($CDCl_3$, 400 MHz) δ 11.31 (s, 1H), 9.83 (s, 1H), 7.48 (d, J=2.4 Hz, 1H), 7.17 (d, J=2.4 Hz, 1H), 2.22-2.17 (m, 1H), 1.07-1.00 (m, 2H), 0.74-0.66 (m, 2H).

55.3 Preparation of 4-bromo-2-cyclopropyl-6-[(E)-
2-(4,4,5,5-tetramethyl-1,3,2-dioxaborolan-2-yl)
vinyl] phenol

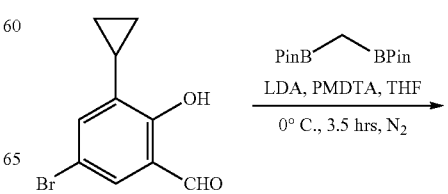

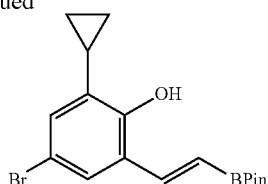

To a solution of LDA (19 mL, 2N, 2 eq) in THF (50 mL) was added N'-[2-(dimethylamino)ethyl]-N, N, N'-trimethylethane-1,2-diamine (6.61 g, 38.1 mmol, 7.97 mL, 2 eq) and 4,4,5,5-tetramethyl-2-[(4,4,5,5-tetramethyl-1,3,2-dioxaborolan-2-yl) methyl]-1,3,2-dioxaborolane (10.2 g, 38.1 mmol, 2 eq) in portions at 0° C. over 10 mins under $N_2$. The mixture was continue stirred at 0° C. for 20 mins. Then a solution of 5-bromo-3-cyclopropyl-2-hydroxy-benzaldehyde (4.6 g, 19.0 mmol, 1 eq) in THF (5 mL) was added at 0° C. The resulting mixture was stirred at 0° C. for another 3 hrs. TLC showed the reaction was completed. The reaction mixture was quenched by addition of sat. aq. $NH_4Cl$ (50 mL) at 0° C., and then extracted with EtOAc (50 mL×3). The combined organic layers were washed with brine (30 mL×3), dried over $Na_2SO_4$, filtered and concentrated under reduced pressure to give a residue. The residue was purified by flash silica gel chromatography (ISCO®; 40 g SepaFlash® Silica Flash Column, Eluent of 0~10% Ethyl acetate/Petroleum ether gradient @ 60 mL/min) to give 4-bromo-2-cyclopropyl-6-[(E)-2-(4,4,5,5-tetramethyl-1,3,2-dioxaborolan-2-yl) vinyl]phenol (6 g, 86.1% yield) as a yellow solid. $^1H$ NMR ($CDCl_3$, 400 MHz) δ=7.64 (d, J=18.4 Hz, 1H), 7.49 (d, J=2.4 Hz, 1H), 7.15 (d, J=2.4 Hz, 1H), 6.15 (d, J=18.4 Hz, 1H), 5.80 (s, 1H), 1.80-1.71 (m, 1H), 1.31 (s, 12H), 1.04-0.98 (m, 2H), 0.67-0.60 (m, 2H).

55.4 Preparation of 6-bromo-8-cyclopropyl-2-hydroxy-1,2-benzoxaborinine

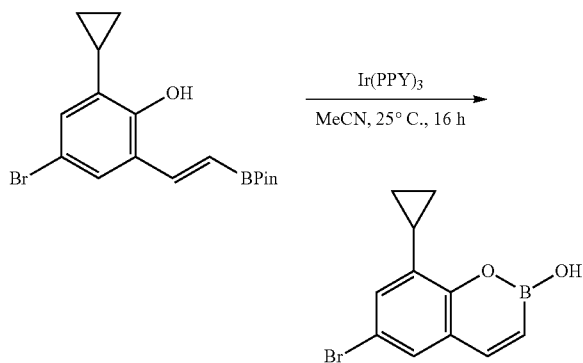

To a mixture of 4-bromo-2-cyclopropyl-6-[(E)-2-(4,4,5,5-tetramethyl-1,3,2-dioxaborolan-2-yl) vinyl]phenol (3 g, 8.22 mmol, 1 eq) in McCN (20 mL) was added tris[2-(2-pyridyl) phenyl] iridium ($Ir(PPY)_3$, 53 mg, 82.1 umol, 0.01 eq). The reaction mixture was stirred at 25° C. and irradiated using 34W blue LED lamps for 16 hrs. TLC showed the reaction was completed. The reaction mixture was quenched with water (30 mL) and extracted with EtOAc (30 mL×3). Then the organic phases were washed with brine (20 mL×2), dried over $Na_2SO_4$, filtered and concentrated under reduced pressure to give a residue. The residue was purified by column chromatography ($SiO_2$, Petroleum ether/Ethyl acetate=1/0 to 20/1) to give 6-bromo-8-cyclopropyl-2-hydroxy-1,2-benzoxaborinine (2.4 g, 55.1% yield) as a yellow solid. $^1H$ NMR ($CDCl_3$, 400 MHz) δ 7.68 (d, J=12.0 Hz, 1H), 7.35 (d, J=2.4 Hz, 1H), 7.00 (d, J=2.4 Hz, 1H), 6.27 (d, J=12.0 Hz, 1H), 4.51 (s, 1H), 2.45-2.39 (m, 1H), 1.08-1.02 (m, 2H), 0.76-0.70 (m, 2H).

55.5 Preparation of 1-(trans-4-cyanotetrahydro-2H-pyran-3-yl)-3-[(8-cyclopropyl-2-hydroxy-1,2-benzoxaborinin-6-yl) amino] pyrazole-4-carboxamide

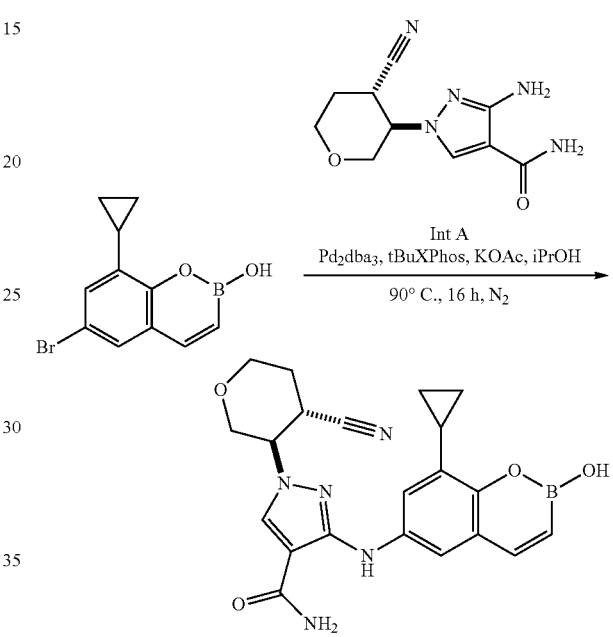

A mixture of 3-amino-1-(trans-4-cyanotetrahydro-2H-pyran-3-yl)pyrazole-4-carboxamide (500 mg, 2.13 mmol, 1 eq), 6-bromo-8-cyclopropyl-2-hydroxy-1,2-benzoxaborinine (844 mg, 3.19 mmol, 1.5 eq), KOAc (417 mg, 4.25 mmol, 2 eq), $Pd_2(dba)_3$ (389 mg, 425 umol, 0.2 eq) and t-Bu Xphos (361 mg, 850 umol, 0.4 eq) in i-PrOH (15 mL) was degassed and purged with $N_2$ for 3 times, and then the mixture was stirred at 90° C. for 16 h under $N_2$ atmosphere. LCMS indicated the reaction was completed and desired MS observed. The reaction was cooled to room temperature and filtered. The filtrate was concentrated under reduced pressure to give a residue. The residue was purified by flash silica gel chromatography (ISCO®; 80 g SepaFlash® Silica Flash Column, Eluent of 0-15% Ethyl acetate/Petroleum ether gradient @ 60 mL/min) to give crude product (2.8 g) as yellow solid, which was further purified by prep-HPLC (column: Phenomenex luna Cis 250*50 mm*10 um; mobile phase: [water(HCl)-ACN]; B %: 30/6-60%, 10 min) to give 1-(4-cyanotetrahydropyran-3-yl)-3-[(8-cyclopropyl-2-hydroxy-1,2-benzoxaborinin-6-yl) amino] pyrazole-4-carboxamide (1.1 g, 2.62 mmol, 61.7% yield, 100% purity) as a yellow solid. $^1H$ NMR ($CDCl_3$, 400 MHz) δ=8.94 (s, 1H), 8.27 (s, 1H), 7.79 (d, J=12.0 Hz, 1H), 7.68 (br s, 1H), 7.52 (d, J=2.4 Hz, 1H), 7.14 (br s, 1H), 7.04 (d, J=2.4 Hz, 1H), 6.11 (d, J=12.0 Hz, 1H), 4.55 (dt, J=4.4, 10.0 Hz, 1H), 4.06 (dd, J=4.4, 11.2 Hz, 1H), 3.94 (br d, J=10.0 Hz, 1H), 3.73-3.60 (m, 2H), 3.52-3.42 (m, 1H), 2.44-2.38 (m, 1H), 2.18 (br d, J=10.0 Hz, 1H), 2.06-1.97 (m, 1H), 1.04-0.94 (m, 2H), 0.79-0.70 (m, 2H). MS (ESI): mass calculated for $C_{21}H_{22}BN_5O_4$ 419.25; m/z found 420.3 [M+H]$^+$. HPLC: 100% (220 nm), 100% (254 nm). 1-(trans-4-cyanotetrahydro-2H-pyran-3-yl)-3-[(8-cyclopropyl-2-hydroxy-1,2-benzoxaborinin-6-yl) amino]pyrazole-4-carboxamide (800 mg) was separated by SFC (condition: column: REGIS(S, S)WHELK-O1 (250 mm×25 mm, 10 um); mobile phase: [0.1% NH$_3$H$_2$O ETOH]; B %: 45%-45%, 6 min) to give 1-[trans-4-cyanotetrahydro-2H-pyran-3-yl]-3-[(8-cyclopropyl-2-hydroxy-1,2-benzoxaborinin-6-yl) amino] pyrazole-4-carboxamide (stereoisomer one) 265.5 mg, 32.8% yield, 99.0% purity, 99.3% ee, first peak, Rt=1.522 min) as a white solid. 1H NMR (DMSO-hd 6, 400 MHz) δ=8.94 (s, 1H), 8.76 (s, 1H), 8.27 (s, 1H), 7.79 (d, J=12.0 Hz, 1H), 7.68 (brs, 1H), 7.52 (d, J=2.4 Hz, 1H), 7.09 (m, 1H), 7.04 (d, J=2.4 Hz, 1H), 6.11 (d, J=11.6 Hz, 1H), 4.56 (dt, J=4.4, 10.2 Hz, 1H), 4.06 (dd, J=4.4, 11.2 Hz, 1H), 3.94 (br d, J=10.0 Hz, 1H), 3.73-3.60 (m, 2H), 3.52-3.42 (m, 1H), 2.44-2.38 (m, 1H), 2.18 (d, J=10.0 Hz, 1H), 2.06-1.97 (m, 1H), 1.04-0.94 (m, 2H), 0.79-0.70 (m, 2H). MS (ESI): mass calculated for $C_{21}H_{22}BN_5O_4$ 419.25; m/z found 420.2 [M+H]$^+$. HPLC: 98.68% (220 nm), 99.53% (254 nm) and 1-[trans-4-cyanotetrahydro-2H-pyran-3-yl]-3-[(8-cyclopropyl-2-hydroxy-1,2-benzoxaborinin-6-yl) amino]pyrazole-4-carboxamide (stereoisomer two) 194.6 mg, 24.0% yield, 98.6% purity, 98.2% ee, second peak, Rt=1.670 min) as a white solid. 1H NMR (DMSO-hd 6, 400 MHz) δ=8.94 (s, 1H), 8.77 (s, 1H), 8.27 (s, 1H), 7.79 (d, J=12.0 Hz, 1H), 7.74-7.61 (m, 1H), 7.52 (d, J=2.4 Hz, 1H), 7.22-7.08 (m, 1H), 7.04 (d, J=2.4 Hz, 1H), 6.11 (d, J=12.0 Hz, 1H), 4.55 (dt, J=4.4, 10.0 Hz, 1H), 4.06 (dd, J=4.4, 11.2 Hz, 1H), 3.98-3.90 (m, 1H), 3.73-3.60 (m, 2H), 3.50-3.45 (m, 1H), 2.43-2.36 (m, 1H), 2.18 (d, J=9.6 Hz, 1H), 2.06-1.92 (m, 1H), 1.06-0.95 (m, 2H), 0.82-0.69 (m, 2H) MS (ESI): mass calculated for $C_{21}H_{22}BN_5O_4$ 419.25, m/z found 420.2 [M+H]$^+$. HPLC: 100.00% (220 nm), 100.00% (254 nm).

56. Preparation of 1-(trans-4-cyanotetrahydro-2H-pyran-3-yl)-3-[(3-ethyl-2-hydroxy-1,2-benzoxaborinin-6-yl)amino]pyrazole-4-carboxamide

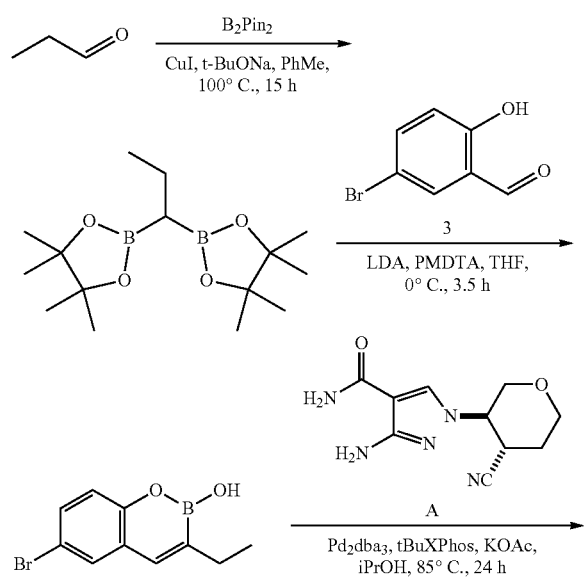

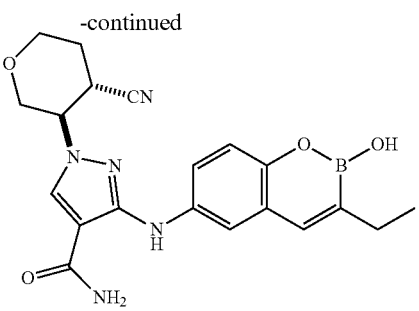

56.1 Preparation of 4,4,5,5-tetramethyl-2-[1-(4,4,5,5-tetramethyl-1,3,2-diaxaborolan-2-yl) propyl]-1,3,2-dioxaborolane

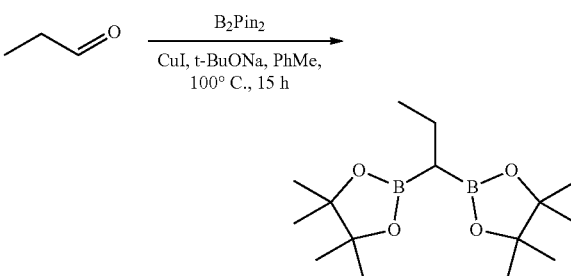

A mixture of propanal (0.5 g, 8.61 mmol, 626 uL, 1 eq), 4,4,5,5-tetramethyl-2-(4,4,5,5-tetramethyl-1,3,2-dioxaborolan-2-yl)-1,3,2-dioxaborolane (B$_2$Pin$_2$, 4.81 g, 18.9 mmol, 2.2 eq), CuI (164 mg, 860 umol, 0.1 eq) and t-BuONa (1.08 g, 11.2 mmol, 1.3 eq) in toluene (14 mL) was degassed and purged with N$_2$ for 3 times, and then the mixture was heated and stirred at 100° C. for 15 h under N$_2$ atmosphere. The reaction was cooled to room temperature and filtered. The filtrate from 8 parallel reactions was concentrated under reduced pressure to give a residue. The residue was purified by flash silica gel chromatography (ISCO®; 220 g Sepa-Flash® Silica Flash Column, Eluent of 0-20% Ethyl acetate/Petroleum ether gradient @ 100 mL/min) to give 4,4,5,5-tetramethyl-2-[1-(4,4,5,5-tetramethyl-1,3,2-dioxaborolan-2-yl)propyl]-1,3,2-dioxaborolane (9 g, 44.1% yield) as colorless oil. $^1$H NMR (CDCl$_3$, 400 MHz) δ 1.60 (q, J=7.6 Hz, 1H), 1.24-1.23 (m, 24H) 0.93 (q, J=7.6 Hz, 1H), 0.67 (q, J=7.6 Hz, 1H).

56.2 Preparation of 6-bromo-3-ethyl-2-hydroxy-1,2-benzoxaborinine

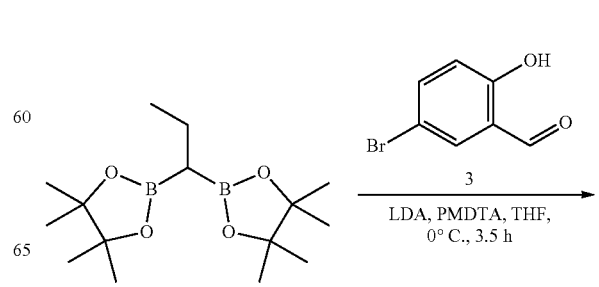

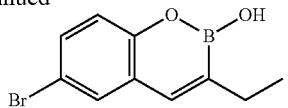

To a solution of LDA (2 M, 5.7 mL, 2.3 eq) in THF (10 mL) was added N'-[2-(dimethylamino)ethyl]-N,N,N'-trimethyl-ethane-1,2-diamine (1.98 g, 11.4 mmol, 2.4 mL, 2.3 eq) and 4,4,5,5-tetramethyl-2-[1-(4,4,5,5-tetramethyl-1,3,2-dioxaborolan-2-yl)propyl]-1,3,2-dioxaborolane (3.38 g, 11.4 mmol, 2.3 eq) in portions at 0° C. over a period of 10 min under $N_2$. The mixture was stirred at 0° C. for additional 20 min. Then a solution of 5-bromo-2-hydroxy-benzaldehyde (1 g, 4.97 mmol, 1 eq) in THF (5 mL) was added to the above mixture at 0° C., the resulting mixture was stirred at 0° C. for 3 h. TLC showed the reaction was completed. The reaction mixture was quenched by addition of sat. aq. $NH_4Cl$ (40 mL) at 0° C., and then extracted with EtOAc (30 mL×3). The combined organic layers were washed with brine (20 mL×3), dried over $Na_2SO_4$, filtered and concentrated under reduced pressure to give a residue. The residue was purified by flash silica gel chromatography (ISCO®; 40 g SepaFlash® Silica Flash Column, Eluent of 0~70% Ethylacetate/Petroleum ether gradient @ 75 mL/min) to give 6-bromo-3-ethyl-2-hydroxy-1,2-benzoxaborinine (500 mg, 39.7% yield) as yellow oil. $^1H$ NMR (DMSO-hd 6, 400 MHz) δ 9.06 (s, 1H), 7.68 (d, J=2.8 Hz, 1H), 7.50-7.43 (m, 2H), 7.15 (d, J=8.8 Hz, 1H), 2.40 (q, J=7.6 Hz, 2H), 1.10 (q, J=7.6 Hz, 3H).

56.3 Preparation of 1-(trans-4-cyanotelrahydr-2H-opyran-3-yl)-3-[(3-ethyl-2-hydroxy-1,2-benzoxaborinin-6-yl)amino]pyrazole-4-carboxamide

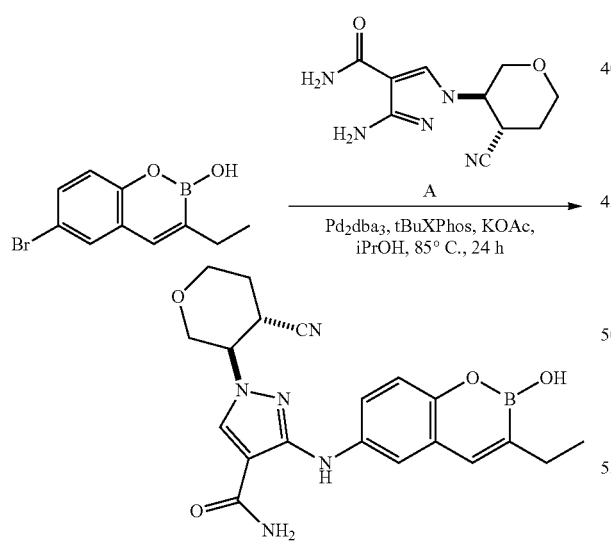

A mixture of 3-amino-1-(trans-4-cyanotetrahydro-2H-pyran-3-yl)pyrazole-4-carboxamide (279 mg, 1.19 mmol, 1.2 eq), 6-bromo-3-ethyl-2-hydroxy-1,2-benzoxaborinine (250 mg, 988 umol, 1 eq), KOAc (145 mg, 1.48 mmol, 1.5 eq), $Pd_2(dba)_3$ (45.2 mg, 49 umol, 0.05 eq) and t-BuXphos (42 mg, 99 umol, 0.1 eq) in i-PrOH (15 mL) was degassed and purged with $N_2$ for 3 times, and then the mixture was stirred at 85° C. for 24 h under $N_2$ atmosphere. LCMS showed the reaction was completed and desired MS observed. The reaction mixture was cooled to room temperature and quenched with sat. aq. $NH_4Cl$ (0.3 mL). The resulting solution was filtered and washed with EtOH (10 mL×3). The filtrate was concentrated under reduced pressure to give a residue. The residue was purified by prep-HPLC (column: Waters Xbridge BEH C18 100*30 mm*10 um; mobile phase: [water (10 mM $NH_4HCO_3$)-ACN]; B %: 25%-55%, 10 min) to give 1-(trans-4-cyanotetrahydro-2H-pyran-3-yl)-3-[(3-ethyl-2-hydroxy-1,2-benzoxaborinin-6-yl)amino]pyrazole-4-carboxamide (107.4 mg, 12.5% yield, 94.0% purity) as a yellow solid. $^1H$ NMR (DMSO-hd 6, 400 MHz) δ 9.06 (s, 1H), 8.73 (s, 1H), 8.28 (s, 1H), 7.69 (br s, 1H), 7.59 (d, J=2.8 Hz, 1H), 7.53-7.44 (m, 2H), 7.15 (br s, 1H), 7.09 (d, J=9.2 Hz, 1H), 4.55 (dt, J=3.6, 10.0 Hz, 1H), 4.04 (dd, J=4.2, 10.8 Hz, 1H), 3.91 (d, J=10.4 Hz, 1H), 3.70 (t, J=10.4 Hz, 2H), 3.51 (t, J=11.2 Hz, 1H), 2.38 (q, J=7.2 Hz, 2H), 2.20-2.10 (m, 1H), 2.05-1.92 (m, 1H), 1.11 (t, J=7.2 Hz, 3H). MS (ESI): mass calculated for $C_{20}H_{22}BN_5O_4$ 407.18; m/z found 406.2 [M−H]−. HPLC: 94.08% (220 nm), 97.39% (254 nm).

57. Preparation of 1-(trans-4-cyanotetrahydro-2H-pyran-3-yl)-3-[(2-hydroxy-1a,7b-dihydro-1H-cyclopropa[c][1,2]benzoxaborinin-6-yl)amino]pyrazole-4-carboxamide

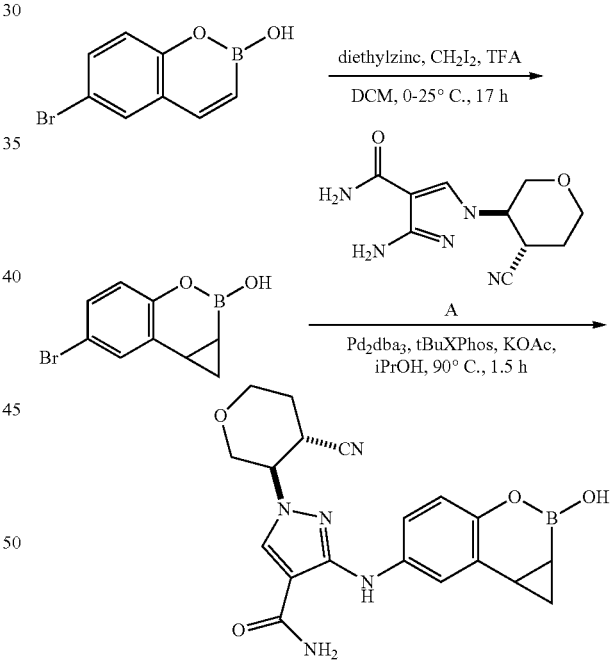

57.1 Preparation of 6-bromo-2-hydroxy-1a,7b-dihydro-1H-cyclopropa[c][1,2] benzoxaborinine

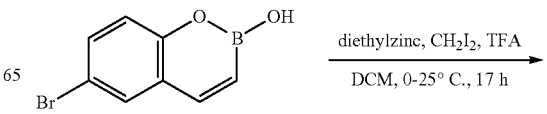

-continued

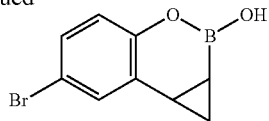

To a mixture of ZnEt₂ (1 M, 16.0 mL, 9 eq) in DCM (8 mL) was added a solution of TFA (1.62 g, 14.2 mmol, 1.1 mL, 8 eq) in DCM (2 mL) dropwise at 0° C. under N₂. The mixture was stirred at 0° C. for 0.5 h. And then added CH₂I₂ (4.29 g, 16.0 mmol, 1.3 mL, 9 eq) drop-wise at 0° C., the mixture was stirred at 0° C. for 0.5 h. Then added a solution of 6-bromo-2-hydroxy-1,2-benzoxaborinine (0.4 g, 1.78 mmol, 1 eq) in DCM (4 mL) dropwise at 0° C. The resulting mixture was allowed to warm to 25° C. and stirred at 25° C. for 16 h. LCMS showed the reaction was completed and desired MS observed. The reaction was poured into ice-water (20 mL) and adjusted pH to 4 with aq·HCl (2 N). The resulting mixture was extracted with DCM (15 mL×3). The combined organic layers were washed with brine (15 mL×2), dried over Na₂SO₄, filtered and concentrated under reduced pressure to give a residue. The residue was purified by prep-HPLC (column: Waters Xbridge BEH C18 100*30 mm*10 um; mobile phase: [water (10 mM NH₄HCO₃)-ACN]; B %: 15%-45%, 10 min) to give 6-bromo-2-hydroxy-1a,7b-dihydro-1H-cyclopropa[c][1,2]benzoxaborinine (180 mg, 41.0% yield, 96.9% purity) as a white solid. ¹H NMR (DMSO-hd 6, 400 MHz) δ 8.94 (br s, 1H), 7.51 (s, 1H), 7.20 (dd, J=2.0, 8.4 Hz, 1H), 7.46 (d, J=8.4 Hz, 1H), 2.29-2.23 (m, 1H), 1.35-1.25 (m, 1H), 0.57-0.46 (m, 1H), 0.35-0.25 (m, 1H). MS (ESI): mass calculated for C₉H₈BBrO₂ 237.98; m/z found 237.1 [M−H]⁻. HPLC: 96.93% (220 nm), 95.61% (254 nm).

57.2 Preparation of 1-(trans-4-cyanotetrahydro-2H-pyran-3-yl)-3-[(2-hydroxy-1a,7b-dihydro-1H-cyclopropa[c][1,2]benzoxaborinin-6-yl)amino]pyrazole-4-carboxamide

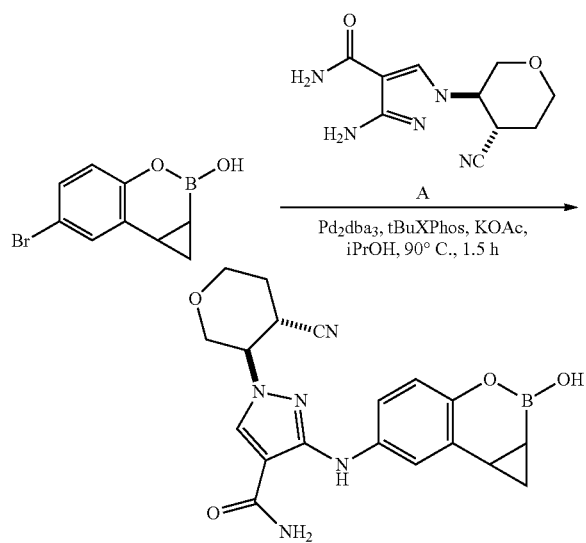

A mixture of 3-amino-1-(trans-4-cyanotetrahydro-2H-pyran-3-yl)pyrazole-4-carboxamide (118 mg, 502umol, 1.5 eq), 6-bromo-2-hydroxy-1a,7b-dihydro-1H-cyclopropa[c][1,2]benzoxaborinine (80 mg, 335 umol, 1 eq), KOAc (99 mg, 1.00 mmol, 3 eq), Pd₂(dba)₃ (92 mg, 100 umol, 0.3 eq) and t-Bu Xphos (85 mg, 201 umol, 0.6 eq) in i-PrOH (2 mL) was degassed and purged with N₂ for 3 times, and then the mixture was stirred at 90° C. for 1.5 h under N₂ atmosphere. LCMS showed the reaction was completed and desired MS observed. The reaction mixture was quenched by addition of sat. aq. NH₄Cl (10 mL) at 0° C., and then extracted with EtOAc (10 mL×3). The combined organic layers were washed with brine (10 mL×2), dried over Na₂SO₄, filtered and concentrated under reduced pressure to give a residue. The residue was purified by prep-HPLC (column: Waters Xbridge BEH C18 100*30 mm*10 um; mobile phase: [water (10 mM NH₄HCO₃)-ACN]; B %: 5%-35%, 10 min) to give 1-(trans-4-cyanotetrahydro-2H-pyran-3-yl)-3-[(2-hydroxy-1a,7b-dihydro-1H-cyclopropa[c][1,2]benzoxaborinin-6-yl)amino]pyrazole-4-carboxamide (27.2 mg, 18.7% yield, 90.7% purity) as a yellow solid. ¹H NMR (DMSO-hd 6, 400 MHz) δ 8.96 (s, 1H), 8.92 (s, 1H), 8.26 (s, 1H), 7.68 (br s, 1H), 7.39 (t, J=3.2 Hz, 1H), 7.29 (dd, J=2.4, 8.4 Hz, 1H), 7.14 (br s, 1H), 6.72 (d, J=8.8 Hz, 1H), 4.53 (dt, J=4.4, 9.6 Hz, 1H), 4.06-3.98 (m, 1H), 3.92-3.85 (m, 1H), 3.72-3.61 (m, 2H), 3.48 (t, J=11.2 Hz, 1H), 2.35-2.25 (m, 1H), 2.20-2.10 (m, 1H), 2.04-1.90 (m, 1H), 1.30 (t, J=7.6 Hz, 1H), 0.56-0.43 (m, 1H), 0.30-0.20 (m, 1H). MS (ESI): mass calculated for C₁₉H₂₀BN₅O₄ 393.16; m/z found 392.2 [M−H]⁻. HPLC: 90.78% (220 nm), 85.19% (254 nm).

Biological Examples

The compounds of the present disclosure were tested in multiple assays as described below. Representative results are compiled in Table 1.

Biochemical Kinase Assay Protocol (JAK)

Reagent: Base Reaction buffer; 20 mM Hepes (pH 7.5), 10 mM MgCl₂, 1 mM EGTA, 0.02% Brij™ 35, 0.02 mg/ml BSA, 0.1 mM Na₃VO₄, 2 mM DTT, 1% DMSO, where required cofactors were added individually to each kinase reaction.

Reaction Procedure:
1. Prepared indicated substrate in freshly prepared Base Reaction Buffer
2. Delivered any required cofactors to the substrate solution above
3. Delivered indicated kinase into the substrate solution and gently mix
4. Delivered compounds in DMSO into the kinase reaction mixture by Acoustic technology (Echo550; nano-liter range), incubated for 20 minutes at room temperature
5. Delivered 33P-ATP into the reaction mixture to initiate the reaction.
6. Incubated kinase reaction for 2 hours at room temperature
7. Reactions were spotted onto P81 ion exchange paper
8. Detected kinase activity by filter-binding method.

Prophetic Cytokine Inhibition Assay Protocol for IL-4 and IL-31

The test compounds are solubilized in DMSO, then diluted to make appropriate stocks for use in the assay, and diluted in culture medium to 20× assay concentrations. PBMC's are plated and allowed to settle for 1 hour at 37° C., 5% CO₂. Test compounds and controls are added to the settled PBMC's and incubated for 1 hour at 37° C., 5% CO₂. The PBMC's are then be treated with PHA (10 µg/mL) and incubated for 24 hours at 37° C., 5% CO₂. DMSO is used as a positive control and dexamethasone (100 nM) was used as a reference inhibitor control. After the main incubation, cell culture supernatants are harvested and assayed for the cytokines listed above, using standard Luminex protocols. Levels of cytokine induction are interpolated from standard curves using 5-parameter non-linear regression analyses, where $y=(A+((B-A)/(1+(((B-E)/(E-A))*((x/C)\hat{}D)))))$. The interpolated data is normalized to DMSO controls and analyzed to determine $IC_{50}$ values using 4-parameter non-linear regression analyses, where $y=(A+((B-A)/(1+((C/x)\hat{}D))))$ Cytokine Function Assay Protocols for IL-4/pSTAT6 and GM-CSF/pSTAT5:

GM-CSF/pSTAT5:

Whole blood from a healthy donor was lysed to remove red blood cells. Cells were plated onto a 96 well plate. Compound was added and incubated for 1 hour (at 37° C.). After 1 hour, cells were stimulated with GM-CSF for 15 minutes. Cells were fixed and stained with anti-pSTAT5 antibody. After staining, cells were read on a Beckman-Coulter CytoFLEX.

IL-4/pSTAT6:

PBMC from a healthy donor was plated onto a 96 w plate. Compound was added and incubated for 1 hour (at 37° C.). After 1 hour, cells were stimulated with IL-4 for 15 minutes. Cells were fixed and stained with anti-pSTAT6 antibody. After staining, cells were read on a Beckman-Coulter Cyto-FLEX.

Cytokine Function Assay Protocols for IL-31:

1. Plate DH82 cells at a density of 125,000 cells per well in a 96-well plate and incubate overnight in EMEM medium (ATCC® 30-2003) containing 15% FBS and 10 ng/mL canine IFNr (R&D, Cat #781-CG-050, Lot #DIA1320011) at 37° C.
2. After 24 hr, wash with 37° C. pre-warmed PBS (100 uL/well).
3. Add serum-free MEM, 90 uL per well, 2 hr, 37° C.
4. Add 10 uL 10×IL-31 (40, 10, 2.5 ug/mL) in duplicate, 5 min, 37° C.
5. Remove medium, add 60 uL lysis buffer per well. Agitate on a plate shaker (~350 rpm) for 10 min at RT.
6. Add 12 uL lysate/50% lysate to 384-well Opaque assay plate, 25% control lysate and lysis buffer were added to the assay plate in duplicate as positive and negative controls.
7. Add 6 uL Acceptor Mix, cover with aluminum foil, quickly spin at 1000 rpm, shake at 120 rpm for 2 min, then incubate at RT for 1 hr.
8. Add 6 uL Donor Mix, cover with aluminum foil, quickly spin at 1000 rpm, shake at 120 rpm for 2 m, then incubate at RT for 3 hr.
9. Measure the fluorescence using EnVision™ plate reader.

Activity of Compounds

Compounds according to the present invention were tested in the Biochemical Kinase Assay Protocol. The results are provided below in Table 1, wherein the potency levels A, B, and C in the columns labeled JAK1 (range) correspond to IC50 as follows: A<10 nM; B=10-50 nM and C>50 nM. The Example Number entries formatted ##a represent stereoisomer one and entries formatted ##b represent stereoisomer two.

TABLE 1

Biochemical Kinase Inhibition Assay Results

| Example Number | JAK1 (range) |
|---|---|
| 1 | B |
| 2 | C |
| 3 | A |
| 3a | A |
| 3b | B |
| 4 | A |
| 5 | A |
| 6 | A |
| 6a | A |
| 6b | B |
| 7 | A |
| 8 | A |
| 9 | A |
| 10 | B |
| 11 | A |
| 12 | A |
| 13 | A |
| 13a | A |
| 13b | A |
| 14 | A |
| 14a | A |
| 14b | B |
| 15 | A |
| 16 | A |
| 16a | C |
| 16b | A |
| 17a | C |
| 17b | C |
| 18 | A |
| 19 | A |
| 20 | B |
| 21 | A |
| 22 | A |
| 23 | A |
| 23a | A |
| 23b | C |
| 24 | B |
| 25 | B |
| 26 | A |
| 27 | A |
| 27a | B |
| 27b | A |
| 28a | C |
| 28b | A |
| 29 | B |
| 30 | A |
| 30a | C |
| 30b | A |
| 31 | A |
| 32 | A |
| 33 | A |
| 34 | B |
| 35 | B |
| 36 | A |
| 36a | A |
| 36b | A |
| 37 | A |
| 38 | A |
| 38a | B |
| 38b | A |
| 39 | A |
| 40 | B |
| 41 | A |
| 41a | A |
| 41b | A |
| 42 | A |
| 42a | A |
| 42b | A |
| 43 | A |
| 43a | A |
| 43b | A |
| 44 | A |
| 44a | A |
| 44b | A |
| 45a | A |

TABLE 1-continued

Biochemical Kinase Inhibition Assay Results

| Example Number | JAK1 (range) |
|---|---|
| 45b | A |
| 46a | C |
| 46b | C |
| 47a | A |
| 47b | A |
| 48 | A |
| 48a | A |
| 48b | A |
| 49 | A |
| 50 | A |
| 51 | A |
| 51a | A |
| 51b | A |
| 52 | A |
| 52a | A |
| 52b | A |
| 53a | C |
| 53b | A |
| 54 | B |
| 55a | A |
| 55b | C |
| 56 | A |
| 57 | A |
| — | — |
| — | — |

In some embodiments, the compounds of the present disclosure are potent JAK inhibitors. As such, the compounds may be used for the treatment or control of inflammation, auto-immune diseases, cancer, and other disorders and indications where modulation of JAK would be desirable.

All publications, patents, and patent applications cited in this specification are incorporated herein by reference for the teaching to which such citation is used.

Test compounds for the experiments described herein were employed in free or salt form.

The specific responses observed may vary according to and depending on the particular active compound selected or whether there are present carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

The invention is further described by the following numbered paragraphs:

1. A compound of formula (IV):

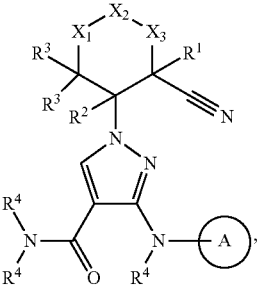

(IV)

or a pharmaceutically acceptable salt or a stereoisomer or a tautomer thereof, wherein $X_1$ is selected from the group consisting of —O—, —N($R^6$)—, and —C($R^7$)($R^8$)—;

$X_2$ is selected from the group consisting of —O—, —N($R^6$)—, and —C($R^7$)($R^8$)—, or $X_2$ comprises a bond between $X_1$ and $X_3$;

$X_3$ is selected from the group consisting of —O—, —N($R^6$)—, and —C($R^7$)($R^8$)—, except $X_1$ and $X_2$ cannot both be —O—, and $X_2$ and $X_3$ cannot both be —O—;

$R^1$ is selected from the group consisting of hydrogen, halogen (when $X_3$ is —C($R^7$)($R^8$)), hydroxy, C1-6 alkyl, $C_{3-7}$ cycloalkyl, C1-6alkyl(oxy), and $C_{3-7}$ cycloalkyl(oxy), wherein the last four members of the of the above-mentioned $R^1$ group may optionally be substituted independently of one another with one or more halogen;

$R^2$ is selected from the group consisting of hydrogen, $C_{1-6}$ alkyl, $C_{3-7}$ cycloalkyl, $C_{1-6}$ alkyl(oxy), and $C_{3-7}$ cycloalkyl(oxy), wherein the last four members of the above-mentioned $R^2$ group may optionally be substituted independently of one another with one or more halogen;

each $R^3$ is independently selected from the group consisting of hydrogen, halogen (when $X_1$ is —C($R^7$)($R^8$)), $C_{1-6}$ alkyl, $C_{3-7}$ cycloalkyl, $C_{1-6}$ alkyl(oxy), and $C_{3-7}$ cycloalkyl(oxy), wherein the last four members of the above-mentioned $R^3$ group may optionally be substituted independently of one another with one or more halogen;

each $R^4$ is independently selected from the group consisting of hydrogen, $C_{1-6}$alkyl, $C_{3-7}$ cycloalkyl, $C_{1-6}$ alkyl (oxy), and $C_{3-7}$ cycloalkyl(oxy), wherein the above-mentioned members of each $R^4$ group, except hydrogen, may optionally be substituted independently of one another with one or more halogen;

A is selected from the group consisting of benzo[c][1,2] oxaborol-1(3H)-ol, 3,4-dihydro-1Hbenzo[c][1,2]oxaborinin-1-ol, and 2H-benzo[e][1,2]oxaborinin-2-ol, or a derivative thereof, such as a moiety selected from any one of $A_1$-$A_6$:

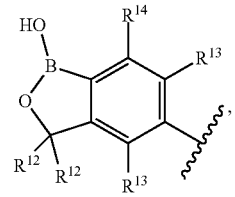

$A_1$

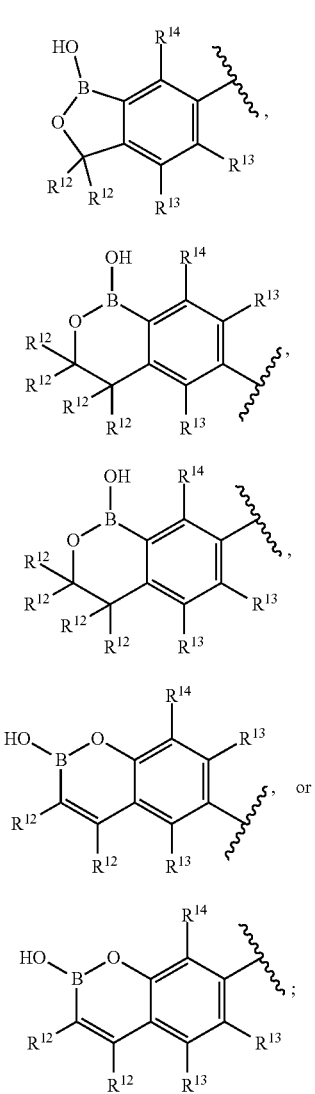

R⁶ is selected from the group consisting of hydrogen, C₁₋₆ alkyl, C₃₋₇ cycloalkyl, C₁₋₆ alkyl(oxy), C₃₋₇ cycloalkyl(oxy), —COO—C₁₋₆ alkyl, —COO—C₃₋₇-cycloalkyl, —(C₁₋₃-alkyl)-(C₃₋₆-cycloalkyl), —(C₂₋₃-alky(oxy)-(C₂₋₆-alkyl), —(C₂₋₃-alkyl(oxy)-(C₃₋₆-cycloalkyl), 4-7-membered heterocycloalkyl, —(C₁₋₃-alkyl)-(4-7-membered heterocycloalkyl), -heteroaryl, and —(C₁₋₃-alkyl)-(heteroaryl), wherein the above-mentioned members of the R⁶ group, except hydrogen, may optionally be substituted independently of one another by one or more substituents selected from the group consisting of C₁₋₆ alkyl and halogen, except halogen may not be adjacent to a heteroatom;

R⁷ and R⁸ are independently selected from the group consisting of hydrogen, halogen, hydroxy, —N(R⁹)(R¹⁰), —O(R¹¹), C₁₋₆ alkyl, C₃₋₇ cycloalkyl, C₁₋₆ alkyl(oxy), C₃₋₇ cycloalkyl(oxy), —COO—C₁₋₆ alkyl, —COO—C₃₋₇-cycloalkyl, —(C₁₋₃-alkyl)-(C₃₋₆-cycloalkyl), —(C₂₋₃-alkyl(oxy)-(C₂₋₆-alkyl), —(C₂₋₃-alkyl(oxy)-(C₃₋₆-cycloalkyl), 4-7-membered heterocycloalkyl, —(C₁₋₃-alkyl)-(4-7-membered heterocycloalkyl), -heteroaryl, and —(C₁₋₃-alkyl)-(heteroaryl), wherein the last fifteen members of the above-mentioned R⁷ and R⁸ groups may optionally be substituted independently of one another by one or more substituents selected from the group consisting of halogen and hydroxy, and wherein R⁷ and R⁸ may be linked together to form a ring;

R⁹ and R¹⁰ are independently selected from the group consisting of hydrogen, C₁₋₆ alkyl, C₃₋₇ cycloalkyl, C₁₋₆ alkyl(oxy), C₃₋₇ cycloalkyl(oxy), —COO—C₁₋₆ alkyl, —COO—C₃₋₇-cycloalkyl, —(C₁₋₃-alkyl)-(C₃₋₆-cycloalkyl), —(C₂₋₃-alkyoxyl)-(C₂₋₆-alkyl), —(C₂₋₃-alkyl(oxy)-(C₃₋₆-cycloalkyl), 4-7-membered heterocycloalkyl, —(C₁₋₃-alkyl)-(4-7-membered heterocycloalkyl), -heteroaryl, and —(C₁₋₃-alkyl)-(heteroaryl); wherein the last fourteen members of the above-mentioned R⁹ and R¹⁰ groups may optionally be substituted independently of one another by one or more halogen, or R⁹ and R¹⁰ may be linked together to form a ring;

R¹¹ is selected from the group consisting of hydrogen, C₁₋₆ alkyl, C₃₋₇ cycloalkyl, C₁₋₆ alkyl(oxy), C₃₋₇ cycloalkyl(oxy), —COO—C₁₋₆ alkyl, —COO—C₃₋₇-cycloalkyl, —(C₁₋₃-alkyl)-(C₃₋₆-cycloalkyl), —(C₂₋₃-alkyoxyl)-(C₂₋₆-alkyl), —(C₂₋₃-alkyl(oxy)-(C₃₋₆-cycloalkyl), 4-7-membered heterocycloalkyl, —(C₁₋₃-alkyl)-(4-7-membered heterocycloalkyl), -heteroaryl, and —(C₁₋₃-alkyl)-(heteroaryl), wherein the last thirteen members of the above-mentioned R¹¹ group may optionally be substituted independently of one another by one or more substituents selected from the group consisting of halogen and hydroxy, except that said optional substitution may not be geminal;

each R¹² is independently selected from the group consisting of hydrogen, halogen, C₁₋₆ alkyl, C₃₋₇ cycloalkyl, 4-7-membered heterocycloalkyl, C₁₋₆ alkyl(oxy), and C₃₋₇ cycloalkyl(oxy), wherein the last four members of the above-mentioned R¹² group may optionally be substituted independently of one another by one or more substituents selected from the group consisting of halogen and hydroxy, except when R¹² is adjacent to oxygen, R¹² is not halogen, and two adjacent R¹² may be connected to provide a fused cycloalkyl, such as cyclopropyl; and R¹³ and R¹⁴ are independently selected from the group consisting of hydrogen, halogen, cyano, C₁₋₆alkyl, C₃₋₇ cycloalkyl, C₁₋₆ alkyl(oxy), C₃₋₇ cycloalkyl(oxy), —(C₁₋₃-alkyl)-(C₃₋₆-cycloalkyl), —(C₂₋₃-alkyl(oxy)-(C₂₋₆-alkyl), —(C₂₋₃-alkyl(oxy)-(C₃₋₆-cycloalkyl), 4-7-membered heterocycloalkyl, —(C₁₋₃-alkyl)-(4-7-membered heterocycloalkyl), —N—(R⁶)(R⁶), —SO₂—(R⁶), —SO₂—(R⁶)(R⁶), —S(O)—(R⁶), and —S—(R⁶), wherein the last fourteen members of the above-mentioned R¹³ and R¹⁴ groups may optionally be substituted independently of one another by one or more substituents selected from the group consisting of halogen and hydroxy.

2. The compound according to paragraph 1, wherein
X₁ is selected from the group consisting of —O—, —N(R⁶)—, and —C(R⁷)(R⁸)—;
X₂ is selected from the group consisting of —O—, —N(R⁶)—, and —C(R⁷)(R⁸)—, or
X₂ comprises a bond between X₁ and X₃;
X₃ is —C(R⁷)(R⁸)—, except X₁ and X₂ cannot both be —O—;
R¹ is selected from the group consisting of hydrogen, C₁₋₆ alkyl, and C₃₋₇ cycloalkyl, wherein the last two members of the above-mentioned group may optionally be substituted independently of one another with one or more halogen;

$R^2$ is selected from the group consisting of hydrogen, $C_{1-6}$ alkyl, and $C_{3-7}$ cycloalkyl, wherein the last two members of the above-mentioned $R^2$ group may optionally be substituted independently of one another with one or more halogen;

each $R^3$ is independently selected from the group consisting of hydrogen, $C_{1-6}$ alkyl, and $C_{3-7}$ cycloalkyl, wherein the last two members of the above-mentioned $R^3$ group may optionally be substituted independently of one another with one or more halogen;

each $R^4$ is independently selected from the group consisting of hydrogen, $C_{1-6}$ alkyl, and $C_{3-7}$ cycloalkyl, wherein the last two members of the above-mentioned $R^4$ group may optionally be substituted independently of one another with one or more halogen;

$R^7$ and $R^8$ are independently selected from the group consisting of hydrogen, —$C_{1-6}$ alkyl, $C_{3-7}$ cycloalkyl, $C_{1-6}$ alkyl(oxy), and $C_{3-7}$ cycloalkyl(oxy), wherein the last four members of the above-mentioned $R^7$ and $R^8$ groups may optionally be substituted independently of one another by one or more substituents selected from the group consisting of halogen and hydroxy, and $R^7$ and $R^8$ may be linked together to form a ring; and each $R^{13}$ is independently selected from the group consisting of hydrogen, halogen, and $C_{1-6}$ alkyl.

3. The compound according to one or more of paragraphs 1 to 2, wherein $X_1$ is selected from the group consisting of —O—, —N($R^6$)—, and —C($R^7$)($R^8$)—;

$X_2$ is selected from the group consisting of —O— and —C($R^7$)($R^8$)—, except $X_1$ and $X_2$ may not both be —O—, or $X_2$ comprises a bond between $X_1$ and $X_3$;

$X_3$ is —C($R^7$)($R^8$)—;

$R^1$ is selected from the group consisting of hydrogen and $C_{1-6}$ alkyl;

$R^2$ is selected from the group consisting of hydrogen and $C_{1-6}$ alkyl;

each $R^3$ is independently selected from the group consisting of hydrogen and $C_{1-6}$ alkyl;

each $R^4$ is independently selected from the group consisting of hydrogen and $C_{1-6}$ alkyl;

$R^7$ and $R^8$ are independently selected from the group consisting of hydrogen and $C_{1-6}$ alkyl, wherein the $C_{1-6}$ alkyl may optionally be substituted with one or more of halogen;

$R^{13}$ is hydrogen; and each $R^{14}$ is independently selected from the group consisting of hydrogen, halogen, cyano, $C_{1-6}$ alkyl, $C_{3-7}$ cycloalkyl, $C_{1-6}$ alkyl(oxy), $C_{3-7}$ cycloalkyl(oxy), —($C_{1-3}$-alkyl)-($C_{3-6}$-cycloalkyl), —($C_{2-3}$-alkyl(oxy)-($C_{2-6}$-alkyl), and 4-7-membered heterocycloalkyl, wherein the last seven members of the above-mentioned $R^{14}$ group may optionally be substituted independently of one another by one or more substituents selected from the group consisting of halogen and hydroxy.

4. The compound according to any one or more of paragraphs 1-3, wherein $X_1$ is selected from the group consisting of —O—, —N($R^6$)—, and —C($R^7$)($R^8$)—;

$X_2$ is —C($R^7$)($R^8$)—;

$X_3$ is —C($R^7$)($R^8$)—;

$R^1$, $R^2$, $R^3$, and $R^4$ are hydrogen;

$R^7$ and $R^8$ are independently selected from the group consisting of hydrogen and $C_{1-6}$ alkyl, wherein $C_{1-6}$ alkyl may optionally be substituted with one or more of halogen;

each $R^{12}$ is independently selected from the group consisting of hydrogen, halogen, $C_{1-6}$ alkyl, and $C_{3-7}$ cycloalkyl, wherein the last two substituents may optionally be substituted independently of one another by one or more halogen;

$R^{13}$ is hydrogen; and each $R^{14}$ is independently selected from the group consisting of hydrogen, halogen, cyano, $C_{1-6}$ alkyl, $C_{3-7}$ cycloalkyl, and $C_{1-6}$ alkyl(oxy), wherein the last three members of the above-mentioned $R^{14}$ group may optionally be substituted independently of one another by one or more halogen.

5. A compound of formula (IVa) or (IVb):

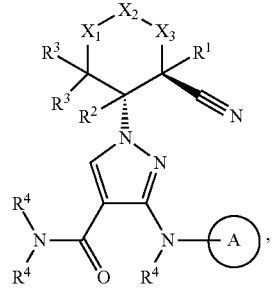

(IVa)

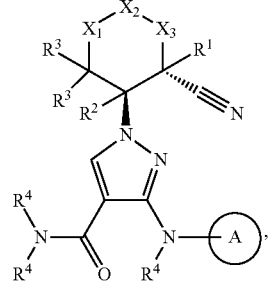

(IVb)

or a pharmaceutically acceptable salt or a stereoisomer or a tautomer thereof wherein $X_1$ is selected from the group consisting of —O—, —N($R^6$)—, and —C($R^7$)($R^8$)—;

$X_2$ is selected from the group consisting of —O—, —N($R^6$)—, and —C($R^7$)($R^8$)—, or $X_2$ comprises a bond between $X_1$ and $X_3$;

$X_3$ is selected from the group consisting of —O—, —N($R^6$)—, and —C($R^7$)($R^8$)—, except $X_1$ and $X_2$ cannot both be —O—, and $X_2$ and $X_3$ cannot both be —O—;

$R^1$ is selected from the group consisting of hydrogen, halogen (when $X_3$ is —C($R^7$)($R^8$)—), hydroxy, $C_{1-6}$ alkyl, $C_{3-7}$ cycloalkyl, $C_{1-6}$ alkyl(oxy), and $C_{3-7}$ cycloalkyl(oxy), wherein the last four members of the of the above-mentioned $R^1$ group may optionally be substituted independently of one another with one or more halogen;

$R^2$ is selected from the group consisting of hydrogen, $C_{1-6}$ alkyl, $C_{3-7}$ cycloalkyl, $C_{1-6}$ alkyl(oxy), and $C_{3-7}$ cycloalkyl(oxy), wherein the last four members of the above-mentioned R² group may optionally be substituted independently of one another with one or more halogen;

each R³ is independently selected from the group consisting of hydrogen, halogen (when $X_1$ is —C(R⁷)(R⁸)), $C_{1-6}$ alkyl, $C_{3-7}$ cycloalkyl, $C_{1-6}$ alkyl(oxy), and $C_{3-7}$ cycloalkyl(oxy), wherein the last four members of the above-mentioned R³ group may optionally be substituted independently of one another with one or more halogen;

each R⁴ is independently selected from the group consisting of hydrogen, $C_{1-6}$ alkyl, $C_{3-7}$ cycloalkyl, $C_{1-6}$ alkyl (oxy), and $C_{3-7}$ cycloalkyl(oxy), wherein the above-mentioned members of each R⁴ group, except hydrogen, may optionally be substituted independently of one another with one or more halogen;

A is selected from the group consisting of benzo[c][1,2]oxaborol-1(3H)-ol, 3,4-dihydro-1Hbenzo[c][1,2]oxaborinin-1-ol, and 2H-benzo[e][1,2]oxaborinin-2-ol, or a derivative thereof, such as a moiety selected from any one of $A_1$-$A_6$:

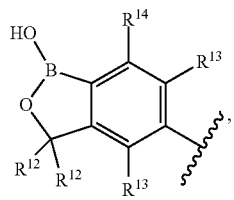
$A_1$

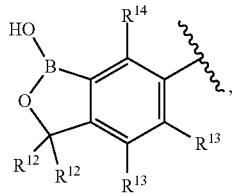
$A_2$

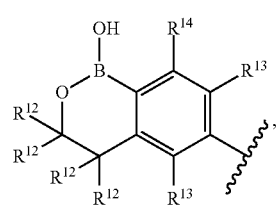
$A_3$

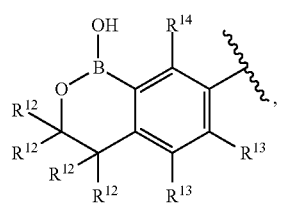
$A_4$

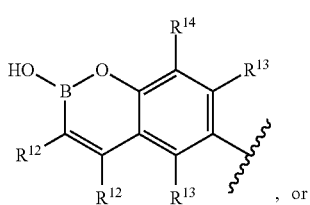
$A_5$, or

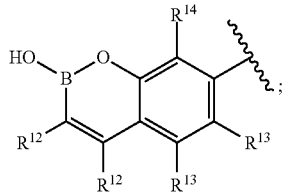
$A_6$;

R⁶ is selected from the group consisting of hydrogen, $C_{1-6}$alkyl, $C_{3-7}$ cycloalkyl, $C_{1-6}$ alkyl(oxy), $C_{3-7}$ cycloalkyl(oxy), —COO—$C_{1-6}$alkyl, —COO—$C_{3-7}$-cycloalkyl, —($C_{1-3}$-alkyl)-($C_{3-6}$-cycloalkyl), —($C_{2-3}$-alky(oxy)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl), wherein the above-mentioned members of the R⁶ group, except hydrogen, may optionally be substituted independently of one another by one or more substituents selected from the group consisting of $C_{1-6}$alkyl and halogen, except halogen may not be adjacent to a heteroatom;

R⁷ and R⁸ are independently selected from the group consisting of hydrogen, halogen, hydroxy, —N(R⁹)(R¹⁰), —O(R¹¹), $C_{1-6}$alkyl, $C_{3-7}$ Cycloalkyl, $C_{1-6}$ alkyl (oxy), $C_{3-7}$ Cycloalkyl(oxy), —COO—$C_{1-6}$ alkyl, —COO—$C_{3-7}$-cycloalkyl, —($C_{1-3}$-alkyly-($C_{3-6}$-Cycloalkyl), —($C_{2-3}$-alkyl(oxy)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl), wherein the last fifteen members of the above-mentioned R⁷ and R⁸ groups may optionally be substituted independently of one another by one or more substituents selected from the group consisting of halogen and hydroxy, and wherein R⁷ and R⁸ may be linked together to form a ring;

R⁹ and R¹⁰ are independently selected from the group consisting of hydrogen, $C_{1-6}$ alkyl, $C_{3-7}$ cycloalkyl, $C_{1-6}$ alkyl(oxy), $C_{3-7}$ cycloalkyl(oxy), —COO—$C_{1-6}$ alkyl, —COO—$C_{3-7}$-cycloalkyl, —($C_{1-3}$-alkyl)-($C_{3-6}$-cycloalkyl), —($C_{2-3}$-alkyoxyl)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl), wherein the last fourteen members of the above-mentioned R⁹ and R¹⁰ groups may optionally be substituted independently of one another by one or more halogen, or R⁹ and R¹⁰ may be linked together to form a ring;

R¹¹ is selected from the group consisting of hydrogen, $C_{1-6}$ alkyl, $C_{3-7}$ cycloalkyl, $C_{1-6}$ alkyl(oxy), $C_{3-7}$ cycloalkyl(oxy), —COO—$C_{1-6}$ alkyl, —COO—$C_{3-7}$-cycloalkyl, —($C_{1-3}$-alkyl)-($C_{3-6}$-cycloalkyl), —($C_{2-3}$-alkyoxyl)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), -heteroaryl, and —($C_{1-3}$-alkyl)-(heteroaryl), wherein the last thirteen members of the above-mentioned R¹¹ group may optionally be substituted independently of one another by one or more substituents selected from the group consisting of halogen and hydroxy, except that said optional substitution may not be geminal;

each R¹² is independently selected from the group consisting of hydrogen, halogen, $C_{1-6}$ alkyl, $C_{3-7}$ cycloalkyl, 4-7-membered heterocycloalkyl, $C_{1-6}$ alkyl(oxy), and $C_{3-7}$ cycloalkyl(oxy), wherein the last four members of the above-mentioned $R^{12}$group may optionally be substituted independently of one another by one or more substituents selected from the group consisting of halogen and hydroxy, except when $R^{12}$ is adjacent to oxygen, $R^{12}$ is not halogen, and two adjacent $R^{12}$ may be connected to provide a fused cycloalkyl, such as cyclopropyl; and $R^{13}$ and $R^{14}$ are independently selected from the group consisting of hydrogen, halogen, cyano, $C_{1-6}$alkyl, $C_{3-7}$ cycloalkyl, $C_{1-6}$ alkyl(oxy), $C_{3-7}$ cycloalkyl(oxy), —($C_{1-3}$-alkyl)-($C_{3-6}$-cycloalkyl), —($C_{2-3}$-alkyl(oxy)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), —N—($R^6$)($R^6$), —SO$_2$—($R^6$), —SO$_2$—($R^6$)($R^6$), —S(O)—($R^6$), and —S—($R^6$), wherein the last fourteen members of the above-mentioned $R^{13}$ and $R^{14}$groups may optionally be substituted independently of one another by one or more substituents selected from the group consisting of halogen and hydroxy.

6. The compound according to paragraph 5, wherein
$X_1$ is selected from the group consisting of —O—, —N($R^6$)—, and —C($R^7$)($R^8$)—;
$X_2$ is selected from the group consisting of —O—, —N($R^6$)—, and —C($R^7$)($R^8$)—, or
$X_2$ comprises a bond between $X_1$ and $X_3$;
$X_3$ is —C($R^7$)($R^8$)—, except $X_1$ and $X_2$ cannot both be —O—;
$R^1$ is selected from the group consisting of hydrogen, $C_{1-6}$ alkyl, and $C_{3-7}$ cycloalkyl, wherein the last two members of the above-mentioned group may optionally be substituted independently of one another with one or more halogen;
$R^2$ is selected from the group consisting of hydrogen, $C_{1-6}$ alkyl, and $C_{3-7}$ cycloalkyl, wherein the last two members of the above-mentioned group may optionally be substituted independently of one another with one or more halogen;
each $R^3$ is independently selected from the group consisting of hydrogen, $C_{1-6}$ alkyl, and $C_{3-7}$ cycloalkyl, wherein the last two members of the above-mentioned group may optionally be substituted independently of one another with one or more halogen;
each $R^4$ is independently selected from the group consisting of hydrogen, $C_{1-6}$ alkyl, and $C_{3-7}$ cycloalkyl, wherein the last two members of the above-mentioned group may optionally be substituted independently of one another with one or more halogen;
$R^7$ and $R^8$ are independently selected from the group consisting of hydrogen, —$C_{1-6}$ alkyl, $C_{3-7}$ cycloalkyl, $C_{1-6}$ alkyl(oxy), and $C_{3-7}$ cycloalkyl(oxy), wherein the last four members of the above-mentioned group may optionally be substituted independently of one another by one or more substituents selected from the group consisting of halogen and hydroxy, and $R^7$ and $R^8$ may be linked together to form a ring; and
each $R^{13}$ is independently selected from the group consisting of hydrogen, halogen, and $C_{1-6}$ alkyl.

7. The compound according to one or more of paragraphs 5 to 6, wherein
$X_1$ is selected from the group consisting of —O—, —N($R^6$)—, and —C($R^7$)($R^8$)—;
$X_2$ is selected from the group consisting of —O— and —C($R^7$)($R^8$)—, except $X_1$ and $X_2$ may not both be —O—, or $X_2$ comprises a bond between $X_1$ and $X_3$;

$X_3$ is —C($R^7$)($R^8$)—;
$R^1$ is selected from the group consisting of hydrogen and $C_{1-6}$ alkyl;
$R^2$ is selected from the group consisting of hydrogen and $C_{1-6}$ alkyl;
each $R^3$ is independently selected from the group consisting of hydrogen and $C_{1-6}$ alkyl;
each $R^4$ is independently selected from the group consisting of hydrogen and $C_{1-6}$ alkyl;
$R^7$ and $R^8$ are independently selected from the group consisting of hydrogen and $C_{1-6}$ alkyl, wherein $C_{1-6}$ alkyl is optionally substituted with one or more of halogen;
$R^{13}$ is hydrogen; and
each $R^{14}$ is independently selected from the group consisting of hydrogen, halogen, cyano, $C_{1-6}$ alkyl, $C_{3-7}$ cycloalkyl, $C_{1-6}$ alkyl(oxy), $C_{3-7}$ cycloalkyl(oxy), —($C_{1-3}$-alkyl)-($C_{3-6}$-cycloalkyl), —($C_{2-3}$-alkyl(oxy)-($C_{2-6}$-alkyl), and 4-7-membered heterocycloalkyl, wherein the last seven members said $R^{14}$group may optionally be substituted independently of one another by one or more substituents selected from the group consisting of halogen and hydroxy.

8. The compound according to any one or more of paragraphs 1 to 7, wherein
$X_2$ is —C($R^7$)($R^8$)—;
$X_3$ is —C($R^7$)($R^8$)—;
$R^1$, $R^2$, $R^3$, and $R^4$ are hydrogen;
$R^7$ and $R^8$ are independently selected from the group consisting of hydrogen and $C_{1-6}$ alkyl, wherein $C_{1-6}$ alkyl is optionally substituted with one or more of halogen;
each $R^{12}$ is independently selected from the group consisting of hydrogen, halogen, $C_{1-6}$ alkyl, and $C_{3-7}$ cycloalkyl, wherein the last two members of the above-mentioned $R^{12}$group may optionally be substituted independently of one another with one or more halogen;
each $R^{13}$ is hydrogen; and
each $R^{14}$ is independently selected from the group consisting hydrogen, halogen, cyano, C1-6 alkyl, $C_{3-7}$ cycloalkyl, and C1-6alkyl(oxy), wherein the last three members of the above-mentioned $R^{14}$ group may optionally be substituted independently of one another by one or more halogen.

9. A compound selected from the group shown in the following table:

| Example Number | Structure |
|---|---|
| 1 | |

| Example Number | Structure |
|---|---|
| 2 | 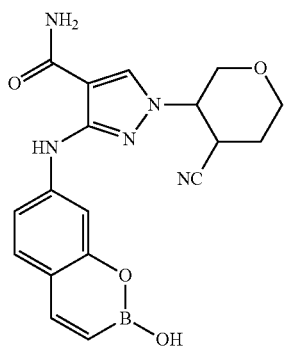 [SMILES: N#CC1CCOCC1n1cc(C(N)=O)c(Nc2ccc3c(c2)OB(O)C=C3)n1] |
| 3 | 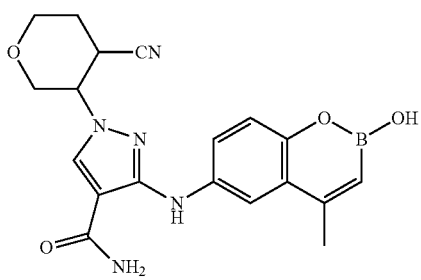 [SMILES: CC1=CB(O)Oc2ccc(Nc3nn(C4COCCC4C#N)cc3C(N)=O)cc21] |
| 4 | 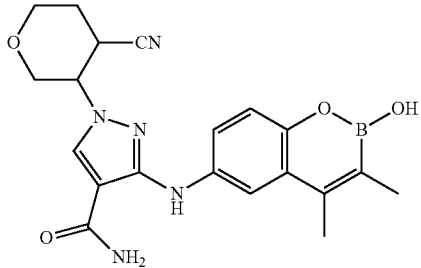 [SMILES: CC1=C(C)c2cc(Nc3nn(C4COCCC4C#N)cc3C(N)=O)ccc2OB1O] |
| 5 | 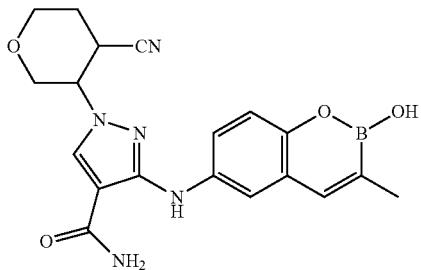 [SMILES: CC1=Cc2cc(Nc3nn(C4COCCC4C#N)cc3C(N)=O)ccc2OB1O] |
| 6 | 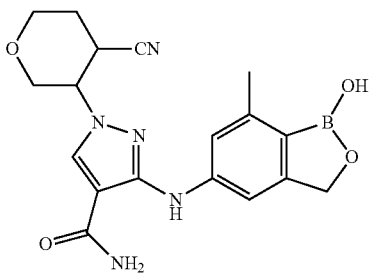 [SMILES: Cc1cc(Nc2nn(C3COCCC3C#N)cc2C(N)=O)cc2c1B(O)OC2] |
| Example Number | Structure |
|---|---|
| 7 | 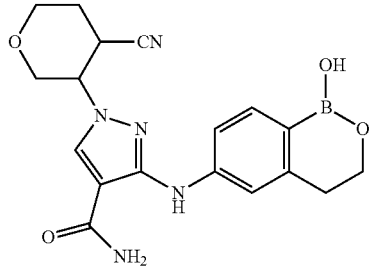 [SMILES: N#CC1CCOCC1n1cc(C(N)=O)c(Nc2ccc3c(c2)CCOB3O)n1] |
| 8 | 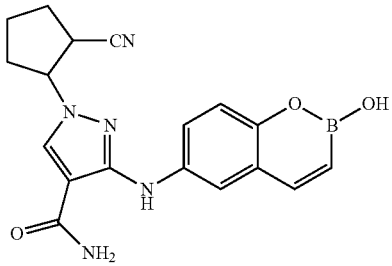 [SMILES: N#CC1CCCC1n1cc(C(N)=O)c(Nc2ccc3c(c2)C=CB(O)O3)n1] |
| 9 | 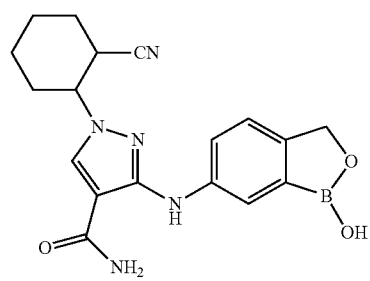 [SMILES: N#CC1CCCCC1n1cc(C(N)=O)c(Nc2ccc3c(c2)B(O)OC3)n1] |
| 10 | 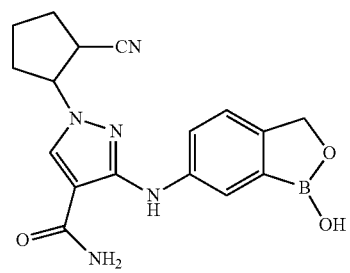 [SMILES: N#CC1CCCC1n1cc(C(N)=O)c(Nc2ccc3c(c2)B(O)OC3)n1] |
| 11 | 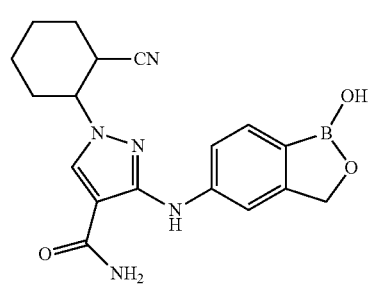 [SMILES: N#CC1CCCCC1n1cc(C(N)=O)c(Nc2ccc3c(c2)COB3O)n1] |

-continued
| Example Number | Structure |
|---|---|
| 12 | 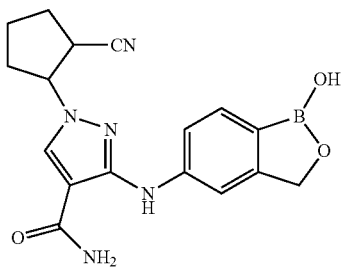 [SMILES: N#CC1CCCC1n1cc(C(N)=O)c(Nc2ccc3c(c2)COB3O)n1] |
| 13 | 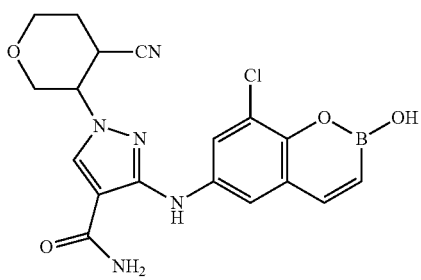 [SMILES: N#CC1CCOCC1n1cc(C(N)=O)c(Nc2cc(Cl)c3c(c2)C=CB(O)O3)n1] |
| 14 | 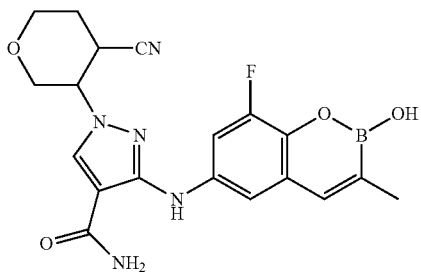 |
| 15 | 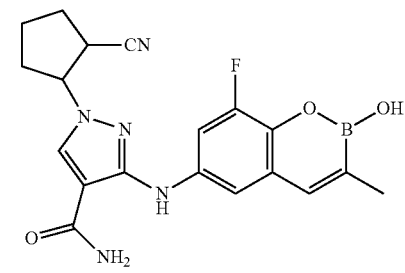 [SMILES: CC1=Cc2cc(Nc3nn(C4CCCC4C#N)cc3C(N)=O)cc(F)c2OB1O] |
| 16 | 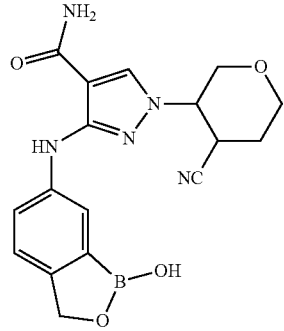 [SMILES: N#CC1CCOCC1n1cc(C(N)=O)c(Nc2ccc3c(c2)B(O)OC3)n1] |
-continued
| Example Number | Structure |
|---|---|
| 17 | 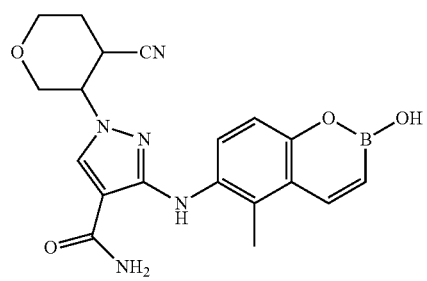 [SMILES: Cc1c(Nc2nn(C3COCCC3C#N)cc2C(N)=O)ccc2c1C=CB(O)O2] |
| 18 | 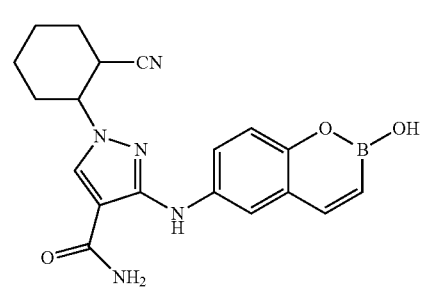 |
| 19 | 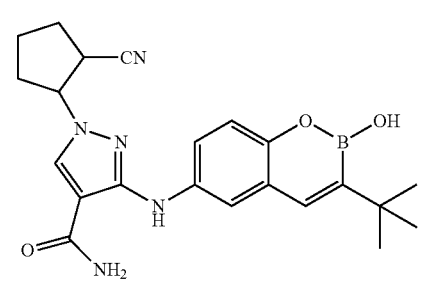 [SMILES: CC(C)(C)C1=Cc2cc(Nc3nn(C4CCCC4C#N)cc3C(N)=O)ccc2OB1O] |
| 20 | 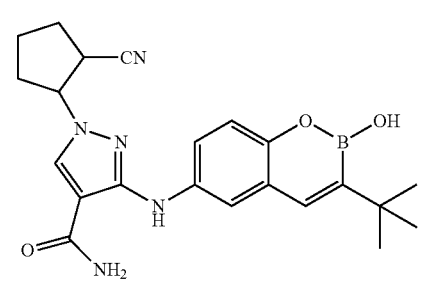 [SMILES: CC(C)(C)C1=Cc2cc(Nc3nn(C4CCCC4C#N)cc3C(N)=O)ccc2OB1O] |
| 21 | 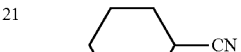 |

| Example Number | Structure |
|---|---|
| 22 | 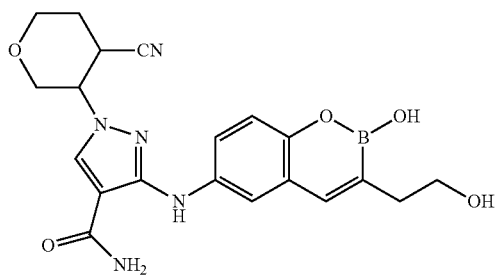 [SMILES: N#CC1CCOCC1n1cc(C(N)=O)c(Nc2ccc3c(c2)C=C(CCO)B(O)O3)n1] |
| 23 | 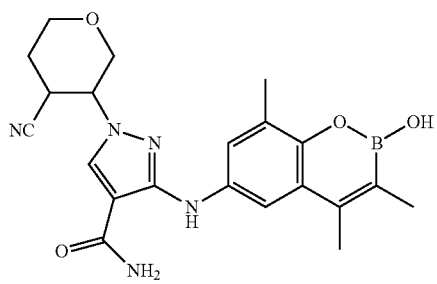 [SMILES: CC1=C(C)c2cc(Nc3nn(C4COCCC4C#N)cc3C(N)=O)cc(C)c2OB1O] |
| 24 | 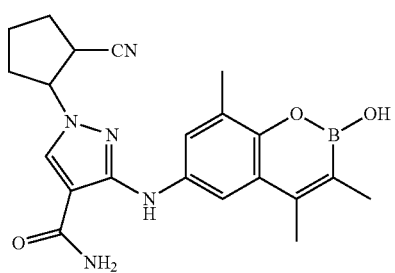 [SMILES: CC1=C(C)c2cc(Nc3nn(C4CCCC4C#N)cc3C(N)=O)cc(C)c2OB1O] |
| 25 | 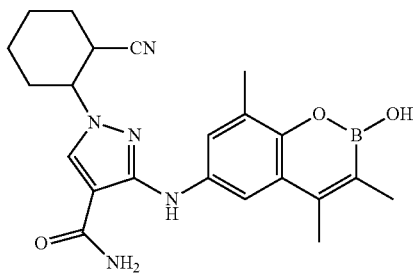 [SMILES: CC1=C(C)c2cc(Nc3nn(C4CCCCC4C#N)cc3C(N)=O)cc(C)c2OB1O] |
| 26 | 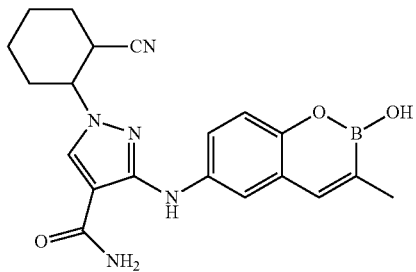 |
| Example Number | Structure |
|---|---|
| 27 | 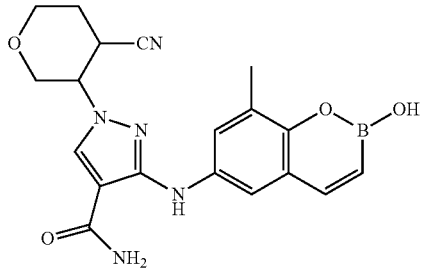 [SMILES: Cc1cc(Nc2nn(C3COCCC3C#N)cc2C(N)=O)cc2c1OB(O)C=C2] |
| 28 | 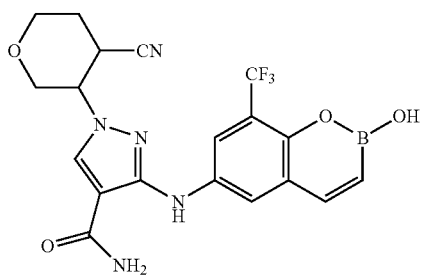 [SMILES: N#CC1CCOCC1n1cc(C(N)=O)c(Nc2cc3c(c(C(F)(F)F)c2)OB(O)C=C3)n1] |
| 29 | 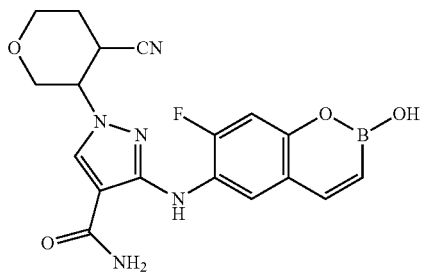 [SMILES: N#CC1CCOCC1n1cc(C(N)=O)c(Nc2cc3c(cc2F)OB(O)C=C3)n1] |
| 30 | 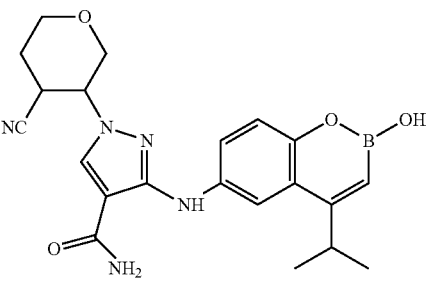 [SMILES: CC(C)C1=CB(O)Oc2ccc(Nc3nn(C4COCCC4C#N)cc3C(N)=O)cc21] |
| 31 | 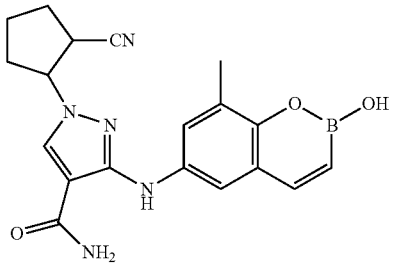 |

| Example Number | Structure |
|---|---|
| 32 | 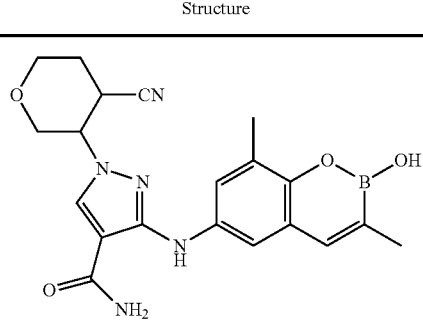 |
| 33 | 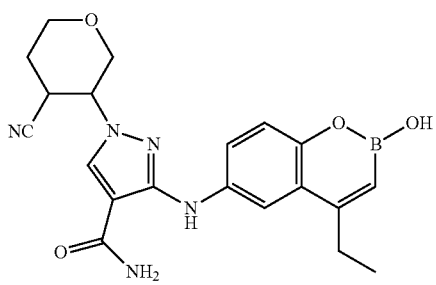 [SMILES: CCC1=CB(O)Oc2ccc(Nc3nn(C4COCCC4C#N)cc3C(N)=O)cc21] |
| 34 | 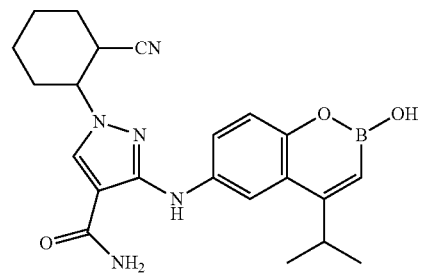 [SMILES: CC(C)C1=CB(O)Oc2ccc(Nc3nn(C4CCCCC4C#N)cc3C(N)=O)cc21] |
| 35 | 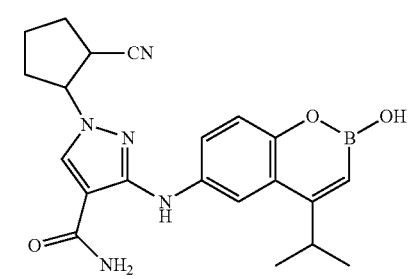 [SMILES: CC(C)C1=CB(O)Oc2ccc(Nc3nn(C4CCCC4C#N)cc3C(N)=O)cc21] |
| 36 | 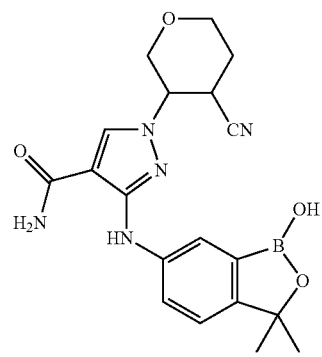 [SMILES: CC1(C)OB(O)c2cc(Nc3nn(C4COCCC4C#N)cc3C(N)=O)ccc21] |
| Example Number | Structure |
|---|---|
| 37 | 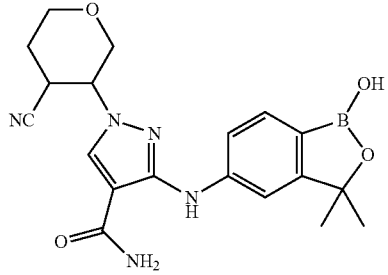 [SMILES: CC1(C)OB(O)c2ccc(Nc3nn(C4COCCC4C#N)cc3C(N)=O)cc21] |
| 38 | 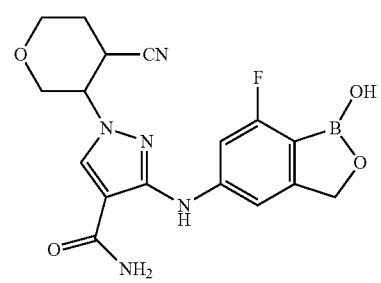 |
| 39 | 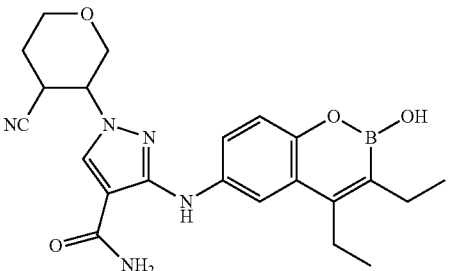 |
| 40 | 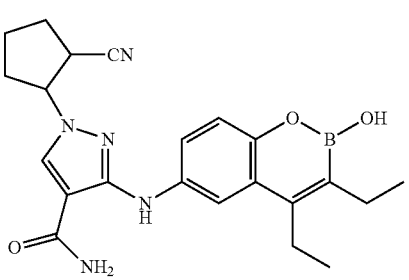 [SMILES: CCC1=C(CC)c2cc(Nc3nn(C4CCCC4C#N)cc3C(N)=O)ccc2OB1O] |
| 41 | 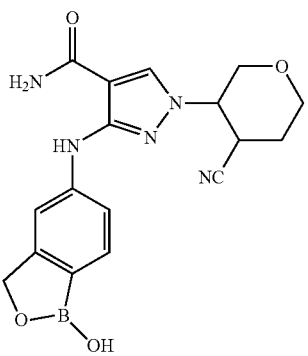 [SMILES: N#CC1CCOCC1n1cc(C(N)=O)c(Nc2ccc3c(c2)COB3O)n1] |

305
-continued
| Example Number | Structure |
|---|---|
| 42 | 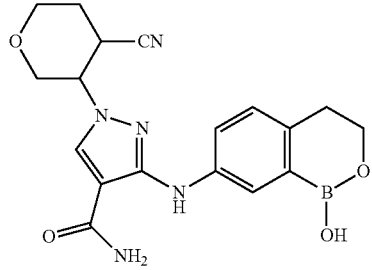 [SMILES: N#CC1CCOCC1n1cc(C(N)=O)c(Nc2ccc3c(c2)B(O)OCC3)n1] |
| 43 | 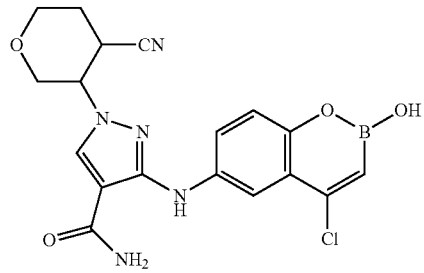 [SMILES: N#CC1CCOCC1n1cc(C(N)=O)c(Nc2ccc3c(c2)C(Cl)=CB(O)O3)n1] |
| 44 | 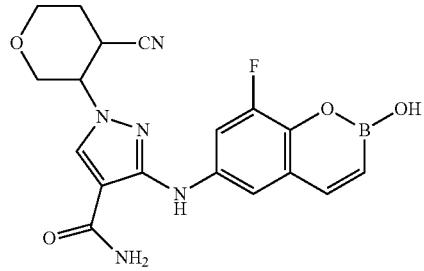 [SMILES: N#CC1CCOCC1n1cc(C(N)=O)c(Nc2cc(F)c3c(c2)C=CB(O)O3)n1] |
| 45 | 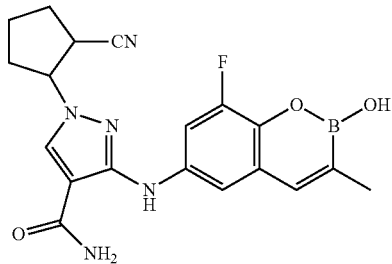 [SMILES: CC1=Cc2cc(Nc3nn(C4CCCC4C#N)cc3C(N)=O)cc(F)c2OB1O] |
| 46 | 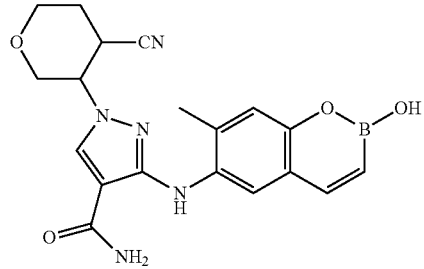 |
306
-continued
| Example Number | Structure |
|---|---|
| 47 | 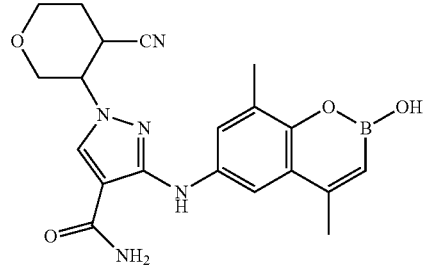 [SMILES: CC1=CB(O)Oc2c(C)cc(Nc3nn(C4COCCC4C#N)cc3C(N)=O)cc21] |
| 48 | 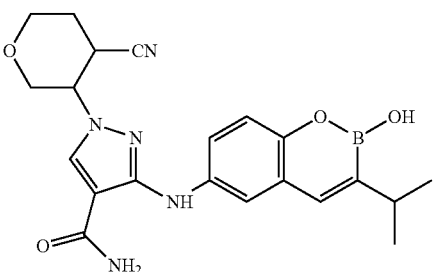 |
| 49 | 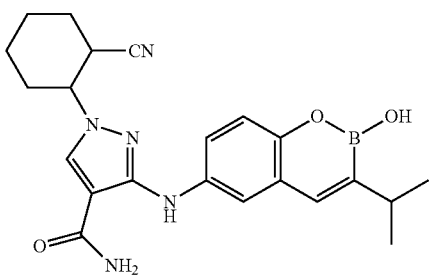 [SMILES: CC(C)C1=Cc2cc(Nc3nn(C4CCCCC4C#N)cc3C(N)=O)ccc2OB1O] |
| 50 | 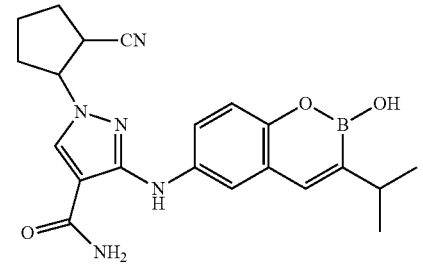 [SMILES: CC(C)C1=Cc2cc(Nc3nn(C4CCCC4C#N)cc3C(N)=O)ccc2OB1O] |
| 51 | 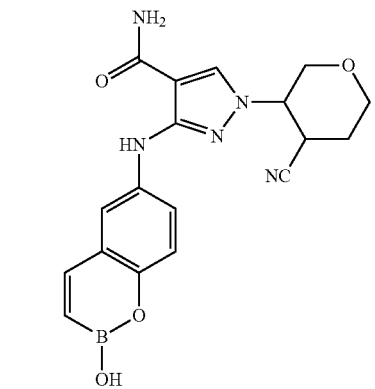 [SMILES: N#CC1CCOCC1n1cc(C(N)=O)c(Nc2ccc3c(c2)C=CB(O)O3)n1] |

| Example Number | Structure |
|---|---|
| 52 | 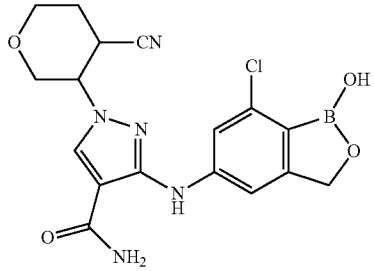 [SMILES: N#CC1CCOCC1n1cc(C(N)=O)c(Nc2cc(Cl)c3c(c2)COB3O)n1] |
| 53 | 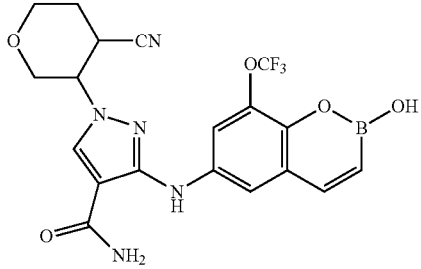 [SMILES: N#CC1CCOCC1n1cc(C(N)=O)c(Nc2cc3c(c(OC(F)(F)F)c2)OB(O)C=C3)n1] |
| 54 | 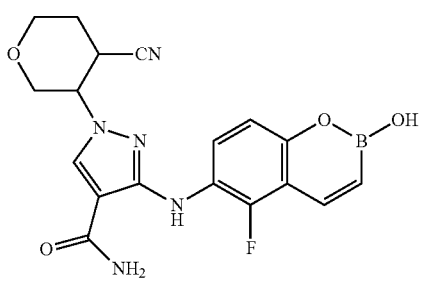 [SMILES: N#CC1CCOCC1n1cc(C(N)=O)c(Nc2ccc3c(c2F)C=CB(O)O3)n1] |
| 55 | 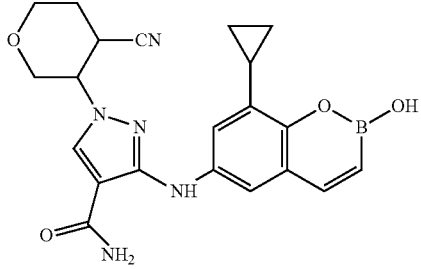 [SMILES: N#CC1CCOCC1n1cc(C(N)=O)c(Nc2cc3c(c(C4CC4)c2)OB(O)C=C3)n1] |
| 56 | 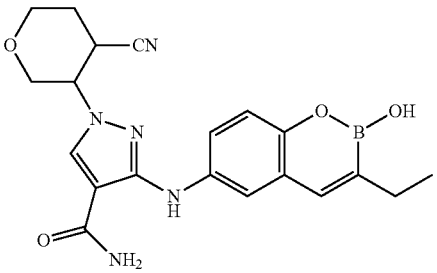 [SMILES: CCC1=Cc2cc(Nc3nn(C4COCCC4C#N)cc3C(N)=O)ccc2OB1O] |

| Example Number | Structure |
|---|---|
| 57 | 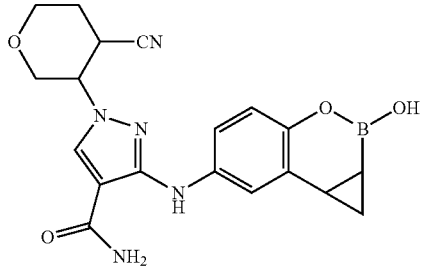 [SMILES: N#CC1CCOCC1n1cc(C(N)=O)c(Nc2ccc3c(c2)C2CC2B(O)O3)n1] |

10. The compound according to any example in paragraph 9 which is a stereoisomer having trans relative stereochemistry as represented in formula (IVa) and (IVb):

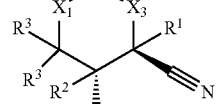

(IVa)

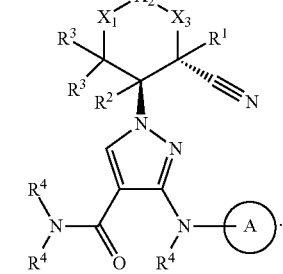

and (IVb)

11. The compound according to one or more of paragraphs 9 and 10, wherein the compound is a single stereoisomer having trans relative stereochemistry.
12. The compound according to paragraph 11, wherein the compound has trans stereochemistry as represented by formula (IVb).
13. A process for preparing a compound according to any one of paragraphs 1-12.
14. A method for treating a patient having a disease or disorder susceptible to modulation of JAK comprising administering a therapeutically effective amount of a compound according to any one of paragraphs 1-12.
15. The method of paragraph 14, wherein the disease or disorder is a condition that can be ameliorated by the selective inhibition of a Janus kinase JAK 1 relative to JAK 2.
16. The method of paragraph 14, wherein the disease or disorder is one or more of atopic dermatitis, flea allergy dermatitis, eczema, pruritus, psoriasis, psoriatic arthritis, inflammatory/autoimmune polyarthritis, Bechet's disease, *Pityriasis rubra* pilaris, alopecia areata, discoid lupus erythematosus, vitiligo, palmoplantar pustulosis, mucocutaneous disease erythema multiforme, mycosis fungoides, graft-versus-host disease, cutaneous lupus, rheumatoid arthritis (RA), arthritis, ulcerative colitis, Crohn's disease, inflammatory bowel disease (IBD), transplant rejection, systemic lupus erythematosus (SLE), dermatomyositis, Sjogren's syndrome, dry eye disease, secondary hypereosinophilic syndrome (HES), allergy, allergic dermatitis, allergic rhinitis, asthma, vasculitis, multiple sclerosis, diabetic nephropathy, cardiovascular disease, artherosclerosis, and cancer.

17. The method of paragraph 16, wherein the disease or disorder is one or more of atopic dermatitis, flea allergy dermatitis, psoriasis, and rheumatoid arthritis.

18. The method according to any one of paragraphs 14-17, wherein the compound is administered in an amount to perturb an immune regulatory pathway in a cell.

19. The method of paragraph 18, wherein the perturbation results in an effect on the JAK-STAT pathway.

20. A method of inhibiting JAK in a mammalian cell comprising contacting the mammalian cell with a compound any one of paragraphs 1-12.

21. The method according to paragraph 20, wherein the mammalian cell is a cell from a subject having an inflammatory condition.

22. A composition comprising a compound of any one of paragraphs 1-12 and a pharmaceutically or veterinary acceptable carrier.

23. A combination comprising a compound of any one of paragraphs 1-12, and one or more other pharmaceutical or veterinary active substances.

24. A method for treating one or more diseases or disorders of inflammation, auto-immune dysfunction, and cancer comprising administering to a subject in need thereof an effective amount of a compound of any one of paragraphs 1-12.

25. The method of paragraph 24, wherein the disease or disorder is atopic dermatitis, flea allergy dermatitis, psoriasis, or rheumatoid arthritis.

26. The method of paragraph 24 or 25, wherein the compound is administered orally, parenterally, or topically.

27. The method of any one of paragraphs 24-26, wherein the subject is a mammal.

28. The method of paragraph 27, wherein the mammal is selected from one or more of livestock mammals, domestic mammals, and companion animals.

29. The method of paragraph 27, wherein the mammal is selected from one or more of humans, cattle, sheep, goats, llamas, alpacas, pigs, horses, donkeys, dogs, and cats.

30. The method of paragraph 27, wherein the mammal is a human, dog, or cat.

31. A compound of any one of paragraphs 1-12 for use in medicine.

32. Use of a compound of any one of paragraphs 1-12 for the manufacture of a medicament for the treatment of one or more diseases or disorder of inflammation, auto-immune dysfunction, and cancer.

33. The use according to paragraph 32, wherein the disease or disorder is atopic dermatitis, flea allergy dermatitis, psoriasis, or rheumatoid arthritis.

34. The use according to paragraph 32, wherein the disease or a disorder is ameliorated by the selective inhibition of a Janus kinase JAK 1 relative to JAK 2.

35. Use of a compound of any one of paragraphs 1-12 and a second active agent in the manufacture of a medicament for the treatment of a disease or a disorder that can be ameliorated by the selective inhibition of a Janus kinase JAK 1 relative to JAK 2.

36. Use of a compound of any one of paragraphs 1-12 for the treatment of one or more diseases or disorders of inflammation, auto-immune dysfunction, and cancer.

37. The use according to paragraph 36, wherein the disease or disorder is atopic dermatitis, flea allergy dermatitis, psoriasis, or rheumatoid arthritis.

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:

1. A compound of formula (IVa) or (IVb):

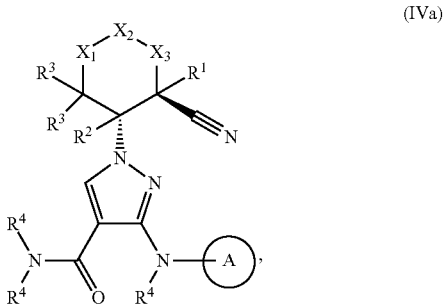
(IVa)

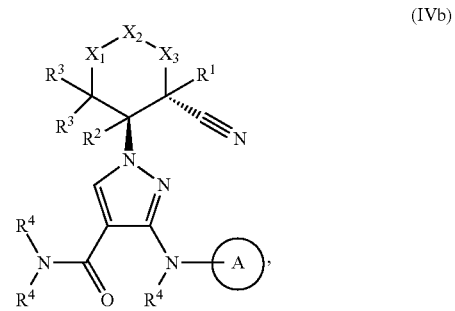
(IVb)

or a pharmaceutically acceptable salt or a stereoisomer or a tautomer thereof wherein $X_1$ is selected from the group consisting of —O—, —N($R^6$)—, and —C($R^7$)($R^8$)—;

$X_2$ is selected from the group consisting of —O—, —N($R^6$)—, and —C($R^7$)($R^8$)—, or $X_2$ comprises a bond between $X_1$ and $X_3$;

$X_3$ is selected from the group consisting of —O—, —N($R^6$)—, and —C($R^7$)($R^8$)—, except $X_1$ and $X_2$ cannot both be —O—, and $X_2$ and $X_3$ cannot both be —O—;

$R^1$ is selected from the group consisting of hydrogen, halogen (when $X_3$ is —C($R^7$)($R^8$)—), hydroxy, $C_{1-6}$ alkyl, $C_{3-7}$ cycloalkyl, $C_{1-6}$ alkyl(oxy), and $C_{3-7}$ cycloalkyl(oxy), wherein the last four members of the of the above-mentioned $R^1$ group may optionally be substituted independently of one another with one or more halogen;

$R^2$ is selected from the group consisting of hydrogen, $C_{1-6}$ alkyl, $C_{3-7}$ cycloalkyl, $C_{1-6}$ alkyl(oxy), and $C_{3-7}$ cycloalkyl(oxy), wherein the last four members of the above-mentioned $R^2$ group may optionally be substituted independently of one another with one or more halogen;

each $R^3$ is independently selected from the group consisting of hydrogen, halogen (when $X_1$ is $-C(R^7)(R^8)$), $C_{1-6}$ alkyl, $C_{3-7}$ cycloalkyl, $C_{1-6}$ alkyl(oxy), and $C_{3-7}$ cycloalkyl(oxy), wherein the last four members of the above-mentioned $R^3$ group may optionally be substituted independently of one another with one or more halogen;

each $R^4$ is independently selected from the group consisting of hydrogen, $C_{1-6}$ alkyl, $C_{3-7}$ cycloalkyl, $C_{1-6}$ alkyl (oxy), and $C_{3-7}$ cycloalkyl(oxy), wherein the above-mentioned members of each $R^4$ group, except hydrogen, may optionally be substituted independently of one another with one or more halogen;

A is selected from the group consisting of benzo[c][1,2]oxaborol-1(3H)-ol, 3,4-dihydro-1 Hbenzo[c][1,2]oxaborinin-1-ol, and 2H-benzo[e][1,2]oxaborinin-2-ol, or a derivative thereof, such as a moiety selected from any one of $A_1$-$A_6$:

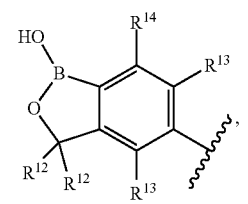

$A_1$

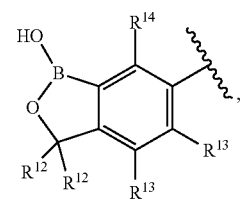

$A_2$

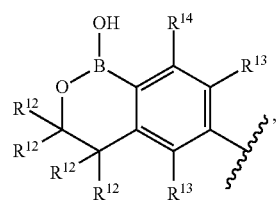

$A_3$

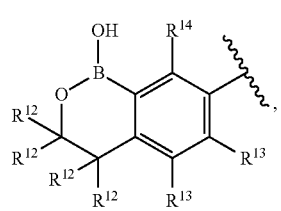

$A_4$

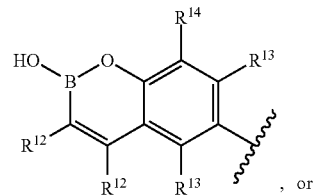

$A_5$, or

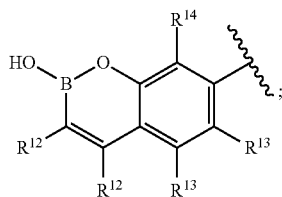

$A_6$;

$R^6$ is selected from the group consisting of hydrogen, $C_{1-6}$ alkyl, $C_{3-7}$ cycloalkyl, $C_{1-6}$ alkyl(oxy), $C_{3-7}$ cycloalkyl (oxy), $-COO-C_{1-6}$ alkyl, $-COO-C_{3-7}$-cycloalkyl, $-(C_{1-3}$-alkyl)-$(C_{3-6}$-cycloalkyl), $-(C_{2-3}$-alky(oxy)-$(C_{2-6}$-alkyl), $-(C_{2-3}$-alkyl(oxy)-$(C_{3-6}$-cycloalkyl), 4-7-membered heterocycloalkyl, $-(C_{1-3}$-alkyl)-(4-7-membered heterocycloalkyl), -heteroaryl, and $-(C_{1-3}$-alkyl)-(heteroaryl), wherein the above-mentioned members of the $R^6$ group, except hydrogen, may optionally be substituted independently of one another by one or more substituents selected from the group consisting of $C_{1-6}$ alkyl and halogen, except halogen may not be adjacent to a heteroatom;

$R^7$ and $R^8$ are independently selected from the group consisting of hydrogen, halogen, hydroxy, $-N(R^9)(R^{10})$, $-O(R^{11})$, $C_{1-6}$alkyl, $C_{3-7}$cycloalkyl, $C_{1-6}$ alkyl (oxy), $C_{3-7}$ cycloalkyl(oxy), $-COO-C_{1-6}$ alkyl, $-COO-C_{3-7}$-cycloalkyl, $-(C_{1-3}$-alkyl)-$(C_{3-6}$-cycloalkyl), $-(C_{2-3}$-alkyl(oxy)-$(C_{2-6}$-alkyl), $-(C_{2-3}$-alkyl(oxy)-$(C_{3-6}$-cycloalkyl), 4-7-membered heterocycloalkyl, $-(C_{1-3}$-alkyl)-(4-7-membered heterocycloalkyl), -heteroaryl, and $-(C_{1-3}$-alkyl)-(heteroaryl), wherein the last fifteen members of the above-mentioned $R^7$ and $R^8$ groups may optionally be substituted independently of one another by one or more substituents selected from the group consisting of halogen and hydroxy, and wherein $R^7$ and $R^8$ may be linked together to form a ring;

$R^9$ and $R^{10}$ are independently selected from the group consisting of hydrogen, $C_{1-6}$ alkyl, $C_{3-7}$ cycloalkyl, $C_{1-6}$ alkyl(oxy), $C_{3-7}$ cycloalkyl(oxy), $-COO-C_{1-6}$ alkyl, $-COO-C_{3-7}$-cycloalkyl, $-(C_{1-3}$-alkyl)-$(C_{3-6}$-cycloalkyl), $-(C_{2-3}$-alkyoxyl)-$(C_{2-6}$-alkyl), $-(C_{2-3}$-alkyl(oxy)-$(C_{3-6}$-cycloalkyl), 4-7-membered heterocycloalkyl, $-(C_{1-3}$-alkyl)-(4-7-membered heterocycloalkyl), -heteroaryl, and $-(C_{1-3}$-alkyl)-(heteroaryl), wherein the last fourteen members of the above-mentioned $R^9$ and $R^{10}$ groups may optionally be substituted independently of one another by one or more halogen, or $R^9$ and $R^{10}$ may be linked together to form a ring;

$R^{11}$ is selected from the group consisting of hydrogen, $C_{1-6}$ alkyl, $C_{3-7}$ cycloalkyl, $C_{1-6}$ alkyl(oxy), $C_{3-7}$ cycloalkyl(oxy), $-COO-C_{1-6}$ alkyl, $-COO-C_{3-7}$-cycloalkyl, $-(C_{1-3}$-alkyl)-$(C_{3-6}$-cycloalkyl), $-(C_{2-3}$-alkyoxyl)-$(C_{2-6}$-alkyl), $-(C_{2-3}$-alkyl(oxy)-$(C_{3-6}$-cycloalkyl), 4-7-membered heterocycloalkyl, $-(C_{1-3}$-alkyl)-(4-7-membered heterocycloalkyl), -heteroaryl, and —($C_{1-3}$-alkyl)-(heteroaryl), wherein the last thirteen members of the above-mentioned $R^{11}$ group may optionally be substituted independently of one another by one or more substituents selected from the group consisting of halogen and hydroxy, except that said optional substitution may not be geminal;

each $R^{12}$ is independently selected from the group consisting of hydrogen, halogen, $C_{1-6}$ alkyl, $C_{3-7}$ cycloalkyl, 4-7-membered heterocycloalkyl, $C_{1-6}$ alkyl(oxy), and $C_{3-7}$ cycloalkyl(oxy), wherein the last four members of the above-mentioned $R^{12}$ group may optionally be substituted independently of one another by one or more substituents selected from the group consisting of halogen and hydroxy, except when $R^{12}$ is adjacent to oxygen, $R^{12}$ is not halogen, and two adjacent $R^{12}$ may be connected to provide a fused cycloalkyl, such as cyclopropyl; and $R^{13}$ and $R^{14}$ are independently selected from the group consisting of hydrogen, halogen, cyano, $C_{1-6}$ alkyl, $C_{3-7}$cycloalkyl, $C_{1-6}$ alkyl(oxy), $C_{3-7}$cycloalkyl(oxy), —($C_{1-3}$-alkyl)-($C_{3-6}$-cycloalkyl), —($C_{2-3}$-alkyl(oxy)-($C_{2-6}$-alkyl), —($C_{2-3}$-alkyl(oxy)-($C_{3-6}$-cycloalkyl), 4-7-membered heterocycloalkyl, —($C_{1-3}$-alkyl)-(4-7-membered heterocycloalkyl), —N—($R^6$)($R^6$), —SO$_2$—($R^6$), —SO$_2$—($R^6$)($R^6$), —S(O)—($R^6$), and —S—($R^6$), wherein the last fourteen members of the above-mentioned $R^{13}$ and $R^{14}$ groups may optionally be substituted independently of one another by one or more substituents selected from the group consisting of halogen and hydroxy.

2. The compound according to claim 1, wherein $X_1$ is selected from the group consisting of —O—, —N($R^6$)—, and —C($R^7$)($R^8$)—;

$X_2$ is selected from the group consisting of —O—, —N($R^6$)—, and —C($R^7$)($R^8$)—, or $X_2$ comprises a bond between $X_1$ and $X_3$;

$X_3$ is —C($R^7$)($R^8$)—, except $X_1$ and $X_2$ cannot both be —O—;

$R^1$ is selected from the group consisting of hydrogen, $C_{1-6}$ alkyl, and $C_{3-7}$ cycloalkyl, wherein the last two members of the above-mentioned group may optionally be substituted independently of one another with one or more halogen;

$R^2$ is selected from the group consisting of hydrogen, $C_{1-6}$ alkyl, and $C_{3-7}$ cycloalkyl, wherein the last two members of the above-mentioned group may optionally be substituted independently of one another with one or more halogen;

each $R^3$ is independently selected from the group consisting of hydrogen, $C_{1-6}$ alkyl, and $C_{3-7}$ cycloalkyl, wherein the last two members of the above-mentioned group may optionally be substituted independently of one another with one or more halogen;

each $R^4$ is independently selected from the group consisting of hydrogen, $C_{1-6}$ alkyl, and $C_{3-7}$ cycloalkyl, wherein the last two members of the above-mentioned group may optionally be substituted independently of one another with one or more halogen;

$R^7$ and $R^8$ are independently selected from the group consisting of hydrogen, —$C_{1-6}$ alkyl, $C_{3-7}$ cycloalkyl, $C_{1-6}$ alkyl(oxy), and $C_{3-7}$ cycloalkyl(oxy), wherein the last four members of the above-mentioned group may optionally be substituted independently of one another by one or more substituents selected from the group consisting of halogen and hydroxy, and $R^7$ and $R^8$ may be linked together to form a ring; and each $R^{13}$ is independently selected from the group consisting of hydrogen, halogen, and $C_{1-6}$ alkyl.

3. The compound according to one or more of claims 1 to 2, wherein $X_1$ is selected from the group consisting of —O—, —N($R^6$)—, and —C($R^7$)($R^8$)—;

$X_2$ is selected from the group consisting of —O— and —C($R^7$)($R^8$)—, except $X_1$ and $X_2$ may not both be —O—, or $X_2$ comprises a bond between $X_1$ and $X_3$;

$X_3$ is —C($R^7$)($R^8$)—;

$R^1$ is selected from the group consisting of hydrogen and $C_{1-6}$ alkyl;

$R^2$ is selected from the group consisting of hydrogen and $C_{1-6}$ alkyl;

each $R^3$ is independently selected from the group consisting of hydrogen and $C_{1-6}$ alkyl;

each $R^4$ is independently selected from the group consisting of hydrogen and $C_{1-6}$ alkyl;

$R^7$ and $R^8$ are independently selected from the group consisting of hydrogen and $C_{1-6}$ alkyl, wherein $C_{1-6}$ alkyl is optionally substituted with one or more of halogen;

$R^{13}$ is hydrogen; and each $R^{14}$ is independently selected from the group consisting of hydrogen, halogen, cyano, $C_{1-6}$ alkyl, $C_{3-7}$ cycloalkyl, $C_{1-6}$ alkyl(oxy), $C_{3-7}$ cycloalkyl(oxy), —($C_{1-3}$-alkyl)-($C_{3-6}$-cycloalkyl), —($C_{2-3}$-alkyl(oxy)-($C_{2-6}$-alkyl), and 4-7-membered heterocycloalkyl, wherein the last seven members said $R^{14}$ group may optionally be substituted independently of one another by one or more substituents selected from the group consisting of halogen and hydroxy.

4. The compound according to claim 3, wherein $X_2$ is —C($R^7$)($R^8$)—;

$X_3$ is —C($R^7$)($R^8$)—;

$R^1$, $R^2$, $R^3$, and $R^4$ are hydrogen;

$R^7$ and $R^8$ are independently selected from the group consisting of hydrogen and $C_{1-6}$ alkyl, wherein $C_{1-6}$ alkyl is optionally substituted with one or more of halogen;

each $R^{12}$ is independently selected from the group consisting of hydrogen, halogen, $C_{1-6}$ alkyl, and $C_{3-7}$ cycloalkyl, wherein the last two members of the above-mentioned $R^{12}$ group may optionally be substituted independently of one another with one or more halogen;

each $R^{13}$ is hydrogen; and each $R^{14}$ is independently selected from the group consisting hydrogen, halogen, cyano, $C_{1-6}$ alkyl, $C_{3-7}$ cycloalkyl, and $C_{1-6}$alkyl(oxy), wherein the last three members of the above-mentioned $R^{14}$ group may optionally be substituted independently of one another by one or more halogen.

5. A compound selected from the group shown in the following table:

| Example Number | Structure |
|---|---|
| 1 | 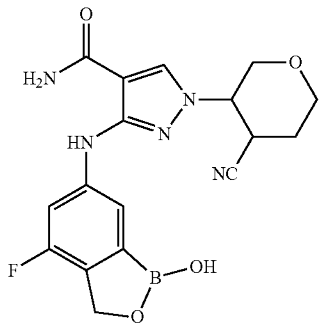 [SMILES: N#CC1CCOCC1n1cc(C(N)=O)c(Nc2cc(F)c3c(c2)B(O)OC3)n1] |
| 2 | 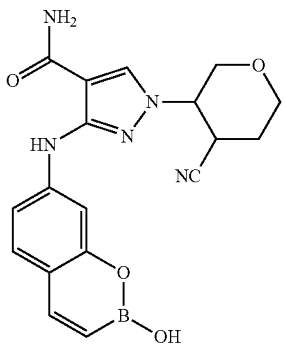 [SMILES: N#CC1CCOCC1n1cc(C(N)=O)c(Nc2ccc3c(c2)OB(O)C=C3)n1] |
| 3 | 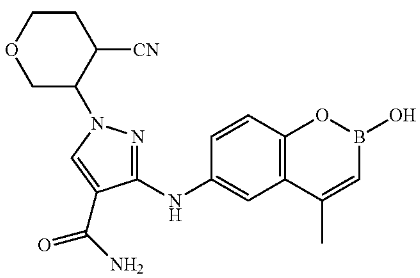 |
| 4 | 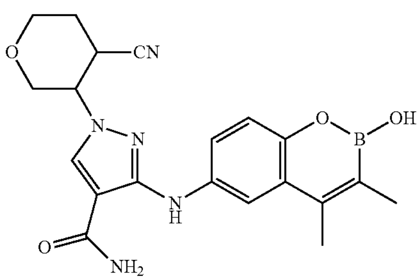 [SMILES: CC1=C(C)c2cc(Nc3nn(C4COCCC4C#N)cc3C(N)=O)ccc2OB1O] |
| 5 | 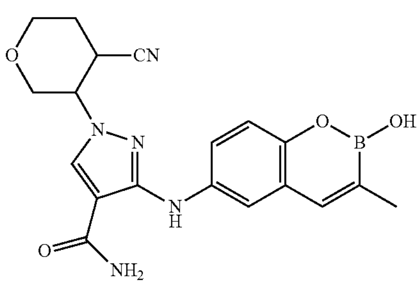 [SMILES: CC1=Cc2cc(Nc3nn(C4COCCC4C#N)cc3C(N)=O)ccc2OB1O] |
| 6 | |
| 7 | |
| 8 | |
| 9 | |
| 10 | |

-continued
| Example Number | Structure |
|---|---|
| 11 | 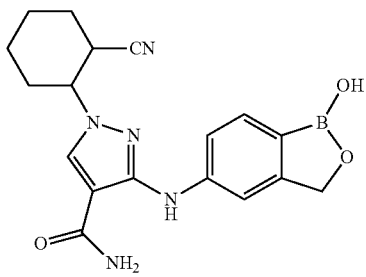 [SMILES: N#CC1CCCCC1n1cc(C(N)=O)c(Nc2ccc3c(c2)COB3O)n1] |
| 12 | 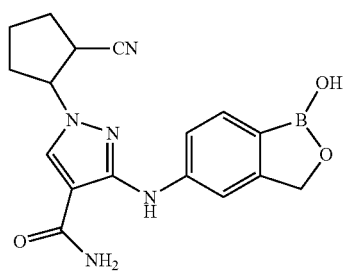 [SMILES: N#CC1CCCC1n1cc(C(N)=O)c(Nc2ccc3c(c2)COB3O)n1] |
| 13 | 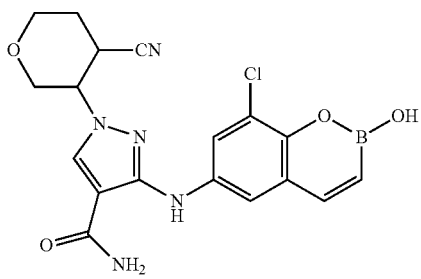 [SMILES: N#CC1CCOCC1n1cc(C(N)=O)c(Nc2cc(Cl)c3c(c2)C=CB(O)O3)n1] |
| 14 | 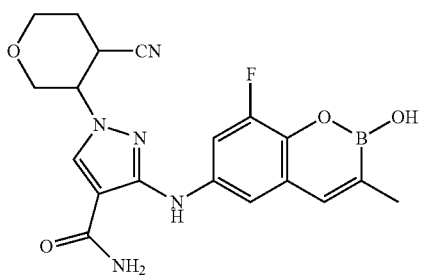 |
| 15 | 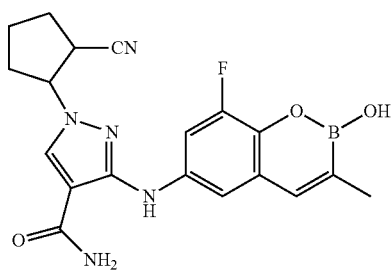 [SMILES: CC1=Cc2cc(Nc3nn(C4CCCC4C#N)cc3C(N)=O)cc(F)c2OB1O] |
-continued
| Example Number | Structure |
|---|---|
| 16 | 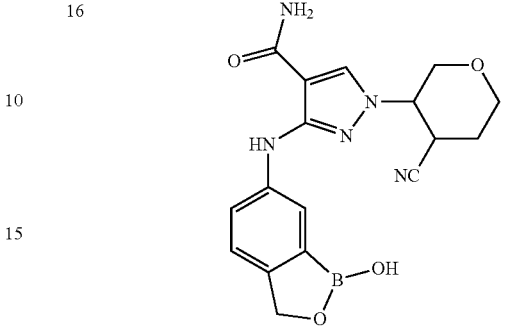 |
| 17 | 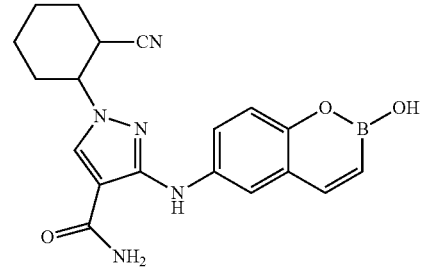 [SMILES: N#CC1CCCCC1n1cc(C(N)=O)c(Nc2ccc3c(c2)C=CB(O)O3)n1] |
| 18 | 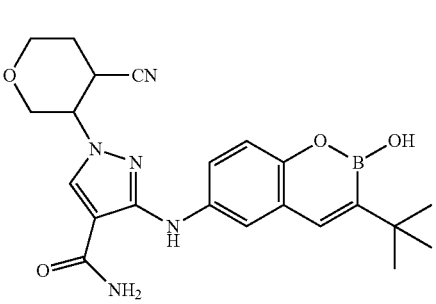 [SMILES: CC(C)(C)C1=Cc2cc(Nc3nn(C4COCCC4C#N)cc3C(N)=O)ccc2OB1O] |
| 19 | 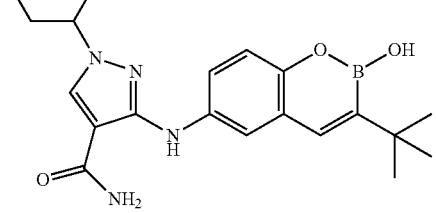 |
| 20 | 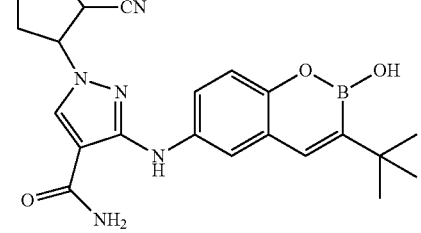 |

| Example Number | Structure |
|---|---|
| 21 | 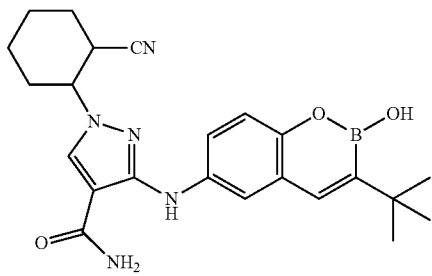 [SMILES: CC(C)(C)C1=Cc2cc(Nc3nn(C4CCCCC4C#N)cc3C(N)=O)ccc2OB1O] |
| 22 | 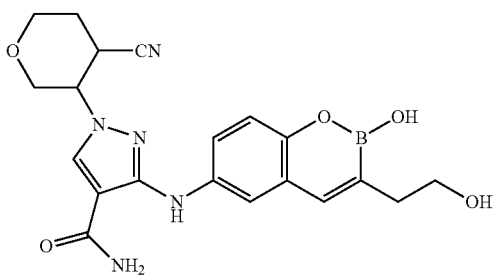 [SMILES: N#CC1CCOCC1n1cc(C(N)=O)c(Nc2ccc3c(c2)C=C(CCO)B(O)O3)n1] |
| 23 | 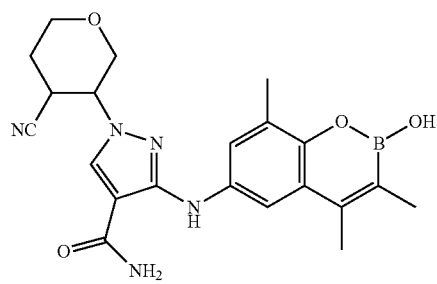 [SMILES: CC1=C(C)c2cc(Nc3nn(C4COCCC4C#N)cc3C(N)=O)cc(C)c2OB1O] |
| 24 | 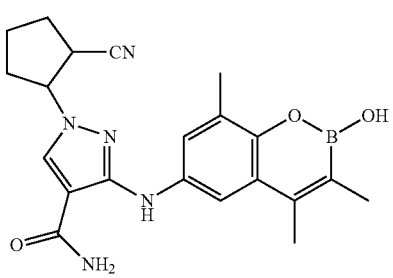 [SMILES: CC1=C(C)c2cc(Nc3nn(C4CCCC4C#N)cc3C(N)=O)cc(C)c2OB1O] |
| 25 | 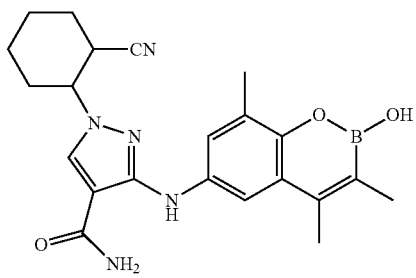 |
| 26 | 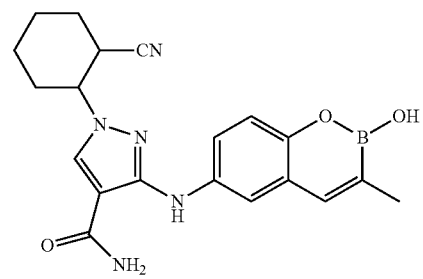 [SMILES: CC1=Cc2cc(Nc3nn(C4CCCCC4C#N)cc3C(N)=O)ccc2OB1O] |
| 27 | 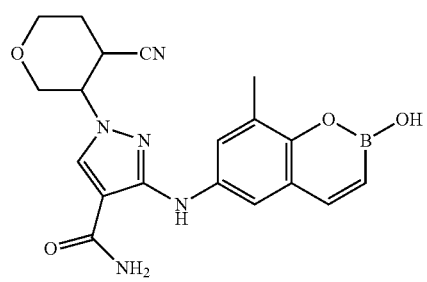 |
| 28 | 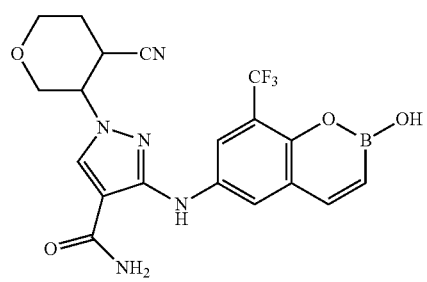 [SMILES: N#CC1CCOCC1n1cc(C(N)=O)c(Nc2cc3c(c(C(F)(F)F)c2)OB(O)C=C3)n1] |
| 29 | 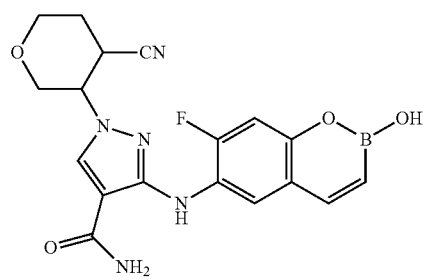 |
| 30 | 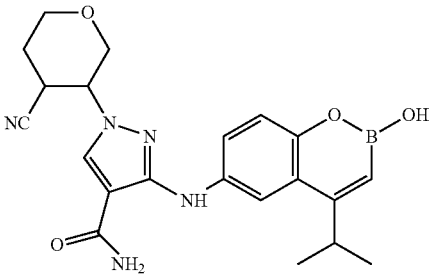 [SMILES: CC(C)C1=CB(O)Oc2ccc(Nc3nn(C4COCCC4C#N)cc3C(N)=O)cc21] |

US 11,827,657 B2
-continued
| Example Number | Structure |
|---|---|
| 31 | 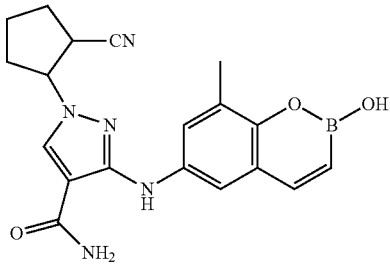 |
| 32 | 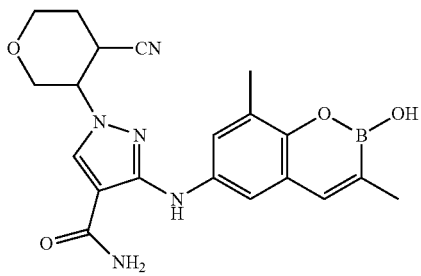 [SMILES: CC1=Cc2cc(Nc3nn(C4COCCC4C#N)cc3C(N)=O)cc(C)c2OB1O] |
| 33 | 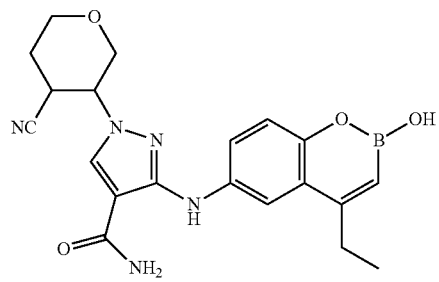 [SMILES: CCC1=CB(O)Oc2ccc(Nc3nn(C4COCCC4C#N)cc3C(N)=O)cc21] |
| 34 | 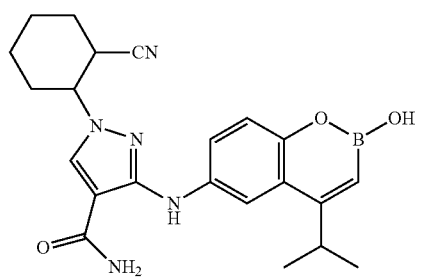 |
| 35 | 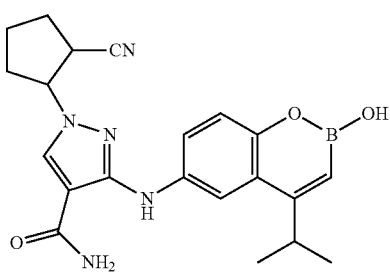 |
-continued
| Example Number | Structure |
|---|---|
| 36 | 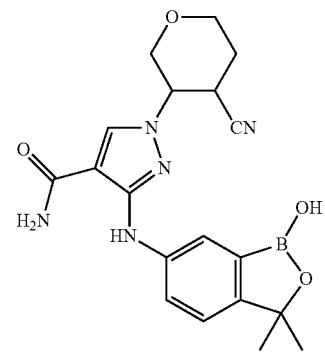 [SMILES: CC1(C)OB(O)c2cc(Nc3nn(C4COCCC4C#N)cc3C(N)=O)ccc21] |
| 37 | 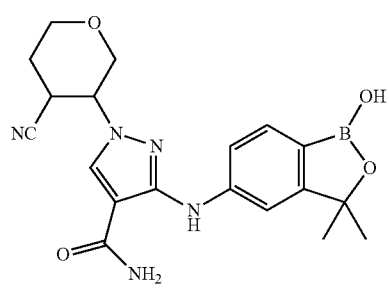 [SMILES: CC1(C)OB(O)c2ccc(Nc3nn(C4COCCC4C#N)cc3C(N)=O)cc21] |
| 38 | 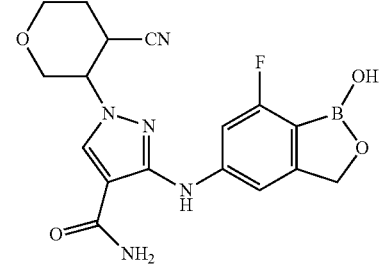 [SMILES: N#CC1CCOCC1n1cc(C(N)=O)c(Nc2cc(F)c3c(c2)COB3O)n1] |
| 39 | 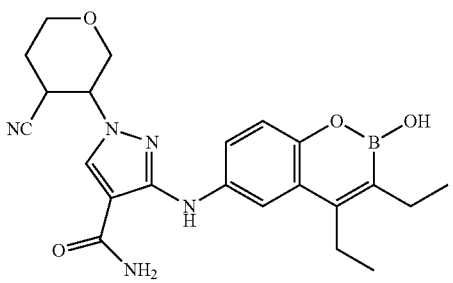 [SMILES: CCC1=C(CC)c2cc(Nc3nn(C4COCCC4C#N)cc3C(N)=O)ccc2OB1O] |
| 40 | 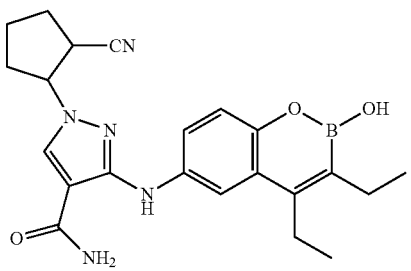 [SMILES: CCC1=C(CC)c2cc(Nc3nn(C4CCCC4C#N)cc3C(N)=O)ccc2OB1O] |

-continued
| Example Number | Structure |
|---|---|
| 41 | 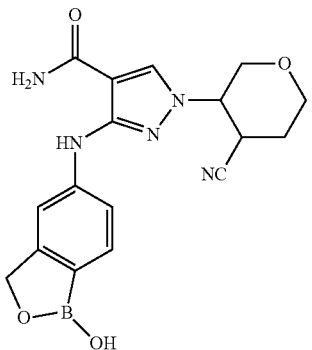 [SMILES: N#CC1CCOCC1n1cc(C(N)=O)c(Nc2ccc3c(c2)COB3O)n1] |
| 42 | 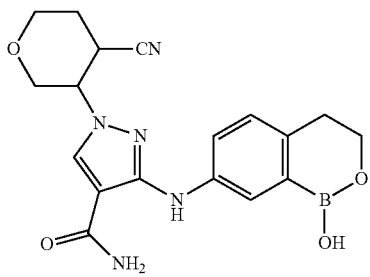 [SMILES: N#CC1CCOCC1n1cc(C(N)=O)c(Nc2ccc3c(c2)B(O)OCC3)n1] |
| 43 | 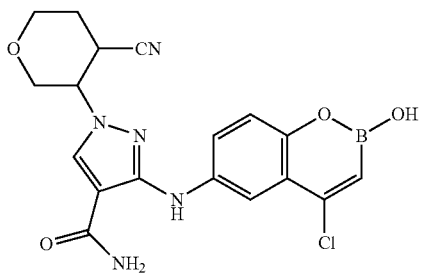 [SMILES: N#CC1CCOCC1n1cc(C(N)=O)c(Nc2ccc3c(c2)C(Cl)=CB(O)O3)n1] |
| 44 | 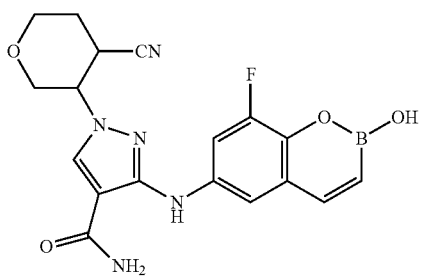 |
| 45 | 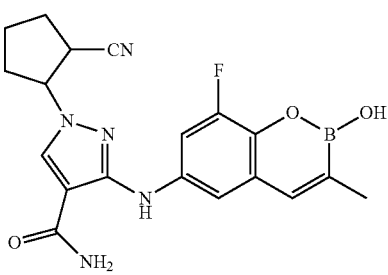 |
-continued
| Example Number | Structure |
|---|---|
| 46 | 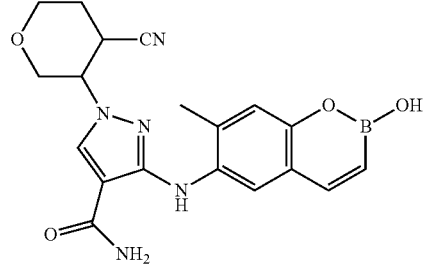 [SMILES: Cc1cc2c(cc1Nc1nn(C3COCCC3C#N)cc1C(N)=O)C=CB(O)O2] |
| 47 | 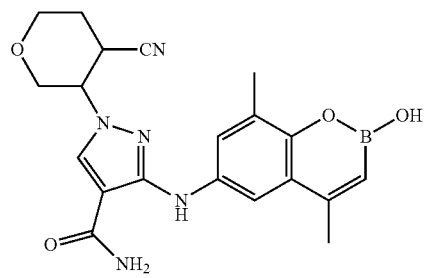 |
| 48 | 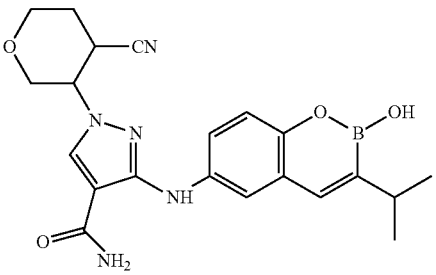 [SMILES: CC(C)C1=Cc2cc(Nc3nn(C4COCCC4C#N)cc3C(N)=O)ccc2OB1O] |
| 49 | 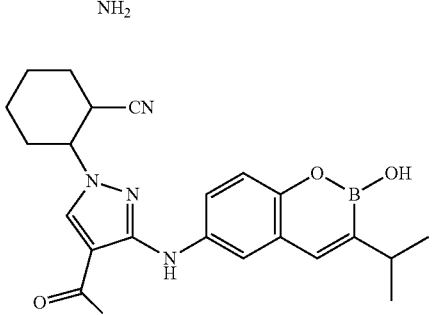 |
| 50 | 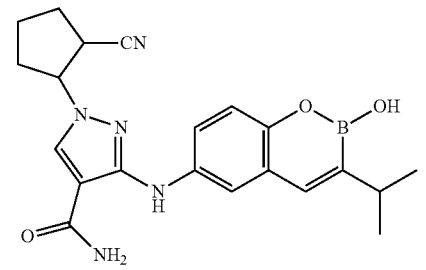 [SMILES: CC(C)C1=Cc2cc(Nc3nn(C4CCCC4C#N)cc3C(N)=O)ccc2OB1O] |

| Example Number | Structure |
|---|---|
| 51 | 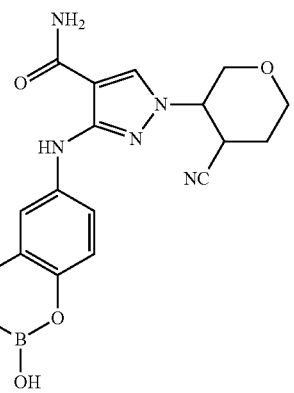 |
| 52 | 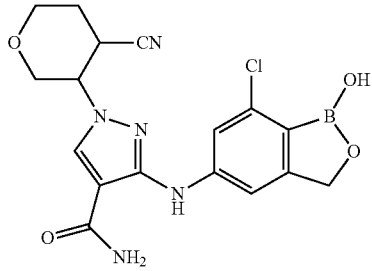 |
| 53 | 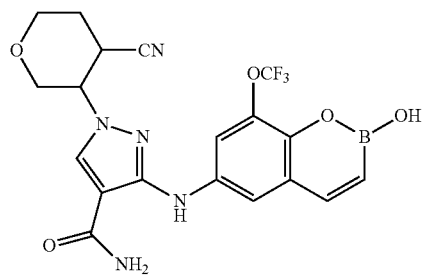 [SMILES: N#CC1CCOCC1n1cc(C(N)=O)c(Nc2cc3c(c(OC(F)(F)F)c2)OB(O)C=C3)n1] |
| 54 | 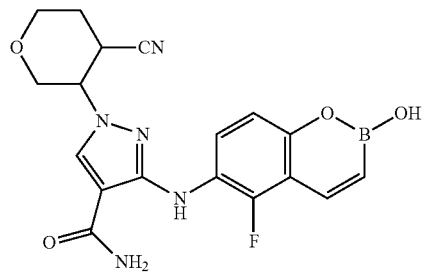 |
| 55 | 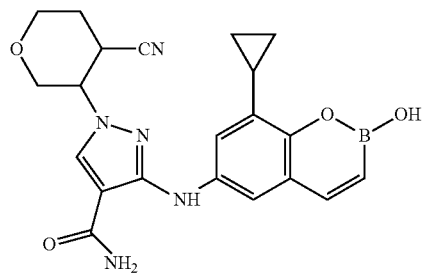 [SMILES: N#CC1CCOCC1n1cc(C(N)=O)c(Nc2cc3c(c(C4CC4)c2)OB(O)C=C3)n1] |
| 56 | 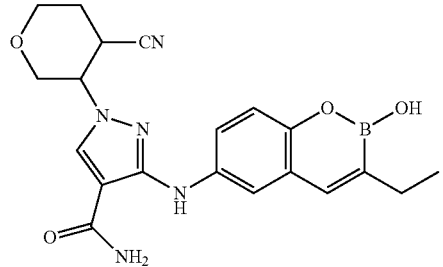 [SMILES: CCC1=Cc2cc(Nc3nn(C4COCCC4C#N)cc3C(N)=O)ccc2OB1O] |
| 57 | 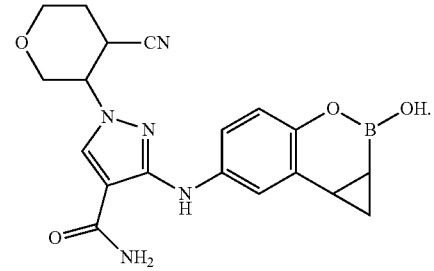 [SMILES: N#CC1CCOCC1n1cc(C(N)=O)c(Nc2ccc3c(c2)C2CC2B(O)O3)n1] |

6. The compound according to claim 5 which is a stereoisomer having trans relative stereochemistry as represented in formula (IVa) and (IVb):

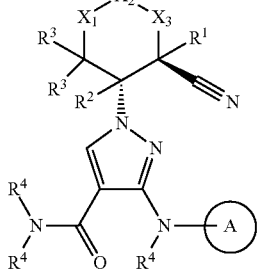

(IVa)

and

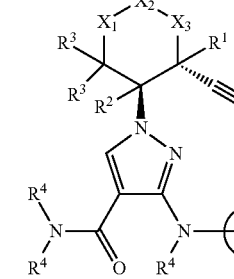

(IVb)

7. The compound according to one or more of claims 5 to 6, wherein the compound is a single stereoisomer having trans relative stereochemistry.

8. The compound according to claim 7, wherein the compound has trans stereochemistry as represented by formula (IVb).

* * * * *